US012559504B2

(12) United States Patent
Komori et al.

(10) Patent No.: US 12,559,504 B2
(45) Date of Patent: Feb. 24, 2026

(54) BENZOTRIAZOLE DERIVATIVE

(71) Applicant: UBE CORPORATION, Ube (JP)

(72) Inventors: Ken-ichi Komori, Ube (JP); Hayato Nishiyama, Ube (JP); Naoya Kinoshita, Ube (JP); Yukinori Wada, Ube (JP); Kousuke Morishita, Ube (JP); Akishi Ninomiya, Ube (JP); Yuusuke Shiraishi, Ube (JP); Kazuhiro Onuma, Ube (JP); Sayaka Ogi, Ube (JP); Hiroyoshi Kawada, Ube (JP); Tomio Kimura, Shinagawa-ku (JP)

(73) Assignee: UBE CORPORATION, Ube (JP)

( * ) Notice: Subject to any disclaimer, the term of this patent is extended or adjusted under 35 U.S.C. 154(b) by 832 days.

(21) Appl. No.: 17/614,941

(22) PCT Filed: May 29, 2020

(86) PCT No.: PCT/JP2020/021426
§ 371 (c)(1),
(2) Date: Nov. 29, 2021

(87) PCT Pub. No.: WO2020/241853
PCT Pub. Date: Dec. 3, 2020

(65) Prior Publication Data

US 2022/0259223 A1 Aug. 18, 2022

(30) Foreign Application Priority Data

May 31, 2019 (JP) ................................ 2019-102529

(51) Int. Cl.

| | |
|---|---|
| ***C07D 498/04*** | (2006.01) |
| ***A61P 1/16*** | (2006.01) |
| ***C07D 413/10*** | (2006.01) |

(52) U.S. Cl.
CPC ............. *C07D 498/04* (2013.01); *A61P 1/16* (2018.01); *C07D 413/10* (2013.01)

(58) Field of Classification Search
CPC .. C07D 498/04; C07D 413/10; C07D 498/14; C07D 215/26; C07D 217/22; C07D 249/18; C07D 267/16; A61P 1/16; A61P 13/12; A61P 43/00; A61K 31/553
See application file for complete search history.

(56) References Cited

U.S. PATENT DOCUMENTS

| | | | |
|---|---|---|---|
| 2017/0210736 | A1 | 7/2017 | Kuroda et al. |
| 2018/0179187 | A1 | 6/2018 | Kerns et al. |
| 2020/0031846 | A1 | 1/2020 | Brooks et al. |
| 2020/0055874 | A1 | 2/2020 | Barbay et al. |
| 2023/0024995 | A1 | 1/2023 | Miyabe et al. |

FOREIGN PATENT DOCUMENTS

| | | | | |
|---|---|---|---|---|
| CN | 108112251 A | 6/2018 | | |
| EA | 030431 B1 | 8/2018 | | |
| RU | 2017 105 836 A | 8/2018 | | |
| WO | WO 2015/092713 A1 | 6/2015 | | |
| WO | WO 2016/203400 A1 | 12/2016 | | |
| WO | WO 2016/203401 A1 | 12/2016 | | |
| WO | WO-2016202253 A1 * | 12/2016 | | ......... A61K 31/4192 |
| WO | WO 2017/060854 A1 | 4/2017 | | |
| WO | WO 2017/060855 A1 | 4/2017 | | |
| WO | WO 2018/104766 A1 | 6/2018 | | |
| WO | WO 2018/109641 A1 | 6/2018 | | |
| WO | WO 2018/109642 A1 | 6/2018 | | |
| WO | WO 2018/109643 A1 | 6/2018 | | |
| WO | WO 2018/109646 A1 | 6/2018 | | |
| WO | WO 2018/109647 A1 | 6/2018 | | |
| WO | WO 2018/109648 A1 | 6/2018 | | |

(Continued)

OTHER PUBLICATIONS

International Search Report issued Apr. 29, 2019 in PCT/JP2020/021426 (submitting English translation only), citing documents AA-AC, AE-AH and AY therein, 3 pages.

International Preliminary Report on Patentability and Written Opinion of the International Searching Authority issued Nov. 16, 2021 in PCT/JP2020/021426 (submitting English translation only), citing documents AE-AH and AY therein, 5 pages.

Tom D. Heightman, et al., "Structure-Activity and Structure-Conformation Relationships of Aryl Propionic Acid Inhibitors of the Kelch-like ECH-Associated Protein 1/Nuclear Factor Erythroid 2-Related Factor 2 (KEAP1/NRF2) Protein-Protein Interaction" Journal of Medicinal Chemistry, vol. 62, 2019, pp. 4683-4702.

(Continued)

*Primary Examiner* — Joseph K McKane
*Assistant Examiner* — Meghan C Heasley
(74) *Attorney, Agent, or Firm* — Oblon, McClelland, Maier & Neustadt, L.L.P.

(57) ABSTRACT

The present invention provides a compound having Keap1 inhibitory effects and a pharmaceutical composition containing the same. Specifically, the present invention provides a compound represented by the following general formula (I):

(I)

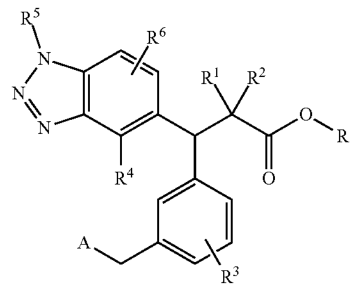

[wherein the symbols have the same meanings as those described in the description] or a pharmaceutically acceptable salt thereof and a pharmaceutical composition containing the same.

20 Claims, No Drawings

(56) References Cited

FOREIGN PATENT DOCUMENTS

| | | | |
|---|---|---|---|
| WO | WO 2018/109649 | A1 | 6/2018 |
| WO | WO 2018/181345 | A1 | 10/2018 |
| WO | WO 2019/116230 | A1 | 6/2019 |
| WO | WO 2019/116231 | A1 | 6/2019 |
| WO | WO 2019/224667 | A1 | 11/2019 |
| WO | WO 2020/041169 | A2 | 2/2020 |
| WO | WO 2020/116660 | A1 | 6/2020 |
| WO | WO 2020/165776 | A1 | 8/2020 |
| WO | WO 2021/002473 | A1 | 1/2021 |
| WO | WO 2021/170774 | A1 | 9/2021 |

OTHER PUBLICATIONS

Ilaria Bellezza, et al., "Nrf2-Keap1 Signaling in Oxidative and Reductive Stress" BBA Molecular Cell Research, vol. 1865, 2018, pp. 721-733.
Melanie P. Chin, et al., "Bardoxolone Methyl Improves Kidney Function in Patients with Chronic Kidney Disease Stage 4 and Type 2 Diabetes: Post-Hoc Analyses from Bardoxolone Methyl Evaluation in Patients with Chronic Kidney Disease and Type 2 Diabetes Study" American Journal of Nephrology, vol. 47, 2018, pp. 40-47.
Rieko Shimozono, et al., "Nrf2 Activators Attenuate the Progression of Nonalcoholic Steatohepatitis-Related Fibrosis in a Dietary Rat Models" Molecular Pharmacology, vol. 84, Jul. 2013, pp. 62-70.
Meng-Chen Lu, et al., "An Inhibitor of the Keap1-Nrf2 Protein-Protein Interaction Protects NCM460 Colonic Cells and Alleviates Experimental Colitis" Scientific Reports, vol. 6, 26585, 2016, pp. 1-13.
John G. Yonchuk, et al., "Characterization of the Potent, Selective Nrf2 Activator, 3-(Pyridin-3-Ylsulfonyl)-5-(Trifluoromethyl)-2H-Chromen-2-One, in Cellular and In Vivo Models of Pulmonary Oxidative Stress" The Journal of Pharmacology and Experimantal Therapeutics, vol. 363, Oct. 2017, pp. 114-125.
Vitali Alexeev, et al., "Radiation Protection of the Gastrointestinal Tract and Growth Inhibition of Prostate Cancer Xenografts by a Single Compound" Molecular Cancer Therapeutics, vol. 13, No. 12, Dec. 2014, pp. 2968-2977.
Ulf Schulze-Topphoffa, et al., "Dimethyl Fumarate Treatment Induces Adaptive and Innate Immune Modulation Independentof Nrf2" Proceeding of the National Academy of Sciences of the United States of America, vol. 113, No. 17, Apr. 26, 2016, pp. 4777-4782.
Junnan Chen, "Dysfunction of Nrf-2 in CF Epithelia Leads to Excess Intracellular H2O2 and Inflammatory Cytokine Production" Plos One, vol. 3, No. 10, Oct. 2008, e3367 pp. 1-12.
Luke M. Shelton, et al., "Role of Nrf2 in Protection Against Acute Kidney Injury" Kidney International, vol. 84, 2013, pp. 1090-1095.
Reuben Howden, "Nrf2 and Cardiovascular Defense" Oxidative Medicine and Cellular Longevity, vol. 2013, Article ID 104308, 2013, pp. 1-10.
Takafumi Mimoto, et al., "Impaired Antioxydative Keap1/Nrf2 System and the Downstream Stress Protein Responses in the Motor Neuron of ALS Model Mice" Brain Research, vol. 1446, 2012, pp. 109-118.
Vincent Paupe, et al., "Impaired Nuclear Nrf2 Translocation Undermines the Oxidative Stress Response in Friedreich Ataxia" Plos One, vol. 4, Issued 1, e4253, Jan. 2009, pp. 1-11.
Maya S. Bitar, et al., "Decline in DJ-1 and Decreased Nuclear Translocation of Nrf2 in Fuchs Endothelial Corneal Dystrophy" Investigative Ophthalmology & Visual Science, vol. 53, No. 9, Aug. 2012, pp. 5806-5813.
Matthias Schäfer, et al., "Nrf2 Establishes a Glutathione-Mediated Gradient of UVB Cytoprotection in the Epidermis" Genes and Development, vol. 24, 2010, pp. 1045-1058.
Jung-Hyun Kim, et al., "NRF2-Mediated Notch Pathway Activation Enhances Hematopoietic Reconstitution Following Myelosuppressive Radiation" The Journal of Clinical Investigation, vol. 124, No. 2, Feb. 2014, pp. 730-741.
Christina Lisk, et al., "Nrf2 Activation: A Potential Strategy for the Prevention of Acute Mountain Sickness" Free Radical Biology and Medicine, vol. 63, Oct. 2013, pp. 264-273.
Thomas G. Davies, et al., "Monoacidic Inhibitors of the Kelch-like ECH-Associated Protein 1: Nuclear Factor Erythroid2-Related Factor 2 (KEAP1:NRF2) Protein-Protein Interaction with High Cell Potency Identified by Fragment-Based Discovery" Journal of Medicinal Chemistry, vol. 59, 2016, pp. 3991-4006.
Office Action issued Jul. 8, 2024, in corresponding Chinese Patent Application No. 202080055155.9 (with English Translation), 9 pages.
Office Action issued Jul. 11, 2024, in corresponding Mexican Patent Application No. MX/a/2021/01 4680 (with English Translation), 8 pages.
Office Action issued Aug. 15, 2024, in corresponding Russian Patent Application No. 2021135307 (with English Translation) citing documents 24 and 25 therein, 20 pages.
Office Action issued Aug. 5, 2024, in corresponding Indian Patent Application No. 202117057337 (with English Translation), 2 pages.
Dayson G., M, Chemistry of Synthetic Drugs, 1964, pp. 12-19 (with English translation).
Bastin R.J. et al., "Salt selection and optimisation procedures for pharmaceutical new chemical entities", Organic process research & development, 2000, V.4, N.5, pp. 427-435.
Japanese Office Action issued Apr. 2, 2024 in Japanese Patent Application No. 2021-522912 (with English translation), 7 pages.
Extended European Search Report issued Jun. 14, 2023 in European Patent Application No. 20815167.0, 5 pages.
Combined Russian Office Action and Search Report issued Oct. 19, 2023 in Russian Patent Application No. 2021135307/04(074592) (with English translation), citing documents 15-16 therein, 16 pages.
Chinese Office Action issued Nov. 1, 2023 in Chinese Patent Application No. 202080055155.9 (with English translation) citing document 17 therein, 10 pages.
Indian Office Action issued Jan. 9, 2024 in Indian Patent Application No. 202117057337, 6 pages.
Belikov, V., "Pharmaceutical Chemistry Manual". Moscow: $4^{th}$ edition, "MEDpress-inform", 2007. 10 pages (with English translation).
Kummerer, K., et al., "Pharmaceuticals in the Environment", The Annual Review of Environment and Resources, vol. 35, 2010, pp. 57-75.
Office Action issued May 23, 2025 in the corresponding Canadian patent application No. 3142295, 4 pages.
Office Action issued Aug. 18, 2025, in the corresponding Korean patent application No. 10-2021-7042003 with machine English translation, 8 pages.
Examination report No. 1 issued Feb. 17, 2025 in the corresponding Australian patent application No. 2020283361, 3 pages.
Examination report No. 2 issued Sep. 1, 2025 in the corresponding Australian patent application No. 2020283361, 2 pages.

* cited by examiner

BENZOTRIAZOLE DERIVATIVE

TECHNICAL FIELD

The present invention relates to benzotriazole derivatives and pharmaceutical compositions comprising the same, especially benzotriazole derivatives and pharmaceutical compositions comprising the same for the prevention, alleviation, and/or treatment of diseases of which symptoms are improved by the inhibition of Keap1.

BACKGROUND ART

Nrf2 (NF-E2 related factor 2) is a transcription factor which belongs to the CNC (cap-n-collar) transcription factor group having a basic leucine zipper structure (bZIPstructure). Keap1 (Kelch-like ECH-associated protein 1) is an adaptor protein which is associated with Cullin3 (Cul3) in cytoplasm to form a proteasomal degradation E3 enzyme complex, and functions as an inhibitory regulatory factor which ubiquitinates Nrf2 and thereby promotes its degradation under basic conditions. Under oxidative stress conditions caused by electrophile materials, reactive oxygen species, or the like, a Keap1-Cul3 complex is inactivated, and Nrf2 is activated. Activated Nrf2 is transferred to a nucleus, and forms a heterodimer with a small Maf transcription factor to bind to an Antioxidant Response Element (ARE) and activate the gene expressions of biological defense enzyme group such as NAD(P)H Quinone Dehydrogenase1 (NQO1) (Nonpatent Document 1). Thus, a Keap1 inhibitor which has an inhibitory effect on the binding of Keap1 and Nrf2 is expected to be useful especially in diseases caused by oxidative stresses.

The treatment caused by an antioxidant function induction effect mediated by the binding inhibition of Keap1 and Nrf2 is expected to be useful in wide range of diseases. Especially, in chronic renal diseases, it is reported that an irreversible Keap1 inhibitor, bardoxolone methyl (CDDO-Me) improved the kidney functions in human patients (Nonpatent Document 2), and a plurality of clinical trials are now in progress. Also, dimethyl fumarate which has an Nrf2 activating effect is approved in U.S. as a therapeutic agent of relapsing-remitting multiple sclerosis. In reports relating to Keap1 inhibitors in preclinical phases, possibilities as therapeutic agents of various diseases have been suggested such as hepatic fibrogenesis inhibitory effects in a NASH model (Nonpatent Document 3), anti-inflammatory effects in a inflammatory bowel disease model and chronic obstructive pulmonary disease model (Nonpatent Documents 4 and 5), anti-tumor effects in solid cancers such as prostate cancer (Nonpatent Document 6), and clinical score improving effects in a multiple sclerosis model (Nonpatent Document 7).

The reports of genetically modified animals or oxidative stresses and pathological models relating to Keap1-Nrf2 pathway suggest the relations to even more diseases. Specific examples thereof include chronic lung infection, al-antitrypsin disease, and cystic fibrosis (Nonpatent Document 8), sepsis-induced acute kidney injury and other acute kidney injuries (Nonpatent Document 9), atherosclerosis, heart failure, acute coronary syndrome, myocardial infarction, myocardial repair, cardiac remodeling, cardiac arrhythmia, heart failure with maintained left ventricular ejection fraction, heart failure with reduced left ventricular ejection fraction, and various cardiovascular diseases including diabetic cardiomyopathy (Nonpatent Document 10), Parkinson's disease, Alzheimer's disease, and Amyotrophic lateral sclerosis (Nonpatent Document 11), Friedreich's ataxia (Nonpatent Document 12), Age-related macular degeneration, Fuchs' endothelial dystrophy, and other inflammatory eye pathologies including uveitis (Nonpatent Document 13), dermatitis caused by radiation or the like (Nonpatent Document 14), immune suppression (Nonpatent Document 15), acute mountain sickness (Nonpatent Document 16), and the others.

To date, triazole compounds are disclosed in Patent Documents 1 to 17, and Nonpatent Documents 17 and 18 as compounds having Keap1 inhibitory activities, but these compounds have different structures from the Present compound.

CITATION LIST

Patent Document

Patent Document 1: WO 2015/092713 pamphlet
Patent Document 2: WO 2016/202253 pamphlet
Patent Document 3: WO 2016/203400 pamphlet
Patent Document 4: WO 2016/203401 pamphlet
Patent Document 5: WO 2017/060854 pamphlet
Patent Document 6: WO 2017/060855 pamphlet
Patent Document 7: WO 2018/104766 pamphlet
Patent Document 8: WO 2018/109641 pamphlet
Patent Document 9: WO 2018/109642 pamphlet
Patent Document 10: WO 2018/109643 pamphlet
Patent Document 11: WO 2018/109646 pamphlet
Patent Document 12: WO 2018/109647 pamphlet
Patent Document 13: WO 2018/109648 pamphlet
Patent Document 14: WO 2018/109649 pamphlet
Patent Document 15: WO 2018/181345 pamphlet
Patent Document 16: WO 2019/224667 pamphlet
Patent Document 17: WO 2020/041169 pamphlet Nonpatent Document Nonpatent Document 1: BBA Molecular Cell Research, 2018, 1865, 721-733.
Nonpatent Document 2: American Journal of Nephrology, 2018, 47, 40-47.
Nonpatent Document 3: Molecular Pharmacology, 2013, 84, 62-70.
Nonpatent Document 4: Scientific Reports, 2016, 6, 26585.
Nonpatent Document 5: The Journal of Pharmacology and Experimental Therapeutics, 2017, 363, 114-125.
Nonpatent Document 6: Molecular Cancer Therapeutics, 2014, 13, 12, 2968-2977.
Nonpatent Document 7: Proceeding of the National Academy of Sciences of the United States of America, 2016, 113, 17, 4777-4782.
Nonpatent Document 8: Plos One, 2008, 3, 10, e3367.
Nonpatent Document 9: Kidney International, 2013, 84, 1090-1095.
Nonpatent Document 10: Oxidative Medicine and Cellular Longevity, 2013, 2013, 104308.
Nonpatent Document 11: Brain Research, 2012, 1446, 109-118.
Nonpatent Document 12: Plos One, 4, 1, e4253.
Nonpatent Document 13: Investigative Ophthalmology & Visual Science, 2012, 53, 9, 5806-5813.
Nonpatent Document 14: Genes and Development, 2010, 24, 1045-1058.
Nonpatent Document 15: Journal of Clinical Investigation, 2014, 124, 2, 730-741.
Nonpatent Document 16: Free Radical Biology and Medicine, 2013, 63, 264-273.

Nonpatent Document 17: Journal of Medicinal Chemistry, 2016, 59, 3991-4006.

Nonpatent Document 18: Journal of Medicinal Chemistry, 2019, 62, 4683-4702.

SUMMARY OF THE INVENTION

Problems to be Solved by Invention

The present invention provides novel compounds and pharmaceutical compositions comprising the same useful in the prevention, alleviation, and/or treatment of diseases of which symptoms are improved by the inhibition of Keap1.

Means to Solve Problems

The present inventors have earnestly studied compounds having Keap1 inhibitory activities. As a result, they have found that a series of benzotriazole derivatives having intramolecular tricyclic structures or pharmaceutically acceptable salts thereof has excellent Keap1 inhibitory activities, and is useful in the prevention, alleviation, and/or treatment of diseases of which symptoms are improved by the inhibition of Keap1, especially the prevention, alleviation, and/or treatment of renal diseases, and finally completed the present invention.

The present invention provides the following [1] to [4].

[I] A compound represented by the following general formula (I):

(I)

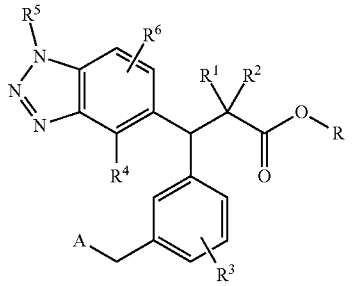

[wherein:

R represents a hydrogen atom or an alkyl group optionally substituted with 1 to 5 substituent(s) independently selected from Group E;

$R^1$ and $R^2$ each independently represent a hydrogen atom, an alkyl group optionally substituted with 1 to 5 substituent(s) independently selected from Group E, an alkenyl group optionally substituted with 1 to 5 substituent(s) independently selected from Group E, or an alkynyl group optionally substituted with 1 to 5 substituent(s) independently selected from Group E;

or $R^1$ and $R^2$ are combined with the carbon atom to which they are attached to form a monocyclic carbocycle optionally substituted with 1 to 5 substituent(s) independently selected from Group E;

$R^3$, $R^4$, and $R^6$ each independently represent a hydrogen atom, a halogen atom, an alkyl group optionally substituted with 1 to 5 substituent(s) independently selected from Group E, an alkenyl group optionally substituted with 1 to 5 substituent(s) independently selected from Group E, an alkynyl group optionally substituted with 1 to 5 substituent(s) independently selected from Group E, an alkoxy group optionally substituted with 1 to 5 substituent(s) independently selected from Group E, a cycloalkyl group optionally substituted with 1 to 5 substituent(s) independently selected from Group E, a nonaromatic heterocyclyl group optionally substituted with 1 to 5 substituent(s) independently selected from Group E, an aryl group optionally substituted with 1 to 5 substituent(s) independently selected from Group E, a heteroaryl group optionally substituted with 1 to 5 substituent(s) independently selected from Group E, or a cyano group;

$R^5$ represents (i) a hydrogen atom, or (ii) an alkyl group optionally substituted with 1 to 5 substituent(s) independently selected from the group consisting of a halogen atom, a hydroxy group, a cycloalkyl group optionally substituted with 1 to 5 substituent(s) independently selected from Group E, a phenyl group optionally substituted with 1 to 5 substituent(s) independently selected from Group E, and an alkoxy group optionally substituted with 1 to 5 substituent(s) independently selected from Group E;

A has a structure represented by the following formula (II)

(II)

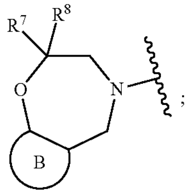

$R^7$ and $R^8$ each independently represent a hydrogen atom, an alkyl group optionally substituted with 1 to 5 substituent(s) independently selected from Group E, an alkenyl group optionally substituted with 1 to 5 substituent(s) independently selected from Group E, or an alkynyl group optionally substituted with 1 to 5 substituent(s) independently selected from Group E;

or $R^7$ and $R^8$ are combined with the carbon atom to which they are attached to form a monocyclic carbocycle optionally substituted with 1 to 5 substituent(s) independently selected from Group E;

ring B represents a bicyclic ring optionally substituted with 1 to 5 substituent(s) independently selected from the group consisting of a halogen atom, an alkyl group optionally substituted with 1 to 5 substituent(s) independently selected from Group E, an alkenyl group optionally substituted with 1 to 5 substituent(s) independently selected from Group E, an alkynyl group optionally substituted with 1 to 5 substituent(s) independently selected from Group E, an alkoxy group optionally substituted with 1 to 5 substituent(s) independently selected from Group E, a cycloalkyl group optionally substituted with 1 to 5 substituent(s) independently selected from Group E, a nonaromatic heterocyclyl group optionally substituted with 1 to 5 substituent(s) independently selected from Group E, an aryl group optionally substituted with 1 to 5 substituent(s) independently selected from Group E, a heteroaryl group optionally substituted with 1 to 5 substituent(s) independently selected from Group E, and a cyano group;

the symbol 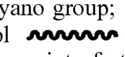 represents the point of attachment to the rest of molecule; and Group E represents a group consisting of a halogen atom, a hydroxy group, and an alkoxy group optionally substituted with 1 to 5 halogen atom(s)]

(hereinafter also referred to as "Compound (I)") or a pharmaceutically acceptable salt thereof.

[2] A pharmaceutical composition comprising the compound according to [1] or a pharmaceutically acceptable salt thereof.

[3] The pharmaceutical composition according to [2] for the prevention, alleviation, and/or treatment of a disease which is improved by the inhibition of Keap1.

[4] The pharmaceutical composition according to [3], wherein the disease which is improved by the inhibition of Keap1 is a renal disease.

The present invention also provides the following [5] to [20].

[5] The compound according to [1] or a pharmaceutically acceptable salt thereof, wherein R represents a hydrogen atom or an alkyl group optionally substituted with 1 to 5 substituent(s) independently selected from Group E;

$R^1$ and $R^2$ each independently represent a hydrogen atom or an alkyl group optionally substituted with 1 to 5 substituent(s) independently selected from Group E;

or $R^1$ and $R^2$ are combined with the carbon atom to which they are attached to form a monocyclic carbocycle optionally substituted with 1 to 5 substituent(s) independently selected from Group E;

$R^3$, $R^4$, and $R^6$ each independently represent a hydrogen atom, a halogen atom, an alkyl group optionally substituted with 1 to 5 substituent(s) independently selected from Group E, or an alkoxy group optionally substituted with 1 to 5 substituent(s) independently selected from Group E;

$R^5$ represents (i) a hydrogen atom, or (ii) an alkyl group optionally substituted with 1 to 5 substituent(s) independently selected from the group consisting of a halogen atom, a hydroxy group, a phenyl group optionally substituted with 1 to 5 substituent(s) independently selected from Group E, and an alkoxy group optionally substituted with 1 to 5 substituent(s) independently selected from Group E;

$R^7$ and $R^8$ each independently represent a hydrogen atom or an alkyl group optionally substituted with 1 to 5 substituent(s) independently selected from Group E;

or $R^7$ and $R^8$ are combined with the carbon atom to which they are attached to form a monocyclic carbocycle optionally substituted with 1 to 5 substituent(s) independently selected from Group E; and ring B represents a bicyclic ring optionally substituted with 1 to 5 substituent(s) independently selected from the group consisting of a halogen atom, an alkyl group optionally substituted with 1 to 5 substituent(s) independently selected from Group E, an alkoxy group optionally substituted with 1 to 5 substituent(s) independently selected from Group E, and a cyano group.

[6] The compound according to [1] or a pharmaceutically acceptable salt thereof, wherein R represents a hydrogen atom or an alkyl group;

$R^1$ and $R^2$ each independently represent a hydrogen atom or an alkyl group;

or $R^1$ and $R^2$ are combined with the carbon atom to which they are attached to form a monocyclic carbocycle;

$R^3$, $R^4$, and $R^6$ each independently represent a hydrogen atom, a halogen atom, an alkyl group, or an alkoxy group;

$R^5$ represents (i) a hydrogen atom, or (ii) an alkyl group optionally substituted with 1 to 5 substituent(s) independently selected from the group consisting of a halogen atom, a hydroxy group, a phenyl group, and an alkoxy group;

$R^7$ and $R^8$ each independently represent a hydrogen atom or an alkyl group;

or $R^7$ and $R^0$ are combined with the carbon atom to which they are attached to form a monocyclic carbocycle optionally substituted with 1 to 5 substituent(s) independently selected from Group E; and ring B represents a bicyclic ring optionally substituted with 1 to 5 substituent(s) independently selected from the group consisting of a halogen atom, an alkyl group optionally substituted with 1 to 5 substituent(s) independently selected from Group E, an alkoxy group optionally substituted with 1 to 5 substituent(s) independently selected from Group E, and a cyano group.

[7] The compound according to any one of [1] or [5] to [6], wherein

The compound has a structure represented by the following general formula (I-1):

(I-1)

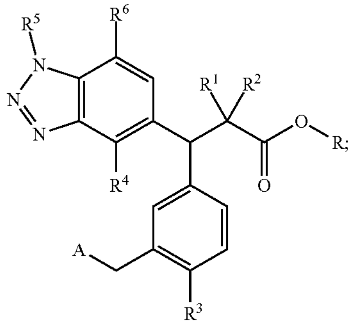

R represents a hydrogen atom or an alkyl group;

$R^1$ and $R^2$ each independently represent a hydrogen atom or an alkyl group;

or $R^1$ and $R^2$ are combined with the carbon atom to which they are attached to form a monocyclic carbocycle;

$R^3$ represents a hydrogen atom, a halogen atom, an alkyl group, or an alkoxy group;

$R^4$ and $R^6$ each independently represent a hydrogen atom, an alkyl group, or an alkoxy group; and $R^5$ represents a hydrogen atom or an alkyl group (hereinafter also referred to as "Compound (1-1)") or a pharmaceutically acceptable salt thereof.

The compound according to any one of [1] or [5] to [7] or a pharmaceutically acceptable salt thereof, wherein R represents a hydrogen atom;

$R^1$ and $R^2$ each independently represent a hydrogen atom or an alkyl group;

or $R^1$ and $R^2$ are combined with the carbon atom to which they are attached to form a monocyclic carbocycle;

$R^3$ represents an alkyl group;

$R^4$ represents an alkyl group;

$R^5$ represents an alkyl group; and $R^6$ represents a hydrogen atom.

[8-1] The compound according to [8] or a pharmaceutically acceptable salt thereof, wherein $R^1$ and $R^2$ each independently represent a hydrogen atom or an alkyl group.

[9] The compound according to any one of [1] or [5] to [8-1], wherein

A has a structure represented by any one of the following formulae (II-1) to (II-3):

(II-1)

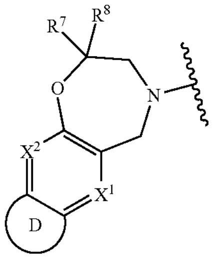

(II-2)

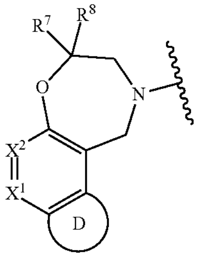

(II-3)

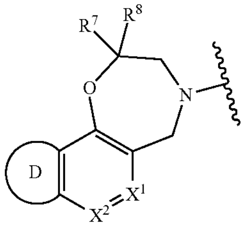

[wherein:

$R^1$ and $R^8$ each independently represent a hydrogen atom or an alkyl group;

or $R^7$ and $R^8$ are combined with the carbon atom to which they are attached to form a monocyclic carbocycle optionally substituted with 1 to 5 substituent(s) independently selected from Group E;

$X^1$ and $X^2$ each independently represent $CR^9$ or a nitrogen atom;

$R^9$ each independently represents a hydrogen atom, a halogen atom, an alkyl group optionally substituted with 1 to 5 substituent(s) independently selected from Group E, an alkoxy group optionally substituted with 1 to 5 substituent(s) independently selected from Group E, or a cyano group; and ring D represents a 5 to 6 membered carbocycle or a 5 to 6 membered heterocycle, each of which is optionally substituted with 1 to 5 substituent(s) independently selected from the group consisting of a halogen atom, an alkyl group optionally substituted with 1 to 5 substituent(s) independently selected from Group E, an alkoxy group optionally substituted with 1 to 5 substituent(s) independently selected from Group E, and a cyano group]

(hereinafter also referred to as "Compound (II-1) to (II-3)") or a pharmaceutically acceptable salt thereof.

[10] The compound according to any one of [1] or [5] to [8], wherein

A has a structure represented by any one of the following formulae (II-1-1) to (II-3-4):

(II-1-1)

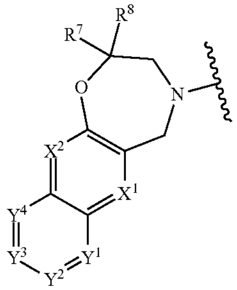

(II-1-2)

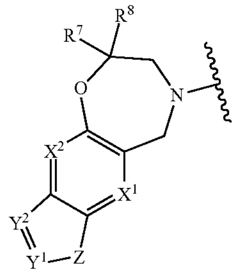

(II-1-3)

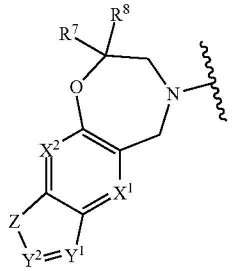

(II-1-4)

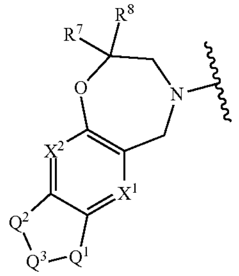

(II-2-1)

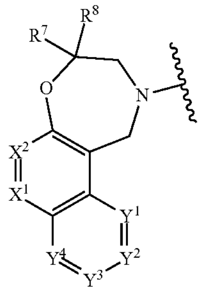

-continued (II-2-2)

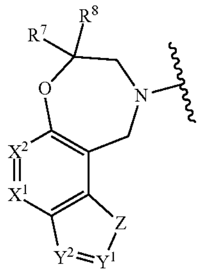

(II-2-3)

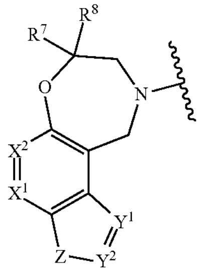

(II-2-4)

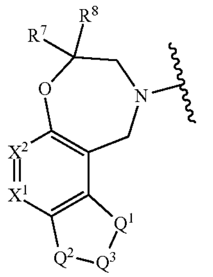

(II-3-1)

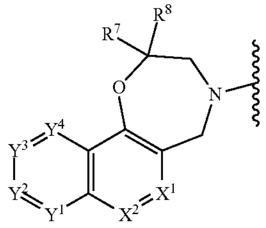

(II-3-2)

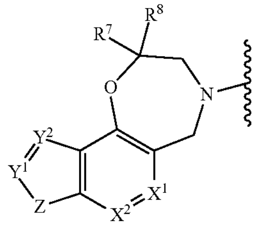

(II-3-3)

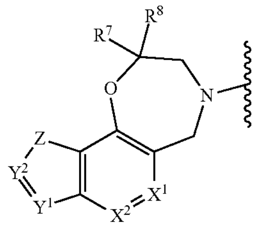

-continued (II-3-4)

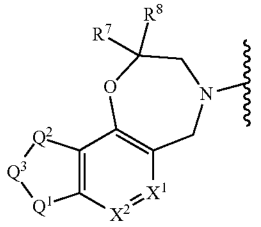

[wherein:

$R^7$ and $R^8$ each independently represent a hydrogen atom or an alkyl group;

or $R^7$ and $R^8$ are combined with the carbon atom to which they are attached to form a monocyclic carbocycle optionally substituted with 1 to 5 substituent(s) independently selected from Group E;

$X^1$ and $X^2$ each independently represent $CR^9$ or a nitrogen atom;

$Y^1$, $Y^2$, $Y^3$, and $Y^4$ each independently represent $CR^{10}$ or a nitrogen atom;

$R^9$ and $R^{10}$ each independently represent a hydrogen atom, a halogen atom, an alkyl group optionally substituted with 1 to 5 substituent(s) independently selected from Group E, an alkoxy group optionally substituted with 1 to 5 substituent(s) independently selected from Group E, or a cyano group;

$Q^1$ and $Q^2$ each independently represent $CR^{11}R^{12}$, $NR^{13}$, an oxygen atom, a sulfur atom, SO, or $SO_2$;

$R^{11}$ and $R^{12}$ each independently represent a hydrogen atom, a halogen atom, or an alkyl group;

$R^{13}$ each independently represents a hydrogen atom or an alkyl group;

Z represents $NR^{14}$, an oxygen atom, or a sulfur atom;

$R^{14}$ represents a hydrogen atom or an alkyl group;

$Q^3$ represents $(CU^1U^2)$;

$U^1$ and $U^2$ each independently represent a hydrogen atom, a halogen atom, or an alkyl group; and n represents 1, 2, or 3]

(hereinafter also referred to as "Compound (II-1-1) to (II-3-4)") or a pharmaceutically acceptable salt thereof.

[10-1] The compound according to [10] or a pharmaceutically acceptable salt thereof, wherein $Q^1$ and $Q^2$ each independently represent $CR^{11}R^{12}$, $NR^{15}$, or an oxygen atom.

[10-2] The compound according to [10] or [10-1] or a pharmaceutically acceptable salt thereof, wherein n represents 1 or 2.

[11] The compound according to any one of [10] to [10-2] or a pharmaceutically acceptable salt thereof, wherein A has a structure represented by any one of the following formula (II-1-1) or (II-3-1):

(II-1-1)

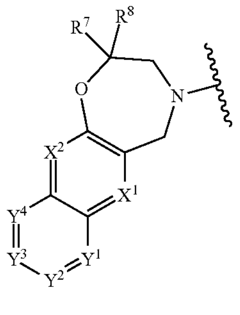

-continued (II-3-1)

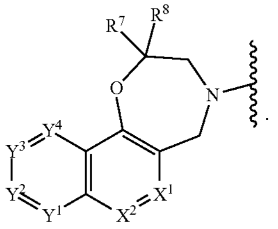

[12] The compound according to any one of (1) or (5) to [11] or a pharmaceutically acceptable salt thereof, wherein A has a structure represented by the following formula (II-1-1):

(II-1-1)

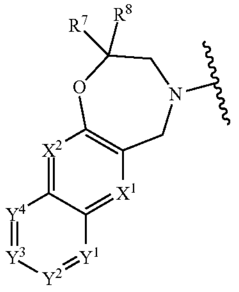

[wherein:

$R^7$ and $R^8$ each independently represent a hydrogen atom or an alkyl group;

or $R^7$ and $R^8$ are combined with the carbon atom to which they are attached to form a monocyclic carbocycle;

$X^1$ and $X^2$ each independently represent $CR^9$;

any one of $Y^1$, $Y^2$, $Y^3$, and $Y^4$ represents a nitrogen atom, and the other three each independently represent $CR^{10}$;

$R^9$ each represents a hydrogen atom; and $R^{10}$ each independently represents a hydrogen atom, a halogen atom, an alkyl group, or an alkoxy group].

[12-1] The compound according to [12] or a pharmaceutically acceptable salt thereof, wherein $R^7$ and $R^8$ each independently represent a hydrogen atom or an alkyl group; and $R^{10}$ each independently represents a hydrogen atom, a halogen atom, or an alkyl group.

[13] The compound according to any one of [1] or [5] to [11] or a pharmaceutically acceptable salt thereof, wherein A has a structure represented by the following formula (II-3-1):

(II-3-1)

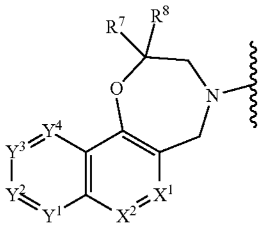

[wherein:

$R^7$ and $R^8$ each independently represent a hydrogen atom or an alkyl group;

any one of $X^1$ and $X^2$ represents a nitrogen atom, and the other one represents $CR^9$;

$Y^1$, $Y^2$, $Y^3$, and $Y^4$ each independently represent $CR^{10}$;

$R^9$ each represents a hydrogen atom; and $R^{10}$ each independently represents a hydrogen atom, a halogen atom, or an alkyl group].

[14] The compound according to [1] represented by the following general formula (I-1-1):

(I-1-1)

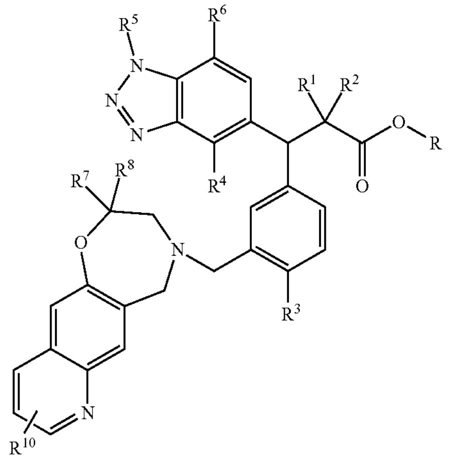

[wherein:

R represents a hydrogen atom or an alkyl group;

$R^1$ and $R^2$ each independently represent a hydrogen atom or an alkyl group;

or $R^1$ and $R^2$ are combined with the carbon atom to which they are attached to form a monocyclic carbocycle;

$R^3$, $R^4$, and $R^6$ each independently represent a hydrogen atom, a halogen atom, an alkyl group, or an alkoxy group;

$R^5$ represents (i) a hydrogen atom, or (ii) an alkyl group optionally substituted with 1 to 5 substituent(s) independently selected from the group consisting of a halogen atom, a hydroxy group, a phenyl group, and an alkoxy group;

$R^7$ and $R^8$ each independently represent a hydrogen atom or an alkyl group;

or $R^7$ and $R^8$ are combined with the carbon atom to which they are attached to form a monocyclic carbocycle optionally substituted with 1 to 5 substituent(s) independently selected from Group E;

$R^{10}$ represents a hydrogen atom, a halogen atom, an alkyl group optionally substituted with 1 to 5 substituent(s) independently selected from Group E, an alkoxy group optionally substituted with 1 to 5 substituent(s) independently selected from Group E, or a cyano group; and Group E represents a group consisting of a halogen atom, a hydroxy group, and an alkoxy group optionally substituted with 1 to 5 halogen atom(s)](hereinafter also referred to as "Compound (I-1-1)") or a pharmaceutically acceptable salt thereof.

[15] The compound according to [14] or a pharmaceutically acceptable salt thereof, wherein R represents a hydrogen atom or an alkyl group;

$R^1$ and $R^2$ each independently represent a hydrogen atom or an alkyl group;

or $R^1$ and $R^2$ are combined with the carbon atom to which they are attached to form a monocyclic carbocycle;
$R^3$ represents a hydrogen atom, a halogen atom, an alkyl group, or an alkoxy group;
$R^4$ represents a hydrogen atom or an alkyl group;
$R^5$ represents an alkyl group;
$R^6$ represents a hydrogen atom;
$R^7$ and $R^8$ each independently represent a hydrogen atom or an alkyl group;
or $R^7$ and $R^8$ are combined with the carbon atom to which they are attached to form a monocyclic carbocycle; and
$R^{10}$ represents a hydrogen atom, a halogen atom, an alkyl group, or an alkoxy group.

The compound according to [1] selected from the group consisting of methyl 3-(1,4-dimethyl-1H-benzo[d][1,2,3]triazol-5-yl)-3-(3-(((R)-6-ethyl-2,2-difluoro-6,7-dihydro-[1,3]dioxolo[4',5':4,5]benzo[1,2-f][1,4]oxazepin-8(9H)-yl)methyl)-4-methylphenyl)-2,2-dimethylpropanoate (Example 1-(a));
3-(1,4-dimethyl-1H-benzo[d][1,2,3]triazol-5-yl)-3-(3-(((R)-6-ethyl-2,2-difluoro-6,7-dihydro-[1,3]dioxolo[4',5':4,5]benzo[1,2-f][1,4]oxazepin-8(9H)-yl)methyl)-4-methylphenyl)-2,2-dimethylpropanoic acid (Example 1-(b), Example 29 (Diastereomer 1), and Example 30 (Diastereomer 2));
methyl 3-(1,4-dimethyl-1H-benzo[d][1,2,3]triazol-5-yl)-3-(3-(((R)-9-ethyl-2,2-difluoro-8,9-dihydro-[1,3]dioxolo[4',5':3,4]benzo[1,2-f][1,4]oxazepin-7 (6H)-yl)methyl)-4-methylphenyl)-2,2-dimethylpropanoate (Example 2-(a));
3-(1,4-dimethyl-1H-benzo[d][1,2,3]triazol-5-yl)-3-(3-(((R)-9-ethyl-2,2-difluoro-8,9-dihydro-[1,3]dioxolo[4',5':3,4]benzo[1,2-f][1,4]oxazepin-7 (6H)-yl)methyl)-4-methylphenyl)-2,2-dimethylpropanoic acid (Example 2-(b));
methyl 3-(1,4-dimethyl-1H-benzo[d][1,2,3]triazol-5-yl)-3-(3-(((R)-2-ethyl-2,3,5,7,8,9-hexahydro-4H-indeno[5,6-f][1,4]oxazepin-4-yl)methyl)-4-methylphenyl)-2,2-dimethylpropanoate (Example 3-(a));
3-(1,4-dimethyl-1H-benzo[d][1,2,3]triazol-5-yl)-3-(3-(((R)-2-ethyl-2,3,5,7,8,9-hexahydro-4H-indeno[5,6-f][1,4]oxazepin-4-yl)methyl)-4-methylphenyl)-2,2-dimethylpropanoic acid (Example 3-(b), Example 31 (Diastereomer 1), and Example 32 (Diastereomer 2));
methyl 3-(1,4-dimethyl-1H-benzo[d][1,2,3]triazol-5-yl)-3-(3-(((R)-2-ethyl-2,3,7,8,9,10-hexahydronaphtho[2,3-f][1,4]oxazepin-4(5H)-yl)methyl)-4-methylphenyl)-2,2-dimethylpropanoate (Example 4-(a));
3-(1,4-dimethyl-1H-benzo[d][1,2,3]triazol-5-yl)-3-(3-(((R)-2-ethyl-2,3,7,8,9,10-hexahydronaphtho[2,3-f][1,4]oxazepin-4(5H)-yl)methyl)-4-methylphenyl)-2,2-dimethylpropanoic acid (Example 4-(b), Example 33 (Diastereomer 1), and Example 34 (Diastereomer 2));
methyl 3-(1,4-dimethyl-1H-benzo[d][1,2,3]triazol-5-yl)-3-(3-(((R)-4-ethyl-3,4,8,9,10,11-hexahydronaphtho[1,2-f][1,4]oxazepin-2(1H)-yl)methyl)-4-methylphenyl)-2,2-dimethylpropanoate (Example 5-(a));
3-(1,4-dimethyl-1H-benzo[d][1,2,3]triazol-5-yl)-3-(3-(((R)-4-ethyl-3,4,8,9,10,11-hexahydronaphtho[1,2-f][1,4]oxazepin-2(1H)-yl)methyl)-4-methylphenyl)-2,2-dimethylpropanoic acid (Example 5-(b));
methyl 3-(1,4-dimethyl-1H-benzo[d][1,2,3]triazol-5-yl)-3-(3-(((R)-2-ethyl-2,3,5,8,9,10-hexahydro-4H-indeno[5,4-f][1,4]oxazepin-4-yl)methyl)-4-methylphenyl)-2,2-dimethylpropanoate (Example 6-(a));
3-(1,4-dimethyl-1H-benzo[d][1,2,3]triazol-5-yl)-3-(3-(((R)-2-ethyl-2,3,5,8,9,10-hexahydro-4H-indeno[5,4-f][1,4]oxazepin-4-yl)methyl)-4-methylphenyl)-2,2-dimethylpropanoic acid (Example 6-(b), Example 35 (Diastereomer 1), and Example 36 (Diastereomer 2));
methyl 3-(1,4-dimethyl-1H-benzo[d][1,2,3]triazol-5-yl)-3-(3-(((R)-2-ethyl-2,3,8,9,10,11-hexahydronaphtho[2,1-f][1,4]oxazepin-4(5H)-yl)methyl)-4-methylphenyl)-2,2-dimethylpropanoate (Example 7-(a));
3-(1,4-dimethyl-1H-benzo[d][1,2,3]triazol-5-yl)-3-(3-(((R)-2-ethyl-2,3,8,9,10,11-hexahydronaphtho[2,1-f][1,4]oxazepin-4(5H)-yl)methyl)-4-methylphenyl)-2,2-dimethylpropanoic acid (Example 7-(b));
methyl 3-(1,4-dimethyl-1H-benzo[d][1,2,3]triazol-5-yl)-3-(3-(((R)-2-ethyl-2,3-dihydronaphtho[2,3-f][1,4]oxazepin-4(5H)-yl)methyl)-4-methylphenyl)-2,2-dimethylpropanoate (Example 8-(a));
3-(1,4-dimethyl-1H-benzo[d][1,2,3]triazol-5-yl)-3-(3-(((R)-2-ethyl-2,3-dihydronaphtho[2,3-f][1,4]oxazepin-4 (5H)-yl)methyl)-4-methylphenyl)-2,2-dimethylpropanoic acid (Example 8-(b));
methyl 3-(1,4-dimethyl-1H-benzo[d][1,2,3]triazol-5-yl)-3-(3-(((R)-2-ethyl-2,3-dihydro-[1,4]oxazepino[7,6-b]quinolin-4(5H)-yl)methyl)-4-methylphenyl)-2,2-dimethylpropanoate (Example 9-(a));
3-(1,4-dimethyl-1H-benzo[d][1,2,3]triazol-5-yl)-3-(3-(((R)-2-ethyl-2,3-dihydro-[1,4]oxazepino[7,6-b]quinolin-4(5H)-yl)methyl)-4-methylphenyl)-2,2-dimethylpropanoic acid (Example 9-(b));
methyl 3-(1,4-dimethyl-1H-benzo[d][1,2,3]triazol-5-yl)-3-(3-(((R)-2-ethyl-2,3-dihydro-[1,4]oxazepino[6,7-b]quinolin-4(5H)-yl)methyl)-4-methylphenyl)-2,2-dimethylpropanoate (Example 10-(a));
3-(1,4-dimethyl-1H-benzo[d][1,2,3]triazol-5-yl)-3-(3-(((R)-2-ethyl-2,3-dihydro-[1,4]oxazepino[6,7-b]quinolin-4(5H)-yl)methyl)-4-methylphenyl)-2,2-dimethylpropanoic acid (Example 10-(b), Example 37 (Diastereomer 1), and Example 38 (Diastereomer 2));
methyl 3-(1,4-dimethyl-1H-benzo[d][1,2,3]triazol-5-yl)-3-(3-(((R)-2-ethyl-2,3-dihydro-[1,4]oxazepino[6,7-g]quinolin-4(5H)-yl)methyl)-4-methylphenyl)-2,2-dimethylpropanoate (Example 11-(a));
3-(1,4-dimethyl-1H-benzo[d][1,2,3]triazol-5-yl)-3-(3-(((R)-2-ethyl-2,3-dihydro-[1,4]oxazepino[6,7-g]quinolin-4(5H)-yl)methyl)-4-methylphenyl)-2,2-dimethylpropanoic acid (Example 11-(b), Example 39 (Diastereomer 1), and Example 40 (Diastereomer 2));
methyl 3-(1,4-dimethyl-1H-benzo[d][1,2,3]triazol-5-yl)-3-(3-(((R)-2-ethyl-2,3-dihydro-[1,4]oxazepino[7,6-g]quinolin-4(5H)-yl)methyl)-4-methylphenyl)-2,2-dimethylpropanoate (Example 12-(a));
3-(1,4-dimethyl-1H-benzo[d][1,2,3]triazol-5-yl)-3-(3-(((R)-2-ethyl-2,3-dihydro-[1,4]oxazepino[7,6-g]quinolin-4(5H)-yl)methyl)-4-methylphenyl)-2,2-dimethylpropanoic acid (Example 12-(b), Example 41 (Diastereomer 1), and Example 42 (Diastereomer 2));
methyl 3-(1,4-dimethyl-1H-benzo[d][1,2,3]triazol-5-yl)-3-(3-(((R)-2-ethyl-10-methyl-2,3-dihydro-[1,4]oxazepino[7,6-b]quinolin-4(5H)-yl)methyl)-4-methylphenyl)-2,2-dimethylpropanoate (Example 13-(a));
3-(1,4-dimethyl-1H-benzo[d][1,2,3]triazol-5-yl)-3-(3-(((R)-2-ethyl-10-methyl-2,3-dihydro-[1,4]oxazepino[7,6-b]quinolin-4(5H)-yl)methyl)-4-methylphenyl)-2,2-dimethylpropanoic acid (Example 13-(b));
methyl 3-(1,4-dimethyl-1H-benzo[d][1,2,3]triazol-5-yl)-3-(3-(((R)-2-ethyl-8-methyl-2,3-dihydro-[1,4]oxazepino[7,6-b]quinolin-4(5H)-yl)methyl)-4-methylphenyl)-2,2-dimethylpropanoate (Example 14-(a));
3-(1,4-dimethyl-1H-benzo[d][1,2,3]triazol-5-yl)-3-(3-(((R)-2-ethyl-8-methyl-2,3-dihydro-[1,4]oxazepino[7,6-b]quinolin-4(5H)-yl)methyl)-4-methylphenyl)-2,2-dimethylpropanoic acid (Example 14-(b));

methyl 3-(1,4-dimethyl-1H-benzo[d][1,2,3]triazol-5-yl)-3-(3-(((R)-8-ethyl-1,5,7,8-tetrahydro-6H-[1,4]oxazepino[6,7-f]indazol-6-yl)methyl)-4-methylphenyl)-2,2-dimethylpropanoate (Example 15-(a));

3-(1,4-dimethyl-1H-benzo[d][1,2,3]triazol-5-yl)-3-(3-(((R)-8-ethyl-1,5,7,8-tetrahydro-6H-[1,4]oxazepino[6,7-f]indazol-6-yl)methyl)-4-methylphenyl)-2,2-dimethylpropanoic acid (Example 15-(b));

methyl 3-(1,4-dimethyl-1H-benzo[d][1,2,3]triazol-5-yl)-3-(3-(((R)-4-ethyl-3,4-dihydronaphtho[1,2-f][1,4]oxazepin-2(1H)-yl)methyl)-4-methylphenyl)-2,2-dimethylpropanoate (Example 16-(a));

3-(1,4-dimethyl-1H-benzo[d][1,2,3]triazol-5-yl)-3-(3-(((R)-4-ethyl-3,4-dihydronaphtho[1,2-f][1,4]oxazepin-2(1H)-yl)methyl)-4-methylphenyl)-2,2-dimethylpropanoic acid (Example 16-(b));

methyl 3-(1,4-dimethyl-1H-benzo[d][1,2,3]triazol-5-yl)-3-(3-(((R)-8-ethyl-8,9-dihydro-[1,4]oxazepino[7,6-h]quinolin-10(11H)-yl)methyl)-4-methylphenyl)-2,2-dimethylpropanoate (Example 17-(a));

3-(1,4-dimethyl-1H-benzo[d][1,2,3]triazol-5-yl)-3-(3-(((R)-8-ethyl-8,9-dihydro-[1,4]oxazepino[7,6-h]quinolin-10(11H)-yl)methyl)-4-methylphenyl)-2,2-dimethylpropanoic acid (Example 17-(b));

methyl 3-(1,4-dimethyl-1H-benzo[d][1,2,3]triazol-5-yl)-3-(3-(((R)-4-ethyl-3,4-dihydro-[1,4]oxazepino[6,7-f]quinolin-2(1H)-yl)methyl)-4-methylphenyl)-2,2-dimethylpropanoate (Example 18-(a));

3-(1,4-dimethyl-1H-benzo[d][1,2,3]triazol-5-yl)-3-(3-(((R)-4-ethyl-3,4-dihydro-[1,4]oxazepino[6,7-f]quinolin-2(1H)-yl)methyl)-4-methylphenyl)-2,2-dimethylpropanoic acid (Example 18-(b));

methyl 3-(1,4-dimethyl-1H-benzo[d][1,2,3]triazol-5-yl)-3-(3-(((R)-4-ethyl-3,4-dihydro-[1,4]oxazepino[7,6-c]quinolin-2(1H)-yl)methyl)-4-methylphenyl)-2,2-dimethylpropanoate (Example 19-(a));

3-(1,4-dimethyl-1H-benzo[d][1,2,3]triazol-5-yl)-3-(3-(((R)-4-ethyl-3,4-dihydro-[1,4]oxazepino[7,6-c]quinolin-2(1H)-yl)methyl)-4-methylphenyl)-2,2-dimethylpropanoic acid (Example 19-(b));

methyl 3-(1,4-dimethyl-1H-benzo[d][1,2,3]triazol-5-yl)-3-(3-(((R)-7-ethyl-1,7,8,10-tetrahydro-9H-[1,4]oxazepino[7,6-g]indazol-9-yl)methyl)-4-methylphenyl)-2,2-dimethylpropanoate (Example 20-(a));

3-(1,4-dimethyl-1H-benzo[d][1,2,3]triazol-5-yl)-3-(3-(((R)-7-ethyl-1,7,8,10-tetrahydro-9H-[1,4]oxazepino[7,6-g]indazol-9-yl)methyl)-4-methylphenyl)-2,2-dimethylpropanoic acid (Example 20-(b), Example 43 (Diastereomer 1), and Example 44 (Diastereomer 2));

methyl 3-(1,4-dimethyl-1H-benzo[d][1,2,3]triazol-5-yl)-3-(3-(((R)-7-ethyl-1-methyl-1,7,8,10-tetrahydro-9H-[1,4]oxazepino[7,6-g]indazol-9-yl)methyl)-4-methylphenyl)-2,2-dimethylpropanoate (Example 21-(a));

3-(1,4-dimethyl-1H-benzo[d][1,2,3]triazol-5-yl)-3-(3-(((R)-7-ethyl-1-methyl-1,7,8,10-tetrahydro-9H-[1,4]oxazepino[7,6-g]indazol-9-yl)methyl)-4-methylphenyl)-2,2-dimethylpropanoic acid (Example 21-(b));

methyl 3-(1,4-dimethyl-1H-benzo[d][1,2,3]triazol-5-yl)-3-(3-(((R)-7-ethyl-2-methyl-2,7,8,10-tetrahydro-9H-[1,4]oxazepino[7,6-g]indazol-9-yl)methyl)-4-methylphenyl)-2,2-dimethylpropanoate (Example 22-(a));

3-(1,4-dimethyl-1H-benzo[d][1,2,3]triazol-5-yl)-3-(3-(((R)-7-ethyl-2-methyl-2,7,8,10-tetrahydro-9H-[1,4]oxazepino[7,6-g]indazol-9-yl)methyl)-4-methylphenyl)-2,2-dimethylpropanoic acid (Example 22-(b));

3-(1,4-dimethyl-1H-benzo[d][1,2,3]triazol-5-yl)-3-(3-(((R)-4-ethyl-1,3,4,9,10,11-hexahydro-2H-pyrimido[1',2':1,6]pyrido[2,3-f][1,4]oxazepin-2-yl)methyl)-4-methylphenyl)-2,2-dimethylpropanoic acid (Example 23);

methyl 3-(1,4-dimethyl-1H-benzo[d][1,2,3]triazol-5-yl)-3-(3-(((R)-2-ethyl-2,3-dihydronaphtho[2,1-f][1,4]oxazepin-4(5H)-yl)methyl)-4-methylphenyl)-2,2-dimethylpropanoate (Example 24-(a));

3-(1,4-dimethyl-1H-benzo[d][1,2,3]triazol-5-yl)-3-(3-(((R)-2-ethyl-2,3-dihydronaphtho[2,1-f][1,4]oxazepin-4 (5H)-yl)methyl)-4-methylphenyl)-2,2-dimethylpropanoic acid (Example 24-(b));

methyl 3-(1,4-dimethyl-1H-benzo[d][1,2,3]triazol-5-yl)-3-(3-(((R)-2-ethyl-2,3-dihydro-[1,4]oxazepino[6,7-c]isoquinolin-4(5H)-yl)methyl)-4-methylphenyl)-2,2-dimethylpropanoate (Example 25-(a));

3-(1,4-dimethyl-1H-benzo[d][1,2,3]triazol-5-yl)-3-(3-(((R)-2-ethyl-2,3-dihydro-[1,4]oxazepino[6,7-c]isoquinolin-4(5H)-yl)methyl)-4-methylphenyl)-2,2-dimethylpropanoic acid (Example 25-(b), Example 45 (Diastereomer 1), and Example 46 (Diastereomer 2));

methyl 3-(1,4-dimethyl-1H-benzo[d][1,2,3]triazol-5-yl)-3-(3-(((R)-2-ethyl-2,3-dihydro-[1,4]oxazepino[6,7-c]quinolin-4(5H)-yl)methyl)-4-methylphenyl)-2,2-dimethylpropanoate (Example 26-(a));

3-(1,4-dimethyl-1H-benzo[d][1,2,3]triazol-5-yl)-3-(3-(((R)-2-ethyl-2,3-dihydro-[1,4]oxazepino[6,7-c]quinolin-4(5H)-yl)methyl)-4-methylphenyl)-2,2-dimethylpropanoic acid (Example 26-(b), Example 47 (Diastereomer 1), and Example 48 (Diastereomer 2));

methyl 3-(1,4-dimethyl-1H-benzo[d][1,2,3]triazol-5-yl)-3-(3-(((R)-2-ethyl-2,3-dihydro-[1,4]oxazepino[6,7-h]quinolin-4(5H)-yl)methyl)-4-methylphenyl)-2,2-dimethylpropanoate (Example 27-(a));

3-(1,4-dimethyl-1H-benzo[d][1,2,3]triazol-5-yl)-3-(3-(((R)-2-ethyl-2,3-dihydro-[1,4]oxazepino[6,7-h]quinolin-4(5H)-yl)methyl)-4-methylphenyl)-2,2-dimethylpropanoic acid (Example 27-(b));

methyl 3-(1,4-dimethyl-1H-benzo[d][1,2,3]triazol-5-yl)-3-(3-(((R)-2-ethyl-2,3-dihydro-[1,4]oxazepino[7,6-f]quinolin-4(5H)-yl)methyl)-4-methylphenyl)-2,2-dimethylpropanoate (Example 28-(a));

3-(1,4-dimethyl-1H-benzo[d][1,2,3]triazol-5-yl)-3-(3-(((R)-2-ethyl-2,3-dihydro-[1,4]oxazepino[7,6-f]quinolin-4(5H)-yl)methyl)-4-methylphenyl)-2,2-dimethylpropanoic acid (Example 28-(b));

methyl 3-(1,4-dimethyl-1H-benzo[d][1,2,3]triazol-5-yl)-3-(3-(((R)-2-ethyl-7-fluoro-2,3-dihydronaphtho[2,1-f][1,4]oxazepin-4(5H)-yl)methyl)-4-methylphenyl)-2,2-dimethylpropanoate (Example 49-(a));

3-(1,4-dimethyl-1H-benzo[d][1,2,3]triazol-5-yl)-3-(3-(((R)-2-ethyl-7-fluoro-2,3-dihydronaphtho[2,1-f][1,4]oxazepin-4(5H)-yl)methyl)-4-methylphenyl)-2,2-dimethylpropanoic acid (Example 49-(b));

methyl 3-(1,4-dimethyl-1H-benzo[d][1,2,3]triazol-5-yl)-3-(3-(((R)-8-ethyl-1-methyl-1,5,7,8-tetrahydro-6H-[1,4]oxazepino[6,7-f]indazol-6-yl)methyl)-4-methylphenyl)-2,2-dimethylpropanoate (Example 50-(a));

3-(1,4-dimethyl-1H-benzo[d][1,2,3]triazol-5-yl)-3-(3-(((R)-8-ethyl-1-methyl-1,5,7,8-tetrahydro-6H-[1,4]oxazepino[6,7-f]indazol-6-yl)methyl)-4-methylphenyl)-2,2-dimethylpropanoic acid (Example 50-(b));

methyl 3-(1,4-dimethyl-1H-benzo[d][1,2,3]triazol-5-yl)-3-(3-(((R)-8-ethyl-2-methyl-2,5,7,8-tetrahydro-6H-[1,4]oxazepino[6,7-f]indazol-6-yl)methyl)-4-methylphenyl)-2,2-dimethylpropanoate (Example 51-(a));

3-(1,4-dimethyl-1H-benzo[d][1,2,3]triazol-5-yl)-3-(3-(((R)-8-ethyl-2-methyl-2,5,7,8-tetrahydro-6H-[1,4]oxazepino[6,7-f]indazol-6-yl)methyl)-4-methylphenyl)-2,2-dimethylpropanoic acid (Example 51-(b));

methyl 3-(1,4-dimethyl-1H-benzo[d][1,2,3]triazol-5-yl)-3-(3-(((R)-2-ethyl-2,3-dihydro-[1,4]oxazepino[6,7-g]isoquinolin-4(5H)-yl)methyl)-4-methylphenyl)-2,2-dimethylpropanoate (Example 52-(a));

3-(1,4-dimethyl-1H-benzo[d][1,2,3]triazol-5-yl)-3-(3-(((R)-2-ethyl-2,3-dihydro-[1,4]oxazepino[6,7-g]isoquinolin-4(5H)-yl)methyl)-4-methylphenyl)-2,2-dimethylpropanoic acid (Example 52-(b));

3-(1,4-dimethyl-1H-benzo[d][1,2,3]triazol-5-yl)-3-(3-(((R)-2-ethyl-2,3-dihydro-[1,4]oxazepino[7,6-g]isoquinolin-4(5H)-yl)methyl)-4-methylphenyl)-2,2-dimethylpropanoic acid (Example 53);

methyl 3-(1,4-dimethyl-1H-benzo[d][1,2,3]triazol-5-yl)-3-(3-(((R)-2-ethyl-7-fluoro-2,3-dihydronaphtho[2,3-f][1,4]oxazepin-4(5H)-yl)methyl)-4-methylphenyl)-2,2-dimethylpropanoate (Example 54-(a));

3-(1,4-dimethyl-1H-benzo[d][1,2,3]triazol-5-yl)-3-(3-(((R)-2-ethyl-7-fluoro-2,3-dihydronaphtho[2,3-f][1,4]oxazepin-4(5H)-yl)methyl)-4-methylphenyl)-2,2-dimethylpropanoic acid (Example 54-(b));

methyl 3-(1,4-dimethyl-1H-benzo[d][1,2,3]triazol-5-yl)-3-(3-(((R)-2-ethyl-2,3-dihydro-[1,4]oxazepino[7,6-f]isoquinolin-4(5H)-yl)methyl)-4-methylphenyl)-2,2-dimethylpropanoate (Example 55-(a));

3-(1,4-dimethyl-1H-benzo[d][1,2,3]triazol-5-yl)-3-(3-(((R)-2-ethyl-2,3-dihydro-[1,4]oxazepino[7,6-f]isoquinolin-4(5H)-yl)methyl)-4-methylphenyl)-2,2-dimethylpropanoic acid ditrifluoroacetate (Example 55-(b));

ethyl 3-(1,4-dimethyl-1H-benzo[d][1,2,3]triazol-5-yl)-3-(3-(((R)-2-ethyl-2,3-dihydro-[1,4]oxazepino[7,6-g]quinolin-4(5H)-yl)methyl)-4-methylphenyl)propanoate (Example 56-(a));

3-(1,4-dimethyl-1H-benzo[d][1,2,3]triazol-5-yl)-3-(3-(((R)-2-ethyl-2,3-dihydro-[1,4]oxazepino[7,6-g]quinolin-4(5H)-yl)methyl)-4-methylphenyl)propanoic acid (Example 56-(b));

methyl 3-(1,4-dimethyl-1H-benzo[d][1,2,3]triazol-5-yl)-3-(3-(((S)-2-ethyl-2,3-dihydro-[1,4]oxazepino[7,6-g]quinolin-4(5H)-yl)methyl)-4-methylphenyl)-2,2-dimethylpropanoate (Example 57-(a));

3-(1,4-dimethyl-1H-benzo[d][1,2,3]triazol-5-yl)-3-(3-(((S)-2-ethyl-2,3-dihydro-[1,4]oxazepino[7,6-g]quinolin-4(5H)-yl)methyl)-4-methylphenyl)-2,2-dimethylpropanoic acid (Example 57-(b), Example 57-(c) (Diastereomer 1), and Example 58 (Diastereomer 2));

methyl 3-(3-(((R)-2-ethyl-2,3-dihydro-[1,4]oxazepino[7,6-g]quinolin-4(5H)-yl)methyl)-4-methylphenyl)-3-(l-ethyl-4-methyl-1H-benzo[d][1,2,3]triazol-5-yl)-2,2-dimethylpropanoate (Example 59-(a));

3-(3-(((R)-2-ethyl-2,3-dihydro-[1,4]oxazepino[7,6-g]quinolin-4(5H)-yl)methyl)-4-methylphenyl)-3-(1-ethyl-4-methyl-1H-benzo[d][1,2,3]triazol-5-yl)-2,2-dimethylpropanoic acid (Example 59-(b));

methyl 3-(1,4-dimethyl-1H-benzo[d][1,2,3]triazol-5-yl)-3-(3-((2,2-dimethyl-2,3-dihydro-[1,4]oxazepino[7,6-g]quinolin-4(5H)-yl)methyl)-4-methylphenyl)-2,2-dimethylpropanoate (Example 60-(a));

3-(1,4-dimethyl-1H-benzo[d][1,2,3]triazol-5-yl)-3-(3-((2,2-dimethyl-2,3-dihydro-[1,4]oxazepino[7,6-g]quinolin-4(5H)-yl)methyl)-4-methylphenyl)-2,2-dimethylpropanoic acid (Example 60-(b));

methyl 3-(1,4-dimethyl-1H-benzo[d][1,2,3]triazol-5-yl)-3-(3-(((R)-6-ethyl-2,2-dimethyl-6,7-dihydro-[1,3]dioxolo[4',5':4,5]benzo[1,2-f][1,4]oxazepin-8(9H)-yl)methyl)-4-methylphenyl)-2,2-dimethylpropanoate (Example 61-(a));

3-(1,4-dimethyl-1H-benzo[d][1,2,3]triazol-5-yl)-3-(3-(((R)-6-ethyl-2,2-dimethyl-6,7-dihydro-[1,3]dioxolo[4',5':4,5]benzo[1,2-f][1,4]oxazepin-8(9H)-yl)methyl)-4-methylphenyl)-2,2-dimethylpropanoic acid (Example 61-(b));

3-(1,4-dimethyl-1H-benzo[d][1,2,3]triazol-5-yl)-3-(3-(((R)-2-ethyl-2,3-dihydro-[1,4]oxazepino[6,7-h]isoquinolin-4(5H)-yl)methyl)-4-methylphenyl)-2,2-dimethylpropanoic acid (Example 62);

methyl 3-(3-((2,3-dihydro-[1,4]oxazepino[7,6-g]quinolin-4(5H)-yl)methyl)-4-methylphenyl)-3-(1,4-dimethyl-1H-benzo[d][1,2,3]triazol-5-yl)-2,2-dimethylpropanoate (Example 63-(a));

3-(3-((2,3-dihydro-[1,4]oxazepino[7,6-g]quinolin-4(5H)-yl)methyl)-4-methylphenyl)-3-(1,4-dimethyl-1H-benzo[d][1,2,3]triazol-5-yl)-2,2-dimethylpropanoic acid (Example 63-(b));

methyl 3-(1,4-dimethyl-1H-benzo[d][1,2,3]triazol-5-yl)-3-(3-(((R)-6-ethyl-1,6,7,9-tetrahydro-8H-[1,4]oxazepino[7,6-f]indazol-8-yl)methyl)-4-methylphenyl)-2,2-dimethylpropanoate (Example 64-(a));

3-(1,4-dimethyl-1H-benzo[d][1,2,3]triazol-5-yl)-3-(3-(((R)-6-ethyl-1,6,7,9-tetrahydro-8H-[1,4]oxazepino[7,6-f]indazol-8-yl)methyl)-4-methylphenyl)-2,2-dimethylpropanoic acid (Example 64-(b));

methyl 3-(1,4-dimethyl-1H-benzo[d][1,2,3]triazol-5-yl)-3-(3-(((R)-6-ethyl-1-methyl-1,6,7,9-tetrahydro-8H-[1,4]oxazepino[7,6-f]indazol-8-yl)methyl)-4-methylphenyl)-2,2-dimethylpropanoate (Example 65-(a));

3-(1,4-dimethyl-1H-benzo[d][1,2,3]triazol-5-yl)-3-(3-(((R)-6-ethyl-1-methyl-1,6,7,9-tetrahydro-8H-[1,4]oxazepino[7,6-f]indazol-8-yl)methyl)-4-methylphenyl)-2,2-dimethylpropanoic acid (Example 65-(b));

methyl 3-(1,4-dimethyl-1H-benzo[d][1,2,3]triazol-5-yl)-3-(3-(((R)-6-ethyl-2-methyl-2,6,7,9-tetrahydro-8H-[1,4]oxazepino[7,6-f]indazol-8-yl)methyl)-4-methylphenyl)-2,2-dimethylpropanoate (Example 66-(a));

3-(1,4-dimethyl-1H-benzo[d][1,2,3]triazol-5-yl)-3-(3-(((R)-6-ethyl-2-methyl-2,6,7,9-tetrahydro-8H-[1,4]oxazepino[7,6-f]indazol-8-yl)methyl)-4-methylphenyl)-2,2-dimethylpropanoic acid (Example 66-(b));

methyl 3-(3-(((R)-7-chloro-2-ethyl-2,3-dihydronaphtho[2,1-f][1,4]oxazepin-4(5H)-yl)methyl)-4-methylphenyl)-3-(1,4-dimethyl-1H-benzo[d][1,2,3]triazol-5-yl)-2,2-dimethylpropanoate (Example 67-(a));

3-(3-(((R)-7-chloro-2-ethyl-2,3-dihydronaphtho[2,1-f][1,4]oxazepin-4(5H)-yl)methyl)-4-methylphenyl)-3-(1,4-dimethyl-1H-benzo[d][1,2,3]triazol-5-yl)-2,2-dimethylpropanoic acid (Example 67-(b));

methyl 3-(3-(((R)-7-chloro-2-ethyl-2,3-dihydronaphtho[2,3-f][1,4]oxazepin-4 (5H)-yl)methyl)-4-methylphenyl)-3-(1,4-dimethyl-1H-benzo[d][1,2,3]triazol-5-yl)-2,2-dimethylpropanoate (Example 68-(a));

3-(3-(((R)-7-chloro-2-ethyl-2,3-dihydronaphtho[2,3-f][1,4]oxazepin-4(5H)-yl)methyl)-4-methylphenyl)-3-(1,4-dimethyl-1H-benzo[d][1,2,3]triazol-5-yl)-2,2-dimethylpropanoic acid (Example 68-(b));

3-(3-(((R)-10-chloro-2-ethyl-2,3-dihydro-[1,4]oxazepino[7,6-g]quinolin-4(5H)-yl)methyl)-4-methylphenyl)-3-(1,4-dimethyl-1H-benzo[d][1,2,3]triazol-5-yl)-2,2-dimethylpropanoic acid (Example 69);

methyl 3-(1,4-dimethyl-1H-benzo[d][1,2,3]triazol-5-yl)-3-(3-(((R)-2-ethyl-10-methoxy-2,3-dihydro-[1,4]oxazepino[7,6-g]quinolin-4(5H)-yl)methyl)-4-methylphenyl)-2,2-dimethylpropanoate (Example 70-(a));

3-(1,4-dimethyl-1H-benzo[d][1,2,3]triazol-5-yl)-3-(3-(((R)-2-ethyl-10-methoxy-2,3-dihydro-[1,4]oxazepino[7,6-g]quinolin-4(5H)-yl)methyl)-4-methylphenyl)-2,2-dimethylpropanoic acid (Example 70-(b));

methyl 3-(1,4-dimethyl-1H-benzo[d][1,2,3]triazol-5-yl)-3-(3-(((R)-2-ethyl-10-methyl-2,3-dihydro-[1,4]oxazepino[7,6-g]quinolin-4 (5H)-yl)methyl)-4-methylphenyl)-2,2-dimethylpropanoate (Example 71-(a));

3-(1,4-dimethyl-1H-benzo[d][1,2,3]triazol-5-yl)-3-(3-(((R)-2-ethyl-10-methyl-2,3-dihydro-[1,4]oxazepino[7,6-g]quinolin-4(5H)-yl)methyl)-4-methylphenyl)-2,2-dimethylpropanoic acid (Example 71-(b));

methyl 3-(1,4-dimethyl-1H-benzo[d][1,2,3]triazol-5-yl)-3-(3-(((R)-2-ethyl-2,3-dihydrothieno[2',3':4,5]benzo[1,2-f][1,4]oxazepin-4(5H)-yl)methyl)-4-methylphenyl)-2,2-dimethylpropanoate (Example 72-(a));

3-(1,4-dimethyl-1H-benzo[d][1,2,3]triazol-5-yl)-3-(3-(((R)-2-ethyl-2,3-dihydrothieno[2',3':4,5]benzo[1,2-f][1,4]oxazepin-4(5H)-yl)methyl)-4-methylphenyl)-2,2-dimethylpropanoic acid (Example 72-(b));

methyl 3-(1,4-dimethyl-1H-benzo[d][1,2,3]triazol-5-yl)-3-(3-(((R)-2-ethyl-2,3,7,8-tetrahydrothieno[2',3':4,5]benzo[1,2-f][1,4]oxazepin-4(5H)-yl)methyl)-4-methylphenyl)-2,2-dimethylpropanoate (Example 73-(a));

3-(1,4-dimethyl-1H-benzo[d][1,2,3]triazol-5-yl)-3-(3-(((R)-2-ethyl-2,3,7,8-tetrahydrothieno[2',3':4,5]benzo[1,2-f][1,4]oxazepin-4(5H)-yl)methyl)-4-methylphenyl)-2,2-dimethylpropanoic acid (Example 73-(b));

methyl 3-(1,4-dimethyl-1H-benzo[d][1,2,3]triazol-5-yl)-3-(3-(((R)-2-ethyl-9,9-dioxide-2,3,7,8-tetrahydrothieno[2',3':4,5]benzo[1,2-f][1,4]oxazepin-4(5H)-yl)methyl)-4-methylphenyl)-2,2-dimethylpropanoate (Example 74-(a));

3-(1,4-dimethyl-1H-benzo[d][1,2,3]triazol-5-yl)-3-(3-(((R)-2-ethyl-9,9-dioxide-2,3,7,8-tetrahydrothieno[2',3':4,5]benzo[1,2-f][1,4]oxazepin-4(5H)-yl)methyl)-4-methylphenyl)-2,2-dimethylpropanoic acid (Example 74-(b));

methyl 3-(1,4-dimethyl-1H-benzo[d][1,2,3]triazol-5-yl)-2,2-dimethyl-3-(4-methyl-3-(((R)-2-methyl-2,3-dihydro-[1,4]oxazepino[7,6-g]quinolin-4 (5H)-yl)methyl)phenyl)propanoate (Example 75-(a));

3-(1,4-dimethyl-1H-benzo[d][1,2,3]triazol-5-yl)-2,2-dimethyl-3-(4-methyl-3-(((R)-2-methyl-2,3-dihydro-[1,4]oxazepino[7,6-g]quinolin-4(5H)-yl)methyl)phenyl)propanoic acid (Example 75-(b));

methyl 3-(3-((3'H-spiro[cyclopropane-1,2'-[1,4]oxazepino[7,6-g]quinoline]-4' (5'H)-yl)methyl)-4-methylphenyl)-3-(1,4-dimethyl-1H-benzo[d][1,2,3]triazol-5-yl)-2,2-dimethylpropanoate (Example 76-(a));

3-(3-((3'H-spiro[cyclopropane-1,2'-[1,4]oxazepino[7,6-g]quinoline]-4' (5'H)-yl)methyl)-4-methylphenyl)-3-(1,4-dimethyl-1H-benzo[d][1,2,3]triazol-5-yl)-2,2-dimethylpropanoic acid (Example 76-(b), Example 85 (Diastereomer 1), and Example 86 (Diastereomer 2));

methyl 3-(1,4-dimethyl-1H-benzo[d][1,2,3]triazol-5-yl)-2,2-dimethyl-3-(4-methyl-3-((2-propyl-2,3-dihydro-[1,4]oxazepino[7,6-g]quinolin-4 (5H)-yl)methyl)phenyl)propanoate (Example 77-(a) and Example 78-(a));

3-(1,4-dimethyl-1H-benzo[d][1,2,3]triazol-5-yl)-2,2-dimethyl-3-(4-methyl-3-((2-propyl-2,3-dihydro-[1,4]oxazepino[7,6-g]quinolin-4(5H)-yl)methyl)phenyl)propanoic acid (Example 77-(b) and Example 78-(b));

methyl 3-(1,4-dimethyl-1H-benzo[d][1,2,3]triazol-5-yl)-3-(3-(((R)-2-ethyl-2,3-dihydro-[1,4]oxazepino[7,6-g]quinolin-4(5H)-yl)methyl)phenyl)-2,2-dimethylpropanoate (Example 79-(a));

3-(1,4-dimethyl-1H-benzo[d][1,2,3]triazol-5-yl)-3-(3-(((R)-2-ethyl-2,3-dihydro-[1,4]oxazepino[7,6-g]quinolin-4 (5H)-yl)methyl)phenyl)-2,2-dimethylpropanoic acid (Example 79-(b));

methyl 3-(4-chloro-3-(((R)-2-ethyl-2,3-dihydro-[1,4]oxazepino[7,6-g]quinolin-4(5H)-yl)methyl)phenyl)-3-(1,4-dimethyl-1H-benzo[d][1,2,3]triazol-5-yl)-2,2-dimethylpropanoate (Example 80-(a));

3-(4-chloro-3-(((R)-2-ethyl-2,3-dihydro-[1,4]oxazepino[7,6-g]quinolin-4(5H)-yl)methyl)phenyl)-3-(1,4-dimethyl-1H-benzo[d][1,2,3]triazol-5-yl)-2,2-dimethylpropanoic acid (Example 80-(b));

methyl 3-(1,4-dimethyl-1H-benzo[d][1,2,3]triazol-5-yl)-3-(3-(((R)-2-ethyl-2,3-dihydro-[1,4]oxazepino[7,6-g]quinolin-4 (5H)-yl)methyl)-4-methoxyphenyl)-2,2-dimethylpropanoate (Example 81-(a));

3-(1,4-dimethyl-1H-benzo[d][1,2,3]triazol-5-yl)-3-(3-(((R)-2-ethyl-2,3-dihydro-[1,4]oxazepino[7,6-g]quinolin-4 (5H)-yl)methyl)-4-methoxyphenyl)-2,2-dimethylpropanoic acid (Example 81-(b));

methyl 3-(3-(((R)-2-ethyl-2,3-dihydro-[1,4]oxazepino[7,6-g]quinolin-4 (5H)-yl)methyl)-4-methylphenyl)-2,2-dimethyl-3-(1-methyl-1H-benzo[d][1,2,3]triazol-5-yl)propanoate (Example 82-(a));

3-(3-(((R)-2-ethyl-2,3-dihydro-[1,4]oxazepino[7,6-g]quinolin-4(5H)-yl)methyl)-4-methylphenyl)-2,2-dimethyl-3-(1-methyl-1H-benzo[d][1,2,3]triazol-5-yl)propanoic acid (Example 82-(b));

methyl 1-((1,4-dimethyl-1H-benzo[d][1,2,3]triazol-5-yl) (3-(((R)-2-ethyl-2,3-dihydro-[1,4]oxazepino[7,6-g]quinolin-4 (5H)-yl)methyl)-4-methylphenyl)methyl)cyclopentane-1-carboxylate (Example 83-(a));

1-((1,4-dimethyl-1H-benzo[d][1,2,3]triazol-5-yl) (3-(((R)-2-ethyl-2,3-dihydro-[1,4]oxazepino[7,6-g]quinolin-4 (5H)-yl)methyl)-4-methylphenyl)methyl)cyclopentane-1-carboxylic acid (Example 83-(b));

methyl 1-((1,4-dimethyl-1H-benzo[d][1,2,3]triazol-5-yl) (3-(((R)-2-ethyl-2,3-dihydro-[1,4]oxazepino[7,6-g]quinolin-4 (5H)-yl)methyl)-4-methylphenyl)methyl)cyclobutane-1-carboxylate (Example 84-(a));

1-((1,4-dimethyl-1H-benzo[d][1,2,3]triazol-5-yl) (3-(((R)-2-ethyl-2,3-dihydro-[1,4]oxazepino[7,6-g]quinolin-4 (5H)-yl)methyl)-4-methylphenyl)methyl)cyclobutane-1-carboxylic acid (Example 84-(b), Example 87 (Diastereomer 1), and Example 88 (Diastereomer 2));

methyl 3-(1,4-dimethyl-1H-benzo[d][1,2,3]triazol-5-yl)-3-(3-(((S)-2-ethyl-2,3-dihydro-[1,4]oxazepino[6,7-c]isoquinolin-4(5H)-yl)methyl)-4-methylphenyl)-2,2-dimethylpropanoate (Example 89-(a)); and 3-(1,4-dimethyl-1H-benzo[d][1,2,3]triazol-5-yl)-3-(3-(((S)-2-ethyl-2,3-dihydro-[1,4]oxazepino[6,7-c]isoquinolin-4 (5H)-yl)methyl)-4-methylphenyl)-2,2-dimethylpropanoic acid (Example 89-(b) (Diastereomer 1) and Example 90 (Diastereomer 2))

or a pharmaceutically acceptable salt thereof.

[17] The compound according to [1] selected from the group consisting of 3-(1,4-dimethyl-1H-benzo[d][1,2,3]triazol-5-yl)-3-(3-(((R)-6-ethyl-2,2-difluoro-6,7-dihydro-[1,3]dioxolo[4',5':4,5]benzo[1,2-f][1,4]oxazepin-8(9H)-yl)methyl)-4-methylphenyl)-2,2-dimethylpropanoic acid (Example 1-(b), Example 29 (Diastereomer 1), and Example 30 (Diastereomer 2));

3-(1,4-dimethyl-1H-benzo[d][1,2,3]triazol-5-yl)-3-(3-(((R)-9-ethyl-2,2-difluoro-8,9-dihydro-[1,3]dioxolo[4',5':3,4]benzo[1,2-f][1,4]oxazepin-7(6H)-yl)methyl)-4-methylphenyl)-2,2-dimethylpropanoic acid (Example 2-(b));

3-(1,4-dimethyl-1H-benzo[d][1,2,3]triazol-5-yl)-3-(3-(((R)-2-ethyl-2,3,5,7,8,9-hexahydro-4H-indeno[5,6-f][1,4]oxazepin-4-yl)methyl)-4-methylphenyl)-2,2-dimethyl-propanoic acid (Example 3-(b), Example 31 (Diastereomer 1), and Example 32 (Diastereomer 2));

3-(1,4-dimethyl-1H-benzo[d][1,2,3]triazol-5-yl)-3-(3-(((R)-2-ethyl-2,3,7,8,9,10-hexahydronaphtho[2,3-f][1,4]oxazepin-4(5H)-yl)methyl)-4-methylphenyl)-2,2-dimethylpropanoic acid (Example 4-(b), Example 33 (Diastereomer 1), and Example 34 (Diastereomer 2));

3-(1,4-dimethyl-1H-benzo[d][1,2,3]triazol-5-yl)-3-(3-(((R)-4-ethyl-3,4,8,9,10,11-hexahydronaphtho[1,2-f][1,4]oxazepin-2(1H)-yl)methyl)-4-methylphenyl)-2,2-dimethylpropanoic acid (Example 5-(b));

3-(1,4-dimethyl-1H-benzo[d][1,2,3]triazol-5-yl)-3-(3-(((R)-2-ethyl-2,3,5,8,9,10-hexahydro-4H-indeno[5,4-f][1,4]oxazepin-4-yl)methyl)-4-methylphenyl)-2,2-dimethyl-propanoic acid (Example 6-(b), Example 35 (Diastereomer 1), and Example 36 (Diastereomer 2));

3-(1,4-dimethyl-1H-benzo[d][1,2,3]triazol-5-yl)-3-(3-(((R)-2-ethyl-2,3,8,9,10,11-hexahydronaphtho[2,1-f][1,4]oxazepin-4(5H)-yl)methyl)-4-methylphenyl)-2,2-dimethylpropanoic acid (Example 7-(b));

3-(1,4-dimethyl-1H-benzo[d][1,2,3]triazol-5-yl)-3-(3-(((R)-2-ethyl-2,3-dihydronaphtho[2,3-f][1,4]oxazepin-4 (5H)-yl)methyl)-4-methylphenyl)-2,2-dimethylpropanoic acid (Example 8-(b));

3-(1,4-dimethyl-1H-benzo[d][1,2,3]triazol-5-yl)-3-(3-(((R)-2-ethyl-2,3-dihydro-[1,4]oxazepino[7,6-b]quinolin-4 (5H)-yl)methyl)-4-methylphenyl)-2,2-dimethylpropanoic acid (Example 9-(b));

3-(1,4-dimethyl-1H-benzo[d][1,2,3]triazol-5-yl)-3-(3-(((R)-2-ethyl-2,3-dihydro-[1,4]oxazepino[6,7-b]quinolin-4 (5H)-yl)methyl)-4-methylphenyl)-2,2-dimethylpropanoic acid (Example 10-(b), Example 37 (Diastereomer 1), and Example 38 (Diastereomer 2));

3-(1,4-dimethyl-1H-benzo[d][1,2,3]triazol-5-yl)-3-(3-(((R)-2-ethyl-2,3-dihydro-[1,4]oxazepino[6,7-g]quinolin-4 (5H)-yl)methyl)-4-methylphenyl)-2,2-dimethylpropanoic acid (Example 11-(b), Example 39 (Diastereomer 1), and Example 40 (Diastereomer 2));

3-(1,4-dimethyl-1H-benzo[d][1,2,3]triazol-5-yl)-3-(3-(((R)-2-ethyl-2,3-dihydro-[1,4]oxazepino[7,6-g]quinolin-4 (5H)-yl)methyl)-4-methylphenyl)-2,2-dimethylpropanoic acid (Example 12-(b), Example 41 (Diastereomer 1), and Example 42 (Diastereomer 2));

3-(1,4-dimethyl-1H-benzo[d][1,2,3]triazol-5-yl)-3-(3-(((R)-2-ethyl-10-methyl-2,3-dihydro-[1,4]oxazepino[7,6-b]quinolin-4(5H)-yl)methyl)-4-methylphenyl)-2,2-dimethylpropanoic acid (Example 13-(b));

3-(1,4-dimethyl-1H-benzo[d][1,2,3]triazol-5-yl)-3-(3-(((R)-2-ethyl-8-methyl-2,3-dihydro-[1,4]oxazepino[7,6-b]quinolin-4(5H)-yl)methyl)-4-methylphenyl)-2,2-dimethyl-propanoic acid (Example 14-(b));

3-(1,4-dimethyl-1H-benzo[d][1,2,3]triazol-5-yl)-3-(3-(((R)-8-ethyl-1,5,7,8-tetrahydro-6H-[1,4]oxazepino[6,7-f]indazol-6-yl)methyl)-4-methylphenyl)-2,2-dimethylpropanoic acid (Example 15-(b));

3-(1,4-dimethyl-1H-benzo[d][1,2,3]triazol-5-yl)-3-(3-(((R)-4-ethyl-3,4-dihydronaphtho[1,2-f][1,4]oxazepin-2(1H)-yl)methyl)-4-methylphenyl)-2,2-dimethylpropanoic acid (Example 16-(b));

3-(1,4-dimethyl-1H-benzo[d][1,2,3]triazol-5-yl)-3-(3-(((R)-8-ethyl-8,9-dihydro-[1,4]oxazepino[7,6-h]quinolin-10 (11H)-yl)methyl)-4-methylphenyl)-2,2-dimethylpropanoic acid (Example 17-(b));

3-(1,4-dimethyl-1H-benzo[d][1,2,3]triazol-5-yl)-3-(3-(((R)-4-ethyl-3,4-dihydro-[1,4]oxazepino[6,7-f]quinolin-2 (1H)-yl)methyl)-4-methylphenyl)-2,2-dimethylpropanoic acid (Example 18-(b));

3-(1,4-dimethyl-1H-benzo[d][1,2,3]triazol-5-yl)-3-(3-(((R)-4-ethyl-3,4-dihydro-[1,4]oxazepino[7,6-c]quinolin-2 (1H)-yl)methyl)-4-methylphenyl)-2,2-dimethylpropanoic acid (Example 19-(b));

3-(1,4-dimethyl-1H-benzo[d][1,2,3]triazol-5-yl)-3-(3-(((R)-7-ethyl-1,7,8,10-tetrahydro-9H-[1,4]oxazepino[7,6-g]indazol-9-yl)methyl)-4-methylphenyl)-2,2-dimethylpropanoic acid (Example 20-(b), Example 43 (Diastereomer 1), and Example 44 (Diastereomer 2));

3-(1,4-dimethyl-1H-benzo[d][1,2,3]triazol-5-yl)-3-(3-(((R)-7-ethyl-1-methyl-1,7,8,10-tetrahydro-9H-[1,4]oxazepino[7,6-g]indazol-9-yl)methyl)-4-methylphenyl)-2,2-dimethylpropanoic acid (Example 21-(b));

3-(1,4-dimethyl-1H-benzo[d][1,2,3]triazol-5-yl)-3-(3-(((R)-7-ethyl-2-methyl-2,7,8,10-tetrahydro-9H-[1,4]oxazepino[7,6-g]indazol-9-yl)methyl)-4-methylphenyl)-2,2-dimethylpropanoic acid (Example 22-(b));

3-(1,4-dimethyl-1H-benzo[d][1,2,3]triazol-5-yl)-3-(3-(((R)-4-ethyl-1,3,4,9,10,11-hexahydro-2H-pyrimido[1',2':1,6]pyrido[2,3-f][1,4]oxazepin-2-yl)methyl)-4-methylphenyl)-2,2-dimethylpropanoic acid (Example 23);

3-(1,4-dimethyl-1H-benzo[d][1,2,3]triazol-5-yl)-3-(3-(((R)-2-ethyl-2,3-dihydronaphtho[2,1-f][1,4]oxazepin-4(5H)-yl)methyl)-4-methylphenyl)-2,2-dimethylpropanoic acid (Example 24-(b));

3-(1,4-dimethyl-1H-benzo[d][1,2,3]triazol-5-yl)-3-(3-(((R)-2-ethyl-2,3-dihydro-[1,4]oxazepino[6,7-c]isoquinolin-4 (5H)-yl)methyl)-4-methylphenyl)-2,2-dimethylpropanoic acid (Example 25-(b), Example 45 (Diastereomer 1), and Example 46 (Diastereomer 2));

3-(1,4-dimethyl-1H-benzo[d][1,2,3]triazol-5-yl)-3-(3-(((R)-2-ethyl-2,3-dihydro-[1,4]oxazepino[6,7-c]quinolin-4 (5H)-yl)methyl)-4-methylphenyl)-2,2-dimethylpropanoic acid (Example 26-(b), Example 47 (Diastereomer 1), and Example 48 (Diastereomer 2));

3-(1,4-dimethyl-1H-benzo[d][1,2,3]triazol-5-yl)-3-(3-(((R)-2-ethyl-2,3-dihydro-[1,4]oxazepino[6,7-h]quinolin-4 (5H)-yl)methyl)-4-methylphenyl)-2,2-dimethylpropanoic acid (Example 27-(b));

3-(1,4-dimethyl-1H-benzo[d][1,2,3]triazol-5-yl)-3-(3-(((R)-2-ethyl-2,3-dihydro-[1,4]oxazepino[7,6-f]quinolin-4 (5H)-yl)methyl)-4-methylphenyl)-2,2-dimethylpropanoic acid (Example 28-(b));

3-(1,4-dimethyl-1H-benzo[d][1,2,3]triazol-5-yl)-3-(3-(((R)-2-ethyl-7-fluoro-2,3-dihydronaphtho[2,1-f][1,4]oxazepin-4(5H)-yl)methyl)-4-methylphenyl)-2,2-dimethylpropanoic acid (Example 49-(b));

3-(1,4-dimethyl-1H-benzo[d][1,2,3]triazol-5-yl)-3-(3-(((R)-8-ethyl-1-methyl-1,5,7,8-tetrahydro-6H-[1,4]oxazepino[6,7-f]indazol-6-yl)methyl)-4-methylphenyl)-2,2-dimethylpropanoic acid (Example 50-(b));

3-(1,4-dimethyl-1H-benzo[d][1,2,3]triazol-5-yl)-3-(3-(((R)-8-ethyl-2-methyl-2,5,7,8-tetrahydro-6H-[1,4]oxazepino[6,7-f]indazol-6-yl)methyl)-4-methylphenyl)-2,2-dimethylpropanoic acid (Example 51-(b));

3-(1,4-dimethyl-1H-benzo[d][1,2,3]triazol-5-yl)-3-(3-(((R)-2-ethyl-2,3-dihydro-[1,4]oxazepino[6,7-g]isoquinolin-4 (5H)-yl)methyl)-4-methylphenyl)-2,2-dimethylpropanoic acid (Example 52-(b));

3-(1,4-dimethyl-1H-benzo[d][1,2,3]triazol-5-yl)-3-(3-(((R)-2-ethyl-2,3-dihydro-[1,4]oxazepino[7,6-g]isoquinolin-4 (5H)-yl)methyl)-4-methylphenyl)-2,2-dimethylpropanoic acid (Example 53);

3-(1,4-dimethyl-1H-benzo[d][1,2,3]triazol-5-yl)-3-(3-(((R)-2-ethyl-7-fluoro-2,3-dihydronaphtho[2,3-f][1,4]oxazepin-4(5H)-yl)methyl)-4-methylphenyl)-2,2-dimethylpropanoic acid (Example 54-(b));

3-(1,4-dimethyl-1H-benzo[d][1,2,3]triazol-5-yl)-3-(3-(((R)-2-ethyl-2,3-dihydro-[1,4]oxazepino[7,6-f]isoquinolin-4(5H)-yl)methyl)-4-methylphenyl)-2,2-dimethylpropanoic acid ditrifluoroacetate (Example 55-(b));

3-(1,4-dimethyl-1H-benzo[d][1,2,3]triazol-5-yl)-3-(3-(((R)-2-ethyl-2,3-dihydro-[1,4]oxazepino[7,6-g]quinolin-4(5H)-yl)methyl)-4-methylphenyl)propanoic acid (Example 56-(b));

3-(1,4-dimethyl-1H-benzo[d][1,2,3]triazol-5-yl)-3-(3-(((S)-2-ethyl-2,3-dihydro-[1,4]oxazepino[7,6-g]quinolin-4(5H)-yl)methyl)-4-methylphenyl)-2,2-dimethylpropanoic acid (Example 57-(b), Example 57-(c) (Diastereomer 1), and Example 58 (Diastereomer 2));

3-(3-(((R)-2-ethyl-2,3-dihydro-[1,4]oxazepino[7,6-g]quinolin-4(5H)-yl)methyl)-4-methylphenyl)-3-(1-ethyl-4-methyl-1H-benzo[d][1,2,3]triazol-5-yl)-2,2-dimethylpropanoic acid (Example 59-(b));

3-(1,4-dimethyl-1H-benzo[d][1,2,3]triazol-5-yl)-3-(3-((2,2-dimethyl-2,3-dihydro-[1,4]oxazepino[7,6-g]quinolin-4(5H)-yl)methyl)-4-methylphenyl)-2,2-dimethylpropanoic acid (Example 60-(b));

3-(1,4-dimethyl-1H-benzo[d][1,2,3]triazol-5-yl)-3-(3-(((R)-6-ethyl-2,2-dimethyl-6,7-dihydro-[1,3]dioxolo[4',5':4,5]benzo[1,2-f][1,4]oxazepin-8(9H)-yl)methyl)-4-methylphenyl)-2,2-dimethylpropanoic acid (Example 61-(b));

3-(1,4-dimethyl-1H-benzo[d][1,2,3]triazol-5-yl)-3-(3-(((R)-2-ethyl-2,3-dihydro-[1,4]oxazepino[6,7-h]isoquinolin-4(5H)-yl)methyl)-4-methylphenyl)-2,2-dimethylpropanoic acid (Example 62);

3-(3-((2,3-dihydro-[1,4]oxazepino[7,6-g]quinolin-4(5H)-yl)methyl)-4-methylphenyl)-3-(1,4-dimethyl-1H-benzo[d][1,2,3]triazol-5-yl)-2,2-dimethylpropanoic acid (Example 63-(b));

3-(1,4-dimethyl-1H-benzo[d][1,2,3]triazol-5-yl)-3-(3-(((R)-6-ethyl-1,6,7,9-tetrahydro-8H-[1,4]oxazepino[7,6-f]indazol-8-yl)methyl)-4-methylphenyl)-2,2-dimethylpropanoic acid (Example 64-(b));

3-(1,4-dimethyl-1H-benzo[d][1,2,3]triazol-5-yl)-3-(3-(((R)-6-ethyl-1-methyl-1,6,7,9-tetrahydro-8H-[1,4]oxazepino[7,6-f]indazol-8-yl)methyl)-4-methylphenyl)-2,2-dimethylpropanoic acid (Example 65-(b));

3-(1,4-dimethyl-1H-benzo[d][1,2,3]triazol-5-yl)-3-(3-(((R)-6-ethyl-2-methyl-2,6,7,9-tetrahydro-8H-[1,4]oxazepino[7,6-f]indazol-8-yl)methyl)-4-methylphenyl)-2,2-dimethylpropanoic acid (Example 66-(b));

3-(3-(((R)-7-chloro-2-ethyl-2,3-dihydronaphtho[2,1-f][1,4]oxazepin-4(5H)-yl)methyl)-4-methylphenyl)-3-(1,4-dimethyl-1H-benzo[d][1,2,3]triazol-5-yl)-2,2-dimethylpropanoic acid (Example 67-(b));

3-(3-(((R)-7-chloro-2-ethyl-2,3-dihydronaphtho[2,3-f][1,4]oxazepin-4(5H)-yl)methyl)-4-methylphenyl)-3-(1,4-dimethyl-1H-benzo[d][1,2,3]triazol-5-yl)-2,2-dimethylpropanoic acid (Example 68-(b));

3-(3-(((R)-10-chloro-2-ethyl-2,3-dihydro-[1,4]oxazepino[7,6-g]quinolin-4(5H)-yl)methyl)-4-methylphenyl)-3-(1,4-dimethyl-1H-benzo[d][1,2,3]triazol-5-yl)-2,2-dimethylpropanoic acid (Example 69);

3-(1,4-dimethyl-1H-benzo[d][1,2,3]triazol-5-yl)-3-(3-(((R)-2-ethyl-10-methoxy-2,3-dihydro-[1,4]oxazepino[7,6-g]quinolin-4(5H)-yl)methyl)-4-methylphenyl)-2,2-dimethylpropanoic acid (Example 70-(b));

3-(1,4-dimethyl-1H-benzo[d][1,2,3]triazol-5-yl)-3-(3-(((R)-2-ethyl-10-methyl-2,3-dihydro-[1,4]oxazepino[7,6-g]quinolin-4(5H)-yl)methyl)-4-methylphenyl)-2,2-dimethylpropanoic acid (Example 71-(b));

3-(1,4-dimethyl-1H-benzo[d][1,2,3]triazol-5-yl)-3-(3-(((R)-2-ethyl-2,3-dihydrothieno[2',3':4,5]benzo[1,2-f][1,4]oxazepin-4(5H)-yl)methyl)-4-methylphenyl)-2,2-dimethylpropanoic acid (Example 72-(b));

3-(1,4-dimethyl-1H-benzo[d][1,2,3]triazol-5-yl)-3-(3-(((R)-2-ethyl-2,3,7,8-tetrahydrothieno[2',3':4,5]benzo[1,2-f][1,4]oxazepin-4(5H)-yl)methyl)-4-methylphenyl)-2,2-dimethylpropanoic acid (Example 73-(b));

3-(1,4-dimethyl-1H-benzo[d][1,2,3]triazol-5-yl)-3-(3-(((R)-2-ethyl-9,9-dioxide-2,3,7,8-tetrahydrothieno[2',3':4,5]benzo[1,2-f][1,4]oxazepin-4(5H)-yl)methyl)-4-methylphenyl)-2,2-dimethylpropanoic acid (Example 74-(b));

3-(1,4-dimethyl-1H-benzo[d][1,2,3]triazol-5-yl)-2,2-dimethyl-3-(4-methyl-3-(((R)-2-methyl-2,3-dihydro-[1,4]oxazepino[7,6-g]quinolin-4 (5H)-yl)methyl)phenyl)propanoic acid (Example 75-(b));

3-(3-((3'H-spiro[cyclopropane-1,2'-[1,4]oxazepino[7,6-g]quinoline]-4' (5'H)-yl)methyl)-4-methylphenyl)-3-(1,4-dimethyl-1H-benzo[d][1,2,3]triazol-5-yl)-2,2-dimethylpropanoic acid (Example 76-(b), Example 85 (Diastereomer 1), and Example 86 (Diastereomer 2));

3-(1,4-dimethyl-1H-benzo[d][1,2,3]triazol-5-yl)-2,2-dimethyl-3-(4-methyl-3-((2-propyl-2,3-dihydro-[1,4]oxazepino[7,6-g]quinolin-4 (5H)-yl)methyl)phenyl)propanoic acid (Example 77-(b) and Example 78-(b));

3-(1,4-dimethyl-1H-benzo[d][1,2,3]triazol-5-yl)-3-(3-(((R)-2-ethyl-2,3-dihydro-[1,4]oxazepino[7,6-g]quinolin-4(5H)-yl)methyl)phenyl)-2,2-dimethylpropanoic acid (Example 79-(b));

3-(4-chloro-3-(((R)-2-ethyl-2,3-dihydro-[1,4]oxazepino[7,6-g]quinolin-4(5H)-yl)methyl)phenyl)-3-(1,4-dimethyl-1H-benzo[d][1,2,3]triazol-5-yl)-2,2-dimethylpropanoic acid (Example 80-(b));

3-(1,4-dimethyl-1H-benzo[d][1,2,3]triazol-5-yl)-3-(3-(((R)-2-ethyl-2,3-dihydro-[1,4]oxazepino[7,6-g]quinolin-4(5H)-yl)methyl)-4-methoxyphenyl)-2,2-dimethylpropanoic acid (Example 81-(b));

3-(3-(((R)-2-ethyl-2,3-dihydro-[1,4]oxazepino[7,6-g]quinolin-4(5H)-yl)methyl)-4-methylphenyl)-2,2-dimethyl-3-(1-methyl-1H-benzo[d][1,2,3]triazol-5-yl)propanoic acid (Example 82-(b));

1-((1,4-dimethyl-1H-benzo[d][1,2,3]triazol-5-yl) (3-(((R)-2-ethyl-2,3-dihydro-[1,4]oxazepino[7,6-g]quinolin-4(5H)-yl)methyl)-4-methylphenyl)methyl)cyclopentane-1-carboxylic acid (Example 83-(b));

1-((1,4-dimethyl-1H-benzo[d][1,2,3]triazol-5-yl) (3-(((R)-2-ethyl-2,3-dihydro-[1,4]oxazepino[7,6-g]quinolin-4(5H)-yl)methyl)-4-methylphenyl)methyl)cyclobutane-1-carboxylic acid (Example 84-(b), Example 87 (Diastereomer 1), and Example 88 (Diastereomer 2)); and 3-(1,4-dimethyl-1H-benzo[d][1,2,3]triazol-5-yl)-3-(3-(((S)-2-ethyl-2,3-dihydro-[1,4]oxazepino[6,7-c]isoquinolin-4(5H)-yl)methyl)-4-methylphenyl)-2,2-dimethylpropanoic acid (Example 89-(b) (Diastereomer 1) and Example 90 (Diastereomer 2))

or a pharmaceutically acceptable salt thereof.

[18] A pharmaceutical composition comprising the compound according to any one of [5] to [17] or a pharmaceutically acceptable salt thereof.

[19] The pharmaceutical composition according to [18] for the prevention, alleviation, and/or treatment of a disease which is improved by the inhibition of Keap1.

[20] The pharmaceutical composition according to [19], wherein the disease which is improved by the inhibition of Keap1 is a renal disease.

Effect of Invention

The compounds represented by general formula (I) or pharmaceutically acceptable salts thereof of the present invention have activities for inhibiting Keap1. Accordingly, the compounds represented by general formula (I) or pharmaceutically acceptable salts thereof are useful as agents for the prevention, alleviation, and/or treatment of various diseases of which symptoms are improved by the inhibition of Keap1 such as renal diseases.

MODE FOR CARRYING OUT THE INVENTION

Embodiments of the present invention are described below. In the present description, "compound represented by general formula (I)" and the like are also conveniently referred to as "Compound (I)" and the like, respectively. Also, the Compound (I) and compounds encompassed by the Compound (I) such as Compound (I-1), the Compounds (II-1) to (II-3), the Compounds (II-1-1) to (II-3-4), the Compound (I-1-1), and Example compounds are also collectively referred to as "Present compound" or "compound of the present invention". Various substituents defined or illustrated below may be optionally selected and combined with each other. Further, embodiments created by optionally selecting and combining each embodiment defined below are also encompassed by the present invention.

The definition of each term used in the present description is as follows.

The term "halogen atom" as described herein refers to a fluorine atom, a chlorine atom, a bromine atom, or an iodine atom.

The term "alkyl group" as described herein refers to a straight or branched saturated hydrocarbon group having 1 to 6 carbon atom(s) ($C_1$-$C_6$) such as 1 to 4 carbon atom(s) ($C_1$-$C_4$), and examples thereof include a methyl group, an ethyl group, a propyl group, an isopropyl group, a n-butyl group, a tert-butyl group, an isobutyl group, a n-pentyl group, a n-hexyl group, and various branched isomers thereof.

The term "alkenyl group" as described herein refers to a straight or branched unsaturated hydrocarbon group having one carbon-carbon double bond and 2 to 6 carbon atoms ($C_2$ to $C_6$) such as 2 to 4 carbon atoms ($C_2$ to $C_4$), and examples thereof include a vinyl group, a propenyl group, an isopropenyl group, a butenyl group, and various branched isomers thereof.

The term "alkynyl group" as described herein refers to a straight or branched unsaturated hydrocarbon group having one carbon-carbon triple bond and 2 to 6 carbon atoms ($C_2$ to $C_6$) such as 2 to 4 carbon atoms ($C_2$ to $C_4$), and examples thereof include an ethynyl group, a 1-propynyl group, a 2-butynyl group, a 4-pentynyl group, a 5-hexynyl group, and various branched isomers thereof.

The term "alkoxy group" as described herein refers to a group in which an oxygen atom is bound to the above straight or branched alkyl group, and examples thereof include a methoxy group, an ethoxy group, a propoxy group, an isopropoxy group, a butoxy group, a tert-butoxy group, an isobutoxy group, and various branched isomers thereof.

The term "cycloalkyl group" as described herein refers to a monocyclic alicyclic saturated hydrocarbon group having 3 to 8 ring-constituting carbon atoms ($C_3$ to $C_0$) such as 3 to 6 ring-constituting carbon atoms ($C_3$ to $C_6$), and examples thereof include a cyclopropyl group, a cyclobutyl group, a cyclopentyl group, a cyclohexyl group, a cycloheptyl group, and a cyclooctyl group.

The term "nonaromatic heterocyclyl group" as described herein refers to a 4 to 8 membered monocyclic nonaromatic heterocyclic group or a 6 to 12 membered bicyclic nonaromatic heterocyclic group comprising 1 to 4 heteroatom(s) selected from an oxygen atom, a sulfur atom, and a nitrogen atom other than carbon atom(s), and examples thereof include an azetidinyl group, an oxetanyl group, a thietanyl group, a pyrrolidinyl group, a piperidinyl group, a piperidino group, a tetrahydrofuryl group, a tetrahydropyranyl group, a tetrahydrothienyl group (i.e., a thiolanyl group), a piperazinyl group, a morpholinyl group, a morpholino group, a perhydroazepinyl group, a perhydroazocinyl group, 6 to 12 membered azabicycloalkyl groups (for example, an azabicyclohexyl group, an azabicycloheptyl group, an azabicyclooctyl group, an azabicyclononyl group, an azabicyclodecyl group, an azabicycloundecyl group, or an azabicyclododecyl group), 6 to 12 membered azabicycloalkenyl groups (for example, an azabicyclohexenyl group, an azabicycloheptenyl group, an azabicyclooctenyl group, an azabicyclononenyl group, an azabicyclodecenyl group, an azabicycloundecenyl group, or an azabicyclododecenyl group), and 6 to 12 membered azaspiroalkyl groups (for example, an azaspirohexyl group, an azaspiroheptyl group, an azaspirooctyl group, an azaspirononyl group, an azaspirodecyl group, an azaspiroundecyl group, or an azaspirododecyl group).

The term "aryl group" as described herein refers to a monocyclic or bicyclic aromatic hydrocarbon group having 6 to 11 ring-constituting carbon atoms (CF to Cn), and examples thereof include monocyclic aryl groups such as a phenyl group; and optionally partially saturated bicyclic aryl groups having 9 to 11 ring-constituting carbon atoms ($C_9$ to $C_{11}$) such as a naphthyl group, a tetrahydronaphthyl group, an indenyl group, and indanyl group.

The term "heteroaryl group" as described herein refers to a 5 to 11 membered monocyclic or bicyclic aromatic heterocyclic group comprising 1 to 4 heteroatom(s) selected from an oxygen atom, a sulfur atom, and a nitrogen atom other than carbon atom(s), and examples thereof include 5 to 6 membered monocyclic heteroaryl groups comprising 1 to 4 heteroatom(s) selected from an oxygen atom, a sulfur atom, and a nitrogen atom other than carbon atom(s) such as a pyrrolyl group, a furyl group, a thienyl group, a pyrazolyl group, an imidazolyl group, an oxazolyl group, an isoxazolyl group, a thiazolyl group, an isothiazolyl group, a thiadiazolyl group, a pyridyl group, a pyrazinyl group, a pyrimidinyl group, a pyridazinyl group, and a triazinyl group; and 8 to 11 membered bicyclic heteroaryl groups comprising 1 to 4 heteroatom(s) selected from an oxygen atom, a sulfur atom, and a nitrogen atom other than carbon atom(s) such as an indolyl group, an indolinyl group, an isoindolinyl group, an indazolyl group, a tetrahydroindazolyl group, a benzofuranyl group, a dihydrobenzofuranyl group, a dihydroisobenzofuranyl group, a benzothiophenyl group, a dihydrobenzothiophenyl group, a dihydroisobenzothiophenyl group, a benzoxazolyl group, a dihydrobenzoxazolyl group, a benzothiazolyl group, a dihydrobenzothiazolyl group, a quinolyl group, a tetrahydroquinolyl group, an isoquinolyl group, a tetrahydroisoquinolyl group, a naphthyridinyl group, a tetrahydronaphthyridinyl group, a quinoxalinyl group, a tetrahydroquinoxalinyl group, and a quinazolinyl group.

The term "monocyclic carbocycle" as described herein refers to a saturated or unsaturated monocyclic hydrocarbon ring such as one formed by combining $R^1$ and $R^2$ or $R^7$ and $R^8$ with the carbon atom to which they are attached in a group represented by $>CR^1R^2$ or $>CR^7R^8$ (wherein $R^1$, $R^2$, $R^7$, and $R^8$ have the same meanings as those described above). The number of ring-constituting carbon atoms is 3 to 8 ($C_3$-$C_8$) such as 3 to 6 ($C_3$-$C_6$).

The term "bicyclic ring" as described herein refers to a saturated or unsaturated 6 to 12 membered, for example 9 to 10 membered bicyclic ring optionally comprising 1 to 4 heteroatom(s) selected from an oxygen atom, a sulfur atom, and a nitrogen atom other than carbon atom(s), and examples thereof include the following rings formed by ring C and ring D.

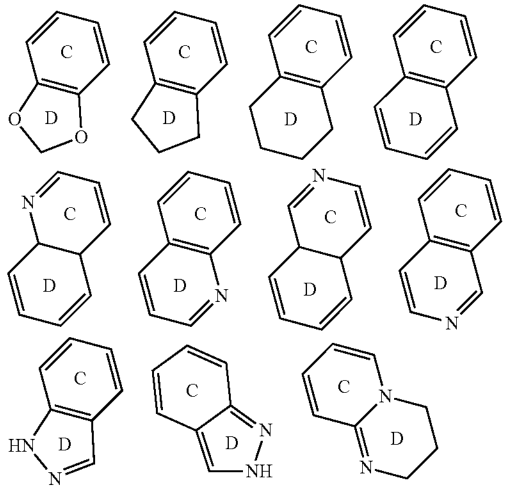

When the bicyclic ring in ring B of the Compound (I) is the above ring formed by ring C and ring D, the ring B is attached to the oxazepine ring at the ring C moiety.

The term "5 to 6 membered carbocycle" as described herein refers to a 5 or 6 membered monocyclic carbocycle, and examples thereof include a ring D in the above "bicyclic ring" which does not comprise a heteroatom.

The term "5 to 6 membered heterocycle" as described herein refers to a 5 or 6 membered monocyclic heterocycle comprising 1 to 4 heteroatom(s) selected from an oxygen atom, a sulfur atom, and a nitrogen atom other than carbon atom(s), and examples thereof include a ring D in the above "bicyclic ring" which comprises heteroatom(s).

Hereinafter, embodiments of each substituent of the Compound (I) are described. Further, embodiments created by optionally selecting and combining each embodiment of the following each substituent are also encompassed by the present invention.

(Embodiment 1) The compound according to any one of the Present compounds or a pharmaceutically acceptable salt thereof, wherein R represents a hydrogen atom or an alkyl group optionally substituted with 1 to 5 substituent(s) independently selected from Group E.

(Embodiment 2) The compound according to any one of the Present compounds or a pharmaceutically acceptable salt thereof, wherein R represents a hydrogen atom or an alkyl group optionally substituted with 1 to 5 halogen atom(s).

(Embodiment 3) The compound according to any one of the Present compounds or a pharmaceutically acceptable salt thereof, wherein R represents a hydrogen atom or an alkyl group.

(Embodiment 4) The compound according to any one of the Present compounds or a pharmaceutically acceptable salt thereof, wherein R represents a hydrogen atom or a methyl group.

(Embodiment 5) The compound according to any one of the Present compounds or a pharmaceutically acceptable salt thereof, wherein R represents a hydrogen atom.

(Embodiment 6) The compound according to any one of the Present compounds or the Embodiments 1 to 5, or a pharmaceutically acceptable salt thereof, wherein $R^1$ and $R^2$ each independently represent a hydrogen atom, an alkyl group optionally substituted with 1 to 5 substituent(s) independently selected from Group E, an alkenyl group optionally substituted with 1 to 5 substituent(s) independently selected from Group E, or an alkynyl group optionally substituted with 1 to 5 substituent(s) independently selected from Group E; or $R^1$ and $R^2$ are combined with the carbon atom to which they are attached to form a monocyclic carbocycle optionally substituted with 1 to 5 substituent(s) independently selected from Group E.

(Embodiment 7) The compound according to any one of the Present compounds or the Embodiments 1 to 5, or a pharmaceutically acceptable salt thereof, wherein $R^1$ and $R^2$ each independently represent a hydrogen atom or an alkyl group optionally substituted with 1 to 5 substituent(s) independently selected from Group E; or $R^1$ and $R^2$ are combined with the carbon atom to which they are attached to form a monocyclic carbocycle optionally substituted with 1 to 5 substituent(s) independently selected from Group E.

(Embodiment 8) The compound according to any one of the Present compounds or the Embodiments 1 to 5, or a pharmaceutically acceptable salt thereof, wherein $R^1$ and $R^2$ each independently represent a hydrogen atom or an alkyl group optionally substituted with 1 to 5 substituent(s) independently selected from Group E; or $R^1$ and $R^2$ are combined with the carbon atom to which they are attached to form a monocyclic carbocycle.

(Embodiment 9) The compound according to any one of the Present compounds or the Embodiments 1 to 5, or a pharmaceutically acceptable salt thereof, wherein $R^1$ and $R^2$ each independently represent a hydrogen atom or an alkyl group optionally substituted with 1 to 5 halogen atom(s); or $R^1$ and $R^2$ are combined with the carbon atom to which they are attached to form a monocyclic carbocycle.

(Embodiment 10) The compound according to any one of the Present compounds or the Embodiments 1 to 5, or a pharmaceutically acceptable salt thereof, wherein $R^1$ and $R^2$ each independently represent a hydrogen atom or an alkyl group; or $R^1$ and $R^2$ are combined with the carbon atom to which they are attached to form a monocyclic carbocycle.

(Embodiment 11) The compound according to any one of the Present compounds or the Embodiments 1 to 5, or a pharmaceutically acceptable salt thereof, wherein $R^1$ and $R^2$ each independently represent a hydrogen atom or an alkyl group.

(Embodiment 12) The compound according to any one of the Present compounds or the Embodiments 1 to 5, or a pharmaceutically acceptable salt thereof, wherein $R^1$ and $R^2$ each independently represent an alkyl group.

(Embodiment 13) The compound according to any one of the Present compounds or the Embodiments 1 to 5, or a pharmaceutically acceptable salt thereof, wherein $R^1$ and $R^2$ each represent a methyl group; or $R^1$ and $R^2$ are combined with the carbon atom to which they are attached to form a cyclobutane ring or a cyclopentane ring.

(Embodiment 14) The compound according to any one of the Present compounds or the Embodiments 1 to 5, or a pharmaceutically acceptable salt thereof, wherein $R^1$ and $R^2$ each represent a methyl group.

(Embodiment 15) The compound according to any one of the Present compounds or the Embodiments 1 to 14, or a pharmaceutically acceptable salt thereof, wherein $R^3$, $R^4$, and $R^6$ each independently represent a hydrogen atom, a halogen atom, an alkyl group optionally substituted with 1 to 5 substituent(s) independently selected from Group E, an alkenyl group optionally substituted with 1 to 5 substituent(s) independently selected from Group E, an alkynyl group optionally substituted with 1 to 5 substituent(s) independently selected from Group E, an alkoxy group optionally substituted with 1 to 5 substituent(s) independently selected from Group E, a cycloalkyl group optionally substituted with 1 to 5 substituent(s) independently selected from Group E, a nonaromatic heterocyclyl group optionally substituted with 1 to 5 substituent(s) independently selected from Group E, an aryl group optionally substituted with 1 to 5 substituent(s) independently selected from Group E, a heteroaryl group optionally substituted with 1 to 5 substituent(s) independently selected from Group E, or a cyano group.

(Embodiment 16) The compound according to any one of the Present compounds or the Embodiments 1 to 14, or a pharmaceutically acceptable salt thereof, wherein $R^3$, $R^4$, and $R^6$ each independently represent a hydrogen atom, a halogen atom, an alkyl group optionally substituted with 1 to 5 substituent(s) independently selected from Group E, or an alkoxy group optionally substituted with 1 to 5 substituent(s) independently selected from Group E.

(Embodiment 17) The compound according to any one of the Present compounds or the Embodiments 1 to 14, or a pharmaceutically acceptable salt thereof, wherein $R^3$, $R^4$, and $R^6$ each independently represent a hydrogen atom, a halogen atom, an alkyl group optionally substituted with 1 to 5 halogen atom(s), or an alkoxy group optionally substituted with 1 to 5 halogen atom(s).

(Embodiment 18) The compound according to any one of the Present compounds or the Embodiments 1 to 14, or a pharmaceutically acceptable salt thereof, wherein $R^3$, $R^4$, and $R^6$ each independently represent a hydrogen atom, a halogen atom, an alkyl group, or an alkoxy group.

(Embodiment 19) The compound according to any one of the Present compounds or the Embodiments 1 to 14, or a pharmaceutically acceptable salt thereof, wherein $R^3$ represents a hydrogen atom, a halogen atom, an alkyl group, or an alkoxy group; and $R^4$ and $R^6$ each independently represent a hydrogen atom, an alkyl group, or an alkoxy group.

(Embodiment 20) The compound according to any one of the Present compounds or the Embodiments 1 to 14, or a pharmaceutically acceptable salt thereof, wherein $R^3$ represents a hydrogen atom, a halogen atom, an alkyl group, or an alkoxy group;

$R^4$ represents a hydrogen atom or an alkyl group; and $R^6$ represents a hydrogen atom.

(Embodiment 21) The compound according to any one of the Present compounds or the Embodiments 1 to 14, or a pharmaceutically acceptable salt thereof, wherein $R^3$ represents an alkyl group;

$R^4$ represents an alkyl group; and $R^6$ represents a hydrogen atom.

(Embodiment 22) The compound according to any one of the Present compounds or the Embodiments 1 to 14, or a pharmaceutically acceptable salt thereof, wherein $R^3$ represents a methyl group;

$R^4$ represents a methyl group; and $R^6$ represents a hydrogen atom.

(Embodiment 23) The compound according to any one of the Present compounds or the Embodiments 1 to 22, or a pharmaceutically acceptable salt thereof, wherein $R^5$ represents (i) a hydrogen atom, or (ii) an alkyl group optionally substituted with 1 to 5 substituent(s) independently selected from the group consisting of a halogen atom, a hydroxy group, a cycloalkyl group optionally substituted with 1 to 5 substituent(s) independently selected from Group E, a phenyl group optionally substituted with 1 to 5 substituent(s) independently selected from Group E, and an alkoxy group optionally substituted with 1 to 5 substituent(s) independently selected from Group E.

(Embodiment 24) The compound according to any one of the Present compounds or the Embodiments 1 to 22, or a pharmaceutically acceptable salt thereof, wherein $R^5$ represents (i) a hydrogen atom, or (ii) an alkyl group optionally substituted with 1 to 5 substituent(s) independently selected from the group consisting of a halogen atom, a hydroxy group, a phenyl group optionally substituted with 1 to 5 substituent(s) independently selected from Group E, and an alkoxy group optionally substituted with 1 to 5 substituent(s) independently selected from Group E.

(Embodiment 25) The compound according to any one of the Present compounds or the Embodiments 1 to 22, or a pharmaceutically acceptable salt thereof, wherein $R^5$ represents (i) a hydrogen atom, or (ii) an alkyl group optionally substituted with 1 to 5 substituent(s) independently selected from the group consisting of a halogen atom, a hydroxy group, a phenyl group, and an alkoxy group.

(Embodiment 26) The compound according to any one of the Present compounds or the Embodiments 1 to 22, or a pharmaceutically acceptable salt thereof, wherein $R^5$ represents a hydrogen atom or an alkyl group.

(Embodiment 27) The compound according to any one of the Present compounds or the Embodiments 1 to 22, or a pharmaceutically acceptable salt thereof, wherein $R^5$ represents an alkyl group.

(Embodiment 28) The compound according to any one of the Present compounds or the Embodiments 1 to 22, or a pharmaceutically acceptable salt thereof, wherein $R^5$ represents a methyl group or an ethyl group.

(Embodiment 29) The compound according to any one of the Present compounds or the Embodiments 1 to 28, or a pharmaceutically acceptable salt thereof, wherein $R^7$ and $R^8$ each independently represent a hydrogen atom, an alkyl group optionally substituted with 1 to 5 substituent(s) independently selected from Group E, an alkenyl group optionally substituted with 1 to 5 substituent(s) independently selected from Group E, or an alkynyl group optionally substituted with 1 to 5 substituent(s) independently selected from Group E; or $R^7$ and $R^8$ are combined with the carbon atom to which they are attached to form a monocyclic carbocycle optionally substituted with 1 to 5 substituent(s) independently selected from Group E.

(Embodiment 30) The compound according to any one of the Present compounds or the Embodiments 1 to 28, or a pharmaceutically acceptable salt thereof, wherein $R^3$ and $R^8$ each independently represent a hydrogen atom or an alkyl group optionally substituted with 1 to 5 substituent(s) independently selected from Group E; or $R^2$ and $R^8$ are combined with the carbon atom to which they are attached to form a monocyclic carbocycle optionally substituted with 1 to 5 substituent(s) independently selected from Group E.

(Embodiment 31) The compound according to any one of the Present compounds or the Embodiments 1 to 28, or a pharmaceutically acceptable salt thereof, wherein $R^7$ and $R^8$ each independently represent a hydrogen atom or an alkyl group; or $R^7$ and $R^8$ are combined with the carbon atom to which they are attached to form a monocyclic carbocycle optionally substituted with 1 to 5 substituent(s) independently selected from Group E.

(Embodiment 32) The compound according to any one of the Present compounds or the Embodiments 1 to 28, or a pharmaceutically acceptable salt thereof, wherein $R^7$ and $R^8$ each independently represent a hydrogen atom or an alkyl group; or $R^7$ and $R^8$ are combined with the carbon atom to which they are attached to form a monocyclic carbocycle.

(Embodiment 33) The compound according to any one of the Present compounds or the Embodiments 1 to 28, or a pharmaceutically acceptable salt thereof, wherein $R^7$ and $R^8$ each independently represent a hydrogen atom or an alkyl group.

(Embodiment 34) The compound according to any one of the Present compounds or the Embodiments 1 to 28, or a pharmaceutically acceptable salt thereof, wherein $R^7$ and $R^8$ each independently represent a hydrogen atom, a methyl group, an ethyl group, or a propyl group; or $R^7$ and $R^8$ are combined with the carbon atom to which they are attached to form a cyclopropane ring.

(Embodiment 35) The compound according to any one of the Present compounds or the Embodiments 1 to 28, or a pharmaceutically acceptable salt thereof, wherein $R^7$ and $R^8$ each independently represent a hydrogen atom, a methyl group, or an ethyl group.

(Embodiment 36) The compound according to any one of the Present compounds or the Embodiments 1 to 35, or a pharmaceutically acceptable salt thereof, wherein ring B represents a bicyclic ring optionally substituted with 1 to 5 substituent(s) independently selected from the group consisting of a halogen atom, an alkyl group optionally substituted with 1 to 5 substituent(s) independently selected from Group E, an alkenyl group optionally substituted with 1 to 5 substituent(s) independently selected from Group E, an alkynyl group optionally substituted with 1 to 5 substituent(s) independently selected from Group E, an alkoxy group optionally substituted with 1 to 5 substituent(s) independently selected from Group E, a cycloalkyl group optionally substituted with 1 to 5 substituent(s) independently selected from Group E, a nonaromatic heterocyclyl group optionally substituted with 1 to 5 substituent(s) independently selected from Group E, an aryl group optionally substituted with 1 to 5 substituent(s) independently selected from Group E, a heteroaryl group optionally substituted with 1 to 5 substituent(s) independently selected from Group E, and a cyano group.

(Embodiment 37) The compound according to any one of the Present compounds or the Embodiments 1 to 35, or a pharmaceutically acceptable salt thereof, wherein ring B represents a bicyclic ring optionally substituted with 1 to 5 substituent(s) independently selected from the group consisting of a halogen atom, an alkyl group optionally substituted with 1 to 5 substituent(s) independently selected from Group E, an alkoxy group optionally substituted with 1 to 5 substituent(s) independently selected from Group E, and a cyano group.

(Embodiment 38) The compound according to any one of the Present compounds or the Embodiments 1 to 37, or a pharmaceutically acceptable salt thereof, wherein $X^1$ and $X^2$ each independently represent $CR^9$ or a nitrogen atom.

(Embodiment 39) The compound according to any one of the Present compounds or the Embodiments 1 to 37, or a pharmaceutically acceptable salt thereof, wherein $X^1$ and $X^2$ each independently represent $CR^9$.

(Embodiment 40) The compound according to any one of the Present compounds or the Embodiments 1 to 37, or a pharmaceutically acceptable salt thereof, wherein $X^1$ and $X^2$ each represent a nitrogen atom.

(Embodiment 41) The compound according to any one of the Present compounds or the Embodiments 1 to 37, or a pharmaceutically acceptable salt thereof, wherein $X^1$ represents $CR^9$; and $X^2$ represents a nitrogen atom.

(Embodiment 42) The compound according to any one of the Present compounds or the Embodiments 1 to 37, or a pharmaceutically acceptable salt thereof, wherein $X^1$ represents a nitrogen atom; and $X^2$ represents $CR^9$.

(Embodiment 43) The compound according to any one of the Present compounds or the Embodiments 1 to 42, or a pharmaceutically acceptable salt thereof, wherein $R^9$ each independently represents a hydrogen atom, a halogen atom, an alkyl group optionally substituted with 1 to 5 substituent(s) independently selected from Group E, an alkoxy group optionally substituted with 1 to 5 substituent(s) independently selected from Group E, or a cyano group.

(Embodiment 44) The compound according to any one of the Present compounds or the Embodiments 1 to 42, or a pharmaceutically acceptable salt thereof, wherein $R^9$ each independently represents a hydrogen atom, a halogen atom, or an alkyl group optionally substituted with 1 to 5 halogen atom(s).

(Embodiment 45) The compound according to any one of the Present compounds or the Embodiments 1 to 42, or a pharmaceutically acceptable salt thereof, wherein $R^9$ each independently represents a hydrogen atom, a halogen atom, or an alkyl group.

(Embodiment 46) The compound according to any one of the Present compounds or the Embodiments 1 to 42, or a pharmaceutically acceptable salt thereof, wherein $R^9$ each independently represents a hydrogen atom or a halogen atom.

(Embodiment 47) The compound according to any one of the Present compounds or the Embodiments 1 to 42, or a pharmaceutically acceptable salt thereof, wherein $R^9$ each independently represents a hydrogen atom, a fluorine atom, or a chlorine atom.

(Embodiment 48) The compound according to any one of the Present compounds or the Embodiments 1 to 42, or a pharmaceutically acceptable salt thereof, wherein $R^9$ each independently represents a hydrogen atom or a fluorine atom.

(Embodiment 49) The compound according to any one of the Present compounds or the Embodiments 1 to 42, or a pharmaceutically acceptable salt thereof, wherein $R^9$ each represents a hydrogen atom.

(Embodiment 50) The compound according to any one of the Present compounds or the Embodiments 1 to 49, or a pharmaceutically acceptable salt thereof, wherein $Y^1$, $Y^2$, $Y^3$, and $Y^4$ each independently represent $CR^{10}$ or a nitrogen atom.

(Embodiment 51) The compound according to any one of the Present compounds or the Embodiments 1 to 49, or a pharmaceutically acceptable salt thereof, wherein $Y^1$, $Y^2$, $Y^3$, and $Y^4$ each independently represent $CR^{10}$.

(Embodiment 52) The compound according to any one of the Present compounds or the Embodiments 1 to 49, or a pharmaceutically acceptable salt thereof, wherein any one of $Y^1$, $Y^2$, $Y^3$, and $Y^4$ represents a nitrogen atom, and the other three each independently represent $CR^{10}$.

(Embodiment 53) The compound according to any one of the Present compounds or the Embodiments 1 to 49, or a pharmaceutically acceptable salt thereof, wherein any two of $Y^1$, $Y^2$, $Y^3$, and $Y^4$ each represent a nitrogen atom, and the other two each independently represent $CR^{10}$.

(Embodiment 54) The compound according to any one of the Present compounds or the Embodiments 1 to 49, or a pharmaceutically acceptable salt thereof, wherein any three of $Y^1$, $Y^2$, $Y^3$, and $Y^4$ each represent a nitrogen atom, and the other one represents $CR^{10}$.

(Embodiment 55) The compound according to any one of the Present compounds or the Embodiments 1 to 49, or a pharmaceutically acceptable salt thereof, wherein $Y^1$, $Y^2$, $Y^3$, and $Y^4$ each represent a nitrogen atom.

(Embodiment 56) The compound according to any one of the Present compounds or the Embodiments 1 to 49, or a pharmaceutically acceptable salt thereof, wherein $Y^1$ and $Y^2$ each independently represent $CR^{10}$ or a nitrogen atom.

(Embodiment 57) The compound according to any one of the Present compounds or the Embodiments 1 to 49, or a pharmaceutically acceptable salt thereof, wherein $Y^1$ and $Y^2$ each independently represent $CR^{11}$.

(Embodiment 58) The compound according to any one of the Present compounds or the Embodiments 1 to 49, or a pharmaceutically acceptable salt thereof, wherein any one of $Y^1$ and $Y^2$ represents a nitrogen atom, and the other one represents $CR^{10}$.

(Embodiment 59) The compound according to any one of the Present compounds or the Embodiments 1 to 49, or a pharmaceutically acceptable salt thereof, wherein $Y^1$ and $Y^2$ each represent a nitrogen atom.

(Embodiment 60) The compound according to any one of the Present compounds or the Embodiments 1 to 59, or a pharmaceutically acceptable salt thereof, wherein $R^{10}$ each independently represents a hydrogen atom, a halogen atom, an alkyl group optionally substituted with 1 to 5 substituent(s) independently selected from Group E, an alkoxy group optionally substituted with 1 to 5 substituent(s) independently selected from Group E, or a cyano group.

(Embodiment 61) The compound according to any one of the Present compounds or the Embodiments 1 to 59, or a pharmaceutically acceptable salt thereof, wherein $R^{10}$ each independently represents a hydrogen atom, a halogen atom, an alkyl group optionally substituted with 1 to 5 halogen atom(s), or an alkoxy group optionally substituted with 1 to 5 halogen atom(s).

(Embodiment 62) The compound according to any one of the Present compounds or the Embodiments 1 to 59, or a pharmaceutically acceptable salt thereof, wherein $R^{10}$ each independently represents a hydrogen atom, a halogen atom, or an alkyl group optionally substituted with 1 to 5 halogen atom(s).

(Embodiment 63) The compound according to any one of the Present compounds or the Embodiments 1 to 59, or a pharmaceutically acceptable salt thereof, wherein $R^{10}$ each independently represents a hydrogen atom, a halogen atom, an alkyl group, or an alkoxy group.

(Embodiment 64) The compound according to any one of the Present compounds or the Embodiments 1 to 59, or a pharmaceutically acceptable salt thereof, wherein $R^{10}$ each independently represents a hydrogen atom, a halogen atom, or an alkyl group.

(Embodiment 65) The compound according to any one of the Present compounds or the Embodiments 1 to 59, or a pharmaceutically acceptable salt thereof, wherein $R^{10}$ each independently represents a hydrogen atom, a fluorine atom, a chlorine atom, a methyl group, or a methoxy group.

(Embodiment 66) The compound according to any one of the Present compounds or the Embodiments 1 to 59, or a pharmaceutically acceptable salt thereof, wherein $R^{10}$ each independently represents a hydrogen atom, a fluorine atom, or a methyl group.

(Embodiment 67) The compound according to any one of the Present compounds or the Embodiments 1 to 59, or a pharmaceutically acceptable salt thereof, wherein $R^{10}$ each represents a hydrogen atom.

(Embodiment 68) The compound according to any one of the Present compounds or the Embodiments 1 to 67, or a pharmaceutically acceptable salt thereof, wherein $Q^1$ and $Q^2$ each independently represent $CR^{11}R^{12}$, $NR^{13}$, an oxygen atom, a sulfur atom, SO, or $SO_2$.

(Embodiment 69) The compound according to any one of the Present compounds or the Embodiments 1 to 67, or a pharmaceutically acceptable salt thereof, wherein $Q^1$ and $Q^2$ each independently represent $CR^{11}R^{12}$, $NR^{13}$, or an oxygen atom.

(Embodiment 70) The compound according to any one of the Present compounds or the Embodiments 1 to 67, or a pharmaceutically acceptable salt thereof, wherein $Q^1$ and $Q^2$ each independently represent $CR^{11}R^{12}$.

(Embodiment 71) The compound according to any one of the Present compounds or the Embodiments 1 to 67, or a pharmaceutically acceptable salt thereof, wherein $Q^1$ and $Q^2$ each represent an oxygen atom.

(Embodiment 72) The compound according to any one of the Present compounds or the Embodiments 1 to 71, or a pharmaceutically acceptable salt thereof, wherein $R^{11}$ and $R^{12}$ each independently represent a hydrogen atom, a halogen atom, or an alkyl group.

(Embodiment 73) The compound according to any one of the Present compounds or the Embodiments 1 to 71, or a pharmaceutically acceptable salt thereof, wherein $R^{11}$ and $R^{12}$ each independently represent a hydrogen atom or an alkyl group.

(Embodiment 74) The compound according to any one of the Present compounds or the Embodiments 1 to 71, or a pharmaceutically acceptable salt thereof, wherein $R^{11}$ and $R^{12}$ each independently represent a hydrogen atom or a methyl group.

(Embodiment 75) The compound according to any one of the Present compounds or the Embodiments 1 to 71, or a pharmaceutically acceptable salt thereof, wherein $R^{11}$ and $R^{12}$ each represent a hydrogen atom.

(Embodiment 76) The compound according to any one of the Present compounds or the Embodiments 1 to 75, or a pharmaceutically acceptable salt thereof, wherein $R^{13}$ each independently represents a hydrogen atom or an alkyl group.

(Embodiment 77) The compound according to any one of the Present compounds or the Embodiments 1 to 75, or a pharmaceutically acceptable salt thereof, wherein $R^{13}$ each independently represents a hydrogen atom or a methyl group.

(Embodiment 78) The compound according to any one of the Present compounds or the Embodiments 1 to 75, or a pharmaceutically acceptable salt thereof, wherein $R^{13}$ each represents a hydrogen atom.

(Embodiment 79) The compound according to any one of the Present compounds or the Embodiments 1 to 78, or a pharmaceutically acceptable salt thereof, wherein Z represents $NR^{14}$, an oxygen atom, or a sulfur atom.

(Embodiment 80) The compound according to any one of the Present compounds or the Embodiments 1 to 78, or a pharmaceutically acceptable salt thereof, wherein Z represents $NR^{14}$.

(Embodiment 81) The compound according to any one of the Present compounds or the Embodiments 1 to 80, or a pharmaceutically acceptable salt thereof, wherein $R^{14}$ represents a hydrogen atom or an alkyl group.

(Embodiment 82) The compound according to any one of the Present compounds or the Embodiments 1 to 80, or a pharmaceutically acceptable salt thereof, wherein $R^{14}$ represents a hydrogen atom or a methyl group.

(Embodiment 83) The compound according to any one of the Present compounds or the Embodiments 1 to 80, or a pharmaceutically acceptable salt thereof, wherein $R^{14}$ represents a hydrogen atom.

(Embodiment 84) The compound according to any one of the Present compounds or the Embodiments 1 to 83, or a pharmaceutically acceptable salt thereof, wherein $Q^3$ represents $(CU^1U^2)_n$;
$U^1$ and $U^2$ each independently represent a hydrogen atom, a halogen atom, or an alkyl group; and
n represents 1, 2, or 3.

(Embodiment 85) The compound according to any one of the Present compounds or the Embodiments 1 to 83, or a pharmaceutically acceptable salt thereof, wherein $Q^3$ represents $(CU^1U^2)_n$;
$U^1$ and $U^2$ each independently represent a hydrogen atom, a halogen atom, or an alkyl group; and
n represents 1 or 2.

(Embodiment 86) The compound according to any one of the Present compounds or the Embodiments 1 to 83, or a pharmaceutically acceptable salt thereof, wherein $Q^3$ represents $(CU^1U^2)_n$;
$U^1$ and $U^2$ each independently represent a hydrogen atom, a halogen atom, or an alkyl group; and
n represents 1.

(Embodiment 87) The compound according to any one of the Present compounds or the Embodiments 1 to 83, or a pharmaceutically acceptable salt thereof, wherein $Q^3$ represents $(CU^1U^2)_n$;
$U^1$ and $U^2$ each independently represent a hydrogen atom, a fluorine atom, or a methyl group; and
n represents 1.

(Embodiment 88) The compound according to any one of the Present compounds or the Embodiments 1 to 83, or a pharmaceutically acceptable salt thereof, wherein $Q^3$ represents $(CU^1U^2)_n$;
$U^1$ and $U^2$ each represent a hydrogen atom; and
n represents 1.

(Embodiment 89) The compound according to any one of the Present compounds or the Embodiments 1 to 83, or a pharmaceutically acceptable salt thereof, wherein $Q^3$ represents $(CU^1U^2)_n$;
$U^1$ and $U^2$ each represent a fluorine atom; and
n represents 1.

(Embodiment 90) The compound according to any one of the Present compounds or the Embodiments 1 to 83, or a pharmaceutically acceptable salt thereof, wherein $Q^3$ represents $(CU^1U^2)$;
$U^1$ and $U^2$ each represent a methyl group; and
n represents 1.

(Embodiment 91) The compound according to any one of the Present compounds or the Embodiments 1 to 90, or a pharmaceutically acceptable salt thereof, wherein ring D represents a 5 to 6 membered carbocycle or a 5 to 6 membered heterocycle, each of which is optionally substituted with 1 to 5 substituent(s) independently selected from the group consisting of a halogen atom, an alkyl group optionally substituted with 1 to 5 substituent(s) independently selected from Group E, an alkoxy group optionally substituted with 1 to 5 substituent(s) independently selected from Group E, and a cyano group.

(Embodiment 92) The compound according to any one of the Present compounds or the Embodiments 1 to 90, or a pharmaceutically acceptable salt thereof, wherein ring D represents a 5 to 6 membered carbocycle or a 5 to 6 membered heterocycle, each of which is optionally substituted with 1 to 5 substituent(s) independently selected from the group consisting of a halogen atom and an alkyl group optionally substituted with 1 to 5 halogen atom(s).

(Embodiment 93) The compound according to any one of the Present compounds or the Embodiments 1 to 90, or a pharmaceutically acceptable salt thereof, wherein ring D represents a 5 to 6 membered carbocycle or a 5 to 6 membered heterocycle, each of which is optionally substituted with 1 to 5 substituent(s) independently selected from the group consisting of a halogen atom and an alkyl group.

(Embodiment 94) The compound according to any one of the Present compounds or the Embodiments 1 to 90, or a pharmaceutically acceptable salt thereof, wherein ring D represents a 5 to 6 membered carbocycle or a 5 to 6 membered heterocycle, each of which is optionally substituted with 1 to 5 substituent(s) independently selected from the group consisting of a fluorine atom and a methyl group.

(Embodiment 95) A compound having a structure represented by the following general formula (I-1):

(I-1)

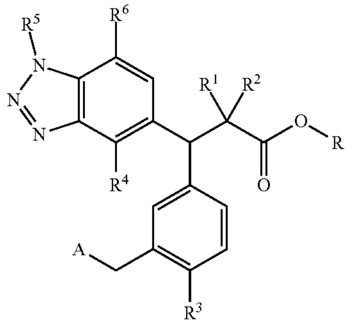

[wherein the symbols have the same meanings as the definitions in any one of the Present compounds or the Embodiments 1 to 94]

or a pharmaceutically acceptable salt thereof.

(Embodiment 96) The compound according to the Compound (I) or the Compound (1-1), or a pharmaceutically acceptable salt thereof, wherein R represents a hydrogen atom or an alkyl group;
$R^1$ and $R^2$ each independently represent a hydrogen atom or an alkyl group;
or $R^1$ and $R^2$ are combined with the carbon atom to which they are attached to form a monocyclic carbocycle;

$R^3$ represents a hydrogen atom, a halogen atom, an alkyl group, or an alkoxy group;

$R^4$ and $R^6$ each independently represent a hydrogen atom, an alkyl group, or an alkoxy group;

$R^5$ represents a hydrogen atom or an alkyl group; and

A has the same meaning as the definition in any one of the Present compounds or the Embodiments 1 to 94.

(Embodiment 97) The compound according to the Compound (I) or the Compound (I-1), or a pharmaceutically acceptable salt thereof, wherein R represents a hydrogen atom;

$R^1$ and $R^2$ each independently represent a hydrogen atom or an alkyl group;

or $R^1$ and $R^2$ are combined with the carbon atom to which they are attached to form a monocyclic carbocycle;

$R^3$ represents an alkyl group;

$R^4$ represents an alkyl group;

$R^5$ represents an alkyl group;

$R^6$ represents a hydrogen atom; and

A has the same meaning as the definition in any one of the Present compounds or the Embodiments 1 to 94.

(Embodiment 98) The compound according to the Compound (I) or the Compound (I-1), or a pharmaceutically acceptable salt thereof, wherein R represents a hydrogen atom;

$R^1$ and $R^2$ each independently represent a hydrogen atom or an alkyl group;

$R^3$ represents an alkyl group;

$R^4$ represents an alkyl group;

$R^5$ represents an alkyl group;

$R^6$ represents a hydrogen atom; and

A has the same meaning as the definition in any one of the Present compounds or the Embodiments 1 to 94.

(Embodiment 99) The compound according to any one of the Present compounds or the Embodiments 1 to 98, or a pharmaceutically acceptable salt thereof, wherein A has a structure represented by any one of the following formulae (II-1) to (II-3):

(II-1)

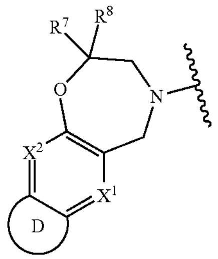

(II-2)

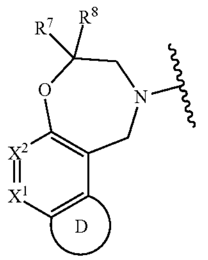

-continued (II-3)

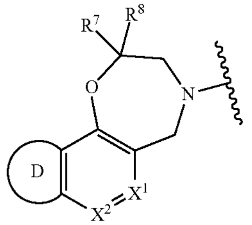

[wherein the symbols have the same meanings as the definitions in any one of the Present compounds or the Embodiments 1 to 94]

or a pharmaceutically acceptable salt thereof.

(Embodiment 100) A compound or a pharmaceutically acceptable salt thereof, wherein in the structure represented by any one of the formulae (II-1) to (II-3), $R^7$ and $R^8$ each independently represent a hydrogen atom or an alkyl group;

or $R^7$ and $R^8$ are combined with the carbon atom to which they are attached to form a monocyclic carbocycle optionally substituted with 1 to 5 substituent(s) independently selected from Group E;

$X^1$ and $X^2$ each independently represent $CR^9$ or a nitrogen atom;

$R^9$ each independently represents a hydrogen atom, a halogen atom, an alkyl group optionally substituted with 1 to 5 substituent(s) independently selected from Group E, an alkoxy group optionally substituted with 1 to 5 substituent(s) independently selected from Group E, or a cyano group; and ring D represents a 5 to 6 membered carbocycle or a 5 to 6 membered heterocycle, each of which is optionally substituted with 1 to 5 substituent(s) independently selected from the group consisting of a halogen atom, an alkyl group optionally substituted with 1 to 5 substituent(s) independently selected from Group E, an alkoxy group optionally substituted with 1 to 5 substituent(s) independently selected from Group E, and a cyano group.

(Embodiment 101) The compound according to any one of the Present compounds or the Embodiments 1 to 100, or a pharmaceutically acceptable salt thereof, wherein A has a structure represented by any one of the following formulae (II-1-1) to (II-3-4):

(II-1-1)

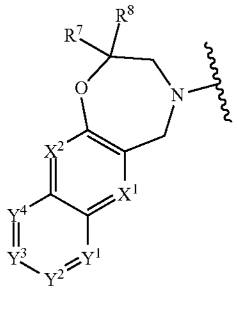

-continued
(II-1-2)
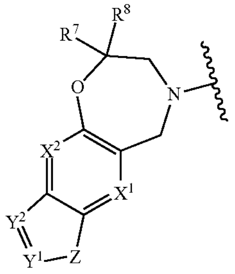
(II-1-3)
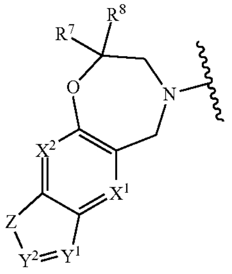
(II-1-4)
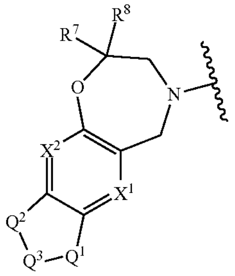
(II-2-1)
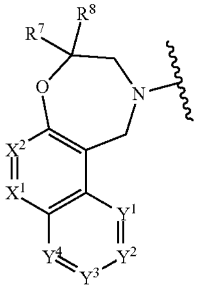
(II-2-2)
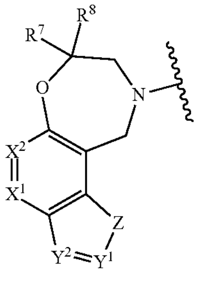
-continued
(II-2-3)
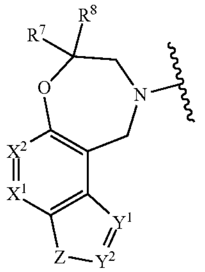
(II-2-4)
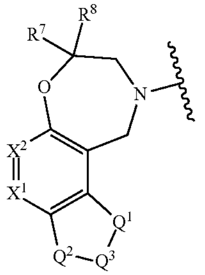
(II-3-1)
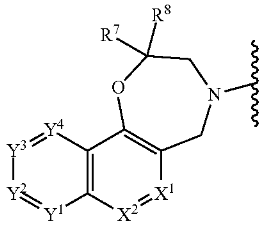
(II-3-2)
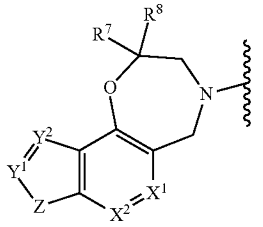
(II-3-3)
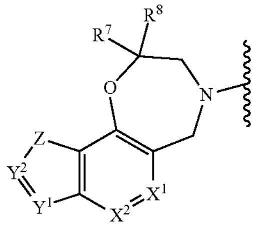
(II-3-4)
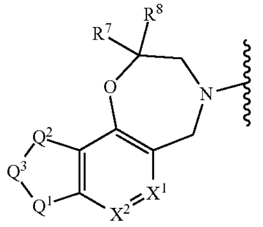
[wherein the symbols have the same meanings as the definitions in any one of the Present compounds or the Embodiments 1 to 100].
(Embodiment 102) The compound according to any one of the Present compounds or the Embodiments 1 to 100, or a pharmaceutically acceptable salt thereof, wherein A has a structure represented by any one of the following formula (II-1-1) or (II-3-1):

(II-1-1)

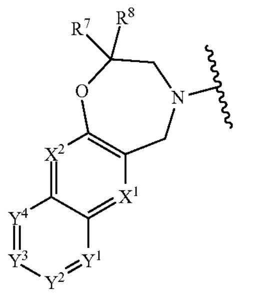

(II-3-1)

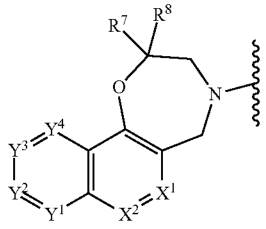

[wherein the symbols have the same meanings as the definitions in any one of the Present compounds or the Embodiments 1 to 100].

(Embodiment 103) A compound or a pharmaceutically acceptable salt thereof, wherein in the structure represented by any one of the formulae (II-1-1) to (II-3-4), $R^7$ and $R^8$ each independently represent a hydrogen atom or an alkyl group;

or $R^7$ and $R^8$ are combined with the carbon atom to which they are attached to form a monocyclic carbocycle optionally substituted with 1 to 5 substituent(s) independently selected from Group E;

$X^1$ and $X^2$ each independently represent $CR^9$ or a nitrogen atom;

$Y^1$, $Y^2$, $Y^3$, and $Y^4$ each independently represent $CR^{10}$ or a nitrogen atom;

$R^9$ and $R^{10}$ each independently represent a hydrogen atom, a halogen atom, an alkyl group optionally substituted with 1 to 5 substituent(s) independently selected from Group E, an alkoxy group optionally substituted with 1 to 5 substituent(s) independently selected from Group E, or a cyano group;

$Q^1$ and $Q^2$ each independently represent $CR^{11}R^{12}$, $NR^{13}$, an oxygen atom, a sulfur atom, SO, or $SO_2$;

$R^{11}$ and $R^{12}$ each independently represent a hydrogen atom, a halogen atom, or an alkyl group;

$R^{13}$ each independently represents a hydrogen atom or an alkyl group;

Z represents $NR^{14}$, an oxygen atom, or a sulfur atom;

$R^{14}$ represents a hydrogen atom or an alkyl group;

$Q^3$ represents $(CU^1U^2)$;

$U^1$ and $U^2$ each independently represent a hydrogen atom, a halogen atom, or an alkyl group; and n represents 1, 2, or 3.

(Embodiment 104) The compound according to the Embodiment 103 or a pharmaceutically acceptable salt thereof, wherein $Q^1$ and $Q^2$ each independently represent $CR^{11}R^{12}$, $NR^{13}$, or an oxygen atom.

(Embodiment 105) The compound according to any one of the Present compounds or the Embodiments 1 to 104, or a pharmaceutically acceptable salt thereof, wherein A has a structure represented by the following formula (II-1-1):

(II-1-1)

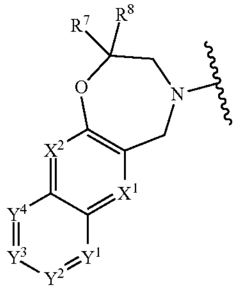

[wherein the symbols have the same meanings as the definitions in any one of the Present compounds or the Embodiments 1 to 104].

(Embodiment 106) A compound or a pharmaceutically acceptable salt thereof, wherein in the structure represented by the formula (II-1-1), $R^7$ and $R^8$ each independently represent a hydrogen atom or an alkyl group;

or $R^7$ and $R^8$ are combined with the carbon atom to which they are attached to form a monocyclic carbocycle;

$X^1$ and $X^2$ each independently represent $CR^9$;

any one of $Y^1$, $Y^2$, $Y^3$, and $Y^4$ represents a nitrogen atom, and the other three each independently represent $CR^{10}$;

$R^9$ each represents a hydrogen atom; and $R^{10}$ each independently represents a hydrogen atom, a halogen atom, an alkyl group, or an alkoxy group.

(Embodiment 107) The compound according to the Embodiment 106 or a pharmaceutically acceptable salt thereof, wherein $R^7$ and $R^8$ each independently represent a hydrogen atom or an alkyl group; and $R^{10}$ each independently represents a hydrogen atom, a halogen atom, or an alkyl group.

(Embodiment 108) The compound according to any one of the Present compounds or the Embodiments 1 to 104, or a pharmaceutically acceptable salt thereof, wherein A has a structure represented by the following formula (II-3-1):

(II-3-1)

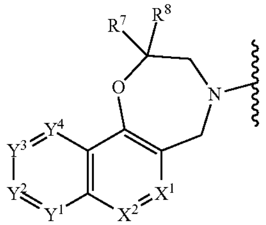

[wherein the symbols have the same meanings as the definitions in any one of the Present compounds or the Embodiments 1 to 104].

(Embodiment 109) A compound or a pharmaceutically acceptable salt thereof, wherein in the structure represented by the formula (II-3-1), $R^7$ and $R^8$ each independently represent a hydrogen atom or an alkyl group;

any one of $X^1$ and $X^2$ represents a nitrogen atom, and the other one represents $CR^9$;

$Y^1$, $Y^2$, $Y^3$, and $Y^4$ each independently represent $CR^{10}$;

$R^9$ each represents a hydrogen atom; and $R^{10}$ each independently represents a hydrogen atom, a halogen atom, or an alkyl group.

(Embodiment 110) A compound having a structure represented by the following general formula (I-1-1):

(I-1-1)

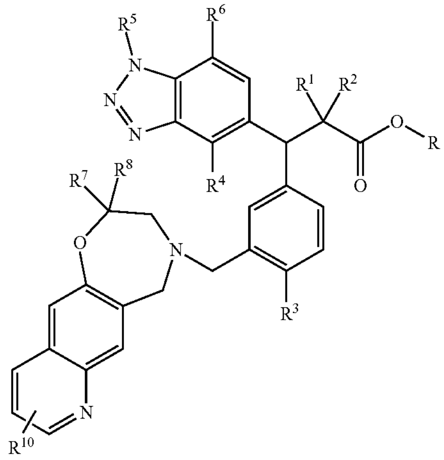

[wherein the symbols have the same meanings as the definitions in any one of the Present compounds or the Embodiments 1 to 94]

or a pharmaceutically acceptable salt thereof.

(Embodiment 111) The Compound (I-1-1) or a pharmaceutically acceptable salt thereof, wherein R represents a hydrogen atom or an alkyl group;

$R^1$ and $R^2$ each independently represent a hydrogen atom or an alkyl group;

or $R^1$ and $R^2$ are combined with the carbon atom to which they are attached to form a monocyclic carbocycle;

$R^3$, $R^4$, and $R^6$ each independently represent a hydrogen atom, a halogen atom, an alkyl group, or an alkoxy group;

$R^5$ represents (i) a hydrogen atom, or (ii) an alkyl group optionally substituted with 1 to 5 substituent(s) independently selected from the group consisting of a halogen atom, a hydroxy group, a phenyl group, and an alkoxy group;

$R^7$ and $R^8$ each independently represent a hydrogen atom or an alkyl group;

or $R^2$ and $R^9$ are combined with the carbon atom to which they are attached to form a monocyclic carbocycle optionally substituted with 1 to 5 substituent(s) independently selected from Group E;

$R^{10}$ represents a hydrogen atom, a halogen atom, an alkyl group optionally substituted with 1 to 5 substituent(s) independently selected from Group E, an alkoxy group optionally substituted with 1 to 5 substituent(s) independently selected from Group E, or a cyano group; and Group E represents a group consisting of a halogen atom, a hydroxy group, and an alkoxy group optionally substituted with 1 to 5 halogen atom(s).

(Embodiment 112) The Compound (I-1-1) or a pharmaceutically acceptable salt thereof, wherein R represents a hydrogen atom or an alkyl group;

$R^1$ and $R^2$ each independently represent a hydrogen atom or an alkyl group;

or $R^1$ and $R^2$ are combined with the carbon atom to which they are attached to form a monocyclic carbocycle;

$R^3$ represents a hydrogen atom, a halogen atom, an alkyl group, or an alkoxy group;

$R^4$ represents a hydrogen atom or an alkyl group;

$R^5$ represents an alkyl group;

$R^6$ represents a hydrogen atom;

$R^7$ and $R^8$ each independently represent a hydrogen atom or an alkyl group;

or $R^7$ and $R^8$ are combined with the carbon atom to which they are attached to form a monocyclic carbocycle; and $R^{10}$ represents a hydrogen atom, a halogen atom, an alkyl group, or an alkoxy group.

Method for Producing Compound (I)

One embodiment of the present invention provides a method for producing the Compound (I). In one embodiment, the method for producing the Compound (I) comprises reacting a compound represented by the following general formula (III)

(III)

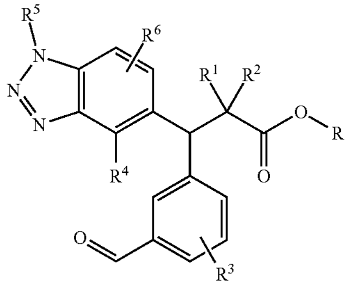

[wherein the symbols have the same meanings as those described above.]

or a salt thereof with a compound represented by the following general formula (IV)

(IV)

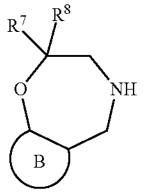

[wherein the symbols have the same meanings as those described above.]

or a salt thereof under appropriate conditions for producing the Compound (I).

In one embodiment, the Compound (I) may be produced by reacting the Compound (III) with the Compound (IV) in a solvent (for example, amides such as dimethylformamide; ethers such as tetrahydrofuran and 1,4-dioxane; halogenated aliphatic hydrocarbons such as chloroform, dichloromethane, and dichloroethane; aromatic hydrocarbons such as toluene; nitriles such as acetonitrile; carboxylic acids such as acetic acid; and mixtures thereof), in the presence of a reducing agent (for example, sodium triacetoxyborohydride and sodium borohydride), in the presence or absence of a base (for example, alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; alkali metal fluorides such as cesium fluoride and potassium fluoride; alkylamines such as triethylamine and N,N-diisopropylethylamine; pyridines such as pyridine and 4-dimethylaminopyridine; and 1,8-diazabicyclo[5.4.0]-7-undecene), and in the presence or absence of an acid (for example, acetic acid).

In another embodiment, the method for producing the Compound (I) comprises reacting a compound represented by the following general formula (III')

(III')

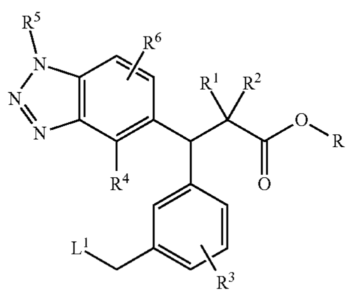

[wherein $L^1$ represents a leaving group such as a halogen atom; and the other symbols have the same meanings as those described above.]
or a salt thereof with a compound represented by the following general formula (IV)

(IV)

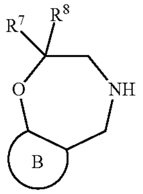

[wherein the symbols have the same meanings as those described above.]
or a salt thereof under appropriate conditions for producing the Compound (I).

In one embodiment, the Compound (I) may be produced by reacting the Compound (III') with the Compound (IV) in a solvent (for example, amides such as dimethylformamide; ethers such as tetrahydrofuran and 1,4-dioxane; halogenated aliphatic hydrocarbons such as chloroform and dichloromethane; aromatic hydrocarbons such as toluene; nitriles such as acetonitrile; carboxylic acids such as acetic acid; and mixtures thereof), and in the presence or absence of a base (for example, alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; alkali metal fluorides such as cesium fluoride and potassium fluoride; alkylamines such as triethylamine and N,N-diisopropylethylamine; pyridines such as pyridine and 4-dimethylaminopyridine; and 1,8-diazabicyclo[5.4.0]-7-undecene).

The Compound (I) of the present invention or a synthetic intermediate compound thereof may exist in the form of a tautomer or a mixture thereof. The Compound (I) of the present invention may exist in the form of a stereoisomer such as an enantiomer or a diastereomer, or a mixture thereof. The Compound (I) of the present invention encompasses a mixture of tautomers or stereoisomers, or an each pure or substantially pure isomer.

When the Compound (I) of the present invention or a synthetic intermediate compound thereof is obtained in the form of a diastereomer or an enantiomer, it may be isolated by a known conventional method in this technical field such as chromatography and fractional crystallization method.

The Compound (I) of the present invention or a synthetic intermediate compound thereof encompasses compounds labeled with an isotope (for example, $^{2}H$, $^{3}H$, $^{13}C$, $^{14}C$, $^{15}N$, $^{18}F$, $^{32}P$, $^{35}S$, and $^{125}I$) and the like, and deuterated products.

Examples of the pharmaceutically acceptable salt of the Compound (I) include alkali metal salts such as lithium, sodium, and potassium salts; alkaline earth metal salts such as magnesium and calcium salts; salts with aluminum or zinc; salts with an amine such as ammonia, choline, diethanolamine, lysine, ethylenediamine, tert-butylamine, tert-octylamine, tris(hydroxymethyl)aminomethane, N-methyl-glucosamine, triethanolamine, and dehydroabietylamine; salts with an inorganic acid such as hydrogen chloride, hydrogen bromide, hydrogen iodide, sulfuric acid, nitric acid, and phosphoric acid; salts with an organic acid such as formic acid, acetic acid, trifluoroacetic acid, propionic acid, oxalic acid, malonic acid, succinic acid, fumaric acid, maleic acid, lactic acid, malic acid, tartaric acid, citric acid, methanesulfonic acid, ethanesulfonic acid, and benzenesulfonic acid; and salts with an acidic amino acid such as aspartic acid and glutamic acid.

A synthetic intermediate compound of the Compound (I) may be in the free form or a salt form. Examples of the salt of synthetic intermediate compound of the Compound (I) include the same salts as those recited in the above "pharmaceutically acceptable salt of the Compound (I)", and pharmaceutically unacceptable salts.

Further, the Compound (I) or a pharmaceutically acceptable salt thereof and a synthetic intermediate compound of the Compound (I) or a salt thereof encompass inner salts, hydrates, and solvates thereof.

The "pharmaceutically acceptable" ingredients in the present description generally mean that they are not harmful to a subject of administration and are compatible with each other in the preparation of a pharmaceutical composition, and include useful ingredients for use as human medicaments as well as useful ingredients for veterinary use.

(Use)

The Compounds (I) or pharmaceutically acceptable salts thereof of the present invention defined by the above each embodiment and combinations thereof are all useful as active ingredients of pharmaceutical compositions, and all the compounds defined by the above embodiments and combinations thereof may be administered to a subject (preferably human). In one embodiment, the Compound (I) or a pharmaceutically acceptable salt thereof wherein R represents a hydrogen atom in any one of embodiments of the above each embodiment and a combination thereof is administered to a subject.

The Compound (I) or a pharmaceutically acceptable salt thereof of the present invention may be orally or parenterally administered alone or as a pharmaceutical composition comprising it and pharmaceutically acceptable carrier(s). Preferably, the pharmaceutical composition of the present invention comprises the Compound (I) or a pharmaceutically acceptable salt thereof of the present invention and pharmaceutically acceptable carrier(s). The pharmaceutically acceptable carrier(s) may be any conventional carrier (s) in this technical field, and examples thereof include diluents, binders (for example, syrup, gum arabic, gelatin, sorbitol, tragacanth, and polyvinylpyrrolidone), excipients (for example, lactose, sucrose, cornstarch, potassium phosphate, sorbitol, and glycine), lubricants (for example, magnesium stearate, talc, polyethylene glycol, and silica), disintegrants (for example, potato starch), and humectants (for example, sodium lauryl sulfate). Also, the dosage form of the pharmaceutical composition is not limited to a specific one, and the pharmaceutical composition may be used as a conventional pharmaceutical formulation such as a tablet, a granule, a capsule, a powder, an injection, an inhalant, and a suppository.

The dose (i.e., effective amount) of the Compound (I) or a pharmaceutically acceptable salt thereof of the present invention varies depending on administration method, age, body weight, and condition of patient, and the like, and normally 0.001 to 500 mg/kg/day, in particular 0.01 to 10 mg/kg/day is preferable and administered at one time or two to four divided doses.

The Compound (I) or a pharmaceutically acceptable salt thereof of the present invention has a Keap1 (Kelch-like ECH-associated protein 1) inhibitory activity, and is useful in the prevention, alleviation, and/or treatment of diseases which are improved by the inhibition of Keap1. Examples of such diseases include renal diseases (for example, chronic renal disease and Alport syndrome).

One embodiment of the present invention relates to a pharmaceutical composition comprising the Compound (I) or a pharmaceutically acceptable salt thereof of the present invention and pharmaceutically acceptable carrier(s). In one embodiment, the above pharmaceutical composition is used in the prevention, alleviation, and/or treatment of diseases of which symptoms are improved by the inhibition of Keap1. In another embodiment, the above pharmaceutical composition is used for the prevention, alleviation, and/or treatment of a renal disease (for example, chronic renal disease and Alport syndrome).

One embodiment of the present invention relates to use of the Compound (I) or a pharmaceutically acceptable salt thereof of the present invention in the manufacture of a medicament. In one embodiment, the above medicament is used in the prevention, alleviation, and/or treatment of diseases of which symptoms are improved by the inhibition of Keap1. In another embodiment, the above medicament is used for the prevention, alleviation, and/or treatment of a renal disease (for example, chronic renal disease and Alport syndrome).

One embodiment of the present invention relates to the Compound (I) or a pharmaceutically acceptable salt thereof of the present invention for the prevention, alleviation, and/or treatment of diseases. One embodiment of the present invention relates to the Compound (I) or a pharmaceutically acceptable salt thereof of the present invention for the prevention, alleviation, and/or treatment of diseases of which symptoms are improved by the inhibition of Keap1. Another embodiment of the present invention relates to the Compound (I) or a pharmaceutically acceptable salt thereof of the present invention for the prevention, alleviation, and/or treatment of a renal disease (for example, chronic renal disease and Alport syndrome).

One embodiment of the present invention relates to a method for preventing, alleviating, and/or treating diseases of which symptoms are improved by the inhibition of Keap1, the method comprising administering the Compound (I) or a pharmaceutically acceptable salt thereof of the present invention. Another embodiment of the present invention relates to a method for preventing, alleviating, and/or treating a renal disease (for example, chronic renal disease and Alport syndrome), the method comprising administering the Compound (I) or a pharmaceutically acceptable salt thereof of the present invention.

The Compound (I) or a pharmaceutically acceptable salt thereof may be produced according to, but are not limited to, the following methods. Also, each step in the following production methods may be carried out in an appropriate combination with each other.

When a functional group in a compound needs to be protected in each production step of the Compound (I) described below, the protection may be appropriately carried out by the specific methods described below or conventional methods. General descriptions of protecting groups and use thereof are described in T. W. Greene et al., "Protective Groups in Organic Synthesis", John Wiley & Sons, New York, Fifth Edition. A protecting group may be removed in a subsequent step by using the specific methods described below or conventional methods. Also, each interconversion of a carboxylic acid compound and a salt thereof to each other, or an amine compound and a salt thereof to each other may be carried out by the specific methods described below or conventional salt formation and conventional desalination.

Production method 1

The Compound (I) may be produced according to, for example, the following scheme.

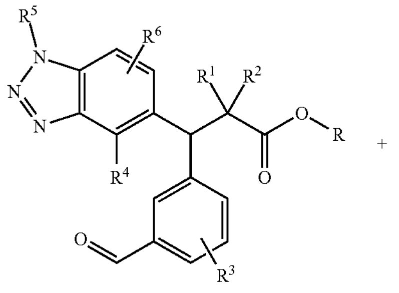

(III)

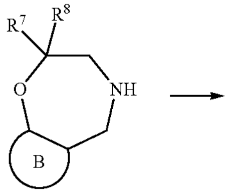

(IV)

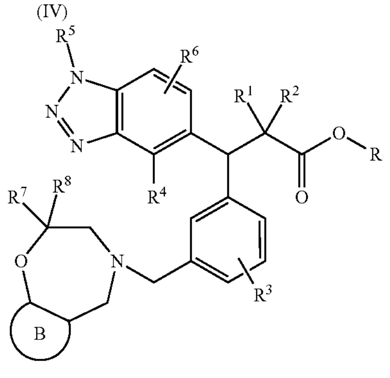

(I)

[wherein the symbols have the same meanings as those described above.]

The Compound (III) may be reacted with the Compound (IV) in a solvent, in the presence of a reducing agent, in the presence or absence of a base, and in the presence or absence of an acid to produce the Compound (I). The Compound (IV) may be in the free body or a salt form such as hydrochloride.

The solvent may be any one which does not affect the reaction, and examples thereof include amides such as dimethylformamide; ethers such as tetrahydrofuran and 1,4-dioxane; alcohols such as methanol, ethanol, and isopropanol; halogenated aliphatic hydrocarbons such as chloroform, dichloromethane, and dichloroethane; aromatic hydrocarbons such as toluene; nitriles such as acetonitrile; carboxylic acids such as acetic acid; and mixtures thereof.

Examples of the reducing agent include sodium triacetoxyborohydride and sodium borohydride.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; alkali metal fluorides such as cesium fluoride and potassium fluoride; alkylamines such as triethylamine and N,N-diisopropylethylamine; pyridines such as pyridine and 4-dimethylaminopyridine; and 1,8-diazabicyclo[5.4.0]-7-undecene.

Examples of the acid include acetic acid.

The amount of the Compound (IV) to be used may be 1.0 to 3.0 molar equivalent(s), preferably 1.0 to 2.0 molar equivalent(s), relative to the Compound (III).

The amount of the reducing agent to be used may be 1.0 to 5.0 molar equivalent(s), preferably 1.5 to 3.0 molar equivalents, relative to the Compound (III).

The amount of the base to be used may be 1.0 to 5.0 molar equivalent(s), preferably 1.0 to 3.0 molar equivalent(s), relative to the Compound (III).

The amount of the acid to be used may be 1.0 to 3.0 molar equivalent(s), preferably 1.0 to 2.0 molar equivalent(s), relative to the Compound (III).

The reaction may be carried out at room temperature to under heating, for example at room temperature to 100° C., preferably at room temperature.

Alternatively, a compound wherein the ring B moiety of the Compound (IV) is a precursor of ring B may also be used as a starting material instead of the Compound (IV) to carry out the same reaction as that described above, produce a compound wherein the ring B moiety of the Compound (I) is the precursor of ring B, and then form a ring B to produce the Compound (I).

Production Method 2

The Compound (I) may also be produced according to the following scheme.

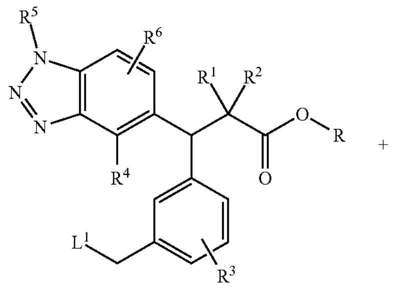
(III')

-continued

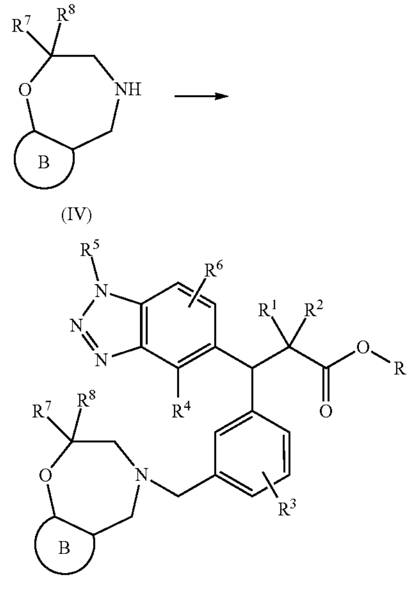
(IV)

(I)

[wherein the symbols have the same meanings as those described above.]

The Compound (III') may be reacted with the Compound (IV) in a solvent and in the presence or absence of a base to produce the Compound (I). The Compound (IV) may be in the free body or a salt form such as hydrochloride.

The solvent may be any one which does not affect the reaction, and examples thereof include amides such as dimethylformamide; ethers such as tetrahydrofuran and 1,4-dioxane; halogenated aliphatic hydrocarbons such as chloroform and dichloromethane; aromatic hydrocarbons such as toluene; nitriles such as acetonitrile; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; alkali metal fluorides such as cesium fluoride and potassium fluoride; alkylamines such as triethylamine and N,N-diisopropylethylamine; pyridines such as pyridine and 4-dimethylaminopyridine; and 1,8-diazabicyclo[5.4.0]-7-undecene.

The amount of the Compound (IV) to be used may be 1.0 to 3.0 molar equivalent(s), preferably 1.0 to 2.0 molar equivalent(s), relative to the Compound (III').

The amount of the base to be used may be 1.0 to 6.0 molar equivalent(s), preferably 1.0 to 4.5 molar equivalent(s), relative to the Compound (III').

The reaction may be carried out at room temperature to under heating, for example at room temperature to 150° C., preferably at room temperature to 100° C.

Alternatively, a compound wherein the ring B moiety of the Compound (IV) is a precursor of ring B may also be used as a starting material instead of the Compound (IV) to carry out the same reaction as that described above, produce a compound wherein the ring B moiety of the Compound (I) is the precursor of ring B, and then form a ring B to produce the Compound (I).

Reference Production Method 1

The Compound (III) may be produced according to, for example, the following scheme.

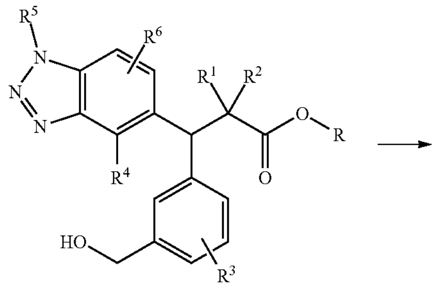

(III-1)

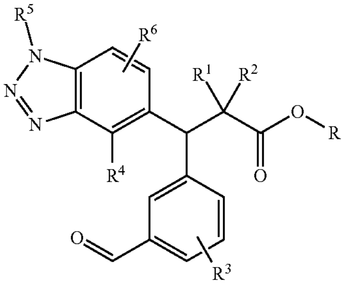

(III)

[wherein the symbols have the same meanings as those described above.]

The Compound (III-1) may be reacted in a solvent and in the presence of an oxidizing agent to produce the Compound (III).

The solvent may be any one which does not affect the reaction, and examples thereof include amides such as dimethylformamide; ethers such as tetrahydrofuran and 1,4-dioxane; halogenated aliphatic hydrocarbons such as chloroform and dichloromethane; aromatic hydrocarbons such as toluene; nitriles such as acetonitrile; carboxylic acids such as acetic acid; and mixtures thereof.

Examples of the oxidizing agent include Dess-Martin periodinane, 2,2,6,6-tetramethylpiperidine 1-oxyl, and iodobenzene diacetate; and mixtures thereof.

The amount of the oxidizing agent to be used may be 1.0 to 5.0 molar equivalent(s), preferably 1.0 to 3.0 molar equivalent(s), relative to the Compound (III-1).

The reaction may be carried out under ice-cooling to under heating, for example under ice-cooling to 100° C., preferably under ice-cooling to room temperature.

Reference Production Method 2

The Compound (III') may be produced according to, for example, the following scheme.

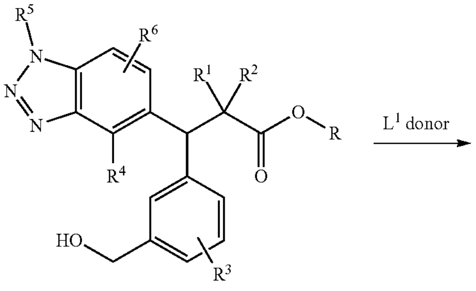

(III-1)

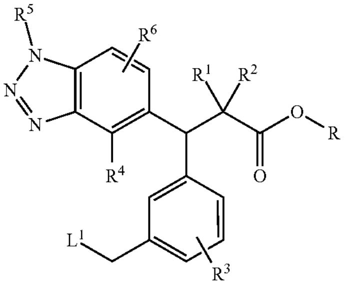

(III')

[wherein the symbols have the same meanings as those described above.]

The Compound (III-1) may be reacted with a $L^1$ donor in a solvent to produce the Compound (III').

The solvent may be any one which does not affect the reaction, and examples thereof include ethers such as tetrahydrofuran and 1,4-dioxane; halogenated aliphatic hydrocarbons such as chloroform and dichloromethane; aromatic hydrocarbons such as toluene; nitriles such as acetonitrile; and mixtures thereof.

Examples of the $L^1$ donor include halogenating agents such as thionyl chloride.

The amount of the $L^1$ donor to be used may be 1.0 to 5.0 molar equivalent(s), preferably 1.0 to 3.0 molar equivalent(s), relative to the Compound (III-1).

The reaction may be carried out at room temperature to under heating, for example at room temperature to 100° C., preferably at room temperature.

Reference Production Method 3

The Compound (III-1) may be produced according to, for example, the following scheme.

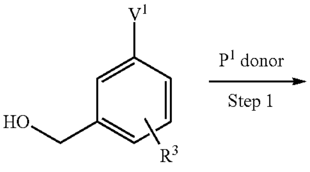

(III-7)

-continued

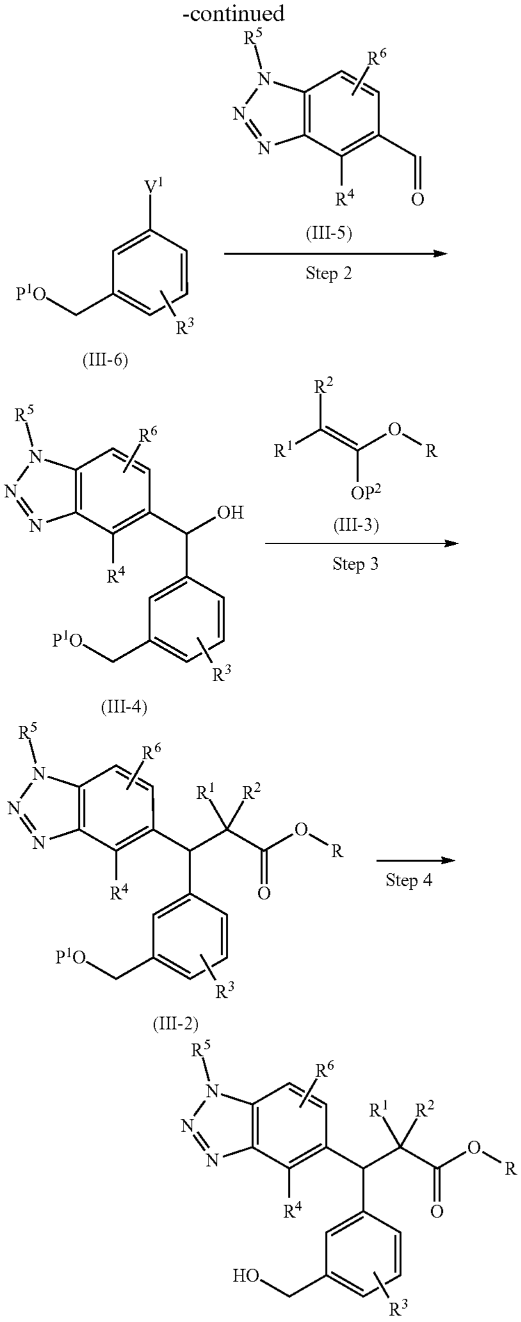

(III-1)

[wherein $V^1$ represents a halogen atom such as a bromine atom; $P^1$ represents a protecting group such as a 4-methoxybenzyl group; P2 represents a protecting group such as a trimethylsilyl group; and the other symbols have the same meanings as those described above.]

Step 1

The Compound (III-7) may be reacted with a $P^1$ donor in a solvent and in the presence of a base to produce the Compound (III-6). The Compound (III-7) may be a commercially available material, or may be produced according to known method(s) from commercially available material(s).

The solvent may be any one which does not affect the reaction, and examples thereof include amides such as dimethylformamide; ethers such as tetrahydrofuran and 1,4-dioxane; halogenated aliphatic hydrocarbons such as chloroform and dichloromethane; aromatic hydrocarbons such as toluene; nitriles such as acetonitrile; and mixtures thereof.

Examples of the base include alkali metal carbonates such as sodium carbonate, potassium carbonate, and sodium hydrogen carbonate; alkali metal hydrides such as sodium hydride; alkylamines such as triethylamine and N,N-diisopropylethylamine; pyridines such as pyridine and 4-dimethylaminopyridine; and 1,8-diazabicyclo[5.4.0]-7-undecene.

Examples of the $P^1$ donor include 4-methoxybenzyl chloride.

The amount of the $P^1$ donor to be used may be 1.0 to 3.0 molar equivalent(s), preferably 1.0 to 2.0 molar equivalent(s), relative to the Compound (III-7).

The amount of the base to be used may be 1.0 to 5.0 molar equivalent(s), preferably 1.0 to 2.0 molar equivalent(s), relative to the Compound (III-7).

The reaction may be carried out under ice-cooling to under heating, for example under ice-cooling to 100° C., preferably under ice-cooling to room temperature.

Step 2

The Compound (III-6) may be reacted with the Compound (III-5) in a solvent and in the presence of alkyllithium to produced the Compound (III-4). The Compound (III-5) may be a commercially available material, or may be produced according to known method(s) from commercially available material(s).

The solvent may be any one which does not affect the reaction, and examples thereof include ethers such as tetrahydrofuran and 1,4-dioxane; aromatic hydrocarbons such as toluene; and mixtures thereof.

Examples of the alkyllithium include n-butyllithium.

The amount of the Compound (III-5) to be used may be 0.8 to 3.0 molar equivalent(s), preferably 1.0 to 2.0 molar equivalent(s), relative to the Compound (III-6).

The amount of the alkyllithium to be used may be 0.8 to 3.0 molar equivalent(s), preferably 0.8 to 2.0 molar equivalent(s), relative to the Compound (III-6).

The reaction may be carried out at −100° C. to under heating, for example at −100° C. to 100° C., preferably at −80° C. to room temperature.

Step 3

The Compound (III-4) may be reacted in a solvent and in the presence of trichloroacetonitrile and a base, and then reacted with the Compound (III-3) in the presence of trifluoromethanesulfonimide to produce the Compound (III-2). The Compound (III-3) may be a commercially available material, or may be produced according to known method(s) from commercially available material(s).

The solvent may be any one which does not affect the reaction, and examples thereof include amides such as dimethylformamide; ethers such as tetrahydrofuran and 1,4-dioxane; halogenated aliphatic hydrocarbons such as chloroform and dichloromethane; aromatic hydrocarbons such as toluene; nitriles such as acetonitrile; and mixtures thereof.

Examples of the base include alkali metal carbonates such as sodium carbonate, potassium carbonate, and sodium hydrogen carbonate; alkali metal hydrides such as sodium hydride; alkyllithiums such as n-butyllithium; alkylamines such as triethylamine and N,N-diisopropylethylamine; pyridines such as pyridine and 4-dimethylaminopyridine; and 1,8-diazabicyclo[5.4.0]-7-undecene.

The amount of the Compound (III-3) to be used may be 1.0 to 10.0 molar equivalent(s), preferably 1.0 to 6.0 molar equivalent(s), relative to the Compound (III-4).

The amount of the trichloroacetonitrile to be used may be 1.0 to 5.0 molar equivalent(s), preferably 1.0 to 3.0 molar equivalent(s), relative to the Compound (III-4).

The amount of the base to be used may be 0.05 to 1.0 molar equivalent, preferably 0.05 to 0.5 molar equivalent, relative to the Compound (III-4).

The amount of the trifluoromethanesulfonimide to be used may be 0.05 to 1.0 molar equivalent, preferably 0.05 to 0.5 molar equivalent, relative to the Compound (III-4).

The reaction may be carried out under ice-cooling to under heating, for example under ice-cooling to 100° C., preferably at room temperature.

Step 4

The Compound (III-2) may be reacted in a solvent and in the presence of an oxidizing agent to produce the Compound (III-1).

The solvent may be any one which does not affect the reaction, and examples thereof include amides such as dimethylformamide; ethers such as tetrahydrofuran and 1,4-dioxane; halogenated aliphatic hydrocarbons such as chloroform and dichloromethane; aromatic hydrocarbons such as toluene; nitriles such as acetonitrile; carboxylic acids such as acetic acid; water; and mixtures thereof.

Examples of the oxidizing agent include cerium (IV) diammonium nitrate.

The amount of the oxidizing agent to be used may be 1.0 to 5.0 molar equivalent(s), preferably 1.0 to 2.0 molar equivalent(s), relative to the Compound (III-2).

The reaction may be carried out under ice-cooling to under heating, for example under ice-cooling to 100° C., preferably at room temperature.

The Compound (III-4) may also be produced according to the following scheme.

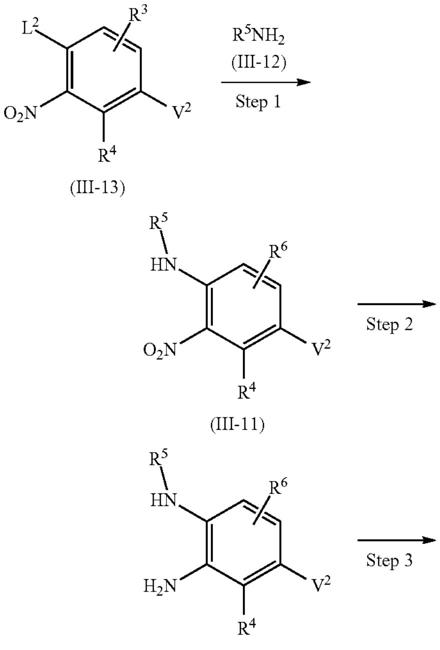

(III-13)

(III-11)

(III-10)

-continued

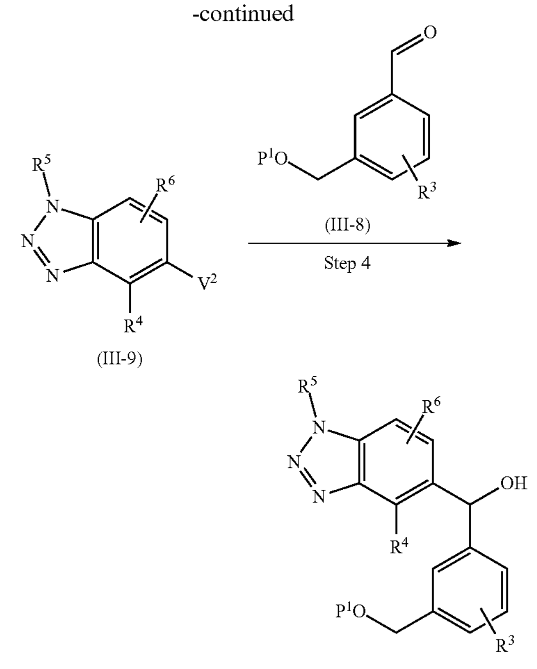

(III-9)

(III-8)

(III-4)

[wherein $L^2$ represents a leaving group such as a halogen atom; $V^2$ represents a halogen atom such as a bromine atom; and the other symbols have the same meanings as those described above.]

Step 1

The Compound (III-13) may be reacted with the Compound (III-12) in a solvent and in the presence of a base to produce the Compound (III-11). The Compound (III-13) and the Compound (111-12) may be commercially available materials, or may be produced according to known methods from commercially available materials. Also, the Compound (III-12) may be in the free body or a salt form such as hydrochloride.

The solvent may be any one which does not affect the reaction, and examples thereof include amides such as dimethylformamide; ethers such as tetrahydrofuran and 1,4-dioxane; alcohols such as methanol, ethanol, and isopropanol; halogenated aliphatic hydrocarbons such as chloroform and dichloromethane; aromatic hydrocarbons such as toluene; nitriles such as acetonitrile; carboxylic acids such as acetic acid; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; alkali metal fluorides such as cesium fluoride and potassium fluoride; alkylamines such as triethylamine and N,N-diisopropylethylamine; pyridines such as pyridine and 4-dimethylaminopyridine; 1,8-diazabicyclo[5.4.0]-7-undecene; and mixtures thereof.

The amount of the Compound (III-12) to be used may be 1.0 to 10.0 molar equivalent(s), preferably 1.0 to 5.0 molar equivalent(s), relative to the Compound (III-13).

The amount of the base to be used may be 1.0 to 5.0 molar equivalent(s), preferably 1.0 to 3.0 molar equivalent(s), relative to the Compound (III-13).

The reaction may be carried out at room temperature to under heating, for example at room temperature to 150° C., preferably at 50 to 100° C.

Step 2

The Compound (III-11) may be reacted in a solvent, in the presence of a catalyst, and in the presence of an acid or a salt thereof to produce the Compound (III-10).

The solvent may be any one which does not affect the reaction, and examples thereof include amides such as dimethylformamide; ethers such as tetrahydrofuran and 1,4-dioxane; alcohols such as methanol, ethanol, and isopropanol; halogenated aliphatic hydrocarbons such as chloroform and dichloromethane; aromatic hydrocarbons such as toluene; nitriles such as acetonitrile; carboxylic acids such as acetic acid; water; and mixtures thereof.

Examples of the catalyst include iron, zinc, and tin.

Examples of the acid or a salt thereof include ammonium chloride, hydrochloric acid, and acetic acid.

The amount of the catalyst to be used may be 1.0 to 15.0 molar equivalent(s), preferably 1.0 to 10.0 molar equivalent(s), relative to the Compound (III-11).

The amount of the acid or a salt thereof to be used may be 1.0 to 10.0 molar equivalent(s), preferably 1.0 to 5.0 molar equivalent(s), relative to the Compound (III-11).

The reaction may be carried out at room temperature to under heating, for example at room temperature to 150° C., preferably at 50 to 100° C.

Step 3

The Compound (III-10) may be reacted with a diazotizing agent in a solvent and in the presence of an acid to produce the Compound (III-9).

The solvent may be any one which does not affect the reaction, and examples thereof include amides such as dimethylformamide; ethers such as tetrahydrofuran and 1,4-dioxane; alcohols such as methanol, ethanol, and isopropanol; halogenated aliphatic hydrocarbons such as chloroform and dichloromethane; aromatic hydrocarbons such as toluene; nitriles such as acetonitrile; carboxylic acids such as acetic acid; water; and mixtures thereof.

Examples of the acid include sulfuric acid.

Examples of the diazotizing agent include sodium nitrite and nitrous acid esters.

The amount of the acid to be used may be 0.1 to 10.0 molar equivalent(s), preferably 1.0 to 5.0 molar equivalent(s), relative to the Compound (III-10).

The amount of the diazotizing agent to be used may be 1.0 to 5.0 molar equivalent(s), preferably 1.0 to 2.0 molar equivalent(s), relative to the Compound (III-10).

The reaction may be carried out under ice-cooling to under heating, for example under ice-cooling to 50° C., preferably under ice-cooling to room temperature.

Step 4

The Compound (III-9) may be reacted with the Compound (III-8) in a solvent, in the presence of an alkyllithium, and in the presence of a Grignard reagent to produce the Compound (III-4). The Compound (III-8) may be a commercially available material, or may be produced according to known method(s) from commercially available material(s).

The solvent may be any one which does not affect the reaction, and examples thereof include ethers such as tetrahydrofuran and 1,4-dioxane; aromatic hydrocarbons such as toluene; and mixtures thereof.

Examples of the alkyllithium include n-butyllithium.

Examples of the Grignard reagent include i-propylmagnesium chloride.

The amount of the Compound (III-8) to be used may be 1.0 to 3.0 molar equivalent(s), preferably 1.0 to 2.0 molar equivalent(s), relative to the Compound (III-9).

The amount of the base to be used may be 1.0 to 5.0 molar equivalent(s), preferably 1.0 to 3.0 molar equivalent(s), relative to the Compound (III-9).

The amount of the Grignard reagent to be used may be 1.0 to 5.0 molar equivalent(s), preferably 1.0 to 3.0 molar equivalent(s), relative to the Compound (III-9).

The reaction may be carried out at −100° C. to under heating, for example at −80° C. to room temperature, preferably at −50° C. to under ice-cooling.

Reference Production Method 4

Among the Compounds (III-1), the Compound (III-1') wherein $R^1$ and $R^2$ each represent a hydrogen atom may also be produced according to the following scheme.

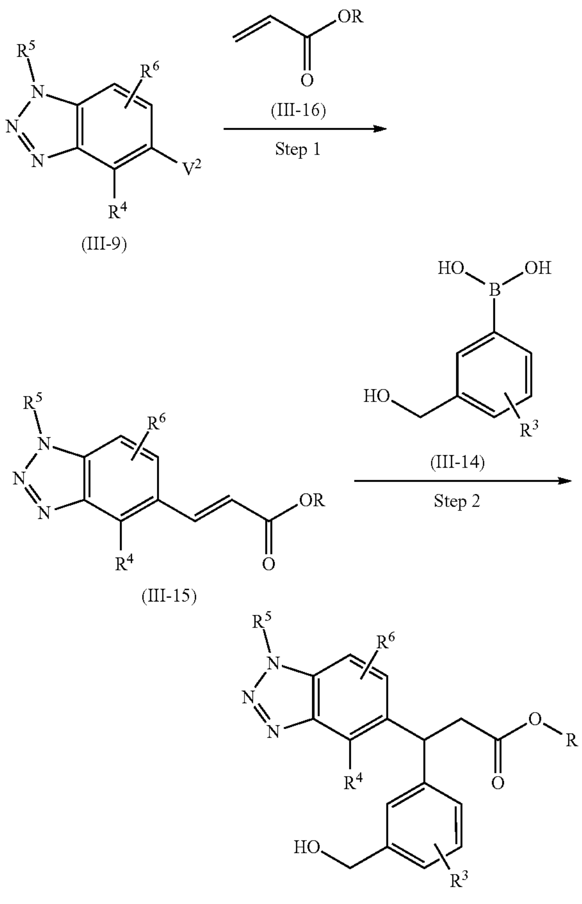

(III-9)
(III-15)
(III-1')

[wherein the symbols have the same meanings as those described above.]

Step 1

The Compound (III-9) may be reacted with the Compound (III-16) in a solvent, in the presence of a base, in the presence of a catalyst, and in the presence or absence of a ligand to produce the Compound (III-15). The Compound (III-16) may be a commercially available material, or may be produced according to known method(s) from commercially available material(s).

The solvent may be any one which does not affect the reaction, and examples thereof include amides such as dimethylformamide; ethers such as tetrahydrofuran and 1,4-dioxane; alcohols such as methanol, ethanol, and isopropanol; halogenated aliphatic hydrocarbons such as chloroform and dichloromethane; aromatic hydrocarbons such as toluene; nitriles such as acetonitrile; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; alkali metal fluorides such as cesium fluoride and potassium fluoride; alkylamines such as triethylamine and N,N-diisopropylethylamine; pyridines such as pyridine and 4-dimethylaminopyridine; 1,8-diazabicyclo[5.4.0]-7-undecene; and mixtures thereof.

Examples of the catalyst include palladium(II) acetate.

Examples of the ligand include tri-o-tolylphosphine.

The amount of the Compound (III-16) to be used may be 1.0 to 10.0 molar equivalent(s), preferably 1.0 to 5.0 molar equivalent(s), relative to the Compound (III-9).

The amount of the base to be used may be 1.0 to 5.0 molar equivalent(s), preferably 1.0 to 3.0 molar equivalent(s), relative to the Compound (III-9).

The amount of the catalyst to be used may be 0.01 to 1.0 molar equivalent, preferably 0.05 to 0.5 molar equivalent, relative to the Compound (III-9).

The amount of the ligand to be used may be 0.01 to 1.0 molar equivalent, preferably 0.05 to 0.5 molar equivalent, relative to the Compound (III-9).

The reaction may be carried out at room temperature to under heating, for example at 50 to 200° C., preferably at 100 to 150° C.

Step 2

The Compound (III-15) may be reacted with the Compound (III-14) in a solvent and in the presence of a base and a catalyst to produce the Compound (III-1'). The Compound (III-14) may be a commercially available material, or may be produced according to known method(s) from commercially available material(s).

The solvent may be any one which does not affect the reaction, and examples thereof include amides such as dimethylformamide; ethers such as tetrahydrofuran and 1,4-dioxane; alcohols such as methanol, ethanol, and isopropanol; halogenated aliphatic hydrocarbons such as chloroform and dichloromethane; aromatic hydrocarbons such as toluene; nitriles such as acetonitrile; water; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; alkali metal fluorides such as cesium fluoride and potassium fluoride; alkylamines such as triethylamine and N,N-diisopropylethylamine; pyridines such as pyridine and 4-dimethylaminopyridine; 1,8-diazabicyclo[5.4.0]-7-undecene; and mixtures thereof.

Examples of the catalyst include di-μ-chlorobis[(η-cycloocta-1,5-diene)rhodium(I)].

The amount of the Compound (III-14) to be used may be 1.0 to 3.0 molar equivalent(s), preferably 1.0 to 2.0 molar equivalent(s), relative to the Compound (III-15).

The amount of the base to be used may be 1.0 to 5.0 molar equivalent(s), preferably 1.0 to 3.0 molar equivalent(s), relative to the Compound (III-15).

The amount of the catalyst to be used may be 0.01 to 1.0 molar equivalent, preferably 0.01 to 0.5 molar equivalent, relative to the Compound (III-15).

The reaction may be carried out at room temperature to under heating, for example at room temperature to 150° C., preferably at 50 to 100° C.

Reference Production Method 5

Among the Compounds (IV), the Compound (IV-1)

(IV-1)

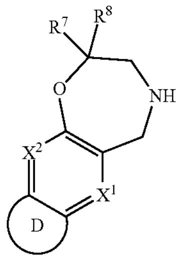

[wherein the symbols have the same meanings as those described above.]

may be produced according to, for example, the following scheme.

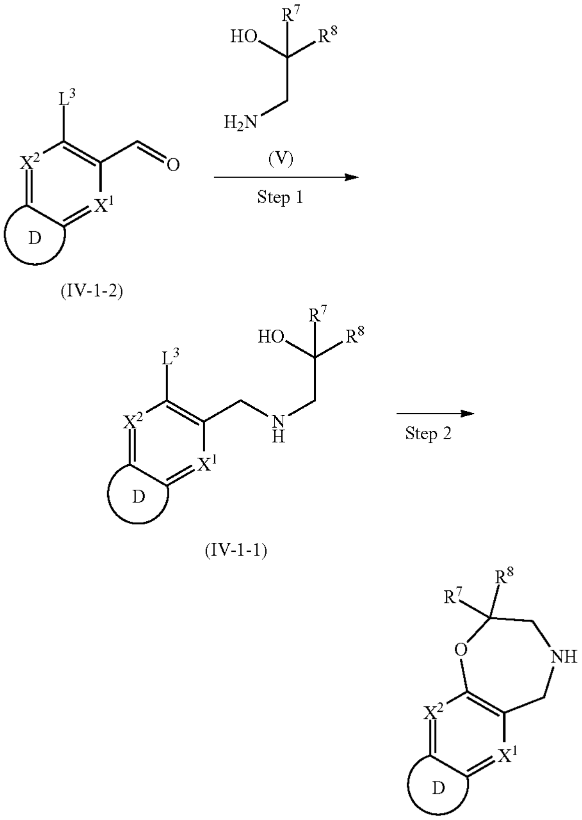

(IV-1-2)

(IV-1-1)

(IV-1)

[wherein $L^3$ represents a leaving group such as a halogen atom; and the other symbols have the same meanings as those described above.]

Step 1

The Compound (IV-1-2) may be reacted with the Compound (V) in a solvent and in the presence of a reducing agent to produce the Compound (IV-1-1). The Compound (IV-1-2) and the Compound (V) may be commercially available materials, or may be produced according to known methods from commercially available materials.

The solvent may be any one which does not affect the reaction, and examples thereof include amides such as dimethylformamide; ethers such as tetrahydrofuran and 1,4-dioxane; alcohols such as methanol, ethanol, and isopropanol; halogenated aliphatic hydrocarbons such as chloroform and dichloromethane; aromatic hydrocarbons such as toluene; nitriles such as acetonitrile; and mixtures thereof.

Examples of the reducing agent include sodium triacetoxyborohydride and sodium borohydride.

The amount of the Compound (V) to be used may be 1.0 to 3.0 molar equivalent(s), preferably 1.0 to 2.0 molar equivalent(s), relative to the Compound (IV-1-2).

The amount of the reducing agent to be used may be 1.0 to 5.0 molar equivalent(s), preferably 1.0 to 3.0 molar equivalent(s), relative to the Compound (IV-1-2).

The reaction may be carried out at room temperature to under heating, for example at room temperature to 100° C., preferably at room temperature to 70° C.

Step 2

The Compound (IV-1-1) may be reacted in a solvent, in the presence or absence of a copper catalyst, in the presence or absence of dimethylglycine, and in the presence of a base to produce the Compound (IV-1). The Compound (IV-1) may be in the free body or a salt form such as hydrochloride.

The solvent may be any one which does not affect the reaction, and examples thereof include amides such as N-methylpyrrolidone and dimethylformamide; ethers such as tetrahydrofuran and 1,4-dioxane; alcohols such as methanol, ethanol, and isopropanol; aromatic hydrocarbons such as toluene; nitriles such as acetonitrile; dimethyl sulfoxide; carboxylic acids such as acetic acid; water; and mixtures thereof.

Examples of the copper catalyst include copper(I) iodide.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; alkali metal fluorides such as cesium fluoride and potassium fluoride; alkali metal tert-butoxides such as sodium tert-butoxide and potassium tert-butoxide; alkali metal hydrides such as sodium hydride; alkylamines such as triethylamine and N,N-diisopropylethylamine; pyridines such as pyridine and 4-dimethylaminopyridine; and 1,8-diazabicyclo[5.4.0]-7-undecene.

The amount of the copper catalyst to be used may be 0.01 to 1.0 molar equivalent, preferably 0.05 to 1.0 molar equivalent, relative to the Compound (IV-1-1).

The amount of the dimethylglycine to be used may be 0.05 to 1.0 molar equivalent, preferably 0.1 to 0.5 molar equivalent, relative to the Compound (IV-1-1).

The amount of the base to be used may be 1.0 to 5.0 molar equivalent(s), preferably 1.0 to 3.0 molar equivalent(s), relative to the Compound (IV-1-1).

The reaction may be carried out under ice-cooling to under heating, for example at 0 to 150° C., preferably at room temperature to 100° C.

Alternatively, the Step 2 may also be carried out in the presence of a $P^3$ donor (wherein $P^3$ represents a protecting group such as a tert-butoxycarbonyl group) to produce a compound wherein the nitrogen atom on the oxazepine ring of the Compound (IV-1) is protected by a protecting group $P^3$, and then the compound is deprotected by reacting in the presence of a solution of hydrogen chloride in dioxane etc. to produce the Compound (IV-1).

Alternatively, a compound wherein the ring D moiety of the Compound (IV-1-2) is a precursor of ring D may also be used as a starting material instead of the Compound (IV-1-2) to carry out the same reaction as that described above, produce a compound wherein the ring D moiety of the Compound (IV-1-1) is the precursor of ring D, or produce a compound wherein the ring D moiety of the Compound (IV-1) is the precursor of ring D, and then form a ring D to produce the Compound (IV-1).

The Compound (IV-1-1) may also be produced according to the following scheme.

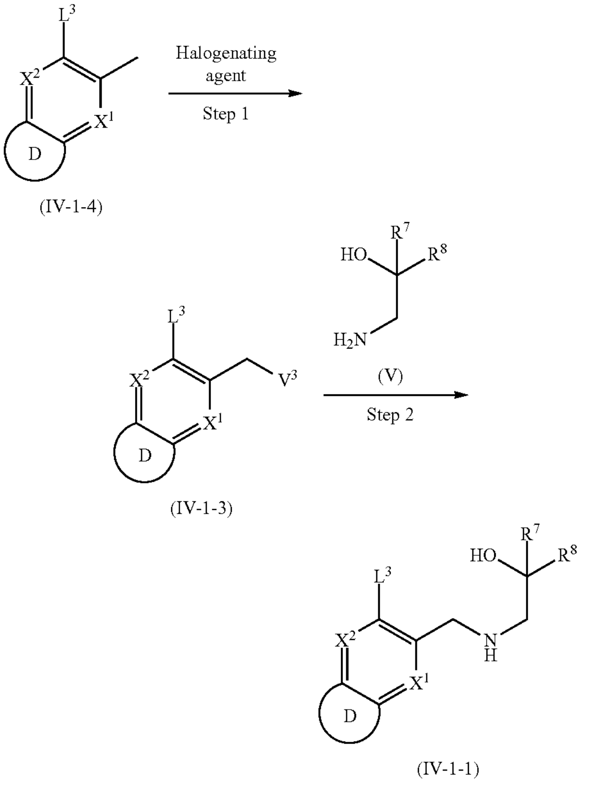

(IV-1-4) (IV-1-3) (V) (IV-1-1)

[wherein $V^3$ represents a halogen atom such as a bromine atom; and the other symbols have the same meanings as those described above.]

Step 1

The Compound (IV-1-4) may be reacted with a halogenating agent in a solvent and in the presence of a radical initiator to produce the Compound (IV-1-3). The Compound (IV-1-4) may be a commercially available material, or may be produced according to known method(s) from commercially available material(s).

The solvent may be any one which does not affect the reaction, and examples thereof include amides such as dimethylformamide; ethers such as tetrahydrofuran and 1,4-dioxane; halogenated aliphatic hydrocarbons such as chloroform, dichloromethane, and dichloroethane; aromatic hydrocarbons such as toluene and chlorobenzene; nitriles such as acetonitrile; and mixtures thereof.

Examples of the radical initiator include 2,2'-azobis(isobutyronitrile) and 2,2'-azobis(2,4-dimethylvaleronitrile).

Examples of the halogenating agent include N-bromosuccinimide.

The amount of the radical initiator to be used may be 0.05 to 1.0 molar equivalent, preferably 0.05 to 0.5 molar equivalent, relative to the Compound (IV-1-4).

The amount of the halogenating agent to be used may be 1.0 to 5.0 molar equivalent(s), preferably 1.0 to 3.0 molar equivalent(s), relative to the Compound (IV-1-4).

The reaction may be carried out at room temperature to under heating, for example at room temperature to 200° C., preferably at 50 to 150° C.

Step 2

The Compound (IV-1-3) may be reacted with the Compound (V) in a solvent and in the presence of a base to produce the Compound (IV-1-1). The Compound (V) may be a commercially available material, or may be produced according to known method(s) from commercially available material(s).

The solvent may be any one which does not affect the reaction, and examples thereof include amides such as dimethylformamide; ethers such as tetrahydrofuran and 1,4-dioxane; halogenated aliphatic hydrocarbons such as chloroform and dichloromethane; aromatic hydrocarbons such as toluene; nitriles such as acetonitrile; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; alkali metal fluorides such as cesium fluoride and potassium fluoride; alkylamines such as triethylamine and N,N-diisopropylethylamine; pyridines such as pyridine and 4-dimethylaminopyridine; and 1,8-diazabicyclo[5.4.0]-7-undecene.

The amount of the Compound (V) to be used may be 1.0 to 5.0 molar equivalent(s), preferably 1.0 to 3.0 molar equivalent(s), relative to the Compound (IV-1-3).

The amount of the base to be used may be 1.0 to 5.0 molar equivalent(s), preferably 1.5 to 3.0 molar equivalents, relative to the Compound (IV-1-3).

The reaction may be carried out at room temperature to under heating, for example at room temperature to 100° C., preferably at room temperature.

Alternatively, a compound wherein the ring D moiety of the Compound (IV-1-4) is a precursor of ring D may also be used as a starting material instead of the Compound (IV-1-4) to carry out the same reaction as that described above, produce a compound wherein the ring D moiety of the Compound (IV-1-3) is the precursor of ring D, or produce a compound wherein the ring D moiety of the Compound (IV-1-1) is the precursor of ring D, and then form a ring D to produce the Compound (IV-1-1).

The Compound (IV-1-2) may also be produced according to the following scheme.

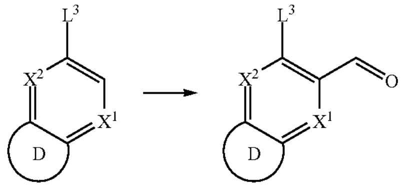

(IV-1-2-1) (IV-1-2)

[wherein the symbols have the same meanings as those described above.]

The Compound (IV-1-2-1) may be reacted with a formylating agent in a solvent and in the presence of a base to produce the Compound (IV-1-2). The Compound (IV-1-2-1) may be a commercially available material, or may be produced according to known method(s) from commercially available material(s).

The solvent may be any one which does not affect the reaction, and examples thereof include ethers such as tetrahydrofuran and 1,4-dioxane; halogenated aliphatic hydrocarbons such as chloroform and dichloromethane; aromatic hydrocarbons such as toluene; nitriles such as acetonitrile; and mixtures thereof.

Examples of the base include a Knochel-Hauser base.

Examples of the formylating agent include dimethylformamide.

The amount of the base to be used may be 1.0 to 5.0 molar equivalent(s), preferably 1.0 to 3.0 molar equivalent(s), relative to the Compound (IV-1-2-1).

The amount of the formylating agent to be used may be 1.0 to 5.0 molar equivalent(s), preferably 1.0 to 3.0 molar equivalent(s), relative to the Compound (IV-1-2-1).

The reaction may be carried out under ice-cooling to under heating, for example under ice-cooling to 50° C., preferably under ice-cooling to room temperature.

Alternatively, a compound wherein the ring D moiety of the Compound (IV-1-2-1) is a precursor of ring D may also be used as a starting material instead of the Compound (IV-1-2-1) to carry out the same reaction as that described above, produce a compound wherein the ring D moiety of the Compound (IV-1-2) is the precursor of ring D, and then form a ring D to produce the Compound (IV-1-2).

Reference Production Method 6

The Compound (IV-1) may also be produced according to the following scheme.

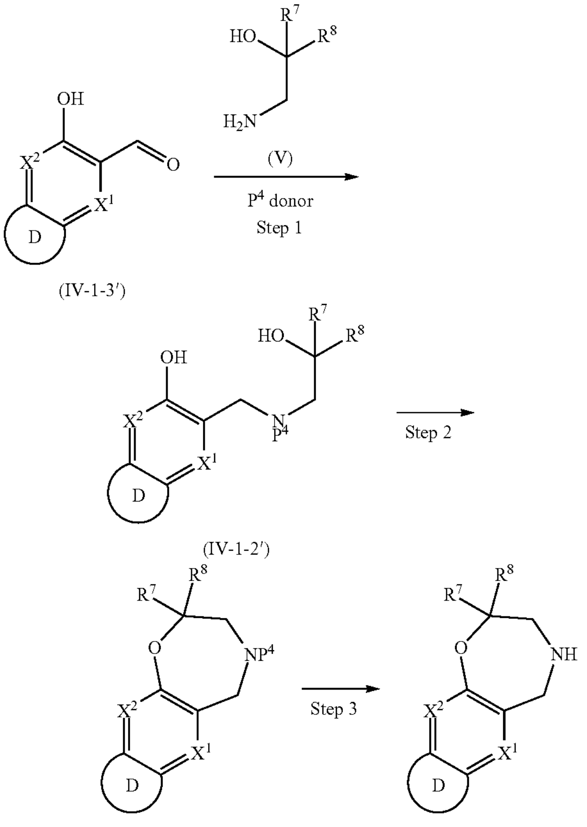

(IV-1-3') (IV-1-2') (IV-1-1') (IV-1)

[wherein $P^4$ represents a protecting group such as a tert-butoxycarbonyl group and a benzyloxycarbonyl group; and the other symbols have the same meanings as those described above.]

Step 1

The Compound (IV-1-3') may be reacted with the Compound (V) in a solvent, in the presence of a reducing agent, and in the presence or absence of an acid, and then reacted with a $P^4$ donor in a solvent and in the presence of a base to produce the Compound (IV-1-2'). The Compound (IV-1-3') and the Compound (V) may be commercially available materials, or may be produced according to known methods from commercially available materials.

The solvent may be any one which does not affect the reaction, and examples of the solvent to be used in the reaction with the Compound (V) include amides such as dimethylformamide; ethers such as tetrahydrofuran and 1,4-dioxane; alcohols such as methanol, ethanol, and isopropanol; halogenated aliphatic hydrocarbons such as chloroform and dichloromethane; aromatic hydrocarbons such as toluene; nitriles such as acetonitrile; and mixtures thereof, and examples of the solvent to be used in the reaction with the $P^4$ donor include ethers such as tetrahydrofuran and 1,4-dioxane; alcohols such as methanol, ethanol, and isopropanol; aromatic hydrocarbons such as toluene; nitriles such as acetonitrile; water; and mixtures thereof.

Examples of the reducing agent include sodium triacetoxyborohydride and sodium borohydride.

Examples of the acid include acetic acid.

Examples of the base include alkali metal carbonates such as cesium carbonate, potassium carbonate, sodium carbonate, and sodium hydrogen carbonate; alkali metal hydroxides such as sodium hydroxide; alkylamines such as triethylamine and N,N-diisopropylethylamine; pyridines such as pyridine and 4-dimethylaminopyridine; and 1,8-diazabicyclo[5.4.0]-7-undecene.

Examples of the $P^4$ donor include di-tert-butyl dicarbonate and benzyl chloroformate.

The amount of the Compound (V) to be used may be 1.0 to 3.0 molar equivalent(s), preferably 1.0 to 2.0 molar equivalent(s), relative to the Compound (IV-1-3').

The amount of the $P^4$ donor to be used may be 1.0 to 30.0 molar equivalent(s), preferably 1.0 to 20.0 molar equivalent(s), relative to the Compound (IV-1-3').

The amount of the reducing agent to be used may be 1.0 to 5.0 molar equivalent(s), preferably 1.3 to 4.0 molar equivalents, relative to the Compound (IV-1-3').

The amount of the acid to be used may be 1.0 to 3.0 molar equivalent(s), preferably 1.0 to 2.0 molar equivalent(s), relative to the Compound (IV-1-3').

The amount of the base to be used may be 1.0 to 100.0 molar equivalent(s), preferably 2.0 to 60.0 molar equivalents, relative to the Compound (IV-1-3').

The reaction may be carried out at room temperature to under heating, for example at room temperature to 100° C., preferably at room temperature.

Step 2

The Compound (IV-1-2') may be reacted in a solvent and in the presence of an azodicarboxylic acid derivative and a phosphine derivative to produce the Compound (IV-1-1').

The solvent may be any one which does not affect the reaction, and examples thereof include ethers such as tetrahydrofuran and 1,4-dioxane; halogenated aliphatic hydrocarbons such as chloroform and dichloromethane; aromatic hydrocarbons such as toluene; nitriles such as acetonitrile; and mixtures thereof.

Examples of the azodicarboxylic acid derivative include azodicarboxylic acid dialkyl esters such as diethyl azodicarboxylate and diisopropyl azodicarboxylate; and azodicarboxamides such as (E)-N1,N1,N2,N2-tetramethyldiazene-1,2-dicarboxamide.

Examples of the phosphine derivative include triarylphosphines such as triphenylphosphine; and trialkylphosphines such as tri-n-butylphosphine.

The amount of the azodicarboxylic acid derivative to be used may be 1.0 to 5.0 molar equivalent(s), preferably 1.0 to 3.0 molar equivalent(s), relative to the Compound (IV-1-2').

The amount of the phosphine derivative to be used may be 1.0 to 5.0 molar equivalent(s), preferably 1.0 to 3.0 molar equivalent(s), relative to the Compound (IV-1-2').

The reaction may be carried out under ice-cooling to under heating, for example under ice-cooling to 50° C., preferably under ice-cooling to room temperature.

Step 3

When the $P^4$ represents a tert-butoxycarbonyl group etc., the Compound (IV-1-1') may be reacted in a solvent and in the presence of an acid to produce the Compound (IV-1). The Compound (IV-1) may be in the free body or a salt form such as hydrochloride.

The solvent may be any one which does not affect the reaction, and examples thereof include ethers such as tetrahydrofuran, 1,4-dioxane, tert-butyl methyl ether, and cyclopentyl methyl ether; halogenated aliphatic hydrocarbons such as chloroform and dichloromethane; aromatic hydrocarbons such as toluene; nitriles such as acetonitrile; and mixtures thereof.

Examples of the acid include hydrogen chloride.

The amount of the acid to be used may be 1.0 to 100.0 molar equivalent(s), preferably 2.0 to 60.0 molar equivalents, relative to the Compound (IV-1-1').

The reaction may be carried out under ice-cooling to under heating, for example under ice-cooling to 150° C., preferably at 0° C. to 100° C.

Alternatively, when the $P^4$ represents a tert-butoxycarbonyl group etc., the Compound (IV-1-1') may also be reacted in a solvent and in the presence of a base and an additive agent to produce the Compound (IV-1).

The solvent may be any one which does not affect the reaction, and examples thereof include ethers such as tetrahydrofuran, 1,4-dioxane, tert-butyl methyl ether, and cyclopentyl methyl ether; halogenated aliphatic hydrocarbons such as chloroform and dichloromethane; aromatic hydrocarbons such as toluene; nitriles such as acetonitrile; and mixtures thereof.

Examples of the base include 2,6-lutidine and triethylamine.

Examples of the additive agent include trifluoromethanesulfonic acid trimethylsilyl ester.

The amount of the base to be used may be 1.0 to 10.0 molar equivalent(s), preferably 1.0 to 5.0 molar equivalent(s), relative to the Compound (IV-1-1').

The amount of the additive agent to be used may be 1.0 to 10.0 molar equivalent(s), preferably 1.0 to 5.0 molar equivalent(s), relative to the Compound (IV-1-1').

The reaction may be carried out under ice-cooling to under heating, for example under ice-cooling to 100° C., preferably under ice-cooling to room temperature.

When the $P^4$ represents a benzyloxycarbonyl group etc., the Compound (IV-1-1') may be treated with a catalyst in a solvent under hydrogen atmosphere to produce the Compound (IV-1).

The solvent may be any one which does not affect the reaction, and examples thereof include ethers such as tetrahydrofuran and 1,4-dioxane; alcohols such as methanol, ethanol, and isopropanol; aromatic hydrocarbons such as toluene; nitriles such as acetonitrile; carboxylic acids such as acetic acid; water; and mixtures thereof.

Examples of the catalyst include palladium carbon.

The amount of the catalyst to be used may be 0.01 to 20.0 molar equivalent(s), preferably 0.01 to 10.0 molar equivalent(s), relative to the Compound (IV-1-1').

The reaction may be carried out at room temperature to under heating, for example at room temperature to 100° C., preferably at room temperature.

Alternatively, a compound wherein the ring D moiety of the Compound (IV-1-3') is a precursor of ring D may also be used as a starting material instead of the Compound (IV-1-3') to carry out the same reaction as that described above, produce a compound wherein the ring D moiety of the Compound (IV-1-2') is the precursor of ring D, then produce a compound wherein the ring D moiety of the Compound (IV-1-1') is the precursor of ring D, or produce a compound wherein the ring D moiety of the Compound (IV-1) is the precursor of ring D, and then form a ring D to produce the Compound (IV-1).

The Compound (IV-1-3') may also be produced according to the following scheme.

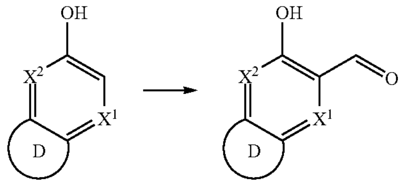

(IV-1-3'-1) (IV-1-3')

[wherein the symbols have the same meanings as those described above.]

The Compound (IV-1-3'-1) may be reacted in a solvent and in the presence of hexamethylenetetramine to produce the Compound (IV-1-3'). The Compound (IV-1-3'-1) may be a commercially available material, or may be produced according to known method(s) from commercially available material(s).

The solvent may be any one which does not affect the reaction, and examples thereof include acids such as acetic acid and trifluoroacetic acid; and mixtures thereof.

The amount of the hexamethylenetetramine to be used may be 1.0 to 3.0 molar equivalent(s), preferably 1.0 to 2.0 molar equivalent(s), relative to the Compound (IV-1-3'-1).

The reaction may be carried out at room temperature to under heating, for example at room temperature to 150° C., preferably at room temperature to 100° C.

Alternatively, the Compound (IV-1-3'-1) may also be reacted with paraformaldehyde in a solvent and in the presence of magnesium chloride and a base to produce the Compound (IV-1-3').

The solvent may be any one which does not affect the reaction, and examples thereof include ethers such as tetrahydrofuran, 1,4-dioxane, and tert-butyl methyl ether; halogenated aliphatic hydrocarbons such as chloroform and dichloromethane; aromatic hydrocarbons such as toluene; nitriles such as acetonitrile; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; alkali metal fluorides such as cesium fluoride and potassium fluoride; alkylamines such as triethylamine and N,N-diisopropylethylamine; pyridines such as pyridine and 4-dimethylaminopyridine; and 1,8-diazabicyclo[5.4.0]-7-undecene.

The amount of the magnesium chloride to be used may be 1.0 to 5.0 molar equivalent(s), preferably 1.0 to 3.0 molar equivalent(s), relative to the Compound (IV-1-3'-1).

The amount of the base to be used may be 1.0 to 5.0 molar equivalent(s), preferably 1.0 to 4.0 molar equivalent(s), relative to the Compound (IV-1-3'-1).

The amount of the paraformaldehyde to be used may be 1.0 to 15.0 molar equivalent(s), preferably 1.0 to 10.0 molar equivalent(s), relative to the Compound (IV-1-3'-1).

The reaction may be carried out at room temperature to under heating, for example at room temperature to 150° C., preferably at room temperature to 100° C.

Alternatively, the Compound (IV-1-3'-1) may also be reacted in the presence of chloroform and a base to produce the Compound (IV-1-3').

Examples of the base include alkali metal hydroxides such as sodium hydroxide.

The amount of the base to be used may be 1.0 to 20.0 molar equivalent(s), preferably 1.0 to 15.0 molar equivalent(s), relative to the Compound (IV-1-3'-1).

The reaction may be carried out at room temperature to under heating, for example at room temperature to 150° C., preferably at room temperature to 100° C.

Alternatively, the Compound (IV-1-3'-1) may also be reacted with a formylating agent in a solvent and in the presence of a catalyst to produce the Compound (IV-1-3').

The solvent may be any one which does not affect the reaction, and examples thereof include ethers such as tetrahydrofuran, 1,4-dioxane, diethyl ether, and tert-butyl methyl ether; halogenated aliphatic hydrocarbons such as chloroform and dichloromethane; aromatic hydrocarbons such as toluene; nitriles such as acetonitrile; water; and mixtures thereof.

Examples of the catalyst include aluminum(III) chloride.

Examples of the formylating agent include triethyl orthoformate.

The amount of the catalyst to be used may be 0.01 to 1.0 molar equivalent, preferably 0.05 to 0.5 molar equivalent, relative to the Compound (IV-1-3'-1).

The amount of the formylating agent to be used may be 1.0 to 5.0 molar equivalent(s), preferably 1.0 to 3.0 molar equivalent(s), relative to the Compound (IV-1-3'-1).

The reaction may be carried out at room temperature to under heating, for example at room temperature to 150° C., preferably at room temperature to 100° C.

Alternatively, a compound wherein the ring D moiety of the Compound (IV-1-3'-1) is a precursor of ring D may also be used as a starting material instead of the Compound (IV-1-3'-1) to carry out the same reaction as that described above, produce a compound wherein the ring D moiety of the Compound (IV-1-3') is the precursor of ring D, and then form a ring D to produce the Compound (IV-1-3').

Reference Production Method 7

The Compound (IV-1) may also be produced according to the following scheme.

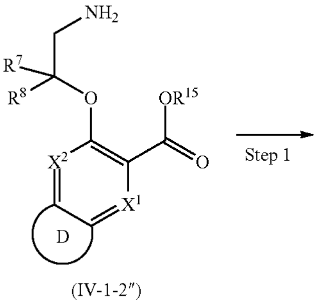

(IV-1-2'')

-continued

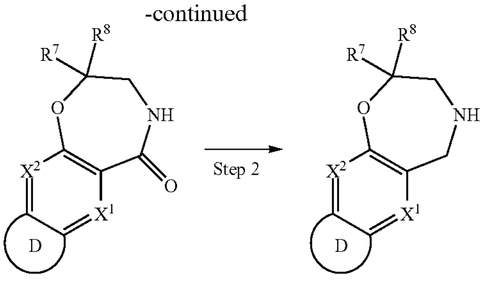

(IV-1-1″) (IV-1)

[wherein $R^{15}$ represents an alkyl group such as a methyl group and an ethyl group; and the other symbols have the same meanings as those described above.]

Step 1

The Compound (IV-1-2") may be reacted in a solvent and in the presence of a base to produce the Compound (IV-1-1"). The Compound (IV-1-2") may be in the free body or a salt form such as hydrochloride.

The solvent may be any one which does not affect the reaction, and examples thereof include ethers such as tetrahydrofuran and 1,4-dioxane; alcohols such as methanol, ethanol, and isopropanol; aromatic hydrocarbons such as toluene; nitriles such as acetonitrile; water; and mixtures thereof.

Examples of the base include alkali metal carbonates such as sodium carbonate, potassium carbonate, and sodium hydrogen carbonate; alkali metal hydrides such as sodium hydride; alkylamines such as triethylamine and N,N-diisopropylethylamine; pyridines such as pyridine and 4-dimethylaminopyridine; and 1,8-diazabicyclo[5.4.0]-7-undecene.

The amount of the base to be used may be 1.0 to 10.0 molar equivalent(s), preferably 1.0 to 5.0 molar equivalent(s), relative to the Compound (IV-1-2").

The reaction may be carried out under ice-cooling to under heating, for example under ice-cooling to 100° C., preferably under ice-cooling to room temperature.

Step 2

The Compound (IV-1-1") may be reacted in a solvent and in the presence of a reducing agent to produce the Compound (IV-1).

The solvent may be any one which does not affect the reaction, and examples thereof include ethers such as tetrahydrofuran and 1,4-dioxane; alcohols such as methanol, ethanol, and isopropanol; aromatic hydrocarbons such as toluene; nitriles such as acetonitrile; and mixtures thereof.

Examples of the reducing agent include sodium cyanoborohydride, sodium borohydride, lithium aluminum hydride, and borane-tetrahydrofuran complex.

The amount of the reducing agent to be used may be 1.0 to 10.0 molar equivalent(s), preferably 1.0 to 5.0 molar equivalent(s), relative to the Compound (IV-1-1").

The reaction may be carried out under ice-cooling to under heating, for example under ice-cooling to 100° C., preferably under ice-cooling to 80° C.

Alternatively, a compound wherein the ring D moiety of the Compound (IV-1-2") is a precursor of ring D may also be used as a starting material instead of the Compound (IV-1-2") to carry out the same reaction as that described above, produce a compound wherein the ring D moiety of the Compound (IV-1-1') is the precursor of ring D, or produce a compound wherein the ring D moiety of the Compound (IV-1) is the precursor of ring D, and then form a ring D to produce the Compound (IV-1).

The Compound (IV-1-2") may be produced according to, for example, the following scheme.

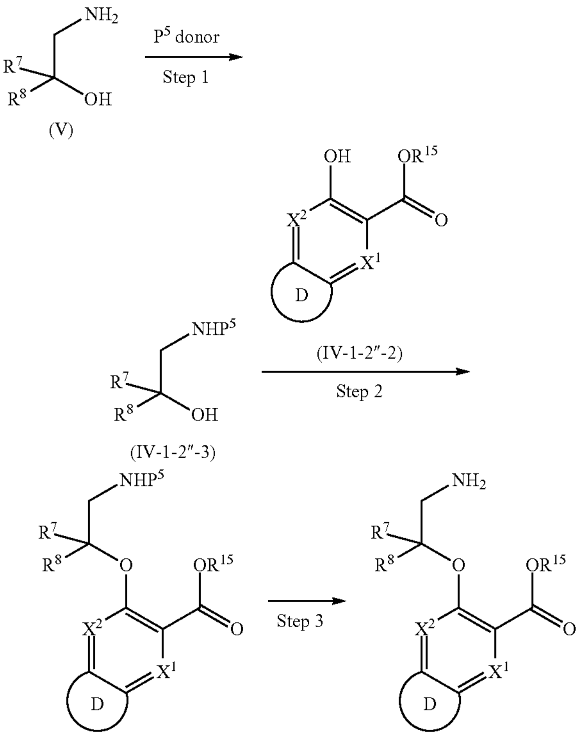

(V) (IV-1-2″-2) (IV-1-2″-3) (IV-1-2″-1) (IV-1-2″)

[wherein $P^5$ represents a protecting group such as a tert-butoxycarbonyl group; and the other symbols have the same meanings as those described above.]

Step 1

The Compound (V) may be reacted with a $P^5$ donor in a solvent to produce the Compound (IV-1-2"-3). The Compound (V) may be a commercially available material, or may be produced according to known method(s) from commercially available material(s).

The solvent may be any one which does not affect the reaction, and examples thereof include ethers such as tetrahydrofuran and 1,4-dioxane; halogenated aliphatic hydrocarbons such as chloroform and dichloromethane; alcohols such as methanol, ethanol, and isopropanol; aromatic hydrocarbons such as toluene; nitriles such as acetonitrile; carboxylic acids such as acetic acid; water; and mixtures thereof.

Examples of the $P^5$ donor include di-tert-butyl dicarbonate.

The amount of the $P^5$ donor to be used may be 1.0 to 3.0 molar equivalent(s), preferably 1.0 to 2.0 molar equivalent(s), relative to the Compound (V).

The reaction may be carried out at room temperature to under heating, for example at room temperature to 100° C., preferably at room temperature.

Step 2

The Compound (IV-1-2"-3) may be reacted with the Compound (IV-1-2"-2) in a solvent and in the presence of an azodicarboxylic acid derivative and a phosphine derivative to produce the Compound (IV-1-2"-1). The Compound (IV-1-2"-2) may be a commercially available material, or may be produced according to known method(s) from commercially available material(s).

The solvent may be any one which does not affect the reaction, and examples thereof include ethers such as tetrahydrofuran and 1,4-dioxane; halogenated aliphatic hydrocarbons such as chloroform and dichloromethane; aromatic hydrocarbons such as toluene; nitriles such as acetonitrile; and mixtures thereof.

Examples of the azodicarboxylic acid derivative include azodicarboxylic acid dialkyl esters such as diethyl azodicarboxylate and diisopropyl azodicarboxylate; and azodicarboxamides such as (E)-N1,N1,N2,N2-tetramethyldiazene-1,2-dicarboxamide.

Examples of the phosphine derivative include triarylphosphines such as triphenylphosphine; and trialkylphosphines such as tri-n-butylphosphine.

The amount of the Compound (IV-1-2"-2) to be used may be 1.0 to 3.0 molar equivalent(s), preferably 1.0 to 2.0 molar equivalent(s), relative to the Compound (IV-1-2"-3).

The amount of the azodicarboxylic acid derivative to be used may be 1.0 to 5.0 molar equivalent(s), preferably 1.0 to 3.0 molar equivalent(s), relative to the Compound (IV-1-2"-3).

The amount of the phosphine derivative to be used may be 1.0 to 5.0 molar equivalent(s), preferably 1.0 to 3.0 molar equivalent(s), relative to the Compound (IV-1-2"-3).

The reaction may be carried out under ice-cooling to under heating, for example under ice-cooling to 50° C., preferably under ice-cooling to room temperature.

Step 3

The Compound (IV-1-2"-1) may be reacted in a solvent and in the presence of an acid to produce the Compound (IV-1-2").

The solvent may be any one which does not affect the reaction, and examples thereof include ethers such as tetrahydrofuran, 1,4-dioxane, and cyclopentyl methyl ether; halogenated aliphatic hydrocarbons such as chloroform and dichloromethane; aromatic hydrocarbons such as toluene; nitriles such as acetonitrile; and mixtures thereof.

Examples of the acid include hydrogen chloride.

The amount of the acid to be used may be 1.0 to 10.0 molar equivalent(s), preferably 1.0 to 5.0 molar equivalent(s), relative to the Compound (IV-1-2"-1).

The reaction may be carried out under ice-cooling to under heating, for example under ice-cooling to 100° C., preferably under ice-cooling to 80° C.

Further, when a protecting group such as a tetrahydropyranyl group is present on the ring D of the Compound (IV-1-2"-1), the protecting group on the ring D may also be removed by the present reaction.

Alternatively, a compound wherein the ring D moiety of the Compound (IV-1-2"-2) is a precursor of ring D may also be used as a starting material instead of the Compound (IV-1-2"-2) to carry out the same reaction as that described above, produce a compound wherein the ring D moiety of the Compound (IV-1-2"-1) is the precursor of ring D, or produce a compound wherein the ring D moiety of the Compound (IV-1-2") is the precursor of ring D, and then form a ring D to produce the Compound (IV-1-2").

Reference Production Method 8

Among the Compounds (IV), the Compound (IV-2)

(IV-2)

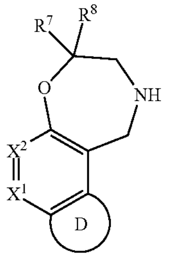

[wherein the symbols have the same meanings as those described above.]

may be produced according to the same method as the method described in the Reference production method 5, 6, or 7 by using the Compound (IV-2-2), the Compound (IV-2-4), the Compound (IV-2-2-1), the Compound (IV-2-3'), the Compound (IV-2-3'-1), or the Compound (IV-2-2"-2)

(IV-2-2)

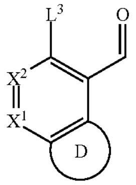

(IV-2-4)

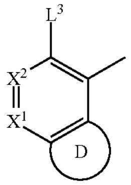

(IV-2-2-1)

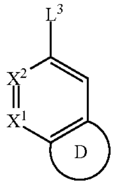

(IV-2-3′)

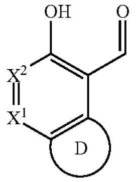

(IV-2-3′1)

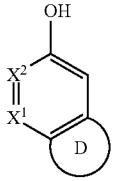

-continued (IV-2-2″-2)

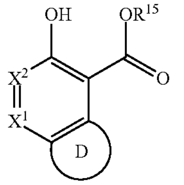

[wherein the symbols have the same meanings as those described above.]
or a compound wherein the ring D moiety of anyone of these compounds is a precursor of ring D as a starting material instead of the Compound (IV-1-2), the Compound (IV-1-4), the Compound (IV-1-2-1), the Compound (IV-1-3'), the Compound (IV-1-3'-1), or the Compound (IV-1-2"-2).
Reference Production Method 9

Among the Compounds (IV), the Compound (IV-3)

(IV-3)

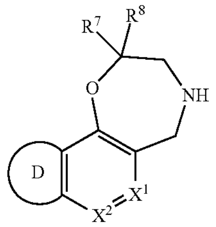

[wherein the symbols have the same meanings as those described above.]
may be produced according to the same method as the method described in the Reference production method 5, 6, or 7 by using the Compound (IV-3-2), the Compound (IV-3-4), the Compound (IV-3-2-1), the Compound (IV-3-3'), the Compound (IV-3-3'-1), or the Compound (IV-3-2"-2)

(IV-3-2)

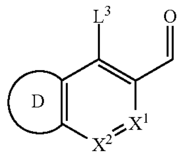

(IV-3-4)

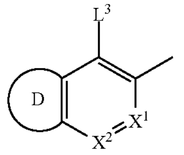

(IV-3-2-1)

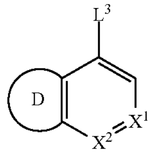

(IV-3-3')

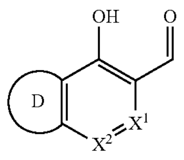

-continued (IV-3-3'-1)

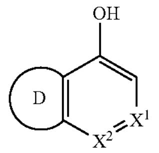

(IV-3-2″-2)

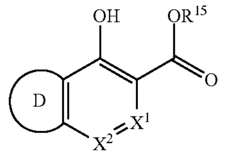

[wherein the symbols have the same meanings as those described above.]
or a compound wherein the ring D moiety of anyone of these compounds is a precursor of ring D as a starting material instead of the Compound (IV-1-2), the Compound (IV-1-4), the Compound (IV-1-2-1), the Compound (IV-1-3'), the Compound (IV-1-3'-1), or the Compound (IV-1-2"-2).

The resulting target compound may be separated or purified if necessary, by appropriately combining conventional method(s) such as recrystallization, reprecipitation, filtration, concentration, and drying, or methods usually used in the separation or purification of organic compounds (for example, column chromatography).

The Compounds (I) of the present invention and intermediate compounds thereof may be produced according to the above Production methods, as well as the methods described in the following Examples and Reference Examples. Further, the Compounds (I) of the present invention and intermediate compounds thereof may be converted into other target compounds and intermediate compounds thereof by the above Production methods, methods described in the following Examples and Reference Examples, and/or known methods, or combined methods thereof. Examples of such methods include the methods described in the following (1) to (26).

(1) Conversion of Alkoxycarbonyl Group into Carboxy Group

A compound having an alkoxycarbonyl group may be reacted in a solvent (for example, dimethyl sulfoxide, tetrahydrofuran, methanol, ethanol, water, and a mixture thereof) and in the presence of a base (for example, potassium hydroxide and lithium hydroxide) or an acid (for example, sulfuric acid) to produce a compound having a corresponding carboxy group.

(2) Alkylation of Nitrogen Atom on Nitrogen-Containing Ring

A compound having a nitrogen-containing ring may be reacted with an alkylating agent (for example, a methylating agent such as methyl iodide) in a solvent (for example, dimethylformamide) and in the presence of a base (for example, sodium hydride) to produce a corresponding compound in which a nitrogen atom on the nitrogen-containing ring is alkylated.

(3) Conversion of Nitro Group into Tert-Butyl Carbamate Group

A compound having a nitro group may be reacted with a tert-butyl group donor (for example, di-tert-butyl dicarbonate) in a solvent (for example, ethanol), under hydrogen atmosphere, and in the presence of a catalyst (for example, palladium carbon) to produce a compound having a corresponding tert-butyl carbamate group.

(4) Acetylation of Amino Group

A compound having an amino group may be reacted with an acetylating agent (for example, acetic anhydride) in a solvent (for example, ethyl acetate) to acetylate the amino group.

(5) Removal of N-Acetyl Group

A compound having an N-acetyl group may be reacted in a solvent (for example, tetrahydrofuran) and in the presence of a base (for example, sodium hydroxide) to remove the acetyl group.

(6) Conversion of 8-acetamide-7-methyl-2,3-dihydrobenzo[f][1,4]oxazepinyl group into 1-acetyl-8-ethyl-1,5,7,8-tetrahydro-6H-[1,4]oxazepino[6,7-f] indazolyl group A compound having a 8-acetamide-7-methyl-2,3-dihydrobenzo[f][1,4]oxazepinyl group may be reacted in a solvent (for example, ethyl acetate) and in the presence of a base (for example, potassium acetate), a diazotizing agent (for example, n-amyl nitrite), a catalyst (for example, tetrabutylammonium bromide), and acetic anhydride to produce a compound having a corresponding 1-acetyl-8-ethyl-1,5,7,8-tetrahydro-6H-[1,4]oxazepino[6,7-f]indazolyl group.

(7) Conversion of Cyano Group into Formyl Group

A compound having a cyano group may be reacted in a solvent (for example, toluene) and in the presence of a reducing agent (for example, diisobutylaluminum hydride) to produce a compound having a corresponding formyl group.

(8) Conversion of Alkoxycarbonyl Group into Hydroxymethyl Group

A compound having an alkoxycarbonyl group may be reacted in a solvent (for example, toluene and tert-butyl methyl ether) and in the presence of a reducing agent (for example, diisobutylaluminum hydride and sodium bis(2-methoxyethoxy)aluminum hydride) to produce a compound having a corresponding hydroxymethyl group.

(9) Conversion of Hydroxymethyl Group into Formyl Group

A compound having a hydroxymethyl group may be reacted in a solvent (for example, dichloromethane) and in the presence of an oxidizing agent (for example, Dess-Martin periodinane) to produce a compound having a corresponding formyl group.

(10) Conversion of Halogen Atom into Azetidin-1-yl Group

A compound having a halogen atom may be reacted with azetidine in a solvent (for example, toluene) and in the presence of a base (for example, sodium tert-butoxide), a catalyst (for example, tris(dibenzylideneacetone)dipalladium(0)), and a ligand (for example, xantphos) to produce a compound having a corresponding azetidin-1-yl group.

(11) Conversion of Azetidin-1-Yl Group into 3-Halogenated Propylamino Group

A compound having an azetidin-1-yl group may be reacted in a solvent (for example, 1,4-dioxane) and in the presence of a hydrogen halide (for example, hydrogen chloride) to produce a compound having a corresponding 3-halogenated propylamino group.

(12) Conversion of 7-((3-chloropropyl)amino)-2,3-dihydropyrido[2,3-f][1,4]oxazepinyl group into 1, 3, 4, 9,10,11-hexahydro-2H-pyrimido[1',2':1,6]pyrido [2,3-f][1,4]oxazepinyl group A compound having a 7-((3-chloropropyl)amino)-2,3-dihydropyrido[2,3-f][1,4]oxazepinyl group may be reacted in a solvent (for example, acetonitrile) to produce a compound having a corresponding 1,3,4,9,10,11-hexahydro-2H-pyrimido[1',2':1,6]pyrido[2,3-f][1,4]oxazepinyl group.

(13) Halogen Atom Exchange Reaction

A compound having a halogen atom may be reacted with a hydrogen halide (for example, hydrogen chloride) in a solvent (for example, tetrahydrofuran), and then reacted with a halogenating agent having another halogen atom (for example, sodium iodide) in a solvent (for example, acetonitrile) to produce a compound having the corresponding another halogen atom.

(14) Conversion of Formylphenyl Group into Isoquinolinyl Group

A compound having a formylphenyl group may be reacted with 2,2-dimethoxyethane-1-amine in a solvent (for example, toluene), and then reacted in the presence of a condensing agent (for example, polyphosphoric acid) to produce a compound having a corresponding isoquinolinyl group.

(15) Conversion of Halogen Atom into Formyl Group

A compound having a halogen atom may be reacted with a formylating agent (for example, dimethylformamide) in a solvent (for example, diethyl ether and tetrahydrofuran) and in the presence of an organic metal reagent (for example, alkyllithiums such as n-butyllithium; and Grignard reagents) to produce a compound having a corresponding formyl group.

(16) Conversion of Alkoxy Group into Hydroxy Group

A compound having an alkoxy group may be reacted in a solvent (for example, dichloromethane) and in the presence of a dealkylating agent (for example, boron tribromide) to produce a compound having a corresponding hydroxy group.

(17) Conversion of 1,2-dihydroxyphenyl Group into 2,2-dimethylbenzo[d][1,3]dioxole Group A compound having a 1,2-dihydroxyphenyl group may be reacted with 2,2-dimethoxypropane in a solvent (for example, toluene) and in the presence of a catalyst (for example, pyridinium p-toluenesulfonate) to produce a compound having a corresponding 2,2-dimethylbenzo[d][1,3] dioxole group.

(18) Protection of Nitrogen Atom of Nitrogen-Containing Ring by Tetrahydropyranyl Group A compound having a nitrogen-containing ring may be reacted with dihydropyran in a solvent (for example, dichloromethane, tetrahydrofuran, and a mixture thereof) and in the presence of an acid (for example, methanesulfonic acid) to protect a nitrogen atom of the nitrogen-containing ring by a tetrahydropyranyl group.

(19) Conversion of Halogen Atom into (Trimethylsilyl)Ethynyl Group

A compound having a halogen atom may be reacted with ethynyltrimethylsilane in a solvent (for example, triethylamine) and in the presence of a catalyst (for example, bis(triphenylphosphine)palladium(II) dichloride, copper(I) iodide, and a mixture thereof) to produce a compound having a corresponding (trimethylsilyl)ethynyl group.

(20) Conversion of Formyl Group into (Methoxycarbonyl)Ethenyl Group

A compound having a formyl group may be reacted with methyl diethylphosphonoacetate in a solvent (for example, tetrahydrofuran) and in the presence of a base (for example, sodium hydride) to produce a compound having a corresponding (methoxycarbonyl)ethenyl group.

(21) Removal of Trimethylsilyl Group

A compound having a trimethylsilyl group may be reacted in a solvent (for example, methanol) and in the presence of a base (for example, potassium carbonate) to remove the trimethylsilyl group.

(22) Conversion of 1-ethynyl-2-(methoxycarbonyl)ethenylphenyl Group into 2-hydroxy-3-methoxycarbonylnaphthyl Group A compound having a 1-ethynyl-2-(methoxycarbonyl) ethenylphenyl group may be reacted with 2,2-dimethoxypropane in a solvent (for example, chlorobenzene), in the presence of an oxidizing agent (for example, pyridine N-oxide) and a catalyst (for example, bis(1,5-cyclooctadiene) rhodium(I) trifluoromethanesulfonate), and in the presence or absence of a ligand (for example, tri-p-tolylphosphine) to produce a compound having a corresponding 2-hydroxy-3-methoxycarbonylnaphthyl group.

(23) Conversion of Alkoxycarbonyl Group into Benzyloxycarbonyl Group

A compound having an alkoxycarbonyl group may be reacted with benzylalcohol to produce a compound having a corresponding benzyloxycarbonyl group.

(24) Conversion of Carboxy Group into Alkoxycarbonyl Group

A compound having a carboxy group may be reacted with an alcohol (for example, methanol and ethanol) in the presence of an acid (for example, sulfuric acid) or a base (for example, sodium hydroxide) to produce a compound having a corresponding alkoxycarbonyl group.

(25) Conversion of Carboxy Group into Benzyloxycarbonyl Group

A compound having a carboxy group may be reacted with benzylalcohol in a solvent (for example, chloroform) and in the presence of an activating agent (for example, 4-dimethylaminopyridine) and a condensing agent (for example, 1-(3-dimethylaminopropyl)-3-ethylcarbodiimide hydrochloride) to produce a compound having a corresponding benzyloxycarbonyl group. Alternatively, a compound having a carboxy group may be reacted with a halogenated benzyl (for example, benzyl bromide) in a solvent (for example, dimethylformamide) and in the presence of a base (for example, cesium carbonate) to produce a compound having a corresponding benzyloxycarbonyl group.

(26) Ester Exchange Reaction of Alkoxycarbonyl Group

A compound having an alkoxycarbonyl group may be reacted with an alcohol having another alkyl group (for example, methanol and ethanol) in the presence of an acid (for example, sulfuric acid) or a base (for example, sodium hydroxide) to produce a compound having a corresponding another alkoxycarbonyl group.

Further, different starting materials from the starting materials described in the above Production methods, and the following Examples and Reference Examples may be used, and the above Production methods, methods described in the following Examples and Reference Examples, and/or known methods, or combined methods thereof may be used, to produce other Compounds (I) of the present invention or intermediate compounds thereof.

EXAMPLES

Hereinafter, the present invention is illustrated more in detail by way of Examples, Reference Examples, Test Examples, and the like, but the present invention is not limited to them.

The term "DIOL silica gel" in silica gel column chromatography refers to CHROMATOREX (trade name) DIOL manufactured by Fuji Silysia Chemical Ltd.

The term "Bond Elut" refers to Bond Elut C18 (trade name) manufactured by Agilent Technologies, Inc.

When two or more mass spectrum values are observed due to the presence of isotope(s), only the minimum m/z value is described. The term "DUIS" in the ionization mode of mass spectrum refers to a mixed mode of ESI and APCI.

Unless otherwise specified, a $^1$H-NMR is expressed as a chemical shift (δ) using tetramethylsilane as an internal standard (0 ppm), and a coupling constant (J value) is expressed by Hz. Also, abbreviations of splitting pattern of each peak are as follows. s: singlet, d: doublet, t: triplet, br: broad, m: multiplet.

Abbreviations described in Examples, Reference Examples, and chemical structures have meanings usually used in the field of organic chemistry or pharmacy. Specifically, each abbreviation is understood by a skilled person as follows.

Boc: tert-butoxycarbonyl group
Cbz: benzyloxycarbonyl group
DMSO: dimethyl sulfoxide PMB: p-methoxybenzyl group
TFA: trifluoroacetic acid
THP: tetrahydropyranyl group
tert-: tertiary
n-: normal
M: molar concentration
ESI: electrospray ionization
APCI: atmospheric pressure chemical ionization

EXAMPLES

Example 1-(a)

Production of methyl 3-(1,4-dimethyl-1H-benzo[d][1,2,3]triazol-5-yl)-3-(3-(((R)-6-ethyl-2,2-difluoro-6,7-dihydro-[1,3]dioxolo[4',5':4,5]benzo[1,2-f][1,4]oxazepin-8(9H)-yl)methyl)-4-methylphenyl)-2,2-dimethylpropanoate

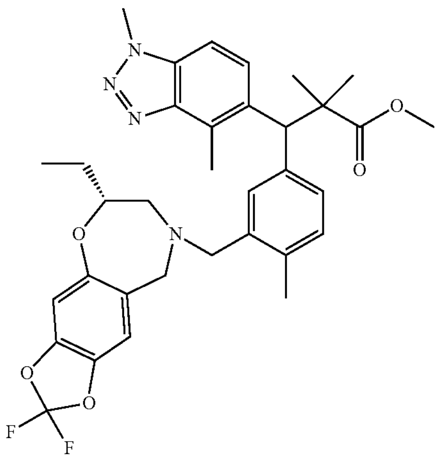 [SMILES: CC[C@@H]1CN(Cc2cc(C(c3ccc4c(nnn4C)c3C)C(C)(C)C(=O)OC)ccc2C)Cc2cc3c(cc2O1)OC(F)(F)O3]

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (20 mg) in dichloromethane (1 mL) was added (R)-6-ethyl-2,2-difluoro-6,7,8,9-tetrahydro-[1,3]dioxolo[4',5':4,5]benzo[1,2-f][1,4]oxazepine hydrochloride produced in the Reference Example 1-(d) (24 mg) under argon gas flow with stirring at room temperature, and the resulting mixture was stirred at room temperature for 1 hour. Then, sodium triacetoxyborohydride (25 mg) was added thereto with stirring at room temperature, and the resulting mixture was stirred at room temperature for 3 hours. After the reaction was completed, to the reaction solution was added a saturated aqueous solution of sodium hydrogen carbonate, and the resulting mixed solution was subjected to extraction twice with dichloromethane. The resulting organic layer was concentrated under reduced pressure, and the resulting residues were purified by a silica gel column (elution solvent; hexane:ethyl acetate) to give the title compound (24 mg) as a colorless oil.

As an alternative method, the title compound was also produced according to the following method.

(1) To a solution of methyl 3-(1,4-dimethyl-1H-benzo[d][1,2,3]triazol-5-yl)-3-(3-(hydroxymethyl)-4-methylphenyl)-2,2-dimethylpropanoate produced according to the same manner as the Reference Example 1-(h) (200 mg) in dichloromethane (4 mL) was added thionyl chloride (0.077 mL) under argon gas flow with stirring at room temperature, and the resulting mixture was stirred at room temperature for 1 hour. After the reaction was completed, the reaction solution was concentrated under reduced pressure to give a crude product comprising methyl 3-(3-(chloromethyl)-4-methylphenyl)-3-(1,4-dimethyl-1H-benzo[d][1,2,3]triazol-5-yl)-2,2-dimethylpropanoate.

(2) To a solution of the crude product comprising methyl 3-(3-(chloromethyl)-4-methylphenyl)-3-(1,4-dimethyl-1H-benzo[d][1,2,3]triazol-5-yl)-2,2-dimethylpropanoate produced in (1) in acetonitrile (4 mL) were added (R)-6-ethyl-2,2-difluoro-6,7,8,9-tetrahydro-[1,3]dioxolo[4',5':4,5]benzo[1,2-f][1,4]oxazepine produced in the Reference Example 1-(k) (162 mg) and N,N-diisopropylethylamine (0.27 mL) under argon gas flow with stirring, and the resulting mixture was stirred at room temperature for 1 hour, and then stirred at 60° C. for 2.5 hours. After the reaction was completed, the reaction solution was diluted with ethyl acetate, washed sequentially with water and saturated brine, dried over anhydrous magnesium sulfate, filtered, and concentrated under reduced pressure. The resulting residues were purified by a silica gel column (elution solvent; hexane ethyl acetate) to give the title compound (260 mg) as a white foam.

Mass spectrum (ESI, m/z): 621 $[M+H]^+$ $^1$H-NMR spectrum (400 MHz, DMSO-$d_6$) δ: 7.63-7.53 (m, 2H), 7.15-6.99 (m, 5H), 4.78-4.71 (m, 1H), 4.28-4.20 (m, 3H), 3.93-3.85 (m, 1H), 3.81-3.55 (m, 2H), 3.53-3.38 (m, 5H), 2.77-2.62 (m, 5H), 2.25-2.16 (m, 3H), 1.47-1.35 (m, 1H), 1.33-1.08 (m, 7H), 0.97-0.78 (m, 3H)

Example 1-(b)

Production of 3-(1,4-dimethyl-1H-benzo[d][1,2,3]triazol-5-yl)-3-(3-(((R)-6-ethyl-2,2-difluoro-6,7-dihydro-[1,3]dioxolo[4',5':4,5]benzo[1,2-f][1,4]oxazepin-8(9H)-yl)methyl)-4-methylphenyl)-2,2-dimethylpropanoic Acid

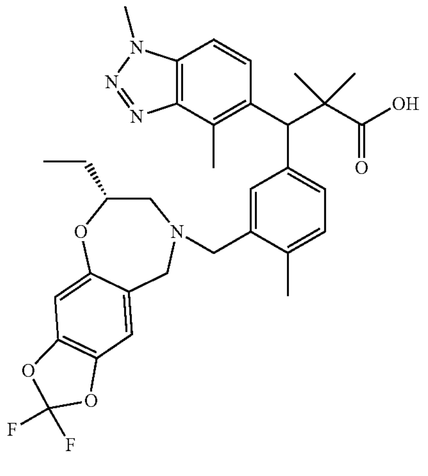 [SMILES: CC[C@@H]1CN(Cc2cc(C(c3ccc4c(nnn4C)c3C)C(C)(C)C(=O)O)ccc2C)Cc2cc3c(cc2O1)OC(F)(F)O3]

To a solution of methyl 3-(1,4-dimethyl-1H-benzo[d][1,2,3]triazol-5-yl)-3-(3-(((R)-6-ethyl-2,2-difluoro-6,7-dihydro-[1,3]dioxolo[4',5':4,5]benzo[1,2-f][1,4]oxazepin-8(9H)-yl)methyl)-4-methylphenyl)-2,2-dimethylpropanoate produced in the Example 1-(a) (23 mg) in dimethyl sulfoxide (2 mL) was added dropwise a 1 M aqueous solution of potassium hydroxide (0.371 mL) with stirring at room temperature, and the resulting mixture was stirred at 70° C.

for 2 hours. After the reaction was completed, to the reaction solution was added water (5 mL), 1 M hydrochloric acid was added thereto to adjust the pH to 5.0, and the resulting mixture was stirred overnight. The resulting solids were collected by filtration, washed with water, and dried under reduced pressure at 65° C. to give the title compound (16 mg) as white solids.

Mass spectrum (ESI, m/z): 607 $[M+H]^+$ $^1$H-NMR spectrum (400 MHz, $CD_3OD$) δ: 7.77-7.68 (m, 1H), 7.53-7.46 (m, 1H), 7.24-7.17 (m, 1H), 7.11-7.06 (m, 1H), 7.04-6.97 (m, 1H), 6.88-6.83 (m, 1H), 6.71-6.62 (m, 1H), 4.97-4.71 (m, 1H), 4.30-4.24 (m, 3H), 3.92-3.82 (m, 1H), 3.77-3.64 (m, 1H), 3.60-3.45 (m, 3H), 2.90-2.66 (m, 5H), 2.30-2.23 (m, 3H), 1.55-1.12 (m, 8H), 1.01-0.87 (m, 3H)

Example 2-(a)

Production of methyl 3-(1,4-dimethyl-1H-benzo[d][(1,2,3]triazol-5-yl)-3-(3-(((R)-9-ethyl-2,2-difluoro-8,9-dihydro-[1,3]dioxolo[4',5':3,4]benzo[1,2-f][1,4]oxazepin-7 (6H)-yl)methyl)-4-methylphenyl)-2,2-dimethylpropanoate

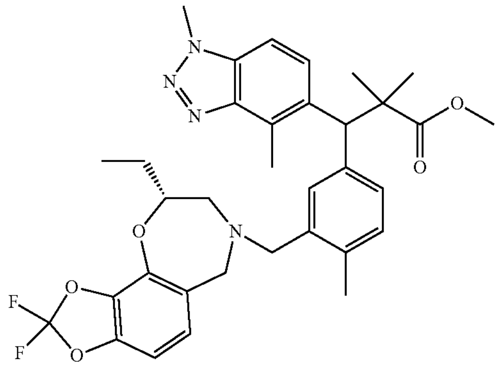 [SMILES: CC[C@@H]1CN(Cc2cc(C(c3ccc4c(nnn4C)c3C)C(C)(C)C(=O)OC)ccc2C)Cc2ccc3c(c2O1)OC(F)(F)O3]

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (20 mg) in dichloromethane (1 mL) was added (R)-9-ethyl-2,2-difluoro-6,7,8,9-tetrahydro-[1,3]dioxolo[4',5':3,4]benzo[1,2-f][1,4]oxazepine produced in the Reference Example 2-(d) (23 mg) under argon gas flow with stirring at room temperature, and the resulting mixture was stirred at room temperature for 1 hour. Then, sodium triacetoxyborohydride (25 mg) was added thereto with stirring at room temperature, and the resulting mixture was stirred at room temperature overnight. After the reaction was completed, to the reaction solution was added a saturated aqueous solution of sodium hydrogen carbonate, and the resulting mixed solution was subjected to extraction twice with dichloromethane. The resulting organic layer was concentrated under reduced pressure, and the resulting residues were purified by a silica gel column (elution solvent; hexane:ethyl acetate) to give the title compound (35 mg) as a colorless oil.

Mass spectrum (ESI, m/z): 621 $[M+H]^+$ $^1$H-NMR spectrum (400 MHz, DMSO-$d_6$) δ: 7.60-7.54 (m, 2H), 7.15-6.97 (m, 3H), 6.95-6.81 (m, 1H), 6.73-6.56 (m, 1H), 4.78-4.71 (m, 1H), 4.28-4.21 (m, 3H), 4.07-3.82 (m, 2H), 3.68-3.56 (m, 1H), 3.49-3.38 (m, 5H), 2.83-2.77 (m, 2H), 2.72-2.63 (m, 3H), 2.21 (s, 3H), 1.55-1.39 (m, 1H), 1.36-1.14 (m, 7H), 0.96-0.88 (m, 3H)

Example 2-(b)

Production of 3-(1,4-dimethyl-1H-benzo[d][1,2,3]triazol-5-yl)-3-(3-(((R)-9-ethyl-2,2-difluoro-8,9-dihydro-[1,3]dioxolo[4',5':3,4]benzo[1,2-f][1,4]oxazepin-7(6H)-yl)methyl)-4-methylphenyl)-2,2-dimethylpropanoic Acid

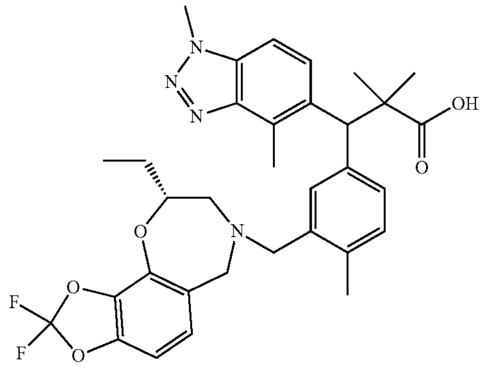 [SMILES: CC[C@@H]1CN(Cc2cc(C(c3ccc4c(nnn4C)c3C)C(C)(C)C(=O)O)ccc2C)Cc2ccc3c(c2O1)OC(F)(F)O3]

To a solution of methyl 3-(1,4-dimethyl-1H-benzo[d][1,2,3]triazol-5-yl)-3-(3-(((R)-9-ethyl-2,2-difluoro-8,9-dihydro-[1,3]dioxolo[4',5':3,4]benzo[1,2-f][1,4]oxazepin-7 (6H)-yl)methyl)-4-methylphenyl)-2,2-dimethylpropanoate produced in the Example 2-(a) (33 mg) in dimethyl sulfoxide (2 mL) was added dropwise a 1 M aqueous solution of potassium hydroxide (0.532 mL) with stirring at room temperature, and the resulting mixture was stirred at 70° C. for 2 hours. After the reaction was completed, to the reaction solution was added water (5 mL), 1 M hydrochloric acid was added thereto to adjust the pH to 5.0, and the resulting mixture was stirred overnight. The resulting solids were collected by filtration, washed with water, and dried under reduced pressure at 65° C. to give the title compound (23 mg) as white solids.

Mass spectrum (ESI, m/z): 607 $[M+H]^+$ $^1$H-NMR spectrum (400 MHz, $CD_3OD$) δ: 7.73-7.68 (m, 1H), 7.52-7.46 (m, 1H), 7.24-7.17 (m, 1H), 7.11-7.05 (m, 1H), 7.04-6.94 (m, 1H), 6.62-6.30 (m, 2H), 4.96-4.79 (m, 1H), 4.31-4.24 (m, 3H), 3.92-3.77 (m, 2H), 3.63-3.44 (m, 3H), 2.96-2.79 (m, 2H), 2.77-2.68 (m, 3H), 2.30-2.22 (m, 3H), 1.61-1.47 (m, 1H), 1.42-1.20 (m, 7H), 1.03-0.94 (m, 3H)

Example 3-(a)

Production of methyl 3-(1,4-dimethyl-1H-benzo[d][1,2,3]triazol-5-yl)-3-(3-(((R)-2-ethyl-2,3,5,7,8,9-hexahydro-4H-indeno[5,6-f][1,4]oxazepin-4-yl)methyl)-4-methylphenyl)-2,2-dimethylpropanoate

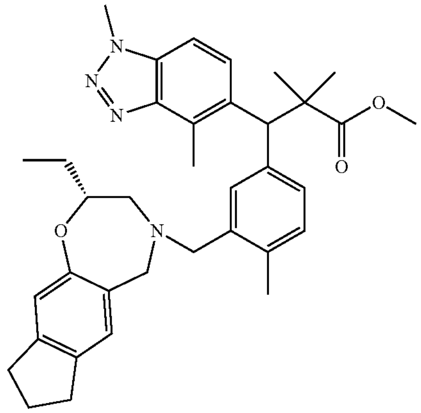 [SMILES: CC[C@@H]1CN(Cc2cc(C(c3ccc4c(nnn4C)c3C)C(C)(C)C(=O)OC)ccc2C)Cc2cc3c(cc2O1)CCC3]

A solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (54 mg) and (R)-2-ethyl-3,4,5,7,8,9-hexahydro-2H-indeno[5,6-f][1,4]oxazepine produced in the Reference Example 3-(d) (46 mg) in dichloromethane (1 mL) was stirred under argon gas flow at room temperature for 0.5 hour. Then, sodium triacetoxyborohydride (63 mg) was added thereto with stirring at room temperature, and the resulting mixture was stirred at room temperature overnight. After the reaction was completed, to the reaction solution was added a saturated aqueous solution of sodium hydrogen carbonate, and the resulting mixed solution was subjected to extraction twice with dichloromethane. The resulting organic layer was concentrated under reduced pressure, and the resulting residues were purified by a silica gel column (elution solvent; hexane:ethyl acetate) to give the title compound (72 mg) as a colorless oil.

As an alternative method, the title compound was also produced according to the following method.

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (235 mg) in acetonitrile (5 mL) were sequentially added (R)-2-ethyl-3,4,5,7,8,9-hexahydro-2H-indeno[5,6-f][1,4]oxazepine produced according to the same manner as the Reference Example 3-(d) (150 mg) and N,N-diisopropylethylamine (0.307 mL) under argon gas flow with stirring at room temperature, and the resulting mixture was stirred at room temperature for 6.5 hours and at 60° C. for 2 hours. After the reaction was completed, the reaction solution was concentrated under reduced pressure. The resulting residues were purified by a silica gel column (elution solvent; hexane:ethyl acetate) to give the title compound (291 mg) as a colorless oil.

Mass spectrum (ESI, m/z): 581 $[M+H]^+$ $^1$H-NMR spectrum (400 MHz, DMSO-$d_6$) δ: 7.63-7.53 (m, 2H), 7.14-7.01 (m, 3H), 6.85-6.76 (m, 2H), 4.78-4.73 (m, 1H), 4.26-4.21 (m, 31), 3.83-3.75 (m, 1H), 3.69-3.17 (m, 7H), 2.84-2.64 (m, 9H), 2.24-2.17 (m, 3H), 2.05-1.97 (m, 2H), 1.49-1.35 (m, 1H), 1.34-1.08 (m, 7H), 0.95-0.87 (m, 3H)

Example 3-(b)

Production of 3-(1,4-dimethyl-1H-benzo[d][1,2,3]triazol-5-yl)-3-(3-(((R)-2-ethyl-2,3,5,7,8,9-hexahydro-4H-indeno[5,6-f][1,4]oxazepin-4-yl)methyl)-4-methylphenyl)-2,2-dimethylpropanoic Acid

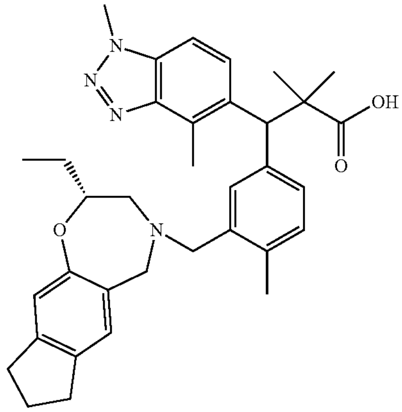 [SMILES: CC[C@@H]1CN(Cc2cc(C(c3ccc4c(nnn4C)c3C)C(C)(C)C(=O)O)ccc2C)Cc2cc3c(cc2O1)CCC3]

To a solution of methyl 3-(1,4-dimethyl-1H-benzo[d][1,2,3]triazol-5-yl)-3-(3-(((R)-2-ethyl-2,3,5,7,8,9-hexahydro-4H-indeno[5,6-f][1,4]oxazepin-4-yl)methyl)-4-methylphenyl)-2,2-dimethylpropanoate produced in the Example 3-(a) (72 mg) in dimethyl sulfoxide (4 mL) was added dropwise a 1 M aqueous solution of potassium hydroxide (1.04 mL) with stirring at room temperature, and the resulting mixture was stirred at 70° C. for 2 hours. After the reaction was completed, to the reaction solution was added water (5 mL), 1 M hydrochloric acid was added thereto to adjust the pH to 5.0, and the resulting mixture was stirred overnight. The resulting solids were collected by filtration, washed with water, and dried under reduced pressure at 65° C. to give the title compound (53 mg) as white solids.

Mass spectrum (ESI, m/z): 567 $[M+H]^+$ $^1$H-NMR spectrum (400 MHz, $CD_3OD$) δ: 7.78-7.68 (m, 1H), 7.51-7.45 (m, 1H), 7.25-7.17 (m, 1H), 7.13-7.06 (m, 2H), 6.85-6.69 (m, 2H), 4.96-4.78 (m, 1H), 4.27 (s, 3H), 3.94-3.86 (m, 1H), 3.72-3.53 (m, 4H), 2.94-2.70 (m, 9H), 2.29-2.23 (m, 3H), 2.11-2.02 (m, 2H), 1.52-1.42 (m, 1H), 1.42-1.36 (m, 3H), 1.36-1.17 (m, 4H), 1.02-0.93 (m, 3H)

Example 4-(a)

Production of methyl 3-(1,4-dimethyl-1H-benzo[d][1,2,3]triazol-5-yl)-3-(3-(((R)-2-ethyl-2,3,7,8,9,10-hexahydronaphtho[2,3-f][1,4]oxazepin-4(5H)-yl)methyl)-4-methylphenyl)-2,2-dimethylpropanoate

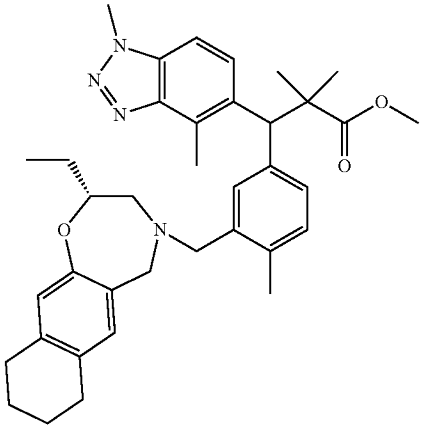 [SMILES: CC[C@@H]1CN(Cc2cc(C(c3ccc4c(nnn4C)c3C)C(C)(C)C(=O)OC)ccc2C)Cc2cc3c(cc2O1)CCCC3]

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (27 mg) in dichloromethane (1.0 mL) were added (R)-2-ethyl-2,3,4,5,7,8,9,10-octahydronaphtho[2,3-f][1,4]oxazepine hydrochloride produced in the Reference Example 4-(d) (21 mg) and triethylamine (0.025 mL) under argon atmosphere with stirring at room temperature, and the resulting mixture was stirred at room temperature for 2 hours. Then, sodium triacetoxyborohydride (30 mg) was added dividedly thereto with stirring under ice-cooling, and the resulting mixture was stirred at room temperature for 16 hours. Additionally, sodium triacetoxyborohydride (30 mg) was added thereto with stirring at room temperature, and the resulting mixture was stirred at room temperature for 24 hours. After the reaction was completed, to the reaction solution was added water, then a saturated aqueous solution of sodium hydrogen carbonate was added thereto, and the resulting mixed solution was subjected to extraction with dichloromethane. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (35 mg) as a colorless oil.

As an alternative method, the title compound was also produced according to the following method.

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (231 mg) in acetonitrile (10 mL) were sequentially added (R)-2-ethyl-2,3,4,5,7,8,9,10-octahydronaphtho[2,3-f][1,4]oxazepine hydrochloride produced according to the same manner as the Reference Example 4-(d) (187 mg) and N,N-diisopropylethylamine (0.415 mL) under argon gas flow with stirring at room temperature, and the resulting mixture was stirred at room temperature for 16.5 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (314 mg) as a colorless oil.

Mass spectrum (ESI, m/z): 595 $[M+H]^+$ $^1$H-NMR spectrum (400 MHz, $CDCl_3$) δ: 7.66-7.57 (m, 1H), 7.29-7.21 (m, 1H), 7.08-6.98 (m, 3H), 6.75-6.71 (m, 1H), 6.70-6.63 (m, 1H), 4.86-4.80 (m, 1H), 4.26-4.21 (m, 3H), 3.93-3.85 (m, 1H), 3.76-3.62 (m, 1H), 3.56-3.39 (m, 6H), 2.86-2.61 (m, 9H), 2.28-2.23 (m, 3H), 1.83-1.72 (m, 4H), 1.61-1.47 (m, 2H), 1.42-1.35 (m, 3H), 1.34-1.29 (m, 3H), 1.03-0.94 (m, 3H)

Example 4-(b)

Production of 3-(1,4-dimethyl-1H-benzo[d][1,2,3]triazol-5-yl)-3-(3-(((R)-2-ethyl-2,3,7,8,9,10-hexahydronaphtho[2,3-f][1,4]oxazepin-4(5H)-yl)methyl)-4-methylphenyl)-2,2-dimethylpropanoic Acid

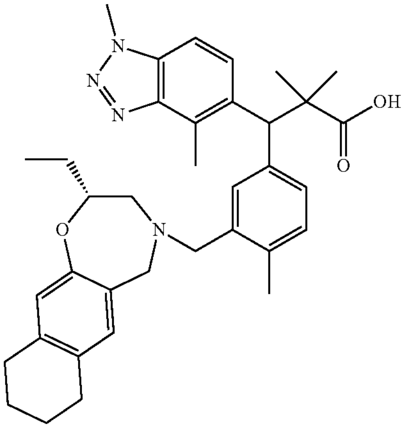 [SMILES: CC[C@@H]1CN(Cc2cc(C(c3ccc4c(nnn4C)c3C)C(C)(C)C(=O)O)ccc2C)Cc2cc3c(cc2O1)CCCC3]

To a solution of methyl 3-(1,4-dimethyl-1H-benzo[d][1,2,3]triazol-5-yl)-3-(3-(((R)-2-ethyl-2,3,7,8,9,10-hexahydronaphtho[2,3-f][1,4]oxazepin-4(5H)-yl)methyl)-4-methylphenyl)-2,2-dimethylpropanoate produced in the Example 4-(a) (35 mg) in dimethyl sulfoxide (1.2 mL) was added a 1 M aqueous solution of potassium hydroxide (0.600 mL) with stirring at room temperature, and the resulting mixture was stirred at 70° C. for 4 hours. Then, to the reaction solution was added water (2.0 mL), and 1 M hydrochloric acid was added thereto to adjust the pH to 5.0. The precipitated solids were collected by filtration, and dried under reduced pressure at 50° C. to give white solids.

To a solution of the resulting solids in dimethyl sulfoxide (1.2 mL) was added a 1 M aqueous solution of potassium hydroxide (0.600 mL) with stirring at room temperature, and the resulting mixture was stirred at 70° C. for 4 hours. After the reaction was completed, to the reaction solution was added water (2.0 mL), and 1 M hydrochloric acid was added thereto to adjust the pH to 5.0. The precipitated solids were collected by filtration, and dried under reduced pressure at 50° C. to give the title compound (26 mg) as white solids.

Mass spectrum (ESI, m/z): 581 $[M+H]^+$ $^1$H-NMR spectrum (400 MHz, $CD_3OD$) δ: 7.80-7.67 (m, 1H), 7.51-7.44 (m, 1H), 7.21-7.13 (m, 1H), 7.11-7.03 (m, 2H), 6.68-6.56 (m, 2H), 4.96-4.77 (m, 1H), 4.29-4.24 (m, 3H), 3.86-3.78 (m, 1H), 3.71-3.45 (m, 4H), 2.91-2.81 (m, 1H), 2.77-2.57 (m, 8H), 2.29-2.21 (m, 3H), 1.82-1.71 (m, 4H), 1.51-1.35 (m, 4H), 1.32-1.14 (m, 4H), 0.99-0.89 (m, 3H)

Example 5-(a)

Production of methyl 3-(1,4-dimethyl-1H-benzo[d][1,2,3]triazol-5-yl)-3-(3-(((R)-4-ethyl-3,4, 8, 9, 10, 11-hexahydronaphtho[1,2-f][1,4]oxazepin-2(1H)-yl)methyl)-4-methylphenyl)-2,2-dimethylpropanoate

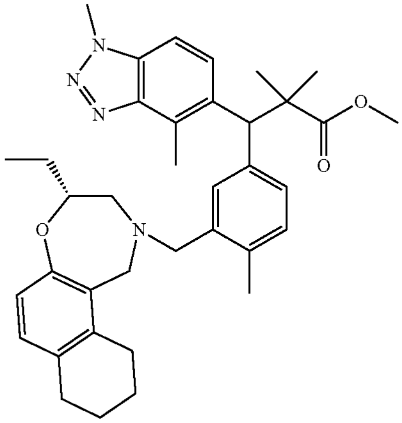 [SMILES: CC[C@@H]1CN(Cc2cc(C(c3ccc4c(nnn4C)c3C)C(C)(C)C(=O)OC)ccc2C)Cc2c(ccc3c2CCCC3)O1]

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (33 mg) in dichloromethane (1.0 mL) were added (R)-4-ethyl-1,2,3,4,8,9,10,11-octahydronaphtho[1,2-f][1,4]oxazepine hydrochloride produced in the Reference Example 5-(d) (25 mg) and triethylamine (0.030 mL) under argon atmosphere with stirring at room temperature, and the resulting mixture was stirred at room temperature for 2 hours. Then, sodium triacetoxyborohydride (36 mg) was added dividedly thereto with stirring under ice-cooling, and the resulting mixture was stirred at room temperature for 16 hours. Additionally, sodium triacetoxyborohydride (36 mg) was added thereto with stirring at room temperature, and the resulting mixture was stirred at room temperature for 24 hours. After the reaction was completed, to the reaction solution was added water, then a saturated aqueous solution of sodium hydrogen carbonate was added thereto, and the resulting mixed solution was subjected to extraction with dichloromethane. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (44 mg) as a colorless oil.

Mass spectrum (ESI, m/z): 595 $[M+H]^+$ $^1$H-NMR spectrum (400 MHz, $CDCl_6$) δ: 7.69-7.59 (m, 1H), 7.29-7.21 (m, 11H), 7.13-6.97 (m, 3H), 6.88-6.82 (m, 1H), 6.80-6.74 (m, 1H), 4.86-4.80 (m, 1H), 4.26-4.21 (m, 3H), 3.88-3.78 (m, 1H), 3.70-3.53 (m, 3H), 3.49-3.38 (m, 4H), 2.85-2.62 (m, 71), 2.36-2.07 (m, 5H), 1.69-1.43 (m, 5H), 1.41-1.23 (m, 7H), 1.04-0.95 (m, 3H)

Example 5-(b)

Production of 3-(1,4-dimethyl-1H-benzo[d][1,2,3)triazol-5-yl)-3-(3-(((R)-4-ethyl-3,4,8,9,10,11-hexahydronaphtho(1,2-f) (1,4]oxazepin-2(1H)-yl)methyl)-4-methylphenyl)-2,2-dimethylpropanoic Acid

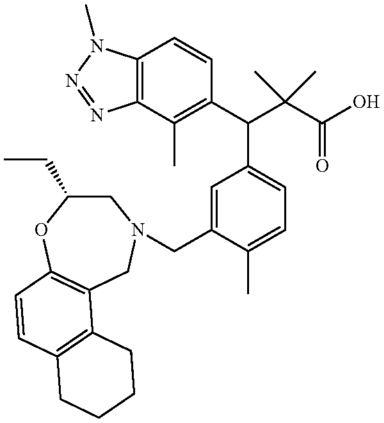 [SMILES: CC[C@@H]1CN(Cc2cc(C(c3ccc4c(nnn4C)c3C)C(C)(C)C(=O)O)ccc2C)Cc2c(ccc3c2CCCC3)O1]

To a solution of methyl 3-(1,4-dimethyl-1H-benzo[d][1,2,3]triazol-5-yl)-3-(3-(((R)-4-ethyl-3,4,8,9,10,11-hexahydronaphtho[1,2-f][1,4]oxazepin-2(1H)-yl)methyl)-4-methylphenyl)-2,2-dimethylpropanoate produced in the Example 5-(a) (44 mg) in dimethyl sulfoxide (1.4 mL) was added a 1 M aqueous solution of potassium hydroxide (0.750 mL) with stirring at room temperature, and the resulting mixture was stirred at 70° C. for 4 hours. After the reaction was completed, to the reaction solution was added water (2.0 mL), and 1 M hydrochloric acid was added thereto to adjust the pH to 5.0. The resulting solids were collected by filtration, and dried under reduced pressure at 50° C. to give the title compound (32 mg) as white solids.

Mass spectrum (ESI, m/z): 581 $[M+H]^+$ $^1$H-NMR spectrum (400 MHz, $CD_3OD$) δ: 7.90-7.73 (m, 1H), 7.52-7.42 (m, 1H), 7.28-7.16 (m, 2H), 7.10-7.04 (m, 1H), 6.84-6.78 (m, 1H), 6.72-6.64 (m, 1H), 4.97-4.90 (m, 1H), 4.29-4.24 (m, 3H), 3.88-3.56 (m, 3H), 3.54-3.41 (m, 2H), 3.01-2.91 (m, 1H), 2.80-2.68 (m, 4H), 2.62-2.53 (m, 2H), 2.27-2.18 (m, 3H), 2.17-2.06 (m, 0.5H), 1.94-1.67 (m, 1.5H), 1.61-1.23 (m, 12H), 1.06-0.97 (m, 3H)

Example 6-(a)

Production of methyl 3-(1,4-dimethyl-1H-benzo[d][1,2,3]triazol-5-yl)-3-(3-(((R)-2-ethyl-2,3,5,8,9,10-hexahydro-4H-indeno[5,4-f][1,4]oxazepin-4-yl)methyl)-4-methylphenyl)-2,2-dimethylpropanoate

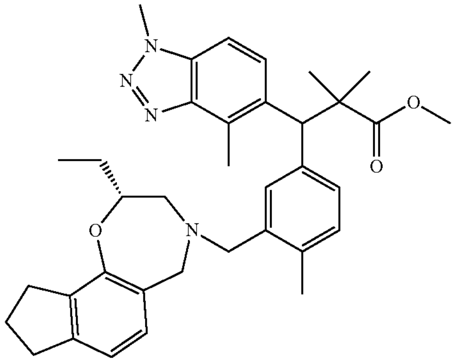 [SMILES: CC[C@@H]1CN(Cc2cc(C(c3ccc4c(nnn4C)c3C)C(C)(C)C(=O)OC)ccc2C)Cc2ccc3c(c2O1)CCC3]

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (41 mg) in dichloromethane (1.0 mL) were added (R)-2-ethyl-3,4,5,8,9,10-hexahydro-2H-indeno[5,4-f][1,4]oxazepine hydrochloride produced in the Reference Example 6-(d) (30 mg) and triethylamine (0.040 mL) under argon atmosphere with stirring at room temperature, and the resulting mixture was stirred at room temperature for 2 hours. Then, sodium triacetoxyborohydride (46 mg) was added dividedly thereto with stirring under ice-cooling, and the resulting mixture was stirred at room temperature for 16 hours. Additionally, sodium triacetoxyborohydride (91 mg) was added thereto with stirring at room temperature, and the resulting mixture was stirred at room temperature for 3 hours. Then, methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (41 mg) was added thereto with stirring at room temperature, and the resulting mixture was stirred at room temperature for 16 hours. After the reaction was completed, to the reaction solution was added water, then a saturated aqueous solution of sodium hydrogen carbonate was added thereto, and the resulting mixed solution was subjected to extraction with dichloromethane. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (62 mg) as a white foam.

As an alternative method, the title compound was also produced according to the following method.

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (188 mg) in acetonitrile (5 mL) were sequentially added (R)-2-ethyl-3,4,5,8,9,10-hexahydro-2H-indeno[5,4-f][1,4]oxazepine hydrochloride produced according to the same manner as the Reference Example 6-(d) (143 mg) and N,N-diisopropylethylamine (0.241 mL) under argon gas flow with stirring at room temperature, and the resulting mixture was stirred at 60° C. for 2 hours and then at 80° C. for 1 hour. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (247 mg) as a white foam.

Mass spectrum (ESI, m/z): 581 $[M+H]^+$ $^1$H-NMR spectrum (400 MHz, $CDCl_3$) δ: 7.62-7.55 (m, 1H), 7.28-7.22 (m, 1H), 7.11-6.99 (m, 2.5H), 6.98-6.95 (m, 0.5H), 6.78-6.73 (m, 0.5H), 6.68-6.61 (m, 1H), 6.43-6.39 (m, 0.5H), 4.87-4.82 (m, 1H), 4.26-4.22 (m, 3H), 3.93-3.82 (m, 1H), 3.79-3.64 (m, 1H), 3.58-3.39 (m, 6H), 2.99-2.77 (m, 9H), 2.28-2.24 (m, 3H), 2.16-1.98 (m, 2H), 1.65-1.50 (m, 1H), 1.42-1.22 (m, 7H), 1.08-0.99 (m, 3H)

Example 6-(b)

Production of 3-(1,4-dimethyl-1H-benzo[d][1,2,3]triazol-5-yl)-3-(3-(((R)-2-ethyl-2,3,5,8,9,10-hexahydro-4H-indeno[5,4-f][1,4]oxazepin-4-yl)methyl)-4-methylphenyl)-2,2-dimethylpropanoic Acid

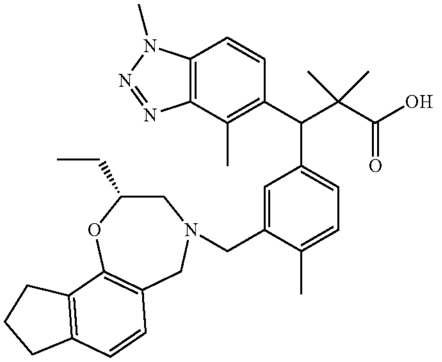 [SMILES: CC[C@@H]1CN(Cc2cc(C(c3ccc4c(nnn4C)c3C)C(C)(C)C(=O)O)ccc2C)Cc2ccc3c(c2O1)CCC3]

To a solution of methyl 3-(1,4-dimethyl-1H-benzo[d][1,2,3]triazol-5-yl)-3-(3-(((R)-2-ethyl-2,3,5,8,9,10-hexahydro-4H-indeno[5,4-f][1,4]oxazepin-4-yl)methyl)-4-methylphenyl)-2,2-dimethylpropanoate produced in the Example 6-(a) (62 mg) in dimethyl sulfoxide (2.20 mL) was added a 1 M aqueous solution of potassium hydroxide (1.10 mL) with stirring at room temperature, and the resulting mixture was stirred at 70° C. for 2 hours. After the reaction was completed, to the reaction solution was added water (2.0 mL), and 1 M hydrochloric acid was added thereto to adjust the pH to 5.0. The resulting solids were collected by filtration, and dried under reduced pressure at 50° C. to give the title compound (48 mg) as white solids.

Mass spectrum (ESI, m/z): 567 $[M+H]^+$ $^1$H-NMR spectrum (400 MHz, $CD_3OD$) δ: 7.74-7.66 (m, 1H), 7.53-7.45 (m, 1H), 7.27-7.18 (m, 1H), 7.12-6.95 (m, 2H), 6.72-6.65 (m, 0.5H), 6.64-6.58 (n, 0.5H), 6.56-6.49 (n, 0.5H), 6.35-6.29 (m, 0.5H), 5.02-4.71 (m, 1H), 4.31-4.22 (m, 3H), 3.86-3.63 (m, 2H), 3.61-3.44 (m, 3H), 2.97-2.68 (m, 9H), 2.31-2.22 (m, 3H), 2.15-1.95 (m, 2H), 1.57-1.42 (m, 1H), 1.41-1.34 (m, 3H), 1.34-1.20 (m, 4H), 1.01 (t, J=7.4 Hz, 3H)

Example 7-(a)

Production of methyl 3-(1,4-dimethyl-1H-benzo[d][1,2,3]triazol-5-yl)-3-(3-(((R)-2-ethyl-2,3,8,9,10,11-hexahydronaphtho[2,1-f][1,4]oxazepin-4(5H)-yl)methyl)-4-methylphenyl)-2,2-dimethylpropanoate

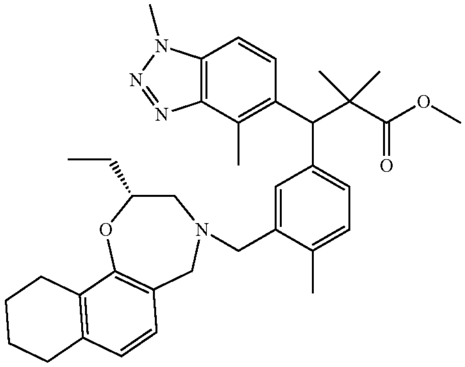 [SMILES: CC[C@@H]1CN(Cc2cc(C(c3ccc4c(nnn4C)c3C)C(C)(C)C(=O)OC)ccc2C)Cc2ccc3c(c2O1)CCCC3]

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (40 mg) in dichloromethane (2 mL) was added (R)-2-ethyl-2,3,4,5,8,9,10,11-octahydronaphtho[2,1-f][1,4]oxazepine hydrochloride produced in the Reference Example 7-(d) (37 mg) under argon gas flow with stirring at room temperature, then triethylamine (0.019 mL) was added thereto, then acetic acid (0.009 mL) was added thereto with stirring at room temperature, and the resulting mixture was stirred at room temperature for 30 minutes. Then, sodium triacetoxyborohydride (45 mg) was added thereto at one time with stirring at room temperature, and the resulting mixture was stirred at room temperature for 16 hours. After the reaction was completed, to the reaction solution was added a saturated aqueous solution of sodium hydrogen carbonate, and the resulting mixed solution was subjected to extraction with ethyl acetate. The resulting organic layer was dried over anhydrous magnesium sulfate, filtered, and concentrated under reduced pressure. The resulting residues were purified by a silica gel column (elution solvent; hexane:ethyl acetate) to give the title compound (58 mg) as a colorless foam.

Mass spectrum (ESI, m/z): 595 $[M+H]^+$ $^1$H-NMR spectrum (400 MHz, DMSO-$d_6$) δ: 7.61-7.53 (m, 2H), 7.15-7.09 (m, 1H), 7.07-7.03 (m, 1H), 7.00-6.95 (m, 1H), 6.56-6.39 (m, 2H), 4.77-4.73 (m, 1H), 4.27-4.23 (m, 3H), 3.77-3.62 (m, 2H), 3.47-3.37 (m, 6H), 2.86-2.78 (m, 1H), 2.74-2.64 (m, 8H), 2.21 (s, 3H), 1.84-1.63 (m, 4H), 1.59-1.21 (m, 8H), 0.97-0.89 (m, 3H)

Example 7-(b)

Production of 3-(1,4-dimethyl-1H-benzo[d][1,2,3]triazol-5-yl)-3-(3-(((R)-2-ethyl-2,3,8,9,10,11-hexahydronaphtho[2,1-f][1,4]oxazepin-4(5H)-yl)methyl)-4-methylphenyl)-2,2-dimethylpropanoic Acid

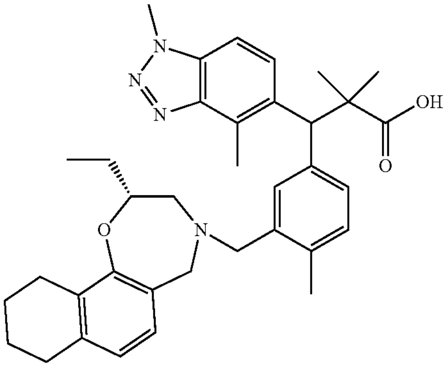 [SMILES: CC[C@@H]1CN(Cc2cc(C(c3ccc4c(nnn4C)c3C)C(C)(C)C(=O)O)ccc2C)Cc2ccc3c(c2O1)CCCC3]

To a solution of methyl 3-(1,4-dimethyl-1H-benzo[d][1,2,3]triazol-5-yl)-3-(3-(((R)-2-ethyl-2,3, 8, 9, 10, 11-hexahydronaphtho[2,1-f][1,4]oxazepin-4 (5H)-yl)methyl)-4-methylphenyl)-2,2-dimethylpropanoate produced in the Example 7-(a) (58 mg) in dimethyl sulfoxide (2 mL) was added a 1 M aqueous solution of potassium hydroxide (0.975 mL) under argon gas flow with stirring at room temperature, and the resulting mixture was stirred at 70° C. for 2 hours. After the reaction was completed, to the reaction solution was added 1 M hydrochloric acid (0.975 mL), and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (DIOL silica gel, elution solvent; hexane:ethyl acetate) to give the title compound (45 mg) as white solids.

Mass spectrum (ESI, m/z): 581 $[M+H]^+$ $^1$H-NMR spectrum (400 MHz, DMSO-$d_6$) δ: 12.30 (s, 1H), 7.66-7.52 (m, 2H), 7.19-7.11 (m, 1H), 7.08-7.01 (m, 1H), 6.98-6.87 (m, 1H), 6.55-6.33 (m, 2H), 4.78 (s, 1H), 4.31-4.19 (m, 3H), 3.80-3.59 (m, 2H), 3.45-3.19 (m, 3H), 2.86-2.77 (m, 1H), 2.75-2.61 (m, 8H), 2.20 (s, 3H), 1.82-1.61 (m, 4H), 1.56-1.14 (m, 8H), 0.97-0.89 (n, 3H)

Example 8-(a)

Production of methyl 3-(1,4-dimethyl-1H-benzo[d][(1,2,3]triazol-5-yl)-3-(3-(((R)-2-ethyl-2,3-dihydronaphtho[2,3-f][1,4]oxazepin-4(5H)-yl)methyl)-4-methylphenyl)-2,2-dimethylpropanoate

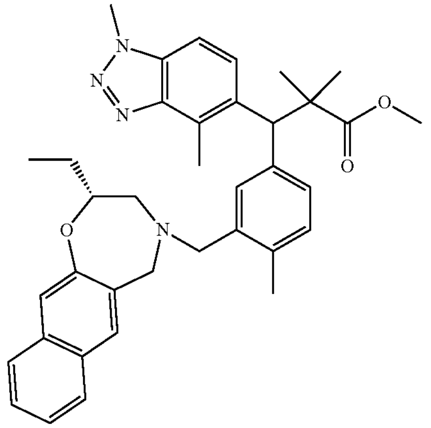 [SMILES: CC[C@@H]1CN(Cc2cc(C(c3ccc4c(nnn4C)c3C)C(C)(C)C(=O)OC)ccc2C)Cc2cc3ccccc3cc2O1]

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (40 mg) in dichloromethane (3 mL) was added (R)-2-ethyl-2,3,4,5-tetrahydronaphtho[2,3-f][1,4]oxazepine produced in the Reference Example 8-(d) (34 mg) under argon gas flow with stirring at room temperature, and the resulting mixture was stirred at room temperature for 30 minutes. Then, sodium triacetoxyborohydride (45 mg) was added thereto at one time with stirring at room temperature, and the resulting mixture was stirred at room temperature for 24 hours. After the reaction was completed, to the reaction solution was added a saturated aqueous solution of sodium hydrogen carbonate, and the resulting mixed solution was subjected to extraction twice with ethyl acetate. The resulting organic layer was dried over anhydrous magnesium sulfate, filtered, and concentrated under reduced pressure. The resulting residues were purified by a silica gel column (elution solvent; hexane:ethyl acetate) to give the title compound (53 mg) as white solids.

Mass spectrum (ESI, m/z): 591 $[M+H]^+$ $^1$H-NMR spectrum (400 MHz, $CDCl_3$) δ: 7.78-7.55 (m, 3H), 7.48-7.35 (m, 4H), 7.23-7.16 (m, 1H), 7.11-6.99 (m, 3H), 4.87-4.81 (m, 1H), 4.24-4.18 (m, 3H), 4.16-4.09 (m, 1H), 3.88-3.72 (m, 2H), 3.62-3.52 (m, 1H), 3.49-3.41 (m, 4H), 2.97-2.84 (m, 2H), 2.82-2.73 (m, 3H), 2.29-2.22 (m, 3H), 1.69-1.49 (m, 1H), 1.44-1.36 (m, 3H), 1.35-1.23 (m, 4H), 1.12-1.01 (m, 3H)

Example 8-(b)

Production of 3-(1,4-dimethyl-1H-benzo[d][1,2,3]triazol-5-yl)-3-(3-(((R)-2-ethyl-2,3-dihydronaphtho[2,3-f][1,4]oxazepin-4(5H)-yl)methyl)-4-methylphenyl)-2,2-dimethylpropanoic Acid

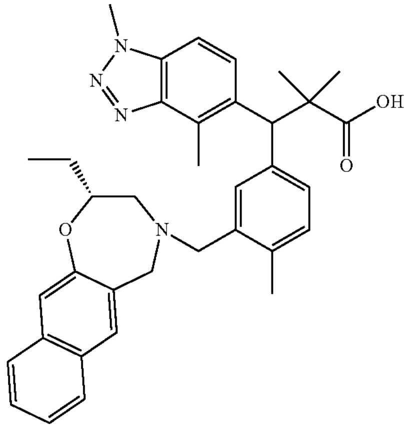 [SMILES: CC[C@@H]1CN(Cc2cc(C(c3ccc4c(nnn4C)c3C)C(C)(C)C(=O)O)ccc2C)Cc2cc3ccccc3cc2O1]

To a solution of methyl 3-(1,4-dimethyl-1H-benzo[d][1,2,3]triazol-5-yl)-3-(3-(((R)-2-ethyl-2,3-dihydronaphtho[2,3-f][1,4]oxazepin-4(5H)-yl)methyl)-4-methylphenyl)-2,2-dimethylpropanoate produced in the Example 8-(a) (53 mg) in dimethyl sulfoxide (2.5 mL) was added dropwise a 1 M aqueous solution of potassium hydroxide (0.897 mL) under argon gas flow with stirring at room temperature, and the resulting mixture was stirred at 70° C. for 3 hours. After the reaction was completed, water (5 mL) was added thereto, and 1 M hydrochloric acid was added thereto to adjust the pH to 5.2. The resulting mixture was stirred at room temperature for 1 hour, the resulting solids were collected by filtration, washed with water, and dried under reduced pressure at 60° C. to give the title compound (47 mg) as white solids.

Mass spectrum (ESI, m/z): 577 $[M+H]^+$ $^1$H-NMR spectrum (400 MHz, $CD_3OD$) δ: 7.81-7.63 (m, 3H), 7.49-7.32 (m, 5H), 7.25-7.14 (m, 1H), 7.12-7.03 (m, 2H), 4.98-4.78 (m, 1H), 4.27-4.18 (m, 3H), 4.07-3.97 (m, 1H), 3.85-3.67 (m, 2H), 3.64-3.46 (m, 2H), 2.96-2.77 (m, 2H), 2.71-2.67 (m, 3H), 2.30-2.22 (m, 3H), 1.61-1.47 (m, 1H), 1.42-1.19 (m, 7H), 1.07-0.97 (m, 3H)

Example 9-(a)

Production of methyl 3-(1,4-dimethyl-1H-benzo[d][1,2,3]triazol-5-yl)-3-(3-(((R)-2-ethyl-2,3-dihydro-[1,4]oxazepino[7,6-b]quinolin-4 (5H)-yl)methyl)-4-methylphenyl)-2,2-dimethylpropanoate

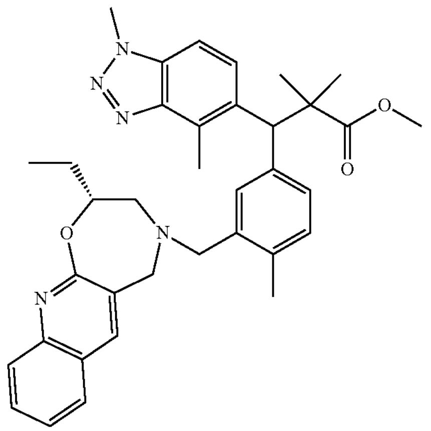 [SMILES: CC[C@@H]1CN(Cc2cc(C(c3ccc4c(nnn4C)c3C)C(C)(C)C(=O)OC)ccc2C)Cc2cc3ccccc3nc2O1]

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (40 mg) in dichloromethane (5 mL) was added (R)-2-ethyl-2,3,4,5-tetrahydro-[1,4]oxazepino[7,6-b]quinoline produced in the Reference Example 9-(b) (72 mg) under argon gas flow with stirring at room temperature, and the resulting mixture was stirred at room temperature for 30 minutes. Then, sodium triacetoxyborohydride (45 mg) was added thereto with stirring at room temperature, and the resulting mixture was stirred at room temperature for 24 hours. After the reaction was completed, to the reaction solution was added a saturated aqueous solution of sodium hydrogen carbonate, and the resulting mixed solution was subjected to extraction twice with ethyl acetate. The resulting organic layer was dried over anhydrous magnesium sulfate, filtered, and concentrated under reduced pressure. The resulting residues were purified by a silica gel column (elution solvent; hexane:ethyl acetate) to give the title compound (56 mg) as a colorless oil.

Mass spectrum (ESI, m/z): 592 $[M+H]^+$ $^1$H-NMR spectrum (400 MHz, $CDCl_3$) δ: 8.01-7.92 (m, 1H), 7.79-7.71 (m, 1H), 7.69-7.55 (m, 3H), 7.50-7.41 (m, 1H), 7.22-7.15 (m, 1H), 7.13-7.03 (m, 3H), 4.88-4.81 (m, 1H), 4.24-4.03 (m, 4H), 3.97-3.87 (m, 1H), 3.86-3.77 (m, 1H), 3.66-3.51 (m, 2H), 3.49-3.42 (m, 3H), 3.03-2.89 (m, 2H), 2.82-2.74 (m, 3H), 2.30-2.23 (m, 3H), 1.86-1.70 (m, 1H), 1.67-1.49 (m, 1H), 1.43-1.36 (m, 3H), 1.35-1.23 (m, 3H), 1.07-0.95 (m, 3H)

Example 9-(b)

Production of 3-(1,4-dimethyl-1H-benzo[d][1,2,3]triazol-5-yl)-3-(3-(((R)-2-ethyl-2,3-dihydro-[1,4]oxazepino[7,6-b]quinolin-4 (5H)-yl)methyl)-4-methylphenyl)-2,2-dimethylpropanoic Acid

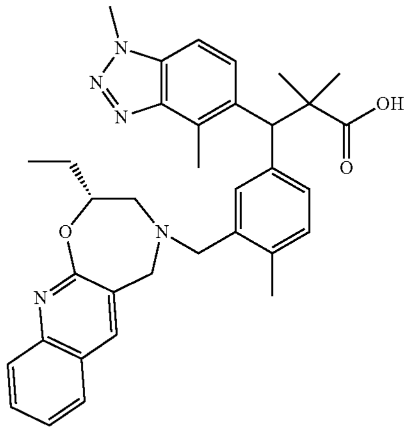 [SMILES: CC[C@@H]1CN(Cc2cc(C(c3ccc4c(nnn4C)c3C)C(C)(C)C(=O)O)ccc2C)Cc2cc3ccccc3nc2O1]

To a solution of methyl 3-(1,4-dimethyl-1H-benzo[d][1,2,3]triazol-5-yl)-3-(3-(((R)-2-ethyl-2,3-dihydro-[1,4]oxazepino[7,6-b]quinolin-4(5H)-yl)methyl)-4-methylphenyl)-2,2-dimethylpropanoate produced in the Example 9-(a) (56 mg) in dimethyl sulfoxide (2.5 mL) was added dropwise a 1 M aqueous solution of potassium hydroxide (0.95 mL) under argon gas flow with stirring at room temperature, and the resulting mixture was stirred at 70° C. for 3 hours. After the reaction was completed, the resulting mixture was allowed to cool to room temperature, water (5 mL) was added thereto, and 1 M hydrochloric acid was added thereto to adjust the pH to 5.2. The resulting mixture was stirred at room temperature for 1 hour, the resulting solids were collected by filtration, washed with water, and dried under reduced pressure at 60° C. to give the title compound (49 mg) as white solids.

Mass spectrum (ESI, m/z): 578 $[M+H]^+$ $^1$H-NMR spectrum (400 MHz, $CD_3OD$) δ: 7.97-7.89 (m, 1H), 7.87-7.62 (m, 4H), 7.55-7.46 (m, 1H), 7.43-7.33 (m, 1H), 7.24-7.05 (m, 3H), 4.96-4.81 (m, 1H), 4.26-4.17 (m, 3H), 4.16-3.99 (m, 1H), 3.94-3.80 (m, 2H), 3.70-3.56 (m, 2H), 2.99-2.86 (m, 2H), 2.72-2.63 (m, 3H), 2.32-2.23 (m, 3H), 1.73-1.59 (m, 1H), 1.55-1.41 (m, 1H), 1.41-1.23 (m, 6H), 1.06-0.94 (m, 3H)

Example 10-(a)

Production of methyl 3-(1,4-dimethyl-1H-benzo[d][1,2,3]triazol-5-yl)-3-(3-(((R)-2-ethyl-2,3-dihydro-[1,4]oxazepino[6,7-b]quinolin-4 (5H)-yl)methyl)-4-methylphenyl)-2,2-dimethylpropanoate

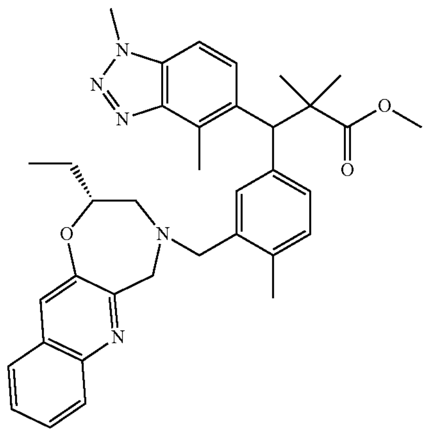 [SMILES: CC[C@@H]1CN(Cc2cc(C(c3ccc4c(nnn4C)c3C)C(C)(C)C(=O)OC)ccc2C)Cc2nc3ccccc3cc2O1]

To a solution of methyl 3-(3-(chloromethyl)-4-methylphenyl)-3-(1,4-dimethyl-1H-benzo[d][1,2,3]triazol-5-yl)-2,2-dimethylpropanoate produced in the Reference Example 10-(c) (52 mg) in acetonitrile (3 mL) were sequentially added (R)-2-ethyl-2,3,4,5-tetrahydro-[1,4]oxazepino[6,7-b]quinoline produced in the Reference Example 10-(b) (27 mg) and N,N-diisopropylethylamine (0.061 mL) under argon gas flow with stirring at room temperature, and the resulting mixture was stirred at room temperature for 15 hours and at 60° C. for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (39 mg) as a white foam.

Mass spectrum (DUIS, m/z): 592 $[M+H]^+$ $^1$H-NMR spectrum (400 MHz, $CDCl_3$) δ: 8.08-8.00 (m, 1H), 7.80-7.58 (m, 4H), 7.55-7.47 (m, 1H), 7.29-7.14 (m, 1H), 7.12-6.98 (m, 3H), 4.84-4.77 (m, 1H), 4.36-4.27 (m, 1H), 4.23-4.14 (m, 4H), 3.88-3.71 (m, 1H), 3.70-3.61 (m, 1H), 3.58-3.48 (m, 1H), 3.46-3.38 (m, 3H), 2.90-2.81 (m, 2H), 2.78-2.71 (m, 3H), 2.27 (s, 3H), 1.67-1.48 (m, 18), 1.41-1.20 (m, 7H), 1.07-0.95 (m, 3H)

Example 10-(b)

Production of 3-(1,4-dimethyl-1H-benzo[d][1,2,3]triazol-5-yl)-3-(3-(((R)-2-ethyl-2,3-dihydro-[1,4]oxazepino[6,7-b]quinolin-4 (5H)-yl)methyl)-4-methylphenyl)-2,2-dimethylpropanoic Acid

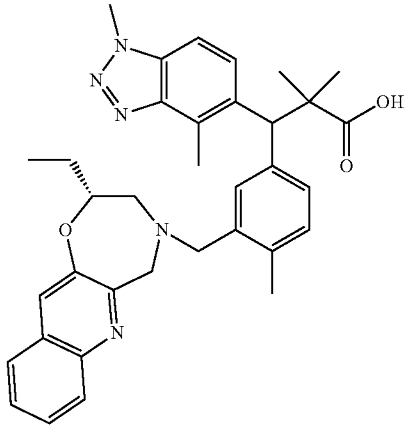 [SMILES: CC[C@@H]1CN(Cc2cc(C(c3ccc4c(nnn4C)c3C)C(C)(C)C(=O)O)ccc2C)Cc2nc3ccccc3cc2O1]

To a solution of methyl 3-(1,4-dimethyl-1H-benzo[d][1,2,3]triazol-5-yl)-3-(3-(((R)-2-ethyl-2,3-dihydro-[1,4]oxazepino[6,7-b]quinolin-4 (5H)-yl)methyl)-4-methylphenyl)-2,2-dimethylpropanoate produced in the Example 10-(a) (39 mg) in dimethyl sulfoxide (2.5 mL) was added dropwise a 1 M aqueous solution of potassium hydroxide (0.66 mL) under argon gas flow with stirring at room temperature, and the resulting mixture was stirred at 70° C. for 3 hours. After the reaction was completed, the resulting mixture was allowed to cool to room temperature, water (5 mL) was added thereto, and 1 M hydrochloric acid was added thereto to adjust the pH to 5.2. The resulting mixed solution was subjected to extraction three times with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate), and the fractions comprising the title compound were concentrated under reduced pressure. The resulting residues were dissolved into a mixed solvent of acetonitrile/water, and the resulting solution was lyophilized to give the title compound (12 mg) as white solids.

As an alternative method, the title compound was also produced according to the following method.

A solution of 3-(1,4-dimethyl-1H-benzo[d][1,2,3]triazol-5-yl)-3-(3-formyl-4-methylphenyl)-2,2-dimethylpropanoic acid produced according to the same manner as the Reference Example 23-(g) (135 mg) and (R)-2-ethyl-2,3,4,5-tetrahydro-[1,4]oxazepino[6,7-b]quinoline produced according to the same manner as the Reference Example 10-(b) (95 mg) in dichloromethane (2 mL) was stirred under argon gas flow at room temperature for 1 hour. Then, sodium triacetoxyborohydride (146 mg) was added thereto with stirring at room temperature, and the resulting mixture was stirred at room temperature overnight. After the reaction was completed, to the reaction solution was added a saturated aqueous solution of sodium hydrogen carbonate, and the resulting mixed solution was subjected to extraction with dichloromethane. Then, the resulting organic layer was concentrated under reduced pressure. The resulting residues were purified by a silica gel column (elution solvent; hexane:ethyl acetate) to give the title compound (18 mg) as a pale yellow oil.

Mass spectrum (ESI, m/z): 578 $[M+H]^+$ $^1$H-NMR spectrum (400 MHz, $CD_3OD$) δ: 8.00-7.91 (m, 1H), 7.89-7.82 (m, 2H), 7.81-7.71 (m, 1H), 7.69-7.61 (m, 1H), 7.60-7.52 (m, 1H), 7.41-7.35 (m, 1H), 7.19-7.09 (m, 2H), 7.08-7.02 (m, 1H), 4.92-4.79 (m, 1H), 4.26-4.17 (m, 4H), 4.16-4.08 (m, 1H), 3.89-3.72 (m, 1H), 3.72-3.64 (m, 1H), 3.60-3.51 (m, 1H), 2.92-2.78 (m, 2H), 2.72-2.63 (m, 3H), 2.31-2.23 (m, 3H), 1.64-1.46 (m, 1H), 1.40-1.18 (m, 7H), 1.02-0.93 (m, 3H)

Example 11-(a)

Production of methyl 3-(1,4-dimethyl-1H-benzo[d][1,2,3]triazol-5-yl)-3-(3-(((R)-2-ethyl-2,3-dihydro-[1,4]oxazepino[6,7-g]quinolin-4 (5H)-yl)methyl)-4-methylphenyl)-2,2-dimethylpropanoate

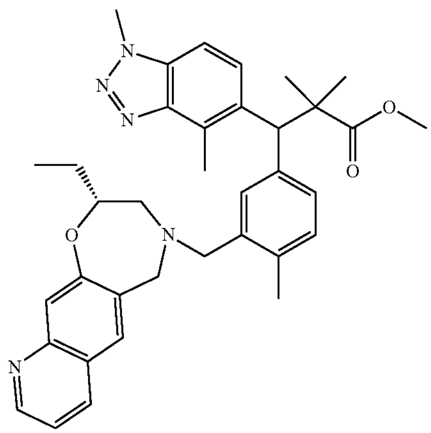 [SMILES: CC[C@@H]1CN(Cc2cc(C(c3ccc4c(nnn4C)c3C)C(C)(C)C(=O)OC)ccc2C)Cc2cc3cccnc3cc2O1]

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (30 mg) in dichloromethane (1 mL) was added (R)-2-ethyl-2,3,4,5-tetrahydro-[1,4]oxazepino[6,7-g]quinoline dihydrochloride produced in the Reference Example 11-(c) (32 mg) under argon gas flow, and the resulting mixture was stirred at room temperature for 0.5 hour. Then, sodium triacetoxyborohydride (35 mg) was added thereto with stirring at room temperature, and the resulting mixture was stirred at room temperature overnight. After the reaction was completed, to the reaction solution was added a saturated aqueous solution of sodium hydrogen carbonate, and the resulting mixed solution was subjected to extraction twice with dichloromethane. The resulting organic layer was concentrated under reduced pressure, and the resulting residues were purified by a silica gel column (elution solvent; hexane:ethyl acetate) to give the title compound (18 mg) as a pale yellow oil.

Mass spectrum (ESI, m/z): 592 $[M+H]^+$ $^1$H-NMR spectrum (400 MHz, DMSO-$d_6$) δ: 8.87-8.82 (m, 1H), 8.25-8.18 (m, 1H), 7.67-7.49 (m, 4H), 7.47-7.42 (m, 1H), 7.13-7.03 (m, 3H), 4.78-4.72 (m, 1H), 4.26-4.19 (m, 3H), 4.10-3.99 (m, 1H), 3.95-3.80 (m, 2H), 3.60-3.19 (m, 5H), 2.84-2.76 (m, 2H), 2.70-2.59 (m, 3H), 2.24-2.20 (m, 3H), 1.58-1.45 (m, 1H), 1.35-1.14 (m, 7H), 1.01-0.93 (m, 3H)

Example 11-(b)

Production of 3-(1,4-dimethyl-1H-benzo[d][1,2,3]triazol-5-yl)-3-(3-(((R)-2-ethyl-2,3-dihydro-[1,4]oxazepino[6,7-g]quinolin-4(5H)-yl)methyl)-4-methylphenyl)-2,2-dimethylpropanoic Acid

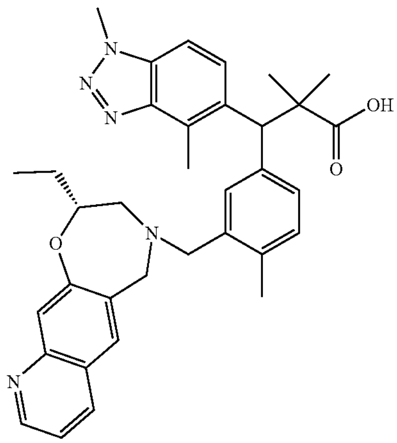 [SMILES: CC[C@@H]1CN(Cc2cc(C(c3ccc4c(nnn4C)c3C)C(C)(C)C(=O)O)ccc2C)Cc2cc3cccnc3cc2O1]

To a solution of methyl 3-(1,4-dimethyl-1H-benzo[d][1,2,3]triazol-5-yl)-3-(3-(((R)-2-ethyl-2,3-dihydro-[1,4]oxazepino[6,7-g]quinolin-4(5H)-yl)methyl)-4-methylphenyl)-2,2-dimethylpropanoate produced in the Example 11-(a) (18 mg) in dimethyl sulfoxide (1 mL) was added dropwise a 1 M aqueous solution of potassium hydroxide (0.304 mL) with stirring at room temperature, and the resulting mixture was stirred at 70° C. for 2 hours. After the reaction was completed, to the reaction solution was added water (5 mL), 1 M hydrochloric acid was added thereto to adjust the pH to 5.0, and the resulting mixture was stirred overnight. The resulting solids were collected by filtration, washed with water, and dried under reduced pressure at 65° C. to give the title compound (11 mg) as white solids.

Mass spectrum (ESI, m/z): 578 $[M+H]^+$ $^1$H-NMR spectrum (400 MHz, $CD_3OD$) δ: 8.84-8.71 (m, 1H), 8.25-8.15 (m, 1H), 7.80-7.65 (m, 1H), 7.59-7.38 (m, 4H), 7.24-7.15 (m, 1H), 7.13-7.03 (m, 2H), 4.97-4.75 (m, 1H), 4.29-4.20 (m, 3H), 4.07-3.97 (m, 1H), 3.94-3.75 (m, 2H), 3.65-3.50 (m, 2H), 2.97-2.82 (m, 2H), 2.73-2.64 (m, 3H), 2.30-2.22 (m, 3H), 1.65-1.51 (m, 1H), 1.42-1.23 (m, 7H), 1.08-0.96 (m, 3H)

Example 12-(a)

Production of methyl 3-(1,4-dimethyl-1H-benzo[d][1,2,3]triazol-5-yl)-3-(3-(((R)-2-ethyl-2,3-dihydro-[1,4]oxazepino[7,6-g]quinolin-4(5H)-yl)methyl)-4-methylphenyl)-2,2-dimethylpropanoate

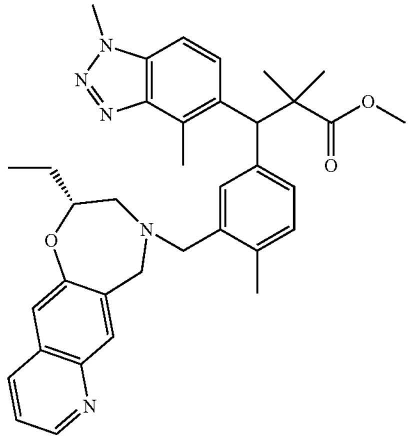 [SMILES: CC[C@@H]1CN(Cc2cc(C(c3ccc4c(nnn4C)c3C)C(C)(C)C(=O)OC)ccc2C)Cc2cc3ncccc3cc2O1]

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (50 mg) in dichloromethane (3 mL) was added (R)-2-ethyl-2,3,4,5-tetrahydro-[1,4]oxazepino[7,6-g]quinoline produced in the Reference Example 12-(c) (38 mg) under argon gas flow with stirring at room temperature, and the resulting mixture was stirred at room temperature for 30 minutes. Then, sodium triacetoxyborohydride (45 mg) was added thereto with stirring at room temperature, and the resulting mixture was stirred at room temperature for 24 hours. After the reaction was completed, to the reaction solution was added a saturated aqueous solution of sodium hydrogen carbonate, and the resulting mixed solution was subjected to extraction twice with ethyl acetate. The resulting organic layer was dried over anhydrous magnesium sulfate, filtered, concentrated under reduced pressure, and the resulting residues were purified by a silica gel column (elution solvent; hexane:ethyl acetate) to give the title compound (59 mg) as a colorless oil.

As an alternative method, the title compound was also produced according to the following method.

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (0.171 g) in acetonitrile (5 mL) were sequentially added (R)-2-ethyl-2,3,4,5-tetrahydro-[1,4]oxazepino[7,6-g]quinoline produced according to the same manner as the Reference Example 12-(c) (0.108 g) and N,N-diisopropylethylamine (0.219 mL) under argon gas flow with stirring at room temperature, and the resulting mixture was stirred at room temperature for 1.25 hours, then at 60° C. for 3 hours, at room temperature for 15 hours, and at 60° C. for 1 hour. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (0.177 g) as a white foam.

Mass spectrum (ESI, m/z): 592 $[M+H]^+$ $^1$H-NMR spectrum (400 MHz, $CDCl_3$) δ: 8.85-8.79 (m, 1H), 8.06 (d, J=8.2 Hz, 1H), 7.79-7.71 (m, 1H), 7.67-7.55 (m, 1H), 7.41-7.38 (m, 1H), 7.36 (dd, J=4.3, 8.2 Hz, 1H), 7.33-7.23 (m, 1H), 7.10-6.99 (m, 3H), 4.89-4.80 (m, 1H), 4.26-4.20 (m, 3H), 4.20-4.09 (m, 1H), 3.93-3.75 (m, 2H), 3.65-3.54 (m, 1H), 3.50-3.40 (m, 4H), 2.95-2.83 (m, 2H), 2.80-2.74 (m, 3H), 2.23 (s, 3H), 1.70-1.50 (m, 1H), 1.42-1.23 (m, 7H), 1.09-0.98 (m, 3H)

Example 12-(b)

Production of 3-(1,4-dimethyl-1H-benzo[d][1,2,3]triazol-5-yl)-3-(3-(((R)-2-ethyl-2,3-dihydro-[1,4]oxazepino[7,6-g]quinolin-4 (5H)-yl)methyl)-4-methylphenyl)-2,2-dimethylpropanoic Acid

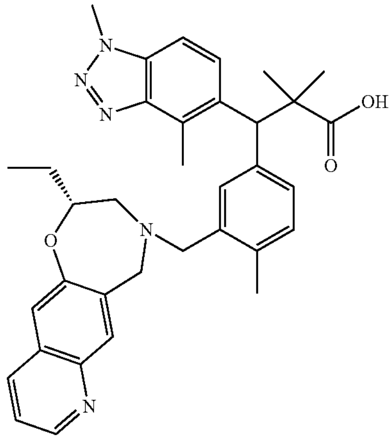 [SMILES: CC[C@@H]1CN(Cc2cc(C(c3ccc4c(nnn4C)c3C)C(C)(C)C(=O)O)ccc2C)Cc2cc3ncccc3cc2O1]

To a solution of methyl 3-(1,4-dimethyl-1H-benzo[d][1,2,3]triazol-5-yl)-3-(3-(((R)-2-ethyl-2,3-dihydro-[1,4]oxazepino[7,6-g]quinolin-4 (5H)-yl)methyl)-4-methylphenyl)-2,2-dimethylpropanoate produced in the Example 12-(a) (59 mg) in dimethyl sulfoxide (2.5 mL) was added dropwise a 1 M aqueous solution of potassium hydroxide (0.997 mL) under argon gas flow with stirring at room temperature, and the resulting mixture was stirred at 70° C. for 3 hours. After the reaction was completed, the resulting mixture was allowed to cool to room temperature, water (5 mL) was added thereto, and 1 M hydrochloric acid was added thereto to adjust the pH to 5.2. The resulting mixture was stirred at room temperature for 1 hour, the resulting solids were collected by filtration, washed with water, and dried under reduced pressure at 60° C. to give the title compound (52 mg) as white solids.

Mass spectrum (ESI, m/z): 578 $[M+H]^+$ $^1$H-NMR spectrum (400 MHz, $CD_3OD$) δ: 8.77-8.70 (m, 1H), 8.31-8.23 (m, 1H), 7.80-7.66 (m, 2H), 7.52-7.42 (m, 3H), 7.21-7.02 (m, 3H), 4.99-4.73 (m, 1H), 4.27-4.22 (m, 3H), 4.13-4.02 (M, 1H), 3.96-3.86 (m, 1H), 3.86-3.70 (m, 1H), 3.68-3.59 (m, 1H), 3.56-3.49 (m, 1H), 2.94-2.77 (m, 2H), 2.73-2.66 (m, 3H), 2.27-2.21 (m, 3H), 1.64-1.46 (m, 1H), 1.41-1.20 (m, 7H), 1.05-0.95 (m, 3H)

Example 13-(a)

Production of methyl 3-(1,4-dimethyl-1H-benzo[d][1,2,3]triazol-5-yl)-3-(3-(((R)-2-ethyl-10-methyl-2,3-dihydro-[1,4]oxazepino[7,6-b]quinolin-4 (5H)-yl)methyl)-4-methylphenyl)-2,2-dimethylpropanoate

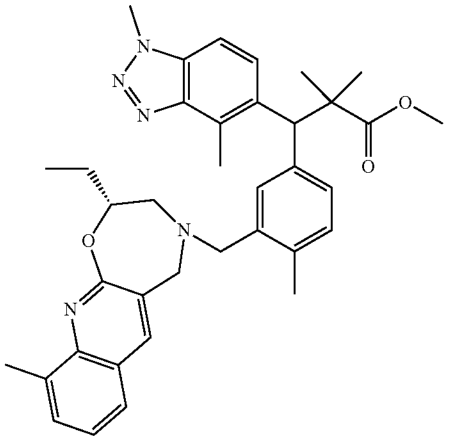

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (35 mg) in dichloromethane (3 mL) was added (R)-2-ethyl-10-methyl-2,3,4,5-tetrahydro-[1,4]oxazepino[7,6-b]quinoline produced in the Reference Example 13-(b) (31 mg) under argon gas flow with stirring at room temperature, and the resulting mixture was stirred at room temperature for 30 minutes. Then, sodium triacetoxyborohydride (40 mg) was added thereto with stirring at room temperature, and the resulting mixture was stirred at room temperature for 24 hours. After the reaction was completed, to the reaction solution was added a saturated aqueous solution of sodium hydrogen carbonate, and the resulting mixed solution was subjected to extraction twice with ethyl acetate. The resulting organic layer was dried over anhydrous magnesium sulfate, filtered, concentrated under reduced pressure, and the resulting residues were purified by a silica gel column (elution solvent; hexane:ethyl acetate) to give the title compound (50 mg) as white solids.

Mass spectrum (ESI, m/z): 606 $[M+H]^+$ $^1$H-NMR spectrum (400 MHz, $CDCl_3$) δ: 7.73-7.68 (m, 1H), 7.64-7.55 (m, 1H), 7.53-7.46 (m, 2H), 7.37-7.30 (m, 1H), 7.22-7.15 (m, 1H), 7.12-7.01 (m, 3H), 4.86-4.81 (m, 1H), 4.22-4.17 (m, 3H), 4.15-4.00 (m, 1H), 3.95-3.86 (m, 1H), 3.82-3.74 (m, 1H), 3.66-3.51 (m, 2H), 3.49-3.42 (m, 3H), 3.01-2.89 (m, 2H), 2.81-2.72 (m, 6H), 2.29-2.23 (m, 3H), 1.83-1.71 (m, 1H), 1.60-1.44 (m, 1H), 1.42-1.36 (m, 3H), 1.35-1.22 (m, 3H), 1.08-0.97 (m, 3H)

Example 13-(b)

Production of 3-(1,4-dimethyl-1H-benzo[d][1,2,3]triazol-5-yl)-3-(3-(((R)-2-ethyl-10-methyl-2,3-dihydro-[1,4]oxazepino[7,6-b]quinolin-4 (5H)-yl)methyl)-4-methylphenyl)-2,2-dimethylpropanoic Acid

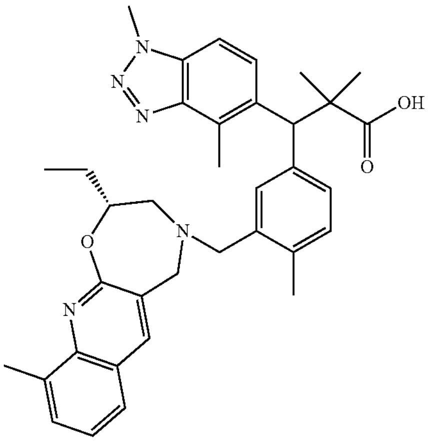 [SMILES: CC[C@@H]1CN(Cc2cc(C(c3ccc4c(nnn4C)c3C)C(C)(C)C(=O)O)ccc2C)Cc2cc3cccc(C)c3nc2O1]

To a solution of methyl 3-(1,4-dimethyl-1H-benzo[d][1,2,3]triazol-5-yl)-3-(3-(((R)-2-ethyl-10-methyl-2,3-dihydro-[1,4]oxazepino[7,6-b]quinolin-4 (5H)-yl)methyl)-4-methylphenyl)-2,2-dimethylpropanoate produced in the Example 13-(a) (50 mg) in dimethyl sulfoxide (3 mL) was added dropwise a 1 M aqueous solution of potassium hydroxide (0.825 mL) under argon gas flow with stirring at room temperature, and the resulting mixture was stirred at 70° C. for 3 hours. After the reaction was completed, water (5 mL) was added thereto, and 1 M hydrochloric acid was added thereto to adjust the pH to 5.2. The resulting mixture was stirred at room temperature for 1 hour, the resulting solids were collected by filtration, washed with water, and dried under reduced pressure at 60° C. to give the title compound (45 mg) as white solids.

Mass spectrum (ESI, m/z): 592 $[M+H]^+$ $^1$H-NMR spectrum (400 MHz, $CD_3OD$) δ: 7.85 (d, J=9.8 Hz, 1H), 7.77-7.63 (m, 1H), 7.61-7.50 (m, 2H), 7.42-7.32 (m, 2H), 7.23-7.15 (m, 1H), 7.13-7.04 (m, 2H), 4.95-4.78 (m, 1H), 4.24-4.17 (m, 3H), 4.13-3.97 (m, 1H), 3.90-3.80 (m, 2H), 3.69-3.54 (m, 2H), 2.99-2.84 (m, 2H), 2.71-2.63 (m, 61), 2.31-2.23 (m, 3H), 1.75-1.60 (m, 1H), 1.56-1.41 (m, 1H), 1.40-1.22 (m, 6H), 1.01-0.92 (m, 3H)

Example 14-(a)

Production of methyl 3-(1,4-dimethyl-1H-benzo[d][1,2,3]triazol-5-yl)-3-(3-(((R)-2-ethyl-8-methyl-2,3-dihydro-[1,4]oxazepino[7,6-b]quinolin-4(5H)-yl)methyl)-4-methylphenyl)-2,2-dimethylpropanoate

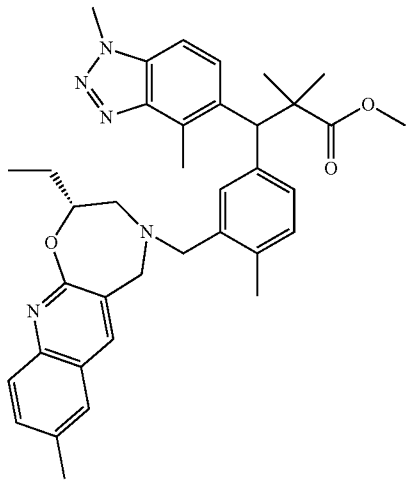 [SMILES: CC[C@@H]1CN(Cc2cc(C(c3ccc4c(nnn4C)c3C)C(C)(C)C(=O)OC)ccc2C)Cc2cc3cc(C)ccc3nc2O1]

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (35 mg) in dichloromethane (3 mL) was added (R)-2-ethyl-8-methyl-2,3,4,5-tetrahydro-[1,4]oxazepino[7,6-b]quinoline produced in the Reference Example 14-(b) (31 mg) under argon gas flow with stirring at room temperature, and the resulting mixture was stirred at room temperature for 30 minutes. Then, sodium triacetoxyborohydride (39 mg) was added thereto with stirring at room temperature, and the resulting mixture was stirred at room temperature for 24 hours. After the reaction was completed, to the reaction solution was added a saturated aqueous solution of sodium hydrogen carbonate, and the resulting mixed solution was subjected to extraction twice with ethyl acetate. The resulting organic layer was dried over anhydrous magnesium sulfate, filtered, concentrated under reduced pressure, and the resulting residues were purified by a silica gel column (elution solvent; hexane:ethyl acetate) to give the title compound (54 mg) as a white foam.

Mass spectrum (ESI, m/z): 606 $[M+H]^+$ $^1$H-NMR spectrum (400 MHz, $CDCl_3$) δ: 7.90-7.82 (m, 1H), 7.67-7.55 (m, 2H), 7.52-7.38 (m, 2H), 7.23-7.15 (m, 1H), 7.13-7.02 (m, 3H), 4.88-4.81 (m, 1H), 4.26-4.16 (m, 3H), 4.16-4.00 (M, 1H), 3.96-3.87 (m, 1H), 3.83-3.75 (m, 1H), 3.65-3.41 (m, 5H), 3.03-2.87 (m, 2H), 2.85-2.74 (m, 3H), 2.59-2.48 (m, 3H), 2.33-2.23 (m, 3H), 1.84-1.70 (m, 1H), 1.67-1.49 (m, 1H), 1.44-1.22 (m, 6H), 1.07-0.94 (m, 3H)

Example 14-(b)

Production of 3-(1,4-dimethyl-1H-benzo[d][1,2,3]triazol-5-yl)-3-(3-(((R)-2-ethyl-8-methyl-2,3-dihydro-[1,4]oxazepino[7,6-b]quinolin-4 (5H)-yl)methyl)-4-methylphenyl)-2,2-dimethylpropanoic Acid

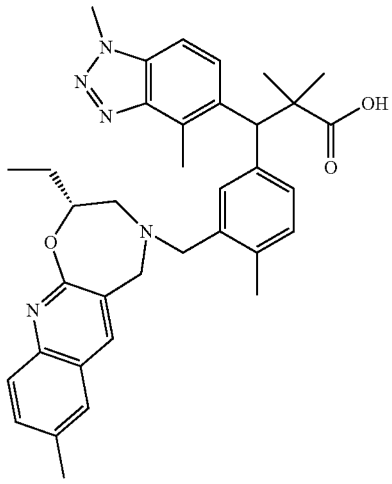 [SMILES: CC[C@@H]1CN(Cc2cc(C(c3ccc4c(nnn4C)c3C)C(C)(C)C(=O)O)ccc2C)Cc2cc3cc(C)ccc3nc2O1]

To a solution of methyl 3-(1,4-dimethyl-1H-benzo[d][1,2,3]triazol-5-yl)-3-(3-(((R)-2-ethyl-8-methyl-2,3-dihydro-[1,4]oxazepino[7,6-b]quinolin-4 (5H)-yl)methyl)-4-methylphenyl)-2,2-dimethylpropanoate produced in the Example 14-(a) (54 mg) in dimethyl sulfoxide (3 mL) was added dropwise a 1 M aqueous solution of potassium hydroxide (0.891 mL) under argon gas flow with stirring at room temperature, and the resulting mixture was stirred at 70° C. for 3 hours. After the reaction was completed, water (5 mL) was added thereto, and 1 M hydrochloric acid was added thereto to adjust the pH to 5.2. The resulting mixture was stirred at room temperature for 1 hour, the resulting solids were collected by filtration, washed with water, and dried under reduced pressure at 60° C. to give the title compound (50 mg) as white solids.

Mass spectrum (ESI, m/z): 592 $[M+H]^+$ $^1$H-NMR spectrum (400 MHz, $CD_3OD$) δ: 7.85-7.62 (m, 3H), 7.58-7.48 (m, 2H), 7.42-7.32 (m, 1H), 7.24-7.04 (m, 3H), 4.95-4.82 (m, 1H), 4.24-4.16 (m, 3H), 4.12-3.95 (m, 1H), 3.90-3.77 (m, 2H), 3.69-3.54 (m, 2H), 2.98-2.81 (m, 2H), 2.72-2.63 (m, 3H), 2.56-2.48 (m, 3H), 2.30-2.22 (m, 3H), 1.73-1.57 (m, 1H), 1.53-1.40 (m, 1H), 1.40-1.22 (m, 6H), 1.04-0.93 (m, 3H)

Example 15-(a)

Production of methyl 3-(1,4-dimethyl-1H-benzo[d][1,2,3]triazol-5-yl)-3-(3-(((R)-8-ethyl-1,5,7,8-tetrahydro-6H-[1,4]oxazepino[6,7-f]indazol-6-yl)methyl)-4-methylphenyl)-2,2-dimethylpropanoate

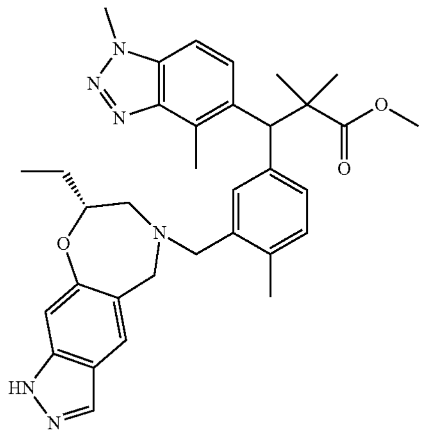 [SMILES: CC[C@@H]1CN(Cc2cc(C(c3ccc4c(nnn4C)c3C)C(C)(C)C(=O)OC)ccc2C)Cc2cc3cn[nH]c3cc2O1]

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (25 mg) in dichloromethane (2 mL) was added (R)-8-ethyl-5,6,7,8-tetrahydro-1H-[1,4]oxazepino[6,7-f]indazole produced in the Reference Example 15-(j) (16 mg) under argon gas flow with stirring at room temperature, and the resulting mixture was stirred at room temperature for 1 hour. Then, sodium triacetoxyborohydride (30 mg) was added thereto with stirring at room temperature, and the resulting mixture was stirred at room temperature for 20 hours. After the reaction was completed, to the reaction solution was added a saturated aqueous solution of sodium hydrogen carbonate, and the resulting mixed solution was subjected to extraction with dichloromethane. The resulting organic layer was washed with saturated brine, dried over anhydrous sodium sulfate, filtered, concentrated under reduced pressure, and the resulting residues were purified by a silica gel column (elution solvent; hexane:ethyl acetate) to give the title compound (29 mg) as a colorless oil.

Mass spectrum (EST, m/z): 581 $[M+H]^+$ $^1$H-NMR spectrum (400 MHz, $CD_3OD$) δ: 7.93-7.83 (m, 1H), 7.76-7.57 (m, 1H), 7.52-7.38 (m, 1H), 7.33-6.97 (m, 5H), 4.91-4.82 (m, 1H), 4.27-4.19 (m, 3H), 3.97-3.88 (m, 1H), 3.79-3.39 (m, 7H), 2.93-2.63 (m, 5H), 2.29-2.15 (m, 3H), 1.65-1.16 (m, 8H), 1.04-0.95 (m, 3H)

Example 15-(b)

Production of 3-(1,4-dimethyl-1H-benzo[d][1,2,3]triazol-5-yl)-3-(3-(((R)-8-ethyl-1,5,7,8-tetrahydro-6H-[1,4]oxazepino[6,7-f]indazol-6-yl)methyl)-4-methylphenyl)-2,2-dimethylpropanoic Acid

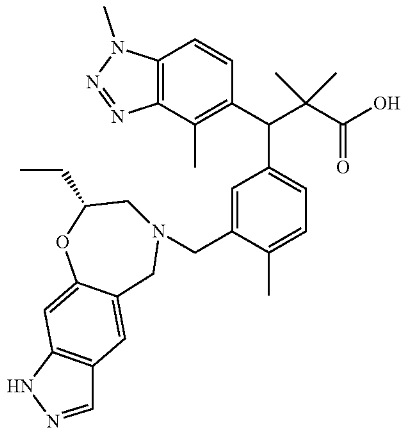 [SMILES: CC[C@@H]1CN(Cc2cc(C(c3ccc4c(nnn4C)c3C)C(C)(C)C(=O)O)ccc2C)Cc2cc3cn[nH]c3cc2O1]

To a solution of methyl 3-(1,4-dimethyl-1H-benzo[d][1,2,3]triazol-5-yl)-3-(3-(((R)-8-ethyl-1,5,7,8-tetrahydro-6H-[1,4]oxazepino[6,7-f]indazol-6-yl)methyl)-4-methylphenyl)-2,2-dimethylpropanoate produced in the Example 15-(a) (29 mg) in dimethyl sulfoxide (2 mL) was added a 2 M aqueous solution of potassium hydroxide (0.250 mL) with stirring at room temperature, and the resulting mixture was stirred at 70° C. for 5 hours. After the reaction was completed, to the reaction solution was added 1 M hydrochloric acid to adjust the pH to about 5, and the resulting mixture was subjected to extraction with ethyl acetate. The resulting organic layer was washed with saturated brine, dried over anhydrous magnesium sulfate, filtered, concentrated under reduced pressure, the resulting residues were purified by a silica gel column (DIOL silica gel, elution solvent; hexane:ethyl acetate), and the fractions comprising the title compound were concentrated under reduced pressure. The resulting residues were dissolved into a mixed solvent of acetonitrile/water, and the resulting solution was lyophilized to give the title compound (17 mg) as white solids.

Mass spectrum (ESI, m/z): 567 $[M+H]^+$ $^1$H-NMR spectrum (400 MHz, $CD_3OD$) δ: 7.93-7.86 (m, 1H), 7.78-7.66 (m, 1H), 7.50-7.40 (m, 1H), 7.36-7.16 (m, 2H), 7.12-7.00 (m, 3H), 4.96-4.77 (m, 1H), 4.29-4.22 (m, 3H), 4.03-3.92 (m, 1H), 3.82-3.44 (m, 4H), 2.93-2.65 (m, 5H), 2.29-2.19 (m, 3H), 1.60-1.46 (m, 1H), 1.43-1.19 (m, 7H), 1.05-0.96 (m, 3H)

Example 16-(a)

Production of methyl 3-(1,4-dimethyl-1H-benzo[d][1,2,3]triazol-5-yl)-3-(3-(((R)-4-ethyl-3,4-dihydronaphtho[1,2-f][1,4]oxazepin-2 (1H)-yl)methyl)-4-methylphenyl)-2,2-dimethylpropanoate

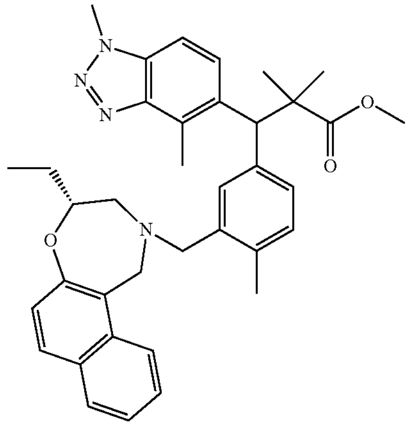 [SMILES: CC[C@@H]1CN(Cc2cc(C(c3ccc4c(nnn4C)c3C)C(C)(C)C(=O)OC)ccc2C)Cc2c(ccc3ccccc23)O1]

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (40 mg) in dichloromethane (2 mL) was added (R)-4-ethyl-1,2,3,4-tetrahydronaphtho[1,2-f][1,4]oxazepine produced in the Reference Example 16-(d) (36 mg) under argon gas flow with stirring at room temperature, then acetic acid (0.009 mL) was added thereto with stirring at room temperature, and the resulting mixture was stirred at room temperature for 30 minutes. Then, sodium triacetoxyborohydride (46 mg) was added thereto with stirring at room temperature, and the resulting mixture was stirred at room temperature for 4 hours. After the reaction was completed, to the reaction solution was added a saturated aqueous solution of sodium hydrogen carbonate, and the resulting mixed solution was subjected to extraction with ethyl acetate. The resulting organic layer was dried over anhydrous magnesium sulfate, filtered, and concentrated under reduced pressure. The resulting residues were purified by a silica gel column (elution solvent; hexane:ethyl acetate) to give the title compound (60 mg) as a colorless foam.

Mass spectrum (ESI, m/z): 591 $[M+H]^+$ $^1$H-NMR spectrum (400 MHz, DMSO-$d_6$) δ: 7.88-7.82 (m, 1H), 7.80-7.73 (m, 1H), 7.65-7.43 (m, 3H), 7.36-7.28 (m, 1H), 7.28-7.07 (m, 4H), 7.06-6.97 (m, 1H), 4.81-4.65 (m, 1H), 4.40-4.31 (m, 1H), 4.23 (s, 3H), 3.96-3.86 (m, 1H), 3.85-3.76 (m, 1H), 3.69-3.51 (m, 2H), 3.44-3.36 (m, 3H), 2.94-2.70 (m, 2H), 2.65-2.55 (m, 3H), 2.17-2.11 (m, 3H), 1.65-1.48 (m, 1H), 1.45-1.30 (m, 1H), 1.29-1.18 (m, 6H), 1.04-0.92 (m, 3H)

Example 16-(b)

Production of 3-(1,4-dimethyl-1H-benzo[d][1,2,3]triazol-5-yl)-3-(3-(((R)-4-ethyl-3,4-dihydronaphtho[1,2-f][1,4]oxazepin-2(1H)-yl)methyl)-4-methylphenyl)-2,2-dimethylpropanoic Acid

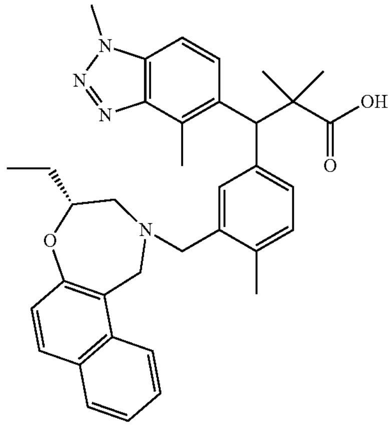 [SMILES: CC[C@@H]1CN(Cc2cc(C(c3ccc4c(nnn4C)c3C)C(C)(C)C(=O)O)ccc2C)Cc2c(ccc3ccccc23)O1]

To a solution of methyl 3-(1,4-dimethyl-1H-benzo[d][1,2,3]triazol-5-yl)-3-(3-(((R)-4-ethyl-3,4-dihydronaphtho[1,2-f][1,4]oxazepin-2 (1H)-yl)methyl)-4-methylphenyl)-2,2-dimethylpropanoate produced in the Example 16-(a) (59 mg) in dimethyl sulfoxide (2 mL) was added a 1 M aqueous solution of potassium hydroxide (1.0 mL) under argon gas flow with stirring at room temperature, and the resulting mixture was stirred at 70° C. for 2 hours. After the reaction was completed, to the reaction solution was added 1 M hydrochloric acid (1.0 mL), and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (DIOL silica gel, elution solvent; hexane:ethyl acetate) to give the title compound (36 mg) as white solids.

Mass spectrum (ESI, m/z): 577 $[M+H]^+$ $^1$H-NMR spectrum (400 MHz, DMSO-$d_6$) δ: 12.18 (s, 1H), 7.87-7.81 (m, 1H), 7.80-7.73 (m, 1H), 7.72-7.56 (m, 1H), 7.54-7.43 (m, 2H), 7.36-7.29 (m, 1H), 7.26-7.07 (m, 4H), 7.05-6.97 (m, 1H), 4.85-4.71 (m, 1H), 4.41-4.31 (m, 1H), 4.22 (s, 3H), 3.95-3.85 (m, 1H), 3.84-3.75 (m, 1H), 3.67-3.48 (m, 2H), 2.94-2.72 (m, 2H), 2.64-2.56 (m, 3H), 2.18-2.08 (m, 3H), 1.66-1.47 (m, 1H), 1.43-1.14 (m, 7H), 1.02-0.93 (m, 3H)

Example 17-(a)

Production of methyl 3-(1,4-dimethyl-1H-benzo[d][1,2,3]triazol-5-yl)-3-(3-(((R)-8-ethyl-8,9-dihydro-[1,4]oxazepino[7,6-h]quinolin-10 (11H)-yl)methyl)-4-methylphenyl)-2,2-dimethylpropanoate

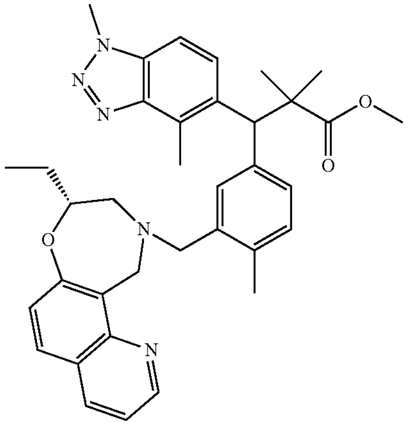 [SMILES: CC[C@@H]1CN(Cc2cc(C(c3ccc4c(nnn4C)c3C)C(C)(C)C(=O)OC)ccc2C)Cc2c(ccc3cccnc23)O1]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (31 mg) in acetonitrile (3 mL) were sequentially added (R)-8-ethyl-8,9,10,11-tetrahydro-[1,4]oxazepino[7,6-h]quinoline dihydrochloride produced in the Reference Example 17-(d) (28 mg) and N,N-diisopropylethylamine (0.040 mL) under argon gas flow with stirring at room temperature, and the resulting mixture was stirred at room temperature for 15 hours and at 60° C. for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (38 mg) as a white foam.

Mass spectrum (ESI, m/z): 592 $[M+H]^+$ $^1$H-NMR spectrum (400 MHz, $CDCl_3$) δ: 8.83-8.76 (m, 1H), 8.12-8.04 (m, 1H), 7.69-7.62 (m, 1H), 7.61-7.51 (m, 1H), 7.34-7.22 (m, 2H), 7.22-7.16 (m, 1H), 7.15-7.08 (m, 1H), 7.04-6.92 (m, 2H), 5.09-5.01 (m, 1H), 4.79-4.71 (m, 1H), 4.42-4.32 (m, 1H), 4.23 (s, 3H), 4.04-3.93 (m, 1H), 3.75-3.57 (m, 2H), 3.46-3.36 (m, 3H), 2.91-2.78 (m, 2H), 2.73-2.65 (m, 3H), 2.26 (s, 3H), 1.69-1.47 (m, 1H), 1.45-1.18 (m, 7H), 1.04-0.95 (m, 3H)

Example 17-(b)

Production of 3-(1,4-dimethyl-1H-benzo[d][1,2,3]triazol-5-yl)-3-(3-(((R)-8-ethyl-8,9-dihydro-[1,4]oxazepino[7,6-h]quinolin-10 (11H)-yl)methyl)-4-methylphenyl)-2,2-dimethylpropanoic Acid

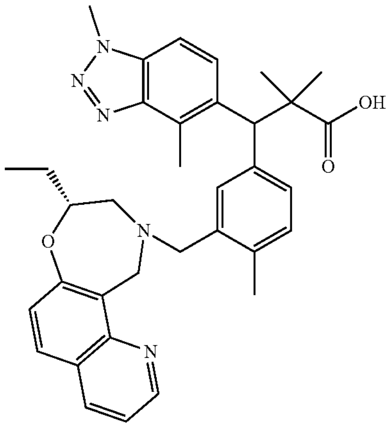 [SMILES: CC[C@@H]1CN(Cc2cc(C(c3ccc4c(nnn4C)c3C)C(C)(C)C(=O)O)ccc2C)Cc2c(ccc3cccnc23)O1]

To a solution of methyl 3-(1,4-dimethyl-1H-benzo[d][1,2,3]triazol-5-yl)-3-(3-(((R)-8-ethyl-8,9-dihydro-[1,4]oxazepino[7,6-h]quinolin-10 (11H)-yl)methyl)-4-methylphenyl)-2,2-dimethylpropanoate produced in the Example 17-(a) (38 mg) in dimethyl sulfoxide (2.5 mL) was added dropwise a 1 M aqueous solution of potassium hydroxide (0.642 mL) under argon gas flow with stirring at room temperature, and the resulting mixture was stirred at 70° C. for 3 hours. After the reaction was completed, water (5 mL) was added thereto, and 1 M hydrochloric acid was added thereto to adjust the pH to 5.2. The resulting mixture was stirred at room temperature for 1 hour, the resulting solids were collected by filtration, washed with water, and dried under reduced pressure at 60° C. to give the title compound (27 mg) as white solids.

Mass spectrum (ESI, m/z): 578 $[M+H]^+$ $^1$H-NMR spectrum (400 MHz, $CD_3OD$) δ: 8.75-8.67 (m, 1H), 8.27-8.19 (m, 1H), 7.82-7.57 (m, 2H), 7.43-7.24 (m, 3H), 7.18-6.99 (m, 3H), 5.05-4.75 (m, 2H), 4.33-4.19 (m, 4H), 4.04-3.89 (m, 1H), 3.79-3.66 (m, 2H), 2.94-2.78 (m, 2H), 2.64-2.55 (m, 3H), 2.32-2.23 (m, 3H), 1.65-1.49 (m, 1H), 1.41-1.09 (m, 7H), 1.03-0.93 (m, 3H)

Example 18-(a)

Production of methyl 3-(1,4-dimethyl-1H-benzo[d][1,2,3]triazol-5-yl)-3-(3-(((R)-4-ethyl-3,4-dihydro-[1,4]oxazepino[6,7-f]quinolin-2 (1H)-yl)methyl)-4-methylphenyl)-2,2-dimethylpropanoate

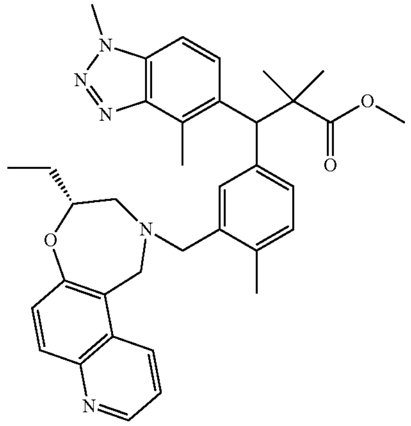 [SMILES: CC[C@@H]1CN(Cc2cc(C(c3ccc4c(nnn4C)c3C)C(C)(C)C(=O)OC)ccc2C)Cc2c(ccc3ncccc23)O1]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (49 mg) in acetonitrile (2.5 mL) was added (R)-4-ethyl-1,2,3,4-tetrahydro-[1,4]oxazepino[6,7-f]quinoline produced in the Reference Example 18-(c) (23 mg) under argon gas flow with stirring at room temperature, and the resulting mixture was stirred at room temperature for 1 hour, at 60° C. for 3.5 hours, and at room temperature for 14.5 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, concentrated under reduced pressure, and the resulting residues were purified by a silica gel column (elution solvent; hexane:ethyl acetate) to give the title compound (44 mg) as a white foam.

Mass spectrum (ESI, m/z): 592 $[M+H]^+$ $^1$H-NMR spectrum (400 MHz, $CDCl_3$) δ: 8.73-8.62 (m, 1H), 7.98-7.90 (m, 1H), 7.65-7.41 (m, 3H), 7.21-6.96 (m, 5H), 4.88-4.81 (m, 1H), 4.32-4.18 (m, 4H), 3.98-3.82 (m, 2H), 3.73-3.41 (m, 5H), 3.03-2.92 (m, 2H), 2.81-2.74 (m, 3H), 2.16-2.09 (m, 3H), 1.55 (m, 2H), 1.39-1.23 (m, 6H), 1.14-1.02 (m, 3H)

Example 18-(b)

Production of 3-(1,4-dimethyl-1H-benzo[d][1,2,3]triazol-5-yl)-3-(3-(((R)-4-ethyl-3,4-dihydro-[1,4]oxazepino[6,7-f]quinolin-2(1H)-yl)methyl)-4-methylphenyl)-2,2-dimethylpropanoic Acid

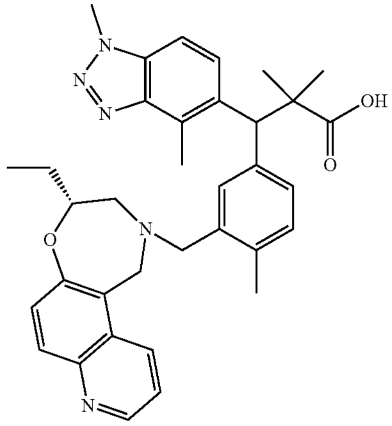 [SMILES: CC[C@@H]1CN(Cc2cc(C(c3ccc4c(nnn4C)c3C)C(C)(C)C(=O)O)ccc2C)Cc2c(ccc3ncccc23)O1]

To a solution of methyl 3-(1,4-dimethyl-1H-benzo[d][1,2,3]triazol-5-yl)-3-(3-(((R)-4-ethyl-3,4-dihydro-[1,4]oxazepino[6,7-f]quinolin-2(1H)-yl)methyl)-4-methylphenyl)-2,2-dimethylpropanoate produced in the Example 18-(a) (44 mg) in dimethyl sulfoxide (2 mL) was added dropwise a 1 M aqueous solution of potassium hydroxide (0.744 mL) under argon gas flow with stirring at room temperature, and the resulting mixture was stirred at 70° C. for 4 hours. After the reaction was completed, the reaction solution was allowed to cool to room temperature, water (4 mL) was added thereto, 1 M hydrochloric acid (0.744 mL) was added thereto, and then the resulting mixture was stirred at room temperature for 1 hour. The resulting solids were collected by filtration, washed with water, and dried under reduced pressure at 60° C. to give the title compound (15 mg) as white solids.

Mass spectrum (ESI, m/z): 578 $[M+H]^+$ $^1$H-NMR spectrum (400 MHz, $CD_3OD$) δ: 8.56-8.46 (m, 1H), 7.89-7.83 (m, 1H), 7.83-7.63 (m, 1H), 7.56-7.50 (m, 1H), 7.49-7.44 (m, 1H), 7.43-7.19 (m, 3H), 7.09-6.98 (m, 2H), 4.95-4.80 (m, 1H), 4.31-4.20 (m, 4H), 3.96-3.54 (m, 4H), 3.11-2.86 (m, 21), 2.69-2.65 (m, 3H), 2.16-2.09 (m, 3H), 1.72-1.41 (m, 2H), 1.37-1.21 (m, 6H), 1.12-1.03 (m, 3H)

Example 19-(a)

Production of methyl 3-(1,4-dimethyl-1H-benzo[d][1,2,3]triazol-5-yl)-3-(3-(((R)-4-ethyl-3,4-dihydro-[1,4]oxazepino[7,6-c]quinolin-2 (1H)-yl)methyl)-4-methylphenyl)-2,2-dimethylpropanoate

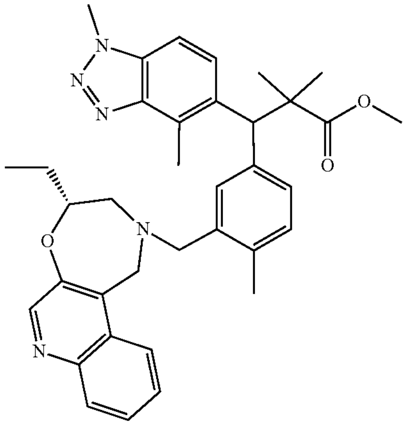 [SMILES: CC[C@@H]1CN(Cc2cc(C(c3ccc4c(nnn4C)c3C)C(C)(C)C(=O)OC)ccc2C)Cc2c(cnc3ccccc23)O1]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (49 mg) in acetonitrile (3 mL) were sequentially added (R)-4-ethyl-1,2,3,4-tetrahydro-[1,4]oxazepino[7,6-c]quinoline dihydrochloride produced in the Reference Example 19-(d) (56 mg) and N,N-diisopropylethylamine (0.085 mL) under argon gas flow with stirring at room temperature, and the resulting mixture was stirred at 60° C. for 2 hours and at 80° C. for 1 hour. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane ethyl acetate) to give the title compound (67 mg) as a white foam.

Mass spectrum (ESI, m/z): 592 $[M+H]^+$

Example 19-(b)

Production of 3-(1,4-dimethyl-1H-benzo[d][1,2,3]triazol-5-yl)-3-(3-(((R)-4-ethyl-3,4-dihydro-[1,4]oxazepino[7,6-c]quinolin-2(1H)-yl)methyl)-4-methylphenyl)-2,2-dimethylpropanoic Acid

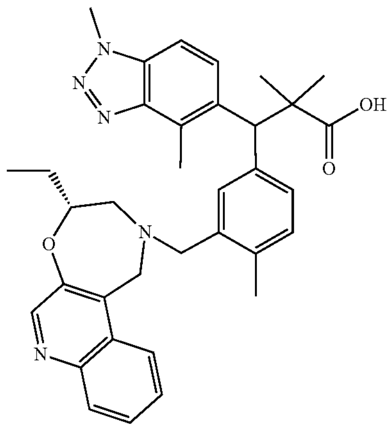 [SMILES: CC[C@@H]1CN(Cc2cc(C(c3ccc4c(nnn4C)c3C)C(C)(C)C(=O)O)ccc2C)Cc2c(cnc3ccccc23)O1]

To a solution of methyl 3-(1,4-dimethyl-1H-benzo[d][1,2,3]triazol-5-yl)-3-(3-(((R)-4-ethyl-3,4-dihydro-[1,4]oxazepino[7,6-c]quinolin-2 (1H)-yl)methyl)-4-methylphenyl)-2,2-dimethylpropanoate produced in the Example 19-(a) (67 mg) in dimethyl sulfoxide (3 mL) was added dropwise a 1 M aqueous solution of potassium hydroxide (1.13 mL) under argon gas flow with stirring at room temperature, and the resulting mixture was stirred at 70° C. for 3 hours. After the reaction was completed, to the reaction solution was added water (5 mL), and 1 M hydrochloric acid was added thereto to adjust the pH to 5.2. The resulting mixed solution was subjected to extraction three times with ethyl acetate. The resulting organic layer was washed with saturated brine, dried over anhydrous magnesium sulfate, filtered, and concentrated under reduced pressure. The resulting residues were purified by a silica gel column (elution solvent; ethyl acetate:methanol) to give a crude product of the title compound (25 mg) as a slightly yellow foam. The resulting crude product was dissolved into methanol, purified by a ODS column (elution solvent; water:acetonitrile), and the fractions comprising the title compound were combined. The resulting solution was lyophilized to give the title compound (15 mg) as white solids.

Mass spectrum (ESI, m/z): 578 $[M+H]^+$ $^1$H-NMR spectrum (400 MHz, $CD_3OD$) δ: 8.53 (s, 1H), 7.96-7.88 (m, 1H), 7.82-7.64 (m, 1H), 7.57-7.48 (m, 1H), 7.43-7.24 (m, 3H), 7.23-7.09 (m, 2H), 7.03-6.95 (m, 1H), 5.01-4.79 (m, 1H), 4.40-4.31 (m, 1H), 4.23 (s, 3H), 3.98-3.84 (m, 2H), 3.77-3.67 (m, 1H), 3.67-3.56 (m, 1H), 3.04-2.85 (m, 2H), 2.68-2.60 (m, 3H), 2.15 (s, 3H), 1.69-1.55 (m, 1H), 1.51-1.38 (m, 1H), 1.35-1.24 (m, 3H), 1.22-1.15 (m, 3H), 1.08-0.98 (m, 3H)

Example 20-(a)

Production of methyl 3-(1,4-dimethyl-1H-benzo[d][1,2,3]triazol-5-yl)-3-(3-(((R)-7-ethyl-1,7,8,10-tetrahydro-9H-[1,4]oxazepino[7,6-g]indazol-9-yl)methyl)-4-methylphenyl)-2,2-dimethylpropanoate

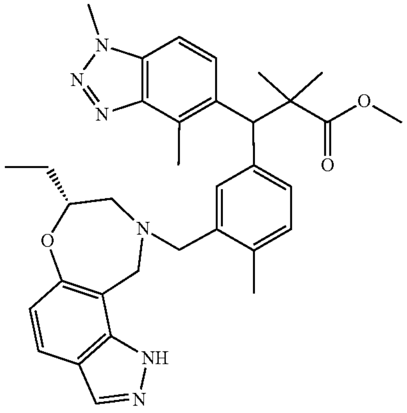 [SMILES: CC[C@@H]1CN(Cc2cc(C(c3ccc4c(nnn4C)c3C)C(C)(C)C(=O)OC)ccc2C)Cc2c(ccc3cn[nH]c23)O1]

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (10 mg) and (R)-7-ethyl-7,8,9,10-tetrahydro-1H-[1,4]oxazepino[7,6-g]indazole dihydrochloride produced in the Reference Example 20-(d) (8 mg) in dichloromethane (2 mL) was added N,N-diisopropylethylamine (0.010 mL) under argon gas flow with stirring at room temperature, and the resulting mixture was stirred at room temperature for 1 hour. Then, sodium triacetoxyborohydride (13 mg) was added thereto with stirring at room temperature, and the resulting mixture was stirred at room temperature for 19 hours. After the reaction was completed, to the reaction solution was added a saturated aqueous solution of sodium hydrogen carbonate, and the resulting mixed solution was subjected to extraction with dichloromethane. The resulting organic layer was concentrated under reduced pressure. The resulting residues were purified by a silica gel column (elution solvent; hexane:ethyl acetate) to give the title compound (13 mg) as a colorless oil.

Mass spectrum (ESI, m/z): 581 $[M+H]^+$ $^1$H-NMR spectrum (400 MHz, DMSO-$d_6$) δ: 13.13-12.87 (br s, 1H), 8.01 (s, 1H), 7.77-7.43 (m, 3H), 7.16-6.95 (m, 3H), 6.88-6.74 (m, 1H), 4.75-4.63 (m, 1H), 4.44-4.32 (m, 1H), 4.30-4.17 (m, 3H), 4.11-3.98 (m, 1H), 3.88-3.71 (m, 1H), 3.66-3.49 (m, 2H), 3.48-3.26 (m, 3H), 2.80-2.43 (m, 5H), 2.35-2.12 (m, 3H), 1.70-0.99 (m, 8H), 0.95-0.71 (m, 3H)

Example 20-(b)

Production of 3-(1,4-dimethyl-1H-benzo[d][1,2,3]triazol-5-yl)-3-(3-(((R)-7-ethyl-1,7,8,10-tetrahydro-9H-[1,4]oxazepino[7,6-g]indazol-9-yl)methyl)-4-methylphenyl)-2,2-dimethylpropanoic Acid

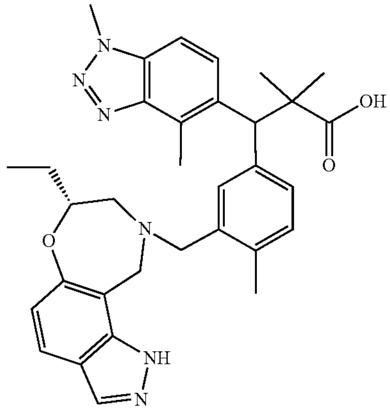 [SMILES: CC[C@@H]1CN(Cc2cc(C(c3ccc4c(nnn4C)c3C)C(C)(C)C(=O)O)ccc2C)Cc2c(ccc3cn[nH]c23)O1]

To a solution of methyl 3-(1,4-dimethyl-1H-benzo[d][1,2,3]triazol-5-yl)-3-(3-(((R)-7-ethyl-1,7,8,10-tetrahydro-9H-[1,4]oxazepino[7,6-g]indazol-9-yl)methyl)-4-methylphenyl)-2,2-dimethylpropanoate produced in the Example 20-(a) (12 mg) in dimethyl sulfoxide (1 mL) was added dropwise a 1 M aqueous solution of potassium hydroxide (0.210 mL) with stirring at room temperature, and the resulting mixture was stirred at 70° C. for 5 hours. After the reaction was completed, to the reaction solution was added water (5 mL), 1 M hydrochloric acid was added thereto to adjust the pH to 5.0, and the resulting mixture was stirred overnight. The resulting solids were collected by filtration, washed with water, and dried under reduced pressure at 65° C. to give the title compound (6 mg) as white solids.

Mass spectrum (ESI, m/z): 567 $[M+H]^+$ $^1$H-NMR spectrum (400 MHz, $CD_3OD$) δ: 7.99-7.92 (m, 1H), 7.74-7.61 (m, 1H), 7.60-7.53 (m, 1H), 7.44-7.36 (m, 1H), 7.19-7.07 (m, 2H), 7.05-7.00 (m, 1H), 6.89-6.81 (m, 1H), 5.07-4.43 (m, 1H), 4.32-4.21 (m, 4H), 4.08-3.98 (m, 1H), 3.89-3.71 (m, 1H), 3.64 (s, 2H), 2.87-2.59 (m, 5H), 2.30-2.19 (m, 3H), 1.54-1.06 (m, 8H), 1.00-0.80 (m, 3H)

Example 21-(a)

Production of methyl 3-(1,4-dimethyl-1H-benzo[d][1,2,3]triazol-5-yl)-3-(3-(((R)-7-ethyl-1-methyl-1,7,8,10-tetrahydro-9H-[1,4]oxazepino[7,6-g]indazol-9-yl)methyl)-4-methylphenyl)-2,2-dimethylpropanoate

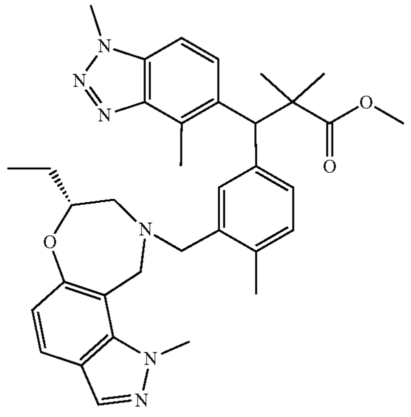 [SMILES: CC[C@@H]1CN(Cc2cc(C(c3ccc4c(nnn4C)c3C)C(C)(C)C(=O)OC)ccc2C)Cc2c(ccc3cnn(C)c23)O1]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (53 mg) in acetonitrile (2 mL) were sequentially added (R)-7-ethyl-1-methyl-7,8,9,10-tetrahydro-1H-[1,4]oxazepino[7,6-g]indazole dihydrochloride produced in the Reference Example 21-(b) (38 mg) and N,N-diisopropylethylamine (0.065 mL) under argon gas flow with stirring at room temperature, and the resulting mixture was stirred at 60° C. for 5 hours and then at room temperature overnight. After the reaction was completed, the reaction solution was concentrated under reduced pressure. The resulting residues were purified by a silica gel column (elution solvent; hexane:ethyl acetate) to give the title compound (77 mg) as a colorless oil.

Mass spectrum (ESI, m/z): 595 $[M+H]^+$ $^1$H-NMR spectrum (400 MHz, $CD_3OD$) δ: 7.76-7.54 (m, 2H), 7.49-7.25 (m, 3H), 7.23-7.14 (m, 1H), 7.10-6.99 (m, 1H), 6.86-6.76 (m, 1H), 4.92-4.81 (m, 1H), 4.27-4.15 (m, 4H), 3.85-3.60 (m, 3H), 3.60-3.39 (m, 4H), 3.17-2.95 (m, 4H), 2.87-2.64 (m, 4H), 2.20-2.07 (m, 3H), 1.69-1.55 (m, 1H), 1.53-1.16 (m, 7H), 1.12-0.97 (m, 3H)

Example 21-(b)

Production of 3-(1,4-dimethyl-1H-benzo[d][1, 2, 3)triazol-5-yl)-3-(3-(((R)-7-ethyl-1-methyl-1,7,8,10-tetrahydro-9H-(1,4]oxazepino[7,6-g]indazol-9-yl) methyl)-4-methylphenyl)-2,2-dimethylpropanoic Acid

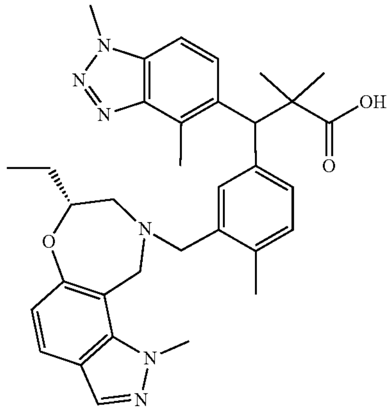 [SMILES: CC[C@@H]1CN(Cc2cc(C(c3ccc4c(nnn4C)c3C)C(C)(C)C(=O)O)ccc2C)Cc2c(ccc3cnn(C)c23)O1]

To a solution of methyl 3-(1,4-dimethyl-1H-benzo[d][1,2,3]triazol-5-yl)-3-(3-3-(((R)-7-ethyl-1-methyl-1,7,8,10-tetrahydro-9H-[1,4]oxazepino[7,6-g]indazol-9-yl)methyl)-4-methylphenyl)-2,2-dimethylpropanoate produced in the Example 21-(a) (77 mg) in dimethyl sulfoxide (2 mL) was added a 2 M aqueous solution of potassium hydroxide (0.58 mL) with stirring at room temperature, and the resulting mixture was stirred at 70° C. for 5 hours. After the reaction was completed, to the reaction solution was added 1 M hydrochloric acid to adjust the pH to about 5, the precipitated solids were filtered, washed with water, and dried under reduced pressure at 40° C. to give the title compound (36 mg) as white solids.

Mass spectrum (ESI, m/z): 581 $[M+H]^+$ $^1$H-NMR spectrum (400 MHz, $CD_3OD$) δ: 7.77-7.59 (m, 2H), 7.52-7.47 (m, 1H), 7.44-7.19 (m, 3H), 7.12-7.04 (m, 1H), 6.88-6.82 (m, 1H), 4.98-4.77 (m, 1H), 4.32-4.22 (m, 4H), 3.86-3.71 (m, 3H), 3.61-3.52 (m, 1H), 3.16-3.06 (m, 4H), 2.93-2.84 (m, 1H), 2.78-2.69 (m, 3H), 2.22-2.13 (m, 3H), 1.72-1.59 (m, 1H), 1.56-1.44 (m, 1H), 1.39-1.18 (m, 6H), 1.14-1.04 (m, 3H)

Example 22-(a)

Production of methyl 3-(1,4-dimethyl-1H-benzo[d][1,2,3]triazol-5-yl)-3-(3-(((R)-7-ethyl-2-methyl-2,7,8,10-tetrahydro-9H-[1,4]oxazepino[7,6-g]indazol-9-yl)methyl)-4-methylphenyl)-2,2-dimethylpropanoate

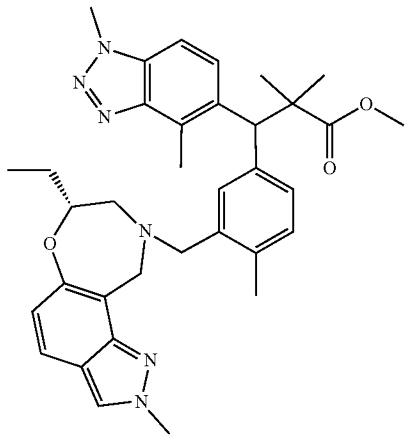 [SMILES: CC[C@@H]1CN(Cc2cc(C(c3ccc4c(nnn4C)c3C)C(C)(C)C(=O)OC)ccc2C)Cc2c(ccc3cn(C)nc23)O1]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (42 mg) in acetonitrile (2 mL) were sequentially added (R)-7-ethyl-2-methyl-7,8,9,10-tetrahydro-2H-[1,4]oxazepino[7,6-g]indazole dihydrochloride produced in the Reference Example 22-(b) (30 mg) and N,N-diisopropylethylamine (0.052 mL) under argon gas flow with stirring at room temperature, and the resulting mixture was stirred at 60° C. for 5 hours and then at room temperature overnight. After the reaction was completed, the reaction solution was concentrated under reduced pressure. The resulting residues were purified by a silica gel column (elution solvent; hexane:ethyl acetate) to give the title compound (40 mg) as a pale yellow oil.

Mass spectrum (ESI, m/z): 595 $[M+H]^+$ $^1$H-NMR spectrum (400 MHz, $CD_3OD$) δ: 8.07-7.98 (m, 1H), 7.69-7.54 (m, 1H), 7.52-7.43 (m, 1H), 7.40-7.30 (m, 1H), 7.20-6.99 (m, 3H), 6.84-6.73 (m, 1H), 4.82-4.75 (m, 1H), 4.44-4.31 (m, 1H), 4.27-4.15 (m, 3H), 4.13-4.04 (m, 3H), 4.03-3.95 (m, 1H), 3.93-3.77 (m, 1H), 3.73-3.59 (m, 2H), 3.45-3.35 (m, 3H), 2.83-2.55 (m, 5H), 2.32-2.20 (m, 3H), 1.54-1.40 (m, 1H), 1.36-1.12 (m, 7H), 0.99-0.80 (m, 3H)

Example 22-(b)

Production of 3-(1,4-dimethyl-1H-benzo[d][1, 2, 3)triazol-5-yl)-3-(3-(((R)-7-ethyl-2-methyl-2,7,8,10-tetrahydro-9H-(1,4]oxazepino[7,6-g]indazol-9-yl) methyl)-4-methylphenyl)-2,2-dimethylpropanoic Acid

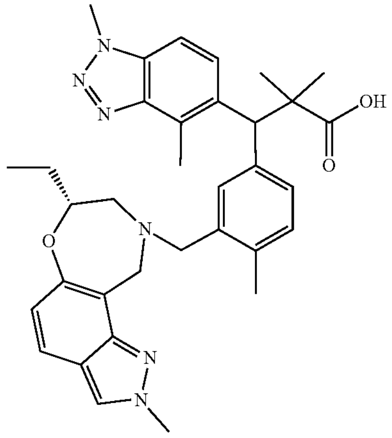 [SMILES: CC[C@@H]1CN(Cc2cc(C(c3ccc4c(nnn4C)c3C)C(C)(C)C(=O)O)ccc2C)Cc2c(ccc3cn(C)nc23)O1]

To a solution of methyl 3-(1,4-dimethyl-1H-benzo[d][1,2,3]triazol-5-yl)-3-(3-(((R)-7-ethyl-2-methyl-2,7,8,10-tetrahydro-9H-[1,4]oxazepino[7,6-g]indazol-9-yl)methyl)-4-methylbiphenyl)-2,2-dimethylpropanoate produced in the Example 22-(a) (40 mg) in dimethyl sulfoxide (8 mL) was added a 2 M aqueous solution of potassium hydroxide (0.30 mL) with stirring at room temperature, and the resulting mixture was stirred at 70° C. for 5 hours. After the reaction was completed, to the reaction solution was added 1 M hydrochloric acid to adjust the pH to about 5, and the precipitated solids were collected by filtration. The resulting filtrate was concentrated, the resulting residues and solids were combined, and purified by Bond Elut (elution solvent; water:acetonitrile). Then, the fractions comprising the target compound were lyophilized. The resulting residues were purified by preparative chromatography (device name: LC-Forte/R, column: T-2000, eluent: acetone). The fractions comprising the target compound were concentrated under reduced pressure, the resulting residues were dissolved into a mixed solvent of acetonitrile/water, and the resulting solution was lyophilized to give the title compound (8 mg) as pale yellow solids.

Mass spectrum (ESI, m/z): 581 $[M+H]^+$ $^1$H-NMR spectrum (400 MHz, $CD_3OD$) δ: 8.10-8.03 (m, 1H), 7.76-7.61 (m, 1H), 7.53-7.46 (m, 1H), 7.41-7.35 (m, 1H), 7.18-7.02 (m, 3H), 6.83-6.77 (m, 1H), 4.96-4.79 (m, 1H), 4.47-4.37 (m, 1H), 4.25 (s, 3H), 4.15-4.08 (m, 3H), 4.05-3.96 (m, 1H), 3.94-3.76 (m, 1H), 3.75-3.66 (m, 2H), 2.88-2.68 (m, 2H), 2.64-2.59 (m, 3H), 2.31-2.25 (m, 3H), 1.55-1.15 (m, 8H), 0.97-0.88 (m, 3H)

Example 23

Production of 3-(1,4-dimethyl-1H-benzo[d][1,2,3]triazol-5-yl)-3-(3-(((R)-4-ethyl-1,3,4,9,10,11-hexahydro-2H-pyrimido[1',2':1,6]pyrido[2,3-f][1,4]oxazepin-2-yl)methyl)-4-methylphenyl)-2,2-dimethylpropanoic Acid

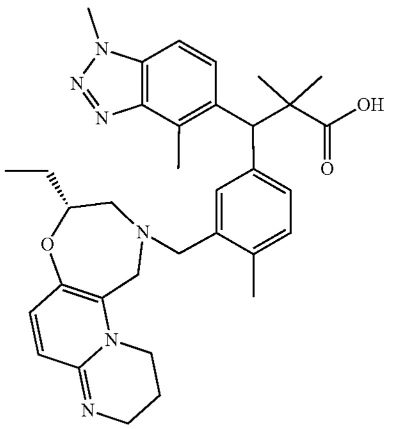 [SMILES: CC[C@@H]1CN(Cc2cc(C(c3ccc4c(nnn4C)c3C)C(C)(C)C(=O)O)ccc2C)CC2=C(C=CC3=NCCCN32)O1]

A solution of 3-(3-(((R)-7-((3-chloropropyl)amino)-2-ethyl-2,3-dihydropyrido[2,3-f][1,4]oxazepin-4(5H)-yl)methyl)-4-methylphenyl)-3-(1,4-dimethyl-1H-benzo[d][1,2,3]triazol-5-yl)-2,2-dimethylpropanoic acid produced in the Reference Example 23-(h) (50 mg) in acetonitrile (4 mL) was stirred under argon gas flow at 90° C. for 4.5 hours. After the reaction was completed, triethylamine (0.010 mL) was added thereto, the reaction solution was stirred, and then concentrated under reduced pressure. The resulting residues were purified by Bond Elut (elution solvent; water:acetonitrile), and the fractions comprising the target compound were concentrated under reduced pressure to give the title compound (42. mg) as yellow solids.

Mass spectrum (DUIS, m/z): 583 $[M+H]^+$ $^1$H-NMR spectrum (400 MHz, $CD_3OD$) δ: 7.70-7.53 (m, 1H), 7.51-7.26 (m, 3H), 7.17-6.99 (m, 2H), 6.72-6.65 (m, 1H), 4.94-4.79 (m, 1H), 4.30-4.25 (m, 3H), 3.98-3.39 (m, 7H), 3.24-2.99 (m, 2H), 2.89-2.76 (m, 5H), 2.28-2.22 (m, 3H), 1.95-1.45 (n, 41), 1.41-1.16 (m, 6H), 1.08-0.98 (m, 3H)

Example 24-(a)

Production of methyl 3-(1,4-dimethyl-1H-benzo[d][1,2,3]triazol-5-yl)-3-(3-(((R)-2-ethyl-2,3-dihydronaphtho[2,1-f][1,4]oxazepin-4 (5H)-yl)methyl)-4-methylphenyl)-2,2-dimethylpropanoate

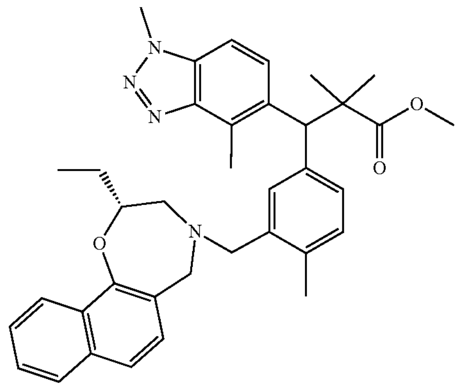 [SMILES: CC[C@@H]1CN(Cc2cc(C(c3ccc4c(nnn4C)c3C)C(C)(C)C(=O)OC)ccc2C)Cc2ccc3ccccc3c2O1]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (51 mg) in acetonitrile (2 mL) were sequentially added (R)-2-ethyl-2,3,4,5-tetrahydronaphtho[2,1-f][1,4]oxazepine produced in the Reference Example 24-(c) (27 mg) and N,N-diisopropylethylamine (0.062 mL) under argon gas flow with stirring at room temperature, and the resulting mixture was stirred at 60° C. for 5 hours and then at room temperature overnight. After the reaction was completed, the reaction solution was concentrated under reduced pressure. The resulting residues were purified by a silica gel column (elution solvent; hexane:ethyl acetate) to give the title compound (51 mg) as a pale yellow foam.

Mass spectrum (ESI, m/z): 591 $[M+H]^+$ $^1$H-NMR spectrum (400 MHz, DMSO-$d_6$) δ: 8.30-8.21 (m, 1H), 7.92-7.85 (m, 1H), 7.61-7.47 (m, 4H), 7.46-7.37 (m, 1H), 7.17-6.90 (m, 4H), 4.75 (s, 1H), 4.32-4.19 (m, 3H), 4.04-3.86 (m, 2H), 3.79-3.66 (m, 1H), 3.63-3.11 (m, 5H), 2.97-2.81 (m, 2H), 2.75-2.38 (m, 3H), 2.22 (s, 3H), 1.80-1.63 (m, 1H), 1.54-1.12 (m, 7H), 1.10-0.99 (m, 3H)

Example 24-(b)

Production of 3-(1,4-dimethyl-1H-benzo[d][1,2,3]triazol-5-yl)-3-(3-(((R)-2-ethyl-2,3-dihydronaphtho[2,1-f][1,4]oxazepin-4(5H)-yl)methyl)-4-methylphenyl)-2,2-dimethylpropanoic Acid

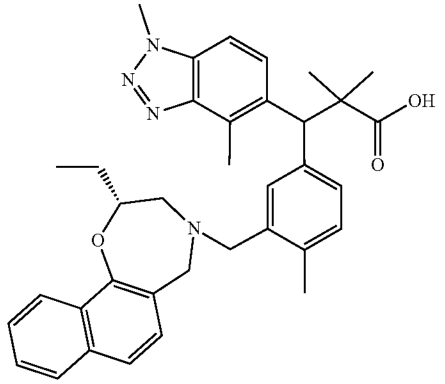

To a solution of methyl 3-(1,4-dimethyl-1H-benzo[d][1,2,3]triazol-5-yl)-3-(3-(((R)-2-ethyl-2,3-dihydronaphtho[2,1-f][1,4]oxazepin-4 (5H)-yl)methyl)-4-methylphenyl)-2,2-dimethylpropanoate produced in the Example 24-(a) (50 mg) in dimethyl sulfoxide (2 mL) was added a 2 M aqueous solution of potassium hydroxide (0.402 mL) with stirring at room temperature, and the resulting mixture was stirred at 70° C. for 3 hours. After the reaction was completed, to the reaction solution was added water, 2 M hydrochloric acid was added thereto to adjust the pH to about 5.6, and the resulting mixture was stirred at room temperature for 1 hour. The resulting solids were collected by filtration, washed with water, dried under reduced pressure, and air-dried overnight to give the title compound (45 mg) as white solids.

Mass spectrum (ESI, m/z): 577 $[M+H]^+$ $^1$H-NMR spectrum (400 MHz, $CD_3OD$) δ: 8.36-8.23 (m, 1H), 7.90-7.65 (m, 2H), 7.56-7.19 (m, 5H), 7.18-7.00 (m, 2H), 6.90-6.61 (m, 1H), 5.04-4.71 (m, 1H), 4.33-4.18 (m, 3H), 4.03-3.80 (m, 2H), 3.80-3.52 (m, 3H), 3.07-2.83 (m, 2H), 2.82-2.64 (m, 3H), 2.38-2.21 (m, 3H), 1.83-1.68 (m, 1H), 1.59-1.46 (m, 1H), 1.44-1.19 (m, 6H), 1.14-1.01 (m, 3H)

Example 25-(a)

Production of methyl 3-(1,4-dimethyl-1H-benzo[d][1,2,3]triazol-5-yl)-3-(3-(((R)-2-ethyl-2,3-dihydro-[1,4]oxazepino[6,7-c]isoquinolin-4 (5H)-yl)methyl)-4-methylphenyl)-2,2-dimethylpropanoate

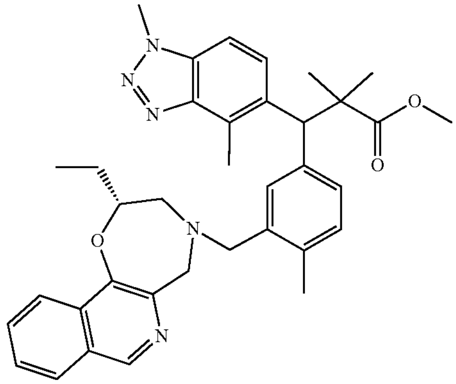 [SMILES: CC[C@@H]1CN(Cc2cc(C(c3ccc4c(nnn4C)c3C)C(C)(C)C(=O)OC)ccc2C)Cc2ncc3ccccc3c2O1]

To a solution of methyl 3-(3-(chloromethyl)-4-methylphenyl)-3-(1,4-dimethyl-1H-benzo (d) [1,2,3]triazol-5-yl)-2,2-dimethylpropanoate produced according to the same manner as the Reference Example 10-(c) (32 mg) in acetonitrile (3 mL) were sequentially added (R)-2-ethyl-2,3,4,5-tetrahydro-[1,4]oxazepino[6,7-c]isoquinoline dihydrochloride produced in the Reference Example 25-(c) (29 mg) and N,N-diisopropylethylamine (0.041 mL) under argon gas flow with stirring at room temperature, and the resulting mixture was stirred at 60° C. for 2 hours and at 80° C. for 1 hour. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane ethyl acetate) to give the title compound (47 mg) as a white foam.

Mass spectrum (DUIS, m/z): 592 $[M+H]^+$ $^1$H-NMR spectrum (400 MHz, $CDCl_3$) δ: 8.90 (s, 1H), 8.32-8.23 (m, 1H), 8.00-7.92 (m, 1H), 7.76-7.55 (m, 3H), 7.22-7.15 (m, 1H), 7.12-6.99 (m, 3H), 4.85-4.77 (m, 1H), 4.28-4.17 (m, 5H), 4.05-3.86 (m, 1H), 3.70-3.51 (m, 2H), 3.47-3.39 (m, 3H), 2.95-2.85 (m, 2H), 2.80-2.72 (m, 3H), 2.28 (s, 3H), 1.83-1.70 (m, 1H), 1.61-1.40 (m, 1H), 1.40-1.19 (m, 6H), 1.14-1.02 (m, 3H)

Example 25-(b)

Production of 3-(1,4-dimethyl-1H-benzo[d][1,2,3]triazol-5-yl)-3-(3-(((R)-2-ethyl-2,3-dihydro-[1,4]oxazepino[6,7-c]isoquinolin-4(5H)-yl)methyl)-4-methylphenyl)-2,2-dimethylpropanoic Acid

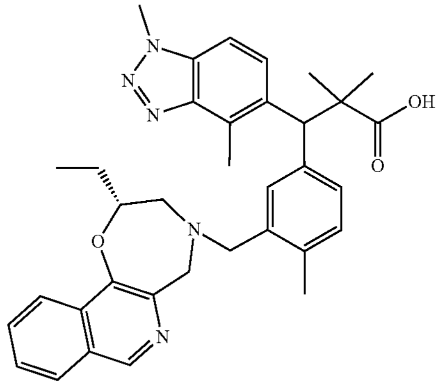 [SMILES: CC[C@@H]1CN(Cc2cc(C(c3ccc4c(nnn4C)c3C)C(C)(C)C(=O)O)ccc2C)Cc2ncc3ccccc3c2O1]

To a solution of methyl 3-(1,4-dimethyl-1H-benzo[d][1,2,3]triazol-5-yl)-3-(3-(((R)-2-ethyl-2,3-dihydro-[1,4]oxazepino[6,7-c]isoquinolin-4(5H)-yl)methyl))-4-methylphenyl)-2,2-dimethylpropanoate produced in the Example 25-(a) (47 mg) in dimethyl sulfoxide (2.5 mL) was added dropwise a 1 M aqueous solution of potassium hydroxide (0.794 mL) under argon gas flow with stirring at room temperature, and the resulting mixture was stirred at 70° C. for 3 hours. After the reaction was completed, water (5 mL) was added thereto, to the reaction solution was added 1 M hydrochloric acid to adjust the pH to 5.2, and the resulting mixture was stirred at room temperature for 15 hours. The resulting solids were collected by filtration, washed with water, and dried under reduced pressure at 60° C. to give the title compound (40 mg) as white solids.

Mass spectrum (DUIS, m/z): 578 $(M+H)^+$ $^1$H-NMR spectrum (400 MHz, $CD_3OD$) δ: 8.90-8.80 (m, 1H), 8.32-8.25 (m, 1H), 8.12-8.05 (m, 1H), 7.85-7.63 (m, 3H), 7.42-7.31 (m, 1H), 7.19-7.11 (m, 2H), 7.09-7.03 (m, 1H), 4.91-4.79 (m, 1H), 4.26-4.06 (m, 5H), 4.06-3.88 (m, 1H), 3.72-3.56 (m, 2H), 3.02-2.82 (m, 2H), 2.72-2.62 (m, 3H), 2.30-2.24 (m, 3H), 1.80-1.65 (m, 1H), 1.56-1.40 (m, 1H), 1.39-1.21 (m, 6H), 1.11-1.00 (m, 3H)

Example 26-(a)

Production of methyl 3-(1,4-dimethyl-1H-benzo[d][1,2,3]triazol-5-yl)-3-(3-(((R)-2-ethyl-2,3-dihydro-[1,4]oxazepino[6,7-c]quinolin-4 (5H)-yl)methyl)-4-methylphenyl)-2,2-dimethylpropanoate

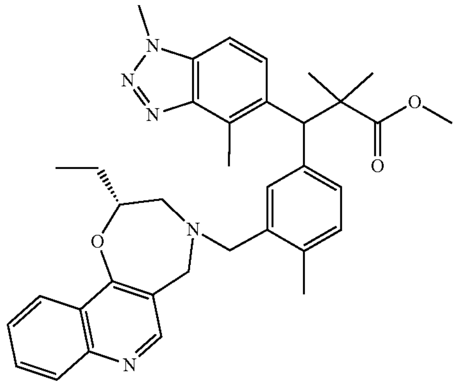 [SMILES: CC[C@@H]1CN(Cc2cc(C(c3ccc4c(nnn4C)c3C)C(C)(C)C(=O)OC)ccc2C)Cc2cnc3ccccc3c2O1]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (36 mg) in acetonitrile (3 mL) were sequentially added (R)-2-ethyl-2,3,4,5-tetrahydro-[1,4]oxazepino[6,7-c]quinoline dihydrochloride produced in the Reference Example 26-(c) (32 mg) and N,N-diisopropylethylamine (0.046 mL) under argon gas flow with stirring at room temperature, and the resulting mixture was stirred at 60° C. for 2 hours and at 80° C. for 1 hour. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane ethyl acetate) to give the title compound (36 mg) as a white foam.

As an alternative method, the title compound was also produced according to the following method.

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (225 mg) in dichloromethane (5 mL) was added (R)-2-ethyl-2,3,4,5-tetrahydro-[1,4]oxazepino[6,7-c]quinoline produced in the Reference Example 26-(h) (142 mg) under argon gas flow with stirring at room temperature, and the resulting mixture was stirred at room temperature for 30 minutes. Then, sodium triacetoxyborohydride (251 mg) was added thereto with stirring at room temperature, and the resulting mixture was stirred at room temperature for 10 hours. After the reaction was completed, to the reaction solution was added a saturated aqueous solution of sodium hydrogen carbonate, and the resulting mixed solution was subjected to extraction with ethyl acetate. The resulting organic layer was dried over anhydrous magnesium sulfate, filtered, and concentrated under reduced pressure. The resulting residues were purified by a silica gel column (elution solvent; hexane:ethyl acetate) to give the title compound (388 mg) as a white foam.

Mass spectrum (ESI, m/z): 592 $[M+H]^+$

$^1$H-NMR spectrum (400 MHz, $CDCl_3$) δ: 8.46-8.33 (m, 1H), 8.32-8.26 (m, 1H), 8.10-8.01 (m, 1H), 7.75-7.65 (m, 1H), 7.62-7.50 (m, 2H), 7.23-7.16 (m, 1H), 7.11-7.00 (m, 3H), 4.87-4.80 (m, 1H), 4.27-4.19 (m, 3H), 4.19-4.06 (m, 1H), 4.03-3.83 (m, 2H), 3.66-3.51 (m, 2H), 3.49-3.42 (m, 3H), 3.03-2.90 (m, 2H), 2.80-2.73 (m, 3H), 2.30-2.21 (m, 3H), 1.88-1.74 (m, 1H), 1.65-1.48 (m, 1H), 1.43-1.22 (m, 6H), 1.14-1.04 (m, 3H)

Example 26-(b)

Production of 3-(1,4-dimethyl-1H-benzo[d][1,2,3]triazol-5-yl)-3-(3-(((R)-2-ethyl-2,3-dihydro-[1,4]oxazepino[6,7-c]quinolin-4(5H)-yl)methyl)-4-methylphenyl)-2,2-dimethylpropanoic Acid

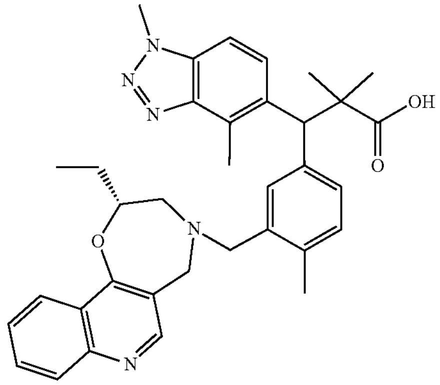 [SMILES: CC[C@@H]1CN(Cc2cc(C(c3ccc4c(nnn4C)c3C)C(C)(C)C(=O)O)ccc2C)Cc2cnc3ccccc3c2O1]

To a solution of methyl 3-(1,4-dimethyl-1H-benzo[d][1,2,3]triazol-5-yl)-3-(3-(((R)-2-ethyl-2,3-dihydro-[1,4]oxazepino[6,7-c]quinolin-4 (5H)-yl)methyl)-4-methylphenyl)-2,2-dimethylpropanoate produced in the Example 26-(a) (36 mg) in dimethyl sulfoxide (2.5 mL) was added dropwise a 1 M aqueous solution of potassium hydroxide (0.608 mL) under argon gas flow with stirring at room temperature, and the resulting mixture was stirred at 70° C. for 3 hours. After the reaction was completed, water (5 mL) was added thereto, and to the reaction solution was added 1 M hydrochloric acid to adjust the pH to 5.2. The resulting mixture was stirred at room temperature for 1 hour, the precipitated solids were collected by filtration, washed with water, and dried under reduced pressure at 60° C. to give the title compound (31 mg) as white solids.

Mass spectrum (ESI, m/z): 578 $[M+H]^+$

$^1$H-NMR spectrum (400 MHz, $CD_3OD$) δ: 8.41-8.27 (m, 2H), 8.01-7.93 (m, 1H), 7.80-7.56 (m, 3H), 7.41-7.27 (m, 1H), 7.21-7.11 (m, 2H), 7.11-7.03 (m, 1H), 4.95-4.80 (m, 1H), 4.29-4.15 (m, 4H), 4.11-3.98 (m, 1H), 3.90-3.79 (m, 1H), 3.72-3.60 (m, 2H), 3.04-2.87 (m, 2H), 2.73-2.63 (m, 3H), 2.27 (s, 3H), 1.82-1.68 (m, 1H), 1.64-1.49 (m, 1H), 1.41-1.23 (m, 6H), 1.10-1.00 (m, 3H)

Example 27-(a)

Production of methyl 3-(1,4-dimethyl-1H-benzo[d][1,2,3]triazol-5-yl)-3-(3-(((R)-2-ethyl-2,3-dihydro-[1,4]oxazepino[6,7-h]quinolin-4(5H)-yl)methyl)-4-methylphenyl)-2,2-dimethylpropanoate

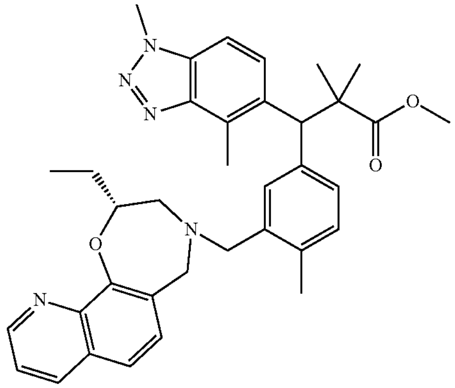 [SMILES: CC[C@@H]1CN(Cc2cc(C(c3ccc4c(nnn4C)c3C)C(C)(C)C(=O)OC)ccc2C)Cc2ccc3cccnc3c2O1]

To a solution of methyl 3-(1,4-dimethyl-1H-benzo[d][1,2,3]triazol-5-yl)-3-(3-(hydroxymethyl)-4-methylphenyl)-2,2-dimethylpropanoate produced according to the same manner as the Reference Example 1-(h) (50 mg) in dichloromethane (2 mL) was added thionyl chloride (0.011 mL) under argon gas flow at room temperature, and the resulting mixture was stirred at room temperature for 1 hour. Thionyl chloride (0.003 mL) was additionally added thereto. After the reaction was completed, the reaction solution was concentrated under reduced pressure. To the resulting residues was added acetonitrile (2 mL), (R)-2-ethyl-2,3,4,5-tetrahydro-[1,4]oxazepino[6,7-h]quinoline dihydrochloride produced in the Reference Example 27-(c) (40 mg) and N,N-diisopropylethylamine (69 mL) were added thereto at room temperature, and the resulting mixture was stirred at 80° C. for 7 hours. After the reaction was completed, to the reaction solution was added ethyl acetate, the resulting mixture was washed sequentially with water and saturated brine, dried over anhydrous magnesium sulfate, filtered, and concentrated under reduced pressure. The resulting residues were purified by a silica gel column (elution solvent; hexane:ethyl acetate) to give the title compound (60 mg) as a white foam.

Mass spectrum (ESI, m/z): 592 $[M+H]^+$

$^1$H-NMR spectrum (400 MHz, $CD_3OD$) δ: 8.88-8.81 (m, 1H), 8.33-8.24 (m, 1H), 7.69-7.59 (m, 1H), 7.55-7.47 (m, 1H), 7.47-7.29 (m, 2H), 7.20-7.12 (m, 1H), 7.11-7.04 (m, 2H), 7.01-6.83 (m, 1H), 4.90-4.85 (m, 1H), 4.27-4.22 (m, 3H), 4.04-3.89 (m, 2H), 3.86-3.70 (m, 1H), 3.69-3.55 (m, 2H), 3.47-3.43 (m, 3H), 3.06-2.90 (m, 2H), 2.75-2.65 (m, 3H), 2.31-2.24 (m, 3H), 1.87-1.73 (m, 1H), 1.60-1.45 (m, 1H), 1.42-1.36 (m, 3H), 1.31-1.27 (m, 3H), 1.00-0.93 (m, 3H)

Example 27-(b)

Production of 3-(1,4-dimethyl-1H-benzo[d][1,2,3]triazol-5-yl)-3-(3-(((R)-2-ethyl-2,3-dihydro-[1,4]oxazepino[6,7-h]quinolin-4 (5H)-yl)methyl)-4-methylphenyl)-2,2-dimethylpropanoic Acid

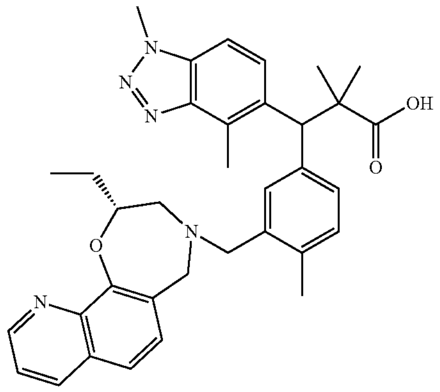 [SMILES: CC[C@@H]1CN(Cc2cc(C(c3ccc4c(nnn4C)c3C)C(C)(C)C(=O)O)ccc2C)Cc2ccc3cccnc3c2O1]

To a solution of methyl 3-(1,4-dimethyl-1H-benzo[d][1,2,3]triazol-5-yl)-3-(3-(((R)-2-ethyl-2,3-dihydro-[1,4]oxazepino[6,7-h]quinolin-4(5H)-yl)methyl)-4-methylphenyl)-2,2-dimethylpropanoate produced in the Example 27-(a) (55 mg) in dimethyl sulfoxide (3 mL) was added dropwise a 1 M aqueous solution of potassium hydroxide (0.232 mL) with stirring at room temperature, and the resulting mixture was stirred at 75° C. for 6 hours. After the reaction was completed, to the reaction solution was added 1 M hydrochloric acid to adjust the pH to 5.5. The resulting mixed solution was subjected to extraction twice with ethyl acetate. The resulting organic layer was washed with saturated brine, dried over anhydrous magnesium sulfate, filtered, and concentrated under reduced pressure. The resulting residues were purified by a silica gel column (DIOL silica gel, elution solvent; hexane:ethyl acetate), and the fractions comprising the target compound were concentrated under reduced pressure. To the resulting residues was added a small amount of acetonitrile to dissolve them, and then water was added thereto to precipitate solids. The resulting solids were collected by filtration, washed with water, and dried under reduced pressure at 60° C. to give the title compound (27 mg) as white solids.

Mass spectrum (ESI, m/z): 578 $[M+H]^+$ $^1$H-NMR spectrum (400 MHz, $CD_3OD$) δ: 8.87-8.82 (m, 1H), 8.32-8.26 (m, 1H), 7.72-7.65 (m, 1H), 7.53-7.48 (m, 1H), 7.47-7.29 (m, 2H), 7.26-7.18 (m, 1H), 7.11-7.05 (m, 2H), 7.03-6.83 (m, 1H), 4.94-4.90 (m, 1H), 4.26-4.21 (m, 3H), 4.04-3.90 (m, 2H), 3.88-3.72 (m, 1H), 3.69-3.56 (m, 2H), 3.07-2.91 (m, 2H), 2.75-2.67 (m, 3H), 2.31-2.25 (m, 3H), 1.87-1.74 (m, 1H), 1.60-1.44 (m, 1H), 1.38 (s, 3H), 1.30-1.24 (m, 3H), 1.00-0.93 (m, 3H)

Example 28-(a)

Production of methyl 3-(1,4-dimethyl-1H-benzo[d][1,2,3]triazol-5-yl)-3-(3-(((R)-2-ethyl-2,3-dihydro-[1,4]oxazepino[7,6-f]quinolin-4 (5H)-yl)methyl)-4-methylphenyl)-2,2-dimethylpropanoate

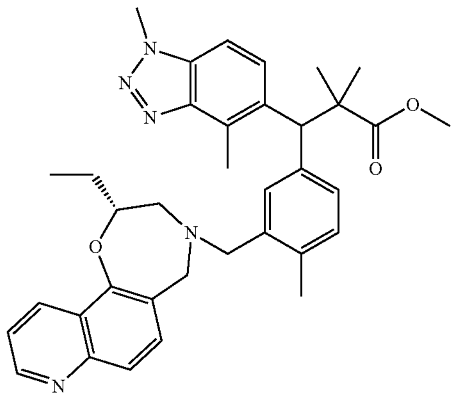 [SMILES: CC[C@@H]1CN(Cc2cc(C(c3ccc4c(nnn4C)c3C)C(C)(C)C(=O)OC)ccc2C)Cc2ccc3ncccc3c2O1]

To a solution of methyl 3-(3-(chloromethyl)-4-methylphenyl)-3-(1,4-dimethyl-1H-benzo (d) [1,2,3]triazol-5-yl)-2,2-dimethylpropanoate produced according to the same manner as the Reference Example 10-(c) (52 mg) in acetonitrile (2.5 mL) were added (R)-2-ethyl-2,3,4,5-tetrahydro-[1,4]oxazepino[7,6-f]quinoline produced in the Reference Example 28-(b) (72 mg) and N,N-diisopropylethylamine (0.045 mL) under argon gas flow with stirring at room temperature, and the resulting mixture was stirred at 60° C. for 3 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (53 mg) as a white foam.

Mass spectrum (ESI, m/z): 592 $[M+H]^+$ $^1$H-NMR spectrum (400 MHz, $CDCl_3$) δ: 8.93-8.86 (m, 1H), 8.69-8.61 (m, 1H), 7.72-7.56 (m, 2H), 7.46-7.37 (m, 1H), 7.31-6.98 (m, 5H), 4.87-4.79 (m, 1H), 4.29-4.19 (m, 3H), 4.08-3.89 (m, 2H), 3.84-3.69 (m, 1H), 3.63-3.39 (m, 5H), 3.05-2.93 (m, 2H), 2.84-2.74 (m, 3H), 2.31-2.19 (m, 3H), 1.89-1.75 (m, 1H), 1.66-1.47 (m, 1H), 1.44-1.29 (m, 6H), 1.17-1.05 (m, 3H)

Example 28-(b)

Production of 3-(1,4-dimethyl-1H-benzo[d][1,2,3]triazol-5-yl)-3-(3-(((R)-2-ethyl-2,3-dihydro-[1,4]oxazepino[7,6-f]quinolin-4(5H)-yl)methyl)-4-methylphenyl)-2,2-dimethylpropanoic Acid

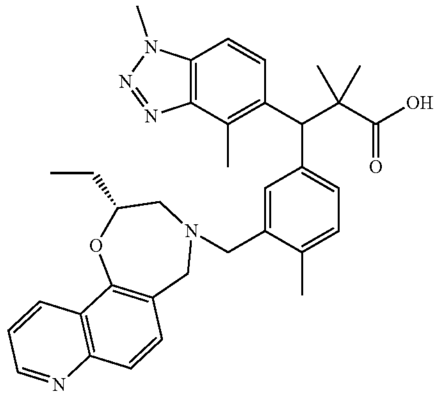 [SMILES: CC[C@@H]1CN(Cc2cc(C(c3ccc4c(nnn4C)c3C)C(C)(C)C(=O)O)ccc2C)Cc2ccc3ncccc3c2O1]

To a solution of methyl 3-(1,4-dimethyl-1H-benzo[d][1,2,3]triazol-5-yl)-3-(3-(((R)-2-ethyl-2,3-dihydro-[1,4]oxazepino[7,6-f]quinolin-4(5H)-yl)methyl)-4-methylphenyl)-2,2-dimethylpropanoate produced in the Example 28-(a) (53 mg) in dimethyl sulfoxide (1.8 mL) was added dropwise a 1 M aqueous solution of potassium hydroxide (0.896 mL) under argon gas flow with stirring at room temperature, and the resulting mixture was stirred at 70° C. for 4 hours. After the reaction was completed, to the reaction solution was added 1 M hydrochloric acid, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (DIOL silica gel, elution solvent; hexane:ethyl acetate) to give the title compound (20 mg) as white solids.

Mass spectrum (ESI, m/z): 578 $[M+H]^+$ $^1$H-NMR spectrum (400 MHz, $CD_3OD$) δ: 8.84-8.78 (m, 1H), 8.76-8.68 (m, 1H), 7.76-7.68 (m, 1H), 7.58-7.49 (m, 2H), 7.48-7.40 (m, 1H), 7.26-7.00 (m, 4H), 4.95-4.81 (m, 1H), 4.30-4.21 (m, 3H), 4.03-3.88 (m, 2H), 3.86-3.75 (m, 1H), 3.65-3.52 (m, 2H), 3.06-2.86 (m, 2H), 2.74-2.66 (m, 3H), 2.28 (s, 3H), 1.83-1.44 (m, 2H), 1.42-1.19 (m, 6H), 1.11-1.01 (m, 3H)

Example 29

3-(1,4-dimethyl-1H-benzo[d][1,2,3)triazol-5-yl)-3-(3-((([]R)-6-ethyl-2,2-difluoro-6,7-dihydro-[1,3]dioxolo[4',5':4,5]benzo[1,2-f][1,4]oxazepin-8(9H)-yl)methyl)-4-methylphenyl)-2,2-dimethylpropanoic Acid (Diastereomer 1) and Example 30

3-(1,4-dimethyl-1N-benzo[d][1,2,3]triazol-5-yl)-3-(3-(((R)-6-ethyl-2,2-difluoro-6,7-dihydro-[1,3]dioxolo[4',5':4,5)benzo[1,2-f](1,4]oxazepin-8(9H)-yl)methyl)-4-methylphenyl)-2,2-dimethylpropanoic Acid (Diastereomer 2)

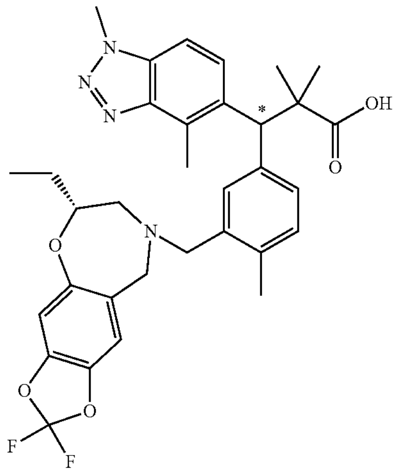 [SMILES: CC[C@@H]1CN(Cc2cc(C(c3ccc4c(nnn4C)c3C)C(C)(C)C(=O)O)ccc2C)Cc2cc3c(cc2O1)OC(F)(F)O3]

3-(1,4-dimethyl-1H-benzo[d][1,2,3]triazol-5-yl)-3-(3-(((R)-6-ethyl-2,2-difluoro-6,7-dihydro-[1,3)dioxolo[4',5':4,5]benzo[1,2-f](1,4]oxazepin-8(9H)-yl)methyl)-4-methylphenyl)-2,2-dimethylpropanoic acid produced according to the same manner as the Example 1-(b) (275 mg) was separated and purified by supercritical fluid chromatography (Column: CHIRALPAK IG, mobile phase: $CO_2$:methanol=85:15). The fractions comprising the first-eluted diastereomer were concentrated under reduced pressure, the resulting residues were dissolved into a mixed solvent of acetonitrile/water, and the resulting solution was lyophilized to give the compound of Example 29 (93 mg) as white solids. Also, the fractions comprising the later-eluted diastereomer were concentrated under reduced pressure, the resulting residues were dissolved into a mixed solvent of acetonitrile/water, and the resulting solution was lyophilized to give the compound of Example 30 (97 mg) as white solids.

(High Performance Liquid Chromatography Analysis)

Column: CHIRALPAK IC-3 4.6×150 mm

Eluent: 0.1% formic acid solution in water/acetonitrile acetonitrile ratio (%)=10 (0 min)→90 (10 min)

Flow rate: 0.8 mL/min

Temperature: 40° C.

Detection wavelength: 254 nm

Retention time: Example 29: 7.59 min, Example 30: 8.03 min

Example 29

Mass spectrum (ESI, m/z): 607 $[M+H]^+$ $^1$H-NMR spectrum (400 MHz, $CD_3OD$) δ: 7.74 (d, J=8.9 Hz, 1H), 7.50 (d, J=8.9 Hz, 1H), 7.20 (dd, J=1.9, 7.9 Hz, 1H), 7.08 (d, J=7.9 Hz, 1H), 6.98 (d, J=1.9 Hz, 1H), 6.85 (s, 1H), 6.68 (s, 1H), 4.98-4.75 (m, 1H), 4.27 (s, 3H), 3.88 (d, J=14.2 Hz, 1H), 3.72-3.61 (m, 1H), 3.56 (d, J=14.2 Hz, 1H), 3.54-3.43 (m, 2H), 2.89-2.71 (m, 2H), 2.70 (s, 3H), 2.27 (s, 3H), 1.51-1.38 (m, 1H), 1.37 (s, 3H), 1.27 (s, 3H), 1.25-1.14 (m, 1H), 0.93 (t, J=7.3 Hz, 3H)

Example 30

Mass spectrum (ESI, m/z): 607 $[M+H]^+$ $^1$H-NMR spectrum (400 MHz, $CD_3OD$) δ: 7.70 (d, J=8.9 Hz, 1H), 7.48 (d, J=8.9 Hz, 1H), 7.21 (dd, J=1.7, 7.8 Hz, 1H), 7.08 (d, J=7.8 Hz, 1H), 6.99 (d, J=1.7 Hz, 1H), 6.86 (s, 1H), 6.63 (s, 1H), 4.96-4.76 (m, 1H), 4.27 (s, 3H), 3.86 (d, J=14.3 Hz, 1H), 3.77-3.67 (m, 1H), 3.56-3.45 (m, 3H), 2.90-2.81 (m, 1H), 2.80-2.71 (m, 1H), 2.71 (s, 3H), 2.26 (s, 3H), 1.53-1.40 (m, 1H), 1.37 (s, 3H), 1.31-1.19 (m, 4H), 0.96 (t, J=7.3 Hz, 3H)

Example 31

3-(1,4-dimethyl-1H-benzo[d][1,2,3]triazol-5-yl)-3-(3-(((R)-2-ethyl-2,3,5,7,8,9-hexahydro-4H-indeno[5,6-f][1,4]oxazepin-4-yl)methyl)-4-methylphenyl)-2,2-dimethylpropanoic Acid (Diastereomer 1) and Example 32

3-(1,4-dimethyl-1H-benzo[d][1, 2, 3]triazol-5-yl)-3-(3-(((R)-2-ethyl-2,3,5,7,8,9-hexahydro-4H-indeno[5,6-f][1,4]oxazepin-4-yl)methyl)-4-methylphenyl)-2,2-dimethylpropanoic Acid (Diastereomer 2)

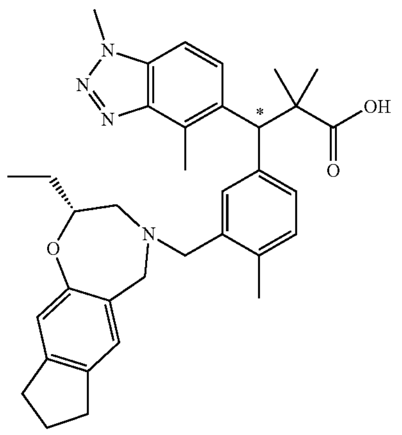 [SMILES: CC[C@@H]1CN(Cc2cc(C(c3ccc4c(nnn4C)c3C)C(C)(C)C(=O)O)ccc2C)Cc2cc3c(cc2O1)CCC3]

3-(1,4-dimethyl-1H-benzo[d][1,2,3)triazol-5-yl)-3-(3-(((R)-2-ethyl-2,3,5,7,8,9-hexahydro-4H-indeno[5,6-f](1,4]oxazepin-4-yl)methyl)-4-methylphenyl)-2,2-dimethylpropanoic acid produced according to the same manner as the Example 3-(b) (243 mg) was separated and purified by supercritical fluid chromatography (Column: CHIRALPAK IB, mobile phase: $CO_2$:methanol methanol ratio (%)=30 (0 min)→10 (3 min)→10 (28 min)→30 (28.1 min)→30 (30 min)). The fractions comprising the first-eluted diastereomer were concentrated under reduced pressure, the resulting residues were dissolved into a mixed solvent of acetonitrile/water, and the resulting solution was lyophilized to give the compound of Example 31 (103 mg) as white solids. Also, the fractions comprising the later-eluted diastereomer were concentrated under reduced pressure, the resulting residues were dissolved into a mixed solvent of acetonitrile/water, and the resulting solution was lyophilized to give the compound of Example 32 (108 mg) as white solids.

(High Performance Liquid Chromatography Analysis)

Column: CHIRALPAK IC-3 4.6×150 mm

Eluent: 0.1% formic acid solution in water/acetonitrile acetonitrile ratio (%)=20 (0 min)→60 (10 min)→60 (15 min)

Flow rate: 0.8 mL/min

Temperature: 40° C.

Detection wavelength: 254 nm

Retention time: Example 31: 8.61 min, Example 32: 9.06 min

Example 31

Mass spectrum (ESI, m/z): 567 $[M+H]^+$ $^1$H-NMR spectrum (400 MHz, $CD_3OD$) δ: 7.76 (d, J=8.7 Hz, 1H), 7.47 (d, J=8.7 Hz, 1H), 7.20-7.15 (m, 1H), 7.08-7.04 (m, 1H), 7.02-6.98 (m, 1H), 6.80 (s, 1H), 6.67 (s, 1H), 4.86 (m, 1H), 4.26 (s, 3H), 3.83 (d, J=13.8 Hz, 1H), 3.64-3.56 (m, 1H), 3.55-3.45 (m, 3H), 2.89-2.67 (m, 9H), 2.26 (s, 3H), 2.11-2.01 (m, 2H), 1.49-1.10 (m, 8H), 0.94 (t, J=7.4 Hz, 3H)

Example 32

Mass spectrum (ESI, m/z): 567 $[M+H]^+$ $^1$H-NMR spectrum (400 MHz, $CD_3OD$) δ: 7.70 (d, J=8.8 Hz, 1H), 7.46 (d, J=8.8 Hz, 1H), 7.22-7.15 (m, 1H), 7.11-7.02 (m, 2H), 6.85-6.78 (m, 2H), 4.87 (m, 1H), 4.27 (s, 3H), 3.86 (d, J=13.8 Hz, 1H), 3.70-3.45 (m, 4H), 2.91-2.67 (m, 9H), 2.25 (s, 3H), 2.13-2.01 (m, 2H), 1.52-1.16 (m, 8H), 0.96 (t, J=7.4 Hz, 3H)

Example 33

3-(1,4-dimethyl-1H-benzo[d][1,2,3]triazol-5-yl)-3-(3-(((R)-2-ethyl-2,3,7,8,9,10-hexahydronaphtho[2,3-f][1,4]oxazepin-4 (5H)-yl)methyl)-4-methylphenyl)-2,2-dimethylpropanoic Acid (Diastereomer 1) and Example 34

3-(1,4-dimethyl-1H-benzo[d][1,2,3]triazol-5-yl)-3-(3-(((R)-2-ethyl-2,3,7,8,9,10-hexahydronaphtho[2,3-f][1,4]oxazepin-4(5H)-yl)methyl)-4-methylphenyl)-2,2-dimethylpropanoic Acid (Diastereomer 2)

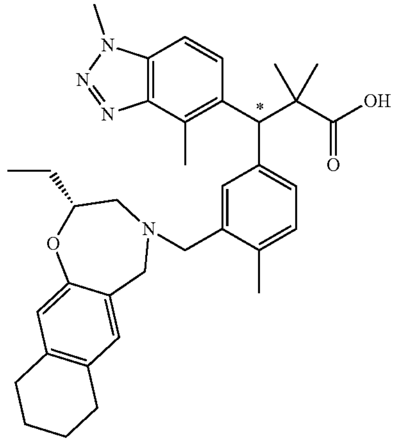 [SMILES: CC[C@@H]1CN(Cc2cc(C(c3ccc4c(nnn4C)c3C)C(C)(C)C(=O)O)ccc2C)Cc2cc3c(cc2O1)CCCC3]

3-(1,4-dimethyl-1H-benzo[d][1,2,3]triazol-5-yl)-3-(3-(((R)-2-ethyl-2,3,7,8,9,10-hexahydronaphtho[2,3-f][1,4]oxazepin-4(5H)-yl)methyl)-4-methylphenyl)-2,2-dimethylpropanoic acid produced according to the same manner as the Example 4-(b) (272 mg) was separated and purified by supercritical fluid chromatography (Column: CHIRALPAK IB, mobile phase: $CO_2$:methanol methanol ratio (%)=30 (0 min)→5 (7 min)→5 (15 min)→30 (16 min)→30 (19 min)). The fractions comprising the first-eluted diastereomer were concentrated under reduced pressure, the resulting residues were dissolved into a mixed solvent of acetonitrile/water, and the resulting solution was lyophilized to give the compound of Example 33 (111 mg) as white solids. Also, the fractions comprising the later-eluted diastereomer were concentrated under reduced pressure, the resulting residues were dissolved into a mixed solvent of acetonitrile/water, and the resulting solution was lyophilized to give the compound of Example 34 (109 mg) as white solids.

(High Performance Liquid Chromatography Analysis)

Column: CHIRALPAK IG-3 4.6×150 mm

Eluent: hexane/ethanol ethanol ratio (%)=10 (0 min)→90 (10 min)→90 (15 min)

Flow rate: 0.8 mL/min

Temperature: 40° C.

Detection wavelength: 254 nm

Retention time: Example 33: 6.11 min, Example 34: 7.80 min

Example 33

Mass spectrum (ESI, m/z): 581 $[M+H]^+$ $^1$H-NMR spectrum (400 MHz, $CD_3OD$) δ: 7.77 (d, J=8.0 Hz, 1H), 7.49 (d, J=8.0 Hz, 1H), 7.21-7.13 (m, 1H), 7.11-7.04 (m, 2H), 6.66 (s, 1H), 6.58 (s, 1H), 4.87 (s, 1H), 4.28 (s, 3H), 3.87-3.77 (m, 1H), 3.66-3.48 (m, 4H), 2.93-2.53 (m, 9H), 2.26 (s, 3H), 1.85-1.70 (m, 4H), 1.52-1.12 (m, 8H), 0.94 (t, J=7.5 Hz, 3H)

Example 34

Mass spectrum (ESI, m/z): 581 $[M+H]^+$ $^1$H-NMR spectrum (400 MHz, $CD_3OD$) δ: 7.70 (d, J=8.0 Hz, 1H), 7.47 (d, J=8.0 Hz, 1H), 7.23-7.16 (m, 1H), 7.14-7.03 (m, 2H), 6.72-6.63 (m, 2H), 4.98-4.80 (m, 1H), 4.28 (s, 3H), 3.90-3.80 (m, 1H), 3.72-3.47 (m, 4H), 2.94-2.57 (m, 9H), 2.25 (s, 3H), 1.83-1.73 (m, 4H), 1.52-1.16 (m, 8H), 0.96 (t, J=7.5 Hz, 3H)

Example 35

3-(1,4-dimethyl-1H-benzo[d][1,2,3]triazol-5-yl)-3-(3-(((R)-2-ethyl-2,3,5,8,9,10-hexahydro-4H-indeno[5,4-f][1,4]oxazepin-4-yl)methyl)-4-methylphenyl)-2,2-dimethylpropanoic Acid (Diastereomer 1) and Example 36

3-(1,4-dimethyl-1H-benzo[d][1,2,3]triazol-5-yl)-3-(3-(((R)-2-ethyl-2,3,5,8,9,10-hexahydro-4H-indeno[5,4-f][1,4]oxazepin-4-yl)methyl)-4-methylphenyl)-2,2-dimethylpropanoic Acid (Diastereomer 2)

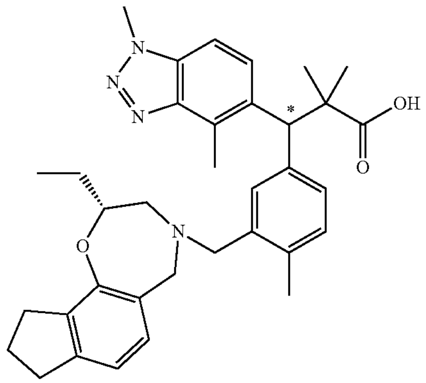 [SMILES: CC[C@@H]1CN(Cc2cc(C(c3ccc4c(nnn4C)c3C)C(C)(C)C(=O)O)ccc2C)Cc2ccc3c(c2O1)CCC3]

3-(1,4-dimethyl-1H-benzo[d][1,2,3]triazol-5-yl)-3-(3-(((R)-2-ethyl-2,3,5,8,9,10-hexahydro-4H-indeno[5,4-f][1,4]oxazepin-4-yl)methyl)-4-methylphenyl)-2,2-dimethylpropanoic acid produced according to the same manner as the Example 6-(b) (227 mg) was separated and purified by supercritical fluid chromatography (Column: CHIRALPAK IF, mobile phase: $CO_2$:methanol methanol ratio (%)=15 (0 min)→15 (40 min)). The fractions comprising the first-eluted diastereomer were concentrated under reduced pressure, the resulting residues were dissolved into a mixed solvent of acetonitrile/water, and the resulting solution was lyophilized to give the compound of Example 35 (65 mg) as white solids. Also, the fractions comprising the later-eluted diastereomer were concentrated under reduced pressure, the resulting residues were dissolved into a mixed solvent of acetonitrile/water, and the resulting solution was lyophilized to give the compound of Example 36 (63 mg) as white solids.

(High Performance Liquid Chromatography Analysis)

Column: CHIRALPAK IG-3 4.6×150 mm

Eluent: hexane/ethanol ethanol ratio (%)=10 (0 min)→90 (10 min)→90 (15 min)

Flow rate: 0.8 mL/min

Temperature: 40° C.

Detection wavelength: 254 nm

Retention time: Example 35: 4.82 min, Example 36: 6.34 min

Example 35

Mass spectrum (ESI, m/z): 567 $[M+H]^+$ $^1$H-NMR spectrum (400 MHz, $CD_3OD$) δ: 7.69 (d, J=8.8 Hz, 1H), 7.49 (d, J=8.8 Hz, 1H), 7.23 (dd, J=1.9, 7.9 Hz, 1H), 7.08 (d, J=7.9 Hz, 1H), 6.96 (d, J=1.9 Hz, 1H), 6.59 (d, J=7.4 Hz, 1H), 6.30 (d, J=7.4 Hz, 1H), 4.94 (s, 1H), 4.27 (s, 3H), 3.77 (d, J=13.7 Hz, 1H), 3.67 (m, 1H), 3.54-3.45 (m, 3H), 2.95-2.84 (m, 5H), 2.83-2.75 (m, 1H), 2.73 (s, 3H), 2.26 (s, 3H), 2.12-1.98 (m, 2H), 1.56-1.42 (m, 1H), 1.38 (s, 3H), 1.30-1.21 (m, 4H), 1.01 (t, J=7.0 Hz, 3H)

Example 36

Mass spectrum (ESI, m/z): 567 $[M+H]^+$ $^1$H-NMR spectrum (400 MHz, $CD_3OD$) δ: 7.71 (d, J=8.7 Hz, 1H), 7.48 (d, J=8.7 Hz, 1H), 7.20 (dd, J=1.8, 7.8 Hz, 1H), 7.07 (d, J=7.8 Hz, 1H), 6.99 (d, J=1.8 Hz, 1H), 6.67 (d, J=7.4 Hz, 1H), 6.50 (d, J=7.4 Hz, 1H), 4.93 (s, 1H), 4.27 (s, 3H), 3.79 (d, J=13.9 Hz, 11H), 3.74-3.65 (m, 1H), 3.58-3.46 (m, 3H), 2.93-2.83 (M, 5H), 2.80-2.67 (m, 4H), 2.26 (s, 3H), 2.16-1.98 (m, 2H), 1.56-1.42 (m, 1H), 1.40-1.19 (m, 7H), 1.01 (t, J=7.3 Hz, 3H)

Example 37

3-(1,4-dimethyl-1H-benzo[d][1,2,3]triazol-5-yl)-3-(3-(((R)-2-ethyl-2,3-dihydro-[1,4]oxazepino[6,7-b]quinolin-4(5H)-yl)methyl)-4-methylphenyl)-2,2-dimethylpropanoic Acid (Diastereomer 1) and Example 38

3-(1,4-dimethyl-1H-benzo[d][1,2,3]triazol-5-yl)-3-(3-(((R)-2-ethyl-2,3-dihydro-[1,4]oxazepino[6,7-b]quinolin-4(5H)-yl)methyl)-4-methylphenyl)-2,2-dimethylpropanoic Acid (Diastereomer 2)

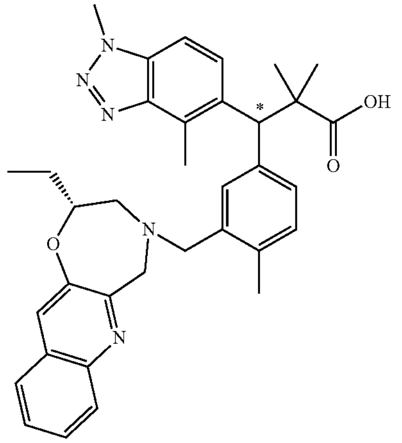 [SMILES: CC[C@@H]1CN(Cc2cc(C(c3ccc4c(nnn4C)c3C)C(C)(C)C(=O)O)ccc2C)Cc2nc3ccccc3cc2O1]

3-(1,4-dimethyl-1H-benzo[d][1,2,3]triazol-5-yl)-3-(3-(((R)-2-ethyl-2,3-dihydro-[1,4]oxazepino[6,7-b]quinolin-4(5H)-yl)methyl)-4-methylphenyl)-2,2-dimethylpropanoic acid produced according to the same manner as the Example 10-(b) (130 mg) was separated and purified by supercritical fluid chromatography (Column: CHIRALPAK IG, mobile phase: $CO_2$ methanol methanol ratio (%)=30 (0 min)→30 (20 min)). The fractions comprising the first-eluted diastereomer were concentrated under reduced pressure, the resulting residues were dissolved into a mixed solvent of acetonitrile/water, and the resulting solution was lyophilized to give the compound of Example 37 (45 mg) as white solids. Also, the fractions comprising the later-eluted diastereomer were concentrated under reduced pressure, the resulting residues were dissolved into a mixed solvent of acetonitrile/water, and the resulting solution was lyophilized twice to give the compound of Example 38 (39 mg) as white solids.

(High Performance Liquid Chromatography Analysis)

Column: CHIRALPAK IG-3 4.6×150 mm

Eluent: hexane/ethanol ethanol ratio (%)=10 (0 min)→90 (15 min)

Flow rate: 0.8 mL/min

Temperature: 40° C.

Detection wavelength: 254 nm

Retention time: Example 37: 6.65 min, Example 38: 8.27 min

Example 37

Mass spectrum (ESI, m/z): 576 $[M-H]^-$ $^1$H-NMR spectrum (400 MHz, $CD_3OD$) δ: 7.97 (d, J=8.5 Hz, 1H), 7.90-7.82 (m, 2H), 7.78 (d, J=8.8 Hz, 1H), 7.70-7.49 (m, 2H), 7.38 (d, J=8.8 Hz, 1H), 7.24-6.99 (m, 3H), 5.21-4.47 (m, 1H), 4.38-4.01 (m, 5H), 3.84-3.43 (m, 3H), 2.94-2.76 (m, 2H), 2.66 (s, 3H), 2.27 (s, 3H), 1.61-1.46 (m, 1H), 1.44-1.07 (m, 7H), 0.97 (t, J=7.3 Hz, 3H)

Example 38

Mass spectrum (ESI, m/z): 576 $[M-H]^-$ $^1$H-NMR spectrum (400 MHz, $CD_3OD$) δ: 7.95 (d, J=8.3 Hz, 1H), 7.89-7.83 (m, 2H), 7.73 (d, J=8.7 Hz, 1H), 7.67-7.61 (m, 1H), 7.59-7.52 (m, 1H), 7.38 (d, J=8.7 Hz, 1H), 7.19-7.10 (m, 2H), 7.05 (d, J=7.9 Hz, 1H), 4.96-4.77 (m, 1H), 4.27-4.17 (m, 4H), 4.17-4.08 (m, 1H), 3.89-3.80 (m, 1H), 3.73-3.65 (m, 1H), 3.60-3.52 (m, 1H), 2.92-2.76 (m, 2H), 2.68 (s, 3H), 2.27 (s, 3H), 1.60-1.48 (m, 1H), 1.39-1.19 (m, 7H), 0.99 (t, J=7.3 Hz, 3H)

Example 39

3-(1,4-dimethyl-1H-benzo[d][1,2,3]triazol-5-yl)-3-(3-(((R)-2-ethyl-2,3-dihydro-[1,4]oxazepino[6,7-g]quinolin-4(5H)-yl)methyl)-4-methylphenyl)-2,2-dimethylpropanoic Acid (Diastereomer 1) and Example 40

3-(1,4-dimethyl-1H-benzo[d][1,2,3]triazol-5-yl)-3-(3-(((R)-2-ethyl-2,3-dihydro-[1,4]oxazepino[6,7-g]quinolin-4 (5H)-yl)methyl)-4-methylphenyl)-2,2-dimethylpropanoic Acid (Diastereomer 2)

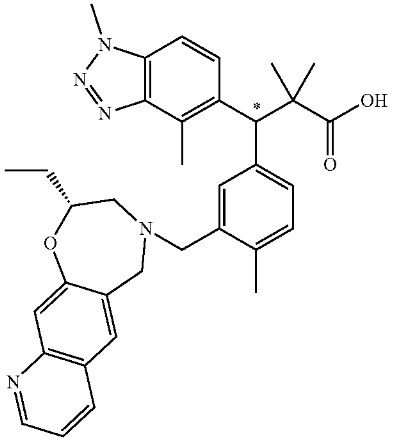 [SMILES: CC[C@@H]1CN(Cc2cc(C(c3ccc4c(nnn4C)c3C)C(C)(C)C(=O)O)ccc2C)Cc2cc3cccnc3cc2O1]

A crude product comprising 3-(1,4-dimethyl-1H-benzo[d][1,2,3]triazol-5-yl)-3-(3-(((R)-2-ethyl-2,3-dihydro-[1,4]oxazepino [6,7-g]quinolin-4 (5H)-yl)methyl)-4-methylphenyl)-2,2-dimethylpropanoic acid produced according to the same manner as the Example 11-(b) (193 mg) was purified by supercritical fluid chromatography (column: Kinetix Biphenyl, mobile phase: $CO_2$:methanol methanol ratio=30%). The fractions comprising the title compound were concentrated under reduced pressure, and the resulting residues were separated and purified by supercritical fluid chromatography (Column: CHIRALPAK IB, mobile phase: $CO_2$:methanol methanol ratio (%)=30 (0 min)→30 (30 min)).

The fractions comprising the first-eluted diastereomer were concentrated under reduced pressure, the resulting residues were dissolved into a mixed solvent of acetonitrile/water, and the resulting solution was lyophilized to give the compound of Example 39 (60 mg) as white solids. Also, the fractions comprising the later-eluted diastereomer were concentrated under reduced pressure, the resulting residues were dissolved into a mixed solvent of acetonitrile/water, and the resulting solution was lyophilized twice to give the compound of Example 40 (56 mg) as white solids.

(High Performance Liquid Chromatography Analysis)

Column: CHIRALPAK IC-3 4.6×150 mm

Eluent: 0.1% formic acid solution in water/0.1% formic acid solution in acetonitrile 0.1% formic acid solution in acetonitrile ratio (%)=30 (0 min)→60 (10 min)

Flow rate: 0.8 mL/min

Temperature: 40° C.

Detection wavelength: 254 nm

Retention time: Example 39: 5.25 min, Example 40: 6.80 min

Example 39

Mass spectrum (ESI, m/z): 578 $[M+H]^+$ $^1$H-NMR spectrum (400 MHz, $CD_3OD$) δ: 8.85-8.70 (m, 1H), 8.23-8.13 (m, 1H), 7.81-7.70 (m, 1H), 7.54 (s, 1H), 7.50 (s, 1H), 7.48-7.40 (m, 2H), 7.21-7.15 (m, 1H), 7.11-7.03 (m, 2H), 4.98-4.75 (m, 1H), 4.24 (s, 3H), 4.08-3.74 (m, 3H), 3.65-3.48 (m, 2H), 2.94-2.81 (m, 2H), 2.68 (s, 3H), 2.27 (s, 3H), 1.63-1.48 (m, 1H), 1.40-1.21 (m, 7H), 1.00 (t, J=7.4 Hz, 3H)

Example 40

Mass spectrum (ESI, m/z): 578 $[M+H]^+$ $^1$H-NMR spectrum (400 MHz, $CD_3OD$) δ: 8.82-8.72 (m, 1H), 8.23 (d, J=8.3 Hz, 1H), 7.68 (d, J=8.8 Hz, 1H), 7.59-7.53 (m, 2H), 7.49-7.37 (m, 2H), 7.20 (dd, J=1.8, 7.7 Hz, 1H), 7.12-7.03 (m, 2H), 5.06-4.72 (m, 1H), 4.22 (s, 3H), 4.01 (d, J=14.1 Hz, 1H), 3.93-3.81 (m, 2H), 3.65-3.50 (m, 2H), 2.97-2.77 (m, 2H), 2.68 (s, 3H), 2.25 (s, 3H), 1.68-1.51 (m, 1H), 1.44-1.20 (m, 7H), 1.03 (t, J=7.3 Hz, 3H)

Example 41

3-(1,4-dimethyl-1H-benzo[d][1,2,3]triazol-5-yl)-3-(3-(((R)-2-ethyl-2,3-dihydro-[1,4]oxazepino[7,6-g]quinolin-4(5H)-yl)methyl)-4-methylphenyl)-2,2-dimethylpropanoic Acid (Diastereomer 1) and Example 42

3-(1,4-dimethyl-1H-benzo[d][1,2,3]triazol-5-yl)-3-(3-(((R)-2-ethyl-2,3-dihydro-[1,4]oxazepino[7,6-g]quinolin-4(5H)-yl)methyl)-4-methylphenyl)-2,2-dimethylpropanoic Acid (Diastereomer 2)

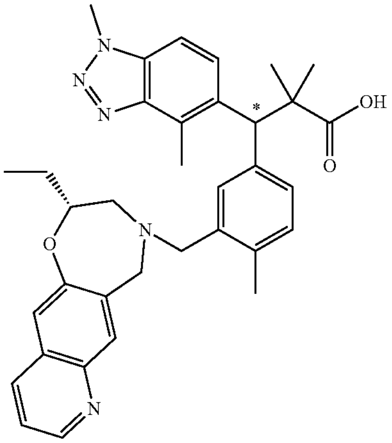 [SMILES: CC[C@@H]1CN(Cc2cc(C(c3ccc4c(nnn4C)c3C)C(C)(C)C(=O)O)ccc2C)Cc2cc3ncccc3cc2O1]

3-(1,4-dimethyl-1H-benzo[d][1,2,3]triazol-5-yl)-3-(3-(((R)-2-ethyl-2,3-dihydro-[1,4]oxazepino[7,6-g]quinolin-4(5H)-yl)methyl)-4-methylphenyl)-2,2-dimethylpropanoic acid produced according to the same manner as the Example 12-(b) (149 mg) was separated and purified by supercritical fluid chromatography (Column: CHIRALPAK IB, mobile phase: $CO_2$:methanol methanol ratio (%)=50 (0 min)→15 (2 min)→15 (13 min)→50 (13.5 min)→50 (15 min)). The fractions comprising the first-eluted diastereomer were concentrated under reduced pressure, the resulting residues were dissolved into a mixed solvent of acetonitrile/water, and the resulting solution was lyophilized to give the compound of Example 41 (51 mg) as white solids. Also, the fractions comprising the later-eluted diastereomer were concentrated under reduced pressure, the resulting residues were dissolved into a mixed solvent of acetonitrile/water, and the resulting solution was lyophilized to give the compound of Example 42 (64 mg) as white solids.

(High Performance Liquid Chromatography Analysis)

Column: CHIRALPAK IC-3 4.6×150 mm

Eluent: 0.1% formic acid solution in water/0.1% formic acid solution in acetonitrile 0.1% formic acid solution in acetonitrile ratio (%)=10 (0 min)→40 (10 min)→40 (15 min)

Flow rate: 0.8 mL/min

Temperature: 40° C.

Detection wavelength: 254 nm

Retention time: Example 41: 12.38 min, Example 42: 13.44 min

Example 41

Mass spectrum (ESI, m/z): 578 $[M+H]^+$ $^1$H-NMR spectrum (400 MHz, $CD_3OD$) δ: 8.77-8.71 (m, 1H), 8.31-8.24 (m, 1H), 7.80-7.74 (m, 1H), 7.70 (s, 1H), 7.52-7.40 (m, 3H), 7.16-7.01 (m, 3H), 4.96-4.75 (m, 1H), 4.25 (s, 3H), 4.09 (d, J=14.1 Hz, 1H), 3.92 (d, J=14.1 Hz, 1H), 3.80-3.71 (m, 1H), 3.63 (d, J=13.1 Hz, 1H), 3.52 (d, J=13.1 Hz, 1H), 2.90-2.76 (m, 2H), 2.67 (s, 3H), 2.25 (s, 3H), 1.59-1.18 (m, 8H), 0.98 (t, J=7.5 Hz, 3H)

Example 42

Mass spectrum (ESI, m/z): 578 $[M+H]^+$ $^1$H-NMR spectrum (400 MHz, $CD_3OD$) δ: 8.73 (dd, J=1.5, 4.2 Hz, 1H), 8.31-8.23 (m, 1H), 7.76-7.65 (m, 2H), 7.52-7.40 (m, 3H), 7.24-6.98 (m, 3H), 5.00-4.76 (m, 1H), 4.25 (a, 3H), 4.06 (d, J=13.9 Hz, 1H), 3.89 (d, J=13.9 Hz, 1H), 3.86-3.75 (m, 1H), 3.67-3.48 (m, 2H), 2.93-2.76 (m, 2H), 2.70 (s, 3H), 2.24 (s, 3H), 1.37 (s, 8H), 1.01 (t, J=7.4 Hz, 3H)

Example 43

3-(1,4-dimethyl-1H-benzo[d](1,2,3)triazol-5-yl)-3-(3-(((R)-7-ethyl-1,7,8,10-tetrahydro-9H-[1,4]oxazepino[7,6-g]indazol-9-yl)methyl)-4-methylphenyl)-2,2-dimethylpropanoic Acid (Diastereomer 1) and Example 44

3-(1,4-dimethyl-1H-benzo[d][1, 2, 3]triazol-s-yl)-3-(3-(((R)-7-ethyl-1,7,8,10-tetrahydro-9H-[1,4]oxazepino[7,6-g]indazol-9-yl)methyl)-4-methylphenyl)-2,2-dimethylpropanoic Acid (Diastereomer 2)

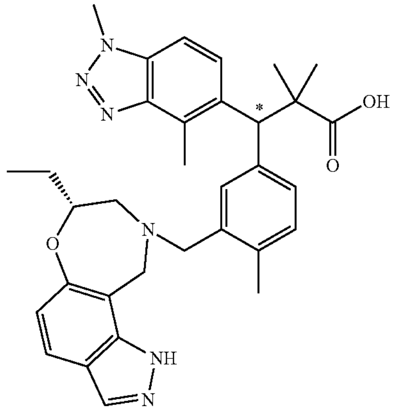 [SMILES: CC[C@@H]1CN(Cc2cc(C(c3ccc4c(nnn4C)c3C)C(C)(C)C(=O)O)ccc2C)Cc2c(ccc3cn[nH]c23)O1]

3-(1,4-dimethyl-1H-benzo[d][1, 2, 3]triazol-5-yl)-3-(3-(((R)-7-ethyl-1,7,8,10-tetrahydro-9H-[1,4]oxazepino[7,6-g]indazol-9-yl)methyl)-4-methylphenyl)-2,2-dimethylpropanoic acid produced according to the same manner as the Example 20-(b) (199 mg) was separated and purified by supercritical fluid chromatography (Column: CHIRALPAK IB, mobile phase: $CO_2$:methanol methanol ratio (%)=30 (0 min)→10 (8 min)→10 (9 min)→30 (10 min)→30(13 min)). The fractions comprising the first-eluted diastereomer were concentrated under reduced pressure, the resulting residues were dissolved into a mixed solvent of acetonitrile/water, and the resulting solution was lyophilized to give the compound of Example 43 (77 mg) as white solids. Also, the fractions comprising the later-eluted diastereomer were concentrated under reduced pressure, the resulting residues were dissolved into a mixed solvent of acetonitrile/water, and the resulting solution was lyophilized to give the compound of Example 44 (79 mg) as white solids.

(High Performance Liquid Chromatography Analysis)

Column: CHIRALPAK IG-3 4.6×150 mm

Eluent: hexane/ethanol ethanol ratio (%)=10 (0 min)→60 (15 min)

Flow rate: 0.8 mL/min

Temperature: 40° C.

Detection wavelength: 254 nm

Retention time: Example 43: 8.14 min, Example 44: 9.33 min

Example 43

Mass spectrum (ESI, m/z): 567 $[M+H]^+$ $^1$H-NMR spectrum (400 MHz, $CD_3OD$) δ: 7.96 (s, 1H), 7.71 (d, J=8.8 Hz, 1H), 7.55 (d, J=8.6 Hz, 1H), 7.41 (d, J=8.8 Hz, 1H), 7.15-7.06 (m, 2H), 7.03 (d, J=7.5 Hz, 1H), 6.85 (d, J=8.6 Hz, 1H), 4.95-4.77 (m, 1H), 4.33-4.22 (m, 4H), 4.12-3.99 (m, 1H), 3.83-3.71 (m, 1H), 3.65 (s, 2H), 2.84-2.60 (m, 5H), 2.25 (s, 3H), 1.53-1.39 (m, 1H), 1.37-1.08 (m, 7H), 0.90 (t, J=7.3 Hz, 3H)

Example 44

Mass spectrum (ESI, m/z): 567 $[M+H]^+$ $^1$H-NMR spectrum (400 MHz, $CD_3OD$) δ: 7.95 (s, 1H), 7.68-7.53 (m, 2H), 7.39 (d, J=8.7 Hz, 1H), 7.19-7.08 (m, 2H), 7.04 (d, J=7.9 Hz, 1H), 6.86 (d, J=8.5 Hz, 1H), 4.96-4.83 (m, 1H), 4.32-4.21 (m, 4H), 4.02 (d, J=14.7 Hz, 1H), 3.89-3.78 (m, 1H), 3.65 (s, 2H), 2.89-2.64 (m, 5H), 2.24 (s, 3H), 1.56-1.40 (m, 1H), 1.39-1.08 (m, 7H), 0.94 (t, J=7.3 Hz, 3H)

Example 45

3-(1,4-dimethyl-1H-benzo[d][1,2,3]triazol-5-yl)-3-(3-(((R)-2-ethyl-2,3-dihydro-[1,4]oxazepino[6,7-c]isoquinolin-4(5H)-yl)methyl)-4-methylphenyl)-2,2-dimethylpropanoic Acid (Diastereomer 1) and Example 46

3-(1,4-dimethyl-1H-benzo[d][1,2,3]triazol-5-yl)-3-(3-(((R)-2-ethyl-2,3-dihydro-[1,4]oxazepino[6,7-c]isoquinolin-4 (5H)-yl)methyl)-4-methylphenyl)-2,2-dimethylpropanoic Acid (Diastereomer 2)

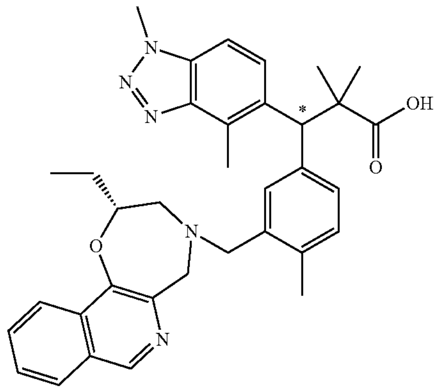 [SMILES: CC[C@@H]1CN(Cc2cc(C(c3ccc4c(nnn4C)c3C)C(C)(C)C(=O)O)ccc2C)Cc2ncc3ccccc3c2O1]

3-(1,4-dimethyl-1H-benzo[d][1,2,3]triazol-5-yl)-3-(3-(((R)-2-ethyl-2,3-dihydro-[1,4]oxazepino[6,7-c]isoquinolin-4 (5H)-yl)methyl)-4-methyl phenyl)-2,2-dimethylpropanoic acid produced according to the same manner as the Example 25-(b) (243 mg) was separated and purified by supercritical fluid chromatography (Column: CHIRALPAK IG, mobile phase: $CO_2$:methanol methanol ratio (t)=30 (0 min)→30 (20 min)). The fractions comprising the first-eluted diastereomer were concentrated under reduced pressure, the resulting residues were dissolved into a mixed solvent of acetonitrile/water, and the resulting solution was lyophilized to give the compound of Example 45 (90 mg) as white solids. Also, the fractions comprising the later-eluted diastereomer were concentrated under reduced pressure, the resulting residues were dissolved into a mixed solvent of acetonitrile/water, and the resulting solution was lyophilized to give the compound of Example 46 (90 mg) as white solids.

(High Performance Liquid Chromatography Analysis)

Column: CHIRALPAK IG-3 4.6×150 mm

Eluent: hexane/ethanol ethanol ratio (%)=10 (0 min)→90 (10 min)→90 (15 min)

Flow rate: 0.8 mL/min

Temperature: 40° C.

Detection wavelength: 254 nm

Retention time: Example 45: 7.15 min, Example 46: 9.01 min

Example 45

Mass spectrum (ESI, m/z): 578 $[M+H]^+$ $^1$H-NMR spectrum (400 MHz, $CD_3OD$) δ: 8.87 (s, 1H), 8.33-8.26 (m, 1H), 8.12-8.04 (m, 1H), 7.85-7.74 (m, 2H), 7.68 (ddd, J=1.1, 7.0, 8.2 Hz, 1H), 7.39 (d, J=8.8 Hz, 1H), 7.19-7.11 (m, 2H), 7.09-7.03 (m, 1H), 4.98-4.76 (m, 1H), 4.26-4.07 (m, 5H), 3.97-3.88 (m, 1H), 3.72-3.57 (m, 2H), 2.99-2.84 (m, 2H), 2.68 (s, 3H), 2.28 (s, 3H), 1.82-1.64 (m, 1H), 1.53-1.40 (m, 1H), 1.32 (s, 3H), 1.27 (s, 3H), 1.04 (t, J=7.5 Hz, 3H)

Example 46

Mass spectrum (ESI, m/z): 578 $[M+H]^+$ $^1$H-NMR spectrum (400 MHz, $CD_3OD$) δ: 8.83 (s, 1H), 8.32-8.27 (m, 1H), 8.11-8.05 (m, 1H), 7.84-7.78 (m, 1H), 7.74-7.65 (m, 2H), 7.34 (d, J=8.9 Hz, 1H), 7.19-7.10 (m, 2H), 7.05 (d, J=7.8 Hz, 1H), 4.98-4.79 (m, 1H), 4.23 (s, 3H), 4.20-4.07 (m, 2H), 4.05-3.96 (m, 1H), 3.71-3.57 (m, 2H), 3.01-2.93 (m, 1H), 2.92-2.83 (m, 1H), 2.67 (8, 3H), 2.27 (s, 3H), 1.82-1.66 (m, 1H), 1.55-1.42 (m, 1H), 1.40-1.17 (m, 6H), 1.05 (t, J=7.4 Hz, 3H)

Example 47

3-(1,4-dimethyl-1H-benzo[d][1,2,3]triazol-5-yl)-3-(3-((((R)-2-ethyl-2,3-dihydro-[1,4]oxazepino[6,7-c]quinolin-4(5H)-yl)methyl)-4-methylphenyl)-2,2-dimethylpropanoic Acid (Diastereomer 1) and Example 48

3-(1,4-dimethyl-1H-benzo[d][1,2,3]triazol-5-yl)-3-(3-(((R)-2-ethyl-2,3-dihydro-[1,4]oxazepino[6,7-c]quinolin-4(5H)-yl)methyl)-4-methylphenyl)-2,2-dimethylpropanoic Acid (Diastereomer 2)

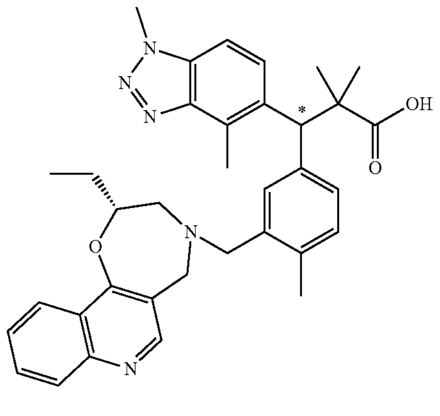 [SMILES: CC[C@@H]1CN(Cc2cc(C(c3ccc4c(nnn4C)c3C)C(C)(C)C(=O)O)ccc2C)Cc2cnc3ccccc3c2O1]

3-(1,4-dimethyl-1H-benzo[d][1,2,3]triazol-5-yl)-3-(3-(((R)-2-ethyl-2,3-dihydro-[1,4]oxazepino[6,7-c]quinolin-4(5H)-yl)methyl)-4-methylphenyl)-2,2-dimethylpropanoic acid produced according to the same manner as the Example 26-(b) (345 mg) was separated and purified by supercritical fluid chromatography (Column: CHIRALPAK IG, mobile phase: $CO_2$ methanol methanol ratio (%)=25 (0 min)→25 (30 min)). The fractions comprising the first-eluted diastereomer were concentrated under reduced pressure, the resulting residues were dissolved into a mixed solvent of acetonitrile/water, and the resulting solution was lyophilized to give the compound of Example 47 (99 mg) as white solids. Also, the fractions comprising the later-eluted diastereomer were concentrated under reduced pressure, the resulting residues were dissolved into a mixed solvent of acetonitrile/water, and the resulting solution was lyophilized to give the compound of Example 48 (99 mg) as white solids.

(High Performance Liquid Chromatography Analysis)

Column: CHIRALPAK IC-3 4.6×150 mm

Eluent: hexane/ethanol ethanol ratio (%)=10 (0 min)→90 (10 min)→90 (15 min)

Flow rate: 0.8 mL/min

Temperature: 40° C.

Detection wavelength: 254 nm

Retention time: Example 47: 7.08 min, Example 48: 8.13 min

Example 47

Mass spectrum (ESI, m/z): 578 $[M+H]^+$ $^1$H-NMR spectrum (400 MHz, $CD_3OD$) δ: 8.38 (s, 1H), 8.33-8.27 (m, 1H), 8.00-7.94 (m, 1H), 7.78-7.69 (m, 2H), 7.63-7.56 (m, 1H), 7.41-7.35 (m, 1H), 7.18-7.12 (m, 2H), 7.09-7.04 (m, 1H), 4.94-4.84 (m, 1H), 4.25-4.15 (m, 4H), 4.07 (d, J=14.9 Hz, 1H), 3.85 (d, J=14.9 Hz, 1H), 3.67 (s, 2H), 3.00-2.89 (m, 2H), 2.67 (s, 3H), 2.26 (s, 3H), 1.82-1.69 (m, 1H), 1.62-1.49 (m, 1H), 1.35 (s, 3H), 1.27 (s, 3H), 1.04 (t, J=7.4 Hz, 3H)

Example 48

Mass spectrum (ESI, m/z): 578 $[M+H]^+$ $^1$H-NMR spectrum (400 MHz, $CD_3OD$) δ: 8.36 (s, 1H), 8.33-8.28 (m, 1H), 8.00-7.96 (m, 1H), 7.80-7.72 (m, 1H), 7.65 (d, J=8.8 Hz, 1H), 7.63-7.57 (m, 1H), 7.30 (d, J=8.8 Hz, 1H), 7.20-7.11 (m, 2H), 7.09-7.04 (m, 1H), 4.90 (s, 1H), 4.30-4.19 (m, 4H), 4.02 (d, J=14.9 Hz, 1H), 3.84 (d, J=14.9 Hz, 1H), 3.73-3.58 (m, 2H), 3.04-2.88 (m, 2H), 2.68 (s, 3H), 2.26 (s, 3H), 1.80-1.69 (m, 1H), 1.62-1.50 (m, 1H), 1.37 (s, 3H), 1.26 (s, 3H), 1.05 (t, J=7.4 Hz, 3H)

Example 49-(a)

Production of methyl 3-(1,4-dimethyl-1H-benzo[d][1,2,3]triazol-5-yl)-3-(3-(((R)-2-ethyl-7-fluoro-2,3-dihydronaphtho[2,1-f][1,4]oxazepin-4(5H)-yl)methyl)-4-methylphenyl)-2,2-dimethylpropanoate

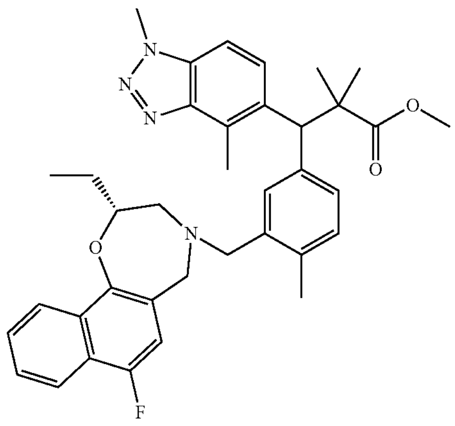 [SMILES: CC[C@@H]1CN(Cc2cc(C(c3ccc4c(nnn4C)c3C)C(C)(C)C(=O)OC)ccc2C)Cc2cc(F)c3ccccc3c2O1]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (41 mg) in acetonitrile (3 mL) were sequentially added (R)-2-ethyl-7-fluoro-2,3,4,5-tetrahydronaphtho[2,1-f][1,4]oxazepine hydrochloride produced in the Reference Example 49-(d) (43 mg) and N,N-diisopropylethylamine (0.053 mL) under argon gas flow with stirring at room temperature, and the resulting mixture was stirred at 60° C. for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (60 mg) as a white foam.

Mass spectrum (DUIS, m/z): 609 $[M+H]^+$ $^1$H-NMR spectrum (400 MHz, $CDCl_3$) δ: 8.36-8.26 (m, 1H), 8.10-8.00 (m, 1H), 7.66-7.50 (m, 3H), 7.38-7.19 (m, 1H), 7.15-6.98 (m, 3H), 6.75-6.59 (m, 1H), 4.85 (s, 1H), 4.27-4.20 (m, 3H), 4.14-4.02 (m, 1H), 3.97-3.81 (m, 1H), 3.71-3.41 (m, 6H), 3.06-2.94 (m, 2H), 2.85-2.75 (m, 3H), 2.27 (s, 3H), 1.90-1.75 (m, 1H), 1.66-1.46 (m, 1H), 1.43-1.22 (m, 6H), 1.17-1.05 (m, 3H)

Example 49-(b)

Production of 3-(1,4-dimethyl-1H-benzo[d](1, 2, 3)triazol-5-yl)-3-(3-(((R)-2-ethyl-7-fluoro-2,3-dihydronaphtho[2,1-f][1,4]oxazepin-4 (5H)-yl)methyl)-4-methylphenyl)-2,2-dimethylpropanoic Acid

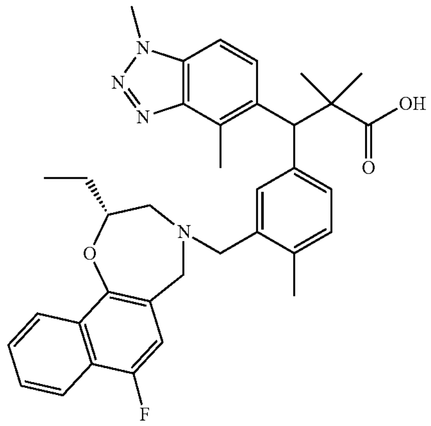 [SMILES: CC[C@@H]1CN(Cc2cc(C(c3ccc4c(nnn4C)c3C)C(C)(C)C(=O)O)ccc2C)Cc2cc(F)c3ccccc3c2O1]

To a solution of methyl 3-(1,4-dimethyl-1H-benzo[d][1,2,3]triazol-5-yl)-3-(3-(((R)-2-ethyl-7-fluoro-2,3-dihydronaphtho[2,1-f][1,4]oxazepin-4 (5H)-yl)methyl)-4-methylphenyl)-2,2-dimethylpropanoate produced in the Example 49-(a) (60 mg) in dimethyl sulfoxide (4 mL) was added dropwise a 2 M aqueous solution of potassium hydroxide (0.493 mL) under argon gas flow with stirring at room temperature, and the resulting mixture was stirred at 70° C. for 3 hours. After the reaction was completed, to the reaction solution was added water (5 mL), 1 M hydrochloric acid was added thereto to adjust the pH to 5.5, and the resulting mixture was stirred for 1 hour. The resulting solids were collected by filtration, washed with water, and dried under reduced pressure at 60° C. to give the title compound (56 mg) as white solids.

Mass spectrum (ESI, m/z): 593 $[M-H]^-$ $^1$H-NMR spectrum (400 MHz, $CD_3OD$) δ: 8.32-8.23 (m, 1H), 8.04-7.96 (m, 1H), 7.78-7.66 (m, 1H), 7.61-7.52 (m, 2H), 7.46-7.37 (m, 1H), 7.24-7.16 (m, 1H), 7.13-7.03 (m, 2H), 6.75-6.65 (m, 1H), 4.96-4.79 (m, 1H), 4.28-4.19 (m, 3H), 4.04-3.66 (m, 3H), 3.64-3.51 (m, 2H), 3.04-2.83 (m, 2H), 2.74-2.68 (m, 3H), 2.32-2.23 (m, 3H), 1.82-1.64 (m, 1H), 1.56-1.23 (m, 7H), 1.10-0.98 (m, 3H)

Example 50-(a)

Production of methyl 3-(1,4-dimethyl-1H-benzo[d][1,2,3]triazol-5-yl)-3-(3-(((R)-8-ethyl-1-methyl-1,5,7,8-tetrahydro-6H-[1,4]oxazepino[6,7-f]indazol-6-yl)methyl)-4-methylphenyl)-2,2-dimethylpropanoate

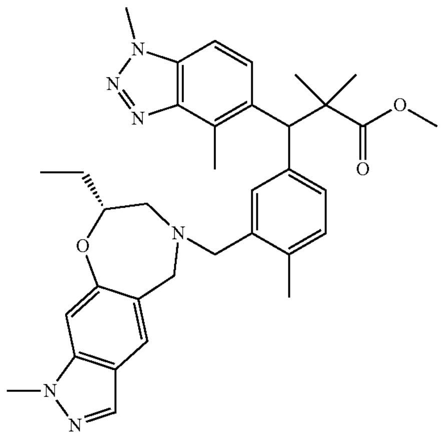

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (72 mg) in acetonitrile (2 mL) were sequentially added (R)-8-ethyl-1-methyl-5,6,7,8-tetrahydro-1H-[1,4]oxazepino[6,7-f]indazole produced in the Reference Example 50-(b) (62 mg) and N,N-diisopropylethylamine (0.16 mL) under argon gas flow with stirring at room temperature, and the resulting mixture was stirred at 60° C. for 4 hours. Then, the resulting mixture was left to stand at room temperature for 14 hours. After the reaction was completed, the reaction solution was concentrated under reduced pressure. The resulting residues were purified by a silica gel column (elution solvent; hexane:ethyl acetate) to give the title compound (118 mg) as a colorless oil.

Mass spectrum (ESI, m/z): 595 $[M+H]^+$ $^1$H-NMR spectrum (400 MHz, $CD_3OD$) δ: 7.88-7.78 (m, 1H), 7.73-7.60 (m, 1H), 7.52-7.42 (m, 1H), 7.33-7.03 (m, 5H), 4.95-4.75 (m, 1H), 4.29-4.21 (m, 3H), 4.03-3.88 (m, 4H), 3.84-3.40 (m, 7H), 2.92-2.63 (m, 5H), 2.33-2.15 (m, 3H), 1.63-1.48 (m, 1H), 1.44-1.20 (m, 7H), 1.06-0.97 (m, 3H)

Example 50-(b)

Production of 3-(1,4-dimethyl-1H-benzo[d][1,2,3]triazol-5-yl)-3-(3-(((R)-8-ethyl-1-methyl-1,5,7,8-tetrahydro-6H-[1,4]oxazepino[6,7-f]indazol-6-yl)methyl)-4-methylphenyl)-2,2-dimethylpropanoic Acid

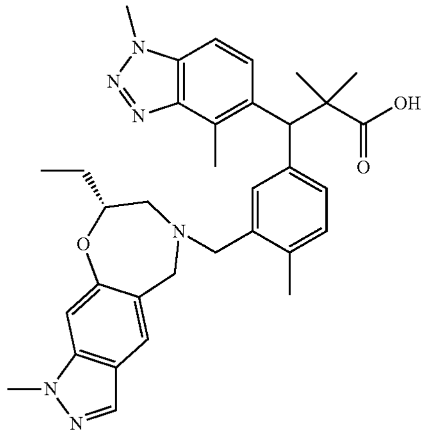 [SMILES: CC[C@@H]1CN(Cc2cc(C(c3ccc4c(nnn4C)c3C)C(C)(C)C(=O)O)ccc2C)Cc2cc3cnn(C)c3cc2O1]

To a solution of methyl 3-(1,4-dimethyl-1H-benzo[d][1,2,3]triazol-5-yl)-3-(3-(((R)-8-ethyl-1-methyl-1,5,7,8-tetrahydro-6H-[1,4]oxazepino[6,7-f]indazol-6-yl)methyl)-4-methylphenyl)-2,2-dimethylpropanoate produced in the Example 50-(a) (115 mg) in dimethyl sulfoxide (2 mL) was added a 1 M aqueous solution of potassium hydroxide (0.145 mL) with stirring at room temperature, and the resulting mixture was stirred at 70° C. for 5 hours. Additionally, a 1 M aqueous solution of potassium hydroxide (0.145 mL) was added thereto with stirring at 70° C., the resulting mixture was stirred at 70° C. for 1.5 hours, and left to stand at room temperature for 13.5 hours. Additionally, a 1 M aqueous solution of potassium hydroxide (0.145 mL) was added thereto with stirring at room temperature, and the resulting mixture was stirred at 70° C. for 3.5 hours. After the reaction was completed, to the reaction mixture was added 2 M hydrochloric acid to adjust the pH to 5.5. The precipitated solids were collected by filtration, washed with water, and dried under reduced pressure at 40° C. to give the title compound (86 mg) as white solids.

Mass spectrum (ESI, m/z): 581 $[M+H]^+$ $^1$H-NMR spectrum (600 MHz, $CD_3OD$) δ: 7.87-7.80 (m, 1H), 7.77-7.65 (m, 1H), 7.49-7.42 (m, 1H), 7.33-7.16 (m, 2H), 7.13-7.04 (m, 3H), 4.96-4.89 (m, 1H), 4.29-4.21 (m, 3H), 4.03-3.93 (m, 4H), 3.82-3.65 (m, 2H), 3.63-3.45 (m, 2H), 2.93-2.76 (m, 2H), 2.76-2.67 (m, 3H), 2.30-2.22 (m, 3H), 1.61-1.48 (m, 1H), 1.44-1.19 (m, 7H), 1.07-0.94 (m, 3H)

Example 51-(a)

Production of methyl 3-(1,4-dimethyl-1H-benzo[d][1,2,3]triazol-5-yl)-3-(3-(((R)-8-ethyl-2-methyl-2,5,7,8-tetrahydro-6H-[1,4]oxazepino[6,7-f]indazol-6-yl)methyl)-4-methylphenyl)-2,2-dimethylpropanoate

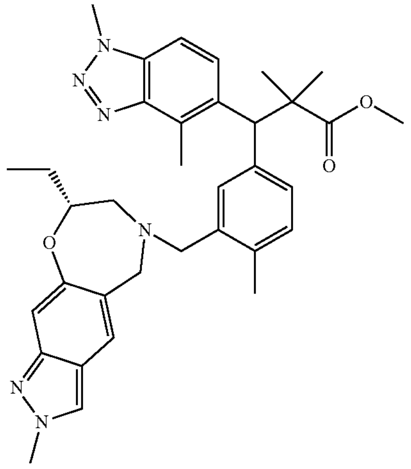 [SMILES: CC[C@@H]1CN(Cc2cc(C(c3ccc4c(nnn4C)c3C)C(C)(C)C(=O)OC)ccc2C)Cc2cc3cn(C)nc3cc2O1]

To a solution of methyl 3-(3-(chloromethyl)-4-methylphenyl)-3-(1,4-dimethyl-1H-benzo (d) [1,2,3]triazol-5-yl)-2,2-dimethylpropanoate produced according to the same manner as the Reference Example 10-(c) (24 mg) in acetonitrile (2 mL) were sequentially added (R)-8-ethyl-2-methyl-5,6,7,8-tetrahydro-2H-[1,4]oxazepino[6,7-f]indazole produced in the Reference Example 51-(b) (21 mg) and N,N-diisopropylethylamine (0.053 mL) under argon gas flow with stirring at room temperature, and the resulting mixture was stirred at 60° C. for 4 hours. Then, the resulting mixture was left to stand at room temperature for 14 hours. After the reaction was completed, the reaction solution was concentrated under reduced pressure. The resulting residues were purified by a silica gel column (elution solvent; ethyl acetate:methanol) to give the title compound (50 mg) as a pale yellow oil.

Mass spectrum (ESI, m/z): 595 $[M+H]^+$ $^1$H-NMR spectrum (400 MHz, $CD_3OD$) δ: 8.05-7.97 (m, 1H), 7.73-7.63 (m, 1H), 7.51-7.42 (m, 1H), 7.26-7.04 (m, 5H), 5.01-4.73 (m, 1H), 4.29-4.21 (m, 3H), 4.20-4.14 (m, 3H), 3.98-3.85 (m, 1H), 3.79-3.40 (m, 7H), 2.89-2.68 (m, 5H), 2.30-2.18 (m, 3H), 1.62-1.46 (m, 1H), 1.43-1.19 (m, 7H), 1.07-0.95 (m, 3H)

Example 51-(b)

Production of 3-(1,4-dimethyl-1H-benzo[d][1,2,3]triazol-5-yl)-3-(3-(((R)-8-ethyl-2-methyl-2,5,7,8-tetrahydro-6H-[1,4]oxazepino[6,7-f]indazol-6-yl)methyl)-4-methylphenyl)-2,2-dimethylpropanoic Acid

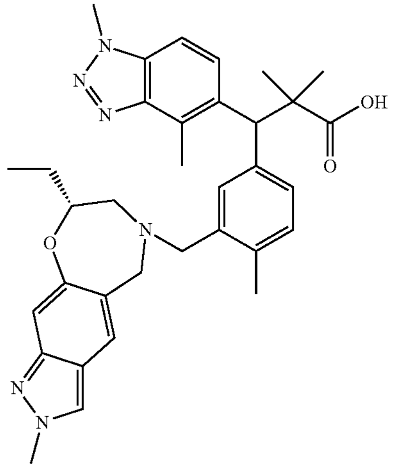 [SMILES: CC[C@@H]1CN(Cc2cc(C(c3ccc4c(nnn4C)c3C)C(C)(C)C(=O)O)ccc2C)Cc2cc3cn(C)nc3cc2O1]

To a solution of methyl 3-(1,4-dimethyl-1H-benzo[d][1,2,3]triazol-5-yl)-3-(3-(((R)-8-ethyl-2-methyl-2,5,7,8-tetrahydro-6H-[1,4]oxazepino [6,7-f]indazol-6-yl)methyl)-4-methylphenyl)-2,2-dimethylpropanoate produced in the Example 51-(a) (48 mg) in dimethyl sulfoxide (2 mL) was added a 1 M aqueous solution of potassium hydroxide (0.061 mL) with stirring at room temperature, and the resulting mixture was stirred at 70° C. for 5 hours. Additionally, a 1 M aqueous solution of potassium hydroxide (0.061 mL) was added thereto with stirring at 70° C., the resulting mixture was stirred at 70° C. for 1.5 hours, and left to stand at room temperature for 14 hours. After the reaction was completed, to the reaction mixture was added 2 M hydrochloric acid to adjust the pH to 5.8. The precipitated solids were collected by filtration, washed with water, and dried under reduced pressure at 40° C. to give the title compound (20 mg) as white solids.

Mass spectrum (ESI, m/z): 581 $[M+H]^+$ $^1$H-NMR spectrum (600 MHz, $CD_3OD$) δ: 8.06-7.98 (m, 1H), 7.77-7.66 (m, 1H), 7.50-7.39 (m, 1H), 7.30-7.04 (m, 5H), 4.95-4.90 (m, 1H), 4.28-4.21 (m, 3H), 4.19-4.13 (m, 3H), 4.02-3.90 (m, 1H), 3.80-3.49 (m, 4H), 2.94-2.69 (m, 5H), 2.33-2.23 (m, 3H), 1.65-1.47 (m, 1H), 1.42-1.20 (m, 7H), 1.06-0.98 (m, 3H)

Example 52-(a)

Production of methyl 3-(1,4-dimethyl-1H-benzo[d][1,2,3]triazol-5-yl)-3-(3-(((R)-2-ethyl-2,3-dihydro-[1,4]oxazepino[6,7-g]isoquinolin-4(5H)-yl)methyl)-4-methylphenyl)-2,2-dimethylpropanoate

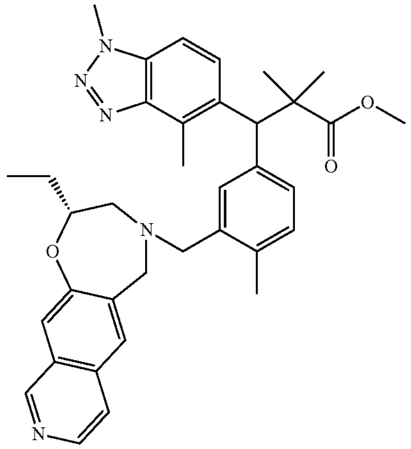 [SMILES: CC[C@@H]1CN(Cc2cc(C(c3ccc4c(nnn4C)c3C)C(C)(C)C(=O)OC)ccc2C)Cc2cc3ccncc3cc2O1]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (25 mg) in acetonitrile (3 mL) were sequentially added (R)-2-ethyl-2,3,4,5-tetrahydro-[1,4]oxazepino[6,7-g]isoquinoline dihydrochloride produced in the Reference Example 52-(d) (19 mg) and N,N-diisopropylethylamine (0.043 mL) under argon gas flow with stirring at room temperature, and the resulting mixture was stirred at 60° C. for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (24 mg) as a white foam.

Mass spectrum (ESI, m/z): 592 $[M+H]^+$ $^1$H-NMR spectrum (400 MHz, $CDCl_3$) δ: 9.16 (s, 1H), 8.48-8.42 (m, 1H), 7.65-7.49 (m, 3H), 7.44 (s, 1H), 7.32-7.17 (m, 1H), 7.12-7.01 (m, 3H), 4.87-4.80 (m, 1H), 4.24-4.18 (m, 3H), 4.15-4.07 (m, 1H), 3.88-3.74 (m, 2H), 3.62-3.42 (m, 5H), 2.96-2.89 (m, 2H), 2.81-2.73 (m, 3H), 2.26-2.21 (m, 3H), 1.71-1.45 (m, 1H), 1.42-1.21 (m, 7H), 1.12-1.02 (m, 3H)

Example 52-(b)

Production of 3-(1,4-dimethyl-1H-benzo[d][1, 2, 3]triazol-5-yl)-3-(3-(((R)-2-ethyl-2,3-dihydro-[1,4]oxazepino[6,7-g]isoquinolin-4 (5H)-yl)methyl)-4-methylphenyl)-2,2-dimethylpropanoic Acid

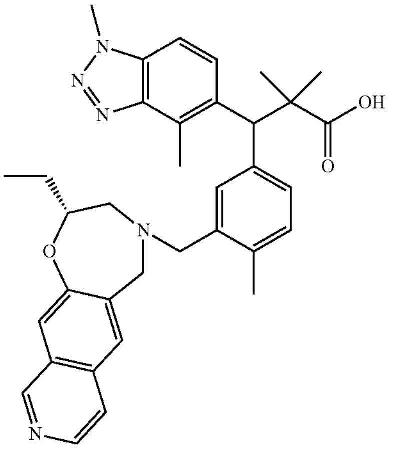 [SMILES: CC[C@@H]1CN(Cc2cc(C(c3ccc4c(nnn4C)c3C)C(C)(C)C(=O)O)ccc2C)Cc2cc3ccncc3cc2O1]

To a solution of methyl 3-(1,4-dimethyl-1H-benzo[d][1,2,3]triazol-5-yl)-3-(3-(((R)-2-ethyl-2,3-dihydro-[1,4]oxazepino[6,7-g]isoquinolin-4 (5H)-yl)methyl)-4-methylphenyl)-2,2-dimethylpropanoate produced in the Example 52-(a) (24 mg) in dimethyl sulfoxide (2.5 mL) was added dropwise a 1 M aqueous solution of potassium hydroxide (0.406 mL) under argon gas flow with stirring at room temperature, and the resulting mixture was stirred at 70° C. for 3 hours. After the reaction was completed, to the reaction solution was added water (5 mL), and 1 M hydrochloric acid was added thereto to adjust the pH to 5.2. The resulting mixed solution was subjected to extraction three times with ethyl acetate. The resulting organic layer was washed with saturated brine, dried over anhydrous magnesium sulfate, filtered, and concentrated under reduced pressure. The resulting residues were purified by a silica gel column (elution solvent; ethyl acetate:methanol), and the fractions comprising the target compound were concentrated under reduced pressure. The resulting residues were dissolved into a mixed solvent of acetonitrile/water, and the resulting solution was lyophilized to give the title compound (11 mg) as white solids.

Mass spectrum (ESI, m/z): 578 $[M+H]^+$ $^1$H-NMR spectrum (400 MHz, $CD_3OD$) δ: 9.12 (s, 1H), 8.38-8.29 (m, 1H), 7.80-7.61 (m, 3H), 7.58-7.50 (m, 1H), 7.46-7.38 (m, 1H), 7.25-7.14 (m, 1H), 7.11-7.04 (m, 2H), 4.96-4.78 (m, 1H), 4.27-4.20 (m, 3H), 4.08-3.99 (m, 1H), 3.91-3.72 (m, 2H), 3.66-3.49 (m, 2H), 2.96-2.80 (m, 2H), 2.71-2.63 (m, 3H), 2.29-2.21 (m, 3H), 1.66-1.49 (m, 1H), 1.41-1.23 (m, 7H), 1.08-0.98 (m, 3H)

Example 53

Production of 3-(1,4-dimethyl-1H-benzo[d][1,2,3]triazol-5-yl)-3-(3-(((R)-2-ethyl-2,3-dihydro-[1,4]oxazepino[7,6-g]isoquinolin-4 (5H)-yl)methyl)-4-methylphenyl)-2,2-dimethylpropanoic Acid

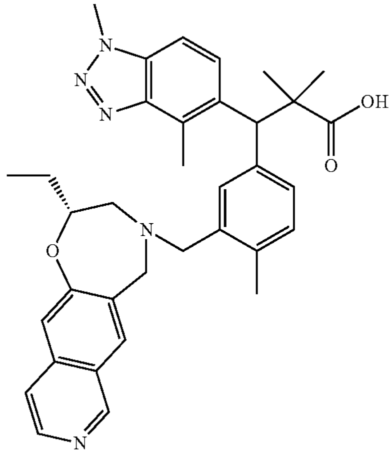 [SMILES: CC[C@@H]1CN(Cc2cc(C(c3ccc4c(nnn4C)c3C)C(C)(C)C(=O)O)ccc2C)Cc2cc3cnccc3cc2O1]

To a suspension of (R)-2-ethyl-2,3,4,5-tetrahydro-[1,4]oxazepino[7,6-g]isoquinoline dihydrochloride produced in the Reference Example 53-(c) (55 mg) in dichloromethane (3 mL) were sequentially added 3-(1,4-dimethyl-1H-benzo[d][1,2,3]triazol-5-yl)-3-(3-formyl-4-methylphenyl)-2,2-dimethylpropanoic acid produced according to the same manner as the Reference Example 23-(g) (63 mg) and N,N-diisopropylethylamine (0.065 mL) under argon gas flow with stirring at room temperature, and the resulting mixture was stirred at room temperature for 1 hour. Then, sodium triacetoxyborohydride (74 mg) was added thereto with stirring at room temperature, and the resulting mixture was stirred at room temperature for 4 hours. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (DIOL silica gel, elution solvent; ethyl acetate:methanol), and the fractions comprising the title compound were concentrated under reduced pressure. The resulting residues were separated and purified by supercritical fluid chromatography (column: SFC-B, mobile phase: $CO_2$/methanol methanol ratio (%)=30 (0 min)→30 (10 min)), and the fractions comprising the target compound were concentrated under reduced pressure. The resulting residues were dissolved into a mixed solvent of acetonitrile/water, and the resulting solution was lyophilized to give the title compound (58 mg) as white solids.

Mass spectrum (ESI, m/z): 578 $[M+H]^+$ $^1$H-NMR spectrum (400 MHz, $CD_3OD$) δ: 9.07 (s, 1H), 8.38-8.30 (m, 1H), 7.81-7.64 (m, 3H), 7.51-7.36 (m, 2H), 7.27-7.00 (m, 3H), 5.06-4.67 (m, 1H), 4.29-4.18 (m, 3H), 4.10-3.72 (m, 3H), 3.69-3.49 (m, 2H), 2.97-2.76 (m, 2H), 2.72-2.61 (Ta, 3H), 2.31-2.21 (m, 3H), 1.69-1.18 (m, 8H), 1.08-0.94 (n, 3H)

Example 54-(a)

Production of methyl 3-(1,4-dimethyl-1H-benzo[d][(1,2,3]triazol-5-yl)-3-(3-(((R)-2-ethyl-7-fluoro-2,3-dihydronaphtho[2,3-f][1,4]oxazepin-4(51H)-yl)methyl)-4-methylphenyl)-2,2-dimethylpropanoate

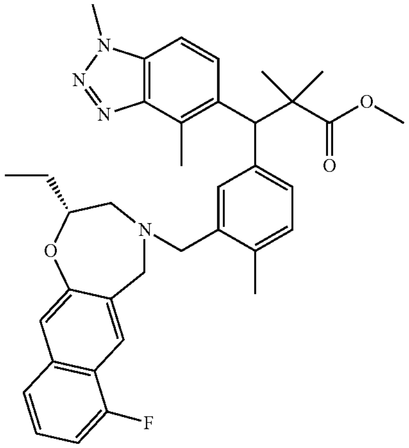 [SMILES: CC[C@@H]1CN(Cc2cc(C(c3ccc4c(nnn4C)c3C)C(C)(C)C(=O)OC)ccc2C)Cc2cc3c(F)cccc3cc2O1]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(C) (31 mg) in acetonitrile (3 mL) were sequentially added (R)-2-ethyl-7-fluoro-2,3,4,5-tetrahydronaphtho[2,3-f][1,4]oxazepine produced in the Reference Example 54-(1) (29 mg) and N,N-diisopropylethylamine (0.053 mL) under argon gas flow with stirring at room temperature, and the resulting mixture was stirred at 60° C. for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (44 mg) as a white foam.

Mass spectrum (ESI, m/z): 609 $[M+H]^+$ $^1$H-NMR spectrum (400 MHz, $CDCl_3$) δ: 7.82-7.74 (m, 1H), 7.70-7.50 (m, 2H), 7.48-7.43 (m, 1H), 7.40-7.32 (m, 1H), 7.30-7.19 (m, 1H), 7.12-7.01 (m, 4H), 4.88-4.80 (m, 1H), 4.23-4.19 (m, 3H), 4.17-4.07 (m, 1H), 3.90-3.72 (m, 2H), 3.62-3.52 (m, 1H), 3.49-3.42 (m, 4H), 2.98-2.82 (m, 2H), 2.79-2.73 (m, 3H), 2.26 (s, 3H), 1.69-1.45 (m, 1H), 1.43-1.21 (m, 7H), 1.11-1.00 (m, 3H)

Example 54-(b)

Production of 3-(1,4-dimethyl-1H-benzo[d][1,2,3]triazol-5-yl)-3-(3-(((R)-2-ethyl-7-fluoro-2,3-dihydronaphtho[2,3-f][1,4]oxazepin-4(5H)-yl)methyl)-4-methylphenyl)-2,2-dimethylpropanoic Acid

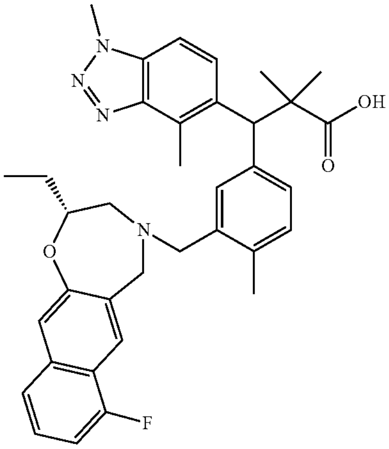 [SMILES: CC[C@@H]1CN(Cc2cc(C(c3ccc4c(nnn4C)c3C)C(C)(C)C(=O)O)ccc2C)Cc2cc3c(F)cccc3cc2O1]

To a solution of methyl 3-(1,4-dimethyl-1H-benzo[d][1,2,3]triazol-5-yl)-3-(3-(((R)-2-ethyl-7-fluoro-2,3-dihydronaphtho[2,3-f][1,4]oxazepin-4(5H)-yl)methyl)-4-methylphenyl)-2,2-dimethylpropanoate produced in the Example 54-(a) (44 mg) in dimethyl sulfoxide (4 mL) was added dropwise a 2 M aqueous solution of potassium hydroxide (0.361 mL) under argon gas flow with stirring at room temperature, and the resulting mixture was stirred at 70° C. for 3 hours. After the reaction was completed, to the reaction solution was added water (5 mL), 1 M hydrochloric acid was added thereto to adjust the pH to 5.5, and the resulting mixture was stirred for 1 hour. The resulting solids were collected by filtration, washed with water, and dried under reduced pressure at 60° C. to give the title compound (37 mg) as white solids.

Mass spectrum (ESI, m/z): 593 $[M-H]^-$ $^1$H-NMR spectrum (400 MHz, $CD_3OD$) δ: 7.84-7.66 (m, 2H), 7.61-7.55 (m, 1H), 7.48-7.35 (m, 3H), 7.22-7.03 (m, 4H), 4.96-4.81 (m, 1H), 4.26-4.20 (m, 3H), 4.09-3.98 (m, 1H), 3.92-3.69 (m, 2H), 3.66-3.56 (m, 1H), 3.56-3.49 (m, 1H), 2.95-2.78 (m, 2H), 2.72-2.63 (m, 3H), 2.29-2.22 (m, 3H), 1.63-1.47 (m, 1H), 1.42-1.20 (m, 7H), 1.06-0.96 (m, 3H)

Example 55-(a)

Production of methyl 3-(1,4-dimethyl-1H-benzo[d][1,2,3]triazol-5-yl)-3-(3-(((R)-2-ethyl-2,3-dihydro-[1,4]oxazepino[7,6-f]isoquinolin-4(5H)-yl)methyl)-4-methylphenyl)-2,2-dimethylpropanoate

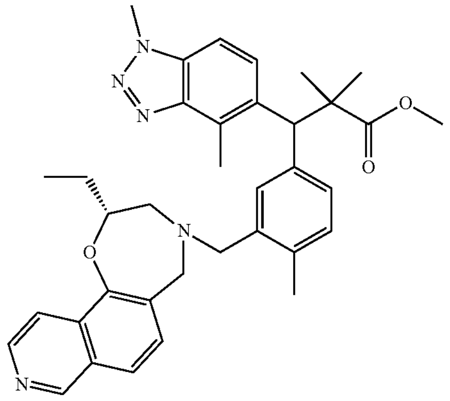 [SMILES: CC[C@@H]1CN(Cc2cc(C(c3ccc4c(nnn4C)c3C)C(C)(C)C(=O)OC)ccc2C)Cc2ccc3cnccc3c2O1]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (63 mg) in acetonitrile (3 mL) were sequentially added (R)-2-ethyl-2,3,4,5-tetrahydro-[1,4]oxazepino[7,6-f]isoquinoline hydrochloride produced in the Reference Example 55-(c) (52 mg) and N,N-diisopropylethylamine (0.113 mL) under argon gas flow with stirring at room temperature, and the resulting mixture was stirred at 60° C. for 3 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (35 mg) as a colorless oil.

Mass spectrum (ESI, m/z): 592 $[M+H]^+$ $^1$H-NMR spectrum (400 MHz, $CDCl_3$) δ: 9.24-9.17 (m, 1H), 8.58-8.50 (m, 1H), 8.10-8.02 (m, 1H), 7.63-7.38 (m, 2H), 7.32-6.81 (m, 5H), 4.88-4.80 (m, 1H), 4.23 (s, 3H), 4.07-3.40 (m, 8H), 3.07-2.94 (m, 2H), 2.87-2.73 (m, 3H), 2.30-2.22 (m, 3H), 1.89-1.75 (m, 1H), 1.72-1.45 (m, 1H), 1.43-1.21 (m, 6H), 1.17-1.07 (m, 3H)

Example 55-(b)

Production of 3-(1,4-dimethyl-1H-benzo[d][1,2,3]triazol-5-yl)-3-(3-(((R)-2-ethyl-2,3-dihydro-[1,4]oxazepino[7,6-f]isoquinolin-4(5H)-yl)methyl)-4-methylphenyl)-2,2-dimethylpropanoic Acid Ditrifluoroacetate

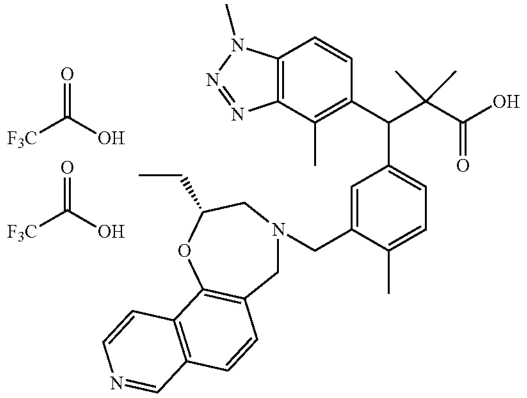

To a solution of methyl 3-(1,4-dimethyl-1H-benzo[d][1,2,3]triazol-5-yl)-3-(3-(((R)-2-ethyl-2,3-dihydro-[1,4]oxazepino[7,6-f]isoquinolin-4 (5H)-yl)methyl)-4-methylphenyl)-2,2-dimethylpropanoate produced in the Example 55-(a) (34 mg) in dimethyl sulfoxide (1.5 mL) was added dropwise a 1 M aqueous solution of potassium hydroxide (0.575 mL) under argon gas flow with stirring at room temperature, and the resulting mixture was stirred at 70° C. for 4 hours. After the reaction was completed, 1 M hydrochloric acid was added thereto to adjust the pH to 5. The resulting mixed solution was subjected to extraction with ethyl acetate. The resulting organic layer was dried over anhydrous sodium sulfate, filtered, and concentrated under reduced pressure. The resulting residues were purified by a silica gel column (DIOL silica gel, elution solvent; hexane:ethyl acetate), and the fractions comprising the title compound were concentrated under reduced pressure. The resulting residues were purified by reverse-phase HPLC (elution solvent; acetonitrile: 0.5% TFA solution in water), and the fractions comprising the title compound were combined. The resulting solution was lyophilized to give the title compound (12 mg) as white solids.

Mass spectrum (ESI, m/z): 578 $[M+H]^+$ $^1$H-NMR spectrum (400 MHz, $DMSO-d_6+D_2O$) δ: 9.47-9.38 (m, 1H), 8.63-8.56 (m, 11H), 8.18-8.07 (m, 1H), 7.93-7.83 (m, 1H), 7.71-7.13 (m, 6H), 4.82-4.73 (m, 1H), 4.26-4.17 (m, 3H), 3.73-3.45 (m, 7H), 2.72-2.61 (m, 3H), 2.36-2.26 (m, 3H), 1.80-1.43 (m, 2H), 1.34-1.14 (m, 6H), 1.09-0.96 (m, 31)

Example 56-(a)

Production of ethyl 3-(1,4-dimethyl-1H-benzo[d][1,2,3]triazol-5-yl)-3-(3-(((R)-2-ethyl-2,3-dihydro-[1,4]oxazepino[7,6-g]quinolin-4 (5H)-yl)methyl)-4-methylphenyl)propanoate

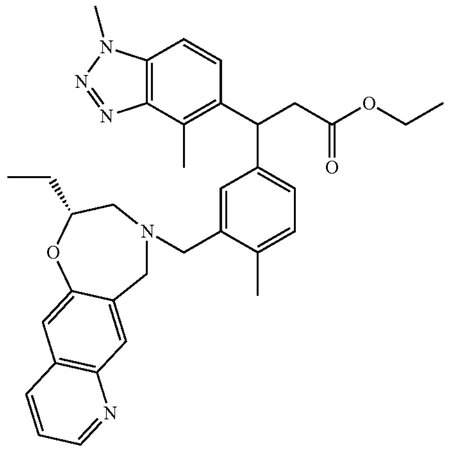 [SMILES: CCOC(=O)CC(c1ccc(C)c(CN2Cc3cc4ncccc4cc3O[C@H](CC)C2)c1)c1ccc2c(nnn2C)c1C]

To a solution of ethyl 3-(1,4-dimethyl-1H-benzo[d][1,2,3]triazol-5-yl)-3-(3-formyl-4-methylphenyl)propanoate produced in the Reference Example 56-(c) (30 mg) in dichloromethane (3 mL) was added (R)-2-ethyl-2,3,4,5-tetrahydro-[1,4]oxazepino[7,6-g]quinoline produced according to the same manner as the Reference Example 12-(c) (20 mg) under argon gas flow with stirring at room temperature, and the resulting mixture was stirred at room temperature for 0.5 hour. Then, sodium triacetoxyborohydride (35 mg) was added thereto with stirring at room temperature, and the resulting mixture was stirred at room temperature for 14 hours. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (37 mg) as a white foam.

Mass spectrum (ESI, m/z): 578 $[M+H]^+$ $^1$H-NMR spectrum (400 MHz, $CD_3OD$) δ: 8.77-8.72 (m, 1H), 8.30-8.24 (m, 1H), 7.70-7.63 (m, 1H), 7.53-7.39 (m, 4H), 7.14-7.04 (m, 3H), 5.01-4.90 (m, 1H), 4.26-4.19 (m, 3H), 4.13-4.03 (m, 1H), 4.00-3.75 (m, 4H), 3.69-3.52 (m, 2H), 3.22-3.01 (m, 2H), 2.94-2.81 (m, 2H), 2.76-2.69 (m, 3H), 2.28-2.21 (m, 3H), 1.65-1.49 (m, 1H), 1.39-1.26 (m, 1H), 1.09-0.96 (m, 6H)

Example 56-(b)

Production of 3-(1,4-dimethyl-1H-benzo[d][1,2,3]triazol-5-yl)-3-(3-(((R)-2-ethyl-2,3-dihydro-[1,4]oxazepino[7,6-g]quinolin-4(5H)-yl)methyl)-4-methylphenyl)propanoic acid

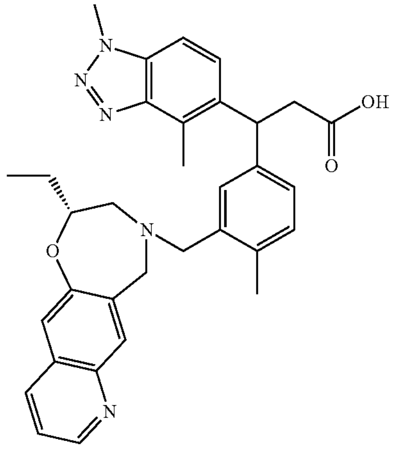 [SMILES: CC[C@@H]1CN(Cc2cc(C(CC(=O)O)c3ccc4c(nnn4C)c3C)ccc2C)Cc2cc3ncccc3cc2O1]

To a solution of ethyl 3-(1,4-dimethyl-1H-benzo[d][1,2,3]triazol-5-yl)-3-(3-(((R)-2-ethyl-2,3-dihydro-[1,4]oxazepino[7,6-g]quinolin-4 (5H)-yl)methyl)-4-methylphenyl)propanoate produced in the Example 56-(a) (35 mg) in a mixture of ethanol (1 mL)/water (1 mL) was added lithium hydroxide (6 mg) with stirring at room temperature, and the resulting mixture was stirred at 85° C. for 2 hours. After the reaction was completed, 1 M hydrochloric acid was added thereto to adjust the pH to 5. The resulting mixed solution was subjected to extraction with ethyl acetate. The resulting organic layer was dried over anhydrous magnesium sulfate, filtered, and concentrated under reduced pressure. The resulting residues were purified by a silica gel column (DIOL silica gel, elution solvent; ethyl acetate:methanol), and the fractions comprising the title compound were concentrated under reduced pressure. The resulting residues were dissolved into a mixed solvent of acetonitrile/water, and the resulting solution was lyophilized to give the title compound (25 mg) as white solids.

Mass spectrum (ESI, m/z): 550 $[M+H]^+$ $^1$H-NMR spectrum (400 MHz, $CD_3OD$) δ: 8.78-8.72 (m, 1H), 8.32-8.24 (m, 1H), 7.72-7.64 (m, 1H), 7.53-7.39 (m, 4H), 7.17-7.04 (m, 3H), 4.98-4.91 (m, 1H), 4.28-4.21 (m, 3H), 4.13-4.02 (m, 1H), 3.94-3.76 (m, 2H), 3.71-3.62 (m, 1H), 3.60-3.54 (m, 1H), 3.19-3.10 (m, 1H), 3.08-2.97 (m, 1H), 2.96-2.83 (m, 2H), 2.76-2.71 (m, 3H), 2.28-2.23 (m, 3H), 1.64-1.50 (m, 1H), 1.40-1.24 (m, 1H), 1.05-0.96 (m, 3H)

Example 57-(a)

Production of methyl 3-(1,4-dimethyl-1H-benzo[d][1,2,3]triazol-5-yl)-3-(3-(((S)-2-ethyl-2,3-dihydro-[1,4]oxazepino[7,6-g]quinolin-4 (5H)-yl)methyl)-4-methylphenyl)-2,2-dimethylpropanoate

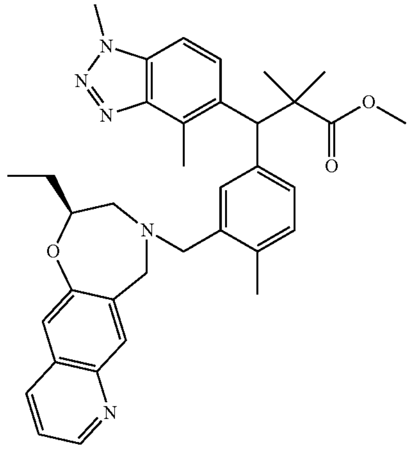 [SMILES: CC[C@H]1CN(Cc2cc(C(c3ccc4c(nnn4C)c3C)C(C)(C)C(=O)OC)ccc2C)Cc2cc3ncccc3cc2O1]

To a solution of methyl 3-(1,4-dimethyl-1H-benzo[d][1,2,3]triazol-5-yl)-3-(3-(hydroxymethyl)-4-methylphenyl)-2,2-dimethylpropanoate produced according to the same manner as the Reference Example 1-(h) (150 mg) in dichloromethane (1.5 mL) was added dropwise thionyl chloride (0.043 mL) under argon gas flow with stirring at room temperature, and the resulting mixture was stirred at room temperature for 15 minutes. Then, the reaction solution was concentrated.

To a solution of the resulting residues in acetonitrile (1.5 mL) were added dropwise N,N-diisopropylethylamine (0.201 mL) and a solution of (S)-2-ethyl-2,3,4,5-tetrahydro-[1,4]oxazepino[7,6-g]quinoline produced in the Reference Example 57-(b) (94 mg) in acetonitrile (1.5 mL) under argon gas flow with stirring at room temperature, and the resulting mixture was stirred at 80° C. for 4 hours. After the reaction was completed, the reaction solution was poured into water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (198 mg) as a slightly yellow oil.

Mass spectrum (ESI, m/z): 592 $[M+H]^+$ $^1$H-NMR spectrum (400 MHz, $CDCl_3$) δ: 8.85-8.80 (m, 1H), 8.10-8.03 (m, 1H), 7.79-7.72 (m, 1H), 7.67-7.55 (m, 1H), 7.44-7.23 (m, 3H), 7.11-6.99 (m, 3H), 4.87-4.82 (m, 1H), 4.27-4.09 (m, 4H), 3.95-3.74 (m, 2H), 3.65-3.55 (m, 1H), 3.52-3.41 (m, 4H), 2.96-2.73 (m, 5H), 2.29-2.20 (m, 3H), 1.70-1.55 (m, 1H), 1.43-1.29 (m, 7H), 1.11-0.98 (m, 3H)

Example 57-(b)

Production of 3-(1,4-dimethyl-1H-benzo[d][1,2,3]triazol-5-yl)-3-(3-(((S)-2-ethyl-2,3-dihydro-[1,4]oxazepino[7,6-g]quinolin-4(5H)-yl)methyl)-4-methylphenyl)-2,2-dimethylpropanoic Acid

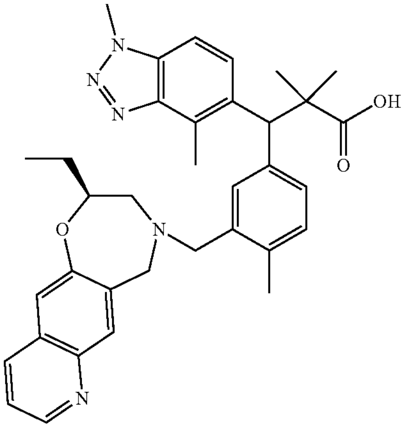 [SMILES: CC[C@H]1CN(Cc2cc(C(c3ccc4c(nnn4C)c3C)C(C)(C)C(=O)O)ccc2C)Cc2cc3ncccc3cc2O1]

To a solution of methyl 3-(1,4-dimethyl-1H-benzo[d][1,2,3]triazol-5-yl)-3-(3-(((S)-2-ethyl-2,3-dihydro-[1,4]oxazepino[7,6-g]quinolin-4 (5H)-yl)methyl)-4-methylphenyl)-2,2-dimethylpropanoate produced in the Example 57-(a) (197 mg) in dimethyl sulfoxide (4 mL) was added dropwise a 1 M aqueous solution of potassium hydroxide (1.66 mL) with stirring at 75° C., and the resulting mixture was stirred at 75° C. for 4 hours. After the reaction was completed, water (4 mL) was added thereto. Then, 2 M hydrochloric acid was added thereto to adjust the pH to 5.5, and the resulting mixed solution was subjected to extraction twice with ethyl acetate. The resulting organic layer was washed sequentially with water and saturated brine, dried over anhydrous magnesium sulfate, filtered, and concentrated under reduced pressure. The resulting residues were purified by a silica gel column (DIOL silica gel, elation solvent; hexane:ethyl acetate) to give the title compound (164 mg) as a slightly yellow foam.

Mass spectrum (ESI, m/z): 578 $[M+H]^+$ $^1$H-NMR spectrum (400 MHz, $CD_3OD$) δ: 8.77-8.71 (m, 1H), 8.31-8.24 (m, 1H), 7.80-7.68 (m, 2H), 7.53-7.42 (m, 3H), 7.21-7.03 (m, 3H), 4.97-4.84 (m, 1H), 4.29-4.22 (m, 3H), 4.13-4.02 (m, 1H), 3.96-3.72 (m, 2H), 3.68-3.50 (m, 2H), 2.96-2.79 (m, 2H), 2.74-2.65 (m, 3H), 2.29-2.20 (m, 3H), 1.64-1.48 (m, 1H), 1.43-1.20 (m, 7H), 1.09-0.96 (m, 3H)

Example 57-(c)

Production of 3-(1,4-dimethyl-1H-benzo[d][1,2,3]triazol-5-yl)-3-(3-(((S)-2-ethyl-2,3-dihydro-[1,4]oxazepino[7,6-g]quinolin-4(5H)-yl)methyl)-4-methylphenyl)-2,2-dimethylpropanoic Acid (Diastereomer 1) and Example 58

Production of 3-(1,4-dimethyl-1H-benzo[d][1,2,3]triazol-5-yl)-3-(3-(((S)-2-ethyl-2,3-dihydro-[1,4]oxazepino[7,6-g]quinolin-4(5H)-yl)methyl)-4-methylphenyl)-2,2-dimethylpropanoic Acid (Diastereomer 2)

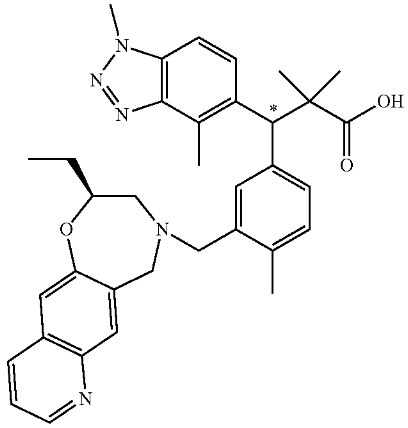 [SMILES: CC[C@H]1CN(Cc2cc(C(c3ccc4c(nnn4C)c3C)C(C)(C)C(=O)O)ccc2C)Cc2cc3ncccc3cc2O1]

3-(1,4-dimethyl-1H-benzo[d][1,2,3]triazol-5-yl)-3-(3-(((S)-2-ethyl-2,3-dihydro-[1,4]oxazepino[7,6-g]quinolin-4(5H)-yl)methyl)-4-methylphenyl)-2,2-dimethylpropanoic acid produced in the Example 57-(b) was separated and purified by chiral high performance liquid chromatography (Column: CHIRALPAK IC, mobile phase: hexane/ethanol). The fractions comprising the first-eluted diastereomer were concentrated under reduced pressure to give the compound of Example 57-(c) (41 mg) as white solids. Also, the later-eluted fractions were concentrated under reduced pressure to give the compound of Example 58 (38 mg) as white solids.

(High Performance Liquid Chromatography Analysis)

Column: CHIRALPAK IC-3 4.6×150 mm

Eluent: hexane/ethanol ethanol ratio (%) 10 (0 min)→90 (10 min)

Flow rate: 0.8 mL/min

Temperature: 40° C.

Detection wavelength: 254 nm

Retention time: Example 57-(C): 6.81 min, Example 58: 7.54 min (Example 57-(c))

Mass spectrum (ESI, m/z): 578 $[M+H]^+$ $^1$H-NMR spectrum (400 MHz, $CD_3OD$) δ: 8.77-8.71 (m, 1H), 8.31-8.23 (m, 1H), 7.77-7.67 (m, 2H), 7.54-7.42 (m, 3H), 7.21-7.12 (m, 2H), 7.09-7.03 (m, 1H), 4.95 (s, 1H), 4.25 (s, 3H), 4.10-3.77 (m, 3H), 3.65 (d, J=13.3 Hz, 1H), 3.53 (d, J=13.3 Hz, 1H), 2.95-2.80 (m, 2H), 2.71 (s, 3H), 2.24 (s, 3H), 1.64-1.51 (m, 1H), 1.42-1.25 (m, 7H), 1.03 (t, J=7.7 Hz, 3H)

Example 58

Mass spectrum (ESI, m/z): 578 $[M+H]^+$ $^1$H-NMR spectrum (400 MHz, $CD_3OD$) δ: 8.78-8.72 (m, 1H), 8.30-8.24 (m, 1H), 7.80-7.74 (m, 1H), 7.70 (s, 1H), 7.53-7.42 (m, 3H), 7.17-7.03 (m, 3H), 4.92 (s, 1H), 4.25 (s, 3H), 4.09 (d, J=14.1 Hz, 1H), 3.92 (d, J=14.1 Hz, 1H), 3.82-3.72 (m, 1H), 3.63 (d, J=13.4 Hz, 1H), 3.54 (d, J=13.4 Hz, 1H), 2.93-2.79 (m, 2H), 2.69 (s, 3H), 2.25 (s, 3H), 1.65-1.48 (m, 1H), 1.37 (s, 3H), 1.32-1.19 (m, 4H), 0.99 (t, J=7.2 Hz, 3H)

Example 59-(a)

Production of methyl 3-(3-(((R)-2-ethyl-2,3-dihydro-[1,4]oxazepino[7,6-g]quinolin-4(5H)-yl)methyl)-4-methylphenyl)-3-(1-ethyl-4-methyl-1H-benzo[d][1,2,3]triazol-5-yl)-2,2-dimethylpropanoate

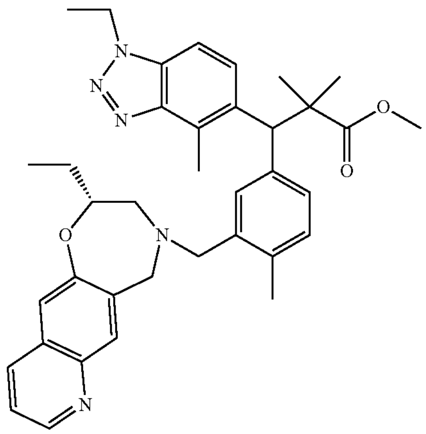 [SMILES: CC[C@@H]1CN(Cc2cc(C(c3ccc4c(nnn4CC)c3C)C(C)(C)C(=O)OC)ccc2C)Cc2cc3ncccc3cc2O1]

To a solution of methyl 3-(1-ethyl-4-methyl-1H-benzo[d][1,2,3]triazol-5-yl)-3-(3-(hydroxymethyl)-4-methylphenyl)-2,2-dimethylpropanoate produced according to the same manner as the Reference Example 59-(f) (33 mg) in dichloromethane (2 mL) was added dropwise thionyl chloride (0.009 mL) under argon gas flow with stirring at room temperature, and the resulting mixture was stirred at room temperature for 15 minutes. Then, the reaction solution was concentrated under reduced pressure. To the resulting residues was added acetonitrile (2 mL), then N,N-diisopropylethylamine (0.044 mL) was added thereto. Additionally, a solution of (R)-2-ethyl-2,3,4,5-tetrahydro-[1,4]oxazepino[7,6-g]quinoline produced according to the same manner as the Reference Example 12-(c) (20 mg) in acetonitrile (2 mL) was added dropwise thereto with stirring at room temperature, and the resulting mixture was stirred at 80° C. for 5 hours. After the reaction was completed, the reaction solution was poured into water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (38 mg) as a slightly yellow oil.

Mass spectrum (ESI, m/z): 606 $[M+H]^+$ $^1$H-NMR spectrum (400 MHz, $CD_3OD$) δ: 8.77-8.70 (m, 1H), 8.31-8.22 (m, 1H), 7.76-7.59 (m, 2H), 7.54-7.43 (m, 3H), 7.18-7.02 (m, 3H), 4.91-4.82 (m, 1H), 4.74-4.61 (m, 2H), 4.14-4.02 (m, 1H), 3.98-3.73 (m, 2H), 3.69-3.61 (m, 1H), 3.59-3.51 (m, 1H), 3.49-3.42 (m, 3H), 2.92-2.75 (m, 2H), 2.74-2.65 (m, 3H), 2.28-2.20 (m, 3H), 1.62-1.47 (m, 4H), 1.42-1.36 (m, 3H), 1.34-1.28 (m, 4H), 1.05-0.94 (m, 3H)

Example 59-(b)

Production of 3-(3-(((R)-2-ethyl-2,3-dihydro-[1,4]oxazepino[7,6-g]quinolin-4(5H)-yl)methyl)-4-methylphenyl)-3-(1-ethyl-4-methyl-1H-benzo[d][1,2,3]triazol-5-yl)-2,2-dimethylpropanoic Acid

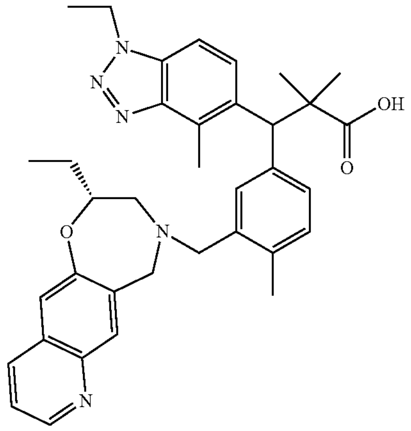 [SMILES: CC[C@@H]1CN(Cc2cc(C(c3ccc4c(nnn4CC)c3C)C(C)(C)C(=O)O)ccc2C)Cc2cc3ncccc3cc2O1]

To a solution of methyl 3-(3-(((R)-2-ethyl-2,3-dihydro-[1,4]oxazepino[7,6-g]quinolin-4 (5H)-yl)methyl)-4-methylphenyl)-3-(1-ethyl-4-methyl-1H-benzo[d][1,2,3]triazol-5-yl)-2,2-dimethylpropanoate produced in the Example 59-(a) (36 mg) in dimethyl sulfoxide (1 mL) was added dropwise a 1 M aqueous solution of potassium hydroxide (0.090 mL) with stirring at 75° C., and the resulting mixture was stirred at 75° C. for 4 hours. After the reaction was completed, to the reaction solution was added water (4 mL), and 2 M hydrochloric acid was added thereto to adjust the pH to 5.5. The resulting mixed solution was subjected to extraction twice with ethyl acetate. The resulting organic layer was washed sequentially with water and saturated brine, dried over anhydrous magnesium sulfate, filtered, and concentrated under reduced pressure. The resulting residues were purified by a silica gel column (DIOL silica gel, elution solvent; hexane:ethyl acetate) to give the title compound (26 mg) as a slightly yellow foam.

Mass spectrum (ESI, m/z): 592 $[M+H]^+$ $^1$H-NMR spectrum (400 MHz, $CD_3OD$) δ: 8.78-8.71 (m, 1H), 8.31-8.24 (m, 1H), 7.79-7.68 (m, 2H), 7.53-7.44 (m, 3H), 7.23-7.11 (m, 2H), 7.10-7.04 (m, 1H), 4.98-4.90 (m, 1H), 4.72-4.63 (m, 2H), 4.13-4.02 (m, 1H), 3.96-3.73 (m, 2H), 3.69-3.60 (n, 11), 3.58-3.50 (m, 1H), 2.97-2.79 (m, 2H), 2.76-2.67 (m, 3H), 2.31-2.20 (m, 3H), 1.65-1.49 (m, 4H), 1.43-1.26 (m, 7H), 1.06-0.95 (m, 3H)

Example 60-(a)

Production of methyl 3-(1,4-dimethyl-1H-benzo[d][1, 2, 3]triazol-5-yl)-3-(3-((2,2-dimethyl-2,3-dihydro-[1,4]oxazepino[7,6-g]quinolin-4 (5H)-yl)methyl)-4-methylphenyl)-2,2-dimethylpropanoate

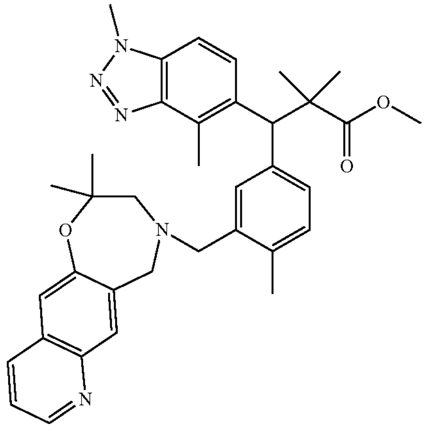 [SMILES: COC(=O)C(C)(C)C(c1ccc(C)c(CN2Cc3cc4ncccc4cc3OC(C)(C)C2)c1)c1ccc2c(nnn2C)c1C]

To a solution of methyl 3-(1,4-dimethyl-1H-benzo[d][1,2,3]triazol-5-yl)-3-(3-(hydroxymethyl)-4-methylphenyl)-2,2-dimethylpropanoate produced according to the same manner as the Reference Example 1-(h) (70 mg) in dichloromethane (3 mL) was added dropwise thionyl chloride (0.020 mL) under argon gas flow with stirring at room temperature, and the resulting mixture was stirred at room temperature for 15 minutes. Then, the reaction solution was concentrated.

To a solution of the resulting residues in acetonitrile (1 mL) were added dropwise N,N-diisopropylethylamine (0.10 mL) and a solution of 2,2-dimethyl-2,3,4,5-tetrahydro-[1,4]oxazepino[7,6-g]quinoline produced in the Reference Example 60-(b) (44 mg) in acetonitrile (2 mL) under argon gas flow with stirring at room temperature, and the resulting mixture was stirred at 80° C. for 3 hours. After the reaction was completed, the reaction solution was poured into water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (64 mg) as a slightly yellow oil.

Mass spectrum (ESI, m/z): 592 $[M+H]^+$ $^1$H-NMR spectrum (400 MHz, $CD_3OD$) δ: 8.74-8.68 (m, 1H), 8.25-8.20 (m, 1H), 7.68-7.63 (m, 1H), 7.53-7.50 (m, 1H), 7.48-7.43 (m, 1H), 7.39-7.33 (m, 2H), 7.23-7.19 (m, 1H), 7.14-7.04 (m, 2H), 4.89-4.84 (m, 11H), 4.21 (s, 3H), 3.75-3.62 (m, 4H), 3.46 (s, 3H), 2.77-2.68 (m, 2H), 2.65 (s, 3H), 2.28 (s, 3H), 1.37 (s, 3H), 1.29 (s, 3H), 1.15 (s, 3H), 1.08 (s, 3H)

Example 60-(b)

Production of 3-(1,4-dimethyl-1H-benzo[d][1,2,3]triazol-5-yl)-3-(3-((2,2-dimethyl-2,3-dihydro-[1,4]oxazepino[7,6-g]quinolin-4 (5H)-yl)methyl)-4-methylphenyl)-2,2-dimethylpropanoic Acid

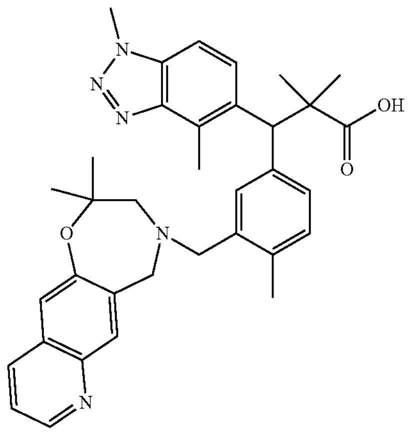 [SMILES: Cc1ccc(C(c2ccc3c(nnn3C)c2C)C(C)(C)C(=O)O)cc1CN1Cc2cc3ncccc3cc2OC(C)(C)C1]

To a solution of methyl 3-(1,4-dimethyl-1H-benzo[d][1,2,3]triazol-5-yl)-3-(3-((2,2-dimethyl-2,3-dihydro-[1,4]oxazepino[7,6-g]quinolin-4 (5H)-yl)methyl)-4-methylphenyl)-2,2-dimethylpropanoate produced in the Example 60-(a) (62 mg) in dimethyl sulfoxide (1 mL) was added dropwise a 1 M aqueous solution of potassium hydroxide (0.157 mL) with stirring at 75° C., and the resulting mixture was stirred at 75° C. for 4 hours. After the reaction was completed, water (4 mL) was added thereto. Then, 2 M hydrochloric acid was added thereto to adjust the pH to 5.5, and the resulting mixed solution was subjected to extraction twice with ethyl acetate. The resulting organic layer was washed sequentially with water and saturated brine, dried over anhydrous magnesium sulfate, filtered, and concentrated under reduced pressure. The resulting residues were purified by a silica gel column (DIOL silica gel, elution solvent; hexane:ethyl acetate) to give the title compound (46 mg) as a slightly yellow foam.

Mass spectrum (ESI, m/z): 578 $[M+H]^+$ $^1$H-NMR spectrum (400 MHz, $CD_3OD$) δ: 8.73-8.67 (m, 1H), 8.26-8.19 (m, 1H), 7.75-7.67 (m, 1H), 7.54-7.49 (m, 1H), 7.49-7.42 (m, 1H), 7.40-7.32 (m, 2H), 7.26-7.21 (m, 1H), 7.18-7.12 (m, 1H), 7.09-7.02 (m, 1H), 4.93 (s, 1H), 4.21 (s, 3H), 3.77-3.60 (m, 4H), 2.79-2.70 (m, 2H), 2.68 (s, 3H), 2.27 (s, 3H), 1.38 (s, 3H), 1.28 (s, 3H), 1.15 (s, 3H), 1.09 (s, 3H)

Example 61-(a)

Production of methyl 3-(1,4-dimethyl-1H-benzo[d][1,2,3]triazol-5-yl)-3-(3-(((R)-6-ethyl-2,2-dimethyl-6,7-dihydro-[1,3]dioxolo[4',5':4,5]benzo[1,2-f][1,4]oxazepin-8(9H)-yl)methyl)-4-methylphenyl)-2,2-dimethylpropanoate

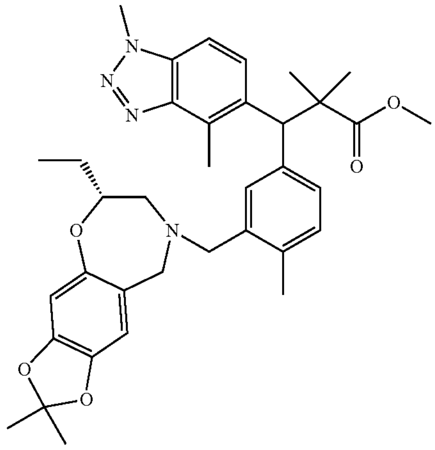

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (25 mg) in acetonitrile (3 mL) were sequentially added (R)-6-ethyl-2,2-dimethyl-6,7,8,9-tetrahydro-[1,3]dioxolo[4',5':4,5]benzo[1,2-f][1,4]oxazepine produced in the Reference Example 61-(e) (17 mg) and N,N-diisopropylethylamine (0.043 mL) under argon gas flow with stirring at room temperature, and the resulting mixture was stirred at 60° C. for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (32 mg) as a white foam.

Mass spectrum (ESI, m/z): 613 $[M+H]^+$ $^1$H-NMR spectrum (400 MHz, $CDCl_6$) δ: 7.64-7.55 (m, 1H), 7.33-7.20 (m, 1H), 7.16-6.95 (m, 3H), 6.49-6.42 (m, 1H), 6.26-6.12 (m, 1H), 4.88-4.81 (m, 1H), 4.27-4.20 (m, 3H), 3.94-3.84 (m, 1H), 3.75-3.60 (m, 1H), 3.53-3.32 (m, 6H), 2.86-2.75 (m, 5H), 2.28-2.22 (m, 3H), 1.73-1.60 (m, 6H), 1.59-1.45 (m, 1H), 1.43-1.17 (m, 7H), 1.04-0.92 (m, 3H)

Example 61-(b)

Production of 3-(1,4-dimethyl-1H-benzo[d][1,2,3)triazol-5-yl)-3-(3-(((R)-6-ethyl-2,2-dimethyl-6,7-dihydro-(1,3]dioxolo[4',5':4,5]benzo[1,2-f][1,4]oxazepin-8(9H)-yl)methyl)-4-methylphenyl)-2,2-dimethylpropanoic Acid

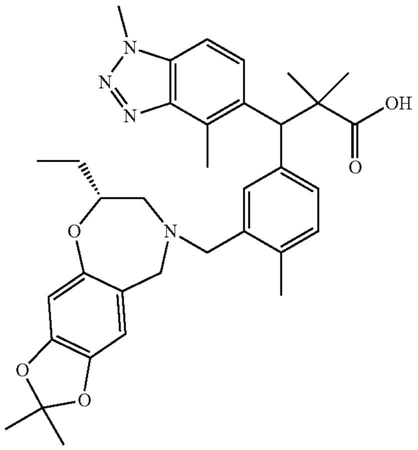 [SMILES: CC[C@@H]1CN(Cc2cc(C(c3ccc4c(nnn4C)c3C)C(C)(C)C(=O)O)ccc2C)Cc2cc3c(cc2O1)OC(C)(C)O3]

To a solution of methyl 3-(1,4-dimethyl-1H-benzo[d][1,2,3]triazol-5-yl)-3-(3-(((R)-6-ethyl-2,2-dimethyl-6,7-dihydro-[1,3]dioxolo[4',5':4,5]benzo[1,2-f][1,4]oxazepin-8(9H)-yl)methyl)-4-methylphenyl)-2,2-dimethylpropanoate produced in the Example 61-(a) (32 mg) in dimethyl sulfoxide (4 mL) was added dropwise a 2 M aqueous solution of potassium hydroxide (0.216 mL) under argon gas flow with stirring at room temperature, and the resulting mixture was stirred at 70° C. for 3 hours. After the reaction was completed, to the reaction solution was added water (5 mL), and 1 M hydrochloric acid was added thereto to adjust the pH to 5.5. The resulting mixed solution was subjected to extraction three times with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate), and the fractions comprising the title compound were concentrated under reduced pressure. The resulting residues were dissolved into a mixed solvent of acetonitrile/water, and the resulting solution was lyophilized to give the title compound (17 mg) as white solids.

Mass spectrum (ESI, m/z): 599 $[M+H]^+$ $^1$H-NMR spectrum (400 MHz, $CD_3OD$) δ: 7.74-7.67 (m, 1H), 7.54-7.46 (m, 1H), 7.25-7.18 (m, 1H), 7.11-6.95 (m, 2H), 6.42-6.36 (m, 1H), 6.22-6.03 (m, 1H), 4.97-4.92 (m, 1H), 4.30-4.25 (m, 3H), 3.85-3.77 (m, 1H), 3.70-3.36 (m, 4H), 2.92-2.84 (m, 1H), 2.80-2.68 (m, 4H), 2.30-2.23 (m, 3H), 1.68-1.56 (m, 6H), 1.50-1.13 (m, 8H), 1.01-0.87 (m, 3H)

Example 62

Production of 3-(1,4-dimethyl-1H-benzo[d][1,2,3]triazol-5-yl)-3-(3-(((R)-2-ethyl-2,3-dihydro-[1,4]oxazepino[6,7-h]isoquinolin-4 (5H)-yl)methyl)-4-methylphenyl)-2,2-dimethylpropanoic Acid

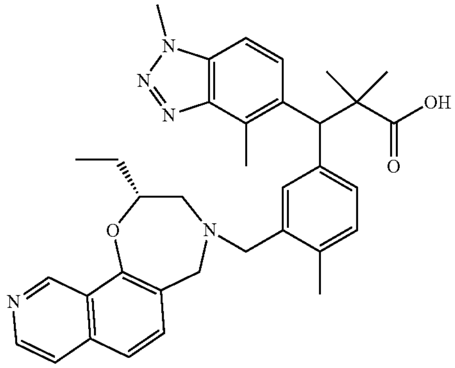 [SMILES: CC[C@@H]1CN(Cc2cc(C(c3ccc4c(nnn4C)c3C)C(C)(C)C(=O)O)ccc2C)Cc2ccc3ccncc3c2O1]

To a suspension of (R)-2-ethyl-2,3,4,5-tetrahydro-[1,4]oxazepino[6,7-h]isoquinoline dihydrochloride produced in the Reference Example 62-(d) (32 mg) in dichloromethane (2 mL) were sequentially added 3-(1,4-dimethyl-1H-benzo[d][1,2,3]triazol-5-yl)-3-(3-formyl-4-methylphenyl)-2,2-dimethylpropanoic Acid produced according to the same manner as the Reference Example 23-(g) (38 mg) and N,N-diisopropylethylamine (0.038 mL) under argon gas flow with stirring at room temperature, and the resulting mixture was stirred at room temperature for 1 hour. Then, sodium triacetoxyborohydride (44 mg) was added thereto, and the resulting mixture was stirred at room temperature for 4 hours. After the reaction was completed, to the reaction solution was added a saturated aqueous solution of sodium hydrogen carbonate, and the resulting mixed solution was subjected to extraction with ethyl acetate. The resulting organic layer was washed with a saturated aqueous solution of sodium hydrogen carbonate, dried over anhydrous sodium sulfate, filtered, and concentrated under reduced pressure. The resulting residues were subjected to achiral preparative isolation and the fractions comprising the title compound were concentrated under reduced pressure. The resulting residues were dissolved into a mixed solvent of acetonitrile/water, and the resulting solution was lyophilized to give the title compound (21 mg) as white solids.

Mass spectrum (ESI, m/z): 578 $[M+H]^+$ $^1$H-NMR spectrum (400 MHz, $CD_3OD$) δ: 9.61-9.53 (m, 1H), 8.44-8.36 (m, 1H), 7.79-7.64 (m, 2H), 7.49-6.94 (m, 6H), 5.05-4.73 (m, 1H), 4.24 (s, 3H), 4.14-3.95 (m, 1H), 3.95-3.67 (m, 2H), 3.63-3.53 (m, 2H), 3.08-2.87 (m, 2H), 2.76-2.65 (m, 3H), 2.35-2.23 (m, 3H), 1.85-1.46 (m, 2H), 1.42-1.18 (m, 6H), 1.15-1.01 (m, 3H)

Example 63-(a)

Production of methyl 3-(3-((2,3-dihydro-[1,4]oxazepino[7,6-g]quinolin-4(5H)-yl)methyl)-4-methylphenyl)-3-(1,4-dimethyl-1H-benzo[d][1,2,3]triazol-5-yl)-2,2-dimethylpropanoate

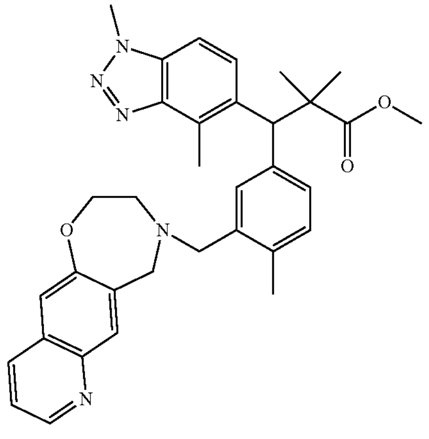 [SMILES: COC(=O)C(C)(C)C(c1ccc(C)c(CN2CCOc3cc4cccnc4cc3C2)c1)c1ccc2c(nnn2C)c1C]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (201 mg) in acetonitrile (10 mL) were sequentially added 2,3,4,5-tetrahydro-[1,4]oxazepino[7,6-g]quinoline produced in the Reference Example 63-(b) (106 mg) and N,N-diisopropylethylamine (0.259 mL) under argon gas flow with stirring at room temperature, and the resulting mixture was stirred at 60° C. for 3 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (221 mg) as a slightly yellow oil.

Mass spectrum (DUIS, m/z): 564 $[M+H]^+$ $^1$H-NMR spectrum (400 MHz, $CDCl_3$) δ: 8.83 (dd, J=1.6, 4.3 Hz, 1H), 8.11-8.04 (m, 1H), 7.77 (s, 1H), 7.61 (d, J=8.7 Hz, 1H), 7.41 (s, 1H), 7.36 (dd, J=4.3, 8.3 Hz, 1H), 7.29 (d, J=8.7 Hz, 1H), 7.15-6.98 (m, 3H), 4.86 (s, 1H), 4.23 (s, 3H), 4.17-4.07 (m, 2H), 4.06-3.94 (m, 2H), 3.63-3.51 (m, 21), 3.47 (s, 3H), 3.09-2.98 (m, 2H), 2.79 (s, 3H), 2.23 (s, 3H), 1.43-1.29 (m, 6H)

Example 63-(b)

Production of 3-(3-((2,3-dihydro-[1,4]oxazepino[7,6-g]quinolin-4 (5H)-yl)methyl)-4-methylphenyl)-3-(1,4-dimethyl-1H-benzo[d][1,2,3]triazol-5-yl)-2,2-dimethylpropanoic Acid

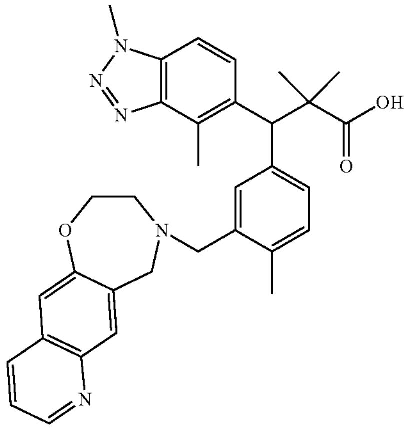 [SMILES: Cc1ccc(C(c2ccc3c(nnn3C)c2C)C(C)(C)C(=O)O)cc1CN1CCOc2cc3cccnc3cc2C1]

To a solution of methyl 3-(3-((2,3-dihydro-[1,4]oxazepino[7,6-g]quinolin-4 (5H)-yl)methyl)-4-methylphenyl)-3-(1,4-dimethyl-1H-benzo[d][1,2,3]triazol-5-yl)-2,2-dimethylpropanoate produced in the Example 63-(a) (208 mg) in dimethyl sulfoxide (8 mL) was added a 1 M aqueous solution of potassium hydroxide (0.553 mL) under argon gas flow with stirring at room temperature, and the resulting mixture was stirred at 70° C. for 4 hours. After the reaction was completed, to the reaction solution was added 1 M hydrochloric acid to neutralize the solution, and the resulting mixed solution was subjected to extraction with ethyl acetate. The resulting organic layer was dried over anhydrous magnesium sulfate, filtered, and concentrated under reduced pressure. The resulting residues were purified by a silica gel column (DIOL silica gel, elution solvent; hexane: ethyl acetate) to give the title compound (159 mg) as white solids.

Mass spectrum (ESI, m/z): 550 $[M+H]^+$ $^1$H-NMR spectrum (400 MHz, $CD_3OD$) δ: 8.77-8.71 (m, 1H), 8.29-8.23 (m, 1H), 7.78-7.67 (m, 2H), 7.52-7.44 (m, 3H), 7.27-7.21 (m, 1H), 7.16-7.09 (m, 1H), 7.08-7.02 (m, 1H), 4.98-4.79 (m, 1H), 4.25 (s, 3H), 4.15-4.08 (m, 2H), 3.97 (s, 2H), 3.69-3.56 (m, 2H), 3.10-3.02 (m, 2H), 2.72 (s, 3H), 2.24 (s, 3H), 1.42-1.25 (m, 6H)

Example 64-(a)

Production of methyl 3-(1,4-dimethyl-1H-benzo[d][1,2,3]triazol-5-yl)-3-(3-(((R)-6-ethyl-1,6,7,9-tetrahydro-8H-[1,4]oxazepino[7,6-f]indazol-8-yl)methyl)-4-methylphenyl)-2,2-dimethylpropanoate

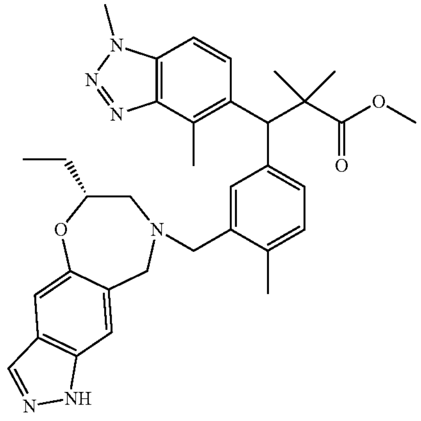 [SMILES: CC[C@@H]1CN(Cc2cc(C(c3ccc4c(nnn4C)c3C)C(C)(C)C(=O)OC)ccc2C)Cc2cc3[nH]ncc3cc2O1]

To a solution of methyl 3-(1,4-dimethyl-1H-benzo[d][1,2,3]triazol-5-yl)-3-(3-formyl-4-methylphenyl)-2,2-dimethylpropanoate produced according to the same manner as the Reference Example 1-(i) (22 mg) and (R)-6-ethyl-6,7,8,9-tetrahydro-1H-[1,4]oxazepino[7,6-f]indazole produced in the Reference Example 64-(e) (10 mg) in dichloromethane (2 mL) was added sodium triacetoxyborohydride (20 mg) under argon gas flow with stirring at room temperature, and the resulting mixture was stirred at room temperature overnight. After the reaction was completed, to the reaction solution was added a saturated aqueous solution of sodium hydrogen carbonate, and the resulting mixed solution was subjected to extraction with dichloromethane. The resulting organic layer was washed with saturated brine, dried over anhydrous sodium sulfate, filtered, and concentrated under reduced pressure. The resulting residues were purified by a silica gel column (elution solvent; hexane:ethyl acetate, then ethyl acetate:methanol) to give the title compound (29 mg) as a pale yellow oil.

Mass spectrum (ESI, m/z): 581 $[M+H]^+$ $^1$H-NMR spectrum (400 MHz, $CD_3OD$) δ: 7.99-7.00 (m, 8H), 5.06-4.73 (m, 1H), 4.32-4.19 (m, 3H), 4.13-3.97 (m, 1H), 3.81-3.24 (m, 7H), 2.89-2.66 (m, 5H), 2.31-2.16 (m, 3H), 1.80-0.75 (m, 11H)

Example 64-(b)

Production of 3-(1,4-dimethyl-1H-benzo[d][1,2,3)triazol-5-yl)-3-(3-(((R)-6-ethyl-1,6,7,9-tetrahydro-8H-(1,4]oxazepino[7,6-f]indazol-8-yl)methyl)-4-methylphenyl)-2,2-dimethylpropanoic Acid

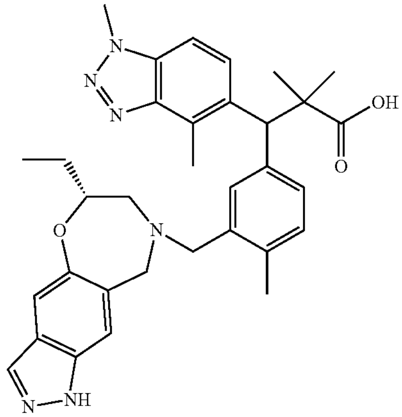 [SMILES: CC[C@@H]1CN(Cc2cc(C(c3ccc4c(nnn4C)c3C)C(C)(C)C(=O)O)ccc2C)Cc2cc3[nH]ncc3cc2O1]

To a solution of methyl 3-(1,4-dimethyl-1H-benzo[d][1,2,3]triazol-5-yl)-3-(3-(((R)-6-ethyl-1,6,7,9-tetrahydro-8H-[1,4]oxazepino[7,6-f]indazol-8-yl)methyl)-4-methylphenyl)-2,2-dimethylpropanoate produced in the Example 64-(a) (29 mg) in dimethyl sulfoxide (2 mL) was added dropwise a 1 M aqueous solution of potassium hydroxide (0.100 mL) with stirring at room temperature, and the resulting mixture was stirred at 70° C. for 3 hours. After the reaction was completed, to the reaction solution were added water and 2 M hydrochloric acid, and the resulting mixture was stirred. The precipitated solids were collected by filtration, washed with water, and dried under reduced pressure at 50° C. Also, the resulting filtrate was subjected to extraction with ethyl acetate, and concentrated under reduced pressure. The dried solids and the resulting residues were combined, and separated and purified by supercritical fluid chromatography (column: Kinetex Biphenyl, mobile phase: $CO_2$: methanol methanol ratio (%)=10 (0 min)→35 (4 min)→35 (5 min)→10 (5.5 min)→10 (7 min)). The fractions comprising the title compound were concentrated under reduced pressure, the resulting residues were dissolved into a mixed solvent of acetonitrile/water, and the resulting solution was lyophilized to give the title compound (4 mg) as white solids.

Mass spectrum (ESI, m/z): 567 $[M+H]^+$ $^1$H-NMR spectrum (400 MHz, $CD_3OD$) δ: 7.98-7.91 (m, 1H), 7.84-7.64 (m, 1H), 7.45-7.37 (m, 1H), 7.35-7.30 (m, 1H), 7.22-7.10 (m, 2H), 7.08-7.01 (m, 2H), 4.98-4.77 (m, 1H), 4.29-4.21 (m, 3H), 4.06-3.98 (m, 1H), 3.78-3.53 (m, 3H), 3.49-3.42 (m, 1H), 2.90-2.83 (m, 1H), 2.82-2.73 (m, 1H), 2.70-2.63 (m, 3H), 2.27-2.20 (m, 3H), 1.56-1.44 (m, 1H), 1.40-1.19 (m, 7H), 1.05-0.95 (m, 3H)

Example 65-(a)

Production of methyl 3-(1,4-dimethyl-1H-benzo[d][1,2,3]triazol-5-yl)-3-(3-(((R)-6-ethyl-1-methyl-1,6,7,9-tetrahydro-8H-1,4 oxazepino[7,6-f]indazol-8-yl)methyl)-4-methylphenyl)-2,2-dimethylpropanoate and Example 66-(a)

Production of methyl 3-(1,4-dimethyl-1H-benzo[d][1,2,3]triazol-5-yl)-3-(3-(((R)-6-ethyl-2-methyl-2,6,7,9-tetrahydro-8H-[1,4]oxazepino[7,6-f]indazol-8-yl)methyl)-4-methylphenyl)-2,2-dimethylpropanoate

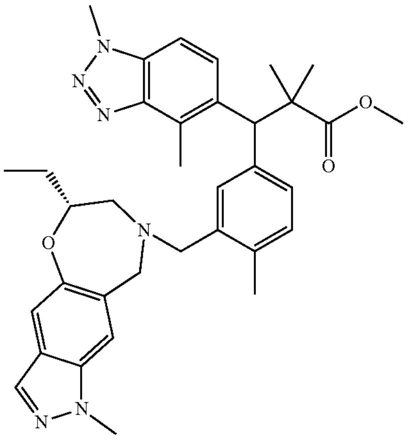

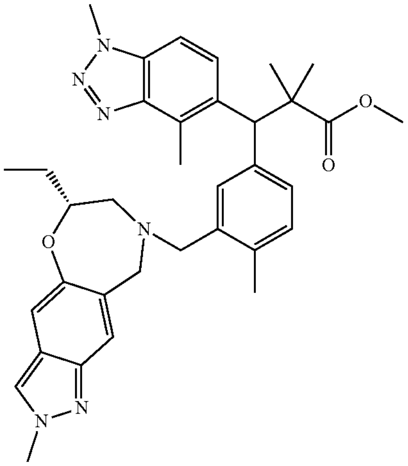

To a solution of (R)-6-ethyl-7,8-dihydro-1H-[1,4]oxazepino[7,6-f]indazol-9 (6H)-one produced according to the same manner as the Reference Example 64-(d) (261 mg) and potassium carbonate (199 mg) in dimethylformamide (7 mL) was added methyl iodide (0.092 mL) under argon gas flow with stirring at room temperature, and the resulting mixture was stirred at 80° C. for 1.5 hours. Then, methyl iodide (0.045 mL) and potassium carbonate (106 mg) were added thereto with stirring at 80° C., and the resulting mixture was stirred at 80° C. for 1 hour. Additionally, methyl iodide (0.045 mL) was added thereto with stirring at 80° C., and the resulting mixture was stirred at 80° C. for 1 hour. Additionally, methyl iodide (0.045 mL) was added thereto with stirring at 80° C., and the resulting mixture was stirred at 80° C. for 3.5 hours. Then, the resulting mixture was allowed to cool to room temperature, and left to stand overnight. Then, methyl iodide (0.045 mL) was added thereto with stirring at 80° C., and the resulting mixture was stirred at 80° C. for 1.5 hours. Additionally, methyl iodide (0.045 mL) was added thereto with stirring at 80° C., and the resulting mixture was stirred at 80° C. for 1 hour. After the reaction was completed, the resulting mixture was allowed to cool to room temperature, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: ethyl acetate methanol) to give a mixture (224 mg) of (R)-7-ethyl-2-methyl-8,9-dihydro-2H-[1,4]oxazepino[7,6-g]indazol-10(7H)-one and (R)-7-ethyl-1-methyl-8,9-dihydro-1H-[1,4]oxazepino[7,6-g]indazol-10(7H)-one as a yellow oil.

To a solution of the mixture (224 mg) of (R)-7-ethyl-2-methyl-8,9-dihydro-2H-[1,4]oxazepino[7,6-g]indazol-10 (7H)-one and (R)-7-ethyl-1-methyl-8,9-dihydro-1H-[1,4]oxazepino[7,6-g]indazol-10(7H)-one in tetrahydrofuran (5 mL) was added a 2.5 M solution of lithium aluminum hydride in tetrahydrofuran (0.8 mL) under argon gas flow with stirring at room temperature, and the resulting mixture was stirred at 50° C. for 3.5 hours. Then, a 2.5 M solution of lithium aluminum hydride in tetrahydrofuran (0.5 mL) was added thereto with stirring at 50° C., and the resulting mixture was stirred at 50° C. for 1.5 hours. After the reaction was completed, to the reaction solution was added a saturated aqueous solution of potassium sodium tartrate, and the resulting mixture was stirred for 1 hour. Then, the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (eluent: ethyl acetate:methanol) to give a mixture (71 mg) of (R)-6-ethyl-1-methyl-6,7,8,9-tetrahydro-1H-[1,4]oxazepino[7,6-f]indazole and (R)-6-ethyl-2-methyl-6,7,8,9-tetrahydro-2H-[1,4]oxazepino[7,6-f]indazole as a colorless oil.

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (160 mg) in acetonitrile (3 mL) were sequentially added a mixture (71 mg) of (R)-6-ethyl-1-methyl-6,7,8,9-tetrahydro-1H-[1,4]oxazepino[7,6-f]indazole and (R)-6-ethyl-2-methyl-6,7,8,9-tetrahydro-2H-[1,4]oxazepino[7,6-f]indazole, and N,N-diisopropylethylamine (0.159 mL) under argon gas flow with stirring at room temperature, and the resulting mixture was stirred at 60° C. for 3 hours. After the reaction was completed, the reaction solution was concentrated under reduced pressure. The resulting residues were purified by a silica gel column (eluent: hexane:ethyl acetate) to give Example 65-(a) (55 mg) as white solids, and also Example 66-(a) (40 mg) as a yellow oil.

Example 65-(a)

Mass spectrum (ESI, m/z): 595 $[M+H]^+$ $^1$H NMR (400 MHz, $CDCl_3$) δ=7.88 (s, 1H), 7.66-7.57 (m, 1H), 7.36-7.31 (m, 1H), 7.25-7.17 (m, 1H), 7.12-7.01 (m, 4H), 4.86-4.81 (m, 1H), 4.24-4.14 (m, 4H), 4.06-3.99 (m, 3H), 3.78-3.63 (m, 2H), 3.61-3.53 (m, 1H), 3.48-3.39

(m, 4H), 2.90-2.81 (m, 2H), 2.77 (s, 3H), 2.26-2.21 (m, 3H), 1.66-1.18 (m, 8H), 1.09-0.97 (m, 3H)

Example 66-(a)

Mass spectrum (ESI, m/z): 595 $[M+H]^+$ $^1H$ NMR (400 MHz, $CDCl_3$) δ=7.81-7.76 (m, 1H), 7.67-7.56 (m, 1H), 7.35-7.30 (m, 1H), 7.29-7.24 (m, 1H), 7.23-7.20 (m, 1H), 7.10-6.98 (m, 3H), 4.87-4.81 (m, 1H), 4.26-4.16 (m, 6H), 4.16-4.08 (m, 1H), 3.81-3.51 (m, 3H), 3.50-3.36 (m, 4H), 2.92-2.73 (m, 5H), 2.26-2.20 (m, 3H), 1.67-1.17 (m, 8H), 1.08-0.96 (m, 3H)

Example 65-(b)

Production of 3-(1,4-dimethyl-1H-benzo[d][1,2,3]triazol-5-yl)-3-(3-(((R)-6-ethyl-1-methyl-1,6,7,9-tetrahydro-8H-[1,4]oxazepino[7,6-f]indazol-8-yl)methyl)-4-methylphenyl)-2,2-dimethylpropanoic Acid

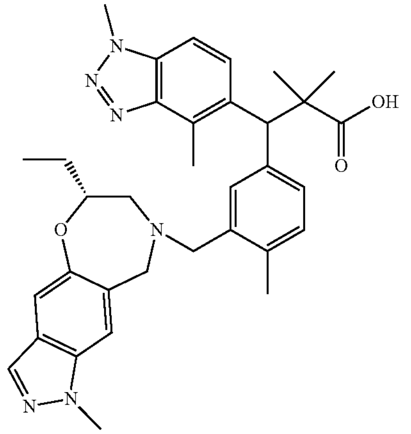 [SMILES: CC[C@@H]1CN(Cc2cc(C(c3ccc4c(nnn4C)c3C)C(C)(C)C(=O)O)ccc2C)Cc2cc3c(cnn3C)cc2O1]

To a solution of methyl 3-(1,4-dimethyl-1H-benzo[d][1,2,3]triazol-5-yl)-3-(3-(((R)-6-ethyl-1-methyl-1,6,7,9-tetrahydro-8H-[1,4]oxazepino[7,6-f]indazol-8-yl)methyl)-4-methylphenyl)-2,2-dimethylpropanoate produced in the Example 65-(a) (48 mg) in dimethyl sulfoxide (1 mL) was added a 1 M aqueous solution of potassium hydroxide (0.121 mL) under argon gas flow with stirring at room temperature, and the resulting mixture was stirred at 70° C. for 2 hours. Then, a 1 M aqueous solution of potassium hydroxide (0.040 mL) was added thereto with stirring at 70° C., and the resulting mixture was stirred at 70° C. for 0.5 hour. After the reaction was completed, to the reaction solution was added water, 1 M hydrochloric acid was added thereto to adjust the pH to 4.7, and further saturated brine was added thereto. The resulting mixed solution was subjected to extraction with ethyl acetate. The resulting organic layer was dried over anhydrous sodium sulfate, filtered, and concentrated under reduced pressure. The resulting residues were purified by a silica gel column (eluent: ethyl acetate: methanol) to give the title compound (21 mg) as a slightly yellow foam.

Mass spectrum (ESI, m/z): 581 $[M+H]^+$ $^1H$ NMR (400 MHz, $CD_3OD$) δ=7.91-7.86 (m, 1H), 7.81-7.66 (m, 1H), 7.48-7.39 (m, 1H), 7.34-7.28 (m, 1H), 7.26-7.04 (m, 4H), 4.96-4.82 (m, 1H), 4.28-4.22 (m, 3H), 4.11-4.04 (m, 1H), 4.02-3.97 (m, 3H), 3.86-3.78 (m, 1H), 3.75-3.58 (m, 2H), 3.53-3.44 (m, 1H), 2.89-2.72 (m, 2H), 2.71-2.66 (m, 3H), 2.29-2.21 (m, 3H), 1.56-1.43 (m, 1H), 1.41-1.36 (m, 3H), 1.31-1.10 (m, 4H), 1.05-0.94 (m, 3H)

Example 66-(b)

Production of 3-(1,4-dimethyl-1H-benzo[d][1,2,3]triazol-5-yl)-3-(3-(((R)-6-ethyl-2-methyl-2,6,7,9-tetrahydro-8H-[1,4]oxazepino[7,6-f]indazol-8-yl)methyl)-4-methylphenyl)-2,2-dimethylpropanoic Acid

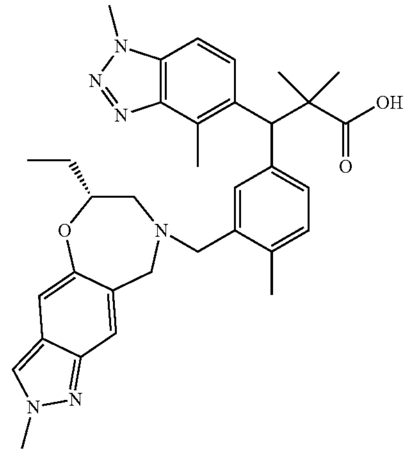 [SMILES: CC[C@@H]1CN(Cc2cc(C(c3ccc4c(nnn4C)c3C)C(C)(C)C(=O)O)ccc2C)Cc2cc3nn(C)cc3cc2O1]

To a solution of methyl 3-(1,4-dimethyl-1H-benzo[d][1,2,3]triazol-5-yl)-3-(3-(((R)-6-ethyl-2-methyl-2,6,7,9-tetrahydro-8H-[1,4]oxazepino[7,6-f]indazol-8-yl)methyl)-4-methylphenyl)-2,2-dimethylpropanoate produced in the Example 66-(a) (36 mg) in dimethyl sulfoxide (1 mL) was added a 1 M aqueous solution of potassium hydroxide (0.089 mL) under argon gas flow with stirring at room temperature, and the resulting mixture was stirred at 70° C. for 1 hour. Then, a 1 M aqueous solution of potassium hydroxide (0.089 mL) was added thereto with stirring at 70° C., and the resulting mixture was stirred at 70° C. for 5.5 hours. After the reaction was completed, to the reaction solution was added 1 M hydrochloric acid to adjust the pH to 5.4, and further saturated brine was added thereto. The resulting mixed solution was subjected to extraction with ethyl acetate. The resulting organic layer was dried over anhydrous sodium sulfate, filtered, and concentrated under reduced pressure. The resulting residues were purified by a silica gel column (eluent: ethyl acetate:methanol) to give the title compound (29 mg) as a slightly yellow foam.

Mass spectrum (ESI, m/z): 581 $[M+H]^+$ $^1H$ NMR (400 MHz, $CD_3OD$) δ=8.05 (s, 1H), 7.82-7.68 (m, 1H), 7.53-7.44 (m, 1H), 7.27-7.03 (m, 5H), 4.96-4.89 (m, 1H), 4.26 (s, 3H), 4.17 (s, 31), 4.08-3.96 (m, 1H), 3.80-3.57 (m, 3H), 3.53-3.45 (m, 1H), 2.89-2.67 (m, 5H), 2.27-2.20 (m, 3H), 1.57-1.42 (m, 1H), 1.41-1.35 (m, 3H), 1.31-1.12 (m, 4H), 1.04-0.94 (m, 3H)

Example 67-(a)

Production of methyl 3-(3-(((R)-7-chloro-2-ethyl-2,3-dihydronaphtho[2,1-f][1,4]oxazepin-4(5H)-yl)methyl)-4-methylphenyl)-3-(1,4-dimethyl-1H-benzo[d][1,2,3]triazol-5-yl)-2,2-dimethylpropanoate

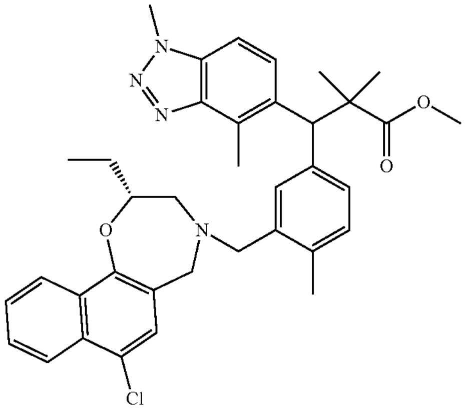 [SMILES: CC[C@@H]1CN(Cc2cc(C(c3ccc4c(nnn4C)c3C)C(C)(C)C(=O)OC)ccc2C)Cc2cc(Cl)c3ccccc3c2O1]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (37 mg) in acetonitrile (3 mL) were sequentially added (R)-7-chloro-2-ethyl-2,3,4,5-tetrahydronaphtho[2,1-f][1,4]oxazepine hydrochloride produced in the Reference Example 67-(d) (33 mg) and N,N-diisopropylethylamine (0.063 mL) under argon gas flow with stirring at room temperature, and the resulting mixture was stirred at 60° C. for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (42 mg) as a white foam.

Mass spectrum (ESI, m/z): 625 $[M+H]^+$ $^1$H NMR (400 MHz, $CDCl_3$) δ=8.39-8.32 (m, 1H), 8.24-8.17 (m, 1H), 7.67-7.53 (m, 3H), 7.24-7.18 (m, 2H), 7.12-7.02 (m, 3H), 4.88-4.81 (m, 1H), 4.24-4.18 (m, 3H), 4.10-3.85 (m, 2H), 3.79-3.67 (m, 1H), 3.62-3.43 (m, 5H), 3.03-2.93 (m, 2H), 2.80-2.76 (m, 3H), 2.29-2.23 (m, 3H), 1.89-1.75 (m, 1H), 1.66-1.47 (m, 1H), 1.43-1.37 (m, 3H), 1.36-1.22 (m, 3H), 1.14-1.03 (m, 3H)

Example 67-(b)

Production of 3-(3-(((R)-7-chloro-2-ethyl-2,3-dihydronaphtho[2,1-f][1,4]oxazepin-4 (5H)-yl)methyl)-4-methylphenyl)-3-(1,4-dimethyl-1H-benzo[d][1,2,3]triazol-5-yl)-2,2-dimethylpropanoic Acid

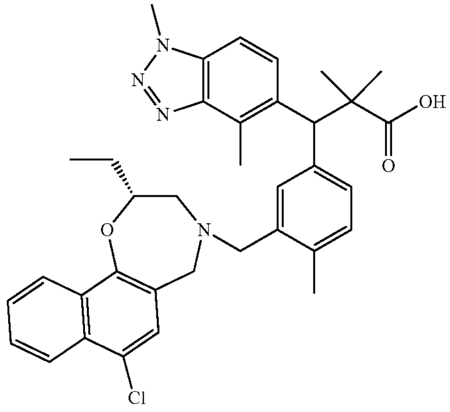 [SMILES: CC[C@@H]1CN(Cc2cc(C(c3ccc4c(nnn4C)c3C)C(C)(C)C(=O)O)ccc2C)Cc2cc(Cl)c3ccccc3c2O1]

To a solution of methyl 3-(3-(((R)-7-chloro-2-ethyl-2,3-dihydronaphtho[2,1-f][1,4]oxazepin-4 (5H)-yl)methyl)-4-methylphenyl)-3-(1,4-dimethyl-1H-benzo[d][1,2,3]triazol-5-yl)-2,2-dimethylpropanoate produced in the Example 67-(a) (42 mg) in dimethyl sulfoxide (4 mL) was added dropwise a 2 M aqueous solution of potassium hydroxide (0.336 mL) under argon gas flow with stirring at room temperature, and the resulting mixture was stirred at 70° C. for 3 hours. After the reaction was completed, to the reaction solution was added water (5 mL), 1 M hydrochloric acid was added thereto to adjust the pH to 5.5, and the resulting mixture was stirred for 1 hour. The resulting solids were collected by filtration, washed with water, and dried under reduced pressure at 60° C. to give the title compound (40 mg) as white solids.

Mass spectrum (ESI, m/z): 611 $[M+H]^+$ $^1$H NMR (400 MHz, $CD_3OD$) δ=8.39-8.29 (m, 1H), 8.22-8.12 (m, 1H), 7.81-7.55 (m, 3H), 7.44-7.31 (m, 1H), 7.26-7.15 (m, 2H), 7.13-7.04 (m, 2H), 4.95-4.78 (m, 1H), 4.25-4.18 (m, 3H), 4.03-3.74 (m, 3H), 3.66-3.52 (m, 2H), 3.05-2.83 (m, 2H), 2.73-2.67 (m, 3H), 2.29-2.23 (m, 3H), 1.82-1.66 (m, 1H), 1.58-1.44 (m, 1H), 1.42-1.36 (m, 3H), 1.31-1.26 (m, 3H), 1.08-1.00 (m, 3H)

Example 68-(a)

Production of methyl 3-(3-(((R)-7-chloro-2-ethyl-2,3-dihydronaphtho[2,3-f][1,4]oxazepin-4 (5H)-yl) methyl)-4-methylphenyl)-3-(1,4-dimethyl-1H-benzo [d][1,2,3]triazol-5-yl)-2,2-dimethylpropanoate

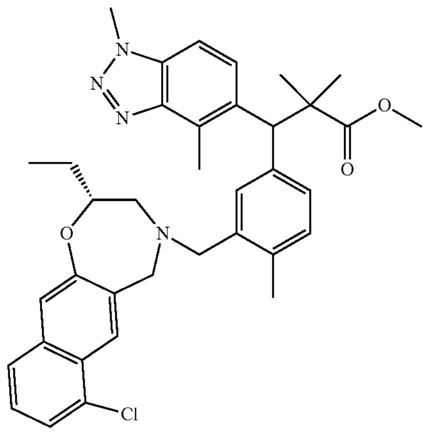 [SMILES: CC[C@@H]1CN(Cc2cc(C(c3ccc4c(nnn4C)c3C)C(C)(C)C(=O)OC)ccc2C)Cc2cc3c(Cl)cccc3cc2O1]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (31 mg) in acetonitrile (3 mL) were sequentially added (R)-7-chloro-2-ethyl-2,3,4,5-tetrahydronaphtho[2,3-f][1,4]oxazepine produced in the Reference Example 68-(g) (25 mg) and N,N-diisopropylethylamine (0.053 mL) under argon gas flow with stirring at room temperature, and the resulting mixture was stirred at 60° C. for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (47 mg) as a white foam.

Mass spectrum (ESI, m/z): 625 $[M+H]^+$ $^1$H NMR (400 MHz, $CDCl_3$) δ=7.99-7.90 (m, 1H), 7.70-7.54 (m, 2H), 7.50-7.43 (m, 2H), 7.38-7.31 (m, 1H), 7.25-7.17 (m, 1H), 7.11-7.00 (m, 3H), 4.88-4.80 (m, 1H), 4.23-4.19 (m, 3H), 4.18-4.09 (m, 1H), 3.96-3.72 (m, 2H), 3.64-3.55 (m, 1H), 3.51-3.41 (m, 4H), 2.96-2.83 (m, 2H), 2.79-2.73 (m, 3H), 2.27-2.24 (m, 3H), 1.69-1.48 (m, 1H), 1.43-1.20 (m, 7H), 1.10-0.98 (m, 3H)

Example 68-(b)

Production of 3-(3-(((R)-7-chloro-2-ethyl-2,3-dihydronaphtho[2,3-f][1,4]oxazepin-4 (5H)-yl)methyl)-4-methylphenyl)-3-(1,4-dimethyl-1H-benzo[d][1,2,3]triazol-5-yl)-2,2-dimethylpropanoic Acid

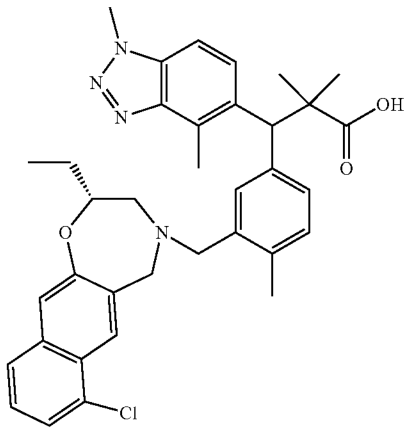 [SMILES: CC[C@@H]1CN(Cc2cc(C(c3ccc4c(nnn4C)c3C)C(C)(C)C(=O)O)ccc2C)Cc2cc3c(Cl)cccc3cc2O1]

To a solution of methyl 3-(3-(((R)-7-chloro-2-ethyl-2,3-dihydronaphtho[2,3-f][1,4]oxazepin-4 (5H)-yl)methyl)-4-methylphenyl)-3-(1,4-dimethyl-1H-benzo[d][1,2,3]triazol-5-yl)-2,2-dimethylpropanoate produced in the Example 68-(a) (47 mg) in dimethyl sulfoxide (4 mL) was added dropwise a 2 M aqueous solution of potassium hydroxide (0.376 mL) under argon gas flow with stirring at room temperature, and the resulting mixture was stirred at 70° C. for 3 hours. After the reaction was completed, to the reaction solution was added water (5 mL), 1 M hydrochloric acid was added thereto to adjust the pH to 5.5, and the resulting mixture was stirred for 1 hour. The resulting solids were collected by filtration, washed with water, and dried under reduced pressure at 60° C. to give the title compound (41 mg) as white solids.

Mass spectrum (ESI, m/z): 611 $[M+H]^+$ $^1$H NMR (400 MHz, DMSO-$d_6$+$D_2O$) δ=7.94-7.83 (m, 2H), 7.75-7.42 (m, 5H), 7.20-7.02 (m, 3H), 4.82-4.73 (m, 1H), 4.26-4.17 (m, 3H), 4.09-4.00 (m, 1H), 3.96-3.74 (m, 2H), 3.68-3.51 (m, 1H), 3.51-3.40 (m, 1H), 2.87-2.75 (m, 2H), 2.67-2.58 (m, 3H), 2.25-2.17 (m, 3H), 1.58-1.41 (m, 1H), 1.35-1.14 (m, 7H), 1.02-0.89 (m, 3H)

Example 69

Production of 3-(3-(((R)-10-chloro-2-ethyl-2,3-dihydro-[1,4]oxazepino[7,6-g]quinolin-4 (5H)-yl) methyl)-4-methylphenyl)-3-(1,4-dimethyl-1H-benzo [d][1, 2, 3]triazol-5-yl)-2,2-dimethylpropanoic Acid

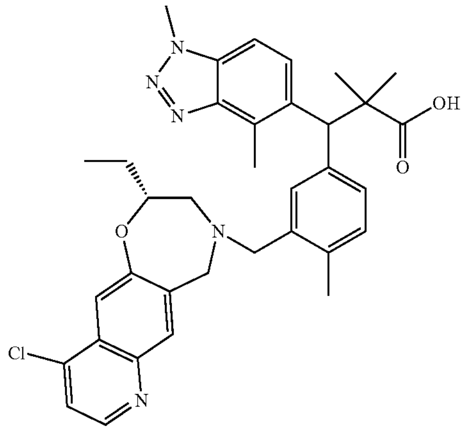 [SMILES: CC[C@@H]1CN(Cc2cc(C(c3ccc4c(nnn4C)c3C)C(C)(C)C(=O)O)ccc2C)Cc2cc3nccc(Cl)c3cc2O1]

To a solution of 3-(1,4-dimethyl-1H-benzo[d][1,2,3]triazol-5-yl)-3-(3-formyl-4-methylphenyl)-2,2-dimethylpropanoic acid produced according to the same manner as the Reference Example 23-(g) (50 mg) in dichloromethane (2 mL) was added (R)-10-chloro-2-ethyl-2,3,4,5-tetrahydro-[1,4]oxazepino[7,6-g]quinoline produced in the Reference Example 69-(c) (40 mg) under argon gas flow with stirring at room temperature, and the resulting mixture was stirred at room temperature for 1 hour. Then, sodium triacetoxyborohydride (59 mg) was added thereto, and the resulting mixture was stirred at room temperature for 18 hours. Then, sodium triacetoxyborohydride (58 mg) was added thereto, and the resulting mixture was stirred at room temperature for 2.5 hours. After the reaction was completed, to the reaction solution was added a saturated aqueous solution of sodium hydrogen carbonate, and the resulting mixed solution was subjected to extraction with ethyl acetate. The resulting organic layer was washed with a saturated aqueous solution of sodium hydrogen carbonate, dried over anhydrous sodium sulfate, filtered, and concentrated under reduced pressure. The resulting residues were purified by a silica gel column (eluent: hexane:ethyl acetate), and the fractions comprising the title compound were concentrated under reduced pressure. The resulting residues were dissolved into a mixed solvent of acetonitrile/water, and the resulting solution was lyophilized to give the title compound (45 mg) as white solids.

Mass spectrum (ESI, m/z): 612 $[M+H]^+$ $^1H$ NMR (400 MHz, $CD_3OD$) δ=8.69-8.63 (m, 1H), 7.81-7.69 (m, 3H), 7.63 (d, J=4.9 Hz, 1H), 7.50-7.42 (m, 1H), 7.22-7.03 (m, 3H), 4.98-4.73 (m, 1H), 4.31-4.23 (m, 3H), 4.13-3.99 (m, 1H), 3.98-3.75 (m, 2H), 3.70-3.50 (m, 2H), 2.99-2.83 (m, 2H), 2.75-2.65 (m, 3H), 2.30-2.21 (m, 3H), 1.74-1.20 (m, 8H), 1.07-0.96 (m, 3H)

Example 70-(a)

Production of methyl 3-(1,4-dimethyl-1H-benzo[d][1,2,3]triazol-5-yl)-3-(3-(((R)-2-ethyl-10-methoxy-2,3-dihydro-[1,4]oxazepino[7,6-g]quinolin-4 (5H)-yl) methyl)-4-methylphenyl)-2,2-dimethylpropanoate

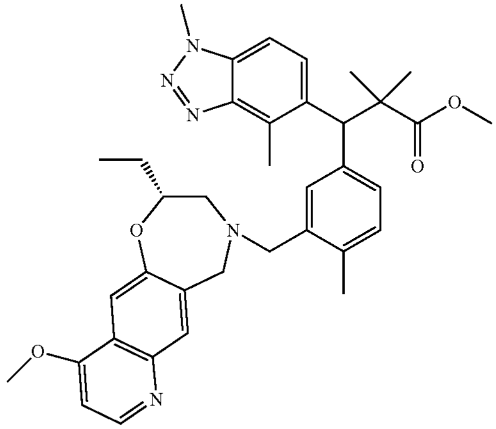

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (54 mg) in acetonitrile (2.5 mL) were sequentially added (R)-2-ethyl-10-methoxy-2,3,4,5-tetrahydro-[1,4]oxazepino[7,6-g]quinoline dihydrochloride produced in the Reference Example 70-(c) (49 mg) and N,N-diisopropylethylamine (0.095 mL) under argon gas flow with stirring at room temperature, and the resulting mixture was stirred at 60° C. for 3 hours and at room temperature for 14 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (eluent: hexane:ethyl acetate) to give the title compound (65 mg) as a slightly yellow oil.

Mass spectrum (ESI, m/z): 622 $[M+H]^+$ $^1H$ NMR (400 MHz, $CDCl_3$) δ=8.70-8.64 (m, 1H), 7.78-7.67 (m, 2H), 7.66-7.54 (m, 1H), 7.33-7.22 (m, 1H), 7.10-6.99 (m, 3H), 6.75-6.68 (m, 1H), 4.87-4.80 (m, 1H), 4.26-4.21 (m, 3H), 4.20-4.09 (m, 1H), 4.08-4.02 (m, 3H), 3.93-3.71 (m, 2H), 3.64-3.53 (m, 1H), 3.50-3.39 (m, 4H), 2.93-2.73 (m, 5H), 2.26-2.19 (m, 3H), 1.42-1.22 (m, 8H), 1.09-0.97 (m, 3H)

Example 70-(b)

Production of 3-(1,4-dimethyl-1H-benzo[d][1,2,3]triazol-5-yl)-3-(3-(((R)-2-ethyl-10-methoxy-2,3-dihydro-[1,4]oxazepino[7,6-g]quinolin-4(5H)-yl)methyl)-4-methylphenyl)-2,2-dimethylpropanoic Acid

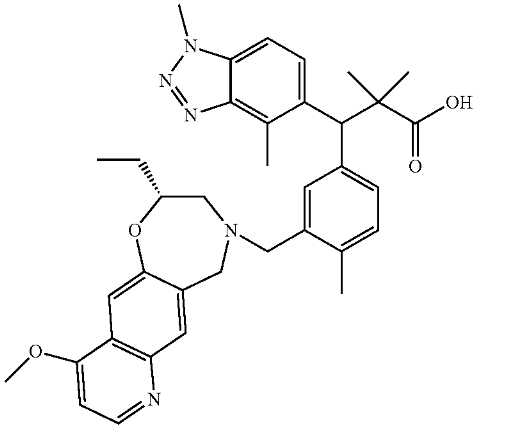 [SMILES: CC[C@@H]1CN(Cc2cc(C(c3ccc4c(nnn4C)c3C)C(C)(C)C(=O)O)ccc2C)Cc2cc3nccc(OC)c3cc2O1]

To a solution of methyl 3-(1,4-dimethyl-1H-benzo[d][1,2,3]triazol-5-yl)-3-(3-(((R)-2-ethyl-10-methoxy-2,3-dihydro-[1,4]oxazepino[7,6-g]quinolin-4 (5H)-yl)methyl)-4-methylphenyl)-2,2-dimethylpropanoate produced in the Example 70-(a) (64 mg) in dimethyl sulfoxide (2.6 mL) was added dropwise a 1 M aqueous solution of potassium hydroxide (0.154 mL) under argon gas flow with stirring at room temperature, and the resulting mixture was stirred at 70° C. for 3 hours. After the reaction was completed, to the reaction solution was added water (5 mL), 1 M hydrochloric acid was added thereto to adjust the pH to 5.0, the resulting solids were collected by filtration, washed with water, and dried under reduced pressure at 60° C. to give the title compound (40 mg) as white solids.

Mass spectrum (ESI, m/z): 608 [M+H]-$^1$H NMR (400 MHz, $CD_3OD$) δ=8.62-8.57 (m, 1H), 7.78-7.67 (m, 2H), 7.64 (s, 1H), 7.49-7.41 (m, 1H), 7.11 (s, 2H), 7.08-7.02 (m, 1H), 7.00-6.95 (m, 1H), 5.01-4.72 (m, 1H), 4.29-4.22 (m, 3H), 4.15-3.99 (m, 4H), 3.93-3.68 (m, 2H), 3.66-3.59 (m, 1H), 3.56-3.49 (M, 1H), 2.96-2.80 (m, 2H), 2.73-2.67 (m, 3H), 2.27-2.21 (m, 3H), 1.64-1.46 (m, 1H), 1.45-1.16 (m, 7H), 1.06-0.94 (m, 3H)

Example 71-(a)

Production of methyl 3-(1,4-dimethyl-1H-benzo[d][1,2,3]triazol-5-yl)-3-(3-(((R)-2-ethyl-10-methyl-2,3-dihydro-[1,4]oxazepino[7,6-g]quinolin-4 (5H)-yl)methyl)-4-methylphenyl)-2,2-dimethylpropanoate

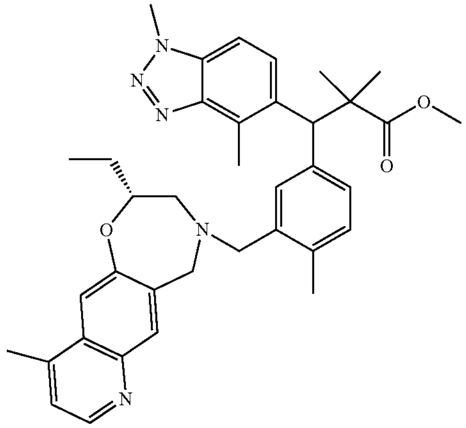

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (52 mg) in acetonitrile (3 mL) were sequentially added (R)-2-ethyl-10-methyl-2, 3, 4, 5-tetrahydro-[1,4]oxazepino[7,6-g]quinoline dihydrochloride produced in the Reference Example 71-(c) (46 mg) and N,N-diisopropylethylamine (0.092 mL) under argon gas flow with stirring at room temperature, and the resulting mixture was stirred at 70° C. for 4 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (eluent: hexane:ethyl acetate) to give the title compound (50 mg) as a slightly yellow oil.

Mass spectrum (ESI, m/z): 606 $[M+H]^+$ $^1$H NMR (400 MHz, $CDCl_3$) δ=8.71-8.65 (m, 1H), 7.79-7.72 (m, 1H), 7.66-7.50 (m, 2H), 7.34-7.16 (m, 2H), 7.11-6.99 (m, 3H), 4.87-4.81 (m, 1H), 4.26-4.20 (m, 3H), 4.20-4.08 (m, 1H), 3.95-3.77 (m, 2H), 3.66-3.56 (m, 1H), 3.51-3.39 (m, 4H), 2.96-2.82 (m, 2H), 2.80-2.74 (m, 3H), 2.67 (s, 3H), 2.23 (s, 3H), 1.72-1.46 (m, 1H), 1.46-1.29 (m, 7H), 1.09-0.98 (m, 3H)

Example 71-(b)

Production of 3-(1,4-dimethyl-1H-benzo[d][1,2,3]triazol-5-yl)-3-(3-(((R)-2-ethyl-10-methyl-2,3-dihydro-[1,4]oxazepino[7,6-g]quinolin-4 (5H)-yl)methyl)-4-methylphenyl)-2,2-dimethylpropanoic Acid

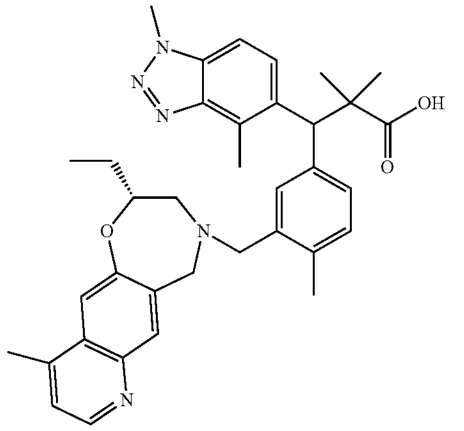 [SMILES: CC[C@@H]1CN(Cc2cc(C(c3ccc4c(nnn4C)c3C)C(C)(C)C(=O)O)ccc2C)Cc2cc3nccc(C)c3cc2O1]

To a solution of methyl 3-(1,4-dimethyl-1H-benzo[d][1,2,3]triazol-5-yl)-3-(3-(((R)-2-ethyl-10-methyl-2,3-dihydro-[1,4]oxazepino[7,6-g]quinolin-4 (5H)-yl)methyl)-4-methylphenyl)-2,2-dimethylpropanoate produced in the Example 71-(a) (48 mg) in dimethyl sulfoxide (2 mL) was added dropwise a 1 M aqueous solution of potassium hydroxide (0.119 mL) under argon gas flow with stirring at room temperature, and the resulting mixture was stirred at 70° C. for 4 hours. After the reaction was completed, to the reaction solution was added 1 M hydrochloric acid to adjust the pH to 5.0, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate), and the fractions comprising the title compound were concentrated under reduced pressure. The resulting residues were dissolved into a mixed solvent of acetonitrile/water, and the resulting solution was lyophilized to give the title compound (19 mg) as white solids.

Mass spectrum (ESI, m/z): 592 $[M+H]^+$ $^1$H NMR (400 MHz, $CD_3OD$) δ=8.62-8.56 (m, 1H), 7.80-7.66 (m, 2H), 7.62-7.57 (m, 1H), 7.50-7.42 (m, 1H), 7.37-7.31 (m, 1H), 7.21-7.02 (m, 3H), 5.00-4.76 (m, 1H), 4.26-4.23 (m, 3H), 4.12-4.01 (m, 1H), 3.96-3.76 (m, 2H), 3.69-3.49 (m, 2H), 2.96-2.78 (m, 2H), 2.76-2.65 (m, 6H), 2.28-2.21 (m, 3H), 1.66-1.22 (m, 8H), 1.07-0.95 (m, 3H)

Example 72-(a)

Production of methyl 3-(1,4-dimethyl-1H-benzo[d][1,2,3]triazol-5-yl)-3-(3-(((R)-2-ethyl-2,3-dihydrothieno[2',3':4,5]benzo[1,2-f][1,4]oxazepin-4(5H)-yl)methyl)-4-methylphenyl)-2,2-dimethylpropanoate

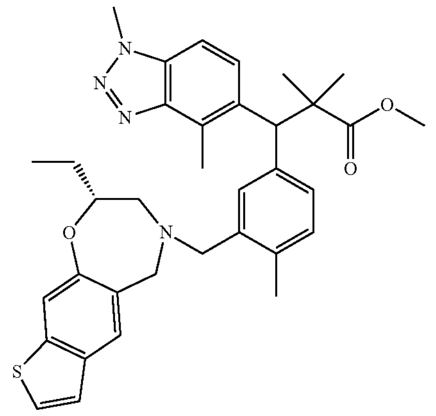 [SMILES: CC[C@@H]1CN(Cc2cc(C(c3ccc4c(nnn4C)c3C)C(C)(C)C(=O)OC)ccc2C)Cc2cc3ccsc3cc2O1]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (50 mg) in acetonitrile (3 mL) were sequentially added (R)-2-ethyl-2,3,4,5-tetrahydrothieno[2',3':4,5]benzo[1,2-f][1,4]oxazepine produced in the Reference Example 72-(b) (35 mg) and N,N-diisopropylethylamine (0.085 mL) under argon gas flow with stirring at room temperature, and the resulting mixture was stirred at 60° C. for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (72 mg) as a white foam.

Mass spectrum (DUIS, m/z): 597 $[M+H]^+$ $^1$H NMR (400 MHz, $CDCl_3$) δ=7.65-7.56 (m, 1H), 7.55-7.51 (m, 1H), 7.41-7.31 (m, 2H), 7.24-7.17 (m, 2H), 7.10-7.00 (m, 3H), 4.86-4.82 (m, 1H), 4.25-4.19 (m, 3H), 4.14-4.05 (m, 1H), 3.85-3.62 (m, 2H), 3.59-3.49 (m, 1H), 3.48-3.40 (m, 4H), 2.96-2.83 (m, 2H), 2.83-2.74 (m, 3H), 2.29-2.21 (m, 3H), 1.67-1.48 (m, 1H), 1.43-1.22 (m, 7H), 1.08-0.99 (m, 3H)

Example 72-(b)

Production of 3-(1,4-dimethyl-1H-benzo[d][1,2,3]triazol-5-yl)-3-(3-(((R)-2-ethyl-2,3-dihydrothieno[2',3':4,5]benzo[1,2-f][1,4]oxazepin-4(5H)-yl)methyl)-4-methylphenyl)-2,2-dimethylpropanoic Acid

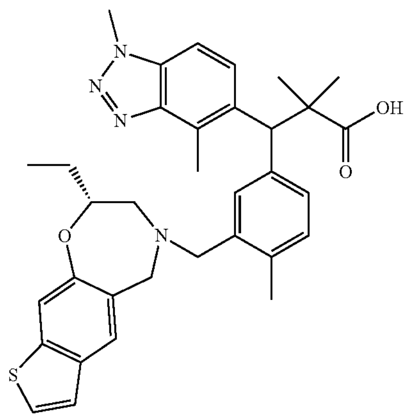 [SMILES: CC[C@@H]1CN(Cc2cc(C(c3ccc4c(nnn4C)c3C)C(C)(C)C(=O)O)ccc2C)Cc2cc3ccsc3cc2O1]

To a solution of methyl 3-(1,4-dimethyl-1H-benzo[d][1,2,3]triazol-5-yl)-3-(3-(((R)-2-ethyl-2,3-dihydrothieno[2',3':4,5]benzo[1,2-f][1,4]oxazepin-4(5H)-yl)methyl)-4-methylphenyl)-2,2-dimethylpropanoate produced in the Example 72-(a) (72 mg) in dimethyl sulfoxide (4 mL) was added dropwise a 2 M aqueous solution of potassium hydroxide (0.603 mL) under argon gas flow with stirring at room temperature, and the resulting mixture was stirred at 70° C. for 3 hours. After the reaction was completed, to the reaction solution was added water (5 mL), 1 M hydrochloric acid was added thereto to adjust the pH to 5.5, and the resulting mixture was stirred for 1 hour. The resulting solids were collected by filtration, washed with water, and dried under reduced pressure at 60° C. to give the title compound (67 mg) as white solids.

Mass spectrum (ESI, m/z): 583 $[M+H]^+$ $^1$H NMR (400 MHz, $CD_3OD$) δ=7.79-7.65 (m, 1H), 7.51-7.31 (m, 4H), 7.24-7.16 (m, 2H), 7.11-7.03 (m, 2H), 4.95-4.84 (m, 1H), 4.27-4.21 (m, 3H), 4.03-3.95 (m, 1H), 3.81-3.65 (m, 2H), 3.64-3.46 (m, 2H), 2.94-2.76 (m, 2H), 2.73-2.67 (m, 3H), 2.29-2.22 (m, 3H), 1.58-1.45 (m, 1H), 1.42-1.17 (m, 7H), 1.05-0.96 (n, 3H)

Example 73-(a)

Production of methyl 3-(1,4-dimethyl-1H-benzo[d][1,2,3]triazol-5-yl)-3-(3-(((R)-2-ethyl-2,3,7,8-tetrahydrothieno[2',3':4,5]benzo[1,2-f][1,4]oxazepin-4(5H)-yl)methyl)-4-methylphenyl)-2,2-dimethylpropanoate

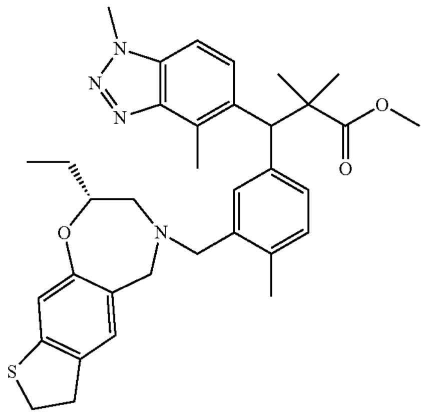 [SMILES: CC[C@@H]1CN(Cc2cc(C(c3ccc4c(nnn4C)c3C)C(C)(C)C(=O)OC)ccc2C)Cc2cc3c(cc2O1)SCC3]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (45 mg) in acetonitrile (3 mL) were sequentially added (R)-2-ethyl-2,3,4,5,7,8-hexahydrothieno[2',3':4,5]benzo[1,2-f][1,4]oxazepine produced in the Reference Example 73-(b) (32 mg) and N,N-diisopropylethylamine (0.077 mL) under argon gas flow with stirring at room temperature, and the resulting mixture was stirred at 60° C. for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (63 mg) as a white foam.

Mass spectrum (DUIS, m/z): 599 $[M+H]^+$ $^1$H NMR (400 MHz, $CDCl_3$) δ=7.65-7.56 (m, 1H), 7.28-7.22 (m, 1H), 7.08-6.99 (m, 3H), 6.91-6.86 (m, 1H), 6.80-6.65 (m, 1H), 4.86-4.80 (m, 1H), 4.26-4.20 (m, 3H), 3.93-3.82 (m, 1H), 3.77-3.61 (m, 1H), 3.55-3.33 (m, 8H), 3.21-3.09 (m, 2H), 2.84-2.74 (m, 5H), 2.27-2.21 (m, 3H), 1.62-1.47 (m, 1H), 1.42-1.15 (m, 7H), 1.03-0.92 (m, 3H)

Example 73-(b)

Production of 3-(1,4-dimethyl-1H-benzo[d][1,2,3]triazol-5-yl)-3-(3-(((R)-2-ethyl-2,3,7,8-tetrahydrothieno[2',3':4,5]benzo[1,2-f][1,4]oxazepin-4(5H)-yl)methyl)-4-methylphenyl)-2,2-dimethylpropanoic Acid

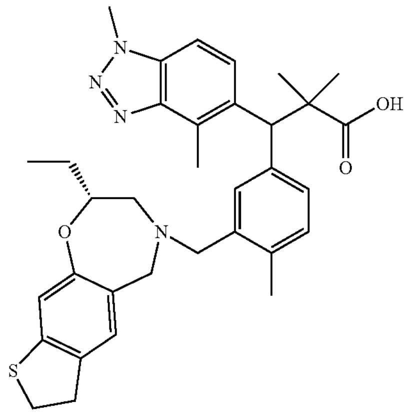 [SMILES: CC[C@@H]1CN(Cc2cc(C(c3ccc4c(nnn4C)c3C)C(C)(C)C(=O)O)ccc2C)Cc2cc3c(cc2O1)SCC3]

To a solution of methyl 3-(1,4-dimethyl-1H-benzo[d][1,2,3]triazol-5-yl)-3-(3-(((R)-2-ethyl-2,3,7,8-tetrahydrothieno[2',3':4,5]benzo[1,2-f][1,4]oxazepin-4(5H)-yl)methyl)-4-methylphenyl)-2,2-dimethylpropanoate produced in the Example 73-(a) (63 mg) in dimethyl sulfoxide (4 mL) was added dropwise a 2 M aqueous solution of potassium hydroxide (0.526 mL) under argon gas flow with stirring at room temperature, and the resulting mixture was stirred at 70° C. for 3 hours. After the reaction was completed, to the reaction solution was added water (5 mL), 1 M hydrochloric acid was added thereto to adjust the pH to 5.5, and the resulting mixture was stirred for 1 hour. The resulting solids were collected by filtration, washed with water, and dried under reduced pressure at 60° C. to give the title compound (54 mg) as white solids.

Mass spectrum (ESI, m/z): 585 $[M+H]^+$ $^1$H NMR (400 MHz, $CD_3OD$) δ=7.79-7.66 (m, 1H), 7.51-7.43 (m, 1H), 7.20-7.14 (m, 1H), 7.11-7.03 (m, 2H), 6.83-6.67 (m, 2H), 4.95-4.88 (m, 1H), 4.29-4.22 (m, 3H), 3.84-3.45 (m, 5H), 3.38-3.25 (m, 2H), 3.19-3.06 (m, 2H), 2.90-2.81 (m, 1H), 2.76-2.68 (m, 4H), 2.29-2.21 (m, 3H), 1.52-1.13 (m, 8H), 0.98-0.88 (m, 3H)

Example 74-(a)

Production of methyl 3-(1,4-dimethyl-1H-benzo([d][1,2,3]triazol-5-yl)-3-(3-(((R)-2-ethyl-9,9-dioxide-2,3,7,8-tetrahydrothieno[2',3':4,5]benzo[1,2-f][1,4]oxazepin-4(5H)-yl)methyl)-4-methylphenyl)-2,2-dimethylpropanoate

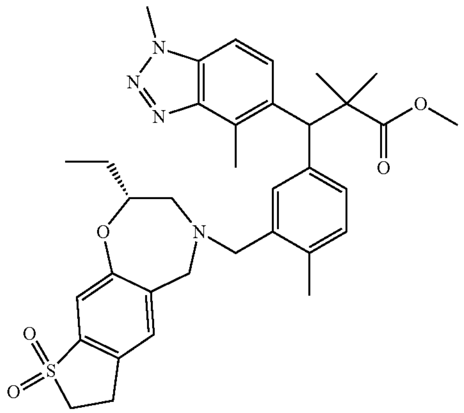 [SMILES: CC[C@@H]1CN(Cc2cc(C(c3ccc4c(nnn4C)c3C)C(C)(C)C(=O)OC)ccc2C)Cc2cc3c(cc2O1)S(=O)(=O)CC3]

To a solution of methyl 3-(3-(chloromethyl)-4-methylphenyl)-3-(1,4-dimethyl-1H-benzo[d][1,2,3]triazol-5-yl)-2,2-dimethylpropanoate produced according to the same manner as the Reference Example 10-(c) (50 mg) in acetonitrile (3 mL) were sequentially added (R)-2-ethyl-2, 3, 4, 5,7,8-hexahydrothieno[2',3':4,5]benzo[1,2-f][1,4]oxazepine 9,9-dioxide produced in the Reference Example 74-(b) (40 mg) and N,N-diisopropylethylamine (0.085 mL) under argon gas flow with stirring at room temperature, and the resulting mixture was stirred at 60° C. for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (67 mg) as a white foam.

Mass spectrum (ESI, m/z): 631 $[M+H]^+$ $^1$H NMR (400 MHz, $CDCl_3$) δ=7.64-7.56 (m, 1H), 7.38-7.33 (m, 1H), 7.29-7.22 (m, 1H), 7.11-6.84 (m, 4H), 4.84-4.82 (m, 1H), 4.26-4.21 (m, 3H), 4.00-3.89 (m, 1H), 3.83-3.38 (m, 9H), 3.33-3.17 (m, 2H), 2.91-2.81 (m, 2H), 2.80-2.73 (m, 3H), 2.27-2.19 (m, 3H), 1.65-1.49 (m, 1H), 1.42-1.18 (m, 7H), 1.06-0.93 (m, 3H)

Example 74-(b)

Production of 3-(1,4-dimethyl-1H-benzo[d][1,2,3]triazol-5-yl)-3-(3-(((R)-2-ethyl-9,9-dioxide-2,3,7,8-tetrahydrothieno[2',3':4,5]benzo[1,2-f][1,4]oxazepin-4(5H)-yl)methyl)-4-methylphenyl)-2,2-dimethylpropanoic Acid

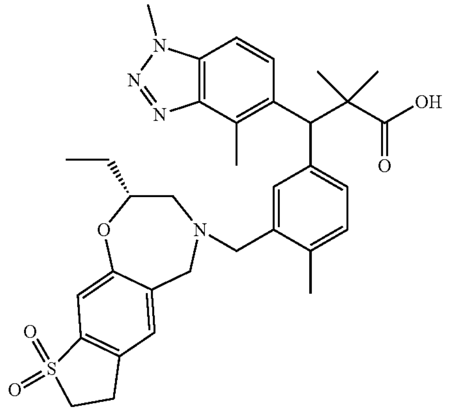 [SMILES: CC[C@@H]1CN(Cc2cc(C(c3ccc4c(nnn4C)c3C)C(C)(C)C(=O)O)ccc2C)Cc2cc3c(cc2O1)S(=O)(=O)CC3]

To a solution of methyl 3-(1,4-dimethyl-1H-benzo[d][1,2,3]triazol-5-yl)-3-(3-(((R)-2-ethyl-9,9-dioxide-2,3,7,8-tetrahydrothieno[2',3':4,5)benzo[1,2-f](1,4]oxazepin-4 (5H)-yl)methyl)-4-methylphenyl)-2,2-dimethylpropanoate produced in the Example 74-(a) (67 mg) in dimethyl sulfoxide (4 mL) was added dropwise a 2 M aqueous solution of potassium hydroxide (0.531 mL) under argon gas flow with stirring at room temperature, and the resulting mixture was stirred at 70° C. for 3 hours. After the reaction was completed, to the reaction solution was added water (5 mL), 1 M hydrochloric acid was added thereto to adjust the pH to 5.5, and the resulting mixed solution was subjected to extraction twice with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate), and the fractions comprising the title compound were concentrated under reduced pressure. The resulting residues were dissolved into a mixed solvent of acetonitrile/water, and the resulting solution was lyophilized to give the title compound (30 mg) as white solids.

Mass spectrum (ESI, m/z): 617 [M+H]$^+$ $^1$H NMR (400 MHz, $CD_3OD$) δ=7.79-7.64 (m, 1H), 7.50-7.41 (m, 1H), 7.24-7.14 (m, 2H), 7.11-6.99 (m, 3H), 4.94-4.79 (m, 1H), 4.30-4.24 (m, 3H), 3.93-3.83 (m, 1H), 3.82-3.45 (m, 6H), 3.35-3.22 (m, 2H), 2.91-2.73 (m, 2H), 2.72-2.66 (m, 3H), 2.28-2.21 (m, 3H), 1.57-1.16 (m, 8H), 1.01-0.87 (m, 3H)

Example 75-(a)

Production of methyl 3-(1,4-dimethyl-1H-benzo[d][1,2,3]triazol-5-yl)-2,2-dimethyl-3-(4-methyl-3-(((R)-2-methyl-2,3-dihydro-[1,4]oxazepino[7,6-g]quinolin-4 (5H)-yl)methyl)phenyl)propanoate

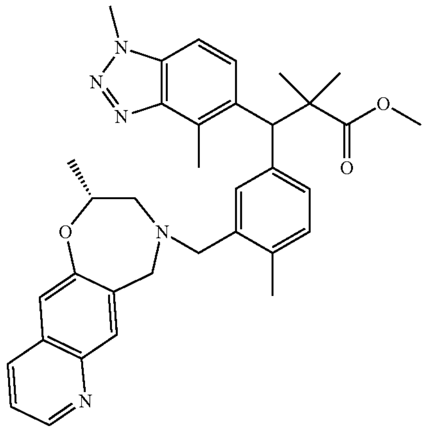 [SMILES: COC(=O)C(C)(C)C(c1ccc(C)c(CN2Cc3cc4ncccc4cc3O[C@H](C)C2)c1)c1ccc2c(nnn2C)c1C]

To a solution of methyl 3-(1,4-dimethyl-1H-benzo[d][1,2,3]triazol-5-yl)-3-(3-(hydroxymethyl)-4-methylphenyl)-2,2-dimethylpropanoate produced according to the same manner as the Reference Example 1-(h) (100 mg) in dichloromethane (2 mL) was added dropwise thionyl chloride (0.03 mL) under argon gas flow with stirring at room temperature, and the resulting mixture was stirred at room temperature for 15 minutes. Then, the reaction solution was concentrated under reduced pressure.

To a solution of the resulting residues in acetonitrile (2 mL) were added N,N-diisopropylethylamine (0.137 mL) and (R)-2-methyl-2,3,4,5-tetrahydro-[1,4]oxazepino[7,6-g]quinoline produced in the Reference Example 75-(b) (59 mg) under argon gas flow with stirring at room temperature, and the resulting mixture was stirred at 80° C. for 6 hours. After the reaction was completed, the reaction solution was poured into water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (110 mg) as a slightly yellow oil.

Mass spectrum (ESI, m/z): 578 [M+H]$^+$ $^1$H NMR (400 MHz, $CD_3OD$) δ=8.77-8.71 (m, 1H), 8.29-8.22 (m, 1H), 7.78-7.61 (m, 2H), 7.52-7.44 (m, 3H), 7.22-7.04 (m, 3H), 4.92-4.82 (m, 1H), 4.29-4.22 (m, 3H), 4.20-4.00 (m, 21), 3.94-3.82 (m, 1H), 3.69-3.51 (m, 2H), 3.47-3.40 (m, 3H), 2.96-2.76 (m, 2H), 2.73-2.65 (m, 3H), 2.27-2.19 (m, 3H), 1.41-1.35 (m, 3H), 1.33-1.28 (m, 3H), 1.27-1.09 (m, 3H)

Example 75-(b)

Production of 3-(1,4-dimethyl-1H-benzo[d][1,2,3]triazol-5-yl)-2,2-dimethyl-3-(4-methyl-3-(((R)-2-methyl-2,3-dihydro-[1,4]oxazepino[7,6-g]quinolin-4(5H)-yl)methyl)phenyl) propanoic Acid

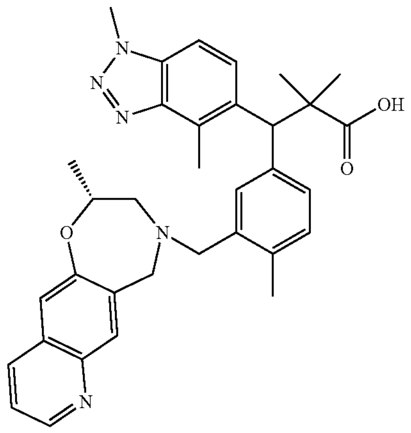 [SMILES: Cc1ccc(C(c2ccc3c(nnn3C)c2C)C(C)(C)C(=O)O)cc1CN1Cc2cc3ncccc3cc2O[C@H](C)C1]

To a solution of methyl 3-(1,4-dimethyl-1H-benzo[d][1,2,3]triazol-5-yl)-2,2-dimethyl-3-(4-methyl-3-(((R)-2-methyl-2,3-dihydro-[1,4]oxazepino[7,6-g]quinolin-4(5H)-yl)methyl)phenyl)propanoate produced in the Example 75-(a) (108 mg) in dimethyl sulfoxide (2 mL) was added dropwise a 1 M aqueous solution of potassium hydroxide (0.28 mL) with stirring at room temperature, and the resulting mixture was stirred at 75° C. for 2 hours. After the reaction was completed, water (38 mL) was added thereto. Then, 2 M hydrochloric acid was added thereto to adjust the pH to 5.5, and the resulting mixed solution was subjected to extraction twice with ethyl acetate. The resulting organic layer was washed sequentially with water and saturated brine, dried over anhydrous magnesium sulfate, filtered, and concentrated under reduced pressure. The resulting residues were purified by a silica gel column (DIOL silica gel, eluent: hexane:ethyl acetate) to give the title compound (55 mg) as a slightly yellow foam.

Mass spectrum (ESI, m/z): 564 $[M+H]^+$ $^1H$ NMR (400 MHz, $CD_3OD$) δ=8.78-8.71 (m, 1H), 8.29-8.24 (m, 1H), 7.81-7.64 (m, 2H), 7.53-7.43 (m, 3H), 7.21-7.02 (m, 3H), 4.97-4.91 (m, 1H), 4.27-4.22 (m, 3H), 4.21-4.01 (m, 2H), 3.94-3.84 (m, 1H), 3.71-3.50 (m, 2H), 2.99-2.79 (m, 2H), 2.75-2.65 (m, 3H), 2.30-2.18 (m, 3H), 1.45-1.13 (m, 9H)

Example 76-(a)

Production of methyl 3-(3-((3'H-spiro[cyclopropane-1,2'-[1,4]oxazepino[7,6-g]quinoline]-4' (5'H)-yl)methyl)-4-methylphenyl)-3-(1,4-dimethyl-1H-benzo[d][1,2,3]triazol-5-yl)-2,2-dimethylpropanoate

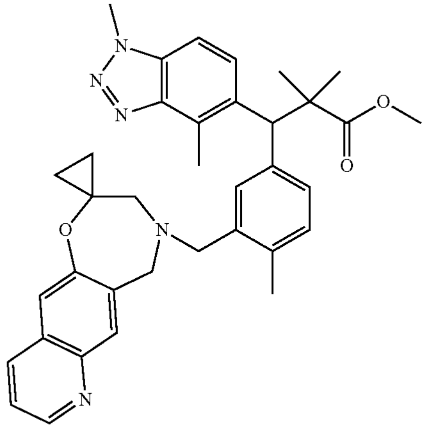 [SMILES: COC(=O)C(C)(C)C(c1ccc(C)c(CN2Cc3cc4ncccc4cc3OC3(CC3)C2)c1)c1ccc2c(nnn2C)c1C]

To a solution of methyl 3-(1,4-dimethyl-1H-benzo[d][1,2,3]triazol-5-yl)-3-(3-(hydroxymethyl)-4-methylphenyl)-2,2-dimethylpropanoate produced according to the same manner as the Reference Example 1-(h) (270 mg) in dichloromethane (2 mL) was added dropwise thionyl chloride (0.08 mL) under argon gas flow with stirring at room temperature, and the resulting mixture was stirred at room temperature for 15 minutes. Then, the reaction solution was concentrated under reduced pressure.

To a solution of the resulting residues in acetonitrile (1 mL) were added dropwise N,N-diisopropylethylamine (0.37 mL) and a solution of 4',5'-dihydro-3'H-spiro(cyclopropane-1,2'-[1,4]oxazepino[7,6-g]quinoline) produced in the Reference Example 76-(b) (168 mg) in acetonitrile (2 mL) under argon gas flow with stirring at room temperature, and the resulting mixture was stirred at 80° C. for 3 hours. After the reaction was completed, the reaction solution was poured into water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (299 mg) as a white foam.

Mass spectrum (ESI, m/z): 590 $[M+H]^+$ $^1H$ NMR (400 MHz, $CD_3OD$) δ=8.77-8.73 (m, 1H), 8.27-8.20 (m, 1H), 7.72-7.62 (m, 2H), 7.53-7.45 (m, 2H), 7.32-7.28 (m, 1H), 7.18-7.00 (m, 3H), 4.92-4.82 (m, 1H), 4.28-4.23 (m, 3H), 4.14-4.04 (m, 2H), 3.65-3.58 (m, 2H), 3.50-3.42 (m, 3H), 3.09-2.98 (m, 2H), 2.71-2.64 (m, 3H), 2.19-2.14 (m, 3H), 1.42-1.36 (m, 3H), 1.32-1.27 (m, 3H), 0.95-0.85 (m, 2H), 0.44-0.34 (m, 2H)

Example 76-(b)

Production of 3-(3-((3'H-spiro[cyclopropane-1,2'-[1,4]oxazepino[7,6-g]quinoline]-4' (5'H)-yl)methyl)-4-methylphenyl)-3-(1,4-dimethyl-1H-benzo[d][1,2,3]triazol-5-yl)-2,2-dimethylpropanoic Acid

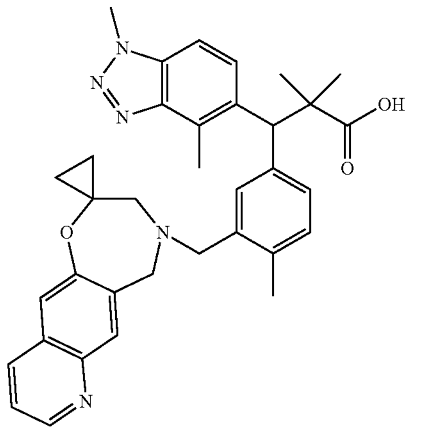 [SMILES: Cc1ccc(C(c2ccc3c(nnn3C)c2C)C(C)(C)C(=O)O)cc1CN1Cc2cc3ncccc3cc2OC2(CC2)C1]

To a solution of methyl 3-(3-((3'H-spiro[cyclopropane-1,2'-[1,4]oxazepino[7,6-g]quinoline]-4' (5'H)-yl)methyl)-4-methylphenyl)-3-(1,4-dimethyl-1H-benzo[d][1,2,3]triazol-5-yl)-2,2-dimethylpropanoate produced in the Example 76-(a) (298 mg) in dimethyl sulfoxide (4.5 m) was added dropwise a 1 M aqueous solution of potassium hydroxide (0.758 mL) with stirring at room temperature, and the resulting mixture was stirred at 75° C. for 5 hours. After the reaction was completed, water (38 mL) was added thereto. Then, 2 M hydrochloric acid was added thereto to adjust the pH to 5.5, and the resulting mixed solution was subjected to extraction twice with ethyl acetate. The resulting organic layer was washed sequentially with water and saturated brine, dried over anhydrous magnesium sulfate, filtered, and concentrated under reduced pressure. The resulting residues were purified by a silica gel column (eluent: hexane:ethyl acetate) to give the title compound (205 mg) as a white foam.

Mass spectrum (ESI, m/z): 576 $[M+H]^+$ $^1H$ NMR (400 MHz, $CD_3OD$) δ=8.79-8.71 (m, 1H), 8.29-8.21 (m, 1H), 7.79-7.66 (m, 2H), 7.52-7.45 (m, 2H), 7.33-7.28 (m, 1H), 7.18-7.01 (m, 3H), 4.98-4.93 (m, 1H), 4.30-4.23 (m, 3H), 4.11-4.05 (m, 2H), 3.67-3.57 (m, 2H), 3.12-3.01 (m, 2H), 2.72-2.66 (m, 3H), 2.24-2.15 (m, 3H), 1.45-1.35 (m, 3H), 1.33-1.25 (m, 3H), 0.94-0.86 (m, 2H), 0.44-0.35 (m, 2H)

Example 77-(a)

Production of methyl 3-(1,4-dimethyl-1H-benzo[d][1,2,3]triazol-5-yl)-2,2-dimethyl-3-(4-methyl-3-((2-propyl-2,3-dihydro-[1,4]oxazepino[7,6-g]quinolin-4(5H)-yl)methyl)phenyl) propanoate

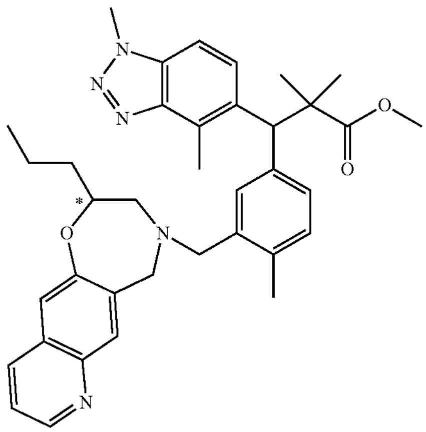 [SMILES: CCCC1CN(Cc2cc(C(c3ccc4c(nnn4C)c3C)C(C)(C)C(=O)OC)ccc2C)Cc2cc3ncccc3cc2O1]

To a solution of methyl 3-(1,4-dimethyl-1H-benzo[d][1,2,3]triazol-5-yl)-3-(3-(hydroxymethyl)-4-methylphenyl)-2,2-dimethylpropanoate produced according to the same manner as the Reference Example 1-(h) (105 mg) in dichloromethane (2 mL) was added dropwise thionyl chloride (0.02 mL) under argon gas flow with stirring at room temperature, and the resulting mixture was stirred at room temperature for 30 minutes. Then, the reaction solution was concentrated under reduced pressure.

To a solution of the resulting residues in acetonitrile (2 mL) were added N,N-diisopropylethylamine (0.14 mL) and 2-propyl-2,3,4,5-tetrahydro-[1,4]oxazepino[7,6-g]quinoline produced in the Reference Example 77-(c) (70 mg) under argon gas flow with stirring at room temperature, and the resulting mixture was stirred at 80° C. for 7 hours. After the reaction was completed, the reaction solution was diluted with ethyl acetate. The resulting organic layer was washed sequentially with water and saturated brine, dried over anhydrous magnesium sulfate, filtered, and concentrated under reduced pressure. The resulting residues were purified by a silica gel column (eluent: hexane:ethyl acetate) to give the title compound (148 mg) as a slightly yellow foam.

Mass spectrum (ESI, m/z): 606 $[M+H]^+$ $^1H$ NMR (400 MHz, $CD_3OD$) δ=8.83-8.68 (m, 1H), 8.33-8.18 (m, 1H), 7.80-7.59 (m, 2H), 7.56-7.36 (m, 3H), 7.22-7.00 (m, 3H), 4.90-4.82 (m, 1H), 4.29-4.21 (m, 3H), 4.13-4.03 (m, 1H), 4.00-3.85 (m, 2H), 3.71-3.51 (m, 2H), 3.47-3.40 (m, 3H), 2.95-2.79 (m, 2H), 2.73-2.65 (m, 3H), 2.27-2.19 (m, 3H), 1.72-1.19 (m, 10H), 1.01-0.86 (m, 3H)

Example 77-(b)

Production of 3-(1,4-dimethyl-1H-benzo[d][1,2,3] triazol-5-yl)-2,2-dimethyl-3-(4-methyl-3-((2-propyl-2,3-dihydro-[1,4]oxazepino[7,6-g]quinolin-4 (5H)-yl)methyl)phenyl)propanoic Acid

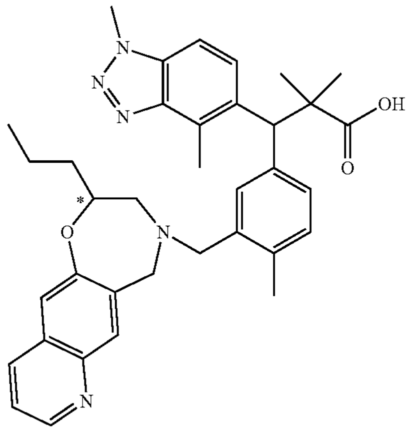 [SMILES: CCCC1CN(Cc2cc(C(c3ccc4c(nnn4C)c3C)C(C)(C)C(=O)O)ccc2C)Cc2cc3ncccc3cc2O1]

To a solution of methyl 3-(1,4-dimethyl-1H-benzo[d][1,2,3]triazol-5-yl)-2,2-dimethyl-3-(4-methyl-3-((2-propyl-2,3-dihydro-[1,4]oxazepino[7,6-g]quinolin-4(5H)-yl)methyl)phenyl)propanoate produced in the Example 77-(a) (147 mg) in dimethyl sulfoxide (2 mL) was added dropwise a 1 M aqueous solution of potassium hydroxide (0.364 mL) with stirring at room temperature, and the resulting mixture was stirred at 75° C. for 5 hours. After the reaction was completed, water (2 mL) was added thereto. Then, 2 M hydrochloric acid was added thereto to adjust the pH to 5.5, and the resulting mixed solution was subjected to extraction twice with ethyl acetate. The resulting organic layer was washed sequentially with water and saturated brine, dried over anhydrous magnesium sulfate, filtered, and concentrated under reduced pressure. The resulting residues were purified by a silica gel column (DIOL silica gel, eluent: hexane:ethyl acetate) to give the title compound (107 mg) as a white foam.

Mass spectrum (ESI, m/z): 592 $[M+H]^+$ $^1$H NMR (400 MHz, $CD_3OD$) δ=8.77-8.71 (m, 1H), 8.32-8.23 (m, 1H), 7.80-7.66 (m, 2H), 7.54-7.41 (m, 3H), 7.22-7.01 (m, 3H), 4.96-4.90 (m, 1H), 4.28-4.21 (m, 3H), 4.14-4.01 (m, 1H), 3.99-3.84 (m, 2H), 3.69-3.50 (m, 2H), 2.96-2.81 (m, 2H), 2.75-2.66 (m, 3H), 2.27-2.20 (m, 3H), 1.72-1.20 (m, 10H), 0.98-0.86 (m, 3H)

Example 78-(a)

Production of methyl 3-(1,4-dimethyl-1H-benzo[d][1,2,3]triazol-5-yl)-2,2-dimethyl-3-(4-methyl-3-((2-propyl-2,3-dihydro-[1,4]oxazepino[7,6-g]quinolin-4 (5H)-yl)methyl)phenyl)propanoate

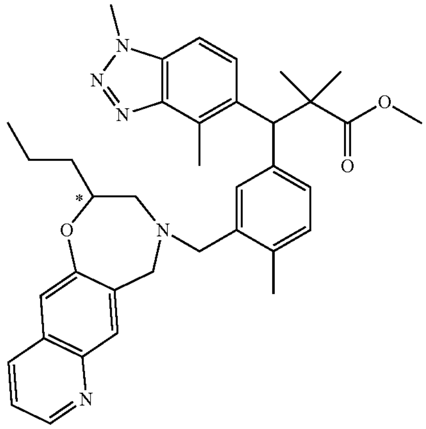 [SMILES: CCCC1CN(Cc2cc(C(c3ccc4c(nnn4C)c3C)C(C)(C)C(=O)OC)ccc2C)Cc2cc3ncccc3cc2O1]

To a solution of methyl 3-(1,4-dimethyl-1H-benzo[d][1,2,3]triazol-5-yl)-3-(3-(hydroxymethyl)-4-methylphenyl)-2,2-dimethylpropanoate produced according to the same manner as the Reference Example 1-(h) (105 mg) in dichloromethane (2 mL) was added dropwise thionyl chloride (0.02 mL) under argon gas flow with stirring at room temperature, and the resulting mixture was stirred at room temperature for 30 minutes. Then, the reaction solution was concentrated under reduced pressure.

To a solution of the resulting residues in acetonitrile (2 mL) were added N,N-diisopropylethylamine (0.14 mL) and 2-propyl-2,3,4,5-tetrahydro-[1,4]oxazepino[7,6-g]quinoline produced in the Reference Example 78-(a) (70 mg) under argon gas flow with stirring at room temperature, and the resulting mixture was stirred at 80° C. for 7 hours. After the reaction was completed, the reaction solution was diluted with ethyl acetate. The resulting organic layer was washed sequentially with water and saturated brine, dried over anhydrous magnesium sulfate, filtered, and concentrated under reduced pressure. The resulting residues were purified by a silica gel column (eluent: hexane:ethyl acetate) to give the title compound (153 mg) as a slightly yellow foam.

Mass spectrum (ESI, m/z): 606 $[M+H]^+$ $^1$H NMR (400 MHz, $CD_3OD$) δ=8.77-8.72 (m, 1H), 8.30-8.24 (m, 1H), 7.76-7.64 (m, 2H), 7.52-7.44 (m, 3H), 7.20-7.03 (m, 3H), 5.04-4.77 (m, 1H), 4.27-4.23 (m, 3H), 4.14-4.04 (m, 1H), 3.99-3.82 (m, 2H), 3.70-3.52 (m, 2H), 3.47-3.42 (m, 3H), 2.94-2.79 (m, 2H), 2.74-2.66 (m, 3H), 2.27-2.20 (m, 3H), 1.72-1.21 (m, 10H), 0.99-0.87 (m, 3H)

Example 78-(b)

Production of 3-(1,4-dimethyl-1H-benzo[d][1,2,3]triazol-5-yl)-2,2-dimethyl-3-(4-methyl-3-((2-propyl-2,3-dihydro-[1,4]oxazepino[7,6-g]quinolin-4 (5H)-yl)methyl)phenyl)propanoic Acid

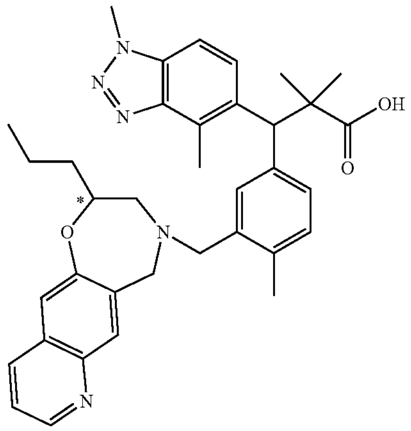 [SMILES: CCCC1CN(Cc2cc(C(c3ccc4c(nnn4C)c3C)C(C)(C)C(=O)O)ccc2C)Cc2cc3ncccc3cc2O1]

To a solution of methyl 3-(1,4-dimethyl-1H-benzo[d][1,2,3]triazol-5-yl)-2,2-dimethyl-3-(4-methyl-3-((2-propyl-2,3-dihydro-[1,4]oxazepino[7,6-g]quinolin-4(5H)-yl)methyl)phenyl)propanoate produced in the Example 78-(a) (152 mg) in dimethyl sulfoxide (2 mL) was added dropwise a 1 M aqueous solution of potassium hydroxide (0.376 mL) with stirring at room temperature, and the resulting mixture was stirred at 75° C. for 6 hours. After the reaction was completed, water (2 mL) was added thereto. Then, 2 M hydrochloric acid was added thereto to adjust the pH to 5.5, and the resulting mixed solution was subjected to extraction twice with ethyl acetate. The resulting organic layer was washed sequentially with water and saturated brine, dried over anhydrous magnesium sulfate, filtered, and concentrated under reduced pressure. The resulting residues were purified by a silica gel column (DIOL silica gel, eluent: hexane:ethyl acetate) to give the title compound (108 mg) as a white foam.

Mass spectrum (ESI, m/z): 592 $[M+H]^+$ $^1$H NMR (400 MHz, $CD_3OD$) δ=8.76-8.71 (m, 1H), 8.30-8.25 (m, 1H), 7.79-7.67 (m, 2H), 7.51-7.41 (m, 3H), 7.20-7.03 (m, 3H), 4.96-4.90 (m, 1H), 4.29-4.21 (m, 3H), 4.12-4.02 (m, 1H), 4.00-3.86 (m, 2H), 3.68-3.51 (m, 2H), 2.96-2.81 (m, 2H), 2.74-2.68 (m, 3H), 2.28-2.21 (m, 3H), 1.72-1.20 (m, 10H), 0.98-0.88 (m, 3H)

Example 79-(a)

Production of methyl 3-(1,4-dimethyl-1H-benzo[d][1,2,3]triazol-5-yl)-3-(3-(((R)-2-ethyl-2,3-dihydro-[1,4]oxazepino[7,6-g]quinolin-4 (5H)-yl)methyl)phenyl)-2,2-dimethylpropanoate

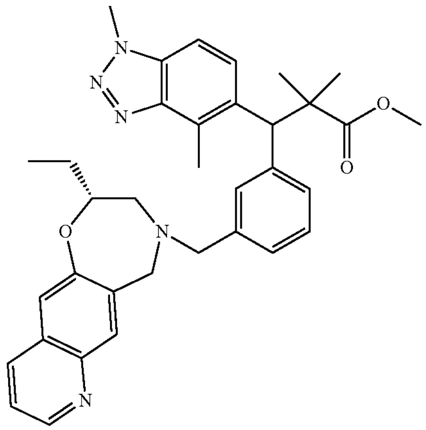 [SMILES: CC[C@@H]1CN(Cc2cccc(C(c3ccc4c(nnn4C)c3C)C(C)(C)C(=O)OC)c2)Cc2cc3ncccc3cc2O1]

To a solution of methyl 3-(1,4-dimethyl-1H-benzo[d][1,2,3]triazol-5-yl)-3-(3-(hydroxymethyl)phenyl)-2,2-dimethylpropanoate produced in the Reference Example 79-(d) (60 mg) in dichloromethane (1.5 mL) was added dropwise thionyl chloride (0.02 mL) under argon gas flow with stirring at room temperature, and the resulting mixture was stirred at room temperature for 15 minutes. Then, the reaction solution was concentrated under reduced pressure.

To a solution of the resulting residues in acetonitrile (1.5 mL) were added dropwise N,N-diisopropylethylamine (0.08 mL) and a solution of (R)-2-ethyl-2,3,4,5-tetrahydro-[1,4]oxazepino[7,6-g]quinoline produced according to the same manner as the Reference Example 12-(c) (39 mg) in acetonitrile (1.5 mL) under argon gas flow with stirring at room temperature, and the resulting mixture was stirred at 80° C. for 4 hours. After the reaction was completed, the reaction solution was poured into water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (80 mg) as a slightly yellow oil.

Mass spectrum (ESI, m/z): 578 $[M+H]^+$ $^1$H NMR (400 MHz, $CD_3OD$) δ=8.75-8.71 (m, 1H), 8.30-8.24 (m, 1H), 7.76-7.62 (m, 2H), 7.52-7.45 (m, 3H), 7.33-7.21 (m, 3H), 7.18-7.11 (m, 1H), 4.95-4.90 (m, 1H), 4.29-4.23 (m, 3H), 4.06-3.59 (m, 5H), 3.47-3.42 (m, 3H), 3.01-2.91 (m, 1H), 2.88-2.78 (m, 1H), 2.75-2.67 (m, 3H), 1.69-1.52 (m, 1H), 1.47-1.26 (m, 7H), 1.12-0.99 (m, 3H)

Example 79-(b)

Production of 3-(1,4-dimethyl-1H-benzo[d][1,2,3]triazol-5-yl)-3-(3-(((R)-2-ethyl-2,3-dihydro-[1,4]oxazepino[7,6-g]quinolin-4(5H)-yl)methyl)phenyl)-2,2-dimethylpropanoic Acid

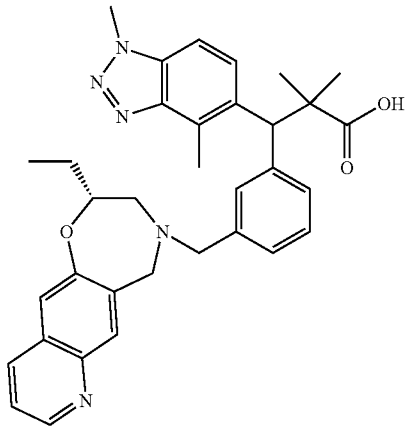 [SMILES: CC[C@@H]1CN(Cc2cccc(C(c3ccc4c(nnn4C)c3C)C(C)(C)C(=O)O)c2)Cc2cc3ncccc3cc2O1]

To a solution of methyl 3-(1,4-dimethyl-1H-benzo[d][1,2,3]triazol-5-yl)-3-(3-(((R)-2-ethyl-2,3-dihydro-[1,4]oxazepino[7,6-g]quinolin-4 (5H)-yl)methyl)phenyl)-2,2-dimethylpropanoate produced in the Example 79-(a) (78 mg) in dimethyl sulfoxide (2 mL) was added dropwise a 1 M aqueous solution of potassium hydroxide (0.203 mL) with stirring at room temperature, and the resulting mixture was stirred at 75° C. for 3 hours. After the reaction was completed, water (38 mL) was added thereto. Then, 2 M hydrochloric acid was added thereto to adjust the pH to 5.5, and the resulting mixed solution was subjected to extraction twice with ethyl acetate. The resulting organic layer was washed sequentially with water and saturated brine, dried over anhydrous magnesium sulfate, filtered, and concentrated under reduced pressure. The resulting residues were purified by a silica gel column (DIOL silica gel, eluent: hexane:ethyl acetate) to give the title compound (55 mg) as a white foam.

Mass spectrum (ESI, m/z): 564 $[M+H]^+$ $^1$H NMR (400 MHz, CD % OD) δ=8.76-8.71 (m, 1H), 8.30-8.25 (m, 1H), 7.79-7.74 (m, 1H), 7.69-7.64 (m, 1H), 7.53-7.44 (m, 3H), 7.35-7.13 (m, 4H), 5.02-4.94 (m, 1H), 4.29-4.22 (m, 3H), 4.08-3.59 (m, 5H), 3.04-2.82 (m, 2H), 2.76-2.69 (m, 3H), 1.72-1.53 (m, 1H), 1.47-1.24 (m, 7H), 1.11-1.00 (n, 3H)

Example 80-(a)

Production of methyl 3-(4-chloro-3-(((R)-2-ethyl-2,3-dihydro-[1,4]oxazepino[7,6-g]quinolin-4 (5H)-yl)methyl)phenyl)-3-(1,4-dimethyl-1H-benzo[d][1,2,3]triazol-5-yl)-2,2-dimethylpropanoate

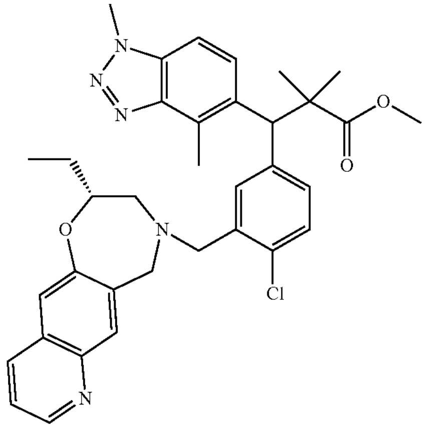 [SMILES: CC[C@@H]1CN(Cc2cc(C(c3ccc4c(nnn4C)c3C)C(C)(C)C(=O)OC)ccc2Cl)Cc2cc3ncccc3cc2O1]

To a solution of methyl 3-(4-chloro-3-(hydroxymethyl)phenyl)-3-(1,4-dimethyl-1H-benzo[d][1,2,3]triazol-5-yl)-2,2-dimethylpropanoate produced in the Reference Example 80-(d) (60 mg) in dichloromethane (1.5 mL) was added dropwise thionyl chloride (0.02 mL) under argon gas flow with stirring at room temperature, and the resulting mixture was stirred at room temperature for 15 minutes. Then, the reaction solution was concentrated under reduced pressure.

To a solution of the resulting residues in acetonitrile (1.5 mL) were added dropwise N,N-diisopropylethylamine (0.08 mL) and a solution of (R)-2-ethyl-2,3,4,5-tetrahydro-[1,4]oxazepino[7,6-g]quinoline produced according to the same method as the Reference Example 12-(c) (36 mg) in acetonitrile (1.5 mL) under argon gas flow with stirring at room temperature, and the resulting mixture was stirred at 80° C. for 5 hours. After the reaction was completed, the reaction solution was poured into water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (61 mg) as a white foam.

Mass spectrum (ESI, m/z): 612 $[M+H]^+$ $^1$H NMR (400 MHz, $CD_3OD$) δ=8.77-8.72 (m, 1H), 8.31-8.25 (m, 1H), 7.71-7.58 (m, 2H), 7.52-7.42 (m, 4H), 7.30-7.25 (m, 1H), 7.24-7.18 (m, 1H), 4.94-4.88 (m, 1H), 4.27-4.21 (m, 3H), 4.16-4.06 (m, 1H), 3.97-3.68 (m, 4H), 3.50-3.43 (m, 3H), 2.99-2.87 (m, 2H), 2.74-2.66 (m, 3H), 1.69-1.54 (m, 1H), 1.46-1.26 (m, 7H), 1.10-1.01 (m, 3H)

Example 80-(b)

Production of 3-(4-chloro-3-(((R)-2-ethyl-2,3-dihydro-[1,4]oxazepino[7,6-g]quinolin-4 (5H)-yl)methyl)phenyl)-3-(1,4-dimethyl-1H-benzo[d][1, 2, 3]triazol-5-yl)-2,2-dimethylpropanoic Acid

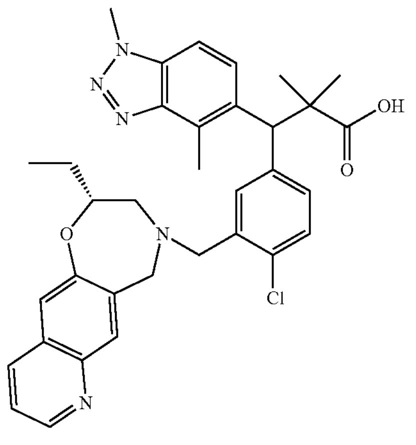 [SMILES: CC[C@@H]1CN(Cc2cc(C(c3ccc4c(nnn4C)c3C)C(C)(C)C(=O)O)ccc2Cl)Cc2cc3ncccc3cc2O1]

To a solution of methyl 3-(4-chloro-3-(((R)-2-ethyl-2,3-dihydro-[1,4]oxazepino[7,6-g]quinolin-4(5H)-yl)methyl)phenyl)-3-(l, 4-dimethyl-1H-benzo[d][1,2,3]triazol-5-yl)-2, 2-dimethylpropanoate produced in the Example 80-(a) (59 mg) in dimethyl sulfoxide (2 mL) was added dropwise a 1 M aqueous solution of potassium hydroxide (0.145 mL) with stirring at room temperature, and the resulting mixture was stirred at 75° C. for 5 hours. After the reaction was completed, water (38 mL) was added thereto. Then, 2 M hydrochloric acid was added thereto to adjust the pH to 5.5, and the resulting mixed solution was subjected to extraction twice with ethyl acetate. The resulting organic layer was washed sequentially with water and saturated brine, dried over anhydrous magnesium sulfate, filtered, and concentrated under reduced pressure. The resulting residues were purified by a silica gel column (eluent: hexane:ethyl acetate) to give the title compound (24 mg) as a white foam.

Mass spectrum (ESI, m/z): 598 $[M+H]^+$ $^1$H NMR (400 MHz, $CD_3OD$) δ=8.77-8.72 (m, 1H), 8.31-8.24 (m, 1H), 7.75-7.63 (m, 2H), 7.54-7.41 (m, 4H), 7.27 (s, 2H), 5.00-4.93 (m, 1H), 4.27-4.22 (m, 3H), 4.16-4.05 (m, 1H), 3.98-3.65 (m, 4H), 3.00-2.88 (m, 2H), 2.75-2.68 (m, 3H), 1.68-1.53 (m, 1H), 1.46-1.24 (m, 7H), 1.09-1.01 (m, 3H)

Example 81-(a)

Production of methyl 3-(1,4-dimethyl-1H-benzo[d][1,2,3]triazol-5-yl)-3-(3-(((R)-2-ethyl-2,3-dihydro-[1,4]oxazepino[7,6-g]quinolin-4 (5H)-yl)methyl)-4-methoxyphenyl)-2,2-dimethylpropanoate

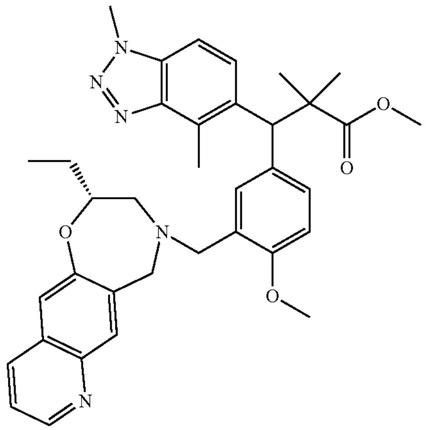 [SMILES: CC[C@@H]1CN(Cc2cc(C(c3ccc4c(nnn4C)c3C)C(C)(C)C(=O)OC)ccc2OC)Cc2cc3ncccc3cc2O1]

To a solution of methyl 3-(1,4-dimethyl-1H-benzo[d][1,2,3]triazol-5-yl)-3-(3-(hydroxymethyl)-4-methoxyphenyl)-2,2-dimethylpropanoate produced in the Reference Example 81-(d) (60 mg) in dichloromethane (1.5 mL) was added dropwise thionyl chloride (0.02 mL) under argon gas flow with stirring at room temperature, and the resulting mixture was stirred at room temperature for 15 minutes. Then, the reaction solution was concentrated under reduced pressure.

To a solution of the resulting residues in acetonitrile (1.5 mL) were added dropwise N,N-diisopropylethylamine (0.08 mL) and a solution of (R)-2-ethyl-2,3,4,5-tetrahydro-[1,4]oxazepino[7,6-g]quinoline produced according to the same method as the Reference Example 12-(c) (36 mg) in acetonitrile (1.5 mL) under argon gas flow with stirring at room temperature, and the resulting mixture was stirred at 80° C. for 4 hours. After the reaction was completed, the reaction solution was poured into water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (84 mg) as a slightly yellow oil.

Mass spectrum (ESI, m/z): 608 $[M+H]^+$ $^1$H NMR (400 MHz, $CD_3OD$) δ=8.77-8.71 (m, 1H), 8.31-8.23 (m, 1H), 7.79-7.66 (m, 2H), 7.52-7.45 (m, 3H), 7.30-7.19 (m, 2H), 6.92-6.86 (m, 1H), 4.93-4.77 (m, 1H), 4.29-4.21 (m, 3H), 4.15-3.57 (m, 8H), 3.50-3.41 (m, 3H), 2.98-2.65 (m, 5H), 1.71-1.49 (m, 1H), 1.45-1.26 (m, 7H), 1.12-1.01 (m, 3H)

Example 81-(b)

Production of 3-(1,4-dimethyl-1H-benzo[d][1,2,3]triazol-5-yl)-3-(3-(((R)-2-ethyl-2,3-dihydro-[1,4]oxazepino[7,6-g]quinolin-4 (5H)-yl)methyl)-4-methoxyphenyl)-2,2-dimethylpropanoic Acid

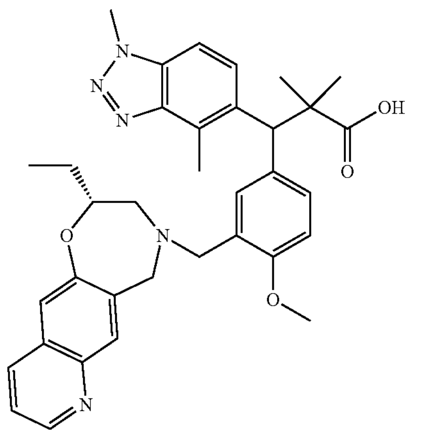 [SMILES: CC[C@@H]1CN(Cc2cc(C(c3ccc4c(nnn4C)c3C)C(C)(C)C(=O)O)ccc2OC)Cc2cc3ncccc3cc2O1]

To a solution of methyl 3-(1,4-dimethyl-1H-benzo[d][1,2,3]triazol-5-yl)-3-(3-(((R)-2-ethyl-2,3-dihydro-[1,4]oxazepino [7,6-g]quinolin-4(5H)-yl)methyl)-4-methoxyphenyl)-2,2-dimethylpropanoate produced in the Example 81-(a) (81 mg) in dimethyl sulfoxide (2 mL) was added dropwise a 1 M aqueous solution of potassium hydroxide (0.20 mL) with stirring at room temperature, and the resulting mixture was stirred at 75° C. for 5 hours. After the reaction was completed, water (38 mL) was added thereto. Then, 2 M hydrochloric acid was added thereto to adjust the pH to 5.5, and the resulting mixed solution was subjected to extraction twice with ethyl acetate. The resulting organic layer was washed sequentially with water and saturated brine, dried over anhydrous magnesium sulfate, filtered, and concentrated under reduced pressure. The resulting residues were purified by a silica gel column (DIOL silica gel, eluent: hexane:ethyl acetate) to give the title compound (50 mg) as a white foam.

Mass spectrum (ESI, m/z): 594 $[M+H]^+$ $^1$H NMR (400 MHz, CD OD) δ=8.77-8.72 (m, 1H), 8.31-8.25 (m, 1H), 7.83-7.71 (m, 2H), 7.53-7.44 (m, 3H), 7.33-7.22 (m, 2H), 6.92-6.85 (m, 1H), 4.95-4.81 (m, 1H), 4.27-4.21 (m, 3H), 4.13-3.94 (m, 2H), 3.91-3.79 (m, 1H), 3.77-3.60 (m, 5H), 3.01-2.67 (m, 5H), 1.67-1.51 (m, 1H), 1.46-1.26 (m, 71), 1.12-1.01 (m, 3H)

Example 82-(a)

Production of methyl 3-(3-(((R)-2-ethyl-2,3-dihydro-[1,4]oxazepino[7,6-g]quinolin-4 (5H)-yl)methyl)-4-methylphenyl)-2,2-dimethyl-3-(1-methyl-1H-benzo[d][1,2,3]triazol-5-yl)propanoate

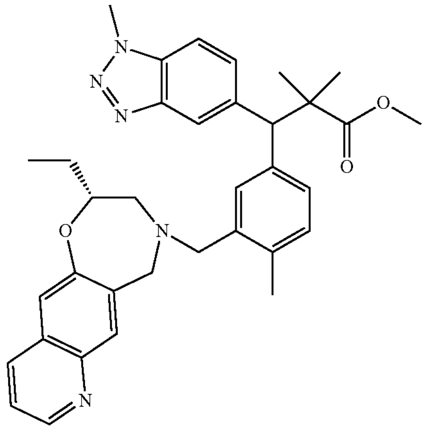 [SMILES: CC[C@@H]1CN(Cc2cc(C(c3ccc4c(c3)nnn4C)C(C)(C)C(=O)OC)ccc2C)Cc2cc3ncccc3cc2O1]

To a solution of methyl 3-(3-(hydroxymethyl)-4-methylphenyl)-2,2-dimethyl-3-(1-methyl-1H-benzo[d][1,2,3]triazol-5-yl)propanoate produced in the Reference Example 82-(c) (60 mg) in dichloromethane (1.5 mL) was added dropwise thionyl chloride (0.018 mL) under argon gas flow with stirring at room temperature, and the resulting mixture was stirred at room temperature for 15 minutes. Then, the reaction solution was concentrated under reduced pressure.

To a solution of the resulting residues in acetonitrile (1.5 mL) were added dropwise N,N-diisopropylethylamine (0.083 mL) and a solution of (R)-2-ethyl-2,3,4,5-tetrahydro-[1,4]oxazepino[7,6-g]quinoline produced according to the same method as the Reference Example 12-(c) (39 mg) in acetonitrile (1.5 mL) under argon gas flow with stirring at room temperature, and the resulting mixture was stirred at 80° C. for 4 hours. After the reaction was completed, the reaction solution was poured into water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (81 mg) as a slightly yellow oil.

Mass spectrum (ESI, m/z): 578 $[M+H]^+$ $^1$H NMR (400 MHz, $CD_3OD$) δ=8.75-8.70 (m, 1H), 8.29-8.23 (m, 1H), 7.99-7.90 (m, 1H), 7.67-7.57 (m, 2H), 7.53-7.43 (m, 3H), 7.28-7.15 (m, 2H), 7.13-7.05 (m, 1H), 4.92-4.80 (m, 1H), 4.30-4.24 (m, 3H), 4.14-4.05 (m, 1H), 3.96-3.78 (m, 2H), 3.72-3.54 (m, 2H), 3.52-3.46 (m, 3H), 2.97-2.81 (m, 2H), 2.30-2.23 (m, 3H), 1.68-1.53 (m, 1H), 1.45-1.26 (m, 7H), 1.07-0.98 (m, 3H)

Example 82-(b)

Production of 3-(3-(((R)-2-ethyl-2,3-dihydro-[1,4]oxazepino[7,6-g]quinolin-4 (5H)-yl)methyl)-4-methylphenyl)-2,2-dimethyl-3-(1-methyl-1H-benzo[d][1,2,3]triazol-5-yl) propanoic Acid

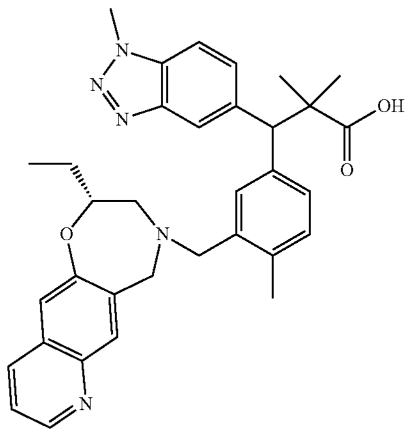 [SMILES: CC[C@@H]1CN(Cc2cc(C(c3ccc4c(c3)nnn4C)C(C)(C)C(=O)O)ccc2C)Cc2cc3ncccc3cc2O1]

To a solution of methyl 3-(3-(((R)-2-ethyl-2,3-dihydro-[1,4]oxazepino[7,6-g]quinolin-4(5H)-yl)methyl)-4-methylphenyl)-2,2-dimethyl-3-(1-methyl-1H-benzo[d][1,2,3]triazol-5-yl)propanoate produced in the Example 82-(a) (79 mg) in dimethyl sulfoxide (2 mL) was added dropwise a 1 M aqueous solution of potassium hydroxide (0.205 mL) with stirring at room temperature, and the resulting mixture was stirred at 75° C. for 5 hours. After the reaction was completed, water (3 mL) was added thereto. Then, 2 M hydrochloric acid was added thereto to adjust the pH to 5.5, and the resulting mixed solution was subjected to extraction twice with ethyl acetate. The resulting organic layer was washed sequentially with water and saturated brine, dried over anhydrous magnesium sulfate, filtered, and concentrated under reduced pressure. The resulting residues were purified by a silica gel column (DIOL silica gel, eluent: hexane:ethyl acetate) to give the title compound (60 mg) as a white foam.

Mass spectrum (ESI, m/z): 564 $[M+H]^+$ $^1H$ NMR (400 MHz, $CD_3OD$) δ=8.76-8.71 (m, 1H), 8.30-8.23 (m, 1H), 8.04-7.95 (m, 1H), 7.70-7.64 (m, 1H), 7.62-7.56 (m, 1H), 7.54-7.44 (m, 3H), 7.29-7.18 (m, 2H), 7.13-7.06 (m, 1H), 4.96-4.79 (m, 1H), 4.30-4.23 (m, 3H), 4.12-4.03 (m, 1H), 3.96-3.79 (m, 2H), 3.72-3.53 (m, 2H), 3.04-2.82 (m, 2H), 2.31-2.21 (m, 3H), 1.71-1.51 (m, 1H), 1.46-1.26 (m, 7H), 1.09-0.98 (m, 3H)

Example 83-(a)

Production of methyl 1-((1,4-dimethyl-1H-benzo[d][1,2,3]triazol-5-yl) (3-(((R)-2-ethyl-2,3-dihydro-[1,4]oxazepino[7,6-g]quinolin-4 (5H)-yl)methyl)-4-methylphenyl)methyl)cyclopentane-1-carboxylate

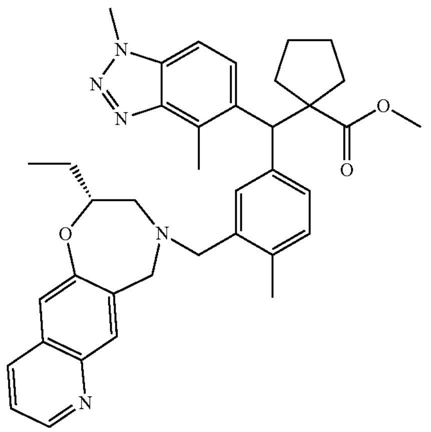 [SMILES: CC[C@@H]1CN(Cc2cc(C(c3ccc4c(nnn4C)c3C)C3(C(=O)OC)CCCC3)ccc2C)Cc2cc3ncccc3cc2O1]

To a solution of methyl 1-((3-(chloromethyl)-4-methylphenyl)(1,4-dimethyl-1H-benzo[d][1,2,3]triazol-5-yl) methyl)cyclopentane-1-carboxylate produced in the Reference Example 83-(c) (104 mg) in acetonitrile (3 mL) were sequentially added (R)-2-ethyl-2,3,4,5-tetrahydro-[1,4]oxazepino[7,6-g]quinoline produced according to the same manner as the Reference Example 12-(c) (62 mg) and N,N-diisopropylethylamine (0.126 mL) under argon gas flow with stirring at room temperature, and the resulting mixture was stirred at room temperature for 15 hours and at 60° C. for 5 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (127 mg) as a white foam.

Mass spectrum (ESI, m/z): 618 $[M+H]^+$ $^1H$ NMR (400 MHz, $CDCl_3$) δ=8.86-8.78 (m, 1H), 8.11-8.03 (m, 1H), 7.82-7.71 (m, 1H), 7.71-7.58 (m, 1H), 7.43-7.21 (m, 3H), 7.13-6.97 (m, 3H), 5.03-4.95 (m, 1H), 4.26-4.14 (m, 4H), 3.96-3.73 (m, 2H), 3.67-3.42 (m, 2H), 3.39-3.32 (m, 3H), 2.96-2.77 (m, 2H), 2.75-2.68 (m, 3H), 2.66-2.50 (m, 1H), 2.37-2.19 (m, 4H), 2.00-1.77 (m, 2H), 1.72-1.17 (m, 6H), 1.11-0.97 (m, 3H)

Example 83-(b)

Production of 1-((1,4-dimethyl-1H-benzo[d][1,2,3]triazol-5-yl) (3-(((R)-2-ethyl-2,3-dihydro-[1,4]oxazepino[7,6-g]quinolin-4 (5H)-yl)methyl)-4-methylphenyl)methyl)cyclopentane-1-carboxylic Acid

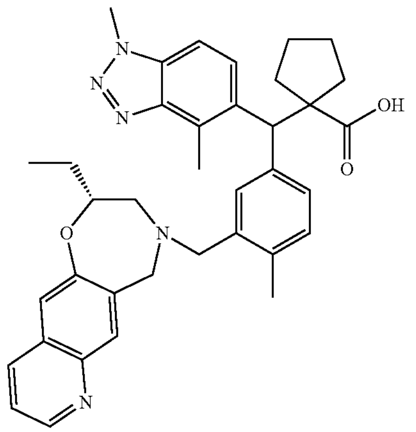 [SMILES: CC[C@@H]1CN(Cc2cc(C(c3ccc4c(nnn4C)c3C)C3(C(=O)O)CCCC3)ccc2C)Cc2cc3ncccc3cc2O1]

To a solution of methyl 1-((1,4-dimethyl-1H-benzo[d][1,2,3]triazol-5-yl) (3-(((R)-2-ethyl-2,3-dihydro-[1,4]oxazepino[7,6-g]quinolin-4 (5H)-yl)methyl)-4-methylphenyl)methyl)cyclopentane-1-carboxylate produced in the Example 83-(a) (125 mg) in dimethyl sulfoxide (5 mL) was added dropwise a 1 M aqueous solution of potassium hydroxide (0.607 mL) under argon gas flow with stirring at room temperature, and the resulting mixture was stirred at 60° C. for 5 hours. After the reaction was completed, to the reaction solution was added 1 M hydrochloric acid to adjust the pH to 5.0, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate), and the fractions comprising the title compound were concentrated under reduced pressure. The resulting residues were dissolved into a mixed solvent of acetonitrile/water, and the resulting solution was lyophilized to give the title compound (70 mg) as white solids.

Mass spectrum (ESI, m/z): 604 $[M+H]^+$ $^1$H NMR (400 MHz, $CD_3OD$) δ=8.78-8.70 (m, 1H), 8.30-8.24 (m, 1H), 7.81-7.63 (m, 2H), 7.52-7.42 (m, 3H), 7.19-7.03 (m, 3H), 5.12-5.03 (m, 1H), 4.27-4.21 (m, 3H), 4.15-4.02 (m, 1H), 3.98-3.88 (m, 1H), 3.88-3.70 (m, 1H), 3.69-3.61 (m, 1H), 3.58-3.50 (m, 1H), 2.95-2.76 (m, 2H), 2.68-2.50 (m, 4H), 2.40-2.20 (m, 4H), 2.08-1.76 (m, 2H), 1.69-1.14 (m, 6H), 1.08-0.93 (m, 3H)

Example 84-(a)

Production of methyl 1-((1,4-dimethyl-1H-benzo[d][1,2,3]triazol-5-yl) (3-(((R)-2-ethyl-2,3-dihydro-[1,4]oxazepino[7,6-g]quinolin-4 (5H)-yl)methyl)-4-methylphenyl)methyl)cyclobutane-1-carboxylate

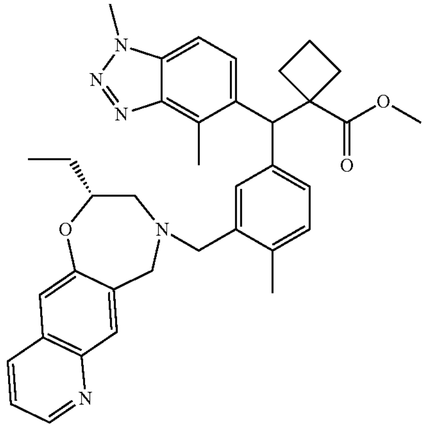 [SMILES: CC[C@@H]1CN(Cc2cc(C(c3ccc4c(nnn4C)c3C)C3(C(=O)OC)CCC3)ccc2C)Cc2cc3ncccc3cc2O1]

To a solution of methyl 1-((3-(chloromethyl)-4-methylphenyl)(1,4-dimethyl-1H-benzo[d][1,2,3]triazol-5-yl)methyl)cyclobutane-1-carboxylate produced in the Reference Example 84-(c) (73 mg) in acetonitrile (4 mL) were sequentially added (R)-2-ethyl-2,3,4,5-tetrahydro-[1,4]oxazepino[7,6-g]quinoline produced according to the same manner as the Reference Example 12-(c) (46 mg) and N,N-diisopropylethylamine (0.091 mL) under argon gas flow with stirring at room temperature, and the resulting mixture was stirred at room temperature for 14 hours and at 60° C. for 1 hour. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (92 mg) as a colorless oil.

Mass spectrum (ESI, m/z): 604 $[M+H]^+$ $^1$H NMR (400 MHz, $CDCl_3$) δ=8.85-8.78 (m, 1H), 8.09-8.03 (m, 1H), 7.79-7.67 (m, 1H), 7.43-7.32 (m, 3H), 7.32-7.23 (m, 1H), 7.10-6.97 (m, 3H), 4.81-4.73 (m, 1H), 4.25-4.16 (m, 4H), 3.95-3.72 (m, 2H), 3.68-3.57 (m, 1H), 3.55-3.41 (m, 4H), 2.95-2.60 (m, 6H), 2.47-2.29 (m, 3H), 2.28-2.23 (m, 3H), 1.93-1.49 (m, 2H), 1.45-1.16 (m, 2H), 1.10-0.95 (m, 3H)

Example 84-(b)

Production of 1-((1,4-dimethyl-1H-benzo[d][1,2,3]triazol-5-yl) (3-(((R)-2-ethyl-2,3-dihydro-[1,4]oxazepino[7,6-g]quinolin-4 (5H)-yl)methyl)-4-methylphenyl)methyl)cyclobutane-1-carboxylic Acid

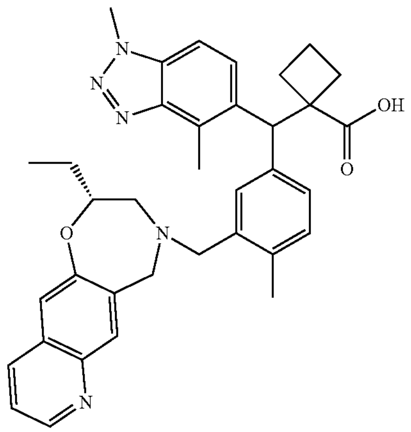 [SMILES: CC[C@@H]1CN(Cc2cc(C(c3ccc4c(nnn4C)c3C)C3(C(=O)O)CCC3)ccc2C)Cc2cc3ncccc3cc2O1]

To a solution of methyl 1-((1,4-dimethyl-1H-benzo[d][1,2,3]triazol-5-yl) (3-(((R)-2-ethyl-2,3-dihydro-[1,4]oxazepino[7,6-g]quinolin-4 (5H)-yl)methyl)-4-methylphenyl)methyl)cyclobutane-1-carboxylate produced in the Example 84-(a) (90 mg) in dimethyl sulfoxide (4 mL) was added dropwise a 1 M aqueous solution of potassium hydroxide (0.224 mL) under argon gas flow with stirring at room temperature, and the resulting mixture was stirred at 70° C. for 3 hours. After the reaction was completed, to the reaction solution was added 1 M hydrochloric acid to adjust the pH to 5.0, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate), and the fractions comprising the title compound were concentrated under reduced pressure. The resulting residues were dissolved into a mixed solvent of acetonitrile/water, and the resulting solution was lyophilized to give the title compound (63 mg) as white solids.

Mass spectrum (ESI, m/z): 590 $[M+H]^+$ $^1$H NMR (400 MHz, $CD_3OD$) 5=8.77-8.69 (m, 1H), 8.30-8.22 (m, 1H), 7.72-7.62 (m, 1H), 7.53-7.41 (m, 4H), 7.15-7.06 (m, 3H), 4.93-4.76 (m, 1H), 4.29-4.22 (m, 3H), 4.16-4.02 (m, 1H), 3.99-3.89 (m, 1H), 3.87-3.63 (m, 2H), 3.59-3.52 (m, 1H), 2.96-2.64 (m, 3H), 2.64-2.52 (m, 3H), 2.50-2.22 (m, 6H), 1.93-1.77 (m, 1H), 1.65-1.44 (m, 1H), 1.41-1.09 (m, 2H), 1.07-0.92 (m, 3H)

Example 85

3-(3-((3'H-spiro[cyclopropane-1,2'-[1,4]oxazepino[7,6-g]quinoline]-4'(5'H)-yl)methyl)-4-methylphenyl)-3-(1,4-dimethyl-1H-benzo[d][1,2,3]triazol-5-yl)-2,2-dimethylpropanoic Acid (Enantiomer 1) and Example 86

3-(3-((3'H-spiro[cyclopropane-1,2'-[1,4]oxazepino[7,6-g]quinoline]-4' (5'H)-yl)methyl)-4-methylphenyl)-3-(1,4-dimethyl-1H-benzo[d][1,2,3]triazol-5-yl)-2,2-dimethylpropanoic Acid (Enantiomer 2)

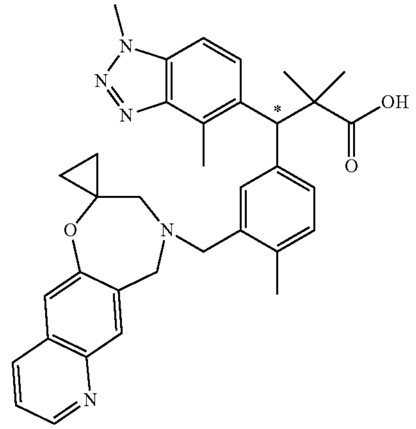 [SMILES: Cc1ccc(C(c2ccc3c(nnn3C)c2C)C(C)(C)C(=O)O)cc1CN1Cc2cc3ncccc3cc2OC2(CC2)C1]

3-(3-((3'H-spiro[cyclopropane-1,2'-[1,4]oxazepino[7,6-g]quinoline]-4'(5'H)-yl)methyl)-4-methylphenyl)-3-(1,4-dimethyl-1H-benzo[d][1,2,3]triazol-5-yl)-2,2-dimethylpropanoic Acid produced according to the same manner as the Example 76-(b) (2.88 g) was separated and purified by high performance liquid chromatography (Column: CHIRALPAK IG, mobile phase: hexane:ethanol ethanol ratio (%)=50-70). The fractions comprising the first-eluted enantiomer were concentrated under reduced pressure, the resulting residues were dissolved into a mixed solvent of acetonitrile/water, and the resulting solution was lyophilized to give the compound of Example 85 (1.26 g) as white solids. Also, the fractions comprising the later-eluted enantiomer were concentrated under reduced pressure, the resulting residues were dissolved into a mixed solvent of acetonitrile/water, and the resulting solution was lyophilized to give the compound of Example 86 (1.25 g) as white solids.

High Performance Liquid Chromatography Analysis:

Column; CHIRALPAK IG-3 4.6×150 mm

Mobile phase; hexane:ethanol ethanol ratio (%)=10 (0 min)→90 (10 min→90 (15 min)

Flow rate; 0.8 mL/min

Temperature; 40° C.

Detection wavelength; 220 nm

Retention time; Example 85: 8.02 min, Example 86: 9.31 min

Example 85

Mass spectrum (ESI, m/z): 576 $[M+H]^+$ $^1$H NMR (400 MHz, $CD_3OD$) δ=8.77-8.73 (m, 1H), 8.27-8.21 (m, 1H), 7.75 (d, J=8.9 Hz, 1H), 7.69 (s, 1H), 7.53-7.44 (m, 2H), 7.30 (s, 1H), 7.18-7.11 (m, 2H), 7.08-

7.01 (m, 1H), 4.95 (s, 1H), 4.26 (s, 3H), 4.07 (s, 2H), 3.66-3.57 (m, 2H), 3.12-3.00 (m, 2H), 2.69 (s, 3H), 2.18 (s, 3H), 1.39 (s, 3H), 1.28 (s, 3H), 0.95-0.84 (m, 2H), 0.43-0.33 (m, 2H)

Example 86

Mass spectrum (ESI, m/z): 576 $[M+H]^+$ $^1H$ NMR (400 MHz, $CD_3OD$) δ=8.78-8.73 (m, 1H), 8.29-8.21 (m, 1H), 7.75 (d, J=8.8 Hz, 1H), 7.69 (s, 1H), 7.52-7.44 (m, 2H), 7.30 (s, 1H), 7.19-7.10 (m, 2H), 7.08-7.01 (m, 1H), 4.95 (s, 1H), 4.26 (s, 3H), 4.07 (s, 2H), 3.70-3.55 (m, 2H), 3.13-2.99 (m, 2H), 2.70 (s, 3H), 2.18 (s, 3H), 1.40 (s, 3H), 1.29 (s, 3H), 0.95-0.86 (m, 2H), 0.45-0.35 (m, 2H)

Example 87

1-((1,4-dimethyl-1H-benzo[d][1,2,3]triazol-5-yl)(3-(((R)-2-ethyl-2,3-dihydro-[1,4]oxazepino[7,6-g]quinolin-4 (5H)-yl)methyl)-4-methylphenyl)methyl)cyclobutane-1-carboxylic acid (Diastereomer 1) and Example 88

1-((1,4-dimethyl-1H-benzo[d][1,2,3]triazol-5-yl)(3-(((R)-2-ethyl-2,3-dihydro-[1,4]oxazepino[7,6-g]quinolin-4 (5H)-yl)methyl)-4-methylphenyl)methyl)cyclobutane-1-carboxylic acid (Diastereomer 2)

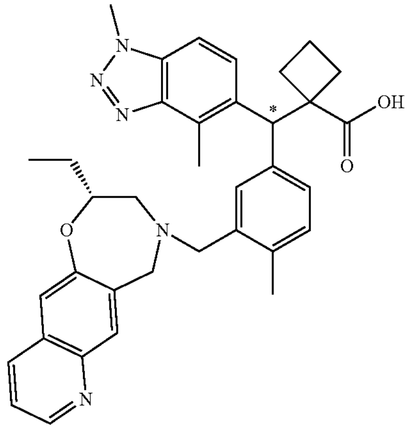 [SMILES: CC[C@@H]1CN(Cc2cc(C(c3ccc4c(nnn4C)c3C)C3(C(=O)O)CCC3)ccc2C)Cc2cc3ncccc3cc2O1]

1-((1,4-dimethyl-1H-benzo[d][1,2,3]triazol-5-yl) (3-(((R)-2-ethyl-2,3-dihydro-[1,4]oxazepino[7,6-g]quinolin-4 (5H)-yl)methyl)-4-methylphenyl)methyl)cyclobutane-1-carboxylic acid produced according to the same manner as the Example 84-(b) (3.00 g) was separated and purified by high performance liquid chromatography (Column: CHIRALPAK IG, mobile phase: hexane:ethanol ethanol ratio (%)=30). The fractions comprising the first-eluted diastereomer were concentrated under reduced pressure, the resulting residues were dissolved into a mixed solvent of acetonitrile/water, and the resulting solution was lyophilized to give the compound of Example 87 (1.22 g) as white solids. Also, the fractions comprising the later-eluted diastereomer were concentrated under reduced pressure, the resulting residues were dissolved into a mixed solvent of acetonitrile/water, and the resulting solution was lyophilized to give the compound of Example 88 (1.21 g) as white solids.

High Performance Liquid Chromatography Analysis:

Column; CHIRALPAK IG-3 4.6×150 mm

Mobile phase; hexane:ethanol ethanol ratio (%)=10 (0 min)→90 (10 min→90 (15 min)

Flow rate; 0.8 mL/min

Temperature; 40° C.

Detection wavelength; 254 nm

Retention time; Example 87: 7.18 min, Example 88: 9.47 min

Example 87

Mass spectrum (ESI, m/z): 590 $[M+H]^+$ $^1H$ NMR (400 MHz, $CD_3OD$) δ=8.78-8.71 (m, 1H), 8.29-8.23 (m, 1H), 7.70 (s, 1H), 7.52-7.42 (m, 4H), 7.17-7.05 (m, 3H), 4.81 (s, 1H), 4.26 (s, 3H), 4.15-3.90 (m, 2H), 3.78-3.52 (m, 3H), 2.87-2.70 (m, 3H), 2.56 (s, 3H), 2.48-2.26 (m, 6H), 1.92-1.76 (m, 1H), 1.59-1.42 (m, 1H), 1.25-1.08 (m, 2H), 0.95 (t, J=7.7 Hz, 3H)

Example 88

Mass spectrum (ESI, m/z): 590 $[M+H]^+$ $^1H$ NMR (400 MHz, $CD_3OD$) δ=8.75-8.70 (m, 1H), 8.29-8.24 (m, 1H), 7.65 (s, 1H), 7.50-7.41 (m, 4H), 7.15-7.08 (m, 3H), 4.91-4.82 (m, 1H), 4.25 (s, 3H), 4.09-3.88 (m, 2H), 3.87-3.79 (m, 1H), 3.72-3.51 (m, 2H), 2.96-2.76 (m, 2H), 2.74-2.65 (m, 1H), 2.61 (s, 3H), 2.49-2.41 (m, 2H), 2.36-2.21 (m, 4H), 1.94-1.79 (m, 1H), 1.66-1.51 (m, 1H), 1.41-1.15 (m, 2H), 1.03 (t, J=7.4 Hz, 3H)

Example 89-(a)

Production of methyl 3-(1,4-dimethyl-1H-benzo[d][1,2,3]triazol-5-yl)-3-(3-(((S)-2-ethyl-2,3-dihydro-[1,4]oxazepino [6,7-c]isoquinolin-4 (5H)-yl)methyl)-4-methylphenyl)-2,2-dimethylpropanoate

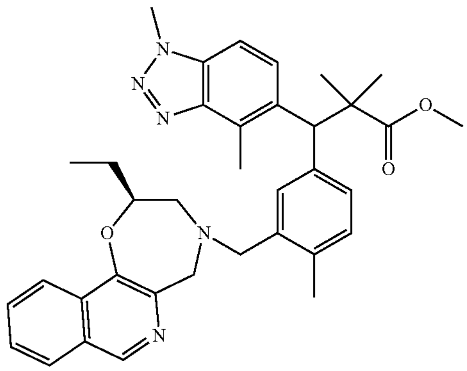 [SMILES: CC[C@H]1CN(Cc2cc(C(c3ccc4c(nnn4C)c3C)C(C)(C)C(=O)OC)ccc2C)Cc2ncc3ccccc3c2O1]

To a solution of methyl 3-(1,4-dimethyl-1H-benzo[d][1,2,3]triazol-5-yl)-3-(3-(hydroxymethyl)-4-methylphenyl)-2,2-dimethylpropanoate produced according to the same manner as the Reference Example 1-(h) (100 mg) in dichloromethane (2 mL) was added dropwise thionyl chloride (0.03 mL) under argon gas flow with stirring at room temperature, and the resulting mixture was stirred at room temperature for 15 minutes. Then, the reaction solution was concentrated under reduced pressure.

To a solution of the resulting residues in acetonitrile (2 mL) were added N,N-diisopropylethylamine (0.18 mL) and (S)-2-ethyl-2,3,4,5-tetrahydro-[1,4]oxazepino[6,7-c]isoquinoline dihydrochloride produced in the Reference Example 89-(c) (83 mg) under argon gas flow with stirring at room temperature, and the resulting mixture was stirred at 80° C. for 6 hours. After the reaction was completed, the reaction solution was poured into water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (131 mg) as a slightly yellow oil.

Mass spectrum (ESI, m/z): 592 $[M+H]^+$ $^1$H NMR (400 MHz, $CD_3OD$) δ=8.87-8.79 (m, 1H), 8.34-8.26 (m, 1H), 8.12-8.02 (m, 1H), 7.84-7.76 (m, 1H), 7.73-7.59 (m, 2H), 7.45-7.29 (m, 1H), 7.20-7.02 (m, 3H), 4.90-4.79 (m, 1H), 4.27-3.88 (m, 6H), 3.72-3.59 (m, 2H), 3.45-3.38 (m, 3H), 3.02-2.81 (m, 2H), 2.72-2.61 (m, 3H), 2.31-2.22 (m, 3H), 1.80-1.64 (m, 1H), 1.55-1.18 (m, 7H), 1.11-0.98 (m, 3H)

Example 89-(b)

3-(1,4-dimethyl-1H-benzo[d][1,2,3]triazol-5-yl)-3-(3-(((S)-2-ethyl-2,3-dihydro-[1,4]oxazepino[6,7-c]isoquinolin-4(5H)-yl)methyl)-4-methylphenyl)-2,2-dimethylpropanoic Acid (Diastereomer 1) and Example 90

3-(1,4-dimethyl-1H-benzo[d][1,2,3]triazol-5-yl)-3-(3-(((S)-2-ethyl-2,3-dihydro-[1,4]oxazepino[6,7-c]isoquinolin-4(5H)-yl)methyl)-4-methylphenyl)-2,2-dimethylpropanoic Acid (Diastereomer 2)

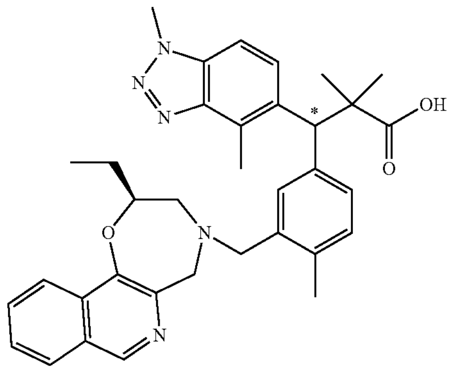 [SMILES: CC[C@H]1CN(Cc2cc(C(c3ccc4c(nnn4C)c3C)C(C)(C)C(=O)O)ccc2C)Cc2ncc3ccccc3c2O1]

To a solution of methyl 3-(1,4-dimethyl-1H-benzo[d][1,2,3]triazol-5-yl)-3-(3-(((S)-2-ethyl-2,3-dihydro-[1,4]oxazepino[6,7-c]isoquinolin-4(5H)-yl)methyl)-4-methylphenyl)-2,2-dimethylpropanoate produced in the Example 89-(a) (130 mg) in dimethyl sulfoxide (2.6 mL) was added dropwise a 1 M aqueous solution of potassium hydroxide (0.33 mL) with stirring at room temperature, and the resulting mixture was stirred at 75° C. for 5 hours. After the reaction was completed, water (3 mL) was added thereto. Then, 2 M hydrochloric acid was added thereto to adjust the pH to 5.5, and the resulting mixed solution was subjected to extraction twice with ethyl acetate. The resulting organic layer was washed sequentially with water and saturated brine, dried over anhydrous magnesium sulfate, filtered, and concentrated under reduced pressure. The resulting residues were purified by a silica gel column (DIOL silica gel, eluent: hexane:ethyl acetate), and the resulting white foam (91 mg) was separated and purified by high performance liquid chromatography (Column: CHIRALPAK IG, mobile phase: hexane:ethanol ethanol ratio (%)=30). The fractions comprising the first-eluted diastereomer were concentrated under reduced pressure, the resulting residues were dissolved into a mixed solvent of acetonitrile/water, and the resulting solution was lyophilized to give the compound of Example 89-(b) (28 mg) as white solids. Also, the fractions comprising the later-eluted diastereomer were concentrated under reduced pressure, the resulting residues were dissolved into a mixed solvent of acetonitrile/water, and the resulting solution was lyophilized to give the compound of Example 90 (36 mg) as white solids.

High Performance Liquid Chromatography Analysis:

Column; CHIRALPAK IG-3 4.6×150 mm

Mobile phase; hexane:ethanol ethanol ratio (%)=20 (0 min)→20 (20 min)

Flow rate; 0.8 mL/min

Temperature; 40° C.

Detection wavelength; 254 nm

Retention time; Example 89-(b): 12.4 min, Example 90: 15.4 min

Example 89-(b)

Mass spectrum (ESI, m/z): 578 $[M+H]^+$ $^1$H NMR (400 MHz, $CD_3OD$) δ=8.83 (s, 1H), 8.35-8.25 (m, 1H), 8.12-8.05 (m, 1H), 7.85-7.63 (m, 3H), 7.38-7.30 (m, 1H), 7.20-7.02 (m, 3H), 4.96-4.78 (m, 1H), 4.30-3.94 (m, 6H), 3.73-3.56 (m, 2H), 3.01-2.81 (m, 2H), 2.67 (s, 3H), 2.27 (s, 3H), 1.80-1.66 (m, 1H), 1.55-1.18 (m, 7H), 1.05 (t, J=7.4 Hz, 3H)

Example 90

Mass spectrum (ESI, m/z): 578 $[M+H]^+$ $^1$H NMR (400 MHz, $CD_3OD$) δ=8.86 (s, 1H), 8.33-8.25 (m, 1H), 8.12-8.05 (m, 1H), 7.85-7.76 (m, 2H), 7.73-7.64 (m, 1H), 7.45-7.35 (m, 1H), 7.20-7.12 (m, 2H), 7.10-7.02 (m, 1H), 4.94-4.79 (m, 1H), 4.22 (s, 3H), 4.19-4.07 (m, 2H), 3.98-3.88 (m, 1H), 3.72-3.58 (m, 2H), 3.00-2.84 (m, 2H), 2.68 (s, 3H), 2.28 (s, 3H), 1.80-1.65 (m, 1H), 1.54-1.23 (m, 7H), 1.04 (t, J=7.4 Hz, 3H)

Reference Examples

Reference Example 1-(a)

Production of 2,2-difluoro-6-hydroxybenzo[d][1,3]dioxole-5-carbaldehyde

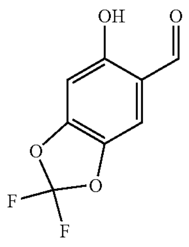 [SMILES: O=Cc1cc2c(cc1O)OC(F)(F)O2]

To a solution of 2,2-difluorobenzo[d][1,3]dioxol-5-ol (1.02 g) in trifluoroacetic acid (10 mL) was added hexamethylenetetramine (1.23 g) under argon gas flow with stirring at room temperature, and the resulting mixture was stirred at 80° C. for 5 hours. After the reaction was completed, to the reaction solution was added water (25 mL), the resulting mixture was stirred at room temperature for 30 minutes, and the resulting mixed solution was subjected to extraction with tert-butyl methyl ether. The resulting organic layer was washed sequentially with water and saturated brine, dried over anhydrous magnesium sulfate, filtered, and concentrated under reduced pressure. The resulting residues were purified by a silica gel column (elution solvent; hexane:ethyl acetate) to give the title compound (0.376 g) as red-purple solids.

Mass spectrum (ESI, m/z): 201 $[M-H]^-$

Reference Example 1-(b)

Production of tert-butyl (S)-((2,2-difluoro-6-hydroxybenzo[d][1,3]dioxol-5-yl)methyl) (2-hydroxybutyl)carbamate

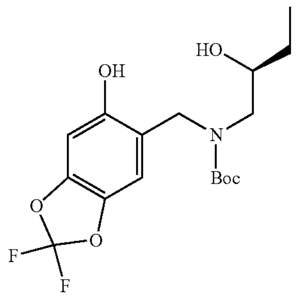 [SMILES: CC[C@H](O)CN(Cc1cc2c(cc1O)OC(F)(F)O2)C(=O)OC(C)(C)C]

A solution of 2,2-difluoro-6-hydroxybenzo[d][1,3]dioxole-5-carbaldehyde produced in the Reference Example 1-(a) (101 mg) and (2S)-1-amino-2-butanol (54 mg) in dichloromethane (2 mL) was stirred under argon gas flow at room temperature for 1 hour. Then, sodium triacetoxyborohydride (220 mg) was added thereto, and the resulting mixture was stirred at room temperature overnight. After the reaction was completed, the reaction solution was concentrated under reduced pressure, to the resulting residues were added methanol (2 mL) and a 8 M aqueous solution of sodium hydroxide (0.825 mL), di-tert-butyl dicarbonate (0.227 mL) was added thereto, and the resulting mixture was stirred at room temperature for 2 hours. Additionally, di-tert-butyl dicarbonate (0.227 mL) was added thereto with stirring at room temperature, and the resulting mixture was stirred at room temperature for 2 hours. Additionally, a 8 M aqueous solution of sodium hydroxide (0.165 mL) and di-tert-butyl dicarbonate (0.227 mL) were added thereto with stirring at room temperature, and the resulting mixture was stirred at room temperature for 2 hours. Additionally, a 8 M aqueous solution of sodium hydroxide (0.825 mL) was added thereto with stirring at room temperature, and the resulting mixture was left to stand at room temperature for 2 days. Then, 1 M hydrochloric acid was added thereto to adjust the pH to 5, and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (181 mg) as a colorless oil.

Mass spectrum (ESI, m/z): 374 $[M-H]^-$

Reference Example 1-(c)

Production of tert-butyl (R)-6-ethyl-2,2-difluoro-6,7-dihydro-[1,3]dioxolo[4',5':4,5]benzo[1,2-f][1,4]oxazepine-8(9H)-carboxylate

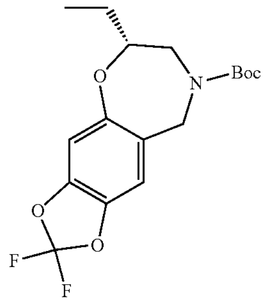 [SMILES: CC[C@@H]1CN(C(=O)OC(C)(C)C)Cc2cc3c(cc2O1)OC(F)(F)O3]

To a solution of tert-butyl (S)-((2,2-difluoro-6-hydroxybenzo[d][1,3]dioxol-5-yl)methyl) (2-hydroxybutyl)carbamate produced in the Reference Example 1-(b) (180 mg) and triphenylphosphine (152 mg) in tetrahydrofuran (2 mL) was added a 1.9 M solution of diisopropyl azodicarboxylate in toluene (0.303 mL) under argon gas flow with stirring at 0° C., and the resulting mixture was stirred at room temperature for 3 hours. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (111 mg) as a colorless oil.

Mass spectrum (ESI, m/z): 356 $[M-H]^-$

Reference Example 1-(d)

Production of (R)-6-ethyl-2,2-difluoro-6,7,8,9-tetrahydro-[1,3]dioxolo[4',5':4,5]benzo[1,2-f][1,4]oxazepine hydrochloride

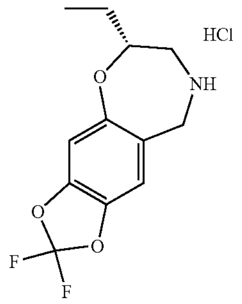 [SMILES: CC[C@@H]1CNCc2cc3c(cc2O1)OC(F)(F)O3 ; Cl]

To a solution of tert-butyl (R)-6-ethyl-2,2-difluoro-6,7-dihydro-[1,3]dioxolo[4',5':4,5]benzo[1,2-f][1,4]oxazepine-8(9H)-carboxylate produced in the Reference Example 1-(c) (111 mg) in tert-butyl methyl ether (1 mL) was added a 4 M solution of hydrogen chloride in 1,4-dioxane (0.311 mL) with stirring at room temperature, and the resulting mixture was stirred at room temperature for 2 hours. The resulting precipitates were filtered, and dried under reduced pressure at 65° C. to give the title compound (28 mg) as white solids.

Mass spectrum (ESI, m/z): 258 [M+H]$^+$

Reference Example 1-(e)

Production of 4-bromo-2-(((4-methoxybenzyl)oxy) methyl)-1-methylbenzene

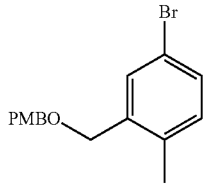

To a solution of (5-bromo-2-methylphenyl)methanol (10.0 g) in dimethylformamide (50 mL) was added sodium hydride (2.28 g) under argon gas flow with stirring at 0° C., and the resulting mixture was stirred at 0° C. for 0.5 hour. Then, 4-methoxybenzyl chloride (7.08 mL) was added dropwise thereto with stirring at 0° C., and the resulting mixture was stirred at room temperature for 2 hours. After the reaction was completed, to the reaction solution was added water, and the resulting mixed solution was subjected to extraction with toluene. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (14.76 g) as a colorless oil.

Mass spectrum (EI, m/z): 320 [M$^+$]

Reference Example 1-(f)

Production of (1,4-dimethyl-1H-benzo[d][1,2,3] triazol-5-yl) (3-(((4-methoxybenzyl)oxy)methyl)-4-methylphenyl)methanol

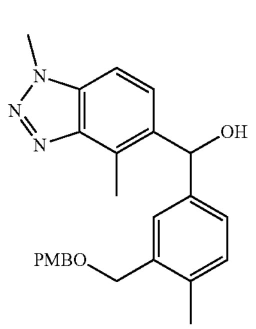

To a solution of 4-bromo-2-(((4-methoxybenzyl)oxy) methyl)-1-methylbenzene produced according to the same manner as the Reference Example 1-(e) (40.0 g) in tetrahydrofuran (523 mL) was added dropwise a 1.6 M solution of n-butyllithium in hexane (0.871 mL) under argon gas flow with stirring at −78° C., and the resulting mixture was stirred at −78° C. for 0.5 hour. Then, a solution of 1,4-dimethyl-1H-benzo[d][1,2,3]triazole-5-carbaldehyde (19.65 g) in tetrahydrofuran (130 mL) was added dropwise thereto with stirring at −78° C., and the resulting mixture was stirred at −78° C. for 0.5 hour. Then, the mixture was gradually warmed to room temperature, and stirred for 3 hours. After the reaction was completed, to the reaction solution was added a saturated aqueous solution of ammonium chloride, and the resulting mixed solution was subjected to extraction twice with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (35.1 g) as a pale yellow foam.

As an alternative method, the title compound was also produced according to the following method.

To a solution of 5-bromo-1,4-dimethyl-1H-benzo[d][1,2,3]triazole (300 mg) in tetrahydrofuran (4 mL) was added toluene (4 mL), added dropwise a 1.6 M solution of n-butyllithium in hexane (0.871 mL) under argon gas flow with stirring at −78° C., and the resulting mixture was stirred at −78° C. for 0.5 hour. Then, a solution of 3-(((4-methoxybenzyl)oxy)methyl)-4-methylbenzaldehyde produced according to the same manner as the Reference Example 1-(j) (395 mg) in tetrahydrofuran (5 mL) was added dropwise thereto with stirring at −78° C., and the resulting mixture was stirred at −78° C. for 1 hour. Then, the mixture was gradually warmed to room temperature, and stirred for 1 hour. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (131 mg) as a yellow foam.

As an alternative method, the title compound was also produced according to the following method.

To a solution of 5-bromo-1,4-dimethyl-1H-benzo[d][1,2,3]triazole (5.00 g) in tetrahydrofuran (50 mL) was added dropwise a 1.0 M solution of i-propylmagnesium chloride in tetrahydrofuran (19.9 mL) under argon gas flow with stirring at −50° C. Then, a 1.6 M solution of n-butyllithium in hexane (24.88 mL) was added dropwise thereto with stirring at −50° C., and the resulting mixture was stirred at −50° C. for 0.5 hour. Additionally, a solution of 3-(((4-methoxybenzyl)oxy)methyl)-4-methylbenzaldehyde produced according to the same manner as the Reference Example 1-(j) (7.17 g) in tetrahydrofuran (7.2 mL) was added dropwise thereto with stirring at −50° C., and the resulting mixture was stirred at −50° C. for 0.5 hour. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (4.05 g) as a yellow foam.

Mass spectrum (EI, m/z): 417 [M$^+$]

Reference Example 1-(g)

Production of methyl 3-(1,4-dimethyl-1H-benzo[d][1,2,3]triazol-5-yl)-3-(3-(((4-methoxybenzyl)oxy)methyl)-4-methylphenyl)-2,2-dimethylpropanoate

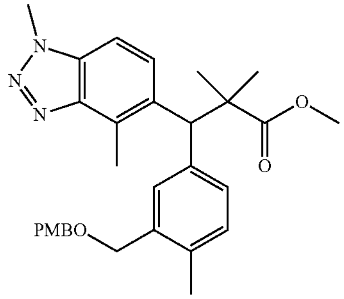

To a solution of (1,4-dimethyl-1H-benzo[d][1, 2, 3]triazol-5-yl) (3-(((4-methoxybenzyl)oxy)methyl)-4-methylphenyl)methanol produced according to the same manner as the Reference Example 1-(f) (55.5 g) in dehydrated acetonitrile (555 mL) were sequentially added trichloroacetonitrile (26.67 mL) and 1,8-diazabicyclo[5.4.0]-7-undecene (3.97 mL) under argon gas flow with stirring at room temperature, and the resulting mixture was stirred at room temperature for 1 hour. Additionally, 1,8-diazabicyclo[5.4.0]-7-undecene (1.99 mL) was added thereto. Then, dimethylketene methyl trimethylsilyl acetal (67.33 mL) and trifluoromethanesulfonimide (11.21 g) were sequentially added thereto with stirring at room temperature, and the resulting mixture was stirred at room temperature for 0.5 hour. Additionally, dimethylketene methyl trimethylsilyl acetal (total: 6.74 mL) and trifluoromethanesulfonimide (total: 9.35 g) were added dividedly thereto. After the reaction was completed, to the reaction solution was added a saturated aqueous solution of sodium hydrogen carbonate, and the resulting mixed solution was subjected to extraction twice with ethyl acetate. The resulting organic layer was washed with saturated brine, dried over anhydrous magnesium sulfate, filtered, and concentrated under reduced pressure to give residues comprising the title compound (138 g).

Mass spectrum (EST, m/z): 502 $[M+H]^+$

Reference Example 1-(h)

Production of methyl 3-(1,4-dimethyl-1H-benzo[d][1,2,3]triazol-5-yl)-3-(3-(hydroxymethyl)-4-methylphenyl)-2,2-dimethylpropanoate

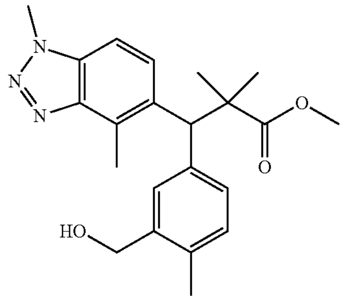 [SMILES: COC(=O)C(C)(C)C(c1ccc(C)c(CO)c1)c1ccc2c(nnn2C)c1C]

To a solution of methyl 3-(1,4-dimethyl-1H-benzo[d][1,2,3]triazol-5-yl)-3-(3-(((4-methoxybenzyl)oxy)methyl)-4-methylphenyl)-2,2-dimethylpropanoate produced in the Reference Example 1-(g) (3.25 g) in a mixture of acetonitrile (22.5 mL)/water (2.5 mL) was added cerium(IV) diammonium nitrate (4.26 g) with stirring at room temperature, and the resulting mixture was stirred at room temperature for 0.5 hour. After the reaction was completed, to the reaction solution was added a saturated aqueous solution of sodium hydrogen carbonate (100 mL), and the resulting mixed solution was subjected to extraction with ethyl acetate. The resulting organic layer was washed with saturated brine (50 mL), dried over anhydrous magnesium sulfate, filtered, and concentrated under reduced pressure. The resulting residues were purified by a silica gel column (elution solvent; hexane:ethyl acetate) to give the title compound (2.01 g) as a pale yellow foam.

Mass spectrum (ESI, m/z): 382 $[M+H]^+$

Reference Example 1-(i)

Production of methyl 3-(1,4-dimethyl-1H-benzo[d][1,2,3]triazol-5-yl)-3-(3-formyl-4-methylphenyl)-2,2-dimethylpropanoate

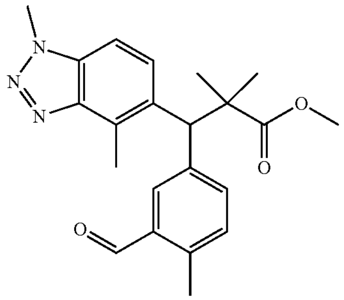 [SMILES: COC(=O)C(C)(C)C(c1ccc(C)c(C=O)c1)c1ccc2c(nnn2C)c1C]

To a solution of methyl 3-(1,4-dimethyl-1H-benzo[d][1,2,3]triazol-5-yl)-3-(3-(hydroxymethyl)-4-methylphenyl)-2,2-dimethylpropanoate produced according to the same manner as the Reference Example 1-(h) (900 mg) in dichloromethane (18 mL) was added Dess-Martin periodinane (1.051 g) under argon gas flow with stirring at 0° C., and the resulting mixture was stirred at 0° C. for 30 minutes. After the reaction was completed, an aqueous solution of sodium thiosulfate and an aqueous solution of sodium hydrogen carbonate were added thereto, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (633 mg) as a white foam.

As an alternative method, the title compound was also produced according to the following method.

To a solution of methyl 3-(1,4-dimethyl-1H-benzo[d][1,2,3]triazol-5-yl)-3-(3-(hydroxymethyl)-4-methylphenyl)-2,2-dimethylpropanoate produced according to the same manner as the Reference Example 1-(h) (1.00 g) in dichloromethane (30 mL) were added 2,2,6,6-tetramethylpiperidine 1-oxyl (20 mg) and iodobenzene diacetate (887 mg) under argon gas flow with stirring at −5° C., and the resulting mixture was stirred at −5° C. for 3 hours. After the reaction was completed, the reaction solution was added to an aqueous solution of sodium thiosulfate, and the resulting mixed solution was subjected to extraction with dichloromethane. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (794 mg) as a white foam.

Mass spectrum (ESI, m/z): 380 [M+H]$^+$

Reference Example 1-(j)

Production of 3-(((4-methoxybenzyl)oxy)methyl)-4-methylbenzaldehyde

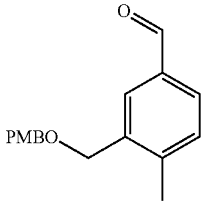

To a solution of 4-bromo-2-(((4-methoxybenzyl)oxy)methyl)-1-methylbenzene produced according to the same manner as the Reference Example 1-(e) (18.0 g) in tetrahydrofuran (180 mL) was added dropwise a 1.6 M solution of n-butyllithium in hexane (42.0 mL) under argon gas flow with stirring at −78° C., and the resulting mixture was stirred at −78° C. for 0.5 hour. Then, dimethylformamide (8.68 mL) was added dropwise thereto with stirring at −78° C., and the resulting mixture was stirred at room temperature for 1 hour. After the reaction was completed, the reaction solution was poured into a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. To the resulting residues was added a mixed solvent of hexane/tert-butyl methyl ether (=19/1), the resulting mixture was stirred, the precipitated solids were filtered, and washed with hexane to give the title compound (10.2 g) as slightly yellow solids.

Alternatively, the filtrate obtained by filtering the precipitated solids was concentrated under reduced pressure, and the resulting residues were purified by a silica gel column (elution solvent; hexane:ethyl acetate) to give the title compound (2.43 g) as a slightly yellow oil.

Mass spectrum (EI, m/z): 270 [M$^+$]

Reference Example 1-(k)

Production of (R)-6-ethyl-2,2-difluoro-6,7,8,9-tetrahydro-[1,3]dioxolo[4',5':4,5]benzo[1,2-f][1,4]oxazepine

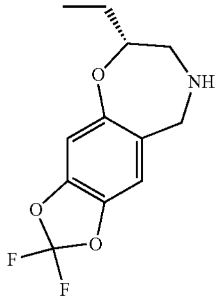 [SMILES: CC[C@@H]1CNCc2cc3c(cc2O1)OC(F)(F)O3]

To a solution of tert-butyl (R)-6-ethyl-2,2-difluoro-6,7-dihydro-[1,3]dioxolo[4',5':4,5]benzo[1,2-f][1,4]oxazepine-8(9H)-carboxylate produced in the Reference Example 1-(c) (495 mg) in tert-butyl methyl ether (5 mL) was added a 4 M solution of hydrogen chloride in cyclopentyl methyl ether (1.4 mL) with stirring at room temperature, and the resulting mixture was stirred at room temperature for 6.5 hours. To the reaction solution was added a saturated aqueous solution of sodium hydrogen carbonate, and the resulting mixed solution was subjected to extraction with ethyl acetate. The resulting organic layer was dried over anhydrous sodium sulfate, filtered, and concentrated under reduced pressure. To a solution of the resulting residues in tert-butyl methyl ether (1 mL) was added a 4 M solution of hydrogen chloride in cyclopentyl methyl ether (5 mL), and the resulting mixture was stirred at room temperature for 24 hours. After the reaction was completed, to the reaction solution was added a saturated aqueous solution of sodium hydrogen carbonate, and the resulting mixed solution was subjected to extraction with ethyl acetate. The resulting organic layer was dried over anhydrous sodium sulfate, filtered, and concentrated under reduced pressure to give the title compound (336 mg) as light brown solids.

Mass spectrum (ESI, m/z): 258 [M+H]$^+$

Reference Example 2-(a)

Production of 2,2-difluoro-4-hydroxybenzo[d][1,3]dioxole-5-carbaldehyde

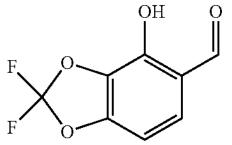 [SMILES: O=Cc1ccc2c(c1O)OC(F)(F)O2]

To a solution of 2,2-difluorobenzo[d][1,3]dioxol-4-ol (1.01 g) in trifluoroacetic acid (10 mL) was added hexamethylenetetramine (1.13 g) under argon gas flow with stirring at room temperature, and the resulting mixture was stirred at 80° C. for 6 hours. After the reaction was completed, to the reaction solution was added water (25 mL), and the resulting mixture was stirred at room temperature for 30 minutes. The resulting mixed solution was subjected to extraction with tert-butyl methyl ether. The resulting organic layer was washed sequentially with water and saturated brine, dried over anhydrous magnesium sulfate, filtered, and concentrated under reduced pressure. The resulting residues were purified by a silica gel column (elution solvent; hexane:ethyl acetate) to give the title compound (0.18 g) as red-purple solids.

Mass spectrum (ESI, m/z): 201 $[M-H]^-$

Reference Example 2-(b)

Production of tert-butyl (S)-((2,2-difluoro-4-hydroxybenzo[d][1,3]dioxol-5-yl)methyl) (2-hydroxybutyl) carbamate

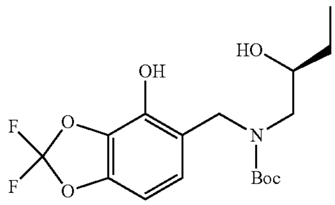 [SMILES: CC[C@H](O)CN(Cc1ccc2c(c1O)OC(F)(F)O2)C(=O)OC(C)(C)C]

A solution of 2,2-difluoro-4-hydroxybenzo[d][1,3]dioxole-5-carbaldehyde produced in the Reference Example 2-(a) (102 mg) and (2S)-1-amino-2-butanol (55 mg) in dichloromethane (2 mL) was stirred under argon gas flow at room temperature for 1 hour. Then, sodium triacetoxyborohydride (211 mg) was added thereto, and the resulting mixture was stirred at room temperature overnight. After the reaction was completed, to the reaction solution was added a saturated aqueous solution of sodium hydrogen carbonate, and the resulting mixed solution was subjected to extraction with dichloromethane. The resulting organic layer was concentrated under reduced pressure, to the resulting residues were added methanol (2.00 mL) and a 8 M aqueous solution of sodium hydroxide (0.618 mL), di-tert-butyl dicarbonate (0.227 mL) was added thereto, and the resulting mixture was stirred at room temperature for 2 hours. Additionally, di-tert-butyl dicarbonate (0.227 mL) was added thereto with stirring at room temperature, and the resulting mixture was stirred at room temperature for 0.5 hour. Additionally, di-tert-butyl dicarbonate (0.227 mL) was added thereto with stirring at room temperature, and the resulting mixture was stirred at room temperature for 0.5 hour. Additionally, di-tert-butyl dicarbonate (0.227 mL) was added thereto with stirring at room temperature, and the resulting mixture was stirred at room temperature for 1.5 hours. Additionally, a 8 M aqueous solution of sodium hydroxide (0.618 mL) was added thereto with stirring at room temperature, the resulting mixture was stirred at room temperature for 0.5 hour, and then left to stand weekend. 1 M hydrochloric acid was added thereto to adjust the pH to 5, and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (178 mg) as a pale yellow oil.

Mass spectrum (ESI, m/z): 376 $[M+H]^+$

Reference Example 2-(c)

Production of tert-butyl (R)-9-ethyl-2,2-difluoro-8,9-dihydro-[1,3]dioxolo[4',5':3,4]benzo[1,2-f][1,4]oxazepine-7(6H)-carboxylate

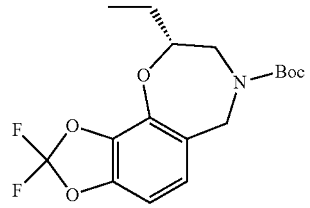 [SMILES: CC[C@@H]1CN(C(=O)OC(C)(C)C)Cc2ccc3c(c2O1)OC(F)(F)O3]

To a solution of tert-butyl (S)-((2,2-difluoro-4-hydroxybenzo[d][1,3]dioxol-5-yl)methyl) (2-hydroxybutyl)carbamate produced in the Reference Example 2-(b) (175 mg) and triphenylphosphine (151 mg) in tetrahydrofuran (2 mL) was added a 1.9 M solution of diisopropyl azodicarboxylate in toluene (0.294 mL) under argon gas flow with stirring at 0° C., and the resulting mixture was stirred at room temperature for 20 hours. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica column (elution solvent; hexane:ethyl acetate) to give the title compound (113 mg) as a yellow oil.

Reference Example 2-(d)

Production of (R)-9-ethyl-2,2-difluoro-6,7,8,9-tetrahydro-[1,3]dioxolo[4',5':3,4]benzo[1,2-f][1,4]oxazepine

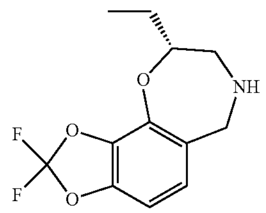 [SMILES: CC[C@@H]1CNCc2ccc3c(c2O1)OC(F)(F)O3]

To a solution of tert-butyl (R)-9-ethyl-2,2-difluoro-8,9-dihydro-[1,3]dioxolo[4',5':3,4]benzo[1,2-f][1,4]oxazepine-7(6H)-carboxylate produced in the Reference Example 2-(c) (113 mg) in tert-butyl methyl ether (1 mL) was added a 4 M solution of hydrogen chloride in 1,4-dioxane (0.237 mL) with stirring at room temperature, and the resulting mixture was stirred at room temperature for 1.5 hours. Additionally, a 4 M solution of hydrogen chloride in 1,4-dioxane (0.237 mL) was added thereto with stirring at room temperature, and the resulting mixture was stirred at room temperature for 17 hours. After the reaction was completed, to the reaction solution was added a saturated aqueous solution of sodium hydrogen carbonate, and the resulting mixed solution was subjected to extraction with ethyl acetate. The resulting organic layer was dried over sodium sulfate, filtered, and dried under reduced pressure. The resulting residues were purified by a silica gel column (elution solvent; ethyl acetate:methanol) to give the title compound (29 mg) as a colorless oil.

Mass spectrum (ESI, m/z): 258 $[M+H]^+$

Reference Example 3-(a)

Production of 6-hydroxy-2,3-dihydro-1H-indene-5-carbaldehyde

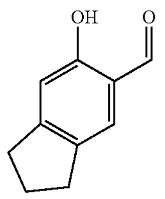 [SMILES: O=Cc1cc2c(cc1O)CCC2]

To a solution of 2,3-dihydro-1H-inden-5-ol. (3.00 g) in trifluoroacetic acid (40 mL) was added hexamethylenetetramine (4.39 g) under argon gas flow with stirring at room temperature, and the resulting mixture was stirred at 80° C. for 5 hours. After the reaction was completed, to the reaction solution was added water, and the resulting mixed solution was subjected to extraction with ethyl acetate. The resulting organic layer was washed sequentially with a saturated aqueous solution of sodium hydrogen carbonate and saturated brine, dried over anhydrous magnesium sulfate, filtered, and concentrated under reduced pressure. The resulting residues were purified by a silica gel column (elution solvent; hexane ethyl acetate) to give the title compound (1.04 g) as white solids.

Mass spectrum (CI, m/z): 163 $[M+H]^+$

Reference Example 3-(b)

Production of tert-butyl (S)-((6-hydroxy-2,3-dihydro-1H-inden-5-yl)methyl) (2-hydroxybutyl)carbamate

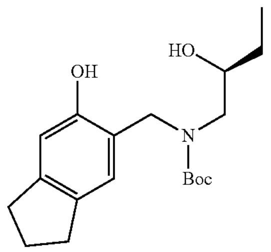 [SMILES: CC[C@H](O)CN(Cc1cc2c(cc1O)CCC2)C(=O)OC(C)(C)C]

A solution of 6-hydroxy-2,3-dihydro-1H-indene-5-carbaldehyde produced in the Reference Example 3-(a) (100 mg) and (2S)-1-amino-2-butanol (66 mg) in dichloromethane (2 mL) was stirred under argon gas flow at room temperature for 1 hour. Then, sodium triacetoxyborohydride (271 mg) was added thereto, and the resulting mixture was stirred at room temperature overnight. After the reaction was completed, to the reaction solution was added a saturated aqueous solution of sodium hydrogen carbonate, and the resulting mixed solution was subjected to extraction with dichloromethane. The resulting organic layer was concentrated under reduced pressure, to the resulting residues were added methanol (2.00 mL), a 8 M aqueous solution of sodium hydroxide (0.771 mL), and di-tert-butyl dicarbonate (0.567 mL), and the resulting mixture was stirred at room temperature for 1 hour. Additionally, a 8 M aqueous solution of sodium hydroxide (0.771 mL) and di-tert-butyl dicarbonate (0.567 mL) were added thereto with stirring at room temperature, and the resulting mixture was stirred at room temperature for 0.5 hour. Additionally, a 8 M aqueous solution of sodium hydroxide (0.771 mL) and di-tert-butyl dicarbonate (0.567 mL) were added thereto with stirring at room temperature, and the resulting mixture was stirred at room temperature for 0.5 hour. Additionally, a 8 M aqueous solution of sodium hydroxide (0.771 mL) and di-tert-butyl dicarbonate (0.567 mL) were added thereto with stirring at room temperature, and the resulting mixture was stirred at room temperature for 0.5 hour. Additionally, a 8 M aqueous solution of sodium hydroxide (0.771 mL) was added thereto with stirring at room temperature, and the resulting mixture was stirred at room temperature overnight. Additionally, a 8 M aqueous solution of sodium hydroxide (0.771 mL) was added thereto with stirring at room temperature, and the resulting mixture was stirred at room temperature for 4 hours. 1 M hydrochloric acid was added thereto to adjust the pH to 5, and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (168 mg) as a colorless oil.

Mass spectrum (ESI, m/z): 334 $[M-H]^-$

Reference Example 3-(c)

Production of tert-butyl (R)-2-ethyl-2,3,5,7,8,9-hexahydro-4H-indeno[5,6-f][1,4]oxazepine-4-carboxylate

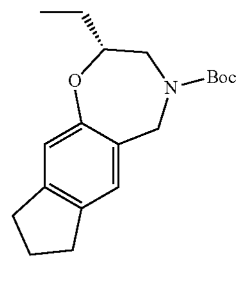 [SMILES: CC[C@@H]1CN(C(=O)OC(C)(C)C)Cc2cc3c(cc2O1)CCC3]

To a solution of tert-butyl (S)-((6-hydroxy-2,3-dihydro-1H-inden-5-yl)methyl) (2-hydroxybutyl)carbamate produced in the Reference Example 3-(b) (168 mg) and triphenylphosphine (145 mg) in tetrahydrofuran (5 mL) was added a 1.9 M solution of diisopropyl azodicarboxylate in toluene (0.290 mL) under argon gas flow with stirring at 0° C., and the resulting mixture was stirred at room temperature for 15 hours. Then, triphenylphosphine (144 mg) and a 1.9 M solution of diisopropyl azodicarboxylate in toluene (0.290 mL) were added thereto with stirring at room temperature, and the resulting mixture was stirred at room temperature for 3.5 hours. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (128 mg) as a colorless oil.

Mass spectrum (ESI, m/z): 318 $[M+H]^+$

Reference Example 3-(d)

Production of (R)-2-ethyl-3,4,5,7,8,9-hexahydro-2H-indeno[5,6-f][1,4]oxazepine

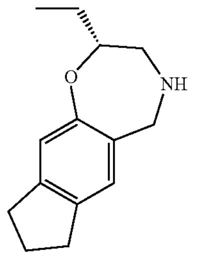 [SMILES: CC[C@@H]1CNCc2cc3c(cc2O1)CCC3]

To a solution of tert-butyl (R)-2-ethyl-2,3,5,7,8,9-hexahydro-4H-indeno[5,6-f][1,4]oxazepine-4-carboxylate produced in the Reference Example 3-(c) (128 mg) in tert-butyl methyl ether (1 mL) was added a 4 M solution of hydrogen chloride in 1,4-dioxane (0.403 mL) with stirring at room temperature, and the resulting mixture was stirred at room temperature for 1.5 hours. Additionally, a 4 M solution of hydrogen chloride in 1,4-dioxane (0.403 mL) was added thereto with stirring at room temperature, and the resulting mixture was stirred at room temperature for 21.5 hours. After the reaction was completed, to the reaction solution were added 2 M hydrochloric acid and tert-butyl methyl ether to separate the solution. To the resulting aqueous layer was added a 1 M aqueous solution of sodium hydroxide, and the resulting mixture was subjected to extraction with ethyl acetate. The resulting organic layer was dried over anhydrous sodium sulfate, filtered, and dried under reduced pressure to give the title compound (46 mg) as a colorless oil.

Mass spectrum (ESI, m/z): 218 $[M+H]^+$

Reference Example 4-(a) and Reference Example 5-(a)

Production of 3-hydroxy-5,6,7,8-tetrahydronaphthalene-2-carbaldehyde and 2-hydroxy-5,6,7,8-tetrahydronaphthalene-1-carbaldehyde

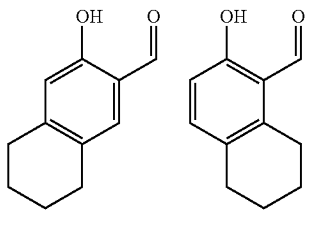

To a solution of 5,6,7,8-tetrahydro-2-naphthol (1.50 g) in trifluoroacetic acid (15 mL) was added dividedly hexamethylenetetramine (2.00 g) under argon atmosphere with stirring at room temperature, and the resulting mixture was stirred at 80° C. under reflux for 6 hours. After the reaction was completed, to the reaction solution was added water (30 mL), and the resulting mixture was stirred at room temperature for 30 minutes. The resulting mixed solution was subjected to extraction with tert-butyl methyl ether. The resulting organic layer was washed sequentially with water and saturated brine, dried over anhydrous magnesium sulfate, filtered, and concentrated under reduced pressure. The resulting residues were purified by a silica gel column (elution solvent; hexane:ethyl acetate) to give a mixture (211 mg) of 3-hydroxy-5,6,7,8-tetrahydronaphthalene-2-carbaldehyde (Reference Example 4-(a)) and 2-hydroxy-5,6,7,8-tetrahydronaphthalene-1-carbaldehyde (Reference Example 5-(a)).

Mass spectrum (ESI, m/z): 177 $[M+H]^+$

Reference Example 4-(b) and Reference Example 5-(b)

Production of tert-butyl. (S)-((3-hydroxy-5,6,7,8-tetrahydronaphthalen-2-yl)methyl) (2-hydroxybutyl) carbamate and tert-butyl (S)-((2-hydroxy-5,6,7,8-tetrahydronaphthalen-1-yl)methyl) (2-hydroxybutyl) carbamate

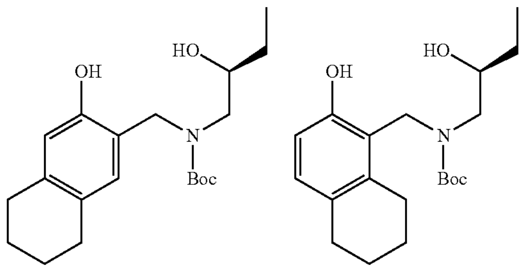 [SMILES: CC[C@H](O)CN(Cc1cc2c(cc1O)CCCC2)C(=O)OC(C)(C)C ; CC[C@H](O)CN(Cc1c(O)ccc2c1CCCC2)C(=O)OC(C)(C)C]

A solution of a mixture (211 mg) of 2-hydroxy-5,6,7,8-tetrahydronaphthalene-1-carbaldehyde and 3-hydroxy-5,6,7,8-tetrahydronaphthalene-2-carbaldehyde produced in the Reference Example 4-(a) and Reference Example 5-(a), and (2S)-1-amino-2-butanol (130 mg) in dichloromethane (2.0 mL) was stirred under argon atmosphere at room temperature for 1 hour. Then, sodium triacetoxyborohydride (510 mg) was added thereto, and the resulting mixture was stirred at room temperature for 16 hours. After the reaction was completed, to the reaction solution was added a saturated aqueous solution of sodium hydrogen carbonate, and the resulting mixed solution was subjected to extraction with dichloromethane. The resulting organic layer was concentrated under reduced pressure, to a solution of the resulting residues in methanol (3.0 mL) was added a 8 M aqueous solution of sodium hydroxide (3.00 mL), di-tert-butyl dicarbonate (2.20 mL) was added thereto under ice-cooling, and the resulting mixture was stirred at room temperature for 2 hours. Additionally, di-tert-butyl dicarbonate (2.20 mL) was added thereto, and the resulting mixture was stirred at room temperature for 2 hours. Additionally, a 8 M aqueous solution of sodium hydroxide (1.50 mL) was added thereto with stirring at room temperature, and the resulting mixture was stirred at room temperature for 16 hours. 1 M hydrochloric acid was added thereto to adjust the pH to 5.0, and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give a mixture (226 mg) of tert-butyl (S)-((3-hydroxy-5,6,7,8-tetrahydronaphthalen-2-yl)methyl) (2-hydroxybutyl)carbamate (Reference Example 4-(b)) and tert-butyl (S)-((2-hydroxy-5,6,7,8-tetrahydronaphthalen-1-yl)methyl) (2-hydroxybutyl)carbamate (Reference Example 5-(b)) as a colorless oil.

Mass spectrum (ESI, m/z): 350 $[M+H]^+$

Reference Example 4-(c)

Production of tert-butyl (R)-2-ethyl-2,3,7,8,9,10-hexahydronaphtho[2,3-f][1,4]oxazepine-4 (5H)-carboxylate

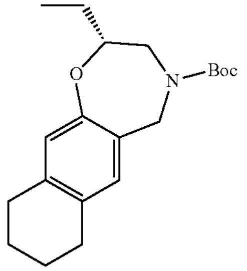 [SMILES: CC[C@@H]1CN(C(=O)OC(C)(C)C)Cc2cc3c(cc2O1)CCCC3]

To a solution of a mixture (226 mg) of tert-butyl (S)-((3-hydroxy-5,6,7,8-tetrahydronaphthalen-2-yl)methyl) (2-hydroxybutyl)carbamate and tert-butyl (S)-((2-hydroxy-5,6,7,8-tetrahydronaphthalen-1-yl)methyl) (2-hydroxybutyl) produced in the Reference Example 4-(b) and Reference Example 5-(b), and triphenylphosphine (205 mg) in tetrahydrofuran (4.0 mL) was added a 1.9 M solution of diisopropyl azodicarboxylate in toluene (0.410 mL) under argon atmosphere with stirring under ice-cooling, and the resulting mixture was stirred at room temperature for 1 hour. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane ethyl acetate) to give a mixture (162 mg) of the title compound and tert-butyl (R)-4-ethyl-3,4,8,9,10,11-hexahydronaphtho[1,2-f][1,4]oxazepine-2 (1H)-carboxylate. The resulting mixture was separated and purified by supercritical fluid chromatography (column: SFC-A, mobile phase: $CO_2$/methanol=95/5) to give the title compound (21 mg) as a colorless oil. Simultaneously, a mixture (116 mg) of tert-butyl (R)-4-ethyl-3,4,8,9,10,11-hexahydronaphtho[1,2-f][1,4]oxazepine-2(1H)-carboxylate and the title compound was produced. The mixture was separated and purified by supercritical fluid chromatography (column: SFC-A, mobile phase: $CO_2$/methanol=95/5) to give the title compound (6 mg) as a colorless oil.

Reference Example 4-(d)

Production of (R)-2-ethyl-2,3,4,5,7,8,9,10-octahydronaphtho[2,3-f][1,4]oxazepine hydrochloride

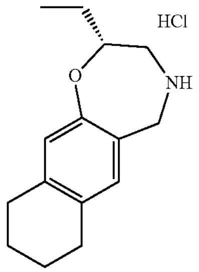 [SMILES: CC[C@@H]1CNCc2cc3c(cc2O1)CCCC3 ; Cl]

To a solution of tert-butyl (R)-2-ethyl-2,3,7,8,9,10-hexahydronaphtho[2,3-f][1,4]oxazepine-4(5H)-carboxylate produced in the Reference Example 4-(c) (27 mg) in 1,4-dioxane (0.500 mL) was added a 4 M solution of hydrogen chloride in 1,4-dioxane (0.100 mL) under argon atmosphere with stirring at room temperature, the resulting mixture was stirred at room temperature for 16 hours, and then concentrated under reduced pressure. Additionally, a 4 M solution of hydrogen chloride in 1,4-dioxane (0.200 mL) was added thereto with stirring at room temperature, and the resulting mixture was stirred at room temperature for 16 hours. The reaction solution was concentrated under reduced pressure. To the resulting residues was added tert-butyl methyl ether, the resulting solids were collected by filtration, and dried under reduced pressure to give the title compound (21 mg) as white solids.

Mass spectrum (ESI, m/z): 232 $[M+H]^+$

Reference Example 5-(c)

Production of tert-butyl (R)-4-ethyl-3,4,8,9,10,11-hexahydronaphtho[1,2-f][1,4]oxazepine-2(1H)-carboxylate

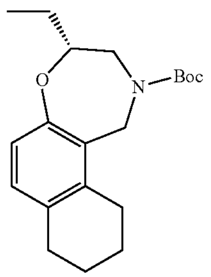 [SMILES: CC[C@@H]1CN(C(=O)OC(C)(C)C)Cc2c(ccc3c2CCCC3)O1]

To a solution of a mixture (226 mg) of tert-butyl (S)-((3-hydroxy-5,6,7,8-tetrahydronaphthalen-2-yl)methyl) (2-hydroxybutyl)carbamate and tert-butyl (S)-((2-hydroxy-5,6,7,8-tetrahydronaphthalen-1-yl)methyl) (2-hydroxybutyl) produced in the Reference Example 4-(b) and Reference Example 5-(b), and triphenylphosphine (205 mg) in tetrahydrofuran (4.0 mL) was added a 1.9 M solution of diisopropyl azodicarboxylate in toluene (0.410 mL) under argon atmosphere with stirring under ice-cooling, and the resulting mixture was stirred at room temperature for 1 hour. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane ethyl acetate) to give a mixture (162 mg) of the title compound and tert-butyl (R)-4-ethyl-3,4,8,9,10,11-hexahydronaphtho[1,2-f][1,4]oxazepine-2(1H)-carboxylate as a colorless oil. The resulting mixture was separated and purified by supercritical fluid chromatography (column: SFC-A, mobile phase: $CO_2$/methanol=95/5) to give a mixture (116 mg) of tert-butyl (R)-2-ethyl-2,3,7,8,9,10-hexahydronaphtho[2,3-f][1,4]oxazepine-4(5H)-carboxylate and the title compound. The mixture was separated and purified by supercritical fluid chromatography (column: SFC-A, mobile phase: $CO_2$/methanol=95/5) to give the title compound (87 mg).

Reference Example 5-(d)

Production of (R)-4-ethyl-1,2,3,4,8,9,10,11-octahydronaphtho[1,2-f][1,4]oxazepine hydrochloride

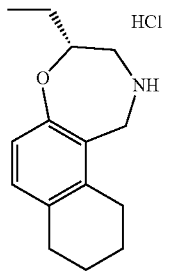 [SMILES: CC[C@@H]1CNCc2c(ccc3c2CCCC3)O1 ; Cl]

To a solution of tert-butyl (R)-4-ethyl-3,4,8,9,10,11-hexahydronaphtho[1,2-f][1,4]oxazepine-2(1H)-carboxylate produced in the Reference Example 5-(c) (87 mg) in 1,4-dioxane (1.50 mL) was added a 4 M solution of hydrogen chloride in 1,4-dioxane (0.300 mL) under argon atmosphere with stirring at room temperature, and the resulting mixture was stirred at room temperature for 16 hours. Additionally, a 4 M solution of hydrogen chloride in 1,4-dioxane (0.700 mL) was added thereto with stirring at room temperature, and the resulting mixture was stirred at room temperature for 16 hours. After the reaction was completed, the reaction solution was concentrated under reduced pressure. To the resulting concentrated residues was added tert-butyl methyl ether, the resulting solids were collected by filtration, and dried under reduced pressure to give the title compound (65 mg) as white solids.

Mass spectrum (ESI, m/z): 232 $[M+H]^+$

Reference Example 6-(a)

Production of 4-hydroxy-2,3-dihydro-1H-indene-5-carbaldehyde

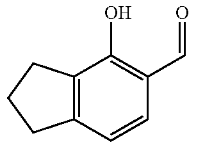 [SMILES: O=Cc1ccc2c(c1O)CCC2]

To a solution of 2,3-dihydro-1H-inden-4-ol. (1.50 g) in trifluoroacetic acid (15 mL) was added dividedly hexamethylenetetramine (1.75 g) under argon atmosphere with stirring at room temperature, and the resulting mixture was stirred at 80° C. under reflux for 6 hours. After the reaction was completed, to the reaction solution was added water (30 mL), and the resulting mixture was stirred at room temperature for 30 minutes. The resulting mixed solution was subjected to extraction with tert-butyl methyl ether. The resulting organic layer was washed sequentially with water and saturated brine, dried over anhydrous magnesium sulfate, filtered, and concentrated under reduced pressure. The resulting residues were purified by a silica gel column (elution solvent; hexane:ethyl acetate) to give the title compound (152 mg) as white solids.

As an alternative method, the title compound was also produced according to the following method.

To a solution of 2,3-dihydro-1H-inden-4-ol (500 mg), triethylamine (1.92 mL), and magnesium chloride (887 mg) in acetonitrile (2 mL) was added paraformaldehyde (683 mg) under argon gas flow with stirring at room temperature, and the resulting mixture was stirred under reflux for 1.5 hours. After the reaction was completed, the reaction solution was allowed to cool to room temperature, a saturated aqueous solution of ammonium chloride was added thereto, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (434 mg) as white solids.

Mass spectrum (CI, m/z): 163 $[M+H]^+$

Reference Example 6-(b)

Production of tert-butyl (S)-((4-hydroxy-2,3-dihydro-1H-inden-5-yl)methyl) (2-hydroxybutyl)carbamate

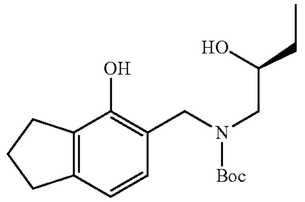 [SMILES: CC[C@H](O)CN(Cc1ccc2c(c1O)CCC2)C(=O)OC(C)(C)C]

A solution of 4-hydroxy-2,3-dihydro-1H-indene-5-carbaldehyde produced in the Reference Example 6-(a) (100 mg) and (2S)-1-amino-2-butanol (66 mg) in dichloromethane (2.0 mL) was stirred under argon atmosphere at room temperature for 1 hour. Then, sodium triacetoxyborohydride (260 mg) was added thereto, and the resulting mixture was stirred at room temperature for 16 hours. Then, (2S)-1-amino-2-butanol (33 mg) and sodium triacetoxyborohydride (260 mg) were added thereto with stirring at room temperature, and the resulting mixture was stirred at room temperature for 3 hours. After the reaction was completed, to the reaction solution was added a saturated aqueous solution of sodium hydrogen carbonate, and the resulting mixed solution was subjected to extraction with dichloromethane. The resulting organic layer was concentrated under reduced pressure, to a solution of the resulting residues in tetrahydrofuran (3.0 mL) was added a 8 M aqueous solution of sodium hydroxide (1.60 mL), di-tert-butyl dicarbonate (1.20 mL) was added thereto under ice-cooling, and the resulting mixture was stirred at room temperature for 4 hours. Then, methanol (3.0 mL) and a 8 M aqueous solution of sodium hydroxide (0.80 mL) were added thereto with stirring at room temperature, and the resulting mixture was stirred at room temperature for 16 hours. 1 M hydrochloric acid was added thereto to adjust the pH to 5.0, and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (107 mg) as a colorless oil.

Mass spectrum (EST, m/z): 336 $[M+H]^+$

Reference Example 6-(c)

Production of tert-butyl (R)-2-ethyl-2,3,5,8,9,10-hexahydro-4H-indeno[5,4-f][1,4]oxazepine-4-carboxylate

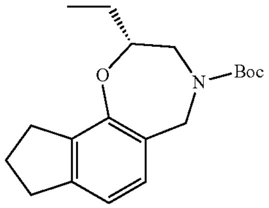 [SMILES: CC[C@@H]1CN(C(=O)OC(C)(C)C)Cc2ccc3c(c2O1)CCC3]

To a solution of tert-butyl (S)-((4-hydroxy-2,3-dihydro-1H-inden-5-yl)methyl) (2-hydroxybutyl)carbamate produced in the Reference Example 6-(b) (107 mg) and triphenylphosphine (100 mg) in tetrahydrofuran (2.0 mL) was added a 1.9 M solution of diisopropyl azodicarboxylate in toluene (0.200 mL) under argon atmosphere with stirring under ice-cooling, and the resulting mixture was stirred at room temperature for 16 hours. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (54 mg) as a colorless oil.

Reference Example 6-(d)

Production of (R)-2-ethyl-3,4,5,8,9,10-hexahydro-2H-indeno[5,4-f][1,4]oxazepine hydrochloride

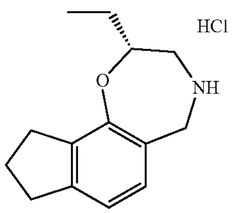 [SMILES: CC[C@@H]1CNCc2ccc3c(c2O1)CCC3 ; Cl]

To a solution of tert-butyl (R)-2-ethyl-2,3,5,8,9,10-hexahydro-4H-indeno[5,4-f][1,4]oxazepine-4-carboxylate produced in the Reference Example 6-(c) (54 mg) in 1,4-dioxane (0.500 mL) was added a 4 M solution of hydrogen chloride in 1,4-dioxane (0.170 mL) under argon atmosphere with stirring at room temperature, the resulting mixture was stirred at room temperature for 16 hours, and then concentrated under reduced pressure. Additionally, a 4 M solution of hydrogen chloride in 1,4-dioxane (0.430 mL) was added thereto with stirring at room temperature, and the resulting mixture was stirred at room temperature for 40 hours. The reaction solution was concentrated under reduced pressure. To the resulting concentrated residues was added tert-butyl methyl ether, the resulting solids were collected by filtration, and dried under reduced pressure to give the title compound (30 mg) as white solids.

Mass spectrum (ESI, m/z): 218 $[M+H]^+$

Reference Example 7-(a)

Production of 1-hydroxy-5,6,7,8-tetrahydronaphthalene-2-carbaldehyde

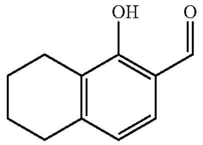 [SMILES: O=Cc1ccc2c(c1O)CCCC2]

To a solution of 5,6,7,8-tetrahydronaphthalen-1-ol (1.0 g) in tetrahydrofuran (10 mL) were added magnesium chloride (0.56 mL), N,N-diisopropylethylamine (2.36 mL), and paraformaldehyde (0.81 g) under argon gas flow with stirring at room temperature, and the resulting mixture was stirred at 70° C. for 6 hours. After the reaction was completed, to the reaction solution was added 1 M hydrochloric acid, and the resulting mixed solution was subjected to extraction with ethyl acetate. The resulting organic layer was washed with water, dried over anhydrous magnesium sulfate, filtered, and concentrated under reduced pressure. The resulting residues were purified by a silica gel column (elution solvent; hexane:ethyl acetate) to give the title compound (372 mg) as a slightly yellow oil.

Mass spectrum (ESI, m/z): 177 $[M+H]^+$

Reference Example 7-(b)

Production of tert-butyl (S)-((1-hydroxy-5,6,7,8-tetrahydronaphthalen-2-yl)methyl) (2-hydroxybutyl) carbamate

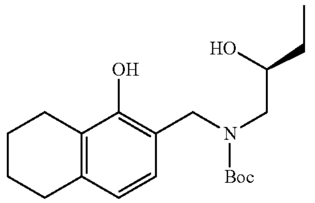 [SMILES: CC[C@H](O)CN(Cc1ccc2c(c1O)CCCC2)C(=O)OC(C)(C)C]

To a solution of 1-hydroxy-5,6,7,8-tetrahydronaphthalene-2-carbaldehyde produced in the Reference Example 7-(a) (372 mg) in dichloromethane (6 mL) were added (2S)-1-amino-2-butanol (232 mg) and acetic acid (0.181 mL) under argon gas flow with stirring at room temperature, and the resulting mixture was stirred at room temperature for 2 hours. Then, sodium triacetoxyborohydride (895 mg) was added thereto with stirring at room temperature, and the resulting mixture was stirred at room temperature for 22 hours. After the reaction was completed, to the reaction solution was added a saturated aqueous solution of sodium hydrogen carbonate, and the resulting mixed solution was subjected to extraction with dichloromethane. The resulting organic layer was concentrated under reduced pressure, to a solution of the resulting residues in methanol (3.0 mL) was added a 8 M aqueous solution of sodium hydroxide (5.30 mL), di-tert-butyl dicarbonate (0.970 mL) was added thereto under ice-cooling, and the resulting mixture was stirred at room temperature for 2 hours. After the reaction was completed, 1 M hydrochloric acid was added thereto to adjust the pH to 5.0, and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane ethyl acetate) to give the title compound (321 mg) as a light brown oil.

Mass spectrum (ESI, m/z): 350 $[M+H]^+$

Reference Example 7-(c)

Production of tert-butyl (R)-2-ethyl-2,3,8,9,10,11-hexahydronaphtho[2,1-f][1,4]oxazepine-4(5H)-carboxylate

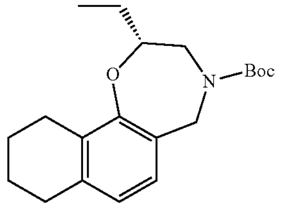 [SMILES: CC[C@@H]1CN(C(=O)OC(C)(C)C)Cc2ccc3c(c2O1)CCCC3]

To a solution of tert-butyl. (S)-((1-hydroxy-5,6,7,8-tetrahydronaphthalen-2-yl)methyl) (2-hydroxybutyl)carbamate produced in the Reference Example 7-(b) (321 mg) in tetrahydrofuran (6 mL) were added triphenylphosphine (291 mg) and a 1.9 M solution of diisopropyl azodicarboxylate in toluene (0.60 mL) under argon gas flow with stirring at 0° C., and the resulting mixture was stirred at room temperature for 22 hours. After the reaction was completed, to the reaction solution was added water, and the resulting mixed solution was subjected to extraction with ethyl acetate. The resulting organic layer was washed with water, dried over anhydrous magnesium sulfate, filtered, and concentrated under reduced pressure. The resulting residues were purified by a silica gel column (elution solvent; hexane:ethyl acetate) to give the title compound (224 mg) as a slightly yellow oil.

Mass spectrum (ESI, m/z): 332 [M+H]

Reference Example 7-(d)

Production of (R)-2-ethyl-2,3,4,5,8,9,10,11-octahydronaphtho[2,1-f][1,4]oxazepine Hydrochloride

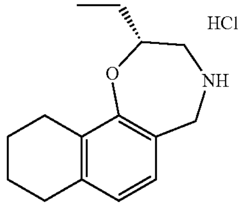 [SMILES: CC[C@@H]1CNCc2ccc3c(c2O1)CCCC3 ; Cl]

To a solution of tert-butyl. (R)-2-ethyl-2,3,8,9,10,11-hexahydronaphtho[2,1-f][1,4]oxazepine-4 (5H)-carboxylate produced in the Reference Example 7-(c) (224 mg) in 1,4-dioxane (2 mL) was added a 4 M solution of hydrogen chloride in 1,4-dioxane (0.845 mL) under argon gas flow with stirring at 0° C., and the resulting mixture was stirred at room temperature for 32 hours. After the reaction was completed, the resulting mixture was concentrated, dried to give a crude product of the title compound (177 mg), and directly used in the next step.

Mass spectrum (ESI, m/z): 232 $[M+H]^+$

Reference Example 8-(a)

Production of methyl (R)-3-((1-((tert-butoxycarbonyl)amino)butan-2-yl)oxy)-2-naphthoate

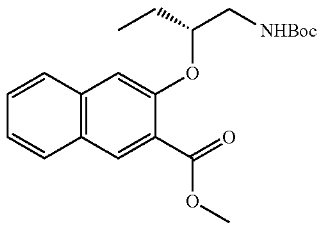 [SMILES: CC[C@H](CNC(=O)OC(C)(C)C)Oc1cc2ccccc2cc1C(=O)OC]

(1) To a solution of (2S)-1-amino-2-butanol (200 mg) in dichloromethane (4 mL) was added di-tert-butyl dicarbonate (0.547 mL) under argon gas flow with stirring at room temperature, and the resulting mixture was stirred at room temperature for 1 hour. After the reaction was completed, the reaction solution was concentrated to give a crude product comprising tert-butyl (S)-(2-hydroxybutyl)carbamate (424 mg).

(2) The crude product (424 mg) comprising tert-butyl (S)-(2-hydroxybutyl)carbamate produced in (1) was subjected to replacement by nitrogen, and dissolved into tetrahydrofuran (7 mL). Methyl 3-hydroxy-2-naphthoate (544 mg), (E)-N1,N1,N2,N2-tetramethyldiazene-1,2-dicarboxamide (579 mg), and tri-n-butylphosphine (0.829 mL) were sequentially added thereto under argon gas flow with stirring at room temperature, and the resulting mixture was stirred at room temperature for 2 hours. After the reaction was completed, the reaction solution was diluted with ethyl acetate, washed sequentially with water and saturated brine, dried over anhydrous magnesium sulfate, and concentrated under reduced pressure. The resulting residues were purified by a silica gel column (elution solvent; hexane:ethyl acetate) to give the title compound (403 mg) as a white foam.

Mass spectrum (ESI, m/z): 374 $[M+H]^+$

Reference Example 8-(b)

Production of methy. (R)-3-((1-aminobutan-2-yl) oxy)-2-naphthoate hydrochloride

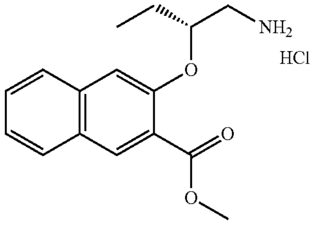 [SMILES: CC[C@H](CN)Oc1cc2ccccc2cc1C(=O)OC ; Cl]

To a solution of methyl (R)-3-((1-((tert-butoxycarbonyl) amino)butan-2-yl)oxy)-2-naphthoate produced in the Reference Example 8-(a) (403 mg) in cyclopentyl methyl ether (3 mL) was added dropwise a 4 M solution of hydrogen chloride in cyclopentyl methyl ether (1.08 mL) under argon gas flow with stirring at room temperature, the resulting mixture was stirred at room temperature for 3 hours, warmed to 60° C., and stirred for 2 hours. After the reaction was completed, the reaction solution was concentrated to give the title compound (334 mg) as white solids.

Mass spectrum (ESI, m/z): 274 $[M+H]^+$

Reference Example 8-(c)

Production of (R)-2-ethyl-3,4-dihydronaphtho[2,3-f] [1,4]oxazepin-5(2H)-one

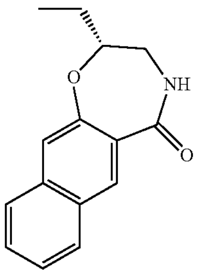 [SMILES: CC[C@@H]1CNC(=O)c2cc3ccccc3cc2O1]

To a solution of methyl (R)-3-((1-aminobutan-2-yl)oxy)-2-naphthoate hydrochloride produced in the Reference Example 8-(b) (334 mg) in methanol (8 mL) was added sodium hydride (188 mg) under argon gas flow with stirring at 0° C., and the resulting mixture was stirred at room temperature for 1 hour. After the reaction was completed, the reaction solution was concentrated, and a saturated aqueous solution of ammonium chloride was added thereto. The resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (218 mg) as white solids.

Mass spectrum (ESI, m/z): 242 $[M+H]^+$

Reference Example 8-(d)

Production of (R)-2-ethyl-2,3,4,5-tetrahydronaphtho [2,3-f][1,4]oxazepine

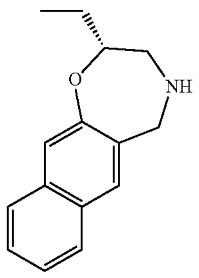 [SMILES: CC[C@@H]1CNCc2cc3ccccc3cc2O1]

To a solution of (R)-2-ethyl-3,4-dihydronaphtho[2,3-f][1,4]oxazepin-5(2H)-one produced in the Reference Example 8-(c) (218 mg) in tetrahydrofuran (4 mL) was added dropwise a 0.9 M solution of borane-tetrahydrofuran complex in tetrahydrofuran (3.01=L) under argon gas flow with stirring at room temperature, and the resulting mixture was stirred at room temperature for 3 hours and at 60° C. for 3 hours. After the reaction was completed, ethanol (0.317 mL) was added thereto, and the resulting mixture was stirred for 1 hour. The reaction solution was concentrated, and then the resulting residues were dissolved into cyclopentyl methyl ether (2 mL). A 4 M solution of hydrogen chloride in cyclopentyl methyl ether (2 mL) was added thereto, and the resulting mixture was stirred for 30 minutes. A 4 M aqueous solution of sodium hydroxide (2 mL) was added thereto, and the resulting mixture was stirred for a while. A saturated aqueous solution of sodium hydrogen carbonate (10 mL) was added thereto. The resulting mixed solution was subjected to extraction three times with ethyl acetate. The resulting organic layer was dried over anhydrous magnesium sulfate, filtered, and concentrated under reduced pressure. The resulting residues were purified by a silica gel column (elution solvent; ethyl acetate:methanol) to give the title compound (113 mg) as a colorless oil.

Mass spectrum (ESI, m/z): 228 $[M+H]^+$

Reference Example 9-(a)

Production of (R)-1-(((2-chloroquinolin-3-yl) methyl)amino)butan-2-ol

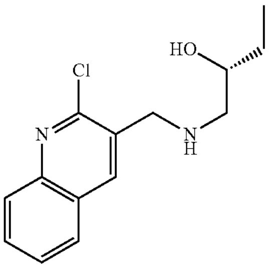 [SMILES: CC[C@@H](O)CNCc1cc2ccccc2nc1Cl]

To a solution of 2-chloroquinoline-3-carbaldehyde (300 mg) in dichloromethane (5 mL) was added (2R)-1-amino- 2-butanol (167 mg) under argon gas flow with stirring at room temperature, and the resulting mixture was stirred at room temperature for 30 minutes. Then, sodium triacetoxyborohydride (664 mg) was added thereto with stirring at room temperature, and the resulting mixture was stirred at room temperature for 24 hours. After the reaction was completed, to the reaction solution was added water, and the resulting mixed solution was subjected to extraction twice with ethyl acetate. The resulting organic layer was dried over anhydrous magnesium sulfate, filtered, and concentrated under reduced pressure. The resulting residues were purified by a silica gel column (elution solvent; hexane:ethyl acetate) to give the title compound (247 mg) as white solids.

Mass spectrum (ESI, m/z): 265 $[M+H]^+$

Reference Example 9-(b)

Production of (R)-2-ethyl-2,3,4,5-tetrahydro-[1,4]oxazepino[7,6-b]quinoline

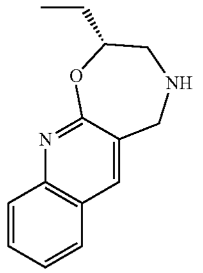 [SMILES: CC[C@@H]1CNCc2cc3ccccc3nc2O1]

To a solution of (R)-1-(((2-chloroquinolin-3-yl)methyl)amino)butan-2-ol produced in the Reference Example 9-(a) (227 mg) in dimethyl sulfoxide (6 mL) was added potassium tert-butoxide (115 mg) under argon atmosphere with stirring at room temperature, and the resulting mixture was stirred at room temperature for 1 hour. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; ethyl acetate:methanol) to give the title compound (204 mg) as a brown oil.

Mass spectrum (ESI, m/z): 229 $[M+H]^+$

Reference Example 10-(a)

Production of (R)-1-(((3-bromoquinolin-2-yl)methyl)amino)butan-2-ol

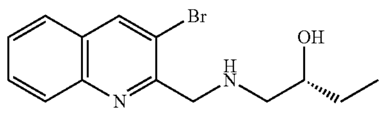 [SMILES: CC[C@@H](O)CNCc1nc2ccccc2cc1Br]

To a solution of 3-bromoquinoline-2-carbaldehyde (300 mg) in dichloromethane (5 mL) was added (2R)-1-amino-2-butanol (0.144 mL) under argon gas flow with stirring at room temperature, and the resulting mixture was stirred at room temperature for 30 minutes. Then, sodium triacetoxyborohydride (539 mg) was added thereto with stirring at room temperature, and the resulting mixture was stirred at room temperature for 24 hours. After the reaction was completed, to the reaction solution was added a saturated aqueous solution of sodium hydrogen carbonate, and the resulting mixed solution was subjected to extraction twice with ethyl acetate. The resulting organic layer was dried over anhydrous magnesium sulfate, filtered, and concentrated under reduced pressure. The resulting residues were purified by a silica gel column (elution solvent; hexane:ethyl acetate) to give the title compound (350 mg) as a colorless oil.

Mass spectrum (ESI, m/z): 309 $[M+H]^+$

Reference Example 10-(b)

Production of (R)-2-ethyl-2,3,4,5-tetrahydro-[1,4]oxazepino[6,7-b]quinoline

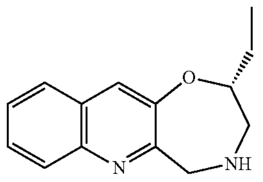 [SMILES: CC[C@@H]1CNCc2nc3ccccc3cc2O1]

To a solution of (R)-1-(((3-bromoquinolin-2-yl)methyl)amino)butan-2-ol produced in the Reference Example 10-(a) (350 mg) in 2-propanol (7 mL) were sequentially added cesium carbonate (738 mg) and copper(I) iodide (108 mg) under argon gas flow with stirring at room temperature, and the resulting mixture was stirred at 90° C. for 3 hours. Copper(I) iodide (100 mg) was added thereto, and the resulting mixture was stirred at 90° C. for 3 hours. After the reaction was completed, the resulting precipitates were removed by filtration, and washed with ethyl acetate. The resulting filtrate was concentrated, and the resulting residues were purified by a silica gel column (elution solvent; ethyl acetate:methanol) to give the title compound (27 mg) as a yellow oil.

As an alternative method, the title compound was also produced according to the following method.

To a solution of (R)-1-(((3-bromoquinolin-2-yl)methyl)amino)butan-2-ol produced according to the same manner as the Reference Example 10-(a) (554 mg) in dimethyl sulfoxide (50 mL) were sequentially added cesium carbonate (1.18 g), N,N-dimethylglycine (36 mg), and copper(I) iodide (31 mg) under argon gas flow with stirring at room temperature, and the resulting mixture was stirred at 100° C. for 2 hours. After the reaction was completed, to the reaction solution was added water, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; ethyl acetate:methanol) to give the title compound (95 mg) as a brown oil.

Mass spectrum (ESI, m/z): 229 $[M+H]^+$

Reference Example 10-(c)

Production of methyl 3-(3-(chloromethyl)-4-methylphenyl)-3-(1,4-dimethyl-1H-benzo[d][1,2,3]triazol-5-yl)-2,2-dimethylpropanoate

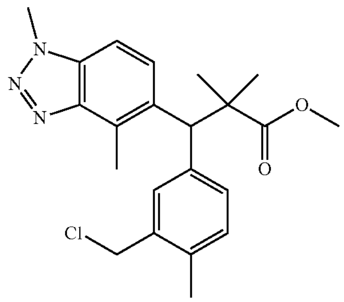 [SMILES: COC(=O)C(C)(C)C(c1ccc(C)c(CCl)c1)c1ccc2c(nnn2C)c1C]

To a solution of methyl 3-(1,4-dimethyl-1H-benzo[d][1,2,3]triazol-5-yl)-3-(3-(hydroxymethyl)-4-methylphenyl)-2,2-dimethylpropanoate produced according to the same manner as the Reference Example 1-(h) (40 mg) in dichloromethane (3 mL) was added dropwise thionyl chloride (0.015 mL) under argon gas flow with stirring at room temperature, and the resulting mixture was stirred at room temperature for 2 hours. After the reaction was completed, the reaction solution was concentrated to give the title compound (41 mg).

Mass spectrum (ESI, m/z): 400 $[M+H]^+$

Reference Example 11-(a)

Production of (R)-1-(((7-fluoroquinolin-6-yl)methyl)amino)butan-2-ol

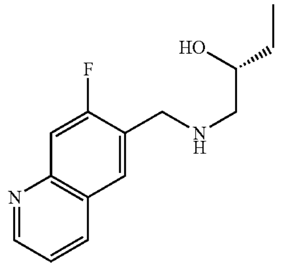 [SMILES: CC[C@@H](O)CNCc1cc2cccnc2cc1F]

A solution of 7-fluoroquinoline-6-carbaldehyde (0.500 g) and (2R)-1-amino-2-butanol (0.383 g) in dichloromethane (10 mL) was stirred under argon gas flow at room temperature for 0.5 hour. Then, sodium triacetoxyborohydride (1.28 g) was added thereto with stirring at room temperature, and the resulting mixture was stirred at room temperature overnight. After the reaction was completed, to the reaction solution was added a saturated aqueous solution of sodium hydrogen carbonate, and the resulting mixed solution was subjected to extraction twice with dichloromethane. The resulting organic layer was concentrated under reduced pressure, and the resulting residues were purified by a silica gel column (elution solvent; ethyl acetate:methanol) to give the title compound (0.723 g) as a yellow oil.

Mass spectrum (ESI, m/z): 249 [M+H]

Reference Example 11-(b)

Production of tert-butyl (R)-2-ethyl-2,3-dihydro-[1,4]oxazepino[6,7-g]quinoline-4(5H)-carboxylate

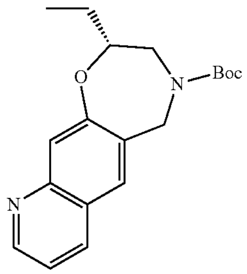 [SMILES: CC[C@@H]1CN(C(=O)OC(C)(C)C)Cc2cc3cccnc3cc2O1]

To a solution of (R)-1-(((7-fluoroquinolin-6-yl)methyl)amino)butan-2-ol produced in the Reference Example 11-(a) (0.723 g) in dimethyl sulfoxide (20 mL) was added potassium tert-butoxide (0.385 g) under argon gas flow with stirring at room temperature, and the resulting mixture was stirred at 90° C. for 1 hour. Then, di-tert-butyl dicarbonate (1.59 mL) was added thereto with stirring at room temperature, and the resulting mixture was stirred at room temperature for 1 hour. After the reaction was completed, to the reaction solution was added a saturated aqueous solution of sodium hydrogen carbonate, and the resulting mixed solution was subjected to extraction with ethyl acetate. The resulting organic layer was dried over anhydrous sodium sulfate, filtered, concentrated under reduced pressure, and the resulting residues were purified by a silica gel column (elution solvent; hexane:ethyl acetate) to give the title compound (0.521 g) as pale yellow solids.

Mass spectrum (ESI, m/z): 329 $[M+H]^+$

Reference Example 11-(c)

Production of (R)-2-ethyl-2,3,4,5-tetrahydro-[1,4]oxazepino[6,7-g]quinoline dihydrochloride

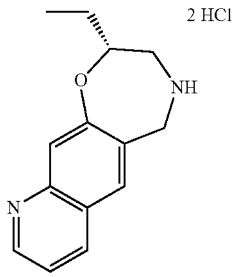 [SMILES: CC[C@@H]1CNCc2cc3cccnc3cc2O1]

2 HCl

To a solution of tert-butyl (R)-2-ethyl-2,3-dihydro-[1,4]oxazepino[6,7-g]quinoline-4(5H)-carboxylate produced in the Reference Example 11-(b) (0.521 g) in 1,4-dioxane (4 ML) was added a 4 M solution of hydrogen chloride in 1,4-dioxane (1.59 mL) with stirring at room temperature, and the resulting mixture was stirred at room temperature for 5 hours. Additionally, a 4 M solution of hydrogen chloride in 1,4-dioxane (1.59 mL) was added thereto with stirring at room temperature, and the resulting mixture was stirred at room temperature for 3 hours. Additionally, a 4 M solution of hydrogen chloride in 1,4-dioxane (1.59 mL) was added thereto with stirring at room temperature, and the resulting mixture was stirred at room temperature for 16 hours. After the reaction was completed, the precipitated solids were filtered, washed with 1,4-dioxane, and dried under reduced pressure at 50° C. to give the title compound (0.340 g) as pale yellow solids.

Mass spectrum (ESI, m/z): 229 $[M+H]^+$

Reference Example 12-(a)

Production of 6-bromo-7-(bromomethyl)quinoline

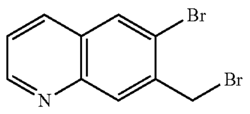 [SMILES: BrCc1cc2ncccc2cc1Br]

To a solution of 6-bromo-7-methylquinoline (500 mg) in dichloroethane (10 mL) were sequentially added N-bromosuccinimide (601 mg) and 2,2'-azobis(isobutyronitrile) (74 mg) under argon gas flow with stirring at room temperature, and the resulting mixture was stirred under heating to reflux for 2 hours. After the reaction was completed, the reaction solution was allowed to cool to room temperature, water was added thereto, and the resulting mixed solution was subjected to extraction with dichloromethane. The resulting organic layer was washed with saturated brine, dried over anhydrous magnesium sulfate, filtered, concentrated under reduced pressure, and the resulting residues were purified by a silica gel column (elution solvent; hexane:ethyl acetate) to give the title compound (265 mg) as white solids.

As an alternative method, the title compound was also produced according to the following method.

To a solution of 6-bromo-7-methylquinoline (1.40 g) in chlorobenzene (30 mL) were sequentially added N-bromosuccinimide (0.895 g) and 2,2'-azobis(2,4-dimethylvaleronitrile) (0.079 g) under argon gas flow with stirring at room temperature, and the resulting mixture was stirred at 60° C. for 4 hours. Then, the reaction solution was allowed to cool to room temperature, N-bromosuccinimide (0.896 g) and 2,2'-azobis(2,4-dimethylvaleronitrile) (0.078 g) were sequentially added thereto with stirring at room temperature, and the resulting mixture was stirred at 60° C. for 3 hours. Then, the resulting mixture was stirred at room temperature overnight. After the reaction was completed, to the reaction solution was added heptane (60 mL), and the resulting mixture was stirred for 10 minutes. The precipitated solids were collected by filtration, a mixed solvent of methanol/water (=1/9) was added thereto, and then subjected to sonication. The resulting solids were collected by filtration, washed with water, and dried under reduced pressure at 40° C. to give the title compound (0.890 g).

Mass spectrum (ESI, m/z): 300 $[M+H]^+$

Reference Example 12-(b)

Production of (R)-1-(((6-bromoquinolin-7-yl) methyl)amino)butan-2-ol

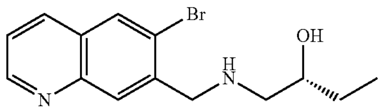 [SMILES: CC[C@@H](O)CNCc1cc2ncccc2cc1Br]

To a solution of 6-bromo-7-(bromomethyl)quinoline produced in the Reference Example 12-(a) (265 mg) in acetonitrile (4 mL) were sequentially added (2R)-1-amino-2-butanol (0.166 mL) and N,N-diisopropylethylamine (0.301 mL) under argon gas flow with stirring at room temperature, and the resulting mixture was stirred at room temperature for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, concentrated under reduced pressure, and the resulting residues were purified by a silica gel column (elution solvent; ethyl acetate:methanol) to give the title compound (185 mg) as white solids.

Mass spectrum (DUIS, m/z): 309 $[M+H]^+$

Reference Example 12-(c)

Production of (R)-2-ethyl-2,3,4,5-tetrahydro-[1,4] oxazepino[7,6-g]quinoline

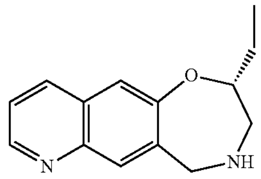 [SMILES: CC[C@@H]1CNCc2cc3ncccc3cc2O1]

To a solution of (R)-1-(((6-bromoquinolin-7-yl)methyl) amino)butan-2-ol produced in the Reference Example 12-(b) (185 mg) in 2-propanol (8 mL) were sequentially added cesium carbonate (390 mg) and copper(I) iodide (57 mg) under argon gas flow with stirring at room temperature, and the resulting mixture was stirred at 90° C. for B hours. Copper (I) iodide (200 mg) was added thereto, and the resulting mixture was stirred at 90° C. for 6 hours. After the reaction was completed, the resulting precipitates were removed by filtration, and washed with ethyl acetate. The resulting filtrate was concentrated, and the resulting residues were purified by a silica gel column (elution solvent; ethyl acetate:methanol) to give the title compound (70 mg) as a yellow oil.

Mass spectrum (ESI, m/z): 229 $[M+H]^+$

Reference Example 13-(a)

Production of (R)-1-(((2-chloro-8-methylquinolin-3-yl)methyl)amino)butan-2-ol

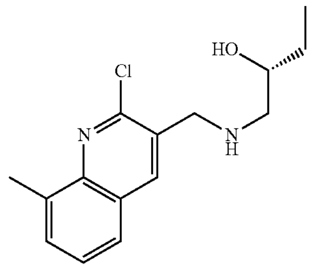 [SMILES: CC[C@@H](O)CNCc1cc2cccc(C)c2nc1Cl]

To a solution of 2-chloro-8-methylquinoline-3-carbaldehyde (200 mg) in dichloromethane (5 mL) was added (2R)-1-amino-2-butanol (0.11 mL) under argon gas flow with stirring at room temperature, and the resulting mixture was stirred at room temperature for 30 minutes. Then, sodium triacetoxyborohydride (412 mg) was added thereto with stirring at room temperature, and the resulting mixture was stirred at room temperature for 24 hours. After the reaction was completed, to the reaction solution was added a saturated aqueous solution of sodium hydrogen carbonate, and the resulting mixed solution was subjected to extraction twice with ethyl acetate. The resulting organic layer was dried over anhydrous magnesium sulfate, filtered, concentrated under reduced pressure, and the resulting residues were purified by a silica gel column (elution solvent; ethyl acetate:methanol) to give the title compound (140 mg) as white solids.

Mass spectrum (ESI, m/z): 279 $[M+H]^+$

Reference Example 13-(b)

Production of (R)-2-ethyl-10-methyl-2,3,4,5-tetrahydro-[1,4]oxazepino[7,6-b]quinoline

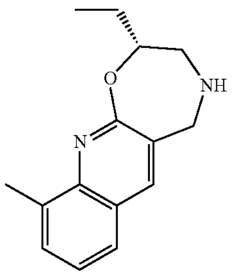 [SMILES: CC[C@@H]1CNCc2cc3cccc(C)c3nc2O1]

To a solution of (R)-1-(((2-chloro-8-methylquinolin-3-yl) methyl)amino)butan-2-ol produced in the Reference Example 13-(a) (140 mg) In tetrahydrofuran (5 mL) was added a 1 M solution of potassium tert-butoxide in tetrahydrofuran (0.603 mL) under argon atmosphere with stirring at room temperature, and the resulting mixture was stirred at room temperature for 1 hour. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, concentrated under reduced pressure, and the resulting residues were purified by a silica gel column (elution solvent; ethyl acetate:methanol) to give the title compound (106 mg) as a colorless oil.

Mass spectrum (ESI, m/z): 243 $[M+H]^4$

Reference Example 14-(a)

Production of (R)-1-(((2-chloro-6-methylquinolin-3-yl)methyl)amino)butan-2-ol

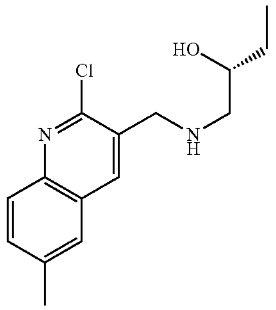 [SMILES: CC[C@@H](O)CNCc1cc2cc(C)ccc2nc1Cl]

To a solution of 2-chloro-6-methylquinoline-3-carbaldehyde (200 mg) in dichloromethane (5 mL) was added (2R)-1-amino-2-butanol (0.110 mL) under argon gas flow with stirring at room temperature, and the resulting mixture was stirred at room temperature for 30 minutes. Then, sodium triacetoxyborohydride (412 mg) was added thereto with stirring at room temperature, and the resulting mixture was stirred at room temperature for 24 hours. After the reaction was completed, to the reaction solution was added a saturated aqueous solution of sodium hydrogen carbonate, and the resulting mixed solution was subjected to extraction twice with ethyl acetate. The resulting organic layer was dried over anhydrous magnesium sulfate, filtered, concentrated under reduced pressure, and the resulting residues were purified by a silica gel column (elution solvent; ethyl acetate:methanol) to give the title compound (157 mg) as white solids.

Mass spectrum (ESI, m/z): 279 $[M+H]^+$

Reference Example 14-(b)

Production of (R)-2-ethyl-8-methyl-2,3,4,5-tetrahydro-[1,4]oxazepino[7,6-b]quinoline

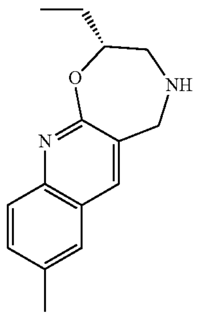 [SMILES: CC[C@@H]1CNCc2cc3cc(C)ccc3nc2O1]

To a solution of (R)-1-(((2-chloro-6-methylquinolin-3-yl) methyl)amino)butan-2-ol produced in the Reference Example 14-(a) (157 mg) in tetrahydrofuran (6 mL) was added a 1 M solution of potassium tert-butoxide in tetrahydrofuran (0.676 mL) under argon atmosphere with stirring at room temperature, and the resulting mixture was stirred at room temperature for 1 hour. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, concentrated under reduced pressure, and the resulting residues were purified by a silica gel column (DIOL silica gel, elution solvent; hexane:ethyl acetate) to give the title compound (121 mg) as a colorless oil.

Mass spectrum (ESI, m/z): 243 $[M+H]^+$

Reference Example 15-(a)

Production of tert-butyl (5-hydroxy-2-methylphenyl)carbamate

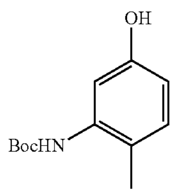 [SMILES: Cc1ccc(O)cc1NC(=O)OC(C)(C)C]

To a solution of 4-methyl-3-nitrophenol (2.06 g) and di-tert-butyl dicarbonate (6.84 mL) in ethanol (40 mL) was added palladium carbon (wetted with 55% water) (2.78 g) with stirring at room temperature, the resulting mixture was subjected to hydrogen atmosphere, and then stirred at room temperature for 20 hours. After the reaction was completed, the reaction solution was filtered through Celite, the resulting filtrate was concentrated under reduced pressure, and the resulting residues were purified by a silica gel column (elution solvent; hexane:ethyl acetate) to give the title compound (2.56 g) as a colorless oil.

Mass spectrum (ESI, m/z): 224 [M+H]

Reference Example 15-(b)

Production of tert-butyl (4-formyl-5-hydroxy-2-methylphenyl) carbamate

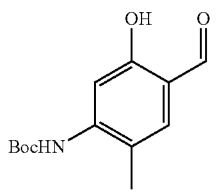 [SMILES: Cc1cc(C=O)c(O)cc1NC(=O)OC(C)(C)C]

To a solution of tert-butyl. (5-hydroxy-2-methylphenyl) carbamate produced in the Reference Example 15-(a) (1.15 g), triethylamine (2.31 mL), and magnesium chloride (1.07 g) in acetonitrile (20 mL) was added paraformaldehyde (0.861 g) under argon gas flow with stirring at room temperature, and the resulting mixture was stirred under reflux for 7.5 hours. After the reaction was completed, the reaction solution was allowed to cool to room temperature, water was added thereto to adjust the pH to 7, and the resulting mixed solution was subjected to extraction with ethyl acetate. The resulting organic layer was washed with saturated brine, dried over anhydrous magnesium sulfate, filtered through Celite, and concentrated under reduced pressure. The resulting residues were purified by a silica gel column (elution solvent; hexane:ethyl acetate) to give the title compound (390 mg) as yellow solids.

Mass spectrum (ESI, m/z): 252 $[M+H]^4$

Reference Example 15-(c)

Production of tert-butyl (S)-(5-hydroxy-4-(((2-hydroxybutyl)amino)methyl)-2-methylphenyl) carbamate

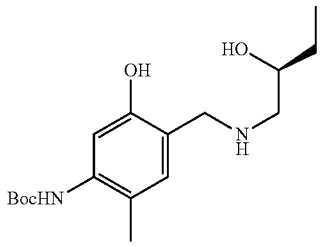 [SMILES: CC[C@H](O)CNCc1cc(C)c(NC(=O)OC(C)(C)C)cc1O]

To a solution of tert-butyl (4-formyl-5-hydroxy-2-methylphenyl)carbamate produced in the Reference Example 15-(b) (390 mg) in ethanol (6 mL) was added (2S)-1-amino-2-butanol (166 mg) under argon gas flow with stirring at room temperature, and the resulting mixture was stirred at room temperature for 2 hours. Then, sodium borohydride (119 mg) was added thereto with stirring at room temperature, and the resulting mixture was stirred at room temperature for 30 minutes. After the reaction was completed, to the reaction solution was added 2 M hydrochloric acid until the bubbling disappeared, and a 1 M aqueous solution of sodium hydroxide was added thereto to adjust the pH to about 5.5. Then, the resulting mixed solution was subjected to extraction with ethyl acetate. The resulting organic layer was washed with saturated brine, dried over anhydrous sodium sulfate, filtered, and concentrated under reduced pressure to give the title compound (552 mg) as a white foam.

Mass spectrum (ESI, m/z): 325 $[M+H]^+$

Reference Example 15-(d)

Production of benzyl (S)-(4-((tert-butoxycarbonyl) amino)-2-hydroxy-5-methylbenzyl) (2-hydroxybutyl) carbamate

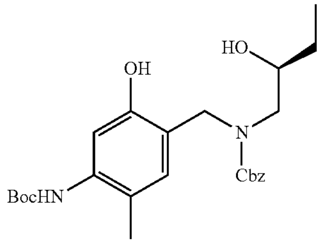 [SMILES: CC[C@H](O)CN(Cc1cc(C)c(NC(=O)OC(C)(C)C)cc1O)C(=O)OCc1ccccc1]

To a solution of tert-butyl (S)-(5-hydroxy-4-(((2-hydroxybutyl)amino)methyl)-2-methylphenyl) carbamate produced in the Reference Example 15-(c) (552 mg) and N,N-diisopropylethylamine (0.410 mL) in tetrahydrofuran (10 mL) was added benzyl chloroformate (0.235 mL) under argon gas flow with stirring at 0° C., and the resulting mixture was stirred at room temperature for 3 hours. Then, N,N-diisopropylethylamine (0.205 mL) and benzyl chloroformate (0.118 mL) were added thereto with stirring at room temperature, and the resulting mixture was stirred at room temperature for 1 hour. After the reaction was completed, to the reaction solution were added water and 2 M hydrochloric acid (2 mL), and the resulting mixed solution was subjected to extraction with ethyl acetate. The resulting organic layer was washed with saturated brine, dried over anhydrous sodium sulfate, filtered, concentrated under reduced pressure, and the resulting residues were purified by a silica gel column (elution solvent; hexane ethyl acetate) to give the title compound (579 mg) as a white foam.

Mass spectrum (ESI, m/z): 457 $[M-H]^-$

Reference Example 15-(e)

Production of benzyl (R)-8-((tert-butoxycarbonyl) amino)-2-ethyl-7-methyl-2,3-dihydrobenzo (f) [1,4] oxazepine-4 (5H)-carboxylate

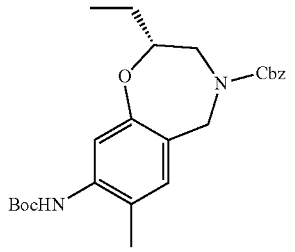 [SMILES: CC[C@@H]1CN(C(=O)OCc2ccccc2)Cc2cc(C)c(NC(=O)OC(C)(C)C)cc2O1]

To a solution of benzyl (S)-(4-((tert-butoxycarbonyl) amino)-2-hydroxy-5-methylbenzyl) (2-hydroxybutyl)carbamate produced in the Reference Example 15-(d) (578 mg) and triphenylphosphine (342 mg) in tetrahydrofuran (20 mL) was added a 1.9 M solution of diisopropyl azodicarboxylate in toluene (0.683 mL) under argon gas flow with stirring at 0° C., and the resulting mixture was stirred at room temperature for 2.5 hours. Additionally, a 1.9 M solution of diisopropyl azodicarboxylate in toluene (0.340 mL) and triphenylphosphine (177 mg) were added thereto with stirring at room temperature, and the resulting mixture was stirred at room temperature for 1 hour. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, concentrated under reduced pressure, and the resulting residues were purified by a silica gel column (elution solvent; hexane:ethyl acetate) to give the title compound (545 mg) as a colorless oil.

Mass spectrum (ESI, m/z): 463 $[M+Na]^+$

Reference Example 15-(f)

Production of benzyl (R)-8-amino-2-ethyl-7-methyl-2,3-dihydrobenzo[f][1,4]oxazepine-4 (5H)-carboxylate

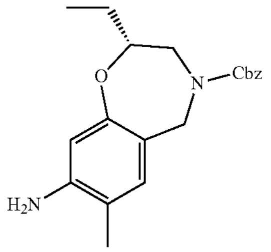 [SMILES: CC[C@@H]1CN(C(=O)OCc2ccccc2)Cc2cc(C)c(N)cc2O1]

To a solution of benzyl (R)-8-((tert-butoxycarbonyl) amino)-2-ethyl-7-methyl-2,3-dihydrobenzo[f][1,4] oxazepine-4(5H)-carboxylate produced in the Reference Example 15-(e) (545 mg) in 1,4-dioxane (2 mL) was added a 4 M solution of hydrogen chloride in 1,4-dioxane (2.69 mL) with stirring at room temperature, and the resulting mixture was stirred at room temperature for 2.5 hours. Additionally, a 4 M solution of hydrogen chloride in 1,4-dioxane (2.69 mL) was added thereto with stirring at room temperature, and the resulting mixture was stirred at room temperature for 15 hours. After the reaction was completed, to the reaction solution was added a saturated aqueous solution of sodium hydrogen carbonate to adjust the pH to about 9, and the resulting mixed solution was subjected to extraction with ethyl acetate. The resulting organic layer was dried over anhydrous sodium sulfate, filtered, and concentrated under reduced pressure to give the title compound (394 mg) as a yellow oil.

Mass spectrum (ESI, m/z): 341 $[M+H]^+$

Reference Example 15-(g)

Production of benzyl (R)-8-acetamide-2-ethyl-7-methyl-2,3-dihydrobenzo[f][1,4]oxazepine-4 (5H)-carboxylate

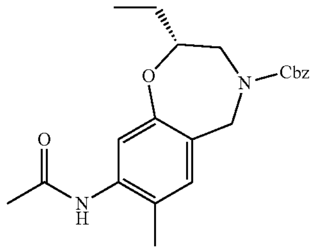 [SMILES: CC[C@@H]1CN(C(=O)OCc2ccccc2)Cc2cc(C)c(NC(C)=O)cc2O1]

To a solution of benzyl (R)-8-amino-2-ethyl-7-methyl-2,3-dihydrobenzo[f][1,4]oxazepine-4(5H)-carboxylate produced in the Reference Example 15-(f) (393 mg) in ethyl acetate (5 mL) was added acetic anhydride (0.139 mL) under argon gas flow with stirring at room temperature, and the resulting mixture was stirred at room temperature for 19 hours. After the reaction was completed, the reaction solution was added to hexane, and the resulting mixed solution was concentrated under reduced pressure. To the resulting residues was added hexane, the precipitated solids were washed by filtration, and dried under reduced pressure at 40° C. to give the title compound (317 mg) as pale yellow solids.

Mass spectrum (ESI, m/z): 383 $[M+H]^+$

Reference Example 15-(h)

Production of benzyl (R)-1-acetyl-8-ethyl-1,5,7,8-tetrahydro-6H-[1,4]oxazepino[6,7-f]indazole-6-carboxylate

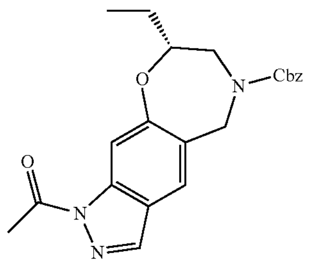 [SMILES: CC[C@@H]1CN(C(=O)OCc2ccccc2)Cc2cc3cnn(C(C)=O)c3cc2O1]

To a solution of benzyl (R)-8-acetamide-2-ethyl-7-methyl-2,3-dihydrobenzo[f][1,4]oxazepine-4(5H)-carboxylate produced in the Reference Example 15-(g) (100 mg) in ethyl acetate (2 mL) were sequentially added tetrabutylammonium bromide (5 mg), potassium acetate (51 mg), acetic anhydride (0.074 mL), and n-amyl nitrite (0.069 mL) under argon gas flow with stirring at room temperature, and the resulting mixture was stirred at 80° C. for 9 hours, at room temperature for 14 hours, and at 80° C. for 8.5 hours. Then, n-amyl nitrite (0.035 mL) was added thereto with stirring at 80° C., and the resulting mixture was stirred at 80° C. for 2 hours and at room temperature for 14.5 hours. After the reaction was completed, to the reaction solution was added a saturated aqueous solution of sodium hydrogen carbonate, and the resulting mixed solution was subjected to extraction with ethyl acetate. The resulting organic layer was washed sequentially with water and saturated brine, dried over anhydrous magnesium sulfate, filtered, concentrated under reduced pressure, and the resulting residues were purified by a silica gel column (elution solvent; hexane:ethyl acetate) to give the title compound (47 mg) as a pale yellow oil.

Mass spectrum (ESI, m/z): 394 $[M+H]^+$

Reference Example 15-(1)

Production of benzyl (R)-8-ethyl-1,5,7,8-tetrahydro-6H-[1,4]oxazepino[6,7-f]indazole-6-carboxylate

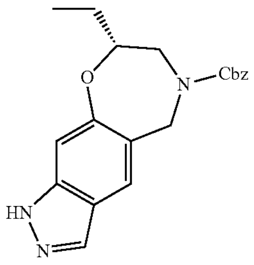 [SMILES: CC[C@@H]1CN(C(=O)OCc2ccccc2)Cc2cc3cn[nH]c3cc2O1]

To a solution of benzyl (R)-1-acetyl-8-ethyl-1,5,7,8-tetrahydro-6H-[1,4]oxazepino[6,7-f]indazole-6-carboxylate produced in the Reference Example 15-(h) (47 mg) in tetrahydrofuran (0.8 mL) was added a 8 M aqueous solution of sodium hydroxide (0.149 mL) with stirring at room temperature, and the resulting mixture was stirred at room temperature for 3 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous sodium sulfate, filtered, and concentrated under reduced pressure to give the title compound (42 mg) as a pale yellow oil.

Mass spectrum (ESI, m/z): 352 $[M+H]^+$

Reference Example 15-(J)

Production of (R)-8-ethyl-5,6,7,8-tetrahydro-1H-[1,4]oxazepino[6,7-f]indazole

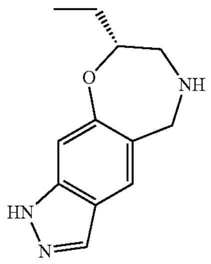 [SMILES: CC[C@@H]1CNCc2cc3cn[nH]c3cc2O1]

To a solution of benzyl (R)-8-ethyl-1,5,7,8-tetrahydro-6H-[1,4]oxazepino[6,7-f]indazole-6-carboxylate produced in the Reference Example 15-(i) (42 mg) in ethanol (2 mL) was added 10% palladium carbon (PE type (trade name) manufactured by N.E. CHEMCAT CORPORATION, wetted with 50% water] (25 mg) with stirring at room temperature, the resulting mixture was subjected to hydrogen atmosphere, and then stirred at room temperature for 3 hours. After the reaction was completed, the reaction solution was filtered through Celite, concentrated under reduced pressure, and the resulting residues were purified by a silica gel column (elution solvent; ethyl acetate:methanol) to give the title compound (16 mg) as a pale yellow oil.

Mass spectrum (ESI, m/z): 218 $[M+H]^+$

Reference Example 16-(a)

Production of methyl (R)-2-((1-((tert-butoxycarbonyl)amino)butan-2-yl)oxy)-1-naphthoate

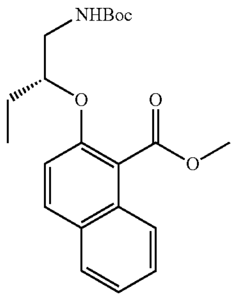 [SMILES: CC[C@H](CNC(=O)OC(C)(C)C)Oc1ccc2ccccc2c1C(=O)OC]

(1) To a solution of (2S)-1-amino-2-butanol (300 mg) in dichloromethane (4 mL) was added di-tert-butyl dicarbonate (0.781 mL) under argon gas flow with stirring at room temperature, and the resulting mixture was stirred at room temperature for 1 hour. After the reaction was completed, the reaction solution was concentrated to give a crude product (637 mg) comprising tert-butyl (S)-(2-hydroxybutyl)carbamate.

(2) The crude product (637 mg) comprising tert-butyl (S)-(2-hydroxybutyl)carbamate produced in (1) was subjected to replacement by nitrogen, and dissolved into tetrahydrofuran (8 mL). Methyl 2-hydroxy-1-naphthoate (815 mg), triphenylphosphine (1.35 g), and a 1.9 M solution of diisopropyl azodicarboxylate in toluene (2.65 mL) were sequentially added thereto under argon gas flow with stirring at room temperature, and the resulting mixture was stirred at room temperature for 2 hours. After the reaction was completed, the reaction solution was diluted with ethyl acetate, washed sequentially with water and saturated brine, dried over anhydrous magnesium sulfate, and concentrated under reduced pressure. The resulting residues were purified by a silica gel column (elution solvent; hexane:ethyl acetate) to give the title compound (1.17 g) as a colorless oil.

Mass spectrum (ESI, m/z): 374 $[M+H]^+$

Reference Example 16-(b)

Production of methyl (R)-2-((1-aminobutan-2-yl)oxy)-1-naphthoate hydrochloride

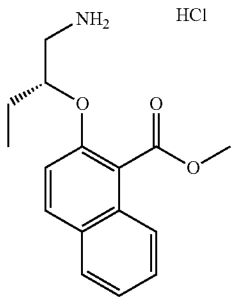 [SMILES: Cl ; CC[C@H](CN)Oc1ccc2ccccc2c1C(=O)OC]

To a solution of methyl (R)-2-((1-((tert-butoxycarbonyl)amino)butan-2-yl)oxy)-1-naphthoate produced in the Reference Example 16-(a) (1.17 g) in 1,4-dioxane (6 mL) was added a 4 M solution of hydrogen chloride in 1,4-dioxane (3.13 mL) under argon gas flow with stirring at 0° C., and the resulting mixture was stirred at room temperature for 16 hours. After the reaction was completed, the reaction solution was concentrated, and dried to give the title compound (0.97 g).

Mass spectrum (ESI, m/z): 274 $[M+H]^+$

Reference Example 16-(c)

Production of (R)-4-ethyl-3,4-dihydronaphtho[1,2-f][1,4]oxazepin-1(2H)-one

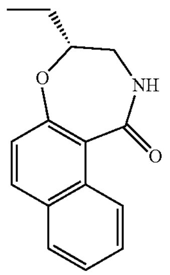 [SMILES: CC[C@@H]1CNC(=O)c2c(ccc3ccccc23)O1]

To a solution of methyl. (R)-2-((1-aminobutan-2-yl)oxy)-1-naphthoate hydrochloride produced in the Reference Example 16-(b) (970 mg) in methanol (10 mL) was added sodium hydride (0.41 g) under argon gas flow with stirring at 0° C., and the resulting mixture was stirred at room temperature for 1 hour. After the reaction was completed, the reaction solution was concentrated, and a saturated aqueous solution of ammonium chloride was added thereto. The resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (683 mg) as a colorless oil.

Mass spectrum (ESI, m/z): 242 $[M+H]^+$

Reference Example 16-(d)

Production of (R)-4-ethyl-1,2,3,4-tetrahydronaphtho[1,2-f][1,4]oxazepine

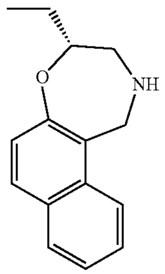 [SMILES: CC[C@@H]1CNCc2c(ccc3ccccc23)O1]

To a solution of (R)-4-ethyl-3,4-dihydronaphtho[1,2-f][1,4]oxazepin-1(2H)-one produced in the Reference Example 16-(c) (683 mg) in tetrahydrofuran (8 mL) was added dropwise borane-tetrahydrofuran complex (9.44 mL) under argon gas flow with stirring at room temperature, and the resulting mixture was stirred at room temperature for 6 hours and at 60° C. for 4 hours. After the reaction was completed, ethanol (1 mL) was added thereto, and the resulting mixture was stirred for 1 hour. The reaction solution was concentrated, and then dissolved into cyclopentyl methyl ether (2 mL). A 4 M solution of hydrogen chloride in cyclopentyl methyl ether (2 mL) was added thereto, and the resulting mixture was stirred for 30 minutes. A 4 M aqueous solution of sodium hydroxide (2 mL) was added thereto, and the resulting mixture was stirred for a while. A saturated aqueous solution of sodium hydrogen carbonate (10 mL) was added thereto, and the resulting mixed solution was subjected to extraction three times with ethyl acetate. The resulting organic layer was dried over anhydrous magnesium sulfate, filtered, and concentrated under reduced pressure. The resulting residues were purified by a silica gel column (elution solvent; ethyl acetate:methanol) to give the title compound (214 mg) as a colorless oil.

Mass spectrum (ESI, m/z): 228 $[M+H]^+$

Reference Example 17-(a)

Production of 7-hydroxyquinoline-8-carbaldehyde

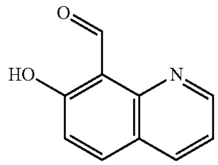 [SMILES: O=Cc1c(O)ccc2cccnc12]

To a suspension of quinolin-7-ol (1.0 g) in chloroform (15 mL) was added dropwise a 8 M aqueous solution of sodium hydroxide (8.61 mL) under argon gas flow with stirring at room temperature, and the resulting mixture was stirred at 90° C. for 2 hours. After the reaction was completed, the reaction solution was allowed to cool to room temperature, water was added thereto, and the resulting mixed solution was subjected to extraction twice with dichloromethane. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (417 mg) as yellow solids.

Mass spectrum (ESI, m/z): 174 $[M+H]^+$

Reference Example 17-(b)

Production of tert-butyl (S)-(2-hydroxybutyl) ((7-hydroxyquinolin-8-yl)methyl) carbamate

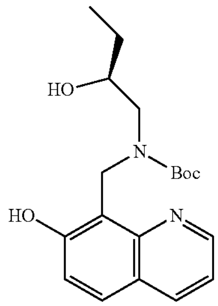 [SMILES: CC[C@H](O)CN(Cc1c(O)ccc2cccnc12)C(=O)OC(C)(C)C]

A solution of 7-hydroxyquinoline-8-carbaldehyde produced in the Reference Example 17-(a) (200 mg) and (2S)-1-amino-2-butanol (0.131 mL) in dichloromethane (5 mL) was stirred under argon gas flow at room temperature for 30 minutes. Then, sodium triacetoxyborohydride (367 mg) was added thereto, and the resulting mixture was stirred at room temperature for 1 hour. After the reaction was completed, the reaction solution was concentrated under reduced pressure, to the resulting residues were added methanol (5.00 mL) and a 8 M aqueous solution of sodium hydroxide (1.44 mL), di-tert-butyl dicarbonate (0.531 mL) was added thereto, and the resulting mixture was stirred at room temperature for 3 hours. Additionally, di-tert-butyl dicarbonate (0.531 mL) was added thereto, and the resulting mixture was stirred at room temperature for 1 hour. Additionally, a 8 M aqueous solution of sodium hydroxide (0.7 mL) was added thereto, and the resulting mixture was stirred at room temperature for 2 hours. 1 M hydrochloric acid was added thereto to adjust the pH to 5, and the resulting mixture was subjected to extraction with ethyl acetate. The resulting organic layer was washed with saturated brine, dried over anhydrous magnesium sulfate, filtered, concentrated under reduced pressure, and the resulting residues were purified by a silica gel column (elution solvent; hexane:ethyl acetate) to give the title compound (190 mg) as a colorless oil.

Mass spectrum (ESI, m/z): 347 $[M+H]^+$

Reference Example 17-(c)

Production of tert-butyl (R)-8-ethyl-8,9-dihydro-[1,4]oxazepino[7,6-h]quinoline-10 (11H)-carboxylate

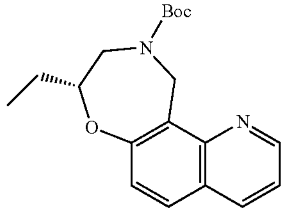 [SMILES: CC[C@@H]1CN(C(=O)OC(C)(C)C)Cc2c(ccc3cccnc23)O1]

To a solution of tert-butyl (S)-(2-hydroxybutyl) ((7-hydroxyquinolin-8-yl)methyl) carbamate produced in the Reference Example 17-(b) (190 mg) in tetrahydrofuran (7 mL) were sequentially added (E)-N1,N1,N2,N2-tetramethyldiazene-1,2-dicarboxamide (142 mg) and tri-n-butylphosphine (0.203 mL) under argon gas flow with stirring at room temperature, and the resulting mixture was stirred at room temperature for 2 hours. After the reaction was completed, the reaction solution was diluted with ethyl acetate, washed sequentially with water and saturated brine, dried over anhydrous magnesium sulfate, and concentrated under reduced pressure. The resulting residues were purified by a silica gel column (elution solvent; hexane:ethyl acetate) to give the title compound (117 mg) as a colorless oil.

Mass spectrum (DUIS, m/z): 329 [M+H]+

Reference Example 17-(d)

Production of (R)-8-ethyl-8,9,10,11-tetrahydro-[1,4]oxazepino[7,6-h]quinoline dihydrochloride

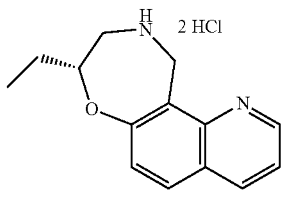 [SMILES: CC[C@@H]1CNCc2c(ccc3cccnc23)O1]

To a solution of tert-butyl (R)-8-ethyl-8,9-dihydro-[1,4]oxazepino[7,6-h]quinoline-10(11H)-carboxylate produced in the Reference Example 17-(c) (117 mg) in 1,4-dioxane (3 mL) was added dropwise a 4 M solution of hydrogen chloride in 1,4-dioxane (0.356 mL) under argon gas flow with stirring at room temperature, and the resulting mixture was stirred at room temperature for 0.5 hour and at 60° C. for 2 hours. After the reaction was completed, the reaction solution was allowed to cool to room temperature, hexane (2 mL) was added thereto, and the resulting mixture was stirred at room temperature for 15 hours. The resulting solids were collected by filtration, washed with tert-butyl methyl ether, and subjected to vacuum drying at room temperature to give the title compound (88 mg) as white solids.

Mass spectrum (ESI, m/z): 229 $[M+H]^+$

Reference Example 18-(a)

Production of 6-bromoquinoline-5-carbaldehyde

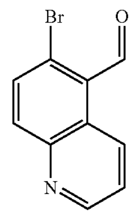 [SMILES: O=Cc1c(Br)ccc2ncccc12]

To a suspension of 6-bromoquinoline-5-carbonitrile (0.501 g) in toluene (40 mL) was added dropwise a 1 M solution of diisobutylaluminum hydride in toluene (4.3 mL) under argon gas flow with stirring at −10° C., and the resulting mixture was stirred at −10° C. for 1 hour. Then, 5% sulfuric acid was added thereto with stirring at −10° C., and the resulting mixture was stirred at room temperature for 1 hour. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (0.111 g) as yellow solids.

Mass spectrum (ESI, m/z): 236 $[M+H]^+$

Reference Example 18-(b)

Production of (R)-1-(((6-bromoquinolin-5-yl)methyl)amino)butan-2-ol

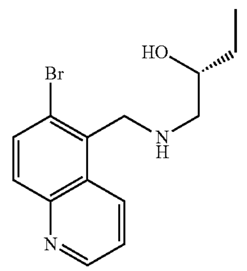 [SMILES: CC[C@@H](O)CNCc1c(Br)ccc2ncccc12]

To a solution of 6-bromoquinoline-5-carbaldehyde produced in the Reference Example 18-(a) (0.111 g) in dichloromethane (4.5 mL) was added (2R)-1-amino-2-butanol (0.050 g) under argon gas flow with stirring at room temperature, and the resulting mixture was stirred at room temperature for 1 hour. Then, sodium triacetoxyborohydride (0.199 g) was added thereto with stirring at room temperature, and the resulting mixture was stirred at room temperature for 20.5 hours. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous sodium sulfate, filtered, concentrated under reduced pressure, and the resulting residues were purified by a silica gel column (elution solvent; ethyl acetate:methanol) to give the title compound (0.105 g) as white solids.

Mass spectrum (DUIS, m/z): 309 $[M+H]^+$

Reference Example 18-(c)

Production of (R)-4-ethyl-1,2,3,4-tetrahydro-[1,4]oxazepino[6,7-f]quinoline

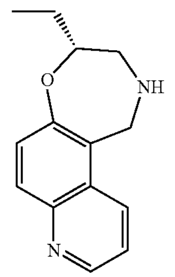 [SMILES: CC[C@@H]1CNCc2c(ccc3ncccc23)O1]

To a solution of (R)-1-(((6-bromoquinolin-5-yl)methyl)amino)butan-2-ol produced in the Reference Example 18-(b) (0.104 g) in 2-propanol (3 mL) were added cesium carbonate (0.222 g) and copper(I) iodide (0.035 g) under argon gas flow with stirring at room temperature, and the resulting mixture was stirred at 90° C. for 2 hours, at room temperature overnight, and at 90° C. for 4.5 hours. After the reaction was completed, the reaction solution was allowed to cool to room temperature, the resulting precipitates were filtered, washed with ethyl acetate, the resulting filtrate was concentrated under reduced pressure, and the resulting residues were purified by a silica gel column (elution solvent; ethyl acetate:methanol) to give the title compound (0.023 g) as slightly yellow solids.

Mass spectrum (ESI, m/z): 229 $[M+H]^+$

Reference Example 19-(a)

Production of 3-hydroxyquinoline-4-carbaldehyde

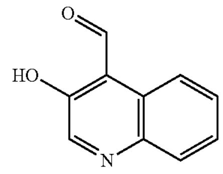 [SMILES: O=Cc1c(O)cnc2ccccc12]

To a suspension of quinolin-3-ol (500 mg) in chloroform (7 mL) was added dropwise a 8 M aqueous solution of sodium hydroxide (4.31 mL) under argon gas flow with stirring at room temperature, and the resulting mixture was stirred at 90° C. for 2 hours. After the reaction was completed, the reaction solution was allowed to cool to room temperature, water was added thereto, and the resulting mixed solution was subjected to extraction twice with dichloromethane. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (70 mg) as yellow solids.

Mass spectrum (DUIS, m/z): 174 $[M+H]^+$

Reference Example 19-(b)

Production of tert-butyl. (S)-(2-hydroxybutyl) ((3-hydroxyquinolin-4-yl)methyl)carbamate

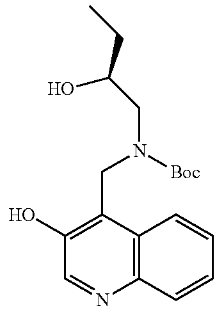 [SMILES: CC[C@H](O)CN(Cc1c(O)cnc2ccccc12)C(=O)OC(C)(C)C]

A solution of 3-hydroxyquinoline-4-carbaldehyde produced in the Reference Example 19-(a) (70 mg) and (2S)-1-amino-2-butanol (0.046 mL) in dichloromethane (4 mL) was stirred under argon gas flow at room temperature for 30 minutes. Then, sodium triacetoxyborohydride (129 mg) was added thereto, and the resulting mixture was stirred at room temperature for 1 hour. After the reaction was completed, the reaction solution was concentrated under reduced pressure, to the resulting residues were added methanol (4 mL) and a 8 M aqueous solution of sodium hydroxide (0.505 mL), di-tert-butyl dicarbonate (0.186 mL) was added thereto, and the resulting mixture was stirred at room temperature for 3 hours. 1 M hydrochloric acid was added thereto to adjust the pH to 5, and the resulting mixture was subjected to extraction with ethyl acetate. The resulting organic layer was washed with saturated brine, dried over anhydrous magnesium sulfate, filtered, concentrated under reduced pressure, and the resulting residues were purified by a silica gel column (elution solvent; hexane:ethyl acetate) to give the title compound (79 mg) as a white foam.

Mass spectrum (ESI, m/z): 347 $[M+H]^+$

Reference Example 19-(c)

Production of tert-butyl (R)-4-ethyl-3,4-dihydro-[1,4]oxazepino[7,6-c]quinoline-2(1H)-carboxylate

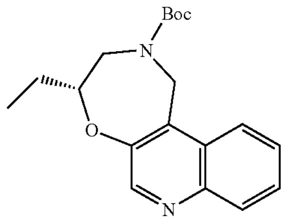 [SMILES: CC[C@@H]1CN(C(=O)OC(C)(C)C)Cc2c(cnc3ccccc23)O1]

To a solution of tert-butyl (S)-(2-hydroxybutyl) ((3-hydroxyquinolin-4-yl)methyl)carbamate produced in the Reference Example 19-(b) (79 mg) in tetrahydrofuran (5 mL) were sequentially added (E)-N1,N1,N2,N2-tetramethyldiazene-1,2-dicarboxamide (59 mg) and tri-n-butylphosphine (0.084 mL) under argon gas flow with stirring at room temperature, and the resulting mixture was stirred at room temperature for 2 hours. After the reaction was completed, the reaction solution was allowed to cool to room temperature, diluted with ethyl acetate, washed sequentially with water and saturated brine, dried over anhydrous magnesium sulfate, and concentrated under reduced pressure. The resulting residues were purified by a silica gel column (elution solvent; hexane:ethyl acetate) to give the title compound (63 mg) as white solids.

Mass spectrum (ESI, m/z): 329 $[M+H]^+$

Reference Example 19-(d)

Production of (R)-4-ethyl-1,2,3,4-tetrahydro-[1,4]oxazepino[7,6-c]quinoline dihydrochloride

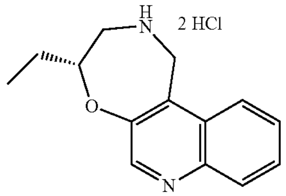 [SMILES: CC[C@@H]1CNCc2c(cnc3ccccc23)O1]

To a solution of tert-butyl (R)-4-ethyl-3,4-dihydro-[1,4]oxazepino[7,6-c]quinoline-2 (1H)-carboxylate produced in the Reference Example 19-(c) (63 mg) in 1,4-dioxane (3 mL) was added dropwise a 4 M solution of hydrogen chloride in 1,4-dioxane (0.192 mL) under argon gas flow with stirring at room temperature, and the resulting mixture was stirred at room temperature for 0.5 hour and at 60° C. for 2 hours. After the reaction was completed, the reaction solution was allowed to cool to room temperature, hexane (2 mL) was added thereto, and the resulting mixture was stirred at room temperature for 15 hours. The resulting solids were collected by filtration, washed with tert-butyl methyl ether, and subjected to vacuum drying at room temperature to give the title compound (56 mg) as white solids.

Mass spectrum (ESI, m/z): 229 $[M+H]^+$

Reference Example 20-(a)

Production of 6-hydroxy-1H-indazole-7-carbaldehyde

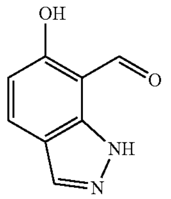 [SMILES: O=Cc1c(O)ccc2cn[nH]c12]

To a solution of 1H-indazol-6-ol (1.01 g) in trifluoroacetic acid (15 mL) was added hexamethylenetetramine (1.46 g) under argon gas flow with stirring at room temperature, and the resulting mixture was stirred at 80° C. for 5 hours. After the reaction was completed, to the reaction solution was added a saturated aqueous solution of sodium hydrogen carbonate, and the resulting mixed solution was subjected to extraction with ethyl acetate. The resulting organic layer was washed sequentially with a saturated aqueous solution of sodium hydrogen carbonate and saturated brine, dried over anhydrous magnesium sulfate, filtered, and concentrated under reduced pressure. The resulting residues were purified by a silica gel column (DIOL silica gel, elution solvent; hexane:ethyl acetate) to give the title compound (368 mg) as milky white solids.

Mass spectrum (ESI, m/z): 161 $[M-H]^-$

Reference Example 20-(b)

Production of tert-butyl (S)-((6-hydroxy-1H-indazol-7-yl)methyl) (2-hydroxybutyl)carbamate

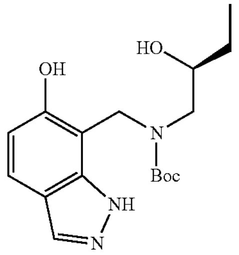 [SMILES: CC[C@H](O)CN(Cc1c(O)ccc2cn[nH]c12)C(=O)OC(C)(C)C]

A solution of 6-hydroxy-1H-indazole-7-carbaldehyde produced in the Reference Example 20-(a) (0.200 g) and (2S)-1-amino-2-butanol (0.166 g) in dichloromethane (5 mL) was stirred under argon gas flow at room temperature for 1 hour. Then, sodium triacetoxyborohydride (0.550 g) was added thereto with stirring at room temperature, and the resulting mixture was stirred at room temperature for 4 hours. After the reaction was completed, the reaction solution was concentrated under reduced pressure. To a solution of the resulting residues in tetrahydrofuran (3 mL) were added a 8 M aqueous solution of sodium hydroxide (1.54 mL) and di-tert-butyl dicarbonate (0.86 mL) with stirring at room temperature, and the resulting mixture was stirred at room temperature for 0.5 hour. Then, di-tert-butyl dicarbonate (0.86 mL) was added thereto with stirring at room temperature, and the resulting mixture was stirred at room temperature for 13.5 hours. Then, a 8 M aqueous solution of sodium hydroxide (1.54 mL) was added thereto with stirring at room temperature, and the resulting mixture was stirred at room temperature for 3 hours. After the reaction was completed, to the reaction solution was added water, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (0.144 g) as a colorless oil.

Mass spectrum (ESI, m/z): 336 $[M+H]^+$

Reference Example 20-(c)

Production of tert-butyl (R)-7-ethyl-1,7,8,10-tetrahydro-9H-[1,4]oxazepino[7,6-g]indazole-9-carboxylate

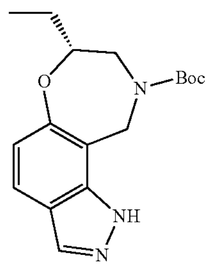 [SMILES: CC[C@@H]1CN(C(=O)OC(C)(C)C)Cc2c(ccc3cn[nH]c23)O1]

To a solution of tert-butyl (S)-((6-hydroxy-1H-indazol-7-yl)methyl) (2-hydroxybutyl)carbamate produced in the Reference Example 20-(b) (50 mg) and tri-n-butylphosphine (0.055 mL) in tetrahydrofuran (1 mL) was added (E)-N1,N1,N2,N2-tetramethyldiazene-1,2-dicarboxamide (38 mg) under argon gas flow with stirring at 0° C., and the resulting mixture was stirred at room temperature for 3 hours. Then, (E)-N1,N1,N2,N2-tetramethyldiazene-1,2-dicarboxamide (39 mg) and tri-n-butylphosphine (0.055 mL) were added thereto with stirring at 0° C., and the resulting mixture was stirred at room temperature for 1.5 hours. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (30 mg) as a colorless oil.

Mass spectrum (ESI, m/z): 318 $[M+H]^+$

Reference Example 20-(d)

Production of (R)-7-ethyl-7,8,9,10-tetrahydro-1H-[1,4]oxazepino[7,6-g]indazole dihydrochloride

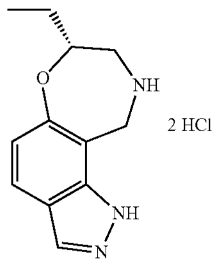 [SMILES: CC[C@@H]1CNCc2c(ccc3cn[nH]c23)O1]

To a solution of tert-butyl. (R)-7-ethyl-1,7,8,10-tetrahydro-9H-[1,4]oxazepino[7,6-g]indazole-9-carboxylate produced in the Reference Example 20-(c) (30 mg) in 1,4-dioxane (1 mL) was added a 4 M solution of hydrogen chloride in 1,4-dioxane (0.087 mL) with stirring at room temperature, and the resulting mixture was stirred at room temperature for 2.5 hours. Additionally, a 4 M solution of hydrogen chloride in 1,4-dioxane (0.087 mL) was added thereto with stirring at room temperature, and the resulting mixture was stirred at room temperature for 1.5 hours. Additionally, a 4 M solution of hydrogen chloride in 1,4-dioxane (0.261 mL) was added thereto with stirring at room temperature, and the resulting mixture was stirred at room temperature for 15.5 hours. The precipitated solids were filtered, washed with tert-butyl methyl ether, and dried under reduced pressure at 50° C. to give the title compound (9 mg) as white solids.

Mass spectrum (ESI, m/z): 218 $[M+H]^+$

Reference Example 21-(a)

Production of tert-butyl (R)-7-ethyl-1-methyl-1,7,8,10-tetrahydro-9H-[1,4]oxazepino[7,6-g]indazole-9-carboxylate

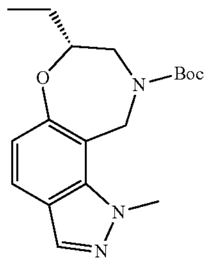 [SMILES: CC[C@@H]1CN(C(=O)OC(C)(C)C)Cc2c(ccc3cnn(C)c23)O1]

To a solution of tert-butyl (R)-7-ethyl-1,7,8,10-tetrahydro-9H-[1,4]oxazepino[7,6-g]indazole-9-carboxylate produced according to the same manner as the Reference Example 20-(c) (50 mg) in dimethylformamide (1 mL) was added sodium hydride (13 mg) under argon gas flow with stirring at 0° C., and the resulting mixture was stirred at 0° C. for 45 minutes. Then, methyl iodide (0.022 mL) was added thereto with stirring at 0° C., and the resulting mixture was stirred at room temperature for 3.25 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate→ethyl acetate:methanol) to give the title compound (22 mg) as white solids.

Mass spectrum (ESI, m/z): 332 $[M+H]^+$

Reference Example 21-(b)

Production of (R)-7-ethyl-1-methyl-7,8,9,10-tetrahydro-1H-[1,4]oxazepino[7,6-g]indazole dihydrochloride

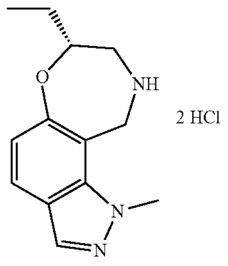 [SMILES: CC[C@@H]1CNCc2c(ccc3cnn(C)c23)O1]

To a solution of tert-butyl (R)-7-ethyl-1-methyl-1,7,8,10-tetrahydro-9H-[1,4]oxazepino[7,6-g]indazole-9-carboxylate produced according to the same manner as the Reference Example 21-(a) (48 mg) in 1,4-dioxane (1 mL) was added a 4 M solution of hydrogen chloride in 1,4-dioxane (0.36 mL) with stirring at room temperature, the resulting mixture was stirred at room temperature for 4 hours, and then left to stand at room temperature for 2 days. A 4 M solution of hydrogen chloride in 1,4-dioxane (0.36 mL) was added thereto at room temperature, and the resulting mixture was stirred for 24 hours. After the reaction was completed, the reaction solution was concentrated under reduced pressure to give the title compound (38 mg) as white solids.

Mass spectrum (ESI, m/z): 232 $[M+H]^+$

Reference Example 22-(a)

Production of tert-butyl (R)-7-ethyl-2-methyl-2,7,8,10-tetrahydro-9H-[1,4]oxazepino[7,6-g]indazole-9-carboxylate

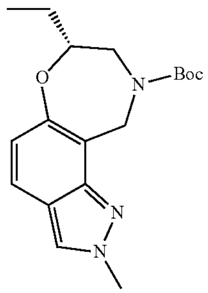 [SMILES: CC[C@@H]1CN(C(=O)OC(C)(C)C)Cc2c(ccc3cn(C)nc23)O1]

To a solution of tert-butyl (R)-7-ethyl-1,7,8,10-tetrahydro-9H-[1,4]oxazepino[7,6-g]indazole-9-carboxylate produced according to the same manner as the Reference Example 20-(c) (50 mg) in dimethylformamide (1 mL) was added sodium hydride (13 mg) under argon gas flow with stirring at 0° C., and the resulting mixture was stirred at 0° C. for 45 minutes. Then, methyl iodide (0.022 mL) was added thereto with stirring at 0° C., and the resulting mixture was stirred at room temperature for 3.25 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate→ethyl acetate:methanol) to give the title compound (16 mg) as a pale yellow oil.

Mass spectrum (ESI, m/z): 332 [M+H]$^+$

Reference Example 22-(b)

Production of (R)-7-ethyl-2-methyl-7,8,9,10-tetrahydro-9H-[1,4]oxazepino[7,6-g]indazole dihydrochloride

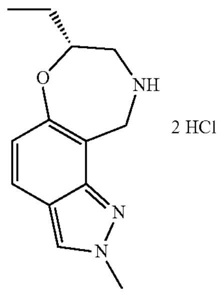 [SMILES: CC[C@@H]1CNCc2c(ccc3cn(C)nc23)O1]

To a solution of tert-butyl. (R)-7-ethyl-2-methyl-2,7,8,10-tetrahydro-9H-[1,4]oxazepino[7,6-g]indazole-9-carboxylate produced according to the same manner as the Reference Example 22-(a) (30 mg) in 1,4-dioxane (1 mL) was added a 4 M solution of hydrogen chloride in 1,4-dioxane (0.226 mL) with stirring at room temperature, the resulting mixture was stirred at room temperature for 4 hours, and then left to stand at room temperature for 2 days. After the reaction was completed, the reaction solution was concentrated under reduced pressure to give the title compound (32 mg) as pale yellow solids.

Mass spectrum (ESI, m/z): 232 [M+H]$^+$

Reference Example 23-(a)

Production of 6-chloro-3-fluoropicolinaldehyde

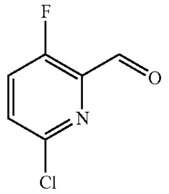

(1) To a solution of methyl 6-chloro-3-fluoropicolinate (0.50 g) in toluene (2.5 mL) was added a 1 M solution of diisobutylaluminum hydride in toluene (5.3 mL) under argon gas flow with stirring at 0° C., and the resulting mixture was stirred at 0° C. for 1 hour. After the reaction was completed, a 10% aqueous solution of potassium sodium tartrate was added thereto, the resulting mixture was stirred at room temperature for 5 minutes, and the resulting mixed solution was subjected to extraction with ethyl acetate. The resulting organic layer was washed with a saturated aqueous solution of sodium hydrogen carbonate, dried over anhydrous magnesium sulfate, filtered, and concentrated under reduced pressure to give a crude product comprising (6-chloro-3-fluoropyridin-2-yl)methanol.

(2) To a solution of the crude product comprising (6-chloro-3-fluoropyridin-2-yl)methanol produced in (1) in dichloromethane (2 mL) was added Dess-Martin periodinane (1.34 g) under argon gas flow with stirring at 0° C., and the resulting mixture was stirred at room temperature for 1.5 hours. After the reaction was completed, to the reaction solution was added an aqueous solution of sodium thiosulfate, and the resulting mixed solution was subjected to extraction with ethyl acetate. The resulting organic layer was washed sequentially with a saturated aqueous solution of sodium hydrogen carbonate and saturated brine, dried over anhydrous magnesium sulfate, filtered, and concentrated under reduced pressure. The resulting residues were purified by a silica gel column (elution solvent; hexane:ethyl acetate) to give the title compound (0.262 g) as white solids.

Mass spectrum (DUIS, m/z): 160 [M+H]$^+$

Reference Example 23-(b)

Production of (R)-1-(((6-chloro-3-fluoropyridin-2-yl)methyl)amino)butan-2-ol

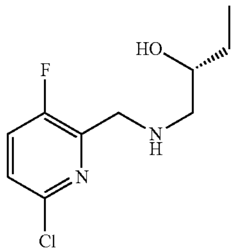

To a solution of 6-chloro-3-fluoropicolinaldehyde produced in the Reference Example 23-(a) (0.260 g) in dichloromethane (10 mL) was added (2R)-1-amino-2-butanol (0.174 g) under argon gas flow with stirring at room temperature, and the resulting mixture was stirred at room temperature for 30 minutes. Then, sodium triacetoxyborohydride (0.691 g) was added thereto with stirring at room temperature, and the resulting mixture was stirred at room temperature for 14.5 hours. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; ethyl acetate:methanol) to give the title compound (0.336 g) as a colorless oil.

Mass spectrum (ESI, m/z): 233 [M+1]$^+$

Reference Example 23-(c)

Production of tert-butyl (R)-7-chloro-2-ethyl-2,3-dihydropyrido[2,3-f][1,4]oxazepine-4(5H)-carboxylate

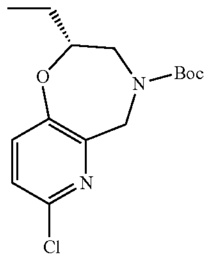 [SMILES: CC[C@@H]1CN(C(=O)OC(C)(C)C)Cc2nc(Cl)ccc2O1]

To a solution of (R)-1-(((6-chloro-3-fluoropyridin-2-yl)methyl)amino)butan-2-ol produced in the Reference Example 23-(b) (0.335 g) in dimethyl sulfoxide (14 mL) was added potassium tert-butoxide (0.198 g) under argon gas flow with stirring at room temperature, and the resulting mixture was stirred at room temperature for 2 hours. Then, di-tert-butyl dicarbonate (0.403 mL) was added thereto with stirring at room temperature, and the resulting mixture was stirred at room temperature for 15 hours. After the reaction was completed, to the reaction solution was added water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (0.325 g) as a slightly yellow oil.

Mass spectrum (ESI, m/z): 313 [M+H]$^+$

Reference Example 23-(d)

Production of tert-butyl (R)-7-(azetidin-1-yl)-2-ethyl-2,3-dihydropyrido[2,3-f][1,4]oxazepine-4(5H)-carboxylate

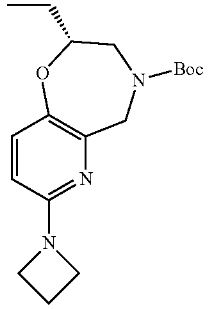 [SMILES: CC[C@@H]1CN(C(=O)OC(C)(C)C)Cc2nc(N3CCC3)ccc2O1]

To a solution of tert-butyl (R)-7-chloro-2-ethyl-2,3-dihydropyrido[2,3-f][1,4]oxazepine-4(5H)-carboxylate produced in the Reference Example 23-(c) (0.200 g) in toluene (15 mL) were added xantphos (0.075 g), azetidine (0.129 mL), sodium tert-butoxide (0.185 g), and tris(dibenzylideneacetone)dipalladium(0) (0.059 g) under argon gas flow with stirring at room temperature, and the resulting mixture was stirred at 100° C. for 1 hour by using a microwave reactor (manufactured by Biotage, Initiator™ 2.0). After the reaction was completed, the reaction solution was concentrated under reduced pressure. The resulting residues were purified by a silica gel column (elution solvent; hexane:ethyl acetate) to give the title compound (0.188 g) as a yellow oil.

Mass spectrum (ESI, m/z): 334 [M+H]$^+$

Reference Example 23-(e)

Production of (R)—N-(3-chloropropyl)-2-ethyl-2, 3, 4, 5-tetrahydropyrido[2,3-f][1,4]oxazepin-7-amine dihydrochloride

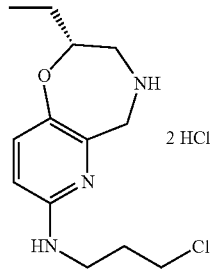 [SMILES: CC[C@@H]1CNCc2nc(NCCCCl)ccc2O1]

To a solution of tert-butyl (R)-7-(azetidin-1-yl)-2-ethyl-2,3-dihydropyrido[2,3-f][1,4]oxazepine-4 (5H)-carboxylate produced in the Reference Example 23-(d) (0.187 g) in 1,4-dioxane (5 mL) was added a 4 M solution of hydrogen chloride in 1,4-dioxane (0.675 mL) under argon atmosphere with stirring at room temperature, and the resulting mixture was stirred at room temperature for 22 hours. A 4 M solution of hydrogen chloride in 1,4-dioxane (0.675 mL) was added thereto, and the resulting mixture was stirred at room temperature for 5 hours. After the reaction was completed, the reaction solution was concentrated under reduced pressure, and dried under reduced pressure to give the title compound (0.172 g).

Mass spectrum (ESI, m/z): 270 [M+H]

Reference Example 23-(f)

Production of 3-(1,4-dimethyl-1H-benzo[d][1,2,3]triazol-5-yl)-3-(3-(hydroxymethyl)-4-methylphenyl)-2,2-dimethylpropanoic Acid

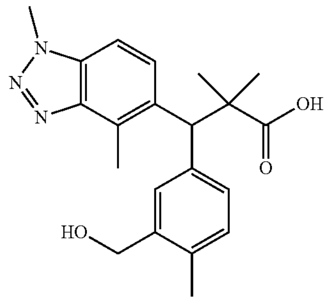 [SMILES: Cc1ccc(C(c2ccc3c(nnn3C)c2C)C(C)(C)C(=O)O)cc1CO]

To a solution of methyl 3-(1,4-dimethyl-1H-benzo[d][1,2,3]triazol-5-yl)-3-(3-(hydroxymethyl)-4-methylphenyl)-2,2-dimethylpropanoate produced according to the same manner as the Reference Example 1-(h) (100 mg) in dimethyl sulfoxide (2.5 mL) was added dropwise a 1 M aqueous solution of potassium hydroxide (2.62 mL) under argon gas flow with stirring at room temperature, and the resulting mixture was stirred at 70° C. for 2 hours. After the reaction was completed, water (5 mL) was added thereto, and to the reaction solution was added 1 M hydrochloric acid to adjust the pH to 5.5. The resulting mixed solution was subjected to extraction three times with ethyl acetate. The resulting organic layer was washed with saturated brine, dried over anhydrous magnesium sulfate, filtered, and concentrated under reduced pressure. The resulting residues were purified by a silica gel column (elution solvent; ethyl acetate) to give the title compound (80 mg) as a white foam.

Mass spectrum (ESI, m/z): 368 [M+H]+

Reference Example 23-(g)

Production of 3-(1,4-dimethyl-1H-benzo[d][1,2,3]triazol-5-yl)-3-(3-formyl-4-methylphenyl)-2,2-dimethylpropanoic Acid

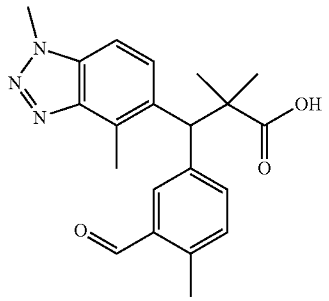 [SMILES: Cc1ccc(C(c2ccc3c(nnn3C)c2C)C(C)(C)C(=O)O)cc1C=O]

To a solution of 3-(1,4-dimethyl-1H-benzo[d][1,2,3]triazol-5-yl)-3-(3-(hydroxymethyl)-4-methylphenyl)-2,2-dimethylpropanoic Acid produced according to the same manner as the Reference Example 23-(f) (409 mg) in dichloromethane (8 mL) was added Dess-Martin periodinane (567 mg) under argon gas flow with stirring at 0° C., and the resulting mixture was stirred at room temperature for 2 hours. After the reaction was completed, to the reaction solution was added a saturated aqueous solution of sodium hydrogen carbonate, further an aqueous solution of sodium thiosulfate was added thereto, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (DIOL silica gel, elution solvent; hexane:ethyl acetate) to give the title compound (295 mg) as a slightly yellow foam.

Mass spectrum (ESI, m/z): 366 [M+H]+

Reference Example 23-(h)

Production of 3-(3-(((R)-7-((3-chloropropyl)amino)-2-ethyl-2,3-dihydropyrido[2,3-f][1,4]oxazepin-4(5H)-yl)methyl)-4-methylphenyl)-3-(1,4-dimethyl-1H-benzo[d][1,2,3]triazol-5-yl)-2,2-dimethylpropanoic Acid

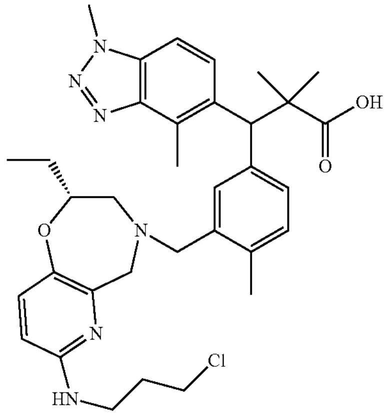 [SMILES: CC[C@@H]1CN(Cc2cc(C(c3ccc4c(nnn4C)c3C)C(C)(C)C(=O)O)ccc2C)Cc2nc(NCCCCl)ccc2O1]

To a solution of 3-(1,4-dimethyl-1H-benzo[d][1,2,3]triazol-5-yl)-3-(3-formyl-4-methylphenyl)-2,2-dimethylpropanoic acid produced according to the same manner as the Reference Example 23-(g) (50 mg) in 1,2-dichloroethane (1.5 mL) were sequentially added (R)—N-(3-chloropropyl)-2-ethyl-2,3,4,5-tetrahydropyrido[2,3-f][1,4]oxazepin-7-amine dihydrochloride produced in the Reference Example 23-(e) (45 mg), N,N-diisopropylethylamine (0.056 mL), and acetic acid (0.009 mL) under argon gas flow with stirring at room temperature, and the resulting mixture was stirred at room temperature for 1 hour. Then, sodium triacetoxyborohydride (59 mg) was added thereto with stirring at room temperature, and the resulting mixture was stirred at room temperature for 16 hours. After the reaction was completed, to the reaction solution was added a saturated aqueous solution of sodium hydrogen carbonate, and the resulting mixed solution was subjected to extraction with ethyl acetate. The resulting organic layer was dried over anhydrous magnesium sulfate, filtered, and concentrated under reduced pressure. The resulting residues were purified three times by a silica gel column (DIOL silica gel, elation solvent; hexane:ethyl acetate) to give the title compound (51 mg) as white solids.

Mass spectrum (ESI, m/z): 619 [M+H]+

Reference Example 24-(a)

Production of tert-butyl (S)-(2-hydroxybutyl) ((1-hydroxynaphthalen-2-yl)methyl) carbamate

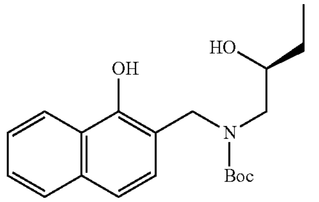 [SMILES: CC[C@H](O)CN(Cc1ccc2ccccc2c1O)C(=O)OC(C)(C)C]

(1) To a solution of 1-hydroxy-2-naphthaldehyde (151 mg) in ethanol (3 mL) was added (2S)-1-amino-2-butanol (91 mg) under argon gas flow with stirring at room temperature, and the resulting mixture was stirred at room temperature for 2 hours. Then, sodium borohydride (51 mg) was added thereto with stirring at room temperature, and the resulting mixture was stirred at room temperature for 30 minutes. After the reaction was completed, to the reaction solution was added 2 M hydrochloric acid until the bubbling disappeared, and a 1 M aqueous solution of sodium hydroxide was added thereto to adjust the pH to about 5.5. Then, the resulting mixed solution was subjected to extraction with ethyl acetate. The resulting organic layer was washed with saturated brine, dried over anhydrous sodium sulfate, filtered, and concentrated under reduced pressure to give (S)-2-(((2-hydroxybutyl)amino)methyl)naphthalen-1-ol (149 mg) as a brown oil.

(2) To a solution of (S)-2-(((2-hydroxybutyl)amino)methyl)naphthalen-1-ol produced in (1) (149 mg) in methanol (5 mL) was added di-tert-butyl dicarbonate (0.225 mL) under argon gas flow with stirring at room temperature, and the resulting mixture was stirred at room temperature overnight. Then, a 8 M aqueous solution of sodium hydroxide (0.550 mL) was added thereto with stirring at room temperature, and the resulting mixture was stirred at room temperature for 3 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (96 mg) as a brown oil.

Mass spectrum (ESI, m/z): 344 $[M-H]^-$

Reference Example 24-(b)

Production of tert-butyl (R)-2-ethyl-2,3-dihydronaphtho[2,1-f][1,4]oxazepine-4(5H)-carboxylate

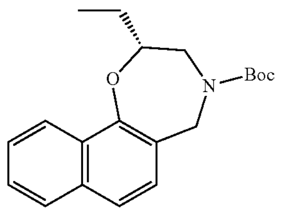 [SMILES: CC[C@@H]1CN(C(=O)OC(C)(C)C)Cc2ccc3ccccc3c2O1]

To a solution of tert-butyl (S)-(2-hydroxybutyl) ((1-hydroxynaphthalen-2-yl)methyl)carbamate produced in the Reference Example 24-(a) (96 mg) and triphenylphosphine (84 mg) in tetrahydrofuran (10 mL) was added a 1.9 M solution of diisopropyl azodicarboxylate in toluene (0.168 mL) under argon gas flow with stirring under ice-cooling, and the resulting mixture was stirred at room temperature for 2 days. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane ethyl acetate) to give the title compound (47 mg) as a colorless oil.

Mass spectrum (ESI, m/z): 328 $[M+H]^+$

Reference Example 24-(c)

Production of (R)-2-ethyl-2,3,4,5-tetrahydronaphtho[2,1-f][1,4]oxazepine

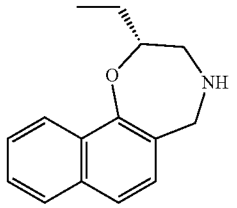 [SMILES: CC[C@@H]1CNCc2ccc3ccccc3c2O1]

To a solution of tert-butyl (R)-2-ethyl-2,3-dihydronaphtho[2,1-f][1,4]oxazepine-4(5H)-carboxylate produced in the Reference Example 24-(b) (47 mg) in tert-butyl methyl ether (1 mL) was added a 4 M solution of hydrogen chloride in 1,4-dioxane (0.359 mL) with stirring at room temperature, and the resulting mixture was stirred at room temperature for 2.5 hours. Additionally, a 4 M solution of hydrogen chloride in 1,4-dioxane (0.72 mL) was added thereto with stirring at room temperature, and the resulting mixture was stirred at room temperature for 3 hours. Additionally, a 4 M solution of hydrogen chloride in 1,4-dioxane (0.72 mL) was added thereto with stirring at room temperature, and the resulting mixture was stirred at room temperature for 3 hours. After the reaction was completed, to the reaction solution was added water, and the resulting mixed solution was washed with tert-butyl methyl ether. To the resulting aqueous layer was added a saturated aqueous solution of sodium hydrogen carbonate to adjust the pH to about 9, and the resulting mixed solution was subjected to extraction with ethyl acetate. The resulting organic layer was dried over anhydrous sodium sulfate, filtered, and concentrated under reduced pressure to give the title compound (27 mg) as a brown oil.

Mass spectrum (ESI, m/z): 228 $[M+H]^+$

Reference Example 25-(a)

Production of (R)-1-(((4-fluoroisoquinolin-3-yl)methyl)amino)butan-2-ol

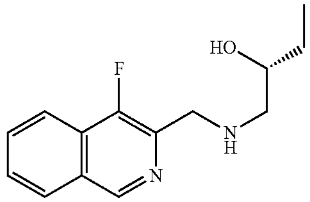 [SMILES: CC[C@@H](O)CNCc1ncc2ccccc2c1F]

To a solution of 4-fluoroisoquinoline-3-carbaldehyde synthesized according to the method described in Chemical Communications, 2013, 49, 8537. (250 mg) in dichloromethane (5 mL) was added (2R)-1-amino-2-butanol (0.162 mL) under argon gas flow with stirring at room temperature, and the resulting mixture was stirred at room temperature for 30 minutes. Then, sodium triacetoxyborohydride (605 mg) was added thereto with stirring at room temperature, and the resulting mixture was stirred at room temperature for 4 hours. After the reaction was completed, to the reaction solution was added water, and the resulting mixed solution was subjected to extraction twice with ethyl acetate. The resulting organic layer was dried over anhydrous magnesium sulfate, filtered, and concentrated under reduced pressure. The resulting residues were purified by a silica gel column (DIOL silica gel, elution solvent; ethyl acetate:methanol) to give the title compound (311 mg) as a slightly yellow oil.

Mass spectrum (ESI, m/z): 249 $[M+H]^+$

Reference Example 25-(b)

Production of tert-butyl (R)-2-ethyl-2,3-dihydro-[1,4]oxazepino[6,7-c]isoquinoline-4(5H)-carboxylate

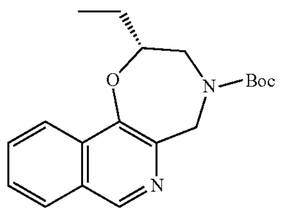 [SMILES: CC[C@@H]1CN(C(=O)OC(C)(C)C)Cc2ncc3ccccc3c2O1]

To a solution of (R)-1-(((4-fluoroisoquinolin-3-yl)methyl)amino)butan-2-ol produced in the Reference Example 25-(a) (311 mg) in dimethyl sulfoxide (8 mL) was added potassium tert-butoxide (169 mg) under argon atmosphere with stirring at room temperature, and the resulting mixture was stirred at room temperature for 1 hour and at 90° C. for 1 hour. After the reaction was completed, the resulting mixture was allowed to cool to room temperature. Di-tert-butyl dicarbonate (0.349 mL) was added thereto, and the resulting mixture was stirred at room temperature for 2 hours. After the reaction was completed, to the reaction solution was added water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (323 mg) as a slightly yellow oil.

Mass spectrum (ESI, m/z): 329 $[M+H]^+$

Reference Example 25-(c)

Production of (R)-2-ethyl-2,3,4,5-tetrahydro-[1,4]oxazepino[6,7-c]isoquinoline dihydrochloride

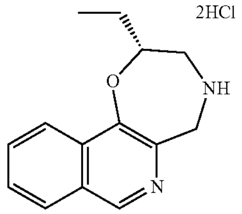 [SMILES: CC[C@@H]1CNCc2ncc3ccccc3c2O1]

To a solution of tert-butyl (R)-2-ethyl-2,3-dihydro-[1,4]oxazepino[6,7-c]isoquinoline-4(5H)-carboxylate produced in the Reference Example 25-(b) (323 mg) in 1,4-dioxane (3 mL) was added dropwise a 4 M solution of hydrogen chloride in 1,4-dioxane (0.984 mL) under argon gas flow with stirring at room temperature, and the resulting mixture was stirred at room temperature for 0.5 hour and at 60° C. for 2 hours. After the reaction was completed, the reaction solution was allowed to cool to room temperature, hexane (4 mL) was added thereto, and the resulting mixture was stirred at room temperature for 15 hours. The precipitated solids were collected by filtration, washed with tert-butyl methyl ether, and subjected to vacuum drying at room temperature to give the title compound (296 mg) as white solids.

Mass spectrum (ESI, m/z): 229 $[M+H]^+$

Reference Example 26-(a)

Production of (R)-1-(((4-chloroquinolin-3-yl)methyl)amino)butan-2-ol

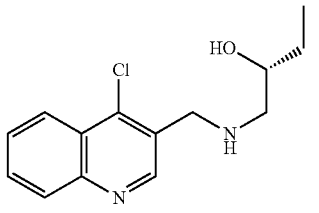 [SMILES: CC[C@@H](O)CNCc1cnc2ccccc2c1Cl]

To a solution of 4-chloroquinoline-3-carbaldehyde (300 mg) in dichloromethane (5 mL) was added (2R)-1-amino-2-butanol (0.178 mL) under argon gas flow with stirring at room temperature, and the resulting mixture was stirred at room temperature for 30 minutes. Then, sodium triacetoxyborohydride (664 mg) was added thereto with stirring at room temperature, and the resulting mixture was stirred at room temperature for 4 hours. After the reaction was completed, to the reaction solution was added water, and the resulting mixed solution was subjected to extraction twice with ethyl acetate. The resulting organic layer was dried over anhydrous magnesium sulfate, filtered, and concentrated under reduced pressure. The resulting residues were purified by a silica gel column (DIOL silica gel, elution solvent; hexane:ethyl acetate) to give the title compound (324 mg) as a slightly yellow oil.

Mass spectrum (ESI, m/z): 265 $[M+H]^+$

Reference Example 26-(b)

Production of tert-butyl (R)-2-ethyl-2,3-dihydro-[1,4]oxazepino[6,7-c]quinoline-4(5H)-carboxylate

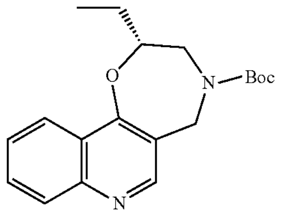 [SMILES: CC[C@@H]1CN(C(=O)OC(C)(C)C)Cc2cnc3ccccc3c2O1]

To a solution of (R)-1-(((4-chloroquinolin-3-yl)methyl)amino)butan-2-ol produced in the Reference Example 26-(a) (324 mg) in dimethyl sulfoxide (8 mL) was added potassium tert-butoxide (165 mg) under argon atmosphere with stirring at room temperature, and the resulting mixture was stirred at room temperature for 0.5 hour and at 90° C. for 1 hour. Then, the resulting mixture was allowed to cool to room temperature. Di-tert-butyl dicarbonate (0.341 mL) was added thereto, and the resulting mixture was stirred at room temperature for 2 hours. After the reaction was completed, to the reaction solution was added water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (43 mg) as a slightly yellow oil.

Mass spectrum (ESI, m/z): 329 [M+H]$^+$

Reference Example 26-(c)

Production of (R)-2-ethyl-2,3,4,5-tetrahydro-[1,4]oxazepino[6,7-c]quinoline dihydrochloride

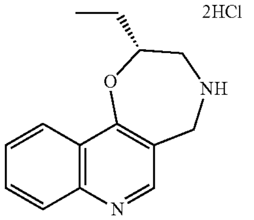 [SMILES: CC[C@@H]1CNCc2cnc3ccccc3c2O1]

To a solution of tert-butyl (R)-2-ethyl-2,3-dihydro-[1,4]oxazepino[6,7-c]quinoline-4(5H)-carboxylate produced in the Reference Example 26-(b) (43 mg) in 1,4-dioxane (3 mL) was added dropwise a 4 M solution of hydrogen chloride in 1,4-dioxane (0.131 mL) under argon gas flow with stirring at room temperature, and the resulting mixture was stirred at room temperature for 0.5 hour and at 60° C. for 2 hours. After the reaction was completed, the reaction solution was concentrated to give the title compound (32 mg).

Mass spectrum (ESI, m/z): 229 [M+H]$^+$

Reference Example 26-(d)

Production of (4-chloroquinolin-3-yl)methanol

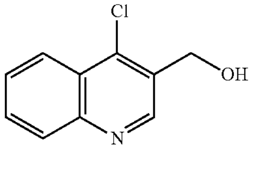 [SMILES: OCc1cnc2ccccc2c1Cl]

To a suspension of ethyl 4-chloroquinoline-3-carboxylate (2.0 g) in tert-butyl methyl ether (20 mL) was added dropwise a 70' solution of sodium bis(2-methoxyethoxy) aluminum hydride in toluene (2.47 mL) under argon gas flow with stirring at −10° C., and the resulting mixture was stirred at room temperature for 0.5 hour. After the reaction was completed, to the reaction solution was added a 5 M aqueous solution of sodium hydroxide, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (587 mg) as pale yellow solids.

Mass spectrum (ESI, m/z): 194 [M+H]$^+$

Reference Example 26-(e)

Production of (4-iodoquinolin-3-yl)methanol

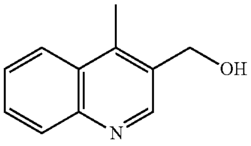

To a suspension of (4-chloroquinolin-3-yl)methanol produced in the Reference Example 26-(d) (0.586 g) in tetrahydrofuran (12 mL) was added dropwise a 4 M solution of hydrogen chloride in 1,4-dioxane (0.37 mL) under argon gas flow with stirring at room temperature, and the resulting mixture was stirred at room temperature for 0.5 hour. Then, the reaction solution was concentrated under reduced pressure, acetonitrile was added thereto, sodium iodide (1.82 g) was added thereto with stirring at room temperature, and the resulting mixture was stirred under reflux for 14 hours. After the reaction was completed, the reaction solution was poured into a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (0.648 g) as yellow solids.

Mass spectrum (ESI, m/z): 286 [M+H]$^+$

Reference Example 26-(f)

Production of 4-iodoquinoline-3-carbaldehyde

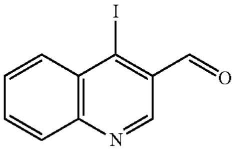 [SMILES: O=Cc1cnc2ccccc2c1I]

To a suspension of (4-iodoquinolin-3-yl)methanol produced in the Reference Example 26-(e) (647 mg) in dichloromethane (50 mL) was added Dess-Martin periodinane (1.16 g) under argon gas flow with stirring at 0° C., and the resulting mixture was stirred at room temperature for 0.5 hour. After the reaction was completed, the reaction solution was poured into a saturated aqueous solution of sodium hydrogen carbonate, washed with an aqueous solution of sodium thiosulfate, and the resulting mixed solution was subjected to extraction with ethyl acetate. The resulting organic layer was washed with saturated brine, dried over anhydrous magnesium sulfate, filtered, and concentrated under reduced pressure. To the resulting residues was added a mixed solvent of ethyl acetate/tert-butyl methyl ether (=8:2), and the resulting mixture was subjected to sonication. The precipitated solids were collected by filtration, and washed with tert-butyl methyl ether to give the title compound (763 mg) as pale yellow solids.

Mass spectrum (ESI, m/z): 284 [M+H]+

Reference Example 26-(g)

Production of (R)-1-(((4-iodoquinolin-3-yl)methyl) amino)butan-2-ol

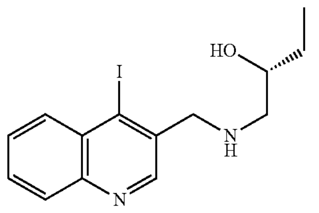 [SMILES: CC[C@@H](O)CNCc1cnc2ccccc2c1I]

To a suspension of 4-iodoquinoline-3-carbaldehyde produced in the Reference Example 26-(f) (642 mg) in ethanol (20 mL) was added (2R)-1-amino-2-butanol (0.24 mL) under argon gas flow with stirring at room temperature, and the resulting mixture was stirred at 50° C. for 1 hour. Then, sodium borohydride (103 mg) was added thereto with stirring at room temperature, and the resulting mixture was stirred at room temperature for 10 hours. After the reaction was completed, to the reaction solution were added water and 2 M hydrochloric acid to adjust the pH to 2.5, and the resulting mixture was stirred for 30 minutes. The resulting mixed solution was washed with tert-butyl methyl ether, to the resulting aqueous layer was added a 5 M aqueous solution of sodium hydroxide to adjust the pH to 9, and the resulting mixture was subjected to extraction with dichloromethane. The resulting organic layer was dried over anhydrous magnesium sulfate, filtered, and concentrated under reduced pressure to give the title compound (585 mg) as slightly yellow solids.

Mass spectrum (ESI, m/z): 357 [M+H]+

Reference Example 26-(h)

Production of (R)-2-ethyl-2,3,4,5-tetrahydro-[1,4] oxazepino[6,7-c]quinoline

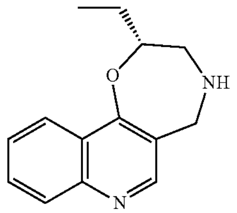 [SMILES: CC[C@@H]1CNCc2cnc3ccccc3c2O1]

To a solution of (R)-1-(((4-iodoquinolin-3-yl)methyl) amino)butan-2-ol produced in the Reference Example 26-(g) (583 mg) in 2-propanol (10 mL) were sequentially added cesium carbonate (1.07 g) and copper(I) iodide (156 mg) under argon gas flow with stirring at room temperature, and the resulting mixture was stirred under reflux for 4 hours. Copper(I) iodide (78 mg) and cesium carbonate (134 mg) were additionally added thereto, and the resulting mixture was stirred under reflux for 3 hours. Additionally, copper (I) iodide (78 mg) and cesium carbonate (134 mg) were added thereto, and the resulting mixture was stirred under reflux for 1 hour. After the reaction was completed, the reaction solution was concentrated under reduced pressure. The resulting residues were purified by a silica gel column (DIOL silica gel, elution solvent; ethyl acetate:methanol) to give the title compound (145 mg) as pale yellow solids.

Mass spectrum (ESI, m/z): 229 [M+H]+

Reference Example 27-(a)

Production of tert-butyl (S)-(2-hydroxybutyl) ((8-hydroxyquinolin-7-yl)methyl) carbamate

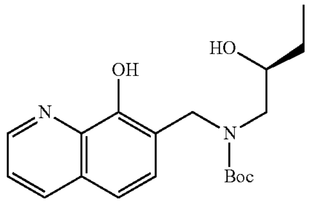 [SMILES: CC[C@H](O)CN(Cc1ccc2cccnc2c1O)C(=O)OC(C)(C)C]

A solution of 8-hydroxyquinoline-7-carbaldehyde (400 mag) and (2S)-1-amino-2-butanol (0.24 mL) in dichloromethane (12 mL) was stirred under argon gas flow at room temperature for 30 minutes. Then, sodium triacetoxyborohydride (734 mg) was added thereto, and the resulting mixture was stirred at room temperature for 10 hours. After the reaction was completed, the reaction solution was concentrated under reduced pressure, to the resulting residues were added methanol (4 mL) and a 8 M aqueous solution of sodium hydroxide (2.89 mL), di-tert-butyl dicarbonate (1.06 mL) was added thereto, and the resulting mixture was stirred at room temperature for 3 hours. Additionally, di-tert-butyl dicarbonate (1.06 mL) was added thereto, and the resulting mixture was stirred at room temperature for 1 hour. Additionally, a 8 M aqueous solution of sodium hydroxide (0.7 mL) was added thereto, and the resulting mixture was stirred at room temperature for 2 hours. 1 M hydrochloric acid was added thereto to adjust the pH to 6.5, and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (DIOL silica gel, elution solvent; hexane:ethyl acetate) to give the title compound (474 mg) as a slightly yellow oil.

Mass spectrum (ESI, m/z): 347 [M+H]+

Reference Example 27-(b)

Production of tert-butyl (R)-2-ethyl-2,3-dihydro-[1,4]oxazepino[6,7-h]quinoline-4 (5H)-carboxylate

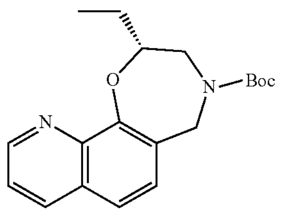 [SMILES: CC[C@@H]1CN(C(=O)OC(C)(C)C)Cc2ccc3cccnc3c2O1]

To a solution of tert-butyl (S)-(2-hydroxybutyl) ((8-hydroxyquinolin-7-yl)methyl)carbamate produced in the Reference Example 27-(a) (470 mg) in tetrahydrofuran (10 mL) were sequentially added (E)-N1,N1,N2,N2-tetramethyldiazene-1,2-dicarboxamide (350 mg) and tri-n-butylphosphine (0.502 mL) under argon gas flow with stirring at room temperature, and the resulting mixture was stirred at room temperature for 10 hours. After the reaction was completed, the reaction solution was diluted with ethyl acetate, washed sequentially with water and saturated brine, dried over anhydrous magnesium sulfate, and concentrated under reduced pressure. The resulting residues were purified by a silica gel column (elution solvent; hexane:ethyl acetate) to give the title compound (336 mg) as a colorless oil.

Mass spectrum (ESI, m/z): 329 [M+H]

Reference Example 27-(c)

Production of (R)-2-ethyl-2,3,4,5-tetrahydro-[1,4]oxazepino[6,7-h]quinoline dihydrochloride

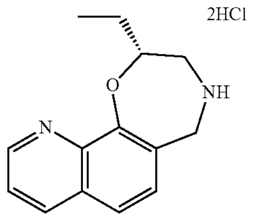 [SMILES: CC[C@@H]1CNCc2ccc3cccnc3c2O1]

To a solution of tert-butyl (R)-2-ethyl-2,3-dihydro-[1,4]oxazepino[6,7-h]quinoline-4(5H)-carboxylate produced in the Reference Example 27-(b) (333 mg) in 1,4-dioxane (3 mL) was added dropwise a 4 M solution of hydrogen chloride in 1,4-dioxane (1.01 mL) under argon gas flow with stirring at room temperature, and the resulting mixture was stirred at room temperature for 1 hour and at 50° C. for 6 hours. After the reaction was completed, tert-butyl methyl ether (5 mL) was added thereto, the resulting mixture was concentrated under reduced pressure, and the resulting residues were dried under reduced pressure to give the title compound (200 mg) as slightly yellow solids.

Mass spectrum (ESI, m/z): 229 $[M+H]^+$

Reference Example 28-(a)

Production of (R)-1-(((5-fluoroquinolin-6-yl)methyl)amino)butan-2-ol

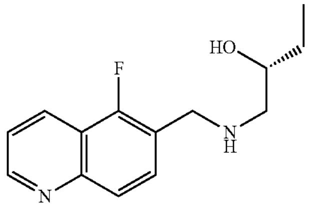 [SMILES: CC[C@@H](O)CNCc1ccc2ncccc2c1F]

To a solution of (2R)-1-amino-2-butanol (0.153 g) in dichloromethane (10 mL) was added 5-fluoroquinoline-6-carbaldehyde (0.251 g) under argon gas flow with stirring at room temperature, and the resulting mixture was stirred at room temperature for 1 hour. Then, sodium triacetoxyborohydride (0.608 g) was added thereto with stirring at room temperature, and the resulting mixture was stirred at room temperature for 17.25 hours. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (DIOL silica gel, elution solvent; ethyl acetate:methanol) to give the title compound (0.263 g) as a colorless oil.

Mass spectrum (DUIS, m/z): 249 $[M+H]^+$

Reference Example 28-(b)

Production of (R)-2-ethyl-2, 3, 4, 5-tetrahydro-[1,4]oxazepino[7,6-f]quinoline

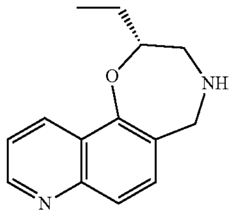 [SMILES: CC[C@@H]1CNCc2ccc3ncccc3c2O1]

To a solution of (R)-1-(((5-fluoroquinolin-6-yl)methyl)amino)butan-2-ol produced in the Reference Example 28-(a) (0.263 g) in dimethyl sulfoxide (10 mL) was added potassium tert-butoxide (0.142 g) under argon gas flow with stirring at room temperature, and the resulting mixture was stirred at room temperature for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (DIOL silica gel, elution solvent; ethyl acetate:methanol) to give the title compound (0.407 g) as a light brown oil.

Mass spectrum (DUIS, m/z): 229 $[M+H]^+$

Reference Example 49-(a)

Production of 4-fluoro-1-hydroxy-2-naphthaldehyde

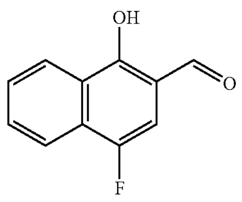 [SMILES: O=Cc1cc(F)c2ccccc2c1O]

To a solution of 4-fluoronaphthalen-1-ol (800 mg) in trifluoroacetic acid (5 mL) was added hexamethylenetetramine (968 mg) under argon gas flow with stirring at room temperature, and the resulting mixture was stirred at 80° C. for 1 hour. After the reaction was completed, the reaction solution was concentrated, and a saturated aqueous solution of sodium hydrogen carbonate was added thereto. The resulting mixed solution was subjected to extraction with ethyl acetate. The resulting organic layer was washed sequentially with a saturated aqueous solution of sodium hydrogen carbonate and saturated brine, dried over anhydrous magnesium sulfate, filtered, and concentrated under reduced pressure. The resulting residues were purified by a silica gel column (elution solvent; hexane:ethyl acetate) to give the title compound (287 mg) as yellow solids.

Mass spectrum (ESI, m/z): 189 $[M-H]^-$

Reference Example 49-(b)

Production of tert-butyl (S)-((4-fluoro-1-hydroxynaphthalen-2-yl)methyl) (2-hydroxybutyl) carbamate

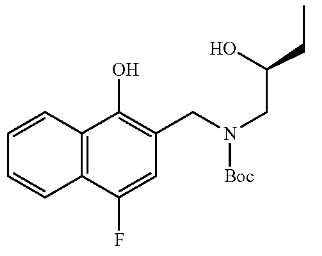 [SMILES: CC[C@H](O)CN(Cc1cc(F)c2ccccc2c1O)C(=O)OC(C)(C)C]

To a solution of 4-fluoro-1-hydroxy-2-naphthaldehyde produced in the Reference Example 49-(a) (287 mg) in dichloromethane (5 mL) was added (2S)-1-amino-2-butanol (0.171 mL) under argon gas flow with stirring at room temperature, and the resulting mixture was stirred at room temperature for 0.5 hour. Then, sodium triacetoxyborohydride (480 mg) was added thereto, and the resulting mixture was stirred at room temperature for 1 hour. After the reaction was completed, the reaction solution was concentrated under reduced pressure, to the resulting residues were added methanol (5 mL) and a 8 M aqueous solution of sodium hydroxide (1.89 mL), di-tert-butyl dicarbonate (0.693 mL) was added thereto, and the resulting mixture was stirred at room temperature for 3 hours. Then, di-tert-butyl dicarbonate (0.300 mL) was added thereto, and the resulting mixture was stirred at room temperature for 1 hour. Then, a 8 M aqueous solution of sodium hydroxide (0.700 mL) was added thereto, and the resulting mixture was stirred at room temperature for 15 hours. Then, 1 M hydrochloric acid was added thereto to adjust the pH to 5, and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (299 mg) as a colorless oil.

Mass spectrum (ESI, m/z): 364 $[M+H]^+$

Reference Example 49-(c)

Production of tert-butyl (R)-2-ethyl-7-fluoro-2,3-dihydronaphtho[2,1-f][1,4]oxazepine-4(5H)-carboxylate

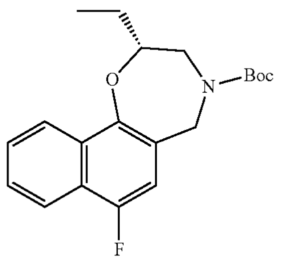 [SMILES: CC[C@@H]1CN(C(=O)OC(C)(C)C)Cc2cc(F)c3ccccc3c2O1]

To a solution of tert-butyl (S)-((4-fluoro-1-hydroxynaphthalen-2-yl)methyl) (2-hydroxybutyl) carbamate produced in the Reference Example 49-(b) (299 mg) in tetrahydrofuran (3 mL) was sequentially added (E)-N1,N1,N2,N2-tetramethyldiazene-1,2-dicarboxamide (212 mg) and tri-n-butylphosphine (0.304 mL) under argon gas flow with stirring at room temperature, and the resulting mixture was stirred at room temperature for 2 hours. After the reaction was completed, the reaction solution was diluted with ethyl acetate, washed sequentially with water and saturated brine, dried over anhydrous magnesium sulfate, filtered, and concentrated under reduced pressure. The resulting residues were purified by a silica gel column (elution solvent; hexane:ethyl acetate) to give the title compound (231 mg) as a colorless oil.

Reference Example 49-(d)

Production of (R)-2-ethyl-7-fluoro-2,3,4,5-tetrahydronaphtho[2,1-f][1,4]oxazepine hydrochloride

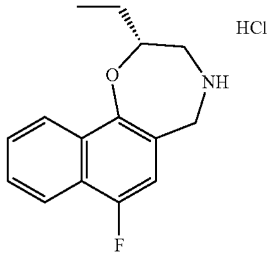 [SMILES: CC[C@@H]1CNCc2cc(F)c3ccccc3c2O1 ; Cl]

To a solution of tert-butyl (R)-2-ethyl-7-fluoro-2,3-dihydronaphtho[2,1-f][1,4]oxazepine-4 (5H)-carboxylate produced in the Reference Example 49-(c) (231 mg) in cyclopentyl methyl ether (2 mL) was added dropwise a 4 M solution of hydrogen chloride in cyclopentyl methyl ether (0.669 mL) under argon gas flow with stirring at room temperature, the resulting mixture was stirred at room temperature for 15 hours, then warmed to 90° C., and stirred for 6 hours. After the reaction was completed, the resulting mixture was allowed to cool to room temperature, hexane (4 mL) was added thereto, and the resulting mixture was stirred for 1 hour. The resulting solids were collected by filtration, washed with tert-butyl methyl ether, and dried under reduced pressure at room temperature to give the title compound (166 mg) as white solids.

Mass spectrum (ESI, m/z): 246 $[M+H]^+$

Reference Example 50-(a)

Production of benzyl (R)-8-ethyl-1-methyl-1,5,7,8-tetrahydro-6H-[1,4]oxazepino[6,7-f]indazole-6-carboxylate

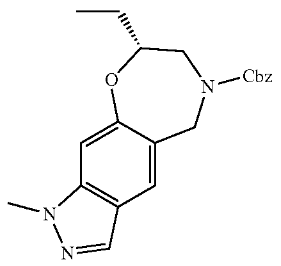 [SMILES: CC[C@@H]1CN(C(=O)OCc2ccccc2)Cc2cc3cnn(C)c3cc2O1]

To a solution of benzyl (R)-8-ethyl-1,5,7,8-tetrahydro-6H-[1,4]oxazepino[6,7-f]indazole-6-carboxylate produced according to the same manner as the Reference Example 15-(1) (186 mg) in dimethylformamide (2 mL) was added sodium hydride (25 mg) under argon gas flow with stirring at 0° C., and the resulting mixture was stirred at 0° C. for 1 hour. Then, iodomethane (0.033 mL) was added thereto with stirring at 0° C., and the resulting mixture was left to stand at room temperature for 54 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (82 mg) as a colorless oil.

Mass spectrum (ESI, m/z): 366 $[M+H]^+$

Reference Example 50-(b)

Production of (R)-8-ethyl-1-methyl-5,6,7,8-tetrahydro-1H-[1,4]oxazepino[6,7-f]indazole

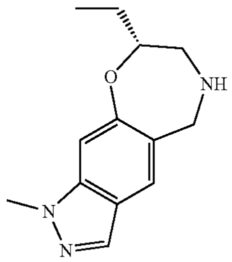 [SMILES: CC[C@@H]1CNCc2cc3cnn(C)c3cc2O1]

To a solution of benzyl (R)-8-ethyl-1-methyl-1,5,7,8-tetrahydro-6H-[1,4]oxazepino[6,7-f]indazole-6-carboxylate produced in the Reference Example 50-(a) (87 mg) in ethanol (2 mL) was added 10% palladium/carbon [PE type (trade name) manufactured by N.E. CHEMCAT CORPORATION, wetted with 50% water] (52 mg) with stirring at room temperature, the resulting mixture was subjected to hydrogen atmosphere, and then stirred at room temperature for 3.5 hours. After the reaction was completed, the reaction solution was filtered through Celite, and the resulting filtrate was concentrated under reduced pressure to give the title compound (62 mg) as a colorless oil.

Mass spectrum (ESI, m/z): 232 $[M+H]^+$

Reference Example 51-(a)

Production of benzyl (R)-8-ethyl-2-methyl-2,5,7,8-tetrahydro-6H-[1,4]oxazepino[6,7-f]indazole-6-carboxylate

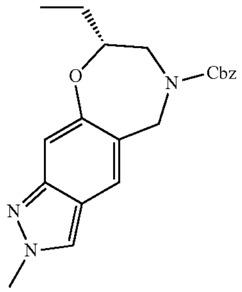 [SMILES: CC[C@@H]1CN(C(=O)OCc2ccccc2)Cc2cc3cn(C)nc3cc2O1]

To a solution of benzyl (R)-8-ethyl-1,5,7,8-tetrahydro-6H-[1,4]oxazepino[6,7-f]indazole-6-carboxylate produced according to the same manner as the Reference Example 15-(i) (186 mg) in dimethylformamide (2 mL) was added sodium hydride (25 mg) under argon gas flow with stirring at 0° C., and the resulting mixture was stirred at 0° C. for 1 hour. Then, iodomethane (0.033 mL) was added thereto with stirring at 0° C., and the resulting mixture was left to stand at room temperature for 54 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (42 mg) as a colorless oil.

Mass spectrum (ESI, m/z): 366 [M+H]$^+$

Reference Example 51-(b)

Production of (R)-8-ethyl-2-methyl-5,6,7,8-tetrahydro-2H-[1,4]oxazepino[6,7-f]indazole

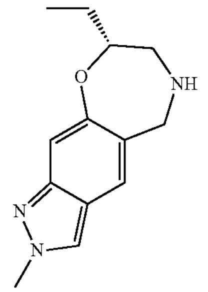 [SMILES: CC[C@@H]1CNCc2cc3cn(C)nc3cc2O1]

To a solution of benzyl. (R)-8-ethyl-2-methyl-2,5,7,8-tetrahydro-6H-[1,4]oxazepino[6,7-f]indazole-6-carboxylate produced in the Reference Example 51-(a) (42 mg) in ethanol (2 mL) was added 10% palladium/carbon [PE type (trade name) manufactured by N.E. CHEMCAT CORPORATION, wetted with 50% water] (25 mg) with stirring at room temperature, the resulting mixture was subjected to hydrogen atmosphere, and then stirred at room temperature for 3.5 hours. After the reaction was completed, the reaction solution was filtered through Celite, and the resulting filtrate was concentrated under reduced pressure to give the title compound (21 mg) as a colorless oil.

Mass spectrum (ESI, m/z): 232 [M+H]

Reference Example 52-(a)

Production of 6-bromo-7-methoxyisoquinoline

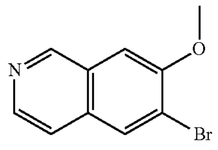

To a solution of 4-bromo-3-methoxybenzaldehyde (2.0 g) in toluene (15 mL) was added dropwise 2,2-dimethoxyethane-1-amine (1.20 mL) under argon gas flow with stirring at room temperature, and the resulting mixture was stirred under heating to reflux for 2 hours by using Dean-Stark trap. Then, the reaction solution was concentrated under reduced pressure. To the resulting residues was added dropwise polyphosphoric acid (10.8 mL) under argon gas flow with stirring at room temperature, and the resulting mixture was stirred at 85° C. for 4 hours. After the reaction was completed, the resulting mixture was allowed to cool to room temperature, and poured into ice-cold water. A 4 M aqueous solution of sodium hydroxide was added thereto to adjust the pH to 7.0, and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (960 mg) as brown solids.

Mass spectrum (ESI, m/z): 238 [M+H]$^+$

Reference Example 52-(b)

Production of tert-butyl (S)-(2-hydroxybutyl) ((7-hydroxyisoquinolin-6-yl)methyl) carbamate

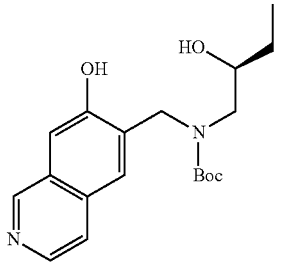 [SMILES: CC[C@H](O)CN(Cc1cc2ccncc2cc1O)C(=O)OC(C)(C)C]

To a solution of 6-bromo-7-methoxyisoquinoline produced in the Reference Example 52-(a) (960 mg) in diethyl ether (15 mL) was added dropwise a 1.6 M solution of n-butyllithium in hexane (2.65 mL) under argon gas flow with stirring at −78° C., and the resulting mixture was stirred at −78° C. for 1 hour. Then, dimethylformamide (0.624 mL) was added dropwise thereto with stirring at −78° C., the resulting mixture was stirred at −78° C. for 1 hour, gradually warmed to room temperature, and stirred at room temperature for 0.5 hour. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate), and the fractions comprising 7-methoxyisoquinoline-6-carbaldehyde were concentrated under reduced pressure.

To a solution of the resulting residues in dichloromethane (6 mL) was added dropwise a 1 M solution of boron tribromide in dichloromethane (3.82 mL) under argon gas flow with stirring at −78° C., the resulting mixture was stirred at −78° C. for 0.5 hour, gradually warmed, and stirred at 0° C. for 2 hours. After the reaction was completed, to the reaction solution was added a saturated aqueous solution of sodium hydrogen carbonate, and the resulting mixed solution was subjected to extraction with dichloromethane. The resulting organic layer was left to stand to precipitate solids. The resulting solids were collected by filtration, washed with tert-butyl methyl ether, and dried under reduced pressure at room temperature.

To a solution of the resulting solids in dichloromethane (8 mL) was added (2S)-1-amino-2-butanol (0.176 mL) under argon gas flow with stirring at room temperature, and the resulting mixture was stirred at room temperature for 0.5 hour. Then, sodium triacetoxyborohydride (494 mg) was added thereto, and the resulting mixture was stirred at room temperature for 1 hour. After the reaction was completed, the reaction solution was concentrated under reduced pressure, to the resulting residues were added methanol (8 mL) and a 8 M aqueous solution of sodium hydroxide (1.94 mL), di-tert-butyl dicarbonate (0.714 mL) was added thereto, and the resulting mixture was stirred at room temperature for 3 hours. Additionally, di-tert-butyl dicarbonate (0.150 mL) was added thereto, and the resulting mixture was stirred at room temperature for 1 hour. Then, 1 M hydrochloric acid was added thereto to adjust the pH to 5, and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; ethyl acetate:methanol) to give the title compound (34 mg) as a colorless oil.

Mass spectrum (DUIS, m/z): 347 $[M+H]^+$

Reference Example 52-(c)

Production of tert-butyl (R)-2-ethyl-2,3-dihydro-[1,4]oxazepino[6,7-g]isoquinoline-4(5H)-carboxylate

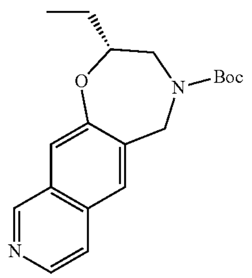 [SMILES: CC[C@@H]1CN(C(=O)OC(C)(C)C)Cc2cc3ccncc3cc2O1]

To a solution of tert-butyl (S)-(2-hydroxybutyl) ((7-hydroxyisoquinolin-6-yl)methyl)carbamate produced in the Reference Example 52-(b) (34 mg) in tetrahydrofuran (4 mL) were sequentially added (E)-N1,N1,N2,N2-tetramethyldiazene-1,2-dicarboxamide (25 mg) and tri-n-butylphosphine (0.036 mL) under argon gas flow with stirring at room temperature, and the resulting mixture was stirred at room temperature for 2 hours. After the reaction was completed, the reaction solution was diluted with ethyl acetate, washed sequentially with water and saturated brine, dried over anhydrous magnesium sulfate, filtered, and concentrated under reduced pressure. The resulting residues were purified by a silica gel column (elution solvent; hexane ethyl acetate) to give the title compound (21 mg) as a colorless oil.

Mass spectrum (ESI, m/z): 329 $[M+H]^+$

Reference Example 52-(d)

Production of (R)-2-ethyl-2,3,4,5-tetrahydro-[1,4]oxazepino[6,7-g]isoquinoline dihydrochloride

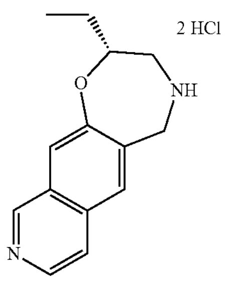 [SMILES: CC[C@@H]1CNCc2cc3ccncc3cc2O1]

To a solution of tert-butyl (R)-2-ethyl-2,3-dihydro-[1,4]oxazepino[6,7-g]isoquinoline-4(5H)-carboxylate produced in the Reference Example 52-(c) (21 mg) in cyclopentyl methyl ether (2 mL) was added dropwise a 4 M solution of hydrogen chloride in cyclopentyl methyl ether (0.064 mL) under argon gas flow with stirring at room temperature, and the resulting mixture was stirred at 60° C. for 4 hours. After the reaction was completed, the resulting mixture was allowed to cool to room temperature, and the reaction solution was concentrated under reduced pressure to give the title compound (19 mg) as a colorless oil.

Mass spectrum (ESI, m/z): 229 $[M+H]^+$

Reference Example 53-(a)

Production of tert-butyl (S)-(2-hydroxybutyl) ((6-hydroxyisoquinolin-7-yl)methyl)carbamate

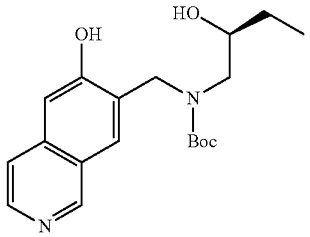 [SMILES: CC[C@H](O)CN(Cc1cc2cnccc2cc1O)C(=O)OC(C)(C)C]

To a suspension of 7-bromo-6-methoxyisoquinoline (0.600 g) in diethyl ether (15 mL) was added dropwise a 1.6 M solution of n-butyllithium in hexane (1.66 mL) under argon gas flow with stirring at −78° C., and the resulting mixture was stirred at −78° C. for 1 hour. Then, dimethylformamide (0.39 mL) was added dropwise thereto with stirring at −78° C., the resulting mixture was stirred at −78° C. for 1 hour, gradually warmed to room temperature, and stirred at room temperature for 0.5 hour. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate), and the fractions comprising 6-methoxyisoquinoline-7-carbaldehyde were concentrated under reduced pressure.

To a solution of the resulting residues in dichloromethane (3.2 mL) was added dropwise a 1 M solution of boron tribromide in dichloromethane (1.07 mL) under argon gas flow with stirring at −78° C., the resulting mixture was stirred at −78° C. for 1 hour, gradually warmed, and stirred at 0° C. for 2 hours. Then, the resulting mixture was stirred at room temperature for 6 hours. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous sodium sulfate, filtered, and concentrated under reduced pressure.

To a solution of the resulting residues in a mixture of dichloromethane (8 mL)/methanol (5 mL) was added (2S)-1-amino-2-butanol (80 mg) under argon gas flow with stirring at room temperature, and the resulting mixture was stirred at room temperature for 1 hour. Then, sodium triacetoxyborohydride (316 mg) was added thereto, and the resulting mixture was stirred at room temperature for 2 hours. After the reaction was completed, to the reaction solution was added a saturated aqueous solution of sodium hydrogen carbonate, and the resulting mixed solution was subjected to extraction with ethyl acetate. The resulting organic layer was dried over anhydrous sodium sulfate, filtered, and concentrated under reduced pressure. To a solution of the resulting residues in methanol (4 mL) were sequentially added a 8 M aqueous solution of sodium hydroxide (1.862 mL) and di-tert-butyl dicarbonate (1.371 mL) under argon gas flow with stirring at 0° C., the resulting mixture was stirred at room temperature for 2 hours, and then left to stand at room temperature weekend. Additionally, di-tert-butyl dicarbonate (0.685 mL) was added thereto at room temperature, and the resulting mixture was stirred at room temperature for 1 hour. Then, a 8 M aqueous solution of sodium hydroxide (1.862 mL) was added thereto at room temperature, and the resulting mixture was stirred at room temperature for 2.5 hours. After the reaction was completed, to the reaction solution was added 1 M hydrochloric acid to adjust the pH to 5, and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; ethyl acetate:methanol) to give the title compound (73 mg) as a slightly yellow oil.

Mass spectrum (ESI, m/z): 347 [M+H]+

Reference Example 53-(b)

Production of tert-butyl (R)-2-ethyl-2,3-dihydro-[1,4]oxazepino[7,6-g]isoquinoline-4 (5H)-carboxylate

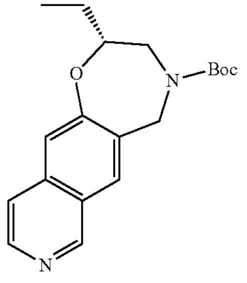 [SMILES: CC[C@@H]1CN(C(=O)OC(C)(C)C)Cc2cc3cnccc3cc2O1]

To a solution of tert-butyl (S)-(2-hydroxybutyl) ((6-hydroxyisoquinolin-7-yl)methyl)carbamate produced in the Reference Example 53-(a) (73 mg) in tetrahydrofuran (3 mL) were sequentially added tri-n-butylphosphine (0.057 mL) and (E)-N1,N1,N2,N2-tetramethyldiazene-1,2-dicarboxamide (40 mg) under argon gas flow with stirring at room temperature, and the resulting mixture was stirred at room temperature for 16 hours. After the reaction was completed, to the reaction solution was added water, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (61 mg) as a slightly yellow oil.

Mass spectrum (ESI, m/z): 329 [M+H]+

Reference Example 53-(c)

Production of (R)-2-ethyl-2,3,4,5-tetrahydro-[1,4]oxazepino[7,6-g]isoquinoline dihydrochloride

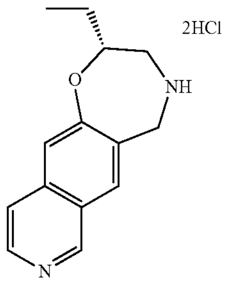 [SMILES: CC[C@@H]1CNCc2cc3cnccc3cc2O1]

To a solution of tert-butyl (R)-2-ethyl-2,3-dihydro-[1,4]oxazepino[7,6-g]isoquinoline-4(5H)-carboxylate produced in the Reference Example 53-(b) (60 mg) in 1,4-dioxane (2 mL) was added a 4 M solution of hydrogen chloride in 1,4-dioxane (0.457 mL) under argon gas flow with stirring at room temperature, and the resulting mixture was stirred at room temperature for 20.5 hours. After the reaction was completed, the reaction solution was concentrated under reduced pressure to give the title compound (59 mg) as white solids.

Mass spectrum (ESI, m/z): 229 [M+H]+

Reference Example 54-(a)

Production of 2-fluoro-6-((trimethylsilyl)ethynyl)benzaldehyde

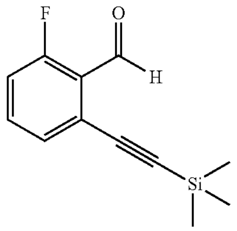

To a solution of 2-bromo-6-fluorobenzaldehyde (2.0 g) in triethylamine (20 mL) were sequentially added bis(triphenylphosphine)palladium(II) dichloride (346 mg), copper(I) iodide (94 mg), and ethynyltrimethylsilane (1.64 mL) under argon gas flow with stirring at room temperature, and the resulting mixture was stirred at 50° C. for 3 hours. After the reaction was completed, the reaction solution was filtered, and the resulting filtrate was concentrated under reduced pressure. The resulting residues were purified by a silica gel column (elution solvent; hexane:ethyl acetate) to give the title compound (1.97 g) as a slightly yellow oil.

Mass spectrum (ESI, m/z): 221 [M+H]$^+$

Reference Example 54-(b) and Reference Example 54-(c)

Production of methyl (E)-3-(2-fluoro-6-((trimethylsilyl)ethynyl)phenyl)acrylate and methyl (E)-3-(2-ethynyl-6-fluorophenyl)acrylate

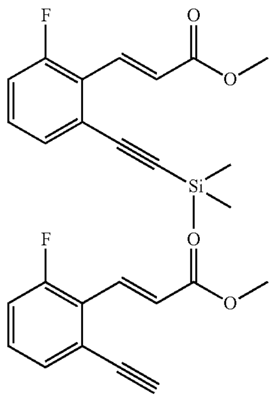

To a solution of methyl diethylphosphonoacetate (8.1 mL) in tetrahydrofuran (20 mL) was added sodium hydride (1.17 g) under argon gas flow with stirring at 0° C., and the resulting mixture was stirred at 0° C. for 0.5 hour. Then, a solution of 2-fluoro-6-((trimethylsilyl)ethynyl)benzaldehyde produced in the Reference Example 54-(a) (1.97 g) in tetrahydrofuran (5 mL) was added thereto with stirring at 0° C., and the resulting mixture was stirred at 0° C. for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give methyl (E)-3-(2-fluoro-6-((trimethylsilyl) ethynyl)phenyl) acrylate (1.18 g) as a colorless oil and also methyl (E)-3-(2-ethynyl-6-fluorophenyl)acrylate (795 mg) as a colorless oil.

As an alternative method, the title compound was also produced according to the following method.

To a solution of methyl (E)-3-(2-fluoro-6-((trimethylsilyl) ethynyl)phenyl)acrylate produced in the Reference Example 54-(b) (1.18 g) in methanol (7 mL) was added potassium carbonate (118 mg) under argon gas flow with stirring at room temperature, and the resulting mixture was stirred at room temperature for 2 hours. After the reaction was completed, the reaction solution was concentrated under reduced pressure. To the resulting residues was added water, and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane ethyl acetate) to give methyl (E)-3-(2-ethynyl-6-fluorophenyl)acrylate (800 mg) as a colorless oil.

Reference Example 54-(b)

Mass spectrum (ESI, m/z): 277 [M+H]$^+$

Reference Example 54-(c)

Mass spectrum (ESI, m/z): 205 [M+H]$^+$

Reference Example 54-(d)

Production of methyl 8-fluoro-3-hydroxy-2-naphthoate

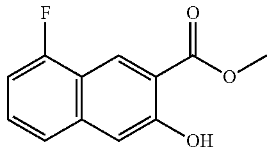 [SMILES: COC(=O)c1cc2c(F)cccc2cc1O]

To a solution of methyl (E)-3-(2-ethynyl-6-fluorophenyl) acrylate produced in the Reference Example 54-(c) (1.59 g) in chlorobenzene (15 mL) were sequentially added bis(1,5-cyclooctadiene)rhodium(I) trifluoromethanesulfonate (0.219 g), tri-p-tolylphosphine (0.569 g), and pyridine N-oxide (1.48 g) under argon gas flow with stirring at room temperature, and the resulting mixture was stirred at 100° C. for 7 hours. After the reaction was completed, the reaction solution was allowed to cool to room temperature, water was added thereto, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (172 mg) as white solids.

Mass spectrum (ESI, m/z): 221 [M+H]$^+$

Reference Example 54-(e)

Production of tert-butyl (S)-(2-hydroxybutyl)carbamate

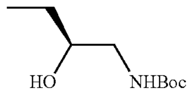

To a solution of (2S)-1-amino-2-butanol (200 mg) in dichloromethane (4 mL) was added di-tert-butyl dicarbonate (0.547 mL) under argon gas flow with stirring at room temperature, and the resulting mixture was stirred at room temperature for 1 hour. After the reaction was completed, the reaction solution was concentrated under reduced pressure. The resulting residues were purified by a silica gel column (elution solvent; hexane:ethyl acetate) to give the title compound (420 mg) as a colorless oil.

Reference Example 54-(f)

Production of methyl (R)-3-((1-((tert-butoxycarbonyl)amino)butan-2-yl)oxy)-8-fluoro-2-naphthoate

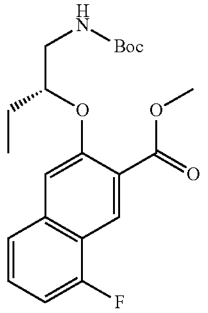

To a solution of tert-butyl (S)-(2-hydroxybutyl)carbamate produced in the Reference Example 54-(e) (177 mg) in tetrahydrofuran (5 mL) were sequentially added methyl 8-fluoro-3-hydroxy-2-naphthoate produced in the Reference Example 54-(d) (172 mg), (E)-N1,N1,N2,N2-tetramethyldiazene-1,2-dicarboxamide (202 mg), and tri-n-butylphosphine (0.289 mL) under argon gas flow with stirring at room temperature, and the resulting mixture was stirred at room temperature for 2 hours. After the reaction was completed, the reaction solution was diluted with ethyl acetate, washed sequentially with water and saturated brine, dried over anhydrous magnesium sulfate, filtered, and concentrated under reduced pressure. The resulting residues were purified by a silica gel column (elution solvent; hexane:ethyl, acetate) to give the title compound (232 mg) as a slightly yellow oil.

Mass spectrum (ESI, m/z): 392 $[M+H]^+$

Reference Example 54-(g)

Production of methyl (R)-3-((1-aminobutan-2-yl)oxy)-8-fluoro-2-naphthoate hydrochloride

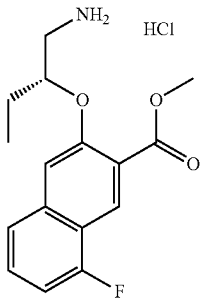 [SMILES: CC[C@H](CN)Oc1cc2cccc(F)c2cc1C(=O)OC ; Cl]

To a solution of methyl (R)-3-((1-((tert-butoxycarbonyl)amino)butan-2-yl)oxy)-8-fluoro-2-naphthoate produced in the Reference Example 54-(f) (232 mg) in cyclopentyl methyl ether (3 mL) was added dropwise a 4 M solution of hydrogen chloride in cyclopentyl methyl ether (0.593 mL) under argon gas flow with stirring at room temperature, the resulting mixture was stirred at room temperature for 3 hours, then warmed to 60° C., and stirred for 2 hours. After the reaction was completed, the reaction solution was allowed to cool to room temperature, and concentrated under reduced pressure to give the title compound (190 mg) as a colorless oil.

Mass spectrum (ESI, m/z): 292 $[M+H]^+$

Reference Example 54-(h)

Production of (R)-2-ethyl-7-fluoro-3,4-dihydronaphtho[2,3-f][1,4]oxazepin-5(2H)-one

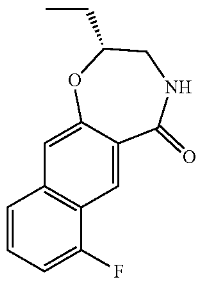 [SMILES: CC[C@@H]1CNC(=O)c2cc3c(F)cccc3cc2O1]

To a solution of methyl (R)-3-((1-aminobutan-2-yl)oxy)-8-fluoro-2-naphthoate hydrochloride produced in the Reference Example 54-(g) (190 mg) in methanol (4 mL) was added sodium hydride (101 mg) under argon gas flow with stirring at 0° C., and the resulting mixture was stirred at room temperature for 1 hour. After the reaction was completed, the reaction solution was concentrated under reduced pressure, a saturated aqueous solution of ammonium chloride was added thereto, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (121 mg) as a white foam.

Mass spectrum (ESI, m/z): 260 $[M+H]^+$

Reference Example 54-(1)

Production of (R)-2-ethyl-7-fluoro-2,3,4,5-tetrahydronaphtho[2,3-f][1,4]oxazepine

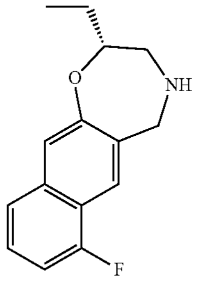 [SMILES: CC[C@@H]1CNCc2cc3c(F)cccc3cc2O1]

To a solution of (R)-2-ethyl-7-fluoro-3,4-dihydronaphtho[2,3-f][1,4]oxazepin-5(2H)-one produced in the Reference Example 54-(h) (121 mg) in tetrahydrofuran (4 mL) was added dropwise a 0.9 M solution of borane-tetrahydrofuran complex in tetrahydrofuran (1.56 mL) under argon gas flow with stirring at room temperature, the resulting mixture was stirred at room temperature for 3 hours, then warmed to 60° C., and stirred for 3 hours. After the reaction was completed, ethanol (0.163 mL) was added thereto, and the resulting mixture was stirred for 1 hour. The reaction solution was concentrated under reduced pressure, and cyclopentyl methyl ether (2 mL) was added thereto. A 4 M solution of hydrogen chloride in cyclopentyl methyl ether (2 mL) was added thereto, and the resulting mixture was stirred for 30 minutes. Then, a 4 M aqueous solution of sodium hydroxide (2 mL) was added thereto, and the resulting mixture was stirred for a while. Additionally, a saturated aqueous solution of sodium hydrogen carbonate (10 mL) was added thereto. The resulting mixed solution was subjected to extraction with ethyl acetate. The resulting organic layer was dried over anhydrous magnesium sulfate, filtered, and concentrated under reduced pressure. The resulting residues were purified by a silica gel column (elution solvent; ethyl acetate:methanol) to give the title compound (97 mg) as a colorless oil.

Mass spectrum (ESI, m/z): 246 $[M+H]^+$

Reference Example 55-(a)

Production of tert-butyl (S)-(2-hydroxybutyl) ((5-hydroxyisoquinolin-6-yl)methyl) carbamate

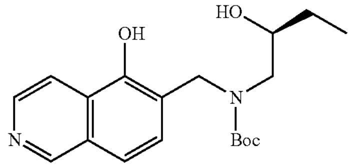 [SMILES: CC[C@H](O)CN(Cc1ccc2cnccc2c1O)C(=O)OC(C)(C)C]

To a suspension of 5-hydroxyisoquinoline (1.00 g) in acetonitrile (15 mL) were sequentially added triethylamine (3.55 mL), magnesium chloride (1.64 g), and paraformaldehyde (1.26 g) under argon gas flow with stirring at room temperature, and the resulting mixture was stirred at 90° C. for 9 hours. After the reaction was completed, the reaction solution was concentrated under reduced pressure. The resulting residues were dissolved into methanol, the resulting insoluble matters were removed by filtration, and the resulting filtrate was concentrated under reduced pressure.

To a solution of the resulting residues in a mixture of dichloromethane (15 mL)/methanol (5 mL) was added (2S)-1-amino-2-butanol (0.735 g) under argon gas flow with stirring at room temperature, and the resulting mixture was stirred at room temperature for 1 hour. Then, sodium triacetoxyborohydride (2.91 g) was added thereto, and the resulting mixture was stirred at room temperature for 13.5 hours. After the reaction was completed, to the reaction solution was added a saturated aqueous solution of sodium hydrogen carbonate, and the resulting mixed solution was subjected to extraction with ethyl acetate. The resulting organic layer was dried over anhydrous sodium sulfate, filtered, and concentrated under reduced pressure. To a solution of the resulting residues in methanol (30 mL) were sequentially added a 8 M aqueous solution of sodium hydroxide (17.2 mL) and di-tert-butyl dicarbonate (12.6 mL) under argon gas flow with stirring at 0° C., and the resulting mixture was stirred at room temperature for 32 hours. After the reaction was completed, to the reaction solution was added 1 M hydrochloric acid to adjust the pH to 5, and the resulting mixture was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (0.422 g) as a yellow foam.

Mass spectrum (DUIS, m/z): 347 $[M+H]^+$

Reference Example 55-(b)

Production of tert-butyl (R)-2-ethyl-2,3-dihydro-[1,4]oxazepino[7,6-f]isoquinoline-4(5H)-carboxylate

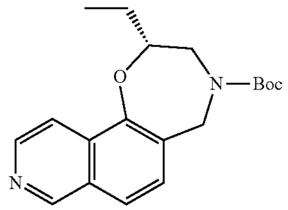 [SMILES: CC[C@@H]1CN(C(=O)OC(C)(C)C)Cc2ccc3cnccc3c2O1]

To a solution of tert-butyl (S)-(2-hydroxybutyl) ((5-hydroxyisoquinolin-6-yl)methyl) carbamate produced in the Reference Example 55-(a) (0.422 g) in tetrahydrofuran (11 mL) were sequentially added tri-n-butylphosphine (0.334 mL) and (E)-N1,N1,N2,N2-tetramethyldiazene-1,2-dicarboxamide (0.231 g) under argon gas flow with stirring at room temperature, and the resulting mixture was stirred at room temperature for 1 hour. After the reaction was completed, to the reaction solution was added water, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (0.355 g) as a colorless oil.

As an alternative method, the title compound was also produced according to the following method.

To a solution of tert-butyl (S)-(2-hydroxybutyl) ((5-hydroxyisoquinolin-6-yl)methyl)carbamate produced according to the same manner as the Reference Example 55-(a) (32 mg) in tetrahydrofuran (3 mL) were sequentially added triphenylphosphine (31 mg) and a 1.9 M solution of diisopropyl azodicarboxylate in toluene (0.060 mL) under argon gas flow with stirring at 0° C., and the resulting mixture was stirred at room temperature for 9 hours. After the reaction was completed, to the reaction solution was added water, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (12 mg) as a colorless oil.

Mass spectrum (ESI, m/z): 329 $[M+H]^+$

Reference Example 55-(c)

Production of (R)-2-ethyl-2,3,4,5-tetrahydro-[1,4]oxazepino[7,6-f]isoquinoline dihydrochloride

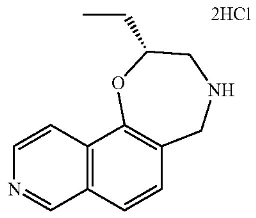 [SMILES: CC[C@@H]1CNCc2ccc3cnccc3c2O1]

To a solution of tert-butyl (R)-2-ethyl-2,3-dihydro-[1,4]oxazepino[7,6-f]isoquinoline-4 (5H)-carboxylate produced according to the same manner as the Reference Example 55-(b) (0.36 g) in 1,4-dioxane (5 mL) was added a 4 M solution of hydrogen chloride in 1,4-dioxane (2.7 mL) under argon gas flow with stirring at room temperature, and the resulting mixture was stirred at room temperature for 17 hours. After the reaction was completed, the reaction solution was concentrated under reduced pressure. To the resulting residues was added tert-butyl methyl ether, the precipitated solids were collected by filtration, and dried under reduced pressure to give the title compound (0.30 g) as white solids.

Mass spectrum (ESI, m/z): 229 $[M+H]^+$

Reference Example 56-(a)

Production of ethyl (E)-3-(1,4-dimethyl-1H-benzo[d][1,2,3]triazol-5-yl)acrylate

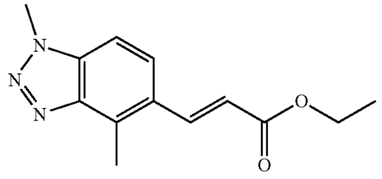 [SMILES: CCOC(=O)/C=C/c1ccc2c(nnn2C)c1C]

To a solution of 5-bromo-1,4-dimethyl-1H-benzo[d][1,2,3]triazole (1.00 g) in dimethylformamide (5 mL) were sequentially added ethyl acrylate (2.41 mL), tri-o-tolylphosphine (269 mg), N,N-diisopropylethylamine (11.1 mL), and palladium(II) acetate (99 mg) under argon gas flow with stirring at room temperature, and the resulting mixture was stirred at 120° C. for 3 hours by using a microwave reactor (manufactured by Anton Paar, Microwave Synthesis: Monowave 300). After the reaction was completed, the reaction solution was allowed to cool to room temperature, poured into water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (903 mg) as pale yellow solids.

Mass spectrum (ESI, m/z): 246 $[M+H]^+$

Reference Example 56-(b)

Production of ethyl 3-(1,4-dimethyl-1H-benzo[d][1,2,3]triazol-5-yl)-3-(3-(hydroxymethyl)-4-methylphenyl)propanoate

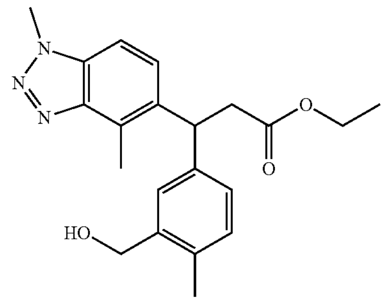 [SMILES: CCOC(=O)CC(c1ccc(C)c(CO)c1)c1ccc2c(nnn2C)c1C]

To a solution of ethyl (E)-3-(1,4-dimethyl-1H-benzo[d][1,2,3]triazol-5-yl)acrylate produced in the Reference Example 56-(a) (900 mg) in a mixture of 1,4-dioxane (13 mL)/water (6.5 mL) were sequentially added (3-(hydroxymethyl)-4-methylphenyl)boronic acid (914 mg), triethylamine (0.77 mL), and di-μ-chlorobis[(η-cycloocta-1,5-diene)rhodium(I)] (36 mg) under argon gas flow with stirring at room temperature, and the resulting mixture was stirred at 95° C. for 1 hour. After the reaction was completed, the reaction solution was allowed to cool to room temperature, water was added thereto, and the resulting mixed solution was subjected to extraction three times with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (919 mg) as a white foam.

Mass spectrum (ESI, m/z): 368 $[M+H]^+$

Reference Example 56-(c)

Production of ethyl 3-(1,4-dimethyl-1H-benzo[d][1,2,3]triazol-5-yl)-3-(3-formyl-4-methylphenyl)propanoate

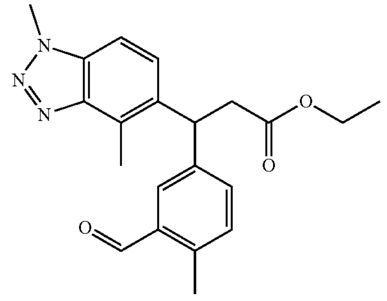 [SMILES: CCOC(=O)CC(c1ccc(C)c(C=O)c1)c1ccc2c(nnn2C)c1C]

To a solution of ethyl 3-(1,4-dimethyl-1H-benzo[d][1,2,3]triazol-5-yl)-3-(3-(hydroxymethyl)-4-methylphenyl)propanoate produced in the Reference Example 56-(b) (918 mg) in dichloromethane (10 mL) was added Dess-Martin periodinane (1.27 g) under argon gas flow with stirring at 0° C., and the resulting mixture was stirred at room temperature for 2 hours. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (862 mg) as a slightly yellow oil.

Mass spectrum (ESI, m/z): 366 $[M+H]^+$

Reference Example 57-(a)

Production of (S)-1-(((6-bromoquinolin-7-yl)methyl)amino)butan-2-ol

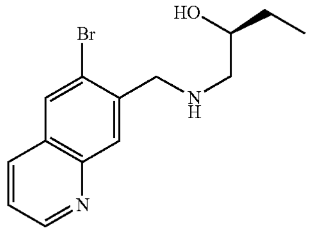 [SMILES: CC[C@H](O)CNCc1cc2ncccc2cc1Br]

To a solution of (2S)-1-amino-2-butanol (0.600 mL) in acetonitrile (19 mL) were added N,N-diisopropylethylamine (2.18 mL) and 6-bromo-7-(bromomethyl)quinoline produced according to the same manner as the Reference Example 12-(a) (1.28 g) under argon gas flow with stirring at room temperature, and the resulting mixture was stirred at room temperature for 3 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; ethyl acetate:methanol) to give the title compound (605 mg) as slightly yellow solids.

Mass spectrum (ESI, m/z): 309 $[M+H]^+$

Reference Example 57-(b)

Production of (S)-2-ethyl-2,3,4,5-tetrahydro-[1,4]oxazepino[7,6-g]quinoline

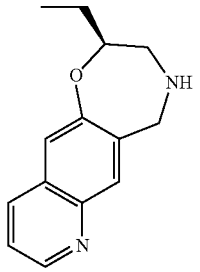 [SMILES: CC[C@H]1CNCc2cc3ncccc3cc2O1]

To a solution of (S)-1-(((6-bromoquinolin-7-yl)methyl)amino)butan-2-ol produced in the Reference Example 57-(b) (604 mg) in 2-propanol (12 mL) were sequentially added cesium carbonate (1.27 g) and copper(I) iodide (186 mg) under argon gas flow with stirring at room temperature, and the resulting mixture was stirred at 90° C. for B hours. Then, copper(I) iodide (186 mg) was added thereto, and the resulting mixture was stirred at 90° C. for 6 hours. After the reaction was completed, the reaction solution was allowed to cool to room temperature, filtered through Celite, washed with ethyl acetate, and the resulting filtrate was concentrated under reduced pressure. The resulting residues were purified by a silica gel column (elution solvent; ethyl acetate:methanol) to give the title compound (242 mg) as a yellow oil.

Mass spectrum (ESI, m/z): 229 $[M+H]^+$

Reference Example 59-(a)

Production of 4-bromo-N-ethyl-3-methyl-2-nitroaniline

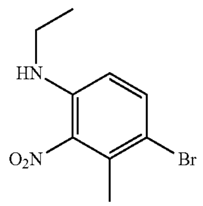

To a solution of 1-bromo-4-fluoro-2-methyl-3-nitrobenzene (1.0 g) and ethylamine hydrochloride (1.74 g) in ethanol (26.9 mL) in a shield tube were sequentially added triethylamine (1.49 mL) and potassium carbonate (1.48 g) at room temperature, the shield tube was covered, and then the resulting mixture was stirred at 90° C. for 7 hours. Then, the resulting mixture was stirred at room temperature for 15.5 hours and additionally at 90° C. for 6.5 hours. After the reaction was completed, to the reaction solution was added water, and the resulting mixed solution was subjected to extraction with ethyl acetate. The resulting organic layer was washed sequentially with a saturated aqueous solution of sodium hydrogen carbonate and saturated brine, dried over anhydrous sodium sulfate, filtered, and concentrated under reduced pressure to give a residue comprising the title compound (1.05 g) as a yellow oil.

Mass spectrum (ESI, m/z): 259 $[M+H]^+$

Reference Example 59-(b)

Production of 4-bromo-N1-ethyl-3-methylbenzene-1,2-diamine

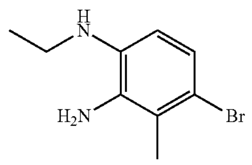

To a solution of 4-bromo-N-ethyl-3-methyl-2-nitroaniline produced in the Reference Example 59-(a) (1.05 g) in a mixture of ethanol (11.25 mL)/water (5 mL) were sequentially added iron powder (1.58 g) and ammonium chloride (0.87 g) at room temperature, and the resulting mixture was stirred at 80° C. for 2 hours. After the reaction was completed, the resulting mixture was allowed to cool to room temperature, and the reaction solution was filtered. The resulting filtrate was subjected to extraction twice with dichloromethane. The resulting organic layer was washed with saturated brine, dried over anhydrous sodium sulfate, filtered, and concentrated under reduced pressure. The resulting residues were purified by a silica gel column (elution solvent; heptane:ethyl acetate) to give the title compound (604 mg) as brown solids.

Mass spectrum (ESI, m/z): 229 $[M+H]^+$

Reference Example 59-(c)

Production of 5-bromo-1-ethyl-4-methyl-1H-benzo[d][1,2,3]triazole

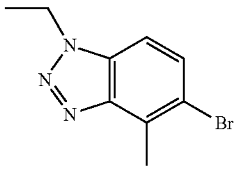

To a suspension of 4-bromo-N1-ethyl-3-methylbenzene-1,2-diamine produced according to the same manner as the Reference Example 59-(b) (3.21 g) in water (56.3 ml) were added concentrated sulfuric acid (3 mL) and sodium nitrite (1.45 g) at 0° C., and the resulting mixture was vigorously stirred at 0° C. After the reaction was completed, the reaction solution was filtered, the resulting solids were collected by filtration, dissolved into chloroform, and the resulting solution was concentrated under reduced pressure. The resulting residues were purified by a silica gel column (elution solvent; heptane:ethyl acetate) to give the title compound (2.62 g) as red-brown solids.

Mass spectrum (ESI, m/z): 240 $[M+H]^+$

Reference Example 59-(d)

Production of (1-ethyl-4-methyl-1H-benzo[d][1,2,3]triazol-5-yl) (3-(((4-methoxybenzyl)oxy)methyl)-4-methylphenyl)methanol

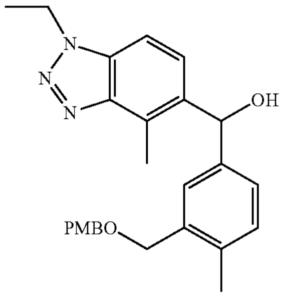

To a solution of 5-bromo-1-ethyl-4-methyl-1H-benzo[d][1,2,3]triazole produced in the Reference Example 59-(c) (2.62 g) in tetrahydrofuran (22 mL) was added dropwise a 1.0 M solution of i-propylmagnesium chloride in tetrahydrofuran (10.9 mL) under argon gas flow with stirring at −40° C. Then, a 1.6 M solution of n-butyllithium in hexane (13.6 mL) was added dropwise thereto with stirring at −40° C., and the resulting mixture was stirred at −40° C. for 1 hour. Additionally, a 8 M solution of 3-(((4-methoxybenzyl)oxy)methyl)-4-methylbenzaldehyde produced according to the same manner as the Reference Example 1-(j) in tetrahydrofuran (2.1 mL) was added dropwise thereto with stirring at −40° C., and the resulting mixture was stirred at −40° C. for 1 hour. Additionally, a 8 M solution of 3-(((4-methoxybenzyl)oxy)methyl)-4-methylbenzaldehyde produced according to the same manner as the Reference Example 1-(j) in tetrahydrofuran (0.4 mL) was added dropwise thereto with stirring at −40° C., and the resulting mixture was stirred at −40° C. for 0.5 hour. After the reaction was completed, to the reaction solution was added a saturated aqueous solution of ammonium chloride, and the resulting mixed solution was subjected to extraction twice with ethyl acetate. The resulting organic layer was washed with saturated brine, dried over anhydrous sodium sulfate, filtered, and concentrated under reduced pressure. The resulting residues were purified by a silica gel column (elution solvent; heptane:ethyl acetate) to give the title compound (2.67 g) as a brown oil.

Mass spectrum (ESI, m/z): 432 $[M+H]^+$

Reference Example 59-(e)

Production of methyl 3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate

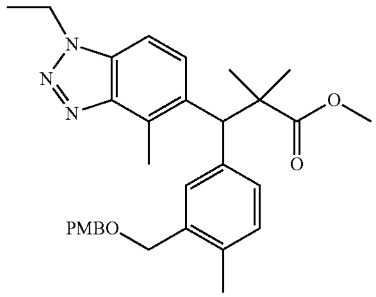

To a solution of (1-ethyl-4-methyl-1H-benzo[d][1,2,3]triazol-5-yl) (3-(((4-methoxybenzyl)oxy)methyl)-4-methylphenyl)methanol produced according to the same manner as the Reference Example 59-(d) (2.93 g) in acetonitrile (29 mL) were sequentially added trichloroacetonitrile (1.96 mL) and 1,8-diazabicyclo[5.4.0]-7-undecene (0.21 mL) under argon atmosphere with stirring at room temperature, and the resulting mixture was stirred at room temperature for 1 hour. Then, dimethylketene methyl trimethylsilyl acetal (3.44 mL) and trifluoromethanesulfonimide (0.57 g) were sequentially added thereto with stirring at room temperature, and the resulting mixture was stirred at room temperature for 1 hour. After the reaction was completed, to the reaction solution was added a saturated aqueous solution of sodium hydrogen carbonate, and the resulting mixed solution was subjected to extraction three times with ethyl acetate. The resulting organic layer was dried over anhydrous sodium sulfate, filtered, and concentrated under reduced pressure. The resulting residues were purified by a silica gel column (elution solvent; heptane:ethyl acetate) to give the title compound (0.379 g) as brown solids.

Mass spectrum (ESI, m/z): 516 $[M+H]^+$

Reference Example 59-(f)

Production of methyl 3-(1-ethyl-4-methyl-1H-benzo[d][1,2,3]triazol-5-yl)-3-(3-(hydroxymethyl)-4-methylphenyl)-2,2-dimethylpropanoate

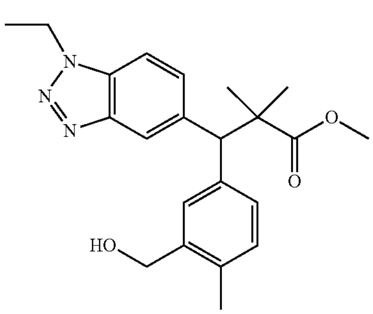 [SMILES: CCn1nnc2cc(C(c3ccc(C)c(CO)c3)C(C)(C)C(=O)OC)ccc21]

To a solution of methyl 3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate produced in the Reference Example 59-(e) (0.379 g) in a mixture of acetonitrile (3.4 mL)/water (0.4 mL) was added cerium (IV) diammonium nitrate (0.16 g) at room temperature, and the resulting mixture was stirred at room temperature for 0.5 hour. Then, cerium(IV) diammonium nitrate (0.16 g) was added thereto at room temperature, and the resulting mixture was stirred at room temperature for 0.5 hour. Additionally, cerium(IV) diammonium nitrate (0.16 g) was added thereto at room temperature, and the resulting mixture was stirred at room temperature for 0.5 hour. After the reaction was completed, to the reaction solution was added a saturated aqueous solution of sodium hydrogen carbonate, and the resulting mixed solution was subjected to extraction twice with ethyl acetate. The resulting organic layer was washed with saturated brine, dried over anhydrous sodium sulfate, filtered, and concentrated under reduced pressure. The resulting residues were purified by a silica gel column (elution solvent; heptane:ethyl acetate) to give the title compound (146 mg) as a brown oil.

Mass spectrum (ESI, m/z): 396 $[M+H]^+$

Reference Example 60-(a)

Production of 1-(((6-bromoquinolin-7-yl)methyl)amino)-2-methylpropan-2-ol

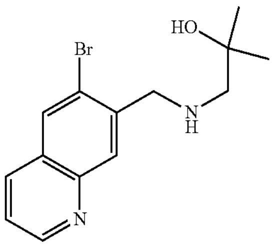 [SMILES: CC(C)(O)CNCc1cc2ncccc2cc1Br]

To a solution of 1-amino-2-methylpropan-2-ol (0.47 mL) in acetonitrile (7.5 mL) were added N,N-diisopropylethylamine (0.85 mL) and 6-bromo-7-(bromomethyl)quinoline produced according to the same manner as the Reference Example 12-(a) (500 mg) under argon gas flow with stirring at room temperature, and the resulting mixture was stirred at room temperature for 3 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; ethyl acetate:methanol) to give the title compound (266 mg) as a dark brown oil.

Mass spectrum (ESI, m/z): 309 $[M+H]^+$

Reference Example 60-(b)

Production of 2,2-dimethyl-2,3,4,5-tetrahydro-[1,4]oxazepino[7,6-g]quinoline

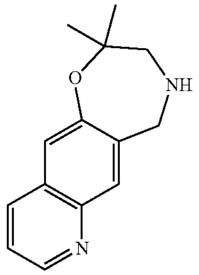 [SMILES: CC1(C)CNCc2cc3ncccc3cc2O1]

To a solution of 1-(((6-bromoquinolin-7-yl)methyl)amino)-2-methylpropan-2-ol produced in the Reference Example 60-(a) (265 mg) in 2-propanol (6 mL) were sequentially added cesium carbonate (558 mg) and copper(I) iodide (82 mg) under argon gas flow with stirring at room temperature, and the resulting mixture was stirred at 90° C. for 8 hours. Then, copper(I) iodide (82 mg) was added thereto, and the resulting mixture was stirred at 90° C. for 6 hours. After the reaction was completed, the reaction solution was allowed to cool to room temperature, filtered through Celite, washed with ethyl acetate, and the resulting filtrate was concentrated under reduced pressure. The resulting residues were purified by a silica gel column (elution solvent; ethyl acetate:methanol) to give the title compound (49 mg) as a yellow oil.

Mass spectrum (ESI, m/z): 229 $[M+H]^+$

Reference Example 61-(a)

Production of 2,2-dimethylbenzo[d][1,3]dioxol-5-ol

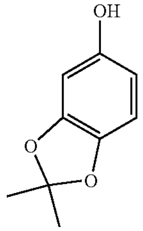

To a solution of benzene-1,2,4-triol (1.0 g) in toluene (80 mL) was added pyridinium p-toluenesulfonate (0.10 g) under argon gas flow with stirring at room temperature, and the resulting mixture was stirred at 130° C. for a while. Then, 2,2-dimethoxypropane (1.65 mL) was added dividedly thereto, and the resulting mixture was stirred at 120° C. for 3 hours. After the reaction was completed, the reaction solution was concentrated under reduced pressure. The resulting residues were purified by a silica gel column (elution solvent; hexane:ethyl acetate) to give the title compound (0.20 g) as a brown oil.

Mass spectrum (ESI, m/z): 167 [M+H]+

Reference Example 61-(b)

Production of 6-hydroxy-2,2-dimethylbenzo[d][1,3]dioxole-5-carbaldehyde

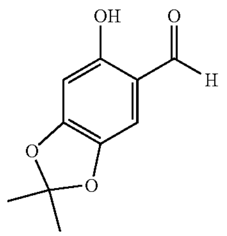

To a solution of 2,2-dimethylbenzo[d][1,3]dioxol-5-ol produced in the Reference Example 61-(a) (200 mg) in diethyl ether (6 mL) was added dropwise triethyl orthoformate (1.4 mL) under argon gas flow with stirring at room temperature, and the resulting mixture was stirred at room temperature for 5 minutes. Then, aluminum(III) chloride (160 mg) was added dividedly thereto with stirring at 0° C., and the resulting mixture was stirred at 0° C. for 10 minutes. After the reaction was completed, to the reaction solution was added 1 M hydrochloric acid (10 mL), and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (93 mg) as slightly yellow solids.

Mass spectrum (ESI, m/z): 195 [M+H]+

Reference Example 61-(c)

Production of tert-butyl (S)-((6-hydroxy-2,2-dimethylbenzo[d][1,3]dioxol-5-yl)methyl) (2-hydroxybutyl) carbamate

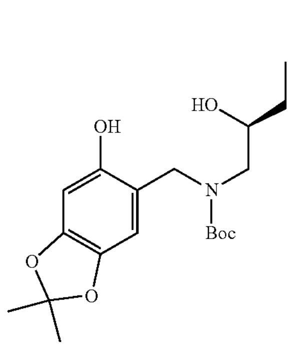 [SMILES: CC[C@H](O)CN(Cc1cc2c(cc1O)OC(C)(C)O2)C(=O)OC(C)(C)C]

To a solution of 6-hydroxy-2,2-dimethylbenzo[d][1,3]dioxole-5-carbaldehyde produced in the Reference Example 61-(b) (93 mg) in dichloromethane (4 mL) was added (2S)-1-amino-2-butanol (0.054 mL) under argon gas flow with stirring at room temperature, and the resulting mixture was stirred at room temperature for 0.5 hour. Then, sodium triacetoxyborohydride (152 mg) was added thereto, and the resulting mixture was stirred at room temperature for 1 hour. After the reaction was completed, the reaction solution was concentrated under reduced pressure, to the resulting residues were added methanol (4 mL) and a 8 M aqueous solution of sodium hydroxide (0.599 mL), di-tert-butyl dicarbonate (0.220 mL) was added thereto, and the resulting mixture was stirred at room temperature for 3 hours. Additionally, di-tert-butyl dicarbonate (0.100 mL) was added thereto, and the resulting mixture was stirred at room temperature for 15 hours. Then, 1 M hydrochloric acid was added thereto to adjust the pH to 5, and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (elution solvent; hexane:ethyl acetate) to give the title compound (76 mg) as a colorless oil.

Mass spectrum (DUIS, m/z): 368 [M+H]+

Reference Example 61-(d)

Production of tert-butyl (R)-6-ethyl-2,2-dimethyl-6,7-dihydro-[1,3]dioxolo[4',5':4,5]benzo[1,2-f][1,4]oxazepine-8(9H)-carboxylate

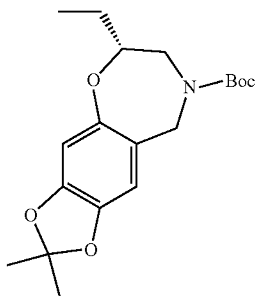 [SMILES: CC[C@@H]1CN(C(=O)OC(C)(C)C)Cc2cc3c(cc2O1)OC(C)(C)O3]

To a solution of tert-butyl (S)-((6-hydroxy-2,2-dimethylbenzo[d][1,3]dioxol-5-yl)methyl) (2-hydroxybutyl)carbamate produced in the Reference Example 61-(c) (76 mg) in tetrahydrofuran (4 mL) were sequentially added (E)-N1,N1,N2,N2-tetramethyldiazene-1,2-dicarboxamide (53 mg) and tri-n-butylphosphine (0.077 mL) under argon gas flow with stirring at room temperature, and the resulting mixture was stirred at room temperature for 2 hours. After the reaction was completed, the reaction solution was diluted with ethyl acetate, washed sequentially with water and saturated brine, dried over anhydrous magnesium sulfate, filtered, and concentrated under reduced pressure. The resulting residues were purified by a silica gel column (elution solvent; hexane:ethyl acetate) to give the title compound (32 mg) as a colorless oil.

Mass spectrum (ESI, m/z): 350 [M+H]+

Reference Example 61-(e)

Production of (R)-6-ethyl-2,2-dimethyl-6,7,8,9-tetrahydro-[1,3]dioxolo[4',5':4,5]benzo[1,2-f][1,4]oxazepine

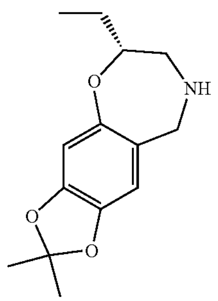 [SMILES: CC[C@@H]1CNCc2cc3c(cc2O1)OC(C)(C)O3]

To a solution of tert-butyl (R)-6-ethyl-2,2-dimethyl-6,7-dihydro-[1,3]dioxolo[4',5':4,5]benzo[1,2-f][1,4]oxazepine-8(9H)-carboxylate produced in the Reference Example 61-(d) (32 mg) in dichloromethane (3 mL) was added dropwise 2,6-lutidine (0.016 mL) under argon gas flow with stirring at room temperature, and the resulting mixture was stirred at room temperature for 5 minutes. Then, trifluoromethanesulfonic acid trimethylsilyl ester (0.020 mL) was added dropwise thereto with stirring at 0° C., and the resulting mixture was stirred at room temperature for 1 hour. Additionally, trifluoromethanesulfonic acid trimethylsilyl ester (0.020 mL) was added dropwise thereto, and the resulting mixture was stirred at room temperature for 1 hour. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (DIOL silica gel, elution solvent; ethyl acetate:methanol) to give the title compound (17 mg) as a colorless oil.

Mass spectrum (ESI, m/z): 250 $[M+H]^+$

Reference Example 62-(a)

Production of 8-hydroxyisoquinoline-7-carbaldehyde

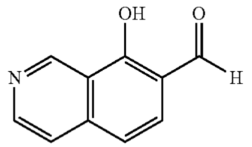 [SMILES: O=Cc1ccc2ccncc2c1O]

To a suspension of isoquinolin-8-ol (2.97 g) in chloroform (40 mL) was added dropwise a 8 M aqueous solution of sodium hydroxide (25.8 mL) under argon gas flow with stirring at 90° C., and the resulting mixture was stirred at 90° C. for 8 hours. After the reaction was completed, the reaction solution was allowed to cool to room temperature, hydrochloric acid was added thereto, and the resulting mixed solution was subjected to extraction with dichloromethane. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (20 mg) as yellow solids.

Mass spectrum (ESI, m/z): 174 $[M+H]^+$

Reference Example 62-(b)

Production of tert-butyl (S)-(2-hydroxybutyl) ((8-hydroxyisoquinolin-7-yl)methyl) carbamate

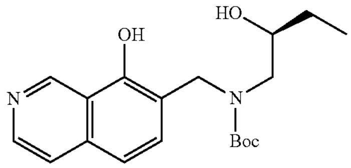 [SMILES: CC[C@H](O)CN(Cc1ccc2ccncc2c1O)C(=O)OC(C)(C)C]

To a solution of 8-hydroxyisoquinoline-7-carbaldehyde produced in the Reference Example 62-(a) (20 mg) in a mixture of dichloromethane (2 mL)/methanol (1 mL) was added (2S)-1-amino-2-butanol (13 mg) under argon gas flow with stirring at room temperature, and the resulting mixture was stirred at room temperature for 1 hour. Then, sodium triacetoxyborohydride (50 mg) was added thereto, and the resulting mixture was stirred at room temperature for 6 hours. After the reaction was completed, to the reaction solution was added a saturated aqueous solution of sodium hydrogen carbonate, and the resulting mixed solution was subjected to extraction with ethyl acetate. The resulting organic layer was dried over anhydrous sodium sulfate, filtered, and concentrated under reduced pressure. To a solution of the resulting residues in methanol (2 mL) was added di-tert-butyl dicarbonate (0.212 mL) under argon gas flow with stirring at room temperature, and the resulting mixture was stirred at room temperature for 14 hours. Then, a 8 M aqueous solution of sodium hydroxide (0.289 mL) was added thereto with stirring at room temperature, the resulting mixture was stirred at room temperature for 10 hours, and then left to stand at room temperature overnight. After the reaction was completed, to the reaction solution was added 1 M hydrochloric acid to adjust the pH to 5, and the resulting mixture was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (32 mg) as a yellow oil.

Mass spectrum (ESI, m/z): 347 $[M+H]^+$

Reference Example 62-(c)

Production of tert-butyl (R)-2-ethyl-2,3-dihydro-[1,4]oxazepino[6,7-h]isoquinoline-4(5H)-carboxylate

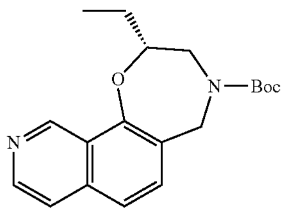 [SMILES: CC[C@@H]1CN(C(=O)OC(C)(C)C)Cc2ccc3ccncc3c2O1]

To a solution of tert-butyl (S)-(2-hydroxybutyl) ((8-hydroxyisoquinolin-7-yl)methyl)carbamate produced in the Reference Example 62-(b) (32 mg) in tetrahydrofuran (2 mL) were sequentially added triphenylphosphine (28 mg) and a 1.9 M solution of diisopropyl azodicarboxylate in toluene (0.055 mL) under argon gas flow with stirring at room temperature, and the resulting mixture was stirred at room temperature for 5 hours. After the reaction was completed, to the reaction solution was added water, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (29 mg) as a slightly yellow oil.

As an alternative method, the title compound was also produced according to the following method.

To a solution of tert-butyl (S)-(2-hydroxybutyl) ((8-hydroxyisoquinolin-7-yl)methyl)carbamate produced according to the same manner as the Reference Example 62-(b) (37 mg) in tetrahydrofuran (3 mL) were added tri-n-butylphosphine (0.029 mL) and (E)-N1,N1,N2,N2-tetramethyldiazene-1,2-dicarboxamide (30 mg) under argon gas flow with stirring at 0° C., and the resulting mixture was stirred at room temperature for 14 hours. After the reaction was completed, to the reaction solution was added water, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; hexane:ethyl acetate) to give the title compound (7 mg) as a colorless oil.

Mass spectrum (ESI, m/z): 329 $[M+H]^+$

Reference Example 62-(d)

Production of (R)-2-ethyl-2,3,4,5-tetrahydro-[1,4]oxazepino[6,7-h]isoquinoline dihydrochloride

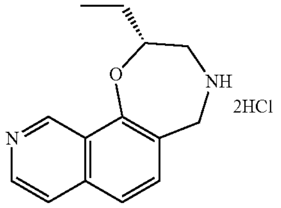 [SMILES: CC[C@@H]1CNCc2ccc3ccncc3c2O1]

To a solution of tert-butyl (R)-2-ethyl-2,3-dihydro-([1,4]oxazepino[6,7-h]isoquinoline-4(5H)-carboxylate produced according to the same manner as the Reference Example 62-(c) (35 mg) in 1,4-dioxane (2 mL) was added a 4 M solution of hydrogen chloride in 1,4-dioxane (0.266 mL) under argon gas flow with stirring at room temperature, the resulting mixture was stirred at room temperature for 20 hours, then warmed to 50° C., and stirred for 5 hours. After the reaction was completed, the reaction solution was concentrated to give the title compound (36 mg) as slightly yellow solids.

Mass spectrum (ESI, m/z): 229 $[M+H]^+$

Reference Example 63-(a)

Production of 2-(((6-bromoquinolin-7-yl)methyl)amino)ethan-1-ol

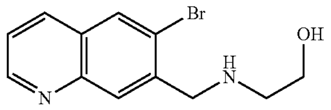 [SMILES: OCCNCc1cc2ncccc2cc1Br]

To a solution of 2-aminoethanol (204 mg) in acetonitrile (17 mL) were sequentially added N,N-diisopropylethylamine (0.568 mL) and 6-bromo-7-(bromomethyl)quinoline produced according to the same manner as the Reference Example 12-(a) (500 mg) under argon gas flow with stirring at room temperature, and the resulting mixture was stirred at room temperature for 4 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; ethyl acetate:methanol) to give the title compound (250 mg) as slightly yellow solids.

Mass spectrum (ESI, m/z): 281 $[M+H]^+$

Reference Example 63-(b)

Production of 2,3,4,5-tetrahydro-[1,4]oxazepino[7,6-g]quinoline

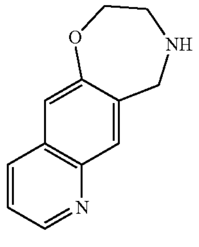 [SMILES: c1cnc2cc3c(cc2c1)OCCNC3]

To a solution of 2-(((6-bromoquinolin-7-yl)methyl)amino)ethan-1-ol produced in the Reference Example 63-(b) (250 mg) in 2-propanol (6 mL) were added cesium carbonate (580 mg) and copper(I) iodide under argon gas flow with stirring at room temperature, and the resulting mixture was stirred at 90° C. for 6 hours, then at room temperature for 14.5 hours, and additionally at 90° C. for 5.5 hours. After the reaction was completed, the reaction solution was allowed to cool to room temperature, filtered, washed with ethyl acetate, and the resulting filtrate was concentrated under reduced pressure. The resulting residues were purified by a silica gel column (elution solvent; ethyl acetate:methanol) to give the title compound (110 mg) as a slightly yellow oil.

Mass spectrum (DUIS, m/z): 201 $[M+H]^+$

Reference Example 64-(a)

Production of ethyl 5-hydroxy-1-(tetrahydro-2H-pyran-2-yl))-1H-indazole-6-carboxylate

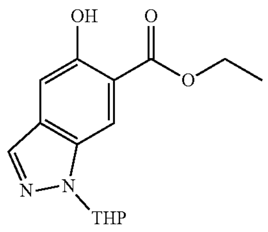

To a solution of ethyl 5-hydroxy-1H-indazole-6-carboxylate (101 mg) in a mixture of dichloromethane (1.2 mL)/tetrahydrofuran (1 mL) was sequentially added dihydropyran (0.047 mL) and methanesulfonic acid (0.0032 mL) under argon gas flow with stirring at room temperature, and the resulting mixture was stirred at room temperature for 16 hours. After the reaction was completed, to the reaction solution was added a saturated aqueous solution of sodium hydrogen carbonate, and the resulting mixed solution was subjected to extraction with dichloromethane. The resulting organic layer was washed with water, dried over anhydrous magnesium sulfate, filtered, and concentrated under reduced pressure. The resulting residues were purified by a silica gel column (elution solvent; hexane ethyl acetate) to give the title compound (109 mg) as a colorless oil.

Mass spectrum (ESI, m/z): 291 $[M+H]^+$

Reference Example 64-(b)

Production of ethyl 5-(((R)-1-((tert-butoxycarbonyl)amino)butan-2-yl)oxy)-1-(tetrahydro-2H-pyran-2-yl)-1H-indazole-6-carboxylate

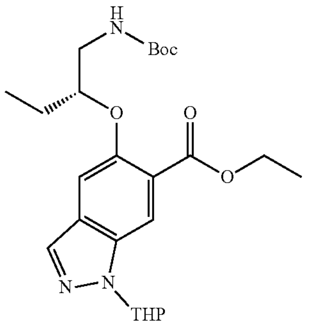

To a solution of ethyl 5-hydroxy-1-(tetrahydro-2H-pyran-2-yl)-1H-indazole-6-carboxylate produced in the Reference Example 64-(a) (108 mg), tert-butyl (S)-(2-hydroxybutyl) carbamate produced according to the same manner as the Reference Example 54-(e) (71 mg), and tri-n-butylphosphine (0.096 mL) in tetrahydrofuran (3 mL) was added (E)-N1,N1,N2,N2-tetramethyldiazene-1,2-dicarboxamide (98 mg) under argon gas flow with stirring at 0° C., and the resulting mixture was stirred at room temperature for 2 hours. After the reaction was completed, to the reaction solution was added water, and the resulting mixed solution was subjected to extraction with ethyl acetate. The resulting organic layer was washed with a saturated aqueous solution of sodium hydrogen carbonate, dried over anhydrous sodium sulfate, filtered, and concentrated under reduced pressure. The resulting residues were purified by a silica gel column (elution solvent; hexane:ethyl acetate) to give the title compound (61 mg) as a pale yellow oil.

Mass spectrum (ESI, m/z): 462 $[M+H]^+$

Reference Example 64-(c)

Production of ethyl (R)-5-((1-aminobutan-2-yl)oxy)-1H-indazole-6-carboxylate dihydrochloride

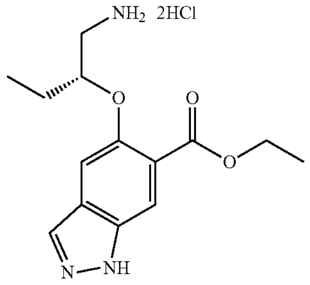 [SMILES: CCOC(=O)c1cc2[nH]ncc2cc1O[C@H](CC)CN]

To a solution of ethyl 5-(((R)-1-((tert-butoxycarbonyl)amino)butan-2-yl)oxy)-1-(tetrahydro-2H-pyran-2-yl)-1H-indazole-6-carboxylate produced in the Reference Example 64-(b) (56 mg) in 1,4-dioxane (2 mL) was added a 4 M solution of hydrogen chloride in 1,4-dioxane (0.230 mL) with stirring at room temperature, and the resulting mixture was stirred at 80° C. for 5 hours. Additionally, a 4 M solution of hydrogen chloride in 1,4-dioxane (0.230 mL) was added thereto with stirring at 80° C., and the resulting mixture was stirred at 80° C. for 3.5 hours. After the reaction was completed, the resulting mixture was allowed to cool to room temperature, and filtered to give the title compound (47 mg) as milky white solids.

Mass spectrum (ESI, m/z): 278 $[M+H]^+$

Reference Example 64-(d)

Production of (R)-6-ethyl-7,8-dihydro-1H-[1,4]oxazepino[7,6-f]indazol-9(6H)-one

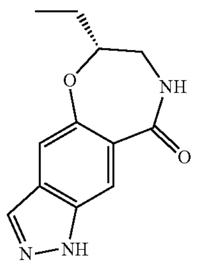 [SMILES: CC[C@@H]1CNC(=O)c2cc3[nH]ncc3cc2O1]

To a solution of ethyl (R)-5-((1-aminobutan-2-yl)oxy)-1H-indazole-6-carboxylate dihydrochloride produced in the Reference Example 64-(c) (47 mg) in ethanol (5 mL) was added sodium hydride (16 mg) under argon gas flow with stirring at room temperature, and the resulting mixture was stirred at room temperature for 3 hours. Additionally, sodium hydride (16 mg) was added thereto with stirring at room temperature, and the resulting mixture was stirred at room temperature for 17 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (elution solvent; ethyl acetate:methanol) to give the title compound (47 mg) as pale yellow solids.

Mass spectrum (ESI, m/z): 232 $[M+H]^+$

Reference Example 64-(e)

Production of (R)-6-ethyl-6,7,8,9-tetrahydro-1H-[1,4]oxazepino[7,6-f]indazole

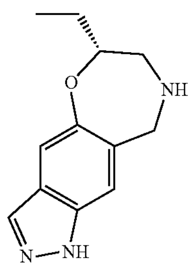 [SMILES: CC[C@@H]1CNCc2cc3[nH]ncc3cc2O1]

To a solution of (R)-6-ethyl-7,8-dihydro-1H-[1,4]oxazepino[7,6-f]indazol-9(6H)-one produced in the Reference Example 64-(d) (47 mg) in tetrahydrofuran (2 mL) was added a 2.5 M solution of lithium aluminum hydride in tetrahydrofuran (0.250 mL) under argon gas flow with stirring at 0° C., and the resulting mixture was stirred at room temperature for 45 minutes. Additionally, a 2.5 M solution of lithium aluminum hydride in tetrahydrofuran (0.250 mL) was added thereto with stirring at room temperature, and the resulting mixture was stirred at room temperature for 14 hours. Additionally, a 2.5 M solution of lithium aluminum hydride in tetrahydrofuran (0.250 mL) was added thereto with stirring at room temperature, and the resulting mixture was stirred at 50° C. for 4 hours. After the reaction was completed, to the reaction solution was added a saturated aqueous solution of potassium sodium tartrate, and the resulting mixture was stirred for 4 hours. Then, the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (DIOL silica gel, elution solvent; ethyl acetate:methanol) to give the title compound (10 mg) as a pale yellow oil.

Mass spectrum (ESI, m/z): 218 $[M+H]^+$

Reference Example 67-(a)

Production of 4-chloro-1-hydroxy-2-naphthaldehyde

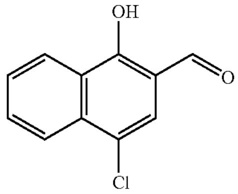 [SMILES: O=Cc1cc(Cl)c2ccccc2c1O]

To a solution of 4-chloronaphthalen-1-ol (800 mg) in trifluoroacetic acid (5 mL) was added hexamethylenetetramine (879 mg) under argon gas flow with stirring at room temperature, and the resulting mixture was stirred at 80° C. for 1 hour. After the reaction was completed, the reaction solution was concentrated under reduced pressure, and a saturated aqueous solution of sodium hydrogen carbonate was added thereto. The resulting mixed solution was subjected to extraction with ethyl acetate. The resulting organic layer was washed sequentially with a saturated aqueous solution of sodium hydrogen carbonate and saturated brine, dried over anhydrous magnesium sulfate, filtered, and concentrated under reduced pressure. The resulting residues were purified by a silica gel column (eluent: hexane:ethyl acetate) to give the title compound (403 mg) as yellow solids.

Mass spectrum (ESI, m/z): 207 $[M+H]^+$

Reference Example 67-(b)

Production of tert-butyl (S)-((4-chloro-1-hydroxynaphthalen-2-yl)methyl) (2-hydroxybutyl)carbamate

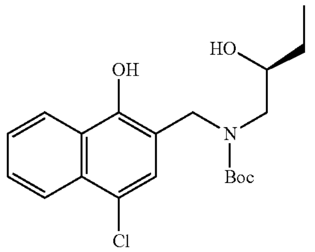 [SMILES: CC[C@H](O)CN(Cc1cc(Cl)c2ccccc2c1O)C(=O)OC(C)(C)C]

To a solution of 4-chloro-1-hydroxy-2-naphthaldehyde produced in the Reference Example 67-(a) (403 mg) in dichloromethane (5 mL) was added (2S)-1-amino-2-butanol (0.221 mL) under argon gas flow with stirring at room temperature, and the resulting mixture was stirred at room temperature for 0.5 hour. Then, sodium triacetoxyborohydride (620 mg) was added thereto, and the resulting mixture was stirred at room temperature for 1 hour. After the reaction was completed, the reaction solution was concentrated under reduced pressure, to the resulting residues were added methanol (5 mL) and a 8 M aqueous solution of sodium hydroxide (2.44 mL), di-tert-butyl dicarbonate (0.896 mL) was added thereto, and the resulting mixture was stirred at room temperature for 3 hours. After the reaction was completed, 1 M hydrochloric acid was added thereto to adjust the pH to 5, and the resulting mixture was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (420 mg) as a colorless oil.

Mass spectrum (ESI, m/z): 380 $[M+H]^+$

Reference Example 67-(c)

Production of tert-butyl (R)-7-chloro-2-ethyl-2,3-dihydronaphtho[2,1-f][1,4]oxazepine-4(5H)-carboxylate

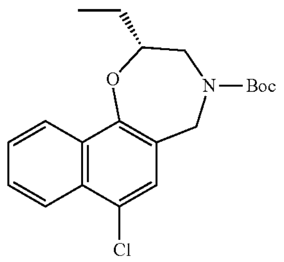 [SMILES: CC[C@@H]1CN(C(=O)OC(C)(C)C)Cc2cc(Cl)c3ccccc3c2O1]

To a solution of tert-butyl. (S)-((4-chloro-1-hydroxynaphthalen-2-yl)methyl) (2-hydroxybutyl)carbamate produced in the Reference Example 67-(b) (420 mg) in tetrahydrofuran (6 mL) were sequentially added (E)-N1,N1,N2,N2-tetramethyldiazene-1,2-dicarboxamide (286 mg) and tri-n-butylphosphine (0.409 mL) under argon gas flow with stirring at room temperature, and the resulting mixture was stirred at room temperature for 3 hours. After the reaction was completed, the reaction solution was diluted with ethyl acetate, washed sequentially with water and saturated brine, dried over anhydrous magnesium sulfate, filtered, and concentrated under reduced pressure. The resulting residues were purified by a silica gel column (eluent: hexane:ethyl acetate) to give the title compound (348 mg) as white solids.

Mass spectrum (ESI, m/z): 362 $[M+H]^+$

Reference Example 67-(d)

Production of (R)-7-chloro-2-ethyl-2,3,4,5-tetrahydronaphtho[2,1-(][1,4]oxazepine hydrochloride

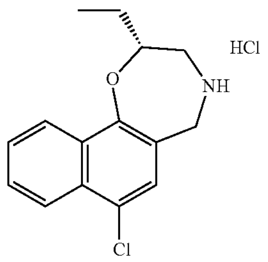 [SMILES: CC[C@@H]1CNCc2cc(Cl)c3ccccc3c2O1 ; Cl]

To a solution of tert-butyl. (R)-7-chloro-2-ethyl-2,3-dihydronaphtho[2,1-f][1,4]oxazepine-4(5H)-carboxylate produced in the Reference Example 67-(c) (348 mg) in cyclopentyl methyl ether (4 mL) was added dropwise a 4 M solution of hydrogen chloride in cyclopentyl methyl ether (0.962 mL) under argon gas flow with stirring at room temperature, and the resulting mixture was stirred at 60° C. for 4 hours. After the reaction was completed, the resulting mixture was allowed to cool to room temperature, and the reaction solution was concentrated to give the title compound (214 mg) as a colorless oil.

Mass spectrum (ESI, m/z): 262 $[M+H]^+$

Reference Example 68-(a)

Production of 2-chloro-6-((trimethylsilyl)ethynyl)benzaldehyde

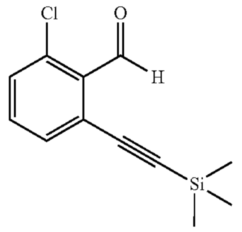

To a solution of 2-bromo-6-chlorobenzaldehyde (2.0 g) in triethylamine (20 mL) were sequentially added bis(triphenylphosphine)palladium(II) dichloride (320 mg), copper(I) iodide (87 mg), and ethynyltrimethylsilane (1.51 mL) under argon gas flow with stirring at room temperature, and the resulting mixture was stirred at 50° C. for 3 hours. After the reaction was completed, the reaction solution was filtered, and the resulting filtrate was concentrated under reduced pressure. The resulting residues were purified by a silica gel column (eluent: hexane:ethyl acetate) to give the title compound (1.94 g) as a slightly yellow oil.

Mass spectrum (ESI, m/z): 237 $[M+H]^+$

Reference Example 68-(b)

Production of methyl (E)-3-(2-chloro-6-ethynylphenyl)acrylate

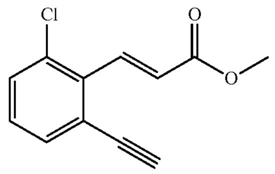

To a solution of methyl diethylphosphonoacetate (7.42 mL) in tetrahydrofuran (20 mL) was added sodium hydride (1.07 g) under argon gas flow with stirring at 0° C., and the resulting mixture was stirred at 0° C. for 0.5 hour. Then, a solution of 2-chloro-6-((trimethylsilyl)ethynyl)benzaldehyde produced in the Reference Example 68-(a) (1.94 g) in tetrahydrofuran (5 mL) was added thereto with stirring at 0° C., and the resulting mixture was stirred at 0° C. for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give a mixture (1.36 g) of the title compound and methyl (E)-3-(2-chloro-6-((trimethylsilyl)ethynyl)phenyl)acrylate as a colorless oil, and also the title compound (513 mg) as white solids.

To a solution of the mixture (1.36 g) of the title compound and methyl (E)-3-(2-chloro-6-((trimethylsilyl)ethynyl)phenyl)acrylate in methanol (7 mL) was added potassium carbonate (128 mg) under argon gas flow with stirring at room temperature, and the resulting mixture was stirred at room temperature for 2 hours. After the reaction was completed, the reaction solution was concentrated under reduced pressure. To the resulting residues was added water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (882 mg) as white solids.

Mass spectrum (ESI, m/z): 221 $[M+H]^+$

Reference Example 68-(c)

Production of methyl 8-chloro-3-hydroxy-2-naphthoate

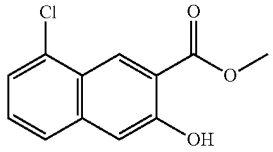 [SMILES: COC(=O)c1cc2c(Cl)cccc2cc1O]

To a solution of methyl (E)-3-(2-chloro-6-ethynylphenyl) acrylate produced according to the same manner as the Reference Example 68-(b) (1.39 g) in chlorobenzene (15 mL) were sequentially added bis(1,5-cyclooctadiene)rhodium(I) trifluoromethanesulfonate (177 mg), tri-p-tolylphosphine (460 mg), and pyridine N-oxide (1.20 g) under argon gas flow with stirring at room temperature, and the resulting mixture was stirred at 100° C. for 7 hours. After the reaction was completed, the reaction solution was allowed to cool to room temperature, water was added thereto, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (299 mg) as white solids.

Mass spectrum (ESI, m/z): 237 $[M+H]^+$

Reference Example 68-(d)

Production of methyl (R)-3-((1-((tert-butoxycarbonyl)amino)butan-2-yl)oxy)-8-chloro-2-naphthoate

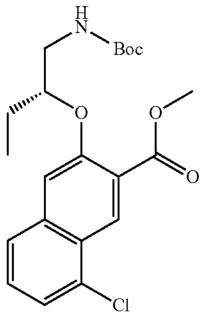 [SMILES: CC[C@H](CNC(=O)OC(C)(C)C)Oc1cc2cccc(Cl)c2cc1C(=O)OC]

To a solution of tert-butyl (S)-(2-hydroxybutyl)carbamate produced according to the same manner as the Reference Example 54-(e) (315 mg) in tetrahydrofuran (5 mL) were sequentially added methyl 8-chloro-3-hydroxy-2-naphthoate produced in the Reference Example 68-(c) (299 mg), (E)-N1,N1,N2,N2-tetramethyldiazene-1,2-dicarboxamide (326 mg), and tri-n-butylphosphine (0.468 mL) under argon gas flow with stirring at room temperature, and the resulting mixture was stirred at room temperature for 2 hours. After the reaction was completed, the reaction solution was diluted with ethyl acetate, washed sequentially with water and saturated brine, dried over anhydrous magnesium sulfate, filtered, and concentrated under reduced pressure. The resulting residues were purified by a silica gel column (eluent: hexane:ethyl acetate) to give the title compound (481 mg) as a slightly yellow oil.

Mass spectrum (ESI, m/z): 408 $[M+H]^+$

Reference Example 68-(e)

Production of methyl (R)-3-((1-aminobutan-2-yl)oxy)-8-chloro-2-naphthoate hydrochloride

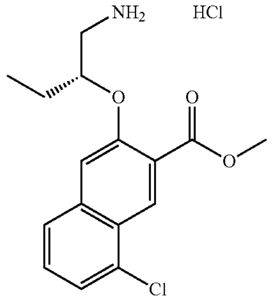 [SMILES: CC[C@H](CN)Oc1cc2cccc(Cl)c2cc1C(=O)OC ; Cl]

To a solution of methyl. (R)-3-((1-((tert-butoxycarbonyl)amino)butan-2-yl)oxy)-8-chloro-2-naphthoate produced in the Reference Example 68-(d) (481 mg) in cyclopentyl methyl ether (3 mL) was added dropwise a 4 M solution of hydrogen chloride in cyclopentyl methyl ether (1.18 mL) under argon gas flow with stirring at room temperature, the resulting mixture was stirred at room temperature for 3 hours, then warmed to 60° C., and stirred for 2 hours. After the reaction was completed, the reaction solution was concentrated under reduced pressure to give the title compound (400 mg) as a white foam.

Mass spectrum (EST, n/z): 308 [M+H]$^+$

Reference Example 68-(f)

Production of (R)-7-chloro-2-ethyl-3,4-dihydronaphtho[2,3-f][1,4]oxazepin-5(2H)-one

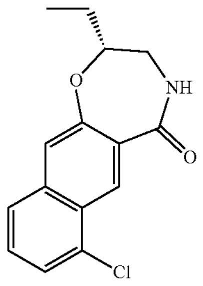

To a solution of methyl. (R)-3-((1-aminobutan-2-yl)oxy)-8-chloro-2-naphthoate hydrochloride produced in the Reference Example 68-(e) (400 mg) in methanol (5 mL) was added sodium hydride (203 mg) under argon gas flow with stirring at 0° C., and the resulting mixture was stirred at room temperature for 1 hour. After the reaction was completed, the reaction solution was concentrated under reduced pressure, a saturated aqueous solution of ammonium chloride was added thereto, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (242 mg) as a white foam.

Mass spectrum (ESI, m/z): 276 [M+H]$^+$

Reference Example 68-(g)

Production of (R)-7-chloro-2-ethyl-2,3,4,5-tetrahydronaphtho[2,3-f][1,4]oxazepine

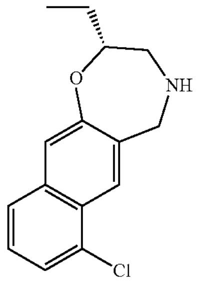 [SMILES: CC[C@@H]1CNCc2cc3c(Cl)cccc3cc2O1]

To a solution of (R)-7-chloro-2-ethyl-3,4-dihydronaphtho[2,3-f][1,4]oxazepin-5(2H)-one produced in the Reference Example 68-(f) (242 mg) in tetrahydrofuran (4 mL) was added dropwise a 0.9 M solution of borane-tetrahydrofuran complex in tetrahydrofuran (2.93 mL) under argon gas flow with stirring at room temperature, the resulting mixture was stirred at room temperature for 3 hours, then warmed to 60° C., and stirred for 3 hours. After the reaction was completed, ethanol (0.307 mL) was added thereto, and the resulting mixture was stirred for 1 hour. The reaction solution was concentrated under reduced pressure, and then dissolved into cyclopentyl methyl ether (2 mL). Additionally, a 4 M solution of hydrogen chloride in cyclopentyl methyl ether (2 mL) was added thereto, and the resulting mixture was stirred for 30 minutes. A 4 M aqueous solution of sodium hydroxide (2 mL) was added thereto, the resulting mixture was stirred, then a saturated aqueous solution of sodium hydrogen carbonate (10 mL) was added thereto, and the resulting mixed solution was subjected to extraction three times with ethyl acetate. The resulting organic layer was washed with saturated brine, dried over anhydrous magnesium sulfate, filtered, and concentrated under reduced pressure. The resulting residues were purified by a silica gel column (eluent: ethyl acetate:methanol) to give the title compound (160 mg) as white solids.

Mass spectrum (ESI, m/z): 262 [M+H]$^+$

Reference Example 69-(a)

Production of 6-bromo-7-(bromomethyl)-4-chloroquinoline

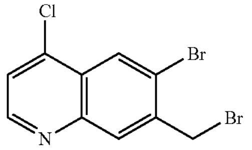 [SMILES: Clc1ccnc2cc(CBr)c(Br)cc12]

To a solution of 6-bromo-4-chloro-7-methylquinoline (2.00 g) in chlorobenzene (50 mL) were sequentially added N-bromosuccinimide (2.09 g) and 2,2'-azobis(2,4-dimethylvaleronitrile) (0.194 g) under argon gas flow with stirring at room temperature, and the resulting mixture was stirred at 60° C. for 8.5 hours and at room temperature for 14.5 hours. N-bromosuccinimide (0.695 g) and 2,2'-azobis(2,4-dimethylvaleronitrile) (0.098 g) were sequentially added thereto with stirring at room temperature, and the resulting mixture was stirred at 60° C. for 3 hours. After the reaction was completed, to the reaction solution was added heptane (10 mL), and the resulting mixture was stirred at room temperature for 10 minutes. The reaction solution was concentrated under reduced pressure, to the resulting residues was added hexane/ethyl acetate, the precipitated solids were collected by filtration, washed with hexane, and dried under reduced pressure at room temperature. To the resulting solids was added a mixed solvent of methanol/water (=1/9), and then the resulting mixture was subjected to sonication. The resulting solids were collected by filtration, washed with water, and dried under reduced pressure at 40° C. to give the title compound (1.10 g) as slightly yellow solids.

Mass spectrum (ESI, m/z): 334 [M+H]$^+$

Reference Example 69-(b)

Production of (R)-1-(((6-bromo-4-chloroquinolin-7-yl)methyl)amino)butan-2-ol

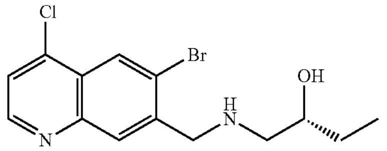 [SMILES: CC[C@@H](O)CNCc1cc2nccc(Cl)c2cc1Br]

To a solution of (2R)-1-amino-2-butanol (0.644 g) in acetonitrile (30 mL) were sequentially added 6-bromo-7-(bromomethyl)-4-chloroquinoline produced in the Reference Example 69-(a) (1.20 g) and N,N-diisopropylethylamine (1.22 mL) under argon gas flow with stirring at room temperature, and the resulting mixture was stirred at room temperature for 2 hours. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous sodium sulfate, filtered, concentrated under reduced pressure, and the resulting residues were purified by a silica gel column (eluent: ethyl acetate:methanol) to give the title compound (1.05 g) as slightly yellow solids.

Mass spectrum (ESI, m/z): 343 $[M+H]^+$

Reference Example 69-(c)

Production of (R)-10-chloro-2-ethyl-2,3,4,5-tetrahydro-[1,4]oxazepino[7,6-g]quinoline

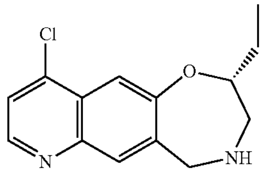 [SMILES: CC[C@@H]1CNCc2cc3nccc(Cl)c3cc2O1]

To a solution of (R)-1-(((6-bromo-4-chloroquinolin-7-yl)methyl)amino)butan-2-ol produced in the Reference Example 69-(b) (1.05 g) in 2-propanol (34 mL) were sequentially added cesium carbonate (2.28 g) and copper(I) iodide (335 mg) under argon gas flow with stirring at room temperature, and the resulting mixture was stirred at 90° C. for 3.5 hours, at room temperature for 14.5 hours, and at 90° C. for 5.5 hours. After the reaction was completed, the resulting precipitates were removed by filtration, and washed with ethyl acetate. The resulting filtrate was concentrated, and the resulting residues were purified by a silica gel column (eluent: ethyl acetate:methanol) to give the title compound (498 mg) as pale yellow solids.

Mass spectrum (EST, m/z): 263 $[M+H]^+$

Reference Example 70-(a)

Production of tert-butyl (R)-10-chloro-2-ethyl-2,3-dihydro-[1,4]oxazepino[7,6-g]quinoline-4(5H)-carboxylate

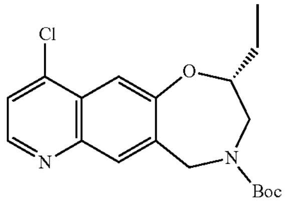 [SMILES: CC[C@@H]1CN(C(=O)OC(C)(C)C)Cc2cc3nccc(Cl)c3cc2O1]

To a solution of (R)-10-chloro-2-ethyl-2,3,4,5-tetrahydro-[1,4]oxazepino[7,6-g]quinoline produced in the Reference Example 69-(c) (306 mg) in methanol (6 mL) was added di-tert-butyl dicarbonate (0.315 mL) under argon gas flow with stirring at room temperature, and the resulting mixture was stirred at room temperature for 2.5 hours. After the reaction was completed, to the reaction solution was added water, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (eluent: hexane:ethyl acetate) to give the title compound (360 mg) as white solids.

Mass spectrum (ESI, m/z): 363 $[M+H]^+$

Reference Example 70-(b)

Production of tert-butyl (R)-2-ethyl-10-methoxy-2,3-dihydro-[1,4]oxazepino[7,6-g]quinoline-4(5H)-carboxylate

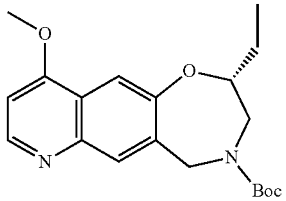 [SMILES: CC[C@@H]1CN(C(=O)OC(C)(C)C)Cc2cc3nccc(OC)c3cc2O1]

To a solution of tert-butyl (R)-10-chloro-2-ethyl-2,3-dihydro-[1,4]oxazepino[7,6-g]quinoline-4(5H)-carboxylate produced in the Reference Example 70-(a) (200 mg) in methanol (2 mL) was added a 5 M solution of sodium methoxide in methanol (0.551 mL) under argon gas flow with stirring at room temperature, and the resulting mixture was stirred at 70° C. for 9 hours. A 5 M solution of sodium methoxide in methanol (0.551 mL) was added thereto at room temperature, and the resulting mixture was stirred at 70° C. for 5 hours. After the reaction was completed, to the reaction solution was added water, and the resulting mixed solution was subjected to extraction with ethyl acetate. The resulting organic layer was washed with saturated brine, dried over anhydrous magnesium sulfate, filtered, concentrated under reduced pressure, and the resulting residues were purified by a silica gel column (eluent: hexane:ethyl acetate) to give the title compound (182 mg) as a white foam.

Mass spectrum (ESI, m/z): 359 $[M+H]^+$

Reference Example 70-(c)

Production of (R)-2-ethyl-10-methoxy-2,3,4,5-tetrahydro-[1,4]oxazepino[7,6-g]quinoline dihydrochloride

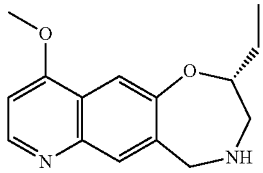

2HCl

To a solution of tert-butyl (R)-2-ethyl-10-methoxy-2,3-dihydro-[1,4]oxazepino[7,6-g]quinoline-4(5H)-carboxylate produced in the Reference Example 70-(b) (180 mg) in 1,4-dioxane (5 mL) was added a 4 M solution of hydrogen chloride in 1,4-dioxane (1.26 mL) under argon gas flow with stirring at room temperature, and the resulting mixture was stirred at room temperature for 19 hours.

After the reaction was completed, the reaction solution was concentrated under reduced pressure, tert-butyl methyl ether was added thereto, the precipitated solids were collected by filtration, washed with tert-butyl methyl ether, and dried under reduced pressure at room temperature to give the title compound (167 mg) as white solids.

Mass spectrum (ESI, m/z): 259 $[M+H]^+$

Reference Example 71-(a)

Production of tert-butyl (R)-2-ethyl-10-methyl-2,3-dihydro-[1,4]oxazepino[7,6-g]quinoline-4(5H)-carboxylate

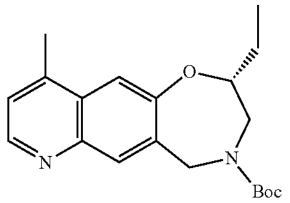 [SMILES: CC[C@@H]1CN(C(=O)OC(C)(C)C)Cc2cc3nccc(C)c3cc2O1]

To a solution of tert-butyl (R)-10-chloro-2-ethyl-2,3-dihydro-[1,4]oxazepino[7,6-g]quinoline-4(5H)-carboxylate produced in the Reference Example 70-(a) (101 mg) in 1,4-dioxane (3 mL) were added tris(dibenzylideneacetone) dipalladium(0) (0.013 g) and 2-dicyclohexylphosphino-2',6'-dimethoxybiphenyl (0.012 g) under argon gas flow with stirring at room temperature, and the resulting mixture was stirred at room temperature for 5 minutes. Then, methylboronic acid (0.051 g) and cesium carbonate (0.270 g) were added thereto at room temperature, and the resulting mixture was stirred at 100° C. for 1 hour. After the reaction was completed, to the reaction solution was added water, and the resulting mixed solution was subjected to extraction with ethyl acetate. The resulting organic layer was washed with saturated brine, dried over anhydrous sodium sulfate, filtered, concentrated under reduced pressure, and the resulting residues were purified by a silica gel column (eluent: hexane:ethyl acetate) to give the title compound (91 mg) as a slightly yellow foam.

Mass spectrum (ESI, m/z): 343 $[M+H]^+$

Reference Example 71-(b)

Production of (R)-2-ethyl-10-methyl-2,3,4,5-tetrahydro-[1,4]oxazepino[7,6-g]quinoline dihydrochloride

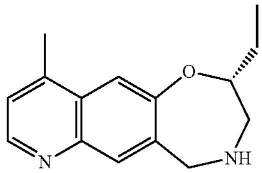

2HCl

To a solution of tert-butyl (R)-2-ethyl-10-methyl-2,3-dihydro-[1,4]oxazepino [7,6-g]quinoline-4 (5H)-carboxylate produced in the Reference Example 71-(a) (89 mg) in 1,4-dioxane (2.5 mL) was added a 4 M solution of hydrogen chloride in 1,4-dioxane (0.657 mL) under argon gas flow with stirring at room temperature, and the resulting mixture was stirred at room temperature for 23 hours. After the reaction was completed, the reaction solution was concentrated under reduced pressure, tert-butyl methyl ether was added thereto, the precipitated solids were collected by filtration, washed with tert-butyl methyl ether, and dried under reduced pressure at room temperature to give the title compound (98 mg) as pale yellow solids. Mass spectrum (DUIS, m/z): 243 $[M+H]^+$ Reference Example 72-(a)

Production of (R)-1-(((6-fluorobenzo[b]thiophen-5-yl)methyl)amino)butan-2-ol

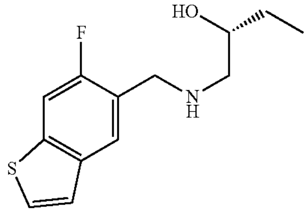 [SMILES: CC[C@@H](O)CNCc1cc2ccsc2cc1F]

To a solution of 6-fluorobenzo[b]thiophene-5-carbaldehyde (300 mg) in dichloromethane (5 mL) was added (R)-1-aminobutan-2-ol (0.189 mL) under argon gas flow with stirring at room temperature, and the resulting mixture was stirred at room temperature for 0.5 hour. Then, sodium triacetoxyborohydride (706 mg) was added thereto with stirring at room temperature, and the resulting mixture was stirred at room temperature for 4 hours. After the reaction was completed, to the reaction solution was added water, and the resulting mixed solution was subjected to extraction twice with ethyl acetate. The resulting organic layer was dried over anhydrous magnesium sulfate, filtered, and concentrated under reduced pressure. The resulting residues were purified by a silica gel column (DIOL silica gel, eluent: hexane:ethyl acetate) to give the title compound (220 mg) as a slightly yellow oil.

Mass spectrum (ESI, m/z): 254 $[M+H]^+$

Reference Example 72-(b)

Production of (R)-2-ethyl-2,3,4,5-tetrahydrothieno[2',3':4,5]benzo[1,2-f][1,4]oxazepine

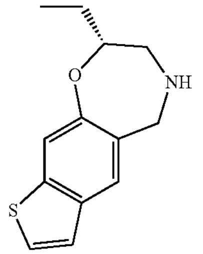 [SMILES: CC[C@@H]1CNCc2cc3ccsc3cc2O1]

To a solution of (R)-1-(((6-fluorobenzo[b]thiophen-5-yl)methyl)amino)butan-2-ol produced in the Reference Example 72-(a) (190 mg) in dimethyl sulfoxide (10 mL) was added potassium tert-butoxide (126 mg) under argon atmosphere with stirring at room temperature, and the resulting mixture was stirred at 70° C. for 2 hours. After the reaction was completed, the reaction solution was allowed to cool to room temperature, water was added thereto, and the resulting mixed solution was subjected to extraction twice with ethyl acetate. The resulting organic layer was washed with saturated brine, dried over anhydrous magnesium sulfate, filtered, and concentrated under reduced pressure. The resulting residues were purified by a silica gel column (DIOL silica gel, eluent: hexane:ethyl acetate) to give the title compound (100 mg) as a slightly yellow oil.

Mass spectrum (ESI, m/z): 234 $[M+H]^+$

Reference Example 73-(a)

Production of 2,2,2-trichloroethyl (R)-2-ethyl-2,3-dihydrothieno[2',3':4,5]benzo[1,2-f][1,4]oxazepine-4(5H)-carboxylate

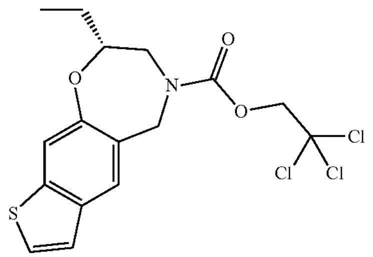 [SMILES: CC[C@@H]1CN(C(=O)OCC(Cl)(Cl)Cl)Cc2cc3ccsc3cc2O1]

To a solution of (R)-2-ethyl-2,3,4,5-tetrahydrothieno[2',3':4,5]benzo[1,2-f][1,4]oxazepine produced according to the same manner as the Reference Example 72-(b) (359 mg) in dichloromethane (5 mL) was added triethylamine (0.322 mL) under argon gas flow with stirring at room temperature. Then, 2,2,2-trichloroethyl carbonochloridate (0.249 mL) was added dropwise thereto with stirring at 0° C., and the resulting mixture was stirred at room temperature for 1 hour. After the reaction was completed, to the reaction solution was added water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (447 mg) as a colorless oil.

Mass spectrum (DUIS, m/z): 408 $[M+H]^+$

Reference Example 73-(b)

Production of (R)-2-ethyl-2,3,4,5,7,8-hexahydrothieno[2',3':4,5]benzo[1,2-f][1,4]oxazepine

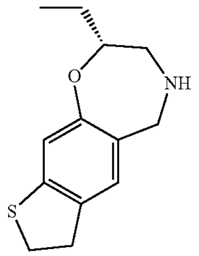 [SMILES: CC[C@@H]1CNCc2cc3c(cc2O1)SCC3]

To a solution of 2,2,2-trichloroethyl (R)-2-ethyl-2,3-dihydrothieno[2',3':4,5]benzo[1,2-f][1,4]oxazepine-4(5H)-carboxylate produced in the Reference Example 73-(a) (447 mg) in trifluoroacetic acid (4 mL) was added dropwise triethylsilane (0.434 mL) under argon gas flow with stirring at room temperature, and the resulting mixture was stirred at 60° C. for 6 hours. After the reaction was completed, to the reaction solution was added a 1 M aqueous solution of sodium hydroxide to adjust the pH to 7.0. The resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate), and the fractions comprising 2,2,2-trichloroethyl (R)-2-ethyl-2,3,7,8-tetrahydrothieno[2',3':4,5]benzo[1,2-f][1,4]oxazepine-4(5H)-carboxylate were concentrated under reduced pressure.

To a solution of the resulting residues (296 mg) in tetrahydrofuran (5 mL) was added zinc powder (105 mg) under argon gas flow with stirring at room temperature, and the resulting mixture was stirred at room temperature for 5 minutes. Then, acetic acid (1 mL) was added thereto, and the resulting mixture was stirred at room temperature for 4 hours. After the reaction was completed, the resulting solids were separated by filtration. To the resulting filtrate was added a saturated aqueous solution of sodium hydrogen carbonate, and the resulting mixed solution was subjected to extraction twice with ethyl acetate. The resulting organic layer was dried over anhydrous magnesium sulfate, filtered, and concentrated under reduced pressure. The resulting residues were purified by a silica gel column (DIOL silica gel, eluent: hexane:ethyl acetate) to give the title compound (48 mg) as white solids.

Mass spectrum (ESI, m/z): 236 $[M+H]^+$

Reference Example 74-(a)

Production of 2,2,2-trichloroethyl (R)-2-ethyl-2,3,7,8-tetrahydrothieno[2',3':4,5]benzo[1,2-f][1,4]oxazepine-4(5H)-carboxylate 9,9-dioxide

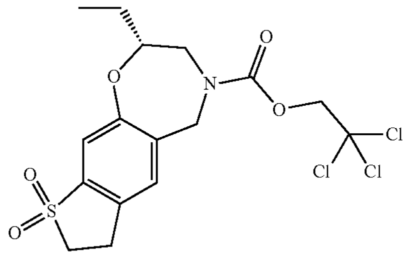 [SMILES: CC[C@@H]1CN(C(=O)OCC(Cl)(Cl)Cl)Cc2cc3c(cc2O1)S(=O)(=O)CC3]

To a solution of 2,2,2-trichloroethyl (R)-2-ethyl-2,3-dihydrothieno[2',3':4,5]benzo[1,2-f][1,4]oxazepine-4(5H)-carboxylate produced in the Reference Example 73-(a) (447 mg) in trifluoroacetic acid (4 mL) was added dropwise triethylsilane (0.434 mL) under argon gas flow with stirring at room temperature, and the resulting mixture was stirred at 60° C. for 6 hours. After the reaction was completed, to the reaction solution was added a 1 M aqueous solution of sodium hydroxide to adjust the pH to 7.0. The resulting mixed solution was subjected to extraction with ethyl acetate. The resulting organic layer was washed with saturated brine, dried over anhydrous magnesium sulfate, filtered, and concentrated under reduced pressure. The resulting residues were purified by silica gel column (eluent: hexane:ethyl acetate), and the fractions comprising 2,2,2-trichloroethyl (R)-2-ethyl-2,3,7,8-tetrahydrothieno[2',3':4,5]benzo[1,2-f][1,4]oxazepine-4(5H)-carboxylate were concentrated under reduced pressure. To a solution of the resulting residues (300 mg) in methanol (3 mL) was added potassium peroxymonosulfate (2.22 g) under argon gas flow with stirring at room temperature, and the resulting mixture was stirred at room temperature for 1 hour. Then, water (1 mL) was added thereto, and the resulting mixture was stirred. After the reaction was completed, the resulting solids were separated by filtration, and washed with ethyl acetate. Then, the resulting filtrate was washed with saturated brine. The resulting organic layer was dried over anhydrous magnesium sulfate, filtered, and concentrated under reduced pressure. The resulting residues were purified by a silica gel column (eluent: hexane:ethyl acetate) to give the title compound (161 mg) as a white foam.

Mass spectrum (ESI, m/z): 442 $[M+H]^+$

Reference Example 74-(b)

Production of (R)-2-ethyl-2,3,4,5,7,8-hexahydrothieno[2',3':4,5]benzo[1,2-f][1,4]oxazepine 9,9-dioxide

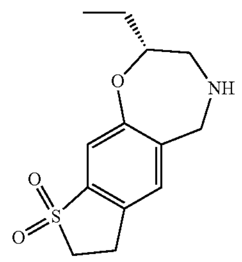 [SMILES: CC[C@@H]1CNCc2cc3c(cc2O1)S(=O)(=O)CC3]

To a solution of 2,2,2-trichloroethyl (R)-2-ethyl-2,3,7,8-tetrahydrothieno[2',3':4,5]benzo[1,2-f][1,4]oxazepine-4(5H)-carboxylate 9,9-dioxide produced in the Reference Example 74-(a) (161 mg) in tetrahydrofuran (5 mL) was added zinc powder (72 mg) under argon gas flow with stirring at room temperature, and the resulting mixture was stirred at room temperature for 5 minutes. Then, acetic acid (1 mL) was added thereto, and the resulting mixture was stirred at room temperature for 4 hours. After the reaction was completed, the resulting solids were separated by filtration. To the resulting filtrate was added a saturated aqueous solution of sodium hydrogen carbonate, and the resulting mixed solution was subjected to extraction twice with ethyl acetate. The resulting organic layer was dried over anhydrous magnesium sulfate, filtered, and concentrated under reduced pressure. The resulting residues were purified by a silica gel column (DIOL silica gel, eluent: ethyl acetate:methanol) to give the title compound (72 mg) as white solids.

Mass spectrum (DUIS, m/z): 268 $[M+H]^+$

Reference Example 75-(a)

Production of (R)-1-(((6-bromoquinolin-7-yl)methyl)amino)propan-2-ol

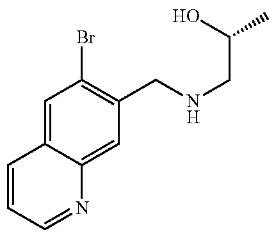 [SMILES: C[C@@H](O)CNCc1cc2ncccc2cc1Br]

To a solution of 6-bromo-7-(bromomethyl)quinoline produced according to the same manner as the Reference Example 12-(a) (570 mg) in acetonitrile (8.7 mL) were sequentially added (2R)-1-amino-2-propanol (0.21 g) and N,N-diisopropylethylamine (0.99 mL) under argon gas flow with stirring at room temperature, and the resulting mixture was stirred at 50° C. for 1.5 hours. After the reaction was completed, to the reaction solution was added a saturated aqueous solution of ammonium chloride (50 mL), and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (eluent: ethyl acetate:methanol) to give the title compound (445 mg) as brown solids.

Mass spectrum (ESI, m/z): 295 $[M+H]^+$

Reference Example 75-(b)

Production of (R)-2-methyl-2,3,4,5-tetrahydro-[1,4]oxazepino[7,6-g]quinoline

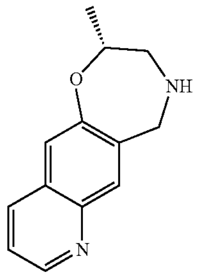 [SMILES: C[C@@H]1CNCc2cc3ncccc3cc2O1]

To a solution of (R)-1-(((6-bromoquinolin-7-yl)methyl)amino)propan-2-ol produced in the Reference Example 75-(a) (445 mg) in 2-propanol (12 mL) were sequentially added cesium carbonate (0.98 g) and copper(I) iodide (0.14 g) under argon gas flow with stirring at room temperature, and the resulting mixture was stirred at 90° C. for 5.7 hours. Then, copper(I) iodide (0.14 g) was added thereto, and the resulting mixture was stirred at 90° C. for 16.7 hours. After the reaction was completed, the reaction solution was allowed to cool to room temperature, filtered through Celite, washed with ethyl acetate, and the resulting filtrate was concentrated under reduced pressure. The resulting residues were purified by a silica gel column (eluent: ethyl acetate:methanol) to give the title compound (209 mg) as brown solids.

Mass spectrum (ESI, m/z): 215 $[M+H]^+$

Reference Example 76-(a)

Production of 1-((((6-bromoquinolin-7-yl)methyl)amino)methyl)cyclopropan-1-ol

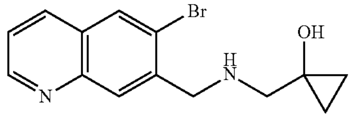 [SMILES: OC1(CNCc2cc3ncccc3cc2Br)CC1]

To a solution of 1-(aminomethyl)cyclopropan-1-ol (4.08 g) in acetonitrile (75 mL) were sequentially added N,N-diisopropylethylamine (8 mL) and 6-bromo-7-(bromomethyl)quinoline produced according to the same manner as the Reference Example 12-(a) (4.70 g) under argon gas flow with stirring at room temperature, and the resulting mixture was stirred at room temperature for 1 hour. After the reaction was completed, to the reaction solution was added a saturated aqueous solution of ammonium chloride, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: ethyl acetate:methanol) to give the title compound (3.24 g) as a light brown oil.

Mass spectrum (ESI, m/z): 307 $[M+H]^+$

Reference Example 76-(b)

Production of 4',5'-dihydro-3'H-spiro(cyclopropane-1,2'-[1,4]oxazepino[7,6-g]quinoline)

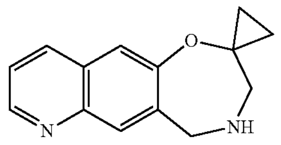 [SMILES: c1cnc2cc3c(cc2c1)OC1(CC1)CNC3]

To a solution of 1-((((6-bromoquinolin-7-yl)methyl)amino)methyl)cyclopropan-1-ol produced in the Reference Example 76-(a) (3.20 g) in 2-propanol (70 mL) were sequentially added cesium carbonate (6.79 g) and copper(I) iodide (0.992 g) under argon gas flow with stirring at room temperature, and the resulting mixture was stirred at 90° C. for 8 hours. Then, copper(I) iodide (0.992 g) was added thereto, and the resulting mixture was stirred at 90° C. for 6 hours. After the reaction was completed, the reaction solution was allowed to cool to room temperature, filtered through Celite, washed with ethyl acetate, and the resulting filtrate was concentrated under reduced pressure. The resulting residues were purified by a silica gel column (eluent: ethyl acetate:methanol) to give the title compound (202 mg) as a light brown oil.

Mass spectrum (ESI, m/z): 227 $[M+H]^+$

Reference Example 77-(a)

Production of 1-(((6-bromoquinolin-7-yl)methyl)amino)pentan-2-ol

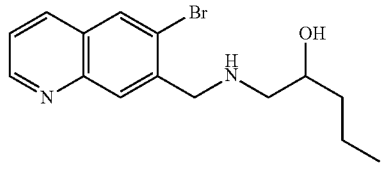 [SMILES: CCCC(O)CNCc1cc2ncccc2cc1Br]

To a solution of 6-bromo-7-(bromomethyl)quinoline produced according to the same manner as the Reference Example 12-(a) (2.1 g) in acetonitrile (32.2 mL) were sequentially added 1-amino-2-pentanol (1.00 g) and N,N-diisopropylethylamine (3.65 mL) under argon gas flow with stirring at room temperature, and the resulting mixture was stirred at 50° C. for 3.5 hours. After the reaction was completed, to the reaction solution was added a saturated aqueous solution of ammonium chloride (50 mL), and the resulting mixed solution was subjected to extraction with ethyl acetate. The resulting organic layer was washed with saturated brine, dried over anhydrous sodium sulfate, filtered, concentrated under reduced pressure, and the resulting residues were purified by a silica gel column (eluent: ethyl acetate:methanol) to give the title compound (1.71 g) as light brown solids.

Mass spectrum (ESI, m/z): 323 [M+H]$^+$

Reference Example 77-(b)

Production of 2-propyl-2,3,4,5-tetrahydro-[1,4]oxazepino[7,6-g]quinoline

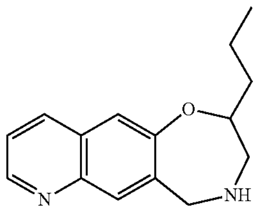 [SMILES: CCCC1CNCc2cc3ncccc3cc2O1]

To a solution of 1-(((6-bromoquinolin-7-yl)methyl)amino)pentan-2-ol produced in the Reference Example 77-(a) (1.71 g) in 2-propanol (40 mL) were sequentially added cesium carbonate (3.45 g) and copper(I) iodide (0.5 g) under argon gas flow with stirring at room temperature, and the resulting mixture was stirred at 90° C. for 3.2 hours. Then, copper(I) iodide (0.5 g) was added thereto, and the resulting mixture was stirred at 90° C. for 16.5 hours. After the reaction was completed, the reaction solution was allowed to cool to room temperature, filtered through Celite, washed with ethyl acetate, and the resulting filtrate was concentrated under reduced pressure. The resulting residues were purified by a silica gel column (eluent: ethyl acetate:methanol) to give the title compound (781 mg) as brown solids.

Mass spectrum (ESI, m/z): 243 [M+H]$^+$

Reference Example 77-(c)

2-propyl-2,3,4,5-tetrahydro-[1,4]oxazepino[7,6-g]quinoline (First Peak)

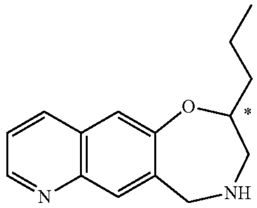 [SMILES: CCCC1CNCc2cc3ncccc3cc2O1]

2-propyl-2,3,4,5-tetrahydro-[1,4]oxazepino[7,6-g]quinoline produced in the Reference Example 77-(b) (760 mg) was separated and purified by high performance liquid chromatography (Column: CHIRALPAK IG, mobile phase: hexane:ethanol ethanol ratio (%): 50 (0 min)→70 (30 min)). The fractions comprising the first-eluted enantiomer were concentrated under reduced pressure to give the compound of Reference Example 78-(a) (339 mg) as slightly yellow solids.

Mass spectrum (ESI, m/z): 243 [M+H]$^+$

Reference Example 78-(a)

2-propyl-2,3,4,5-tetrahydro-[1,4]oxazepino[7,6-g]quinoline (Second Peak)

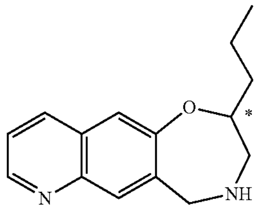 [SMILES: CCCC1CNCc2cc3ncccc3cc2O1]

2-propyl-2,3,4,5-tetrahydro-[1,4]oxazepino[7,6-g]quinoline produced in the Reference Example 77-(b) (760 mg) was separated and purified by high performance liquid chromatography (Column: CHIRALPAK IG, mobile phase: hexane:ethanol ethanol ratio (b): 50 (0 min)→70 (30 min)). The fractions comprising the later-eluted enantiomer were concentrated under reduced pressure to give the compound of Reference Example 78-(b) (352 mg) as slightly yellow solids.

Mass spectrum (ESI, m/z): 243 [M+H]$^+$

Reference Example 79-(a)

Production of 1-bromo-3-(((4-methoxybenzyl)oxy)methyl)benzene

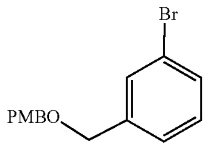

To a solution of (3-bromophenyl)methanol (500 mg) in dimethylformamide (2.5 mL) was added sodium hydride (75 mg) under argon gas flow with stirring at 0° C., and the resulting mixture was stirred at 0° C. for 0.5 hour. Then, 4-methoxybenzyl chloride (0.49 g) was added dropwise thereto with stirring at 0° C., and the resulting mixture was stirred at room temperature for 3 hours. After the reaction was completed, to the reaction solution was added a saturated aqueous solution of ammonium chloride, and the resulting mixed solution was subjected to extraction with toluene. The resulting organic layer was washed with saturated brine, dried over anhydrous sodium sulfate, filtered, and concentrated under reduced pressure. The resulting residues were purified by a silica gel column (eluent: heptane:ethyl acetate) to give the title compound (560 mg) as a colorless oil.

Reference Example 79-(b)

Production of (1,4-dimethyl-1H-benzo[d][1,2,3]triazol-5-yl) (3-(((4-methoxybenzyl)oxy)methyl)phenyl)methanol

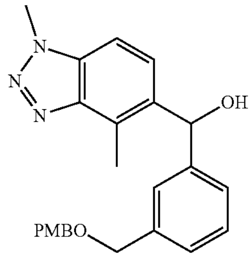

To a solution of 1-bromo-3-(((4-methoxybenzyl)oxy)methyl)benzene produced in the Reference Example 79-(a) (0.52 g) in tetrahydrofuran (7 mL) was added dropwise a 1.6 M solution of n-butyllithium in hexane (1.1 mL) under argon gas flow with stirring at −78° C., and the resulting mixture was stirred at −78° C. for 0.5 hour. Then, a solution of 1,4-dimethyl-1H-benzo[d][1,2,3]triazole-5-carbaldehyde (0.27 g) in tetrahydrofuran (1.8 mL) was added dropwise thereto with stirring at −78° C., and the resulting mixture was stirred at −78° C. for 0.5 hour. Then, the mixture was gradually warmed to room temperature, and stirred for 19.7 hours. After the reaction was completed, to the reaction solution was added a saturated aqueous solution of ammonium chloride, and the resulting mixed solution was subjected to extraction twice with ethyl acetate. The resulting organic layer was washed with saturated brine, dried over anhydrous sodium sulfate, filtered, and concentrated under reduced pressure. The resulting residues were purified by a silica gel column (eluent: heptane:ethyl acetate) to give the title compound (72 mg) as a colorless oil.

Mass spectrum (ESI, m/z): 404 $[M+H]^+$

Reference Example 79-(c)

Production of methyl 3-(1,4-dimethyl-1H-benzo[d][1,2,3]triazol-5-yl)-3-(3-(((4-methoxybenzyl)oxy)methyl)phenyl)-2,2-dimethylpropanoate

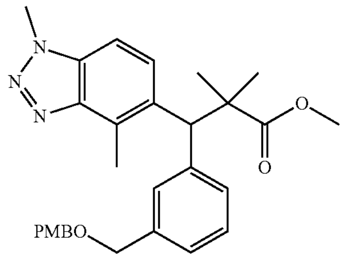

To a solution of (1,4-dimethyl-1H-benzo[d][1,2,3]triazol-5-yl) (3-(((4-methoxybenzyl)oxy)methyl)phenyl)methanol produced according to the same manner as the Reference Example 79-(b) (2.94 g) in dehydrated acetonitrile (29.4 mL) were sequentially added trichloroacetonitrile (1.46 mL) and 1,8-diazabicyclo[5.4.0]-7-undecene (0.218 mL) under argon gas flow with stirring at room temperature, and the resulting mixture was stirred at room temperature for 40 minutes. Then, dimethylketene methyl trimethylsilyl acetal (3.7 mL) and trifluoromethanesulfonimide (0.61 g) were sequentially added thereto with stirring at room temperature, and the resulting mixture was stirred at room temperature for 45 minutes. Additionally, dimethylketene methyl trimethylsilyl acetal (1.47 mL) and trifluoromethanesulfonimide (0.2 g) were added thereto. After the reaction was completed, to the reaction solution was added a saturated aqueous solution of sodium hydrogen carbonate, and the resulting mixed solution was subjected to extraction twice with ethyl acetate. The resulting organic layer was washed with saturated brine, dried over anhydrous sodium sulfate, filtered, and concentrated under reduced pressure to give residues comprising the title compound (4.8 g).

Reference Example 79-(d)

Production of methyl 3-(1,4-dimethyl-1H-benzo[d][1,2,3]triazol-5-yl)-3-(3-(hydroxymethyl)phenyl)-2,2-dimethylpropanoate

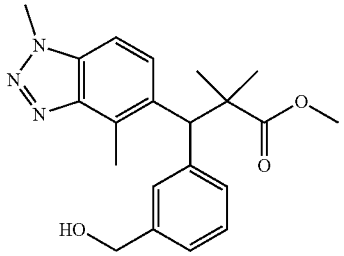 [SMILES: COC(=O)C(C)(C)C(c1cccc(CO)c1)c1ccc2c(nnn2C)c1C]

To a solution of the residues comprising methyl 3-(1,4-dimethyl-1H-benzo[d][1,2,3]triazol-5-yl)-3-(3-(((4-methoxybenzyl)oxy)methyl)phenyl)-2,2-dimethylpropanoate produced in the Reference Example 79-(c) (4.8 g) in a mixture of acetonitrile (32 mL)/water (3.6 mL) was added cerium(IV) diammonium nitrate (2.0 g) with stirring at room temperature, and the resulting mixture was stirred at room temperature for 1.3 hours. Then, cerium (IV) diammonium nitrate (total: 0.81 g) was added thereto in two parts at room temperature. After the reaction was completed, to the reaction solution was added a saturated aqueous solution of sodium hydrogen carbonate (50 mL), the resulting mixture was filtered through Celite, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (eluent: heptane:ethyl acetate) to give the title compound (1.53 g) as a yellow foam.

Mass spectrum (ESI, m/z): 368 [M+Hi]

Reference Example 80-(a)

Production of 4-bromo-1-chloro-2-(((4-methoxybenzyl)oxy)methyl)benzene

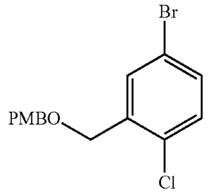

To a solution of (5-bromo-2-chlorophenyl)methanol (2.0 g) in dimethylformamide (10 mL) was added sodium hydride (0.44 g) under argon gas flow with stirring at 0° C., and the resulting mixture was stirred at 0° C. for 0.5 hour. Then, 4-methoxybenzyl chloride (1.48 g) was added dropwise thereto with stirring at 0° C., and the resulting mixture was stirred at room temperature for 4.3 hours. After the reaction was completed, to the reaction solution was added a saturated aqueous solution of ammonium chloride, and the resulting mixed solution was subjected to extraction with toluene. The resulting organic layer was washed with saturated brine, dried over anhydrous sodium sulfate, filtered, and concentrated under reduced pressure. The resulting residues were purified by a silica gel column (eluent: heptane:ethyl acetate) to give the title compound (2.8 g) as a colorless oil.

Reference Example 80-(b)

Production of (4-chloro-3-(((4-methoxybenzyl)oxy)methyl)phenyl)(1,4-dimethyl-1H-benzo[d][1,2,3]triazol-5-yl)methanol

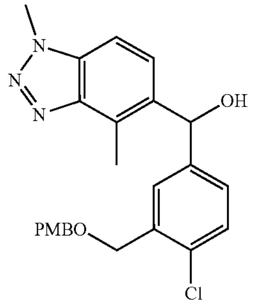

To a solution of 4-bromo-1-chloro-2-(((4-methoxybenzyl)oxy)methyl)benzene produced in the Reference Example 80-(a) (1.13 g) in tetrahydrofuran (13.9 mL) was added dropwise a 1.6 M solution of n-butyllithium in hexane (2.12 mL) under argon gas flow with stirring at −78° C., and the resulting mixture was stirred at −78° C. for 0.5 hour. Then, a solution of 1,4-dimethyl-1H-benzo[d][1,2,3]triazole-5- carbaldehyde (523 mg) in tetrahydrofuran (3.5 mL) was added dropwise thereto with stirring at −78° C., and the resulting mixture was stirred at −78° C. for 0.5 hour. Then, the mixture was gradually warmed to room temperature, and stirred for 1.2 hours. After the reaction was completed, to the reaction solution was added a saturated aqueous solution of ammonium chloride, and the resulting mixed solution was subjected to extraction twice with ethyl acetate. The resulting organic layer was washed with saturated brine, dried over anhydrous sodium sulfate, filtered, and concentrated under reduced pressure. The resulting residues were purified by a silica gel column (eluent: heptane:ethyl acetate) to give the title compound (1.17 g) as a white foam.

Mass spectrum (ESI, m/z): 438 $[M+H]^+$

Reference Example 80-(c)

Production of methyl 3-(4-chloro-3-(((4-methoxybenzyl)oxy)methyl)phenyl)-3-(1,4-dimethyl-1H-benzo[d][1,2,3]triazol-5-yl)-2,2-dimethylpropanoate

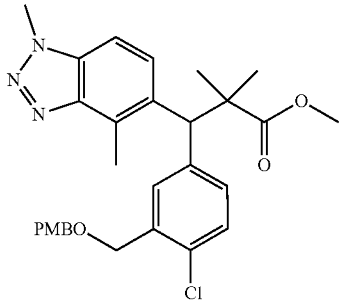

To a solution of (4-chloro-3-(((4-methoxybenzyl)oxy)methyl)phenyl)(1,4-dimethyl-1H-benzo[d][1,2,3]triazol-5-yl)methanol produced in the Reference Example 80-(b) (1.17 g) in dehydrated acetonitrile (11.7 mL) were sequentially added trichloroacetonitrile (0.536 mL) and 1,8-diazabicyclo[5.4.0]-7-undecene (0.08 mL) under argon gas flow with stirring at room temperature, and the resulting mixture was stirred at room temperature for 40 minutes. Then, dimethylketene methyl trimethylsilyl acetal (1.35 mL) and trifluoromethanesulfonimide (0.23 g) were sequentially added thereto with stirring at room temperature, and the resulting mixture was stirred at room temperature for 50 minutes. Additionally, dimethylketene methyl trimethylsilyl acetal (0.056 mL) and trifluoromethanesulfonimide (0.08 g) were added thereto. After the reaction was completed, to the reaction solution was added a saturated aqueous solution of sodium hydrogen carbonate, and the resulting mixed solution was subjected to extraction three times with ethyl acetate. The resulting organic layer was washed with saturated brine, dried over anhydrous sodium sulfate, filtered, and concentrated under reduced pressure to give residues comprising the title compound (2.0 g).

Reference Example 80-(d)

Production of methyl 3-(4-chloro-3-(hydroxymethyl)phenyl)-3-(1,4-dimethyl-1H-benzo[d][1,2,3]triazol-5-yl)-2,2-dimethylpropanoate

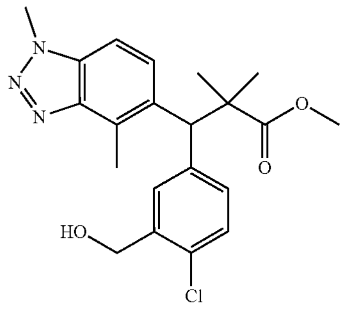 [SMILES: COC(=O)C(C)(C)C(c1ccc(Cl)c(CO)c1)c1ccc2c(nnn2C)c1C]

To a solution of the residues comprising methyl 3-(4-chloro-3-(((4-methoxybenzyl)oxy)methyl)phenyl)-3-(1,4-dimethyl-1H-benzo[d][1,2,3]triazol-5-yl)-2,2-dimethylpropanoate produced in the Reference Example 80-(c) (2.0 g) in a mixture of acetonitrile (12.5 mL)/water (1.4 mL) was added cerium(IV) diammonium nitrate (0.73 g) with stirring at room temperature, and the resulting mixture was stirred at room temperature for 1.3 hours. Then, cerium(IV) diammonium nitrate (total: 0.292 g) was added thereto in two parts at room temperature. After the reaction was completed, to the reaction solution was added a saturated aqueous solution of sodium hydrogen carbonate (50 mL), the resulting mixture was filtered through Celite, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (eluent: heptane:ethyl acetate) to give the title compound (446 mg) as white solids.

Mass spectrum (ESI, m/z): 402 [M+H]$^+$

Reference Example 81-(a)

Production of 4-bromo-1-methoxy-2-(((4-methoxybenzyl)oxy)methyl)benzene

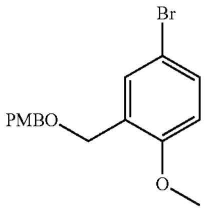

To a solution of (5-bromo-2-methoxyphenyl)methanol (2.0 g) in dimethylformamide (10 mL) was added sodium hydride (0.44 g) under argon gas flow with stirring at 0° C., and the resulting mixture was stirred at 0° C. for 0.5 hour. Then, 4-methoxybenzyl chloride (1.52 g) was added dropwise thereto with stirring at 0° C., and the resulting mixture was stirred at room temperature for 4.8 hours. After the reaction was completed, to the reaction solution was added a saturated aqueous solution of ammonium chloride, and the resulting mixed solution was subjected to extraction twice with toluene. The resulting organic layer was washed with saturated brine, dried over anhydrous sodium sulfate, filtered, and concentrated under reduced pressure. The resulting residues were purified by a silica gel column (eluent: heptane:ethyl acetate) to give the title compound (3.0 g) as a colorless oil.

Reference Example 81-(b)

Production of (1,4-dimethyl-1H-benzo[d][1,2,3]triazol-5-yl) (4-methoxy-3-(((4-methoxybenzyl)oxy)methyl)phenyl)methanol

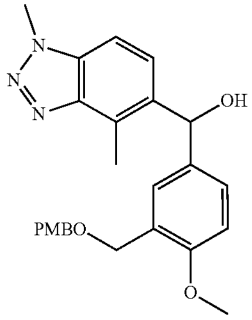

To a solution of 4-bromo-1-methoxy-2-(((4-methoxybenzyl)oxy)methyl)benzene produced in the Reference Example 81-(a) (1.8 g) in tetrahydrofuran (22.3 mL) was added dropwise a 1.6 M solution of n-butyllithium in hexane (3.41 mL) under argon gas flow with stirring at −78° C., and the resulting mixture was stirred at −78° C. for 0.5 hour. Then, a solution of 1,4-dimethyl-1H-benzo[d][1,2,3]triazole-5-carbaldehyde (840 mg) in tetrahydrofuran (6.1 mL) was added dropwise thereto with stirring at −78° C., and the resulting mixture was stirred at −78° C. for 0.5 hour. Then, the mixture was gradually warmed to room temperature, and stirred for 1.3 hours. After the reaction was completed, to the reaction solution was added a saturated aqueous solution of ammonium chloride, and the resulting mixed solution was subjected to extraction twice with ethyl acetate. The resulting organic layer was washed with saturated brine, dried over anhydrous sodium sulfate, filtered, and concentrated under reduced pressure. The resulting residues were purified by a silica gel column (eluent: heptane:ethyl acetate) to give the title compound (1.42 g) as a slightly yellow foam.

Mass spectrum (ESI, m/z): 434 [M+H]$^+$

Reference Example 81-(c)

Production of methyl 3-(1,4-dimethyl-1H-benzo[d][1,2,3]triazol-5-yl)-3-(4-methoxy-3-(((4-methoxybenzyl)oxy)methyl)phenyl)-2,2-dimeth ylpropanoate

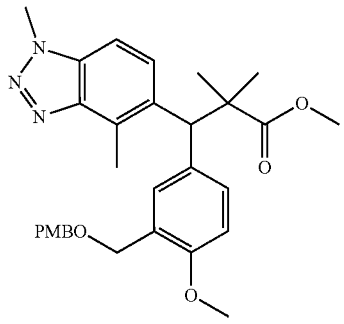

To a solution of (1,4-dimethyl-1H-benzo[d][1,2,3]triazol-5-yl) (4-methoxy-3-(((4-methoxybenzyl)oxy)methyl)phenyl)methanol produced in the Reference Example 81-(b) (1.42 g) in dehydrated acetonitrile (14.2 mL) were sequentially added trichloroacetonitrile (0.657 mL) and 1,8-diazabicyclo[5.4.0]-7-undecene (0.1 mL) under argon gas flow with stirring at room temperature, and the resulting mixture was stirred at room temperature for 40 minutes. Then, dimethylketene methyl trimethylsilyl acetal (1.7 mL) and trifluoromethanesulfonimide (0.28 g) were sequentially added thereto with stirring at room temperature, and the resulting mixture was stirred at room temperature for 40 minutes. After the reaction was completed, to the reaction solution was added a saturated aqueous solution of sodium hydrogen carbonate, and the resulting mixed solution was subjected to extraction twice with ethyl acetate. The resulting organic layer was washed with saturated brine, dried over anhydrous sodium sulfate, filtered, and concentrated under reduced pressure to give residues comprising the title compound (2.5 g).

Reference Example 81-(d)

Production of methyl 3-(1,4-dimethyl-1H-benzo[d][1,2,3]triazol-5-yl)-3-(3-(hydroxymethyl)-4-methoxyphenyl)-2,2-dimethylpropanoate

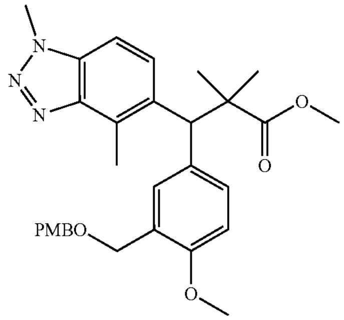

To a solution of the residues comprising methyl 3-(1,4-dimethyl-1H-benzo[d][1,2,3]triazol-5-yl)-3-(4-methoxy-3-(((4-methoxybenzyl)oxy)methyl)phenyl)-2,2-dimethylpropanoate produced in the Reference Example 81-(c) (2.5 g) in a mixture of acetonitrile (15.3 mL)/water (1.7 mL) was added cerium(IV) diammonium nitrate (1.26 g) with stirring at room temperature, and the resulting mixture was stirred at room temperature for 1 hour. Then, cerium(IV) diammonium nitrate (0.51 g) was added thereto at room temperature, and the resulting mixture was stirred at room temperature for 0.75 hour. Additionally, cerium(IV) diammonium nitrate (1.26 g) was added thereto at room temperature, and the resulting mixture was stirred at room temperature for 1 hour. After the reaction was completed, to the reaction solution was added a saturated aqueous solution of sodium hydrogen carbonate, the resulting mixture was filtered through Celite, and the resulting mixed solution was subjected to extraction with ethyl acetate. The resulting organic layer was washed with saturated brine, dried over anhydrous sodium sulfate, filtered, and concentrated under reduced pressure. The resulting residues were purified by a silica gel column (eluent: heptane:ethyl acetate) to give the title compound (303 mg) as a white foam.

Mass spectrum (ESI, m/z): 398 $[M+H]^+$

Reference Example 82-(a)

Production of (3-(((4-methoxybenzyl)oxy)methyl)-4-methylphenyl)(1-methyl-1H-benzo[d][1,2,3]triazol-5-yl)methanol

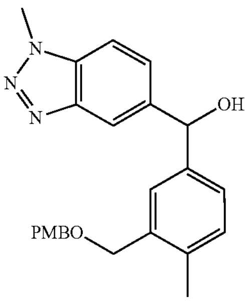

To a solution of 4-bromo-2-(((4-methoxybenzyl)oxy)methyl)-1-methylbenzene produced according to the same manner as the Reference Example 1-(e) (2.5 g) in tetrahydrofuran (32.7 mL) was added dropwise a 1.6 M solution of n-butyllithium in hexane (5 mL) under argon gas flow with stirring at −78° C., and the resulting mixture was stirred at −78° C. for 0.5 hour. Then, a suspension of 1-methyl-1H-benzo (d) [1,2,3]triazole-5-carbaldehyde (1.13 g) in tetrahydrofuran (12.5 mL) was added dropwise thereto with stirring at −78° C., and the resulting mixture was stirred at −78° C. for 0.5 hour. Then, the mixture was gradually warmed to room temperature, and stirred for 1.8 hours. After the reaction was completed, to the reaction solution was added a saturated aqueous solution of ammonium chloride, and the resulting mixed solution was subjected to extraction twice with ethyl acetate. The resulting organic layer was washed with saturated brine, dried over anhydrous sodium sulfate, filtered, and concentrated under reduced pressure. The resulting residues were purified by a silica gel column (eluent: heptane:ethyl acetate) to give the title compound (2.36 g) as a brown foam.

Mass spectrum (ESI, m/z): 404 $[M+H]^+$

Reference Example 82-(b)

Production of methyl 3-(3-(((4-methoxybenzyl)oxy) methyl)-4-methylphenyl)-2,2-dimethyl-3-(1-methyl-1H-benzo[d][1,2,3]triazol-5-yl)propanoate

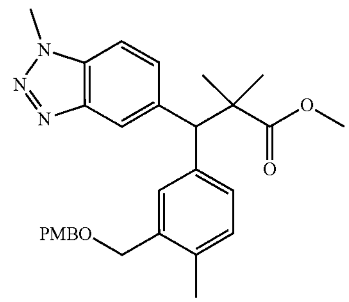

To a solution of (3-(((4-methoxybenzyl)oxy)methyl)-4-methylphenyl)(1-methyl-1H-benzo[d][1,2,3]triazol-5-yl) methanol produced in the Reference Example 82-(a) (2.37 g) in dehydrated acetonitrile (23.7 mL) were sequentially added trichloroacetonitrile (1.18 mL) and 1,8-diazabicyclo [5.4.0]-7-undecene (0.176 mL) under argon gas flow with stirring at room temperature, and the resulting mixture was stirred at room temperature for 1.2 hours. Then, dimethylketene methyl trimethylsilyl acetal (2.98 mL) and trifluoromethanesulfonimide (0.5 g) were sequentially added thereto with stirring at room temperature, and the resulting mixture was stirred at room temperature for 0.5 hour. After the reaction was completed, to the reaction solution was added a saturated aqueous solution of sodium hydrogen carbonate, and the resulting mixed solution was subjected to extraction three times with ethyl acetate. The resulting organic layer was washed with saturated brine, dried over anhydrous sodium sulfate, filtered, and concentrated under reduced pressure to give residues comprising the title compound (4.1 g).

Reference Example 82-(c)

Production of methyl 3-(3-(hydroxymethyl)-4-methylphenyl)-2,2-dimethyl-3-(1-methyl-1H-benzo[d][1,2,3]triazol-5-yl)propanoate

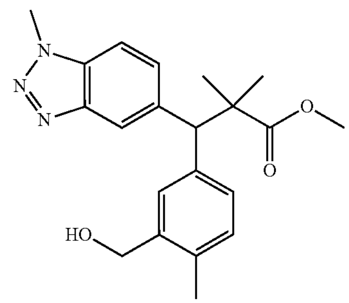 [SMILES: COC(=O)C(C)(C)C(c1ccc(C)c(CO)c1)c1ccc2c(c1)nnn2C]

To a solution of the residues comprising methyl 3-(3-(((4-methoxybenzyl)oxy)methyl)-4-methylphenyl)-2,2-dimethyl-3-(1-methyl-1H-benzo[d][1,2,3]triazol-5-yl)propanoate produced in the Reference Example 82-(b) (4.1 g) in a mixture of acetonitrile (25.8 mL)/water (2.86 mL) was added cerium(IV) diammonium nitrate (1.61 g) with stirring at room temperature, and the resulting mixture was stirred at room temperature for 45 minutes. Then, cerium(IV) diammonium nitrate (1.61 g) was added thereto at room temperature, and the resulting mixture was stirred at room temperature for 0.5 hour. Then, cerium(IV) diammonium nitrate (0.322 g) was added thereto at room temperature, and the resulting mixture was stirred at room temperature for 1 hour. Then, cerium(IV) diammonium nitrate (0.322 g) was added thereto at room temperature, and the resulting mixture was stirred at room temperature for 1 hour. After the reaction was completed, to the reaction solution was added a saturated aqueous solution of sodium hydrogen carbonate, the resulting mixture was filtered through Celite, and the resulting mixed solution was subjected to extraction three times with ethyl acetate. The resulting organic layer was washed with saturated brine, dried over anhydrous sodium sulfate, filtered, and concentrated under reduced pressure. The resulting residues were purified by a silica gel column (eluent: heptane:ethyl acetate) to give the title compound (976 mg) as a slightly yellow foam.

Mass spectrum (ESI, m/z): 368 $[M+H]^+$

Reference Example 83-(a)

Production of methyl 1-((1,4-dimethyl-1H-benzo[d][1,2,3]triazol-5-yl) (3-(((4-methoxybenzyl)oxy)methyl)-4-methylphenyl)methyl)cyclopentane-1-carboxylate

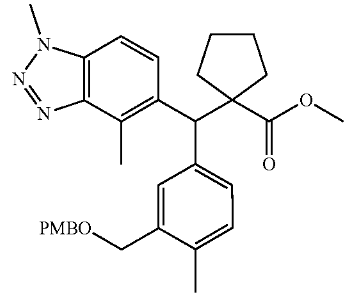

To a solution of (1,4-dimethyl-1H-benzo[d][1,2,3]triazol-5-yl) (3-(((4-methoxybenzyl)oxy)methyl)-4-methylphenyl) methanol produced according to the same manner as the Reference Example 1-(f) (835 mg) in dehydrated acetonitrile (8 mL) were sequentially added trichloroacetonitrile (0.40 mL) and 1,8-diazabicyclo[5.4.0]-7-undecene (0.060 mL) under argon gas flow with stirring at room temperature, and the resulting mixture was stirred at room temperature for 0.5 hour. Then, a solution of (cyclopentylidene(methoxy) methoxy)trimethylsilane (1.00 g) in dehydrated acetonitrile (1 mL) and trifluoromethanesulfonimide (172 mg) were sequentially added thereto with stirring at room temperature, and the resulting mixture was stirred at room temperature for 1.5 hours. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, and concentrated under reduced pressure to give residues comprising the title compound (1.06 g).

Mass spectrum (ESI, m/z): 528 $[M+H]^+$

Reference Example 83-(b)

Production of methyl 1-((1,4-dimethyl-1H-benzo[d][1,2,3]triazol-5-yl) (3-(hydroxymethyl)-4-methylphenyl)methyl)cyclopentane-1-carboxylate

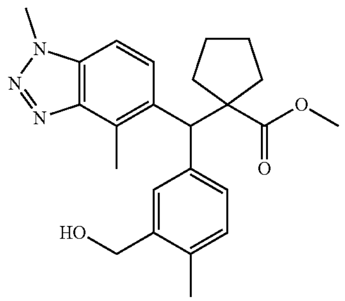 [SMILES: COC(=O)C1(C(c2ccc(C)c(CO)c2)c2ccc3c(nnn3C)c2C)CCCC1]

To a solution of methyl 1-((1,4-dimethyl-1H-benzo[d][1,2,3]triazol-5-yl) (3-(((4-methoxybenzyl)oxy)methyl)-4-methylphenyl)methyl)cyclopentane-1-carboxylate produced in the Reference Example 83-(a) (1.06 g) in a mixture of acetonitrile (9 mL)/water (1 mL) was added cerium(IV) diammonium nitrate (1.10 g) under argon gas flow with stirring at room temperature, and the resulting mixture was stirred at room temperature for 0.5 hour. Cerium(IV) diammonium nitrate (115 mg) was added thereto at room temperature, and the resulting mixture was stirred at room temperature for 0.5 hour. Cerium(IV) diammonium nitrate (112 mg) was added thereto at room temperature, and the resulting mixture was stirred at room temperature for 0.5 hour. Cerium(IV) diammonium nitrate (111 mg) was added thereto at room temperature, and the resulting mixture was stirred at room temperature for 0.5 hour. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (533 mg) as a white foam.

Mass spectrum (ESI, m/z): 408 $[M+H]^+$

Reference Example 83-(c)

Production of methyl 1-((3-(chloromethyl)-4-methylphenyl)(1,4-dimethyl-1H-benzo[d][1,2,3]triazol-5-yl)methyl)cyclopentane-1-carboxylate

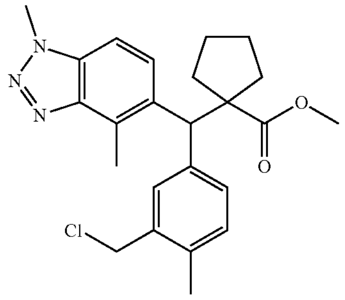 [SMILES: COC(=O)C1(C(c2ccc(C)c(CCl)c2)c2ccc3c(nnn3C)c2C)CCCC1]

To a solution of methyl 1-((1,4-dimethyl-1H-benzo[d][1,2,3]triazol-5-yl) (3-(hydroxymethyl)-4-methylphenyl)methyl)cyclopentane-1-carboxylate produced in the Reference Example 83-(b) (100 mg) in dichloromethane (3 mL) was added dropwise thionyl chloride (0.036 mL) under argon gas flow with stirring at room temperature, and the resulting mixture was stirred at room temperature for 0.5 hour. After the reaction was completed, and the reaction solution was concentrated under reduced pressure to give the title compound (104 mg) as a white foam.

Mass spectrum (DUIS, m/z): 426 $[M+H]^+$

Reference Example 84-(a)

Production of methyl 1-((1,4-dimethyl-1H-benzo[d][1,2,3]triazol-5-yl) (3-(((4-methoxybenzyl)oxy)methyl)-4-methylphenyl)methyl)cyclobutane-1-carboxylate

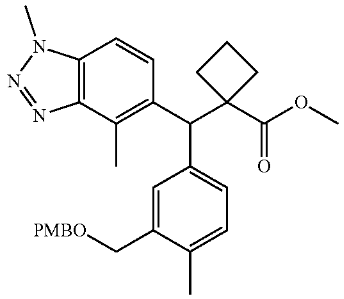

To a solution of (1,4-dimethyl-1H-benzo[d][1,2,3]triazol-5-yl) (3-(((4-methoxybenzyl)oxy)methyl)-4-methylphenyl)methanol produced according to the same manner as the Reference Example 1-(f) (991 mg) in dehydrated acetonitrile (8 mL) were sequentially added trichloroacetonitrile (0.48 mL) and 1,8-diazabicyclo[5.4.0]-7-undecene (0.073 mL) under argon gas flow with stirring at room temperature, and the resulting mixture was stirred at room temperature for 0.5 hour. Then, (cyclobutylidene(methoxy)methoxy)trimethylsilane (1.11 g) and trifluoromethanesulfonimide (203 mg) were sequentially added thereto with stirring at room temperature, and the resulting mixture was stirred at room temperature for 3 hours. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, and concentrated under reduced pressure to give residues comprising the title compound (1.22 g).

Mass spectrum (DUIS, m/z): 514 $(H+H)^+$

Reference Example 84-(b)

Production of methyl 1-((1,4-dimethyl-1H-benzo[d][1,2,3]triazol-5-yl) (3-(hydroxymethyl)-4-methylphenyl)methyl)cyclobutane-1-carboxylate

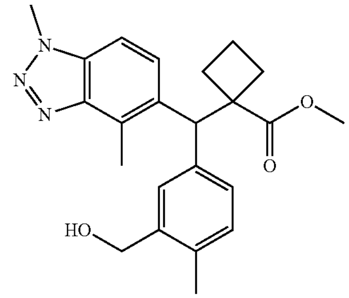 [SMILES: COC(=O)C1(C(c2ccc(C)c(CO)c2)c2ccc3c(nnn3C)c2C)CCC1]

To a solution of methyl 1-((1,4-dimethyl-1H-benzo[d][1,2,3]triazol-5-yl) (3-(((4-methoxybenzyl)oxy)methyl)-4-methylphenyl)methyl)cyclobutane-1-carboxylate produced in the Reference Example 84-(a) (1.22 g) in a mixture of acetonitrile (9 mL)/water (1 mL) was added cerium(IV) diammonium nitrate (1.31 g) under argon gas flow with stirring at room temperature, and the resulting mixture was stirred at room temperature for 0.5 hour. Cerium(IV) diammonium nitrate (130 mg) was added thereto at room temperature, and the resulting mixture was stirred at room temperature for 0.5 hour. Cerium(IV) diammonium nitrate (261 mg) was added thereto at room temperature, and the resulting mixture was stirred at room temperature for 2.5 hours. Cerium(IV) diammonium nitrate (261 mg) was added thereto at room temperature, and the resulting mixture was stirred at room temperature for 0.5 hour. After the reaction was completed, to the reaction solution was added a saturated aqueous solution of sodium hydrogen carbonate, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (332 mg) as a slightly yellow foam.

Mass spectrum (ESI, m/z): 394 $[M+H]^+$

Reference Example 84-(c)

Production of methyl 1-((3-(chloromethyl)-4-methylphenyl)(1,4-dimethyl-1H-benzo[d][1,2,3]triazol-5-yl)methyl)cyclobutane-1-carboxylate

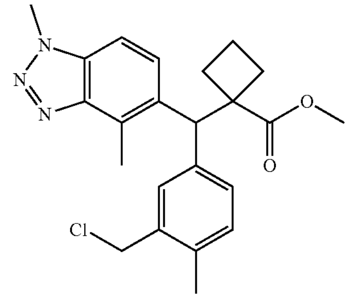 [SMILES: COC(=O)C1(C(c2ccc(C)c(CCl)c2)c2ccc3c(nnn3C)c2C)CCC1]

To a solution of methyl 1-((1,4-dimethyl-1H-benzo[d][1,2,3]triazol-5-yl) (3-(((4-methoxybenzyl)oxy)methyl)-4-methylphenyl)methyl)cyclobutane-1-carboxylate produced in the Reference Example 84-(b) (71 mg) in dichloromethane (2 mL) was added dropwise thionyl chloride (0.026 mL) under argon gas flow with stirring at room temperature, and the resulting mixture was stirred at room temperature for 0.5 hour. After the reaction was completed, the reaction solution was concentrated under reduced pressure to give the title compound (73 mg) as a slightly yellow foam.

Mass spectrum (DUIS, m/z): 412 $[M+H]^+$

Reference Example 89-(a)

Production of (S)-1-(((4-fluoroisoquinolin-3-yl)methyl)amino)butan-2-ol

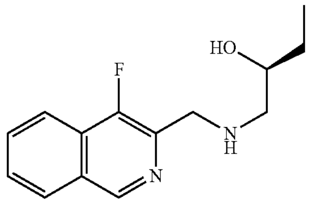 [SMILES: CC[C@H](O)CNCc1ncc2ccccc2c1F]

To a solution of 4-fluoroisoquinoline-3-carbaldehyde synthesized according to the method described in Chemical Communications, 2013, 49, 8537. (473 mg) in dichloromethane (9.5 mL) was added (2S)-1-amino-2-butanol (289 mg) under nitrogen atmosphere with stirring at room temperature, and the resulting mixture was stirred at room temperature for 30 minutes. Then, sodium triacetoxyborohydride (1.14 g) was added thereto with stirring at room temperature, and the resulting mixture was stirred at room temperature for 19 hours. After the reaction was completed, to the reaction solution was added an aqueous solution of sodium hydrogen carbonate, and the resulting mixed solution was subjected to extraction with ethyl acetate. The resulting organic layer was dried over anhydrous magnesium sulfate, filtered, and concentrated under reduced pressure. The resulting residues were purified by a silica gel column (NHsilica gel, eluent: ethyl acetate:methanol) to give the title compound (379 mg) as a yellow oil.

Mass spectrum (ESI, m/z): 249 $[M+H]^+$

Reference Example 89-(b)

Production of tert-butyl (S)-2-ethyl-2,3-dihydro-[1,4]oxazepino[6,7-c]isoquinoline-4(5H)-carboxylate

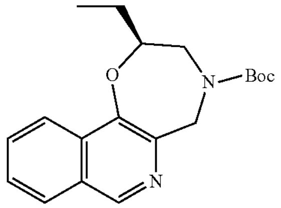 [SMILES: CC[C@H]1CN(C(=O)OC(C)(C)C)Cc2ncc3ccccc3c2O1]

To a solution of (S)-1-(((4-fluoroisoquinolin-3-yl)methyl)amino)butan-2-ol produced in the Reference Example 89-(a) (379 mg) in dimethyl sulfoxide (10 mL) was added potassium tert-butoxide (206 mg) under nitrogen atmosphere with stirring at room temperature, and the resulting mixture was stirred at room temperature for 1 hour and at 90° C. for 1.5 hours. After the reaction was completed, the resulting mixture was allowed to cool to room temperature. Di-tert-butyl dicarbonate (400 mg) was added thereto, and the resulting mixture was stirred at room temperature for 19 hours. After the reaction was completed, to the reaction solution was added water, and the resulting mixed solution was subjected to extraction with ethyl acetate. The resulting organic layer was washed with saturated brine, dried over anhydrous magnesium sulfate, filtered, and concentrated under reduced pressure. The resulting residues were purified by a silica gel column (eluent: hexane:ethyl acetate) to give the title compound (432 mg) as yellow solids.

Mass spectrum (ESI, m/z): 329 $[M+H]^+$

Reference Example 89-(c)

Production of (S)-2-ethyl-2,3,4,5-tetrahydro-[1,4]oxazepino[6,7-c]isoquinoline dihydrochloride

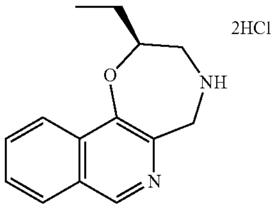 [SMILES: CC[C@H]1CNCc2ncc3ccccc3c2O1]

To a solution of tert-butyl (S)-2-ethyl-2,3-dihydro-[1,4]oxazepino[6,7-c]isoquinoline-4(5H)-carboxylate produced in the Reference Example 89-(b) (432 mg) in 1,4-dioxane (4 mL) was added dropwise a 4 M solution of hydrogen chloride in 1,4-dioxane (1.3 mL) under nitrogen atmosphere with stirring at room temperature, and the resulting mixture was stirred at room temperature for 0.5 hour and at 60° C. for 1 hour. Then, a 4 M solution of hydrogen chloride in 1,4-dioxane (1.3 mL) was added dropwise thereto at room temperature, and the resulting mixture was stirred at 60° C. for 1 hour. After the reaction was completed, the reaction solution was allowed to cool to room temperature, hexane (5.3 mL) was added thereto, and the resulting mixture was stirred at room temperature for 16 hours. The precipitated solids were collected by filtration, washed with tert-butyl methyl ether, and subjected to vacuum drying at room temperature to give the title compound (315 mg) as slightly yellow solids.

Mass spectrum (ESI, m/z): 229 $[M+H]^+$

TABLE 1

| Comparative compounds | | |
|---|---|---|
| Comparative No. | Compound structure | Remarks |
| C1 | 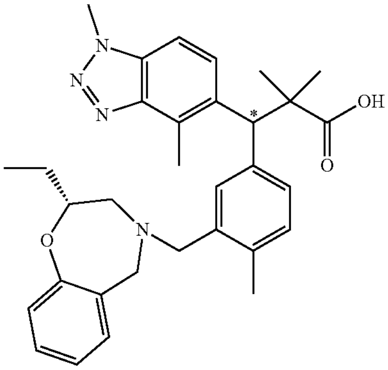 [SMILES: CC[C@@H]1CN(Cc2cc(C(c3ccc4c(nnn4C)c3C)C(C)(C)C(=O)O)ccc2C)Cc2ccccc2O1] | Diastereomer 1 First-eluted ingredient obtained by separating and purifying Example 103 in WO 2016/202253 pamphlet by supercritical fluid chromatography (Column: CHIRALPAK IG, mobile phase: $CO_2$: methanol = 70:30). |
| C2 | 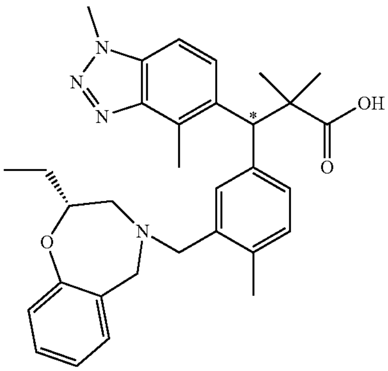 [SMILES: CC[C@@H]1CN(Cc2cc(C(c3ccc4c(nnn4C)c3C)C(C)(C)C(=O)O)ccc2C)Cc2ccccc2O1] | Diastereomer 2 Later-eluted ingredient obtained by separating and purifying Example 103 of WO 2016/202253 pamphlet by supercritical fluid chromatography (Column: CHIRALPAK IG, mobile phase: $CO_2$: methanol = 70:30). |

Pharmacological Test Examples

(Test Example 1): Keap1-Nrf2 Binding Inhibition Test

The inhibitory activity of each test compound on the binding between Nrf2 and Keap1 was measured by the fluorescence polarization method. A solution consisting of 20 mM tris-hydrochloride pH7.5 (NIPPON GENE CO., LTD., REF: 318-90225), 150 mM NaCl [FUJIFILM Wako Pure Chemical. Corporation, REF: 191-01665], 0.05% Tween 20 (BioRAD, REF: 161-0781), and 5 mM DTT (FUJIFILM Wako Pure Chemical Corporation, REF: 049-08972) was used as a buffer solution. To a test compound solution (70 μL) adjusted to each concentration with 10% DMSO (FUJIFILM Wako Pure Chemical Corporation, REF: 043-07216) was added a buffer solution (350 μL) comprising 6 nM FITC-labeled Nrf2 peptide (FITC-Ahx-LDEETGEFL-NH2, Invitrogen) and 0.2 mg/mL of BSA (FUJIFILM Wako Pure Chemical Corporation, REF: 017-22231). Each 120 μL of the resulting mixture was dispensed into a black 96 well plate, and a buffer solution (80 μL) comprising 2.5 nM GST fusion human Keap1 (amino acid residue: 325-624) protein (Protein tech, REF: Ag0779) was added thereto. A Keap1-free buffer solution was added to some wells to prepare negative controls. Meanwhile, compound-free wells were used as positive controls. The plate was incubated at room temperature for 30 minutes, and each fluorescence polarization at excitation wavelength of 482 nm and fluorescence wavelength of 530 nm was measured by using a plate reader Clariostar (BMG Labtech). The fluorescence polarization of the negative control was set to be 100% inhibition, fluorescence polarization of the positive control was set to be 0% inhibition, and the inhibition rate of each test compound at 100 nM was calculated by using the following equation.

Inhibition rate (%)=100−((Fluorescence polarization when test compound was added−Fluorescence polarization of negative control)/(Fluorescence polarization of positive control−Fluorescence polarization of negative control))×100

In this test, compounds of the present invention showed excellent Keap1 inhibitory activities. For example, compounds of Examples 1-(b), 2-(b), 3-(b), 4-(b), 6-(b), 7-(b), 8-(b), 9-(b), 10-(b), 11-(b), 12-(b), 13-(b), 14-(b), 15-(b), 16-(b), 17-(b), 18-(b), 19-(b), 20-(b), 21-(b), 22-(b), 23, 24-(b), 25-(b), 26-(b), 27-(b), 28-(b), 29, 31, 33, 35, 37, 39, 41, 43, 45, 47, 49-(b), 50-(b), 51-(b), 52-(b), 53, 54-(b), 55-(b), 56-(b), 57-(c), 59-(b), 60-(b), 61-(b), 62, 63-(b), 64-(b), 65-(b), 66-(b), 67-(b), 68-(b), 69, 70-(b), 71-(b), 72-(b), 73-(b), 74-(b), 75-(b), 76-(b), 77-(b), 78-(b), 79-(b), 80-(b), 81-(b), 82-(b), 84-(b), 85, 87, and 89-(b), and Comparative compound C1 showed 50% or more of inhibition rates at the compound concentration of 100 nM.

(Test Example 2): NQO1 Enzyme Induction Test (In Vitro)

Each NQO1 assay was carried out by modifying a known method (Anal Biochem 1998; 169: 328-, Methods Enzymol 2004; 382: 243-). Hepa1c1c7 cells (mouse hepatocyte line manufacture by DS Pharma Biomedical Co., Ltd., REF. No. 95090613) were cultured (5% $CO_2$, 37° C.). The cells were cultured in MEMα (manufactured by FUJIFILM Wako Pure Chemical Corporation, REF. 135-15175) medium comprising 10% FBS (manufactured by GIBCO, REF. 10082) and 1 penicillin/streptomycin/amphotericin B (manufactured by GIBCO, REF. 15240), and dispensed into a 96 well plate (manufactured by Costar, REF. 3610) at 2.0×103 cells/well. On the next day, test compound (final concentration of DHSO: 0.1%) dissolved into DMSO (manufactured by FUJIFILM Wako Pure Chemical Corporation, REF. 043-07216) was added to each well, and the plate was further cultured for about 48 hours.

A cell lysate manufactured by Cell signaling Technology, Inc. (REF. 9803) with the addition of a Protease Inhibitor manufactured by Roche Diagnostics K.K. (REF. 11-873580001) was used. A reaction solution (which is a solution comprising trishydrochloric acid (25 mM), albumin (0.07-), Tween-20 (0.01%), glucose-6-phosphate dehydrogenase (2 U/mL), flavin-adenine dinucleotide (5 μM), glucose-6-phosphate (1 μM), nicotinamide adenine dinucleotide phosphate (30 μM), 3-(4,5-dimethyl-2-thiazolyl)-2,5-diphenyltetrazolium bromide (MTT) (0.03%), and menadione (50 μM)), and a stop solution (which is a solution comprising dicumarol (0.3 mM) and potassium dihydrogen phosphate (5 mM), pH 7.4) were prepared. After the medium was removed, cell lysate (50 μL) was added thereto, and the resulting mixture was shaken at room temperature for 20 minutes. The reaction solution (200 μL) was added thereto, and the resulting mixture was left to stand at room temperature for 5 minutes. The stop solution (50 μL) was added thereto, and absorbance at 540 nm (reference 750 nm) was measured.

Cell number was measured by Cell Titer Glo assay (manufactured by Promega Corporation, REF. G9242) by using another plate prepared according to the same conditions as those described above, and correction of absorbance was carried out. The test result was analyzed by Excel, and the $EC_{150}$ value which is the concentration to elevate the NQO1 activity by 1.5 times was calculated.

The results of test compounds in this test are shown in the following Table 2. A: $EC_{150}$<0.5 nM, B: 0.5 nM≤$EC_{150}$<5 nM, C: 5 nM≤$EC_{150}$<50 nM, D: 50 nM≤$EC_{150}$<500 nM, or E: $EC_{150}$≥500 nM.

Table 2

TABLE 2A

Results of NQO1 enzyme induction test about Example compounds

| Example No. | $EC_{150}$ |
|---|---|
| 1-(b) | B |
| 2-(b) | B |
| 3-(b) | C |
| 4-(b) | C |
| 5-(b) | D |
| 6-(b) | C |
| 7-(b) | C |
| 8-(b) | B |
| 9-(b) | B |
| 10-(b) | B |
| 11-(b) | B |
| 12-(b) | B |
| 13-(b) | B |
| 14-(b) | B |
| 15-(b) | B |
| 16-(b) | D |
| 17-(b) | C |
| 18-(b) | C |
| 19-(b) | B |
| 20-(b) | B |
| 21-(b) | D |
| 22-(b) | B |
| 23 | D |
| 24-(b) | C |
| 25-(b) | B |

TABLE 2A-continued

Results of NQO1 enzyme induction test about Example compounds

| Example No. | $EC_{150}$ |
|---|---|
| 26-(b) | B |
| 27-(b) | C |
| 28-(b) | B |
| 29 | B |
| 30 | D |
| 31 | B |
| 32 | E |
| 33 | C |
| 34 | E |
| 35 | C |
| 36 | D |
| 37 | A |
| 38 | D |
| 39 | B |
| 40 | D |
| 41 | A |
| 42 | C |
| 43 | B |
| 44 | D |
| 45 | B |
| 46 | D |
| 47 | B |
| 48 | D |
| 49-(b) | B |
| 50-(b) | B |
| 51-(b) | B |
| 52-(b) | B |
| 53 | B |
| 54-(b) | C |
| 55-(b) | B |
| 56-(b) | B |
| 57-(c) | C |
| 58 | E |
| 59-(b) | B |
| 60-(b) | B |
| 61-(b) | C |
| 62 | B |
| 63-(b) | C |
| 64-(b) | C |
| 65-(b) | B |
| 66-(b) | B |
| 67-(b) | C |
| 68-(b) | C |
| 69 | A |
| 70-(b) | B |
| 71-(b) | B |
| 72-(b) | C |
| 73-(b) | C |
| 74-(b) | B |
| 75-(b) | B |
| 76-(b) | B |
| 77-(b) | B |
| 78-(b) | C |
| 79-(b) | C |
| 80-(b) | C |
| 81-(b) | C |
| 82-(b) | C |
| 83-(b) | C |
| 84-(b) | B |
| 85 | B |
| 86 | — |
| 87 | B |
| 88 | — |
| 89-(b) | C |
| 90 | E |

TABLE 2B

Result of NQO1 enzyme induction test about Comparative compound

| Comparative compound | $EC_{150}$ |
|---|---|
| C1 | C |

(Test Example 3) NQO1 Expression Induction Test in Mouse Kidney (Single Administration)

Each test compound solution for administration was prepared by dissolving or suspending each test compound into a 0.5 w/v % aqueous solution of methylcellulose (0.5% MC) (manufactured by Wako Pure Chemical Industries, Ltd.).

Each prepared test compound was orally administered to a BALB/c mouse (female, provided by Charles River Laboratories Japan, Inc.). Non-treated group was used as a control group. After 6 hours from the administration, each mouse was anesthetized with isoflurane, and euthanized with bloodletting by incising a lower aorta. Immediately, the left kidney was excised, cut into small pieces, and then the cut kidney pieces were transferred to RNA later (Thermo Fisher Scientific).

Then, mRNA was extracted from the collected kidney pieces by using NucleoSpin (registered trademark) RNA Kit (Takara Bio Inc.), each concentration was quantified by FlexStation3 (Molecular Devices), and then the concentration was adjusted to a constant concentration. A reverse transcription synthesis of cDNA was carried out from the mRNA with the constant concentration by using PrimeScript™ RT reagent Kit with gDNA Eraser and PCR Thermal Cycler (Takara Bio Inc.). Then, in addition to the resulting cDNA, SYBR (registered trademark) Premix Ex Taq™ II and NQO1, GAPDH primer (Takara Bio Inc.) were used to carry out Real-time PCR by PCR Thermal Cycler Dice Real time (Takara Bio Inc.), and the NQO1 expression was quantified by using the GAPDH expression as the reference.

In order to evaluate the NQO1 expression induction in each group, the NQO1 expression induction ratio was calculated by using the following equation.

(NQO1 expression induction ratio)=(Average NQO1 expression in test compound administered group)+(Average NQO1 expression in control group)

In this test, compounds of the present invention showed excellent NQO1 expression induction activities. The results of test compounds are shown in the following Table 3. A: NQO1 expression induction ratio>6, B: 3<NQO1 expression induction ratio≤6, or C: NQO1 expression induction ratio≤3.

Table 3

TABLE 3A

| Results of NQO1 expression induction test in mouse kidney about Example compounds | | | |
|---|---|---|---|
| | NQO1 expression induction activity Dose | | |
| Example No. | 30 mg/kg | 20 mg/kg | 10 mg/kg |
| 1-(b) | B | — | — |
| 2-(b) | B | — | — |
| 3-(b) | A | — | — |
| 4-(b) | A | — | — |
| 5-(b) | — | — | — |
| 6-(b) | B | — | — |
| 7-(b) | B | — | — |
| 8-(b) | B | — | — |
| 9-(b) | B | — | — |
| 10-(b) | A | — | — |
| 11-(b) | A | — | — |
| 12-(b) | A | — | — |
| 13-(b) | B | — | — |
| 14-(b) | A | — | — |
| 15-(b) | B | — | — |
| 16-(b) | C | — | — |
| 17-(b) | B | — | — |
| 18-(b) | B | — | — |
| 19-(b) | C | — | — |
| 20-(b) | — | — | — |
| 21-(b) | C | — | — |
| 22-(b) | A | — | — |
| 23 | C | — | — |
| 24-(b) | A | — | — |
| 25-(b) | A | — | — |
| 26-(b) | A | — | — |
| 27-(b) | C | — | — |
| 28-(b) | B | — | — |
| 29 | — | — | A |
| 30 | — | — | — |
| 31 | — | — | B |
| 32 | — | — | — |
| 33 | — | — | B |
| 34 | — | — | — |
| 35 | — | — | A |
| 36 | — | — | — |
| 37 | — | — | A |
| 38 | — | — | — |
| 39 | — | — | B |
| 40 | — | — | — |
| 41 | — | — | A |
| 42 | — | — | — |
| 43 | — | — | A |
| 44 | — | — | — |
| 45 | — | — | A |
| 46 | — | — | — |
| 47 | — | — | A |
| 48 | — | — | — |
| 49-(b) | A | — | — |
| 50-(b) | A | — | — |
| 51-(b) | A | — | — |
| 52-(b) | A | — | — |
| 53 | A | — | — |
| 54-(b) | B | — | — |
| 55-(b) | C | — | — |
| 56-(b) | B | — | — |
| 57-(c) | — | — | — |
| 58 | — | — | — |
| 59-(b) | A | — | — |
| 60-(b) | C | — | — |
| 61-(b) | B | — | — |
| 62 | C | — | — |
| 63-(b) | B | — | — |
| 64-(b) | — | — | — |
| 65-(b) | — | B | — |
| 66-(b) | — | A | — |
| 67-(b) | — | C | — |
| 68-(b) | — | B | — |

TABLE 3A-continued

| Results of NQO1 expression induction test in mouse kidney about Example compounds | | | |
|---|---|---|---|
| | NQO1 expression induction activity Dose | | |
| Example No. | 30 mg/kg | 20 mg/kg | 10 mg/kg |
| 69 | — | B | — |
| 70-(b) | — | A | — |
| 71-(b) | — | A | — |
| 72-(b) | — | C | — |
| 73-(b) | — | A | — |
| 74-(b) | — | B | — |
| 75-(b) | — | A | — |
| 76-(b) | — | A | — |
| 77-(b) | — | A | — |
| 78-(b) | — | B | — |
| 79-(b) | — | B | — |
| 80-(b) | — | A | — |
| 81-(b) | — | B | — |
| 82-(b) | — | A | — |
| 83-(b) | — | A | — |
| 84-(b) | — | A | — |
| 85 | — | — | — |
| 86 | — | — | — |
| 87 | — | — | — |
| 88 | — | — | — |
| 89-(b) | — | — | B |
| 90 | — | — | — |

TABLE 3B

| Result of NQO1 expression induction test in mouse kidney about Comparative compound | | | |
|---|---|---|---|
| Comparative | NQO1 expression induction activity Dose | | |
| compound | 30 mg/kg | 20 mg/kg | 10 mg/kg |
| C1 | — | — | C |

Pharmacokinetic Test Example

(Test Example 4) Metabolism Test Using Human and Monkey Liver Microsome Fractions A reaction composition solution (comprising NADPH Regenerating System, Solution A (manufactured by Corning Inc., REF. 451220) (50 μL), NADPH Regenerating System, Solution B (manufactured by Corning Inc., REF. 451200) (10 μL), 250 mM UDP-glucuronic acid (40 μL), UGT Reaction Mix Solution B (manufactured by Corning Inc., REF. 451320) (200 μL), and distilled water (640 μL)) in which human liver microsomes (manufactured by Xenotech, Cat. No. H610) or monkey liver microsomes (manufactured by Xenotech, Cat. No. P2000) (corresponding to 1 mg of protein) were suspended was prepared. After the solution was incubated at 37° C. for 5 minutes, each test compound dissolved into DMSO (manufactured by FUJIFILM Wako Pure Chemical Corporation, Code No. 043-07216) was added to the solution so that the final concentration was set to be 10 μmol/L, and a reaction was initiated. After 0, 5, 10, 15, 20, and 30 minute(s) from the initiation of the metabolism reaction, 100 μL of the reaction solution was taken out of the reaction system, and added to 200 μL of acetonitrile to stop the reaction. After the reaction was completed, the reaction solution was subjected to a work-up such as deproteinization, and then subjected to an UV-HPLC analysis to carry out the following analysis.

Analysis Method

The peak area of each test compound was calculated by LabSolution software (Shimadzu Corporation), and the residual ratio (%) at each culture time of test material was calculated by the following equation.

Residual ratio (%)=Peak area at each culture time+Peak area at 0 (initial time)

Next, the residual amount (nmol/mg/mL) at each culture time of test material was calculated by the following equation.

Residual amount (nmol/mg/mL)=Initial concentration of reaction solution (10 nmol/mg/mL)×residual ratio÷100

Finally, a graph in which the reaction time was plotted at horizontal axis and the residual amount was plotted at longitudinal axis was prepared on Excel, and the inclination was calculated as the elimination rate (pmol/min/mg-P) within the time range in which the graph was deemed linear.

LC system used in the test is as follows.

LC: LC20 HPLC system manufactured by Shimadzu Corporation

Column: Phenomenex Kinetex C18 (100×2.1 mm, 2.6 μm)

Column temperature: 40° C.

Flow rate: 0.25 mL/min

Mobile phase A: 0.1% formic acid solution in water,

Mobile phase B: 0.1% formic acid solution in a mixture of 50% acetonitrile/methanol Gradient: 0 to 3 min.; A/B=90/10, 3 to 11 min.; 90/10 to 5/95, 11 to 15 min.; A/B=5/95, 15 to 15.1 min; A/B=5/95 to 90/10

Measurement UV wavelength: 200 to 350 nm

In this test, representative compounds of the present invention had excellent metabolic stability.

The results of test compounds in human are shown in the following Table 4. A: metabolic rate<100 pmol/min/mg protein, B: 100≤metabolic rate<150 pmol/min/mg protein, C: 150≤metabolic rate<200 pmol/min/mg protein, D: 200≤metabolic rate<250 pmol/min/me protein, or E: metabolic rate≥250 pmol/min/mg protein.

Table 4

TABLE 4A

Results of metabolism test using human liver microsome fractions about Example compounds

| Example No. | Human metabolic rate |
|---|---|
| 1-(b) | C |
| 2-(b) | A |
| 3-(b) | C |
| 4-(b) | B |
| 5-(b) | — |
| 6-(b) | B |
| 7-(b) | B |
| 8-(b) | A |
| 9-(b) | D |
| 10-(b) | C |
| 11-(b) | D |
| 12-(b) | D |
| 13-(b) | E |
| 14-(b) | — |
| 15-(b) | E |
| 16-(b) | E |
| 17-(b) | E |
| 18-(b) | E |
| 19-(b) | E |
| 20-(b) | D |
| 21-(b) | D |
| 22-(b) | B |
| 23 | — |
| 24-(b) | — |
| 25-(b) | D |
| 26-(b) | E |
| 27-(b) | — |
| 28-(b) | — |
| 29 | A |
| 30 | E |
| 31 | B |
| 32 | D |
| 33 | A |
| 34 | C |
| 35 | B |
| 36 | C |
| 37 | A |
| 38 | E |
| 39 | A |
| 40 | E |
| 41 | A |
| 42 | E |
| 43 | A |
| 44 | E |
| 45 | A |
| 46 | E |
| 47 | B |
| 48 | E |
| 49-(b) | B |
| 50-(b) | C |
| 51-(b) | B |
| 52-(b) | C |
| 53 | C |
| 54-(b) | B |
| 55-(b) | C |
| 56-(b) | E |
| 57-(c) | C |
| 48 | C |
| 59-(b) | D |
| 60-(b) | D |
| 61-(b) | A |
| 62-(b) | — |
| 63-(b) | C |
| 64-(b) | B |
| 65-(b) | D |
| 66-(b) | E |
| 67-(b) | — |
| 68-(b) | A |
| 69 | D |
| 70-(b) | E |
| 71-(b) | D |
| 72-(b) | A |
| 73-(b) | C |
| 74-(b) | B |
| 75-(b) | E |
| 76-(b) | B |
| 77-(b) | B |
| 78-(b) | B |
| 79-(b) | E |
| 80-(b) | D |
| 81-(b) | A |
| 82-(b) | B |
| 83-(b) | C |
| 84-(b) | C |
| 85 | A |
| 86 | E |
| 87 | A |
| 88 | E |

TABLE 4A-continued

| Results of metabolism test using human liver microsome fractions about Example compounds | |
|---|---|
| Example No. | Human metabolic rate |
| 89-(b) | E |
| 90 | C |

TABLE 4B

| Results of metabolism test using human liver microsome fractions about Comparative compounds | |
|---|---|
| Comparative compound | Human metabolic rate |
| C1 | C |
| C2 | E |

INDUSTRIAL APPLICABILITY

The compounds represented by formula (I) or pharmaceutically acceptable salts thereof of the present invention have excellent Keap1 inhibitory effects, and thus are useful in the prevention, alleviation, and/or treatment of diseases of which symptoms are improved by the inhibition of Keap1.

The invention claimed is:

1. A compound represented by the following general formula (I) or a pharmaceutically acceptable salt thereof:

(I)

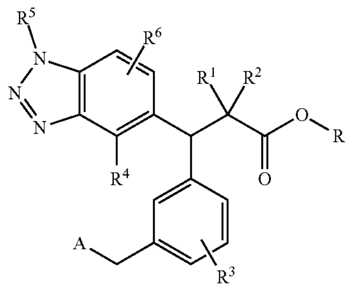

wherein:

R represents a hydrogen atom or an alkyl group optionally substituted with 1 to 5 substituent(s) independently selected from Group E;

$R^1$ and $R^2$ each independently represent a hydrogen atom, an alkyl group optionally substituted with 1 to 5 substituent(s) independently selected from Group E, an alkenyl group optionally substituted with 1 to 5 substituent(s) independently selected from Group E, or an alkynyl group optionally substituted with 1 to 5 substituent(s) independently selected from Group E;

or $R^1$ and $R^2$ are combined with the carbon atom to which they are attached to form a monocyclic carbocycle optionally substituted with 1 to 5 substituent(s) independently selected from Group E;

$R^3$, $R^4$, and $R^6$ each independently represent a hydrogen atom, a halogen atom, an alkyl group optionally substituted with 1 to 5 substituent(s) independently selected from Group E, an alkenyl group optionally substituted with 1 to 5 substituent(s) independently selected from Group E, an alkynyl group optionally substituted with 1 to 5 substituent(s) independently selected from Group E, an alkoxy group optionally substituted with 1 to 5 substituent(s) independently selected from Group E, a cycloalkyl group optionally substituted with 1 to 5 substituent(s) independently selected from Group E, a nonaromatic heterocyclyl group optionally substituted with 1 to 5 substituent(s) independently selected from Group E, an aryl group optionally substituted with 1 to 5 substituent(s) independently selected from Group E, a heteroaryl group optionally substituted with 1 to 5 substituent(s) independently selected from Group E, or a cyano group;

$R^5$ represents (i) a hydrogen atom, or (ii) an alkyl group optionally substituted with 1 to 5 substituent(s) independently selected from the group consisting of a halogen atom, a hydroxy group, a cycloalkyl group optionally substituted with 1 to 5 substituent(s) independently selected from Group E, a phenyl group optionally substituted with 1 to 5 substituent(s) independently selected from Group E, and an alkoxy group optionally substituted with 1 to 5 substituent(s) independently selected from Group E;

A has a structure represented by the following formula (II)

(II)

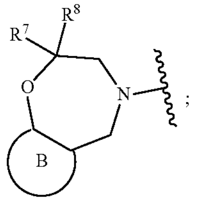

$R^7$ and $R^8$ each independently represent a hydrogen atom, an alkyl group optionally substituted with 1 to 5 substituent(s) independently selected from Group E, an alkenyl group optionally substituted with 1 to 5 substituent(s) independently selected from Group E, or an alkynyl group optionally substituted with 1 to 5 substituent(s) independently selected from Group E;

or $R^7$ and $R^8$ are combined with the carbon atom to which they are attached to form a monocyclic carbocycle optionally substituted with 1 to 5 substituent(s) independently selected from Group E;

ring B represents a bicyclic ring optionally substituted with 1 to 5 substituent(s) independently selected from the group consisting of a halogen atom, an alkyl group optionally substituted with 1 to 5 substituent(s) independently selected from Group E, an alkenyl group optionally substituted with 1 to 5 substituent(s) independently selected from Group E, an alkynyl group optionally substituted with 1 to 5 substituent(s) independently selected from Group E, an alkoxy group optionally substituted with 1 to 5 substituent(s) independently selected from Group E, a cycloalkyl group optionally substituted with 1 to 5 substituent(s) independently selected from Group E, a nonaromatic heterocyclyl group optionally substituted with 1 to 5 substituent(s) independently selected from Group E, an aryl group optionally substituted with 1 to 5 substituent(s) independently selected from Group E, a heteroaryl group optionally substituted with 1 to 5 substituent(s) independently selected from Group E, and a cyano group;

the symbol represents the point of attachment to the rest of molecule; and

Group E represents a group consisting of a halogen atom, a hydroxy group, and an alkoxy group optionally substituted with 1 to 5 halogen atom(s).

2. The compound according to claim 1 or a pharmaceutically acceptable salt thereof, wherein R represents a hydrogen atom or an alkyl group optionally substituted with 1 to 5 substituent(s) independently selected from Group E;

$R^1$ and $R^2$ each independently represent a hydrogen atom or an alkyl group optionally substituted with 1 to 5 substituent(s) independently selected from Group E;

or $R^1$ and $R^2$ are combined with the carbon atom to which they are attached to form a monocyclic carbocycle optionally substituted with 1 to 5 substituent(s) independently selected from Group E;

$R^3$, $R^4$, and $R^6$ each independently represent a hydrogen atom, a halogen atom, an alkyl group optionally substituted with 1 to 5 substituent(s) independently selected from Group E, or an alkoxy group optionally substituted with 1 to 5 substituent(s) independently selected from Group E;

$R^5$ represents (i) a hydrogen atom, or (ii) an alkyl group optionally substituted with 1 to 5 substituent(s) independently selected from the group consisting of a halogen atom, a hydroxy group, a phenyl group optionally substituted with 1 to 5 substituent(s) independently selected from Group E, and an alkoxy group optionally substituted with 1 to 5 substituent(s) independently selected from Group E;

$R^7$ and $R^8$ each independently represent a hydrogen atom or an alkyl group optionally substituted with 1 to 5 substituent(s) independently selected from Group E;

or $R^7$ and $R^8$ are combined with the carbon atom to which they are attached to form a monocyclic carbocycle optionally substituted with 1 to 5 substituent(s) independently selected from Group E; and ring B represents a bicyclic ring optionally substituted with 1 to 5 substituent(s) independently selected from the group consisting of a halogen atom, an alkyl group optionally substituted with 1 to 5 substituent(s) independently selected from Group E, an alkoxy group optionally substituted with 1 to 5 substituent(s) independently selected from Group E, and a cyano group.

3. The compound according to claim 1 or a pharmaceutically acceptable salt thereof, wherein R represents a hydrogen atom or an alkyl group;

$R^1$ and $R^2$ each independently represent a hydrogen atom or an alkyl group;

or $R^1$ and $R^2$ are combined with the carbon atom to which they are attached to form a monocyclic carbocycle;

$R^3$, $R^4$, and $R^6$ each independently represent a hydrogen atom, a halogen atom, an alkyl group, or an alkoxy group;

$R^5$ represents (i) a hydrogen atom, or (ii) an alkyl group optionally substituted with 1 to 5 substituent(s) independently selected from the group consisting of a halogen atom, a hydroxy group, a phenyl group, and an alkoxy group;

$R^7$ and $R^8$ each independently represent a hydrogen atom or an alkyl group;

or $R^7$ and $R^8$ are combined with the carbon atom to which they are attached to form a monocyclic carbocycle optionally substituted with 1 to 5 substituent(s) independently selected from Group E; and ring B represents a bicyclic ring optionally substituted with 1 to 5 substituent(s) independently selected from the group consisting of a halogen atom, an alkyl group optionally substituted with 1 to 5 substituent(s) independently selected from Group E, an alkoxy group optionally substituted with 1 to 5 substituent(s) independently selected from Group E, and a cyano group.

4. The compound according to claim 1 or a pharmaceutically acceptable salt thereof, wherein the compound has a structure represented by the following general formula (I-1):

(I-1)

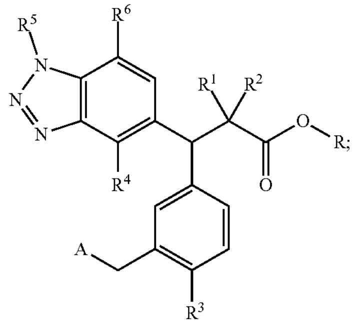

R represents a hydrogen atom or an alkyl group;

$R^1$ and $R^2$ each independently represent a hydrogen atom or an alkyl group;

or $R^1$ and $R^2$ are combined with the carbon atom to which they are attached to form a monocyclic carbocycle;

$R^3$ represents a hydrogen atom, a halogen atom, an alkyl group, or an alkoxy group;

$R^4$ and $R^6$ each independently represent a hydrogen atom, an alkyl group, or an alkoxy group; and $R^5$ represents a hydrogen atom or an alkyl group.

5. The compound according to claim 1 or a pharmaceutically acceptable salt thereof, wherein R represents a hydrogen atom;

$R^1$ and $R^2$ each independently represent a hydrogen atom or an alkyl group;

or $R^1$ and $R^2$ are combined with the carbon atom to which they are attached to form a monocyclic carbocycle;

$R^3$ represents an alkyl group;

$R^4$ represents an alkyl group;

$R^5$ represents an alkyl group; and $R^6$ represents a hydrogen atom.

6. The compound according to claim 1 or a pharmaceutically acceptable salt thereof, wherein A has a structure represented by any one of the following formulae (II-1) to (II-3):

(II-1)

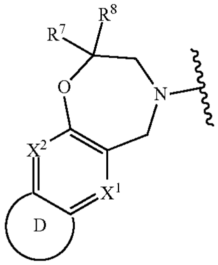

(II-2)

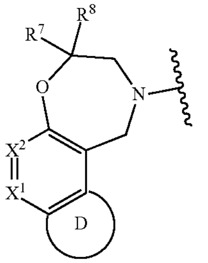

(II-3)

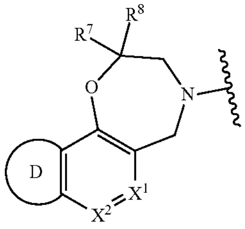

wherein:

$R^7$ and $R^8$ each independently represent a hydrogen atom or an alkyl group;

or $R^7$ and $R^8$ are combined with the carbon atom to which they are attached to form a monocyclic carbocycle optionally substituted with 1 to 5 substituent(s) independently selected from Group E;

$X^1$ and $X^2$ each independently represent $CR^9$ or a nitrogen atom;

$R^9$ each independently represents a hydrogen atom, a halogen atom, an alkyl group optionally substituted with 1 to 5 substituent(s) independently selected from Group E, an alkoxy group optionally substituted with 1 to 5 substituent(s) independently selected from Group E, or a cyano group; and ring D represents a 5 to 6 membered carbocycle or a 5 to 6 membered heterocycle, each of which is optionally substituted with 1 to 5 substituent(s) independently selected from the group consisting of a halogen atom, an alkyl group optionally substituted with 1 to 5 substituent(s) independently selected from Group E, an alkoxy group optionally substituted with 1 to 5 substituent(s) independently selected from Group E, and a cyano group.

7. The compound according to claim 1 or a pharmaceutically acceptable salt thereof, wherein A has a structure represented by any one of the following formulae (II-1-1) to (II-3-4):

(II-1-1)

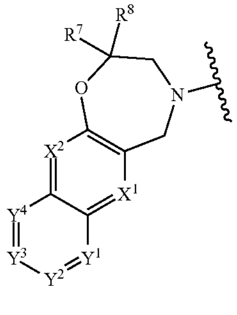

(II-1-2)

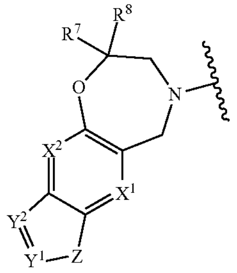

(II-1-3)

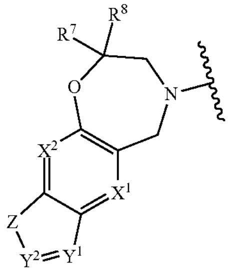

(II-1-4)

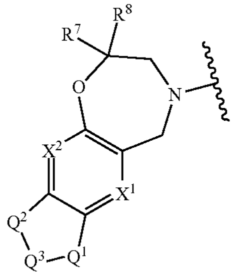

(II-2-1)

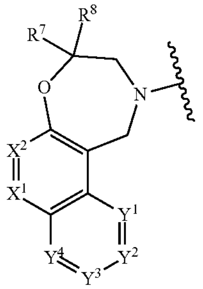

-continued (II-2-2)

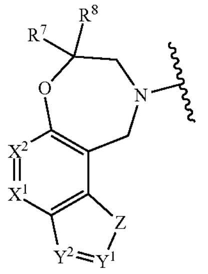

(II-2-3)

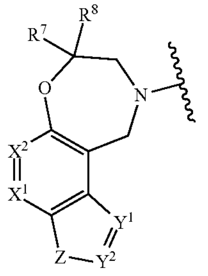

(II-2-4)

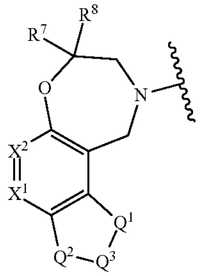

(II-3-1)

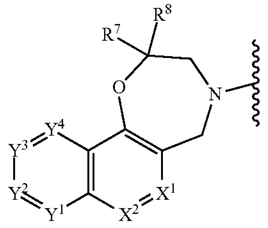

(II-3-2)

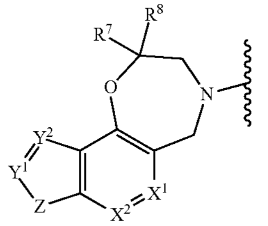

(II-3-3)

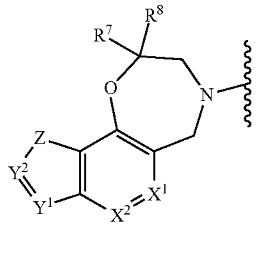

-continued (II-3-4)

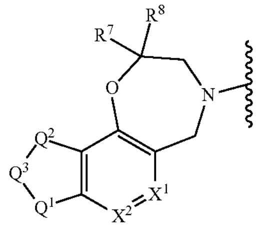

wherein:

$R^7$ and $R^8$ each independently represent a hydrogen atom or an alkyl group;

or $R^7$ and $R^8$ are combined with the carbon atom to which they are attached to form a monocyclic carbocycle optionally substituted with 1 to 5 substituent(s) independently selected from Group E;

$X^1$ and $X^2$ each independently represent $CR^9$ or a nitrogen atom;

$Y^1$, $Y^2$, $Y^3$, and $Y^4$ each independently represent $CR^{10}$ or a nitrogen atom;

$R^9$ and $R^{10}$ each independently represent a hydrogen atom, a halogen atom, an alkyl group optionally substituted with 1 to 5 substituent(s) independently selected from Group E, an alkoxy group optionally substituted with 1 to 5 substituent(s) independently selected from Group E, or a cyano group;

$Q^1$ and $Q^2$ each independently represent $CR^{11}R^{12}$, $NR^{13}$, an oxygen atom, a sulfur atom, SO, or $SO_2$;

$R^{11}$ and $R^{12}$ each independently represent a hydrogen atom, a halogen atom, or an alkyl group;

$R^{13}$ each independently represents a hydrogen atom or an alkyl group;

Z represents $NR^{14}$, an oxygen atom, or a sulfur atom;

$R^{14}$ represents a hydrogen atom or an alkyl group;

$Q^3$ represents $(CU^1U^2)_n$;

$U^1$ and $U^2$ each independently represent a hydrogen atom, a halogen atom, or an alkyl group; and n represents 1, 2, or 3.

8. The compound according to claim 1 or a pharmaceutically acceptable salt thereof, wherein A has a structure represented by the following formula (II-1-1):

(II-1-1)

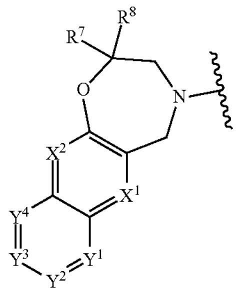

wherein:

$R^7$ and $R^8$ each independently represent a hydrogen atom or an alkyl group;

or $R^7$ and $R^8$ are combined with the carbon atom to which they are attached to form a monocyclic carbocycle;

$X^1$ and $X^2$ each independently represent $CR^9$;

any one of $Y^1$, $Y^2$, $Y^3$, and $Y^4$ represents a nitrogen atom, and the other three each independently represent $CR^{10}$;

$R^9$ each represents a hydrogen atom; and $R^{10}$ each independently represents a hydrogen atom, a halogen atom, an alkyl group, or an alkoxy group.

9. The compound according to claim 1 represented by the following general formula (I-1-1) or a pharmaceutically acceptable salt thereof:

(I-1-1)

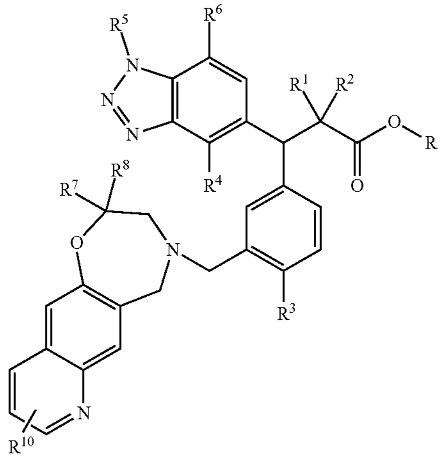

wherein:

R represents a hydrogen atom or an alkyl group;

$R^1$ and $R^2$ each independently represent a hydrogen atom or an alkyl group;

or $R^1$ and $R^2$ are combined with the carbon atom to which they are attached to form a monocyclic carbocycle;

$R^3$, $R^4$, and $R^6$ each independently represent a hydrogen atom, a halogen atom, an alkyl group, or an alkoxy group;

$R^5$ represents (i) a hydrogen atom, or (ii) an alkyl group optionally substituted with 1 to 5 substituent(s) independently selected from the group consisting of a halogen atom, a hydroxy group, a phenyl group, and an alkoxy group;

$R^7$ and $R^8$ each independently represent a hydrogen atom or an alkyl group;

or $R^7$ and $R^8$ are combined with the carbon atom to which they are attached to form a monocyclic carbocycle optionally substituted with 1 to 5 substituent(s) independently selected from Group E;

$R^{10}$ represents a hydrogen atom, a halogen atom, an alkyl group optionally substituted with 1 to 5 substituent(s) independently selected from Group E, an alkoxy group optionally substituted with 1 to 5 substituent(s) independently selected from Group E, or a cyano group; and Group E represents a group consisting of a halogen atom, a hydroxy group, and an alkoxy group optionally substituted with 1 to 5 halogen atom(s).

10. The compound according to claim 9 or a pharmaceutically acceptable salt thereof, wherein R represents a hydrogen atom or an alkyl group;

$R^1$ and $R^2$ each independently represent a hydrogen atom or an alkyl group;

or $R^1$ and $R^2$ are combined with the carbon atom to which they are attached to form a monocyclic carbocycle;

$R^3$ represents a hydrogen atom, a halogen atom, an alkyl group, or an alkoxy group;

$R^4$ represents a hydrogen atom or an alkyl group;

$R^5$ represents an alkyl group;

$R^6$ represents a hydrogen atom;

$R^7$ and $R^8$ each independently represent a hydrogen atom or an alkyl group;

or $R^7$ and $R^8$ are combined with the carbon atom to which they are attached to form a monocyclic carbocycle; and $R^{10}$ represents a hydrogen atom, a halogen atom, an alkyl group, or an alkoxy group.

11. The compound according to claim 1 selected from the group consisting of methyl 3-(1,4-dimethyl-1H-benzo[d][1,2,3]triazol-5-yl)-3-(3-(((R)-6-ethyl-2,2-difluoro-6,7-dihydro-[1,3]dioxolo[4',5':4,5]benzo[1,2-f][1,4]oxazepin-8 (9H)-yl)methyl)-4-methylphenyl)-2,2-dimethylpropanoate;

3-(1,4-dimethyl-1H-benzo[d][1,2,3]triazol-5-yl)-3-(3-(((R)-6-ethyl-2,2-difluoro-6,7-dihydro-[1,3]dioxolo[4',5':4,5]benzo[1,2-f][1,4]oxazepin-8 (9H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-9-ethyl-2,2-difluoro-8,9-dihydro-[1,3]dioxolo[4',5':3,4]benzo[1,2-f][1,4]oxazepin-7 (6H)-yl)methyl)-4-methylphenyl)-2,2-dimethylpropanoate;

3-(1,4-dimethyl-1H-benzo[d][1,2,3]triazol-5-yl)-3-(3-(((R)-9-ethyl-2,2-difluoro-8,9-dihydro-[1,3]dioxolo[4',5':3,4]benzo[1,2-f][1,4]oxazepin-7 (6H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3,5,7,8,9-hexahydro-4H-indeno[5,6-f][1,4]oxazepin-4-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3,5,7,8,9-hexahydro-4H-indeno[5,6-f][1,4]oxazepin-4-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3,7,8,9,10-hexahydronaphtho[2,3-f][1,4]oxazepin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3,7,8,9,10-hexahydronaphtho[2,3-f][1,4]oxazepin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-4-ethyl-3,4,8,9,10,11-hexahydronaphtho[1,2-f][1,4]oxazepin-2 (1H)-yl)methyl)-4-methylphenyl)-2,2-dimethylpropanoate;

3-(1,4-dimethyl-1H-benzo[d][1,2,3]triazol-5-yl)-3-(3-(((R)-4-ethyl-3,4,8,9,10,11-hexahydronaphtho[1,2-f][1,4]oxazepin-2 (1H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3,5,8,9,10-hexahydro-4H-indeno[5,4-f][1,4]oxazepin-4-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3,5,8,9,10-hexahydro-4H-indeno[5,4-f][1,4]oxazepin-4-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3,8,9,10,11-hexahydronaphtho[2,1-f][1,4]oxazepin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3,8,9,10,11-hexahydronaphtho[2,1-f][1,4]oxazepin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3-dihydronaphtho[2,3-f][1,4]oxazepin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3-dihydronaphtho[2,3-f][1,4]oxazepin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3-dihydro-[1,4]oxazepino [7,6-b]quinolin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3-dihydro-[1,4]oxazepino [7,6-b]quinolin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3-dihydro-[1,4]oxazepino [6,7-b]quinolin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3-dihydro-[1,4]oxazepino [6,7-b]quinolin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3-dihydro-[1,4]oxazepino [6,7-g]quinolin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3-dihydro-[1,4]oxazepino [6,7-g]quinolin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3-dihydro-[1,4]oxazepino [7,6-g]quinolin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3-dihydro-[1,4]oxazepino [7,6-g]quinolin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-10-methyl-2,3-dihydro-[1,4]oxazepino [7,6-b]quinolin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-10-methyl-2,3-dihydro-[1,4]oxazepino [7,6-b]quinolin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-8-methyl-2,3-dihydro-[1,4]oxazepino [7,6-b]quinolin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-8-methyl-2,3-dihydro-[1,4]oxazepino [7,6-b]quinolin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-8-ethyl-1,5,7,8-tetrahydro-6H-[1,4]oxazepino [6,7-f]indazol-6-yl)methyl)-4-methylphenyl)-2,2-dimethylpropanoate;

3-(1,4-dimethyl-1H-benzo[d][1,2,3]triazol-5-yl)-3-(3-(((R)-8-ethyl-1,5,7,8-tetrahydro-6H-[1,4]oxazepino [6,7-f]indazol-6-yl)methyl)-4-methylphenyl)-2,2-dimethylpropanoic acid;

methyl 3-(1,4-dimethyl-1H-benzo[d][1,2,3]triazol-5-yl)-3-(3-(((R)-4-ethyl-3,4-dihydronaphtho[1,2-f][1,4]oxazepin-2 (1H)-yl)methyl)-4-methylphenyl)-2,2-dimethylpropanoate;

3-(1,4-dimethyl-1H-benzo[d][1,2,3]triazol-5-yl)-3-(3-(((R)-4-ethyl-3,4-dihydronaphtho[1,2-f][1,4]oxazepin-2 (1H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-8-ethyl-8,9-dihydro-[1,4]oxazepino [7,6-h]quinolin-10 (11H)-yl)methyl)-4-methylphenyl)-2,2-dimethylpropanoate;

3-(1,4-dimethyl-1H-benzo[d][1,2,3]triazol-5-yl)-3-(3-(((R)-8-ethyl-8,9-dihydro-[1,4]oxazepino [7,6-h]quinolin-10 (11H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-4-ethyl-3,4-dihydro-[1,4]oxazepino [6,7-f]quinolin-2 (1H)-yl)methyl)-4-methylphenyl)-2,2-dimethylpropanoate;

3-(1,4-dimethyl-1H-benzo[d][1,2,3]triazol-5-yl)-3-(3-(((R)-4-ethyl-3,4-dihydro-[1,4]oxazepino [6,7-f]quinolin-2 (1H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-4-ethyl-3,4-dihydro-[1,4]oxazepino [7,6-c]quinolin-2 (1H)-yl)methyl)-4-methylphenyl)-2,2-dimethylpropanoate;

3-(1,4-dimethyl-1H-benzo[d][1,2,3]triazol-5-yl)-3-(3-(((R)-4-ethyl-3,4-dihydro-[1,4]oxazepino [7,6-c]quinolin-2 (1H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-7-ethyl-1,7,8,10-tetrahydro-9H-[1,4]oxazepino [7,6-g]indazol-9-yl)methyl)-4-methylphenyl)-2,2-dimethylpropanoate;

3-(1,4-dimethyl-1H-benzo[d][1,2,3]triazol-5-yl)-3-(3-(((R)-7-ethyl-1,7,8,10-tetrahydro-9H-[1,4]oxazepino [7,6-g]indazol-9-yl)methyl)-4-methylphenyl)-2,2-dimethylpropanoic acid;

methyl 3-(1,4-dimethyl-1H-benzo[d][1,2,3]triazol-5-yl)-3-(3-(((R)-7-ethyl-1-methyl-1,7,8,10-tetrahydro-9H-[1,4]oxazepino [7,6-g]indazol-9-yl)methyl)-4-methylphenyl)-2,2-dimethylpropanoate;

3-(1,4-dimethyl-1H-benzo[d][1,2,3]triazol-5-yl)-3-(3-(((R)-7-ethyl-1-methyl-1,7,8,10-tetrahydro-9H-[1,4]oxazepino [7,6-g]indazol-9-yl)methyl)-4-methylphenyl)-2,2-dimethylpropanoic acid;

methyl 3-(1,4-dimethyl-1H-benzo[d][1,2,3]triazol-5-yl)-3-(3-(((R)-7-ethyl-2-methyl-2,7,8,10-tetrahydro-9H-[1,4]oxazepino [7,6-g]indazol-9-yl)methyl)-4-methylphenyl)-2,2-dimethylpropanoate;

3-(1,4-dimethyl-1H-benzo[d][1,2,3]triazol-5-yl)-3-(3-(((R)-7-ethyl-2-methyl-2,7,8,10-tetrahydro-9H-[1,4]oxazepino [7,6-g]indazol-9-yl)methyl)-4-methylphenyl)-2,2-dimethylpropanoic acid;

3-(1,4-dimethyl-1H-benzo[d][1,2,3]triazol-5-yl)-3-(3-(((R)-4-ethyl-1,3,4,9,10,11-hexahydro-2H-pyrimido [1',2': 1,6]pyrido[2,3-f][1,4]oxazepin-2-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3-dihydronaphtho[2,1-f][1,4]oxazepin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3-dihydronaphtho[2,1-f][1,4]oxazepin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3-dihydro-[1,4]oxazepino [6,7-c]isoquinolin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3-dihydro-[1,4]oxazepino [6,7-c]isoquinolin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3-dihydro-[1,4]oxazepino [6,7-c]quinolin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3-dihydro-[1,4]oxazepino [6,7-c]quinolin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3-dihydro-[1,4]oxazepino [6,7-h]quinolin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3-dihydro-[1,4]oxazepino [6,7-h]quinolin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3-dihydro-[1,4]oxazepino [7,6-f]quinolin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3-dihydro-[1,4]oxazepino [7,6-f]quinolin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-7-fluoro-2,3-dihydronaphtho[2,1-f][1,4]oxazepin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-7-fluoro-2,3-dihydronaphtho[2,1-f][1,4]oxazepin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-8-ethyl-1-methyl-1,5,7,8-tetrahydro-6H-[1,4]oxazepino [6,7-f]indazol-6-yl)methyl)-4-methylphenyl)-2,2-dimethylpropanoate;

3-(1,4-dimethyl-1H-benzo[d][1,2,3]triazol-5-yl)-3-(3-(((R)-8-ethyl-1-methyl-1,5,7,8-tetrahydro-6H-[1,4]oxazepino [6,7-f]indazol-6-yl)methyl)-4-methylphenyl)-2,2-dimethylpropanoic acid;

methyl 3-(1,4-dimethyl-1H-benzo[d][1,2,3]triazol-5-yl)-3-(3-(((R)-8-ethyl-2-methyl-2,5,7,8-tetrahydro-6H-[1,4]oxazepino [6,7-f]indazol-6-yl)methyl)-4-methylphenyl)-2,2-dimethylpropanoate;

3-(1,4-dimethyl-1H-benzo[d][1,2,3]triazol-5-yl)-3-(3-(((R)-8-ethyl-2-methyl-2,5,7,8-tetrahydro-6H-[1,4]oxazepino [6,7-f]indazol-6-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3-dihydro-[1,4]oxazepino [6,7-g]isoquinolin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3-dihydro-[1,4]oxazepino [6,7-g]isoquinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [7,6-g]isoquinolin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-7-fluoro-2,3-dihydronaphtho[2,3-f][1,4]oxazepin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-7-fluoro-2,3-dihydronaphtho[2,3-f][1,4]oxazepin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3-dihydro-[1,4]oxazepino [7,6-f]isoquinolin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3-dihydro-[1,4]oxazepino [7,6-f]isoquinolin-4 (5H)-yl)methyl)-4-methylphenyl)-2,2-dimethylpropanoic acid;

ethyl 3-(1,4-dimethyl-1H-benzo[d][1,2,3]triazol-5-yl)-3-(3-(((R)-2-ethyl-2,3-dihydro-[1,4]oxazepino [7,6-g]quinolin-4 (5H)-yl)methyl)-4-methylphenyl) propanoate;

3-(1,4-dimethyl-1H-benzo[d][1,2,3]triazol-5-yl)-3-(3-(((R)-2-ethyl-2,3-dihydro-[1,4]oxazepino [7,6-g]quinolin-4 (5H)-yl)methyl)-4-methylphenyl) propanoic acid;

methyl 3-(1,4-dimethyl-1H-benzo[d][1,2,3]triazol-5-yl)-3-(3-(((S)-2-ethyl-2,3-dihydro-[1,4]oxazepino [7,6-g]quinolin-4 (5H)-yl)methyl)-4-methylphenyl)-2,2-dimethylpropanoate;

3-(1,4-dimethyl-1H-benzo[d][1,2,3]triazol-5-yl)-3-(3-(((S)-2-ethyl-2,3-dihydro-[1,4]oxazepino [7,6-g]quinolin-4 (5H)-yl)methyl)-4-methylphenyl)-2,2-dimethylpropanoic acid;

methyl 3-(3-(((R)-2-ethyl-2,3-dihydro-[1,4]oxazepino [7,6-g]quinolin-4 (5H)-yl)methyl)-4-methylphenyl)-3-(1-ethyl-4-methyl-1H-benzo[d][1,2,3]triazol-5-yl)-2,2-dimethylpropanoate;

3-(3-(((R)-2-ethyl-2,3-dihydro-[1,4]oxazepino [7,6-g]quinolin-4 (5H)-yl)methyl)-4-methylphenyl)-3-(1-ethyl-4-methyl-1H-benzo[d][1,2,3]triazol-5-yl)-2,2-dimethylpropanoic acid;

methyl 3-(1,4-dimethyl-1H-benzo[d][1,2,3]triazol-5-yl)-3-(3-((2,2-dimethyl-2,3-dihydro-[1,4]oxazepino [7,6-g]quinolin-4 (5H)-yl)methyl)-4-methylphenyl)-2,2-dimethylpropanoate;

3-(1,4-dimethyl-1H-benzo[d][1,2,3]triazol-5-yl)-3-(3-((2,2-dimethyl-2,3-dihydro-[1,4]oxazepino [7,6-g]quinolin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-6-ethyl-2,2-dimethyl-6,7-dihydro-[1,3]dioxolo[4',5':4,5]benzo[1,2-f][1,4]oxazepin-8 (9H)-yl)methyl)-4-methylphenyl)-2,2-dimethylpropanoate;

3-(1,4-dimethyl-1H-benzo[d][1,2,3]triazol-5-yl)-3-(3-(((R)-6-ethyl-2,2-dimethyl-6,7-dihydro-[1,3]dioxolo

[4',5':4,5]benzo[1,2-f][1,4]oxazepin-8 (9H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [6,7-h]isoquinolin-4 (5H)-yl)methyl)-4-methylphenyl)-2,2-dimethylpropanoic acid;

methyl 3-(3-((2,3-dihydro-[1,4]oxazepino [7,6-g]quinolin-4 (5H)-yl)methyl)-4-methylphenyl)-3-(1,4-dimethyl-1H-benzo[d][1,2,3]triazol-5-yl)-2,2-dimethylpropanoate;

3-(3-((2,3-dihydro-[1,4]oxazepino [7,6-g]quinolin-4 (5H)-yl)methyl)-4-methylphenyl)-3-(1,4-dimethyl-1H-benzo[d][1,2,3]triazol-5-yl)-2,2-dimethylpropanoic acid;

methyl 3-(1,4-dimethyl-1H-benzo[d][1,2,3]triazol-5-yl)-3-(3-(((R)-6-ethyl-1,6,7,9-tetrahydro-8H-[1,4]oxazepino [7,6-f]indazol-8-yl)methyl)-4-methylphenyl)-2,2-dimethylpropanoate;

3-(1,4-dimethyl-1H-benzo[d][1,2,3]triazol-5-yl)-3-(3-(((R)-6-ethyl-1,6,7,9-tetrahydro-8H-[1,4]oxazepino [7,6-f]indazol-8-yl)methyl)-4-methylphenyl)-2,2-dimethylpropanoic acid;

methyl 3-(1,4-dimethyl-1H-benzo[d][1,2,3]triazol-5-yl)-3-(3-(((R)-6-ethyl-1-methyl-1,6,7,9-tetrahydro-8H-[1,4]oxazepino [7,6-f]indazol-8-yl)methyl)-4-methylphenyl)-2,2-dimethylpropanoate;

3-(1,4-dimethyl-1H-benzo[d][1,2,3]triazol-5-yl)-3-(3-(((R)-6-ethyl-1-methyl-1,6,7,9-tetrahydro-8H-[1,4]oxazepino [7,6-f]indazol-8-yl)methyl)-4-methylphenyl)-2,2-dimethylpropanoic acid;

methyl 3-(1,4-dimethyl-1H-benzo[d][1,2,3]triazol-5-yl)-3-(3-(((R)-6-ethyl-2-methyl-2,6,7,9-tetrahydro-8H-[1,4]oxazepino [7,6-f]indazol-8-yl)methyl)-4-methylphenyl)-2,2-dimethylpropanoate;

3-(1,4-dimethyl-1H-benzo[d][1,2,3]triazol-5-yl)-3-(3-(((R)-6-ethyl-2-methyl-2,6,7,9-tetrahydro-8H-[1,4]oxazepino [7,6-f]indazol-8-yl)methyl)-4-methylphenyl)-2,2-dimethylpropanoic acid;

methyl 3-(3-(((R)-7-chloro-2-ethyl-2,3-dihydronaphtho[2,1-f][1,4]oxazepin-4 (5H)-yl)methyl)-4-methylphenyl)-3-(1,4-dimethyl-1H-benzo[d][1,2,3]triazol-5-yl)-2,2-dimethylpropanoate;

3-(3-(((R)-7-chloro-2-ethyl-2,3-dihydronaphtho[2,1-f][1,4]oxazepin-4 (5H)-yl)methyl)-4-methylphenyl)-3-(1,4-dimethyl-1H-benzo[d][1,2,3]triazol-5-yl)-2,2-dimethylpropanoic acid;

methyl 3-(3-(((R)-7-chloro-2-ethyl-2,3-dihydronaphtho[2,3-f][1,4]oxazepin-4 (5H)-yl)methyl)-4-methylphenyl)-3-(1,4-dimethyl-1H-benzo[d][1,2,3]triazol-5-yl)-2,2-dimethylpropanoate;

3-(3-(((R)-7-chloro-2-ethyl-2,3-dihydronaphtho[2,3-f][1,4]oxazepin-4 (5H)-yl)methyl)-4-methylphenyl)-3-(1,4-dimethyl-1H-benzo[d][1,2,3]triazol-5-yl)-2,2-dimethylpropanoic acid;

3-(3-(((R)-10-chloro-2-ethyl-2,3-dihydro-[1,4]oxazepino [7,6-g]quinolin-4 (5H)-yl)methyl)-4-methylphenyl)-3-(1,4-dimethyl-1H-benzo[d][1,2,3]triazol-5-yl)-2,2-dimethylpropanoic acid;

methyl 3-(1,4-dimethyl-1H-benzo[d][1,2,3]triazol-5-yl)-3-(3-(((R)-2-ethyl-10-methoxy-2,3-dihydro-[1,4]oxazepino [7,6-g]quinolin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-10-methoxy-2,3-dihydro-[1,4]oxazepino [7,6-g]quinolin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-10-methyl-2,3-dihydro-[1,4]oxazepino [7,6-g]quinolin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-10-methyl-2,3-dihydro-[1,4]oxazepino [7,6-g]quinolin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3-dihydrothieno[2',3': 4,5]benzo [1,2-f][1,4]oxazepin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3-dihydrothieno[2',3': 4,5]benzo[1,2-f][1,4]oxazepin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-2,3,7,8-tetrahydrothieno[2',3': 4,5]benzo[1,2-f][1,4]oxazepin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-2,3,7,8-tetrahydrothieno[2',3': 4,5]benzo [1,2-f][1,4]oxazepin-4 (5H)-yl)methyl)-4-methylphenyl)-2,2-dimethylpropanoic acid;

methyl 3-(1,4-dimethyl-1H-benzo[d][1,2,3]triazol-5-yl)-3-(3-(((R)-2-ethyl-9,9-dioxide-2,3,7,8-tetrahydrothieno[2',3': 4,5]benzo[1,2-f][1,4]oxazepin-4 (5H)-yl)methyl)-4-methylphenyl)-2,2-dimethylpropanoate;

3-(1,4-dimethyl-1H-benzo[d][1,2,3]triazol-5-yl)-3-(3-(((R)-2-ethyl-9,9-dioxide-2,3,7,8-tetrahydrothieno[2',3': 4,5]benzo[1,2-f][1,4]oxazepin-4 (5H)-yl)methyl)-4-methylphenyl)-2,2-dimethylpropanoic acid;

methyl 3-(1,4-dimethyl-1H-benzo[d][1,2,3]triazol-5-yl)-2,2-dimethyl-3-(4-methyl-3-(((R)-2-methyl-2,3-dihydro-[1,4]oxazepino [7,6-g]quinolin-4 (5H)-yl)methyl)phenyl) propanoate;

3-(1,4-dimethyl-1H-benzo[d][1,2,3]triazol-5-yl)-2,2-dimethyl-3-(4-methyl-3-(((R)-2-methyl-2,3-dihydro-[1,4]oxazepino [7,6-g]quinolin-4 (5H)-yl)methyl)phenyl) propanoic acid;

methyl 3-(3-((3'H-spiro[cyclopropane-1,2'-[1,4]oxazepino [7,6-g]quinoline]-4' (5'H)-yl)methyl)-4-methylphenyl)-3-(1,4-dimethyl-1H-benzo[d][1,2,3]triazol-5-yl)-2,2-dimethylpropanoate;

3-(3-((3'H-spiro[cyclopropane-1,2'-[1,4]oxazepino [7,6-g]quinoline]-4' (5'H)-yl)methyl)-4-methylphenyl)-3-(1,4-dimethyl-1H-benzo[d][1,2,3]triazol-5-yl)-2,2-dimethylpropanoic acid;

methyl 3-(1,4-dimethyl-1H-benzo[d][1,2,3]triazol-5-yl)-2,2-dimethyl-3-(4-methyl-3-((2-propyl-2,3-dihydro-[1,4]oxazepino [7,6-g]quinolin-4 (5H)-yl)methyl)phenyl) propanoate;

3-(1,4-dimethyl-1H-benzo[d][1,2,3]triazol-5-yl)-2,2-dimethyl-3-(4-methyl-3-((2-propyl-2,3-dihydro-[1,4]oxazepino [7,6-g]quinolin-4 (5H)-yl)methyl)phenyl) propanoic acid;

methyl 3-(1,4-dimethyl-1H-benzo[d][1,2,3]triazol-5-yl)-3-(3-(((R)-2-ethyl-2,3-dihydro-[1,4]oxazepino [7,6-g]quinolin-4 (5H)-yl)methyl)phenyl)-2,2-dimethylpropanoate;

3-(1,4-dimethyl-1H-benzo[d][1,2,3]triazol-5-yl)-3-(3-(((R)-2-ethyl-2,3-dihydro-[1,4]oxazepino [7,6-g]quinolin-4 (5H)-yl)methyl)phenyl)-2,2-dimethylpropanoic acid;

methyl 3-(4-chloro-3-(((R)-2-ethyl-2,3-dihydro-[1,4]oxazepino [7,6-g]quinolin-4 (5H)-yl)methyl)phenyl)-3-(1,4-dimethyl-1H-benzo[d][1,2,3]triazol-5-yl)-2,2-dimethylpropanoate;

3-(4-chloro-3-(((R)-2-ethyl-2,3-dihydro-[1,4]oxazepino [7,6-g]quinolin-4 (5H)-yl)methyl)phenyl)-3-(1,4-dimethyl-1H-benzo[d][1,2,3]triazol-5-yl)-2,2-dimethylpropanoic acid;

methyl 3-(1,4-dimethyl-1H-benzo[d][1,2,3]triazol-5-yl)-3-(3-(((R)-2-ethyl-2,3-dihydro-[1,4]oxazepino [7,6-g] quinolin-4 (5H)-yl)methyl)-4-methoxyphenyl)-2,2-dimethylpropanoate;

3-(1,4-dimethyl-1H-benzo[d][1,2,3]triazol-5-yl)-3-(3-(((R)-2-ethyl-2,3-dihydro-[1,4]oxazepino [7,6-g]quinolin-4 (5H)-yl)methyl)-4-methoxyphenyl)-2,2-dimethylpropanoic acid;

methyl 3-(3-(((R)-2-ethyl-2,3-dihydro-[1,4]oxazepino [7,6-g]quinolin-4 (5H)-yl)methyl)-4-methylphenyl)-2,2-dimethyl-3-(1-methyl-1H-benzo[d][1,2,3]triazol-5-yl) propanoate;

3-(3-(((R)-2-ethyl-2,3-dihydro-[1,4]oxazepino [7,6-g] quinolin-4 (5H)-yl)methyl)-4-methylphenyl)-2,2-dimethyl-3-(1-methyl-1H-benzo[d][1,2,3]triazol-5-yl) propanoic acid;

methyl 1-((1,4-dimethyl-1H-benzo[d][1,2,3]triazol-5-yl) (3-(((R)-2-ethyl-2,3-dihydro-[1,4]oxazepino [7,6-g] quinolin-4 (5H)-yl)methyl)-4-methylphenyl)methyl) cyclopentane-1-carboxylate;

1-((1,4-dimethyl-1H-benzo[d][1,2,3]triazol-5-yl) (3-(((R)-2-ethyl-2,3-dihydro-[1,4]oxazepino [7,6-g]quinolin-4 (5H)-yl)methyl)-4-methylphenyl)methyl)cyclopentane-1-carboxylic acid;

methyl 1-((1,4-dimethyl-1H-benzo[d][1,2,3]triazol-5-yl) (3-(((R)-2-ethyl-2,3-dihydro-[1,4]oxazepino [7,6-g] quinolin-4 (5H)-yl)methyl)-4-methylphenyl)methyl) cyclobutane-1-carboxylate;

1-((1,4-dimethyl-1H-benzo[d][1,2,3]triazol-5-yl) (3-(((R)-2-ethyl-2,3-dihydro-[1,4]oxazepino [7,6-g]quinolin-4 (5H)-yl)methyl)-4-methylphenyl)methyl)cyclobutane-1-carboxylic acid;

methyl 3-(1,4-dimethyl-1H-benzo[d][1,2,3]triazol-5-yl)-3-(3-(((S)-2-ethyl-2,3-dihydro-[1,4]oxazepino [6,7-c] isoquinolin-4 (5H)-yl)methyl)-4-methylphenyl)-2,2-dimethylpropanoate; and 3-(1,4-dimethyl-1H-benzo[d][1,2,3]triazol-5-yl)-3-(3-(((S)-2-ethyl-2,3-dihydro-[1,4]oxazepino [6,7-c]isoquinolin-4 (5H)-yl)methyl)-4-methylphenyl)-2,2-dimethylpropanoic acid or a pharmaceutically acceptable salt thereof.

12. The compound according to claim 1 selected from the group consisting of 3-(1,4-dimethyl-1H-benzo[d][1,2,3]triazol-5-yl)-3-(3-(((R)-6-ethyl-2,2-difluoro-6,7-dihydro-[1,3]dioxolo[4',5':4,5]benzo[1,2-f][1,4]oxazepin-8 (9H)-yl)methyl)-4-methylphenyl)-2,2-dimethylpropanoic acid;

3-(1,4-dimethyl-1H-benzo[d][1,2,3]triazol-5-yl)-3-(3-(((R)-9-ethyl-2,2-difluoro-8,9-dihydro-[1,3]dioxolo[4',5':3,4]benzo[1,2-f][1,4]oxazepin-7 (6H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3,5,7,8,9-hexahydro-4H-indeno[5,6-f][1,4]oxazepin-4-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3,7,8,9,10-hexahydronaphtho[2,3-f][1,4]oxazepin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-4-ethyl-3,4,8,9,10,11-hexahydronaphtho[1,2-f][1,4]oxazepin-2 (1H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3,5,8,9,10-hexahydro-4H-indeno[5,4-f][1,4]oxazepin-4-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3,8,9,10,11-hexahydronaphtho[2,1-f][1,4]oxazepin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydronaphtho[2,3-f][1,4]oxazepin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [7,6-b]quinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [6,7-b]quinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [6,7-g]quinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [7,6-g]quinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-10-methyl-2,3-dihydro-[1,4]oxazepino [7,6-b]quinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-8-methyl-2,3-dihydro-[1,4]oxazepino [7,6-b]quinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-8-ethyl-1,5,7,8-tetrahydro-6H-[1,4]oxazepino [6,7-f]indazol-6-yl)methyl)-4-methylphenyl)-2,2-dimethylpropanoic acid;

3-(1,4-dimethyl-1H-benzo[d][1,2,3]triazol-5-yl)-3-(3-(((R)-4-ethyl-3,4-dihydronaphtho[1,2-f][1,4]oxazepin-2 (1H)-yl)methyl)-4-methylphenyl)-2,2-dimethylpropanoic acid;

3-(1,4-dimethyl-1H-benzo[d][1,2,3]triazol-5-yl)-3-(3-(((R)-8-ethyl-8,9-dihydro-[1,4]oxazepino [7,6-h]quinolin-10 (11H)-yl)methyl)-4-methylphenyl)-2,2-dimethylpropanoic acid;

3-(1,4-dimethyl-1H-benzo[d][1,2,3]triazol-5-yl)-3-(3-(((R)-4-ethyl-3,4-dihydro-[1,4]oxazepino [6,7-f]quinolin-2 (1H)-yl)methyl)-4-methylphenyl)-2,2-dimethylpropanoic acid;

3-(1,4-dimethyl-1H-benzo[d][1,2,3]triazol-5-yl)-3-(3-(((R)-4-ethyl-3,4-dihydro-[1,4]oxazepino [7,6-c]quinolin-2 (1H)-yl)methyl)-4-methylphenyl)-2,2-dimethylpropanoic acid;

3-(1,4-dimethyl-1H-benzo[d][1,2,3]triazol-5-yl)-3-(3-(((R)-7-ethyl-1,7,8,10-tetrahydro-9H-[1,4]oxazepino [7,6-g]indazol-9-yl)methyl)-4-methylphenyl)-2,2-dimethylpropanoic acid;

3-(1,4-dimethyl-1H-benzo[d][1,2,3]triazol-5-yl)-3-(3-(((R)-7-ethyl-1-methyl-1,7,8,10-tetrahydro-9H-[1,4]

oxazepino [7,6-g]indazol-9-yl)methyl)-4-methylphenyl)-2,2-dimethylpropanoic acid;

3-(1,4-dimethyl-1H-benzo[d][1,2,3]triazol-5-yl)-3-(3-(((R)-7-ethyl-2-methyl-2,7,8,10-tetrahydro-9H-[1,4]oxazepino [7,6-g]indazol-9-yl)methyl)-4-methylphenyl)-2,2-dimethylpropanoic acid;

3-(1,4-dimethyl-1H-benzo[d][1,2,3]triazol-5-yl)-3-(3-(((R)-4-ethyl-1,3,4,9,10,11-hexahydro-2H-pyrimido[1',2': 1,6]pyrido[2,3-f][1,4]oxazepin-2-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydronaphtho[2,1-f][1,4]oxazepin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [6,7-c]isoquinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [6,7-c]quinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [6,7-h]quinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [7,6-f]quinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-7-fluoro-2,3-dihydronaphtho[2,1-f][1,4]oxazepin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-8-ethyl-1-methyl-1,5,7,8-tetrahydro-6H-[1,4]oxazepino [6,7-f]indazol-6-yl)methyl)-4-methylphenyl)-2,2-dimethylpropanoic acid;

3-(1,4-dimethyl-1H-benzo[d][1,2,3]triazol-5-yl)-3-(3-(((R)-8-ethyl-2-methyl-2,5,7,8-tetrahydro-6H-[1,4]oxazepino [6,7-f]indazol-6-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [6,7-g]isoquinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [7,6-g]isoquinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-7-fluoro-2,3-dihydronaphtho[2,3-f][1,4]oxazepin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [7,6-f]isoquinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [7,6-g]quinolin-4 (5H)-yl)methyl)-4-methylphenyl) propanoic acid;

3-(1,4-dimethyl-1H-benzo[d][1,2,3]triazol-5-yl)-3-(3-(((S)-2-ethyl-2,3-dihydro-[1,4]oxazepino [7,6-g]quinolin-4 (5H)-yl)methyl)-4-methylphenyl)-2,2-dimethylpropanoic acid;

3-(3-(((R)-2-ethyl-2,3-dihydro-[1,4]oxazepino [7,6-g]quinolin-4 (5H)-yl)methyl)-4-methylphenyl)-3-(1-ethyl-4-methyl-1H-benzo[d][1,2,3]triazol-5-yl)-2,2-dimethylpropanoic acid;

3-(1,4-dimethyl-1H-benzo[d][1,2,3]triazol-5-yl)-3-(3-((2,2-dimethyl-2,3-dihydro-[1,4]oxazepino [7,6-g]quinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-6-ethyl-2,2-dimethyl-6,7-dihydro-[1,3]dioxolo[4',5':4,5]benzo[1,2-f][1,4]oxazepin-8 (9H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [6,7-h]isoquinolin-4 (5H)-yl)methyl)-4-methylphenyl)-2,2-dimethylpropanoic acid;

3-(3-((2,3-dihydro-[1,4]oxazepino [7,6-g]quinolin-4 (5H)-yl)methyl)-4-methylphenyl)-3-(1,4-dimethyl-1H-benzo[d][1,2,3]triazol-5-yl)-2,2-dimethylpropanoic acid;

3-(1,4-dimethyl-1H-benzo[d][1,2,3]triazol-5-yl)-3-(3-(((R)-6-ethyl-1,6,7,9-tetrahydro-8H-[1,4]oxazepino[7,6-f]indazol-8-yl)methyl)-4-methylphenyl)-2,2-dimethylpropanoic acid;

3-(1,4-dimethyl-1H-benzo[d][1,2,3]triazol-5-yl)-3-(3-(((R)-6-ethyl-1-methyl-1,6,7,9-tetrahydro-8H-[1,4]oxazepino [7,6-f]indazol-8-yl)methyl)-4-methylphenyl)-2,2-dimethylpropanoic acid;

3-(1,4-dimethyl-1H-benzo[d][1,2,3]triazol-5-yl)-3-(3-(((R)-6-ethyl-2-methyl-2,6,7,9-tetrahydro-8H-[1,4]oxazepino [7,6-f]indazol-8-yl)methyl)-4-methylphenyl)-2,2-dimethylpropanoic acid;

3-(3-(((R)-7-chloro-2-ethyl-2,3-dihydronaphtho[2,1-f][1,4]oxazepin-4 (5H)-yl)methyl)-4-methylphenyl)-3-(1,4-dimethyl-1H-benzo[d][1,2,3]triazol-5-yl)-2,2-dimethylpropanoic acid;

3-(3-(((R)-7-chloro-2-ethyl-2,3-dihydronaphtho[2,3-f][1,4]oxazepin-4 (5H)-yl)methyl)-4-methylphenyl)-3-(1,4-dimethyl-1H-benzo[d][1,2,3]triazol-5-yl)-2,2-dimethylpropanoic acid;

3-(3-(((R)-10-chloro-2-ethyl-2,3-dihydro-[1,4]oxazepino[7,6-g]quinolin-4 (5H)-yl)methyl)-4-methylphenyl)-3-(1,4-dimethyl-1H-benzo[d][1,2,3]triazol-5-yl)-2,2-dimethylpropanoic acid;

3-(1,4-dimethyl-1H-benzo[d][1,2,3]triazol-5-yl)-3-(3-(((R)-2-ethyl-10-methoxy-2,3-dihydro-[1,4]oxazepino[7,6-g]quinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-10-methyl-2,3-dihydro-[1,4]oxazepino[7,6-g]quinolin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3-dihydrothieno[2',3': 4,5]benzo[1,2-f][1,4]oxazepin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-2,3,7,8-tetrahydrothieno[2',3': 4,5]benzo[1,2-f][1,4]oxazepin-4 (5H)-yl)methyl)-4-methylphenyl)-2,2-dimethylpropanoic acid;

3-(1,4-dimethyl-1H-benzo[d][1,2,3]triazol-5-yl)-3-(3-(((R)-2-ethyl-9,9-dioxide-2,3,7,8-tetrahydrothieno[2',3': 4,5]benzo[1,2-f][1,4]oxazepin-4 (5H)-yl)methyl)-4-methylphenyl)-2,2-dimethylpropanoic acid;

3-(1,4-dimethyl-1H-benzo[d][1,2,3]triazol-5-yl)-2,2-dimethyl-3-(4-methyl-3-(((R)-2-methyl-2,3-dihydro-[1,4]oxazepino [7,6-g]quinolin-4 (5H)-yl)methyl)phenyl) propanoic acid;

3-(3-((3'H-spiro[cyclopropane-1,2'-[1,4]oxazepino [7,6-g]quinoline]-4' (5'H)-yl)methyl)-4-methylphenyl)-3-(1,4-dimethyl-1H-benzo[d][1,2,3]triazol-5-yl)-2,2-dimethylpropanoic acid;

3-(1,4-dimethyl-1H-benzo[d][1,2,3]triazol-5-yl)-2,2-dimethyl-3-(4-methyl-3-((2-propyl-2,3-dihydro-[1,4] oxazepino [7,6-g]quinolin-4 (5H)-yl)methyl)phenyl) propanoic acid;

3-(1,4-dimethyl-1H-benzo[d][1,2,3]triazol-5-yl)-3-(3-(((R)-2-ethyl-2,3-dihydro-[1,4]oxazepino [7,6-g]quinolin-4 (5H)-yl)methyl)phenyl)-2,2-dimethylpropanoic acid;

3-(4-chloro-3-(((R)-2-ethyl-2,3-dihydro-[1,4]oxazepino [7,6-g]quinolin-4 (5H)-yl)methyl)phenyl)-3-(1,4-dimethyl-1H-benzo[d][1,2,3]triazol-5-yl)-2,2-dimethylpropanoic acid;

3-(1,4-dimethyl-1H-benzo[d][1,2,3]triazol-5-yl)-3-(3-(((R)-2-ethyl-2,3-dihydro-[1,4]oxazepino [7,6-g]quinolin-4 (5H)-yl)methyl)-4-methoxyphenyl)-2,2-dimethylpropanoic acid;

3-(3-(((R)-2-ethyl-2,3-dihydro-[1,4]oxazepino [7,6-g] quinolin-4 (5H)-yl)methyl)-4-methylphenyl)-2,2-dimethyl-3-(1-methyl-1H-benzo[d][1,2,3]triazol-5-yl) propanoic acid;

1-((1,4-dimethyl-1H-benzo[d][1,2,3]triazol-5-yl) (3-(((R)-2-ethyl-2,3-dihydro-[1,4]oxazepino [7,6-g]quinolin-4 (5H)-yl)methyl)-4-methylphenyl)methyl)cyclopentane-1-carboxylic acid;

1-((1,4-dimethyl-1H-benzo[d][1,2,3]triazol-5-yl) (3-(((R)-2-ethyl-2,3-dihydro-[1,4]oxazepino [7,6-g]quinolin-4 (5H)-yl)methyl)-4-methylphenyl)methyl)cyclobutane-1-carboxylic acid; and 3-(1,4-dimethyl-1H-benzo[d][1,2,3]triazol-5-yl)-3-(3-(((S)-2-ethyl-2,3-dihydro-[1,4]oxazepino [6,7-c]isoquinolin-4 (5H)-yl)methyl)-4-methylphenyl)-2,2-dimethylpropanoic acid or a pharmaceutically acceptable salt thereof.

13. A pharmaceutical composition comprising the compound according to claim 1 or a pharmaceutically acceptable salt thereof.

14. A method for prevention, alleviation, and/or treatment of a disease which is improved by the inhibition of Keap1, comprising administering the pharmaceutical composition according to claim 13 to a subject in need thereof.

15. The pharmaceutical composition according to claim 14, wherein the disease which is improved by the inhibition of Keap1 is a renal disease.

16. The compound according to claim 1, which is 3-(1,4-dimethyl-1H-benzo [d][1,2,3]triazol-5-yl)-3-(3-(((R)-2-ethyl-2,3-dihydro-[1,4]oxazepino[7,6-g]quinolin- 4(5H)-yl) methyl)-4-methylphenyl)-2,2-dimethylpropanoic acid, or a pharmaceutically acceptable salt thereof.

17. The compound according to claim 1, which is 3-(1,4-dimethyl-1H-benzo [d][1,2,3]triazol-5-yl)-3-(3-(((R)-2-ethyl-2,3-dihydro-[1,4]oxazepino[6,7-c]isoquinolin- 4(5H)-yl)methyl)-4-methylphenyl)-2,2-dimethylpropanoic acid, or a pharmaceutically acceptable salt thereof.

18. The compound according to claim 1, which is 3-(1,4-dimethyl-1H-benzo [d][1,2,3]triazol-5-yl)-3-(3-(((R)-2-ethyl-2,3-dihydro-[1,4]oxazepino[6,7-c]quinolin- 4 (5H)-yl) methyl)-4-methylphenyl)-2,2-dimethylpropanoic acid, or a pharmaceutically acceptable salt thereof.

19. The compound according to claim 1, which is 3-(1,4-dimethyl-1H-benzo [d][1,2,3]triazol-5-yl)-3-(3-(((R)-2-ethyl-10-methoxy-2,3-dihydro-[1,4]oxazepino[7,6- g]quinolin-4 (5H)-yl)methyl)-4-methylphenyl)-2,2-dimethylpropanoic acid, or a pharmaceutically acceptable salt thereof.

20. The compound according to claim 1, which is 1-((1,4-dimethyl-1H-benzo [d][1,2,3]triazol-5-yl)(3-(((R)-2-ethyl-2,3-dihydro-[1,4]oxazepino[7,6-g]quinolin-4(5H)-yl)methyl)-4-methylphenyl)methyl)cyclobutane-1-carboxylic acid, or a pharmaceutically acceptable salt thereof.

* * * * *